US007048931B1

(12) United States Patent
Xu et al.

(10) Patent No.: US 7,048,931 B1
(45) Date of Patent: May 23, 2006

(54) COMPOSITIONS AND METHODS FOR THE THERAPY AND DIAGNOSIS OF PROSTATE CANCER

(75) Inventors: Jiangchun Xu, Bellevue, WA (US); Davin C. Dillon, Issaquah, WA (US); Jennifer L. Mitcham, Redmond, WA (US); Susan L. Harlocker, Seattle, WA (US); Yuqiu Jiang, San Diego, CA (US); Steven G. Reed, Bellevue, WA (US); Michael D. Kalos, Seattle, WA (US); Marc W. Retter, Carnation, WA (US); John A. Stolk, Bothell, WA (US); Craig H. Day, Shoreline, WA (US); Yasir A. W. Skeiky, Silver Spring, MD (US); Aijun Wang, Issaquah, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 10/129,909

(22) PCT Filed: Nov. 9, 2000

(86) PCT No.: PCT/US00/30904

§ 371 (c)(1),
(2), (4) Date: Oct. 17, 2002

(87) PCT Pub. No.: WO01/34802

PCT Pub. Date: May 17, 2001

(51) Int. Cl.
*A61K 39/00* (2006.01)
*A61K 38/00* (2006.01)
*C12Q 1/68* (2006.01)
*C07H 21/02* (2006.01)
*A01N 43/04* (2006.01)

(52) U.S. Cl. .......................... 424/192.1; 435/5; 435/6; 424/94.6; 424/185.1; 424/186.1; 424/226.1; 530/300; 530/350; 536/23.1; 536/24.1; 514/44

(58) Field of Classification Search .................... 435/5, 435/6; 424/94.6, 185.1, 186.1, 226.1, 192.1; 530/300, 350; 536/23.1, 24.1; 514/44
See application file for complete search history.

(56) References Cited

U.S. PATENT DOCUMENTS

| | | | | |
|---|---|---|---|---|
| 4,818,707 | A * | 4/1989 | Breneman | 436/513 |
| 5,776,468 | A * | 7/1998 | Hauser et al. | 424/226.1 |
| 5,786,148 | A | 7/1998 | Bandman et al. | 435/6 |
| 5,846,532 | A * | 12/1998 | Kline | 424/94.6 |
| 6,090,611 | A | 7/2000 | Covacci et al. | 435/252.3 |
| 6,107,090 | A | 8/2000 | Bander | 435/344 |
| 6,130,043 | A * | 10/2000 | Billing-Medel et al. | 435/6 |
| 6,136,311 | A | 10/2000 | Bander | 424/155.1 |
| 6,252,047 | B1 | 6/2001 | Billing-Medel et al. | 530/350 |
| 6,261,562 | B1 * | 7/2001 | Xu et al. | 424/185.1 |
| 6,262,245 | B1 | 7/2001 | Xu et al. | 536/23.5 |
| 6,350,452 | B1 * | 2/2002 | Riss | 424/185.1 |
| 6,375,952 | B1 * | 4/2002 | Koelle et al. | 424/186.1 |
| 6,620,922 | B1 | 9/2003 | Xu et al. | 536/23.1 |
| 2002/0086301 | A1 | 7/2002 | Billing-Medel et al. | 435/6 |

FOREIGN PATENT DOCUMENTS

| | | |
|---|---|---|
| EP | 317 141 A2 | 5/1989 |
| EP | 652 014 A1 | 5/1995 |
| EP | 679 716 A1 | 11/1995 |
| WO | WO 93/14755 | 8/1993 |
| WO | WO 93/25224 | 12/1993 |
| WO | WO 94/09820 | 5/1994 |
| WO | WO 95/04548 | 2/1995 |
| WO | WO 95/14772 | 6/1995 |
| WO | WO 95/30758 | 11/1995 |
| WO | WO 96/21671 | 7/1996 |
| WO | WO 97/33909 | 9/1997 |
| WO | WO 98/12302 | 3/1998 |
| WO | WO 98/17687 | 4/1998 |
| WO | WO 98/20117 | 5/1998 |
| WO | WO 98/31799 | 7/1998 |
| WO | WO 98/37093 | 8/1998 |
| WO | WO 98/38310 | 9/1998 |
| WO | WO 98/39446 | 9/1998 |
| WO | WO 98/45435 | 10/1998 |
| WO | WO 98/50567 | 11/1998 |
| WO | WO 99/06548 | 2/1999 |
| WO | WO 99/06550 | 2/1999 |
| WO | WO 99/06552 | 2/1999 |

(Continued)

OTHER PUBLICATIONS

Stedman, T.L., Stedman's Medical Dictionary, 22nd Edition, The Williams & Williams Company, Baltimore, 1972. See pp. 37 and 952.*
Gygi et al., Molecular and Cellular Biology, vol. 19, pp. 1720-1730, 1999.*
Anderson et al., Electrophoresis, vol. 18, pp. 533-537, 1997.*
Ezzell, C., The J. NIH Research, vol. 7, pp. 46-49. 1995.*
Aspinall et al., Journal of Urology, vol. 154, pp. 622-628, 1996.*
Chen et al., Nature, vol. 407, pp. 916-920, 2000.*
Kajimoto et al., J. Biochem. vol. 112, pp. 28-32, 1993.*

(Continued)

*Primary Examiner*—John Brusca
*Assistant Examiner*—Shubo (Joe) Zhou
(74) *Attorney, Agent, or Firm*—Seed IP Law Group PLLC

(57) ABSTRACT

Compositions and methods for the therapy and diagnosis of cancer, such as prostate cancer, are disclosed. Compositions may comprise one or more prostate-specific proteins, immunogenic portions thereof, or polynucleotides that encode such portions. Alternatively, a therapeutic composition may comprise an antigen presenting cell that expresses a prostate-specific protein, or a T cell that is specific for cells expressing such a protein. Such compositions may be used, for example, for the prevention and treatment of diseases such as prostate cancer. Diagnostic methods based on detecting a prostate-specific protein, or mRNA encoding such a protein, in a sample are also provided.

6 Claims, 10 Drawing Sheets

FOREIGN PATENT DOCUMENTS

| | | |
|---|---|---|
| WO | WO 99/25825 | 5/1999 |
| WO | WO 99/31236 | 6/1999 |
| WO | WO 99/67384 | 12/1999 |
| WO | WO 00/04149 | 1/2000 |
| WO | WO 01/25272 | 4/2001 |
| WO | WO 01/34629 | 5/2001 |
| WO | WO 01/34802 | 5/2001 |
| WO | WO 01/51633 | 7/2001 |
| WO | WO 01/81577 | 11/2001 |

OTHER PUBLICATIONS

Abbas et al., Cellular and Molecular Immunology, Published by W.B. Saunders Company, 1991. See pp. 50-52.*

Xu et al., WO 98/37418-A2, Aug. 27, 1998.*

Ahn and Kunkel, "The structural and functional diversity of dystrophin," *Nature Genetics 3*: 283-291, Apr. 1993.

Alexeyev et al., "Improved antibiotic-resistance gene cassettes and omega elements for *Escherichia coli* vector construction and in vitro deletion/insertion mutagenesis," *Gene 160*:63-67, 1995.

Anderson, W. F., "Human gene therapy," *Nature 392*(Suppl. ): 25-30, Apr. 30, 1998.

Berthon et al., "Predisposing gene for early-onset prostate cancer, localized on chromosome 1q42.2-43," *Am. J. Hum. Genet. 62*(6):1416-1424, Jun. 1998.

Blok et al., "Isolation of cDNA that are differentially expressed between androgen-dependent and androgen-independent prostate carcinoma cells using differential display PCR," *The Prostate 26*:213-224, 1995.

Bowie et al., "Deciphering the Message in Protein Sequences: Tolerance to Amino Acid Substitutions," *Science 247*:1306-10, Mar. 16, 1990.

Busselmakers et al., Genbank Accession No. AF103907, Aug. 14, 2000.

Busselmakers et al., Genbank Accession No. AF103908, Aug. 14, 2000.

Cawthon et al., "cDNA sequence and genomic structure of EVI2B, a gene lying within an intron of the neurofibromatosis type 1 gene," *Genomics 9*:446-460, 1991.

Chu et al., "CpG oligodeoxynucleotides act as adjuvants that switch on T helper 1 (Th1) immunity," *J. Exp. Med. 186*(10): 1623-1631, Nov. 17, 1997.

Coleman et al., *Fundamental Immunology*, Wm. C. Brown Publishers, Dubuque, Iowa, 1989, pp. 465-466.

Database EMBL Accesion No. AA453562, Jun. 5, 1997, Hillier et al., "*Homo sapiens* cDNA clone 788180."

Derwent Geneseq Database, Accession No. AAV58522, Dec. 8 1998.

Derwent Geneseq Database, Accession No. AAV61287, Jan. 6, 1999.

Duerst and Nees, "Nucleic acid characteristic of late or early passage cells immortalized by papilloma virus-and related polypeptide(s) and antibodies, used for diagnosis and treatment of cervical cancer and assessing potential for progression of cervical lesions," Derwent World Patent Index, Accession No. 1998-121623, 1998. See also German Patent DE 19649207 C1.

El-Shirbiny, "Prostatic Specific Antigen," *Advances In Clinical Chemistry 31*:99-133, 1994.

Fannon, M.R., "Gene expression in normal disease states—identification of therapeutic targets," *Trends in Biotechnology 14*: 294-298, Aug. 1996.

Gao et al., "Blinded Evaluation of Reverse Transcriptase-Polymerase Chain Reaction Prostate-Specific Antigen Peripheral Blood Assay for Molecular Staging of Prostate Cancer," *Urology 53*:714-721, 1999.

Garde, S.V. et al., "Prostate inhibin peptide (PIP) in prostate cancer: a comparative immunohistochemical study with prostate-specific antigen (PSA) and prostatic acid phosphatase (PAP)," *Cancer Letters 78*: 11-17, 1994.

GenBank Accession No. AF047020, Feb, 1, 1999.

GenBank Database, Accession No. AA112574, May 29, 2003.

Hara et al., "Characterization of cell phenotype by a novel cDNA library subtraction system: expression of CD8α in a mast cell-derived interleukin-4-dependent cell line," *Blood 84*(1):189-199, Jul. 1, 1994.

Harris et al., "Polycystic Kidney Disease 1: identification and analysis of the primary defect," *J. Am. Soc. of Nephrol. 6*:1125-1133, 1995.

Hillier et al., Genbank Accession No. AA100799, Dec. 23, 1997.

Hillier et al., Genbank Accession No. R20590, Apr. 18, 1995.

Hudson, T., Genbank Accession No. G22461, May 31, 1996.

Kool, M. et al., "Analysis of Expression of *cMoat* (*MRP2*), *MRP3, MRP4,* and *MRP5,* Homologues of the multidrug resistance-associated protein gene (MRP1) in human cancer cell lines," *Cancer Research 57*:3537-3547, Aug. 15, 1997.

Kroger, B. "New serine protease form human prostate, useful for identifying specific inhibitors, antibodies and probes," Derwent World Patent Index, Accession No. 99-432218, 1999. See also European Patent EP 936 270 A2.

Lalvani et al., "Rapid effector function in $CD8^+$ memory T cells ," *J. Exp. Med. 186*(6):859-865, Sep. 15, 1997.

Lee, K. et al., "Isolation of Moat-B, a widely expressed multidrug resistance-associated protein/canalicular multispecific organic anion transporter-relatred transporter" *Cancer Research 58*: 2741-2747, Jul. 1, 1998.

Murphy, G. et al., "Comparison of Prostate Specific Membrane Antigen, and Prostate Specific Antigen Levels in Prostatic Cancer Patients," *Anticancer Research 15*: 1473-1480, 1995.

National Cancer Institute, Cancer Genome Anatomy Project (NCI-CGAP), Genbank Accession No. AA551449, Sep. 5, 1997.

National Cancer Institute, Cancer Genome Anatomy Project (NCI-CGAP), Genbank Accession No. AA551759, Aug. 11, 1997.

National Cancer Institute, Cancer Genome Anatomy Project (NCI-CGAP), Genbank Accession No. AA631143, Oct. 31, 1997.

National Cancer Institute, Cancer Genome Anatomy Project (NCI-CGAP), Genbank Accession No. AA653016, Nov. 25, 1997.

Robson et al., "Indentification of prostatic adrogen regulated genes using the differential display technique," *Proceedings of the American Association for Cancer Research Meeting 86, 36*: p. 266, Abstract No. 1589, 1995.

Schena et al., "Parallel human genome analysis: Microarray-based expression monitoring of 1000 genes," *Proc. Natl. Acad. Sci. USA 93*(19):10614-10619, Oct., 1996.

Schmidt-Wolf et al., "Activated T cells and cytokine-induced $CD3^+$ $CD56^+$ killer cells," *Annals of Hematology 74*:51-56, 1997.

Sherman et al., "Selecting T cell receptors with high affinity for self-MHC by decreasing the contribution of CD8," *Science 258*(5083):815-818, Oct. 30, 1992.

Short et al., "λZAP: a bacteriophage λ expression vector with in vivo excision properties," *Nucleic Acids Research 16*(15):7583-7600, 1988.

Sjögren, H., "Therapeutic Immunization Against Cancer Antigens Using Genetically Engineered Cells," *Immunotechnology 3*: 161-172, 1997.

Small, E.J. et al., "Immunotherapy of hormone-refractory prostate cancer with antigen-loaded dendritic cells" *Journal of Clinical Oncology 18*(23): 3894-3903, Dec. 1, 2000.

Smith et al., "Major susceptibility locus for prostate cancer on chromosome 1 suggested by a genome-wide search," *Science 274*(5291), 1371-1374, Nov. 22, 1996.

Theobald, et al., "Targeting p53 as a general tumor antigen," *Proc. Natl. Sci. USA 92*(25):11993-11997, Dec. 5, 1995.

Tsai et al., "In vitro immunization and expansion of antigen-specific cytotoxic T lymphocytes for adoptive immunotherapy using peptide-pulsed dendritic cells," *Critical Reviews in Immunology 18*:65-75, 1998.

Tusnady and Simon, "Principles governing amino acid compositions of integral membrane proteins: application to topology prediction," *J. Mol. Biol. 283*(2):489-506, Oct. 23, 1998.

Vasmatzis et al., "Discovery of three genes specfically expressed in human prostate by expressed sequence tag database analysis," *Proc. Natl. Acad. Sci USA 95*(1):300-304, Jan. 6, 1998.

Verma and Somia, "Gene therapy—promises, problems and prospects," *Nature 389*: 239-242, Sep. 18, 1997.

Yee et al., "Isolation of tyrosinase-specific $CD8^+$ and $CD4^+$ T cell clones from the peripheral blood of melanoma patients following in vitro stimulation with recombinant vaccinia virus," *The Journal of Immunology 157*(9):4079-4086, Nov. 1, 1996.

Zitvogel et al., "Eradication of Established Murine Tumors Using a Novel Cell-Free Vaccine: Dendritic Cell-Derived Exosomes," *Nature Medicine 4*(5): 594-600, May, 1998.

* cited by examiner

Expression of P501S
by the Baculovirus Expression System

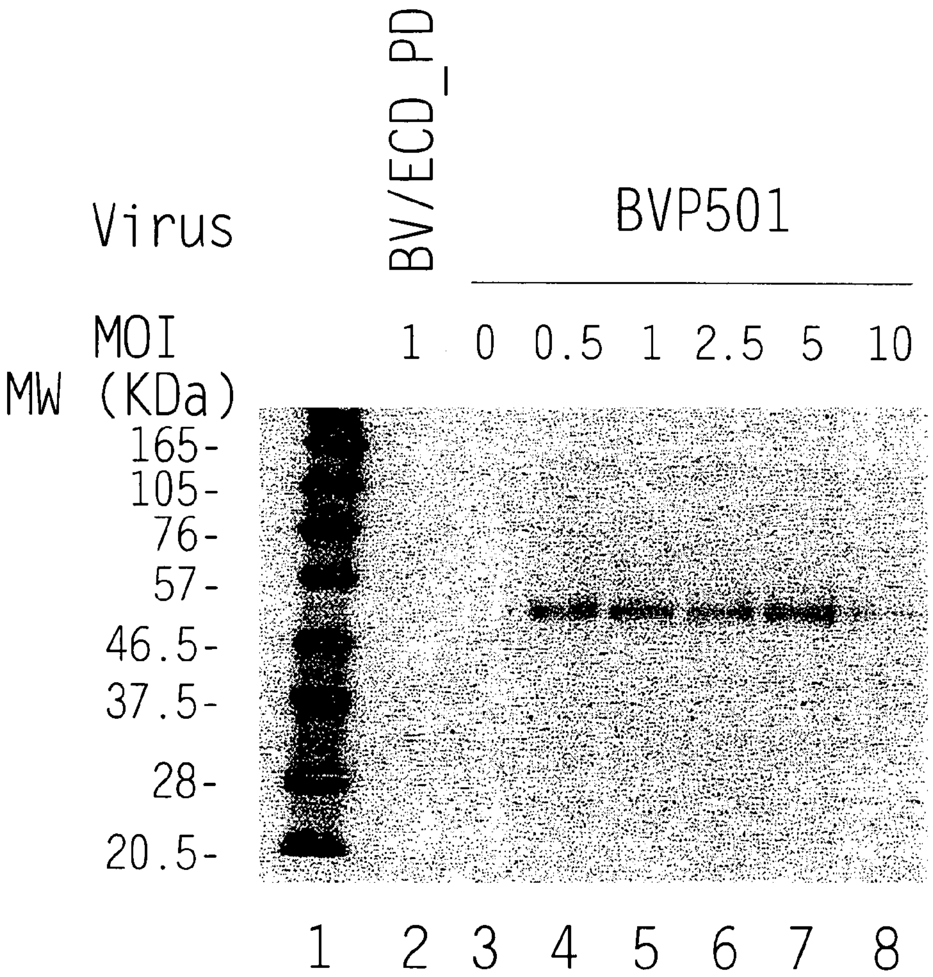

C 6 million high 5 cells in 6-well plate were infected with an unrelated control virus BV/ECD_PD (lane2), without virus (lane3), or with recombinant baculovirus for P501 at different MOIs (lane 4-8). Cell lysates were run on SDS-PAGE under the reducing conditions and analyzed by Western blot with a monoclonal antibody against P501S (P501S-10E3-G4D3). Lane 1 is the biotinylated protein molecular weight marker (BioLabs).

*Fig. 7*

Mapping of the epitope recognized by 10E3-G4-D3

Schematic of P501S with predicted
transmembrane, cytoplasmic, and extracellular regions

*MVQRLWVSRLLRHRK* AQLLLVNLLTFGLEVCLAAGIT YVPPLLLEVGVEEKFM
TMVLGIGPVLGLVCYPLLGSAS

*DHWRGRYGRRRP* FIWALSLGILLSLFLIPRAGWL AGLLCPDPRPLE LALLILGVGLLDFCGQVCFTPL

*EALLSDLFRDPDHCRQ* AYSVYAFMISLGGCLGYLLPAI DWDTSALAPYLGTQEE

CLFGLLTLIFLTCVAATLLV *AEEAALGPTEPAEGLSAPSLSPHCCPCRARLAFRNLGALLPRL*

*HQLCCRMPRTLRR* LFVAELCSWMALMTFTLFYTDF VGEGLYQGVPRAEPGTEARRHYDEGVR

MGSLGLFLQCAISLVFSLVM *DRLVQRFGTRAVYLAS* VAAFPVAAGATCLSHSVAVVTA SAA

LTGFTFSALQILPYTLASLY *HREKQVFLPKYRGDTGGASSEDSLMTSFLPGPKPGAPFPNGHVGAGGSGL*

*LPPPPALCGASACDVSVRVVVGEPTEARVVPGRG* ICLDLAILDSAFLLSQVAPSLF MGSIVQLSQS

VTAYMVSAAGLGLVAIYFAT *QVVFDKSDLAKYSA*

Underlined sequence: Predicted transmembrane domain; Bold sequence: Predicted extracellular domain; *Italic sequence*: Predicted intracellular domain. Sequence in bold/underlined: used generate polyclonal rabbit serum Localization of domains predicted using HMMTOP (G.E. Tusnady an I. Simon (1998) Principles Governing Amino Acid Composition of Integral Membrane Proteins: Applications to topology Prediction.J.Mol Biol. 283, 489-506.

*Fig. 9*

SEQUENCE LISTING

<160> NUMBER OF SEQ ID NOS: 551

<210> SEQ ID NO 1
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 1

```
tttttttttt tttttcacag tataacagct ctttatttct gtgagttcta ctaggaaatc     60
atcaaatctg agggttgtct ggaggacttc aatacacctc cccccatagt gaatcagctt    120
ccagggggtc cagtccctct ccttacttca tccccatccc atgccaaagg aagaccctcc    180
ctccttggct cacagccttc tctaggcttc ccagtgcctc caggacagag tgggttatgt    240
tttcagctcc atccttgctg tgagtgtctg gtgcgttgtg cctccagctt ctgctcagtg    300
cttcatggac agtgtccagc acatgtcact ctccactctc tcagtgtgga tccactagtt    360
ctagagcggc cgccaccgcg gtggagctcc agcttttgtt ccctttagtg agggttaatt    420
gcgcgcttgg cgtaatcatg gtcataactg tttcctgtgt gaaattgtta tccgctcaca    480
attccacaca acatacgagc cggaagcata aagtgtaaag cctggggtgc ctaatgagtg    540
anctaactca cattaattgc gttgcgctca ctgnccgctt tccagtcngg aaaactgtcg    600
tgccagctgc attaatgaat cggccaacgc ncggggaaaa gcggtttgcg ttttgggggc    660
tcttccgctt ctcgctcact nantcctgcg ctcggtcntt cggctgcggg gaacggtatc    720
actcctcaaa ggnggtatta cggttatccn naaatcnggg gatacccngg aaaaaanttt    780
aacaaaaggg cancaaaggg cngaaacgta aaaa                                814
```

<210> SEQ ID NO 2
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 2

```
acagaaatgt tggatggtgg agcacctttc tatacgactt acaggacagc agatggggaa     60
ttcatggctg ttggagcaat agaaccccag ttctacgagc tgctgatcaa aggacttgga    120
ctaaagtctg atgaacttcc caatcagatg agcatggatg attggccaga aatgaagaag    180
aagtttgcag atgtatttgc aaagaagacg aaggcagagt ggtgtcaaat ctttgacggc    240
acagatgcct gtgtgactcc ggttctgact tttgaggagg ttgttcatca tgatcacaac    300
aaggaacggg gctcgtttat caccagtgag gagcaggacg tgagcccccg ccctgcacct    360
ctgctgttaa acaccccagc catcccttct ttcaaaaggg atccactagt tctagaagcg    420
gccgccaccg cggtggagct ccagcttttg ttccctttag tgagggttaa ttgcgcgctt    480
ggcgtaatca tggtcatagc tgtttcctgt gtgaaattgt tatccgctca caattccccc    540
aacatacgag ccggaacata aagtgttaag cctggggtgc ctaatgantg agctaactcn    600
cattaattgc gttgcgctca ctgcccgctt tccagtcggg aaaactgtcg tgccactgcn    660
ttantgaatc ngccaccccc cgggaaaagg cggttgcntt ttgggcctct tccgctttcc    720
```

-continued tcgctcattg atcctngcnc ccggtcttcg gctgcggnga acggttcact cctcaaaggc 780
ggtntnccgg ttatccccaa acnggggata cccnga 816

<210> SEQ ID NO 3
<211> LENGTH: 773
<212> TYPE: DNA
<213> ORGANISM: Homo sapien
<220> FEATURE:
<221> NAME/KEY: misc_feature
<222> LOCATION: (1)...(773)
<223> OTHER INFORMATION: n = A,T,C or G

<400> SEQUENCE: 3
cttttgaaag aagggatggc tggggtgttt aacagcagag gtgcagggcg ggggctcacg 60
tcctgctcct cactggtgat aaacgagccc cgttccttgt tgtgatcatg atgaacaacc 120
tcctcaaaag tcagaaccgg agtcacacag gcatctgtgc cgtcaaagat ttgacaccac 180
tctgccttcg tcttctttgc aaatacatct gcaaacttct tcttcatttc tggccaatca 240
tccatgctca tctgattggg aagttcatca gactttagtc canntccttt gatcagcagc 300
tcgtagaact ggggttctat tgctccaaca gccatgaatt ccccatctgc tgtcctgtaa 360
gtcgtataga aaggtgctcc accatccaac atgttctgtc ctcgaggggg ggcccggtac 420
ccaattcgcc ctatantgag tcgtattacg cgcgctcact ggccgtcgtt ttacaacgtc 480
gtgactggga aaaccctggg cgttaccaac ttaatcgcct tgcagcacat ccccctttcg 540
ccagctgggc gtaatancga aaaggcccgc accgatcgcc cttccaacag ttgcgcacct 600
gaatgggnaa atgggacccc cctgttaccg cgcattnaac ccccgcnggg tttngttgtt 660
acccccacnt nnaccgctta cactttgcca gcgccttanc gcccgctccc tttcnccttt 720
cttcccttcc tttcncnccn ctttcccccg gggtttcccc cntcaaaccc cna 773

<210> SEQ ID NO 4
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 4
cctcctgagt cctactgacc tgtgctttct ggtgtggagt ccagggctgc taggaaaagg 60
aatgggcaga cacaggtgta tgccaatgtt tctgaaatgg gtataatttc gtcctctcct 120
tcggaacact ggctgtctct gaagacttct cgctcagttt cagtgaggac acacacaaag 180
acgtgggtga ccatgttgtt tgtggggtgc agagatggga ggggtggggc ccaccctgga 240
agagtggaca gtgacacaag gtggacactc tctacagatc actgaggata agctggagcc 300
acaatgcatg aggcacacac acagcaagga tgacnctgta aacatagccc acgctgtcct 360
gngggcactg ggaagcctan atnaggccgt gagcanaaag aaggggagga tccactagtt 420
ctanagcggc cgccaccgcg gtgganctcc ancttttgtt ccctttagtg agggttaatt 480
gcgcgcttgg cntaatcatg gtcatanctn tttcctgtgt gaaattgtta tccgctcaca 540
attccacaca acatacganc cggaaacata aantgtaaac ctggggtgcc taatgantga 600
ctaactcaca ttaattgcgt tgcgctcact gcccgctttc caatcnggaa acctgtcttg 660
ccncttgcat tnatgaatcn gccaaccccc ggggaaaagc gtttgcgttt tgggcgctct 720

-continued

```
tccgcttcct cnctcantta ntccctncnc tcggtcattc cggctgcngc aaaccggttc    780

accncctcca aagggggtat tccggtttcc ccnaatccgg gganancc                 828


<210> SEQ ID NO 5
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 5

tttttttttt tttttactga tagatggaat ttattaagct tttcacatgt gatagcacat     60

agttttaatt gcatccaaag tactaacaaa aactctagca atcaagaatg gcagcatgtt    120

attttataac aatcaacacc tgtggctttt aaaatttggt tttcataaga taatttatac    180

tgaagtaaat ctagccatgc ttttaaaaaa tgctttaggt cactccaagc ttggcagtta    240

acatttggca taaacaataa taaaacaatc acaatttaat aaataacaaa tacaacattg    300

taggccataa tcatatacag tataaggaaa aggtggtagt gttgagtaag cagttattag    360

aatagaatac cttggcctct atgcaaatat gtctagacac tttgattcac tcagccctga    420

cattcagttt tcaaagtagg agacaggttc tacagtatca ttttacagtt tccaacacat    480

tgaaaacaag tagaaaatga tgagttgatt tttattaatg cattacatcc tcaagagtta    540

tcaccaaccc ctcagttata aaaaattttc aagttatatt agtcatataa cttggtgtgc    600

ttattttaaa ttagtgctaa atggattaag tgaagacaac aatggtcccc taatgtgatt    660

gatattggtc atttttacca gcttctaaat ctnaactttc aggcttttga actggaacat    720

tgnatnacag tgttccanag ttncaaccta ctggaacatt acagtgtgct tgattcaaaa    780

tgttattttg ttaaaaatta aattttaacc tggtggaaaa ataatttgaa atna          834


<210> SEQ ID NO 6
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 6

tttttttttt tttttttttt aagaccctca tcaatagatg gagacataca gaaatagtca     60

aaccacatct acaaaatgcc agtatcaggc ggcggcttcg aagccaaagt gatgtttgga    120

tgtaaagtga aatattagtt ggcggatgaa gcagatagtg aggaaagttg agccaataat    180

gacgtgaagt ccgtggaagc ctgtggctac aaaaaatgtt gagccgtaga tgccgtcgga    240

aatggtgaag ggagactcga agtactctga ggcttgtagg agggtaaaat agagacccag    300

taaaattgta ataagcagtg cttgaattat ttggtttcgg ttgttttcta ttagactatg    360

gtgagctcag gtgattgata ctcctgatgc gagtaatacg gatgtgttta ggagtgggac    420

ttctagggga tttagcgggg tgatgcctgt tgggggccag tgccctccta gttgggggt     480

aggggctagg ctggagtggt aaaaggctca gaaaaatcct gcgaagaaaa aaacttctga    540

ggtaataaat aggattatcc cgtatcgaag gcctttttgg acaggtggtg tgtggtggcc    600

ttggtatgtg ctttctcgtg ttacatcgcg ccatcattgg tatatggtta gtgtgttggg    660

ttantanggc ctantatgaa gaacttttgg antggaatta aatcaatngc ttggccggaa    720
```

-continued gtcattanga nggctnaaaa ggccctgtta ngggtctggg ctnggtttta cccnacccat 780
ggaatncncc ccccggacna ntgnatccct attcttaa 818

<210> SEQ ID NO 7
<211> LENGTH: 817
<212> TYPE: DNA
<213> ORGANISM: Homo sapien
<220> FEATURE:
<221> NAME/KEY: misc_feature
<222> LOCATION: (1)...(817)
<223> OTHER INFORMATION: n = A,T,C or G

<400> SEQUENCE: 7
tttttttttt tttttttttt tggctctaga gggggtagag ggggtgctat agggtaaata 60
cgggccctat ttcaaagatt tttaggggaa ttaattctag gacgatgggt atgaaactgt 120
ggtttgctcc acagatttca gagcattgac cgtagtatac ccccggtcgt gtagcggtga 180
aagtggtttg gtttagacgt ccgggaattg catctgtttt taagcctaat gtggggacag 240
ctcatgagtg caagacgtct tgtgatgtaa ttattatacn aatgggggct tcaatcggga 300
gtactactcg attgtcaacg tcaaggagtc gcaggtcgcc tggttctagg aataatgggg 360
gaagtatgta ggaattgaag attaatccgc cgtagtcggt gttctcctag gttcaatacc 420
attggtggcc aattgatttg atggtaaggg gagggatcgt tgaactcgtc tgttatgtaa 480
aggatncctt ngggatggga aggcnatnaa ggactangga tnaatggcgg gcangatatt 540
tcaaacngtc tctanttcct gaaacgtctg aaatgttaat aanaattaan tttngttatt 600
gaatnttnng gaaaagggct tacaggacta gaaaccaaat angaaaanta atnntaangg 660
cnttatcntn aaaggtnata accnctccta tnatcccacc caatngnatt ccccacncnn 720
acnattggat nccccanttc canaaanggc cnccccccgg tgnannccnc cttttgttcc 780
cttnantgan ggttattcnc ccctngcntt atcancc 817

<210> SEQ ID NO 8
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 8
catttccggg tttactttct aaggaaagcc gagcggaagc tgctaacgtg ggaatcggtg 60
cataaggaga actttctgct ggcacgcgct agggacaagc gggagagcga ctccgagcgt 120
ctgaagcgca cgtcccagaa ggtggacttg gcactgaaac agctgggaca catccgcgag 180
tacgaacagc gcctgaaagt gctggagcgg gaggtccagc agtgtagccg cgtcctgggg 240
tgggtggccg angcctganc cgctctgcct tgctgccccc angtgggccg ccaccccctg 300
acctgcctgg gtccaaacac tgagccctgc tggcggactt caagganaac ccccacangg 360
ggattttgct cctanantaa ggctcatctg ggcctcggcc cccccacctg gttggccttg 420
tctttgangt gagccccatg tccatctggg ccactgtcng gaccaccttt ngggagtgtt 480
ctccttacaa ccacannatg cccggctcct cccggaaacc antcccancc tgngaaggat 540
caagncctgn atccactnnt nctanaaccg gccnccnccg cngtggaacc cnccttntgt 600
tccttttcnt tnagggttaa tnncgccttg gccttnccan ngtcctncnc nttttccnnt 660

-continued

```
gttnaaattg ttangcnccc nccnntcccn cnncnncnan cccgacccnn annttnnann    720

ncctgggggt nccnncngat tgacccnncc nccctntant tgcnttnggg nncnntgccc    780

ctttccctct nggganncg                                                  799
```

<210> SEQ ID NO 9
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 9

```
acgccttgat cctcccaggc tgggactggt tctgggagga gccgggcatg ctgtggtttg     60

taangatgac actcccaaag gtggtcctga cagtggccca gatggacatg gggctcacct    120

caaggacaag gccaccaggt gcgggggccg aagcccacat gatccttact ctatgagcaa    180

aatcccctgt gggggcttct ccttgaagtc cgccancagg gctcagtctt tggacccang    240

caggtcatgg ggttgtngnc caactggggg ccncaacgca aaanggcnca gggcctcngn    300

cacccatccc angacgcggc tacactnctg gacctcccnc tccaccactt tcatgcgctg    360

ttcntacccg cgnatntgtc ccanctgttt cngtgccnac tccancttct nggacgtgcg    420

ctacatacgc ccggantcnc nctcccgctt tgtccctatc cacgtnccan caacaaattt    480

cnccntantg caccnattcc cacntttnnc agntttccnc nncgngcttc cttntaaaag    540

ggttganccc cggaaaatnc cccaaagggg gggggccngg tacccaactn ccccctnata    600

gctgaantcc ccatnaccnn gnctcnatgg anccntccnt tttaannacn ttctnaactt    660

gggaanancc ctcgnccntn cccccnttaa tcccnccttg cnangnncnt cccccnntcc    720

ncccnnntng gcntntnann cnaaaaaggc ccnnnancaa tctcctnncn cctcanttcg    780

ccancccctcg aaatcggccn c                                              801
```

<210> SEQ ID NO 10
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 10

```
cagtctatnt ggccagtgtg gcagctttcc ctgtggctgc cggtgccaca tgcctgtccc     60

acagtgtggc cgtggtgaca gcttcagccg ccctcaccgg gttcaccttc tcagccctgc    120

agatcctgcc ctacacactg gcctccctct accaccggga gaagcaggtg ttcctgccca    180

aataccgagg ggacactgga ggtgctagca gtgaggacag cctgatgacc agcttcctgc    240

caggccctaa gcctggagct cccttcccta atggacacgt gggtgctgga ggcagtggcc    300

tgctcccacc tccacccgcg ctctgcgggg cctctgcctg tgatgtctcc gtacgtgtgg    360

tggtgggtga gcccaccgan gccagggtgg ttccgggccg gggcatctgc ctggacctcg    420

ccatcctgga tagtgcttcc tgctgtccca ngtggcccca tccctgttta tgggctccat    480

tgtccagctc agccagtctg tcactgccta tatggtgtct gccgcaggcc tgggtctggt    540

cccatttact ttgctacaca ggtantattt gacaagaacg anttggccaa atactcagcg    600

ttaaaaaatt ccagcaacat tgggggtgga aggcctgcct cactgggtcc aactccccgc    660
```

-continued

```
tcctgttaac cccatggggc tgccggcttg gccgccaatt tctgttgctg ccaaantnat    720
gtggctctct gctgccacct gttgctggct gaagtgcnta cngcncanct ngggggggtng    780
ggngttccc                                                            789
```

<210> SEQ ID NO 11
<211> LENGTH: 772
<212> TYPE: DNA
<213> ORGANISM: Homo sapien
<220> FEATURE:
<221> NAME/KEY: misc_feature
<222> LOCATION: (1)...(772)
<223> OTHER INFORMATION: n = A,T,C or G

<400> SEQUENCE: 11

```
cccaccctac ccaaatatta gacaccaaca cagaaaagct agcaatggat tcccttctac     60
tttgttaaat aaataagtta aatatttaaa tgcctgtgtc tctgtgatgg caacagaagg    120
accaacaggc cacatcctga taaaaggtaa gaggggggtg gatcagcaaa aagacagtgc    180
tgtgggctga ggggacctgg ttcttgtgtg ttgcccctca ggactcttcc cctacaaata    240
actttcatat gttcaaatcc catggaggag tgtttcatcc tagaaactcc catgcaagag    300
ctacattaaa cgaagctgca ggttaagggg cttanagatg ggaaaccagg tgactgagtt    360
tattcagctc ccaaaaaccc ttctctaggt gtgtctcaac taggaggcta gctgttaacc    420
ctgagcctgg gtaatccacc tgcagagtcc ccgcattcca gtgcatggaa cccttctggc    480
ctccctgtat aagtccagac tgaaaccccc ttggaaggnc tccagtcagg cagccctana    540
aactggggaa aaaagaaaag gacgccccan cccccagctg tgcanctacg cacctcaaca    600
gcacagggtg gcagcaaaaa aaccacttta ctttggcaca aacaaaaact nggggggca     660
accccggcac cccnangggg gttaacagga ancngggnaa cntggaaccc aattnaggca    720
ggcccnccac cccnaatntt gctgggaaat ttttcctccc ctaaattntt tc            772
```

<210> SEQ ID NO 12
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 12

```
gccccaattc cagctgccac accacccacg gtgactgcat tagttcggat gtcatacaaa     60
agctgattga agcaaccctc tactttttgg tcgtgagcct tttgcttggt gcaggtttca    120
ttggctgtgt tggtgacgtt gtcattgcaa cagaatgggg gaaaggcact gttctctttg    180
aagtanggtg agtcctcaaa atccgtatag ttggtgaagc cacagcactt gagccctttc    240
atggtggtgt tccacacttg agtgaagtct tcctgggaac cataatcttt cttgatggca    300
ggcactacca gcaacgtcag ggaagtgctc agccattgtg gtgtacacca aggcgaccac    360
agcagctgcn acctcagcaa tgaagatgan gaggangatg aagaagaacg tcncgagggc    420
acacttgctc tcagtcttan caccatanca gcccntgaaa accaananca aagaccacna    480
cnccggctgc gatgaagaaa tnaccccncg ttgacaaact tgcatggcac tggganccac    540
agtggcccna aaaatcttca aaaaggatgc cccatcnatt gaccccccaa atgcccactg    600
ccaacagggg ctgccccacn cncnnaacga tganccnatt gnacaagatc tncntggtct    660
```

-continued

```
tnatnaacnt gaaccctgcn tngtggctcc tgttcaggnc cnnggcctga cttctnaann    720

aangaactcn gaagncccca cngganannc g                                   751


<210> SEQ ID NO 13
<211> LENGTH: 729
<212> TYPE: DNA
<213> ORGANISM: Homo sapien
<220> FEATURE:
<221> NAME/KEY: misc_feature
<222> LOCATION: (1)...(729)
<223> OTHER INFORMATION: n = A,T,C or G

<400> SEQUENCE: 13

gagccaggcg tccctctgcc tgcccactca gtggcaacac ccgggagctg ttttgtcctt     60

tgtggancct cagcagtncc ctctttcaga actcantgcc aaganccctg aacaggagcc    120

accatgcagt gcttcagctt cattaagacc atgatgatcc tcttcaattt gctcatcttt    180

ctgtgtggtg cagccctgtt ggcagtgggc atctgggtgt caatcgatgg ggcatccttt    240

ctgaagatct tcgggccact gtcgtccagt gccatgcagt ttgtcaacgt gggctacttc    300

ctcatcgcag ccggcgttgt ggtcttagct ctaggtttcc tgggctgcta tggtgctaag    360

actgagagca agtgtgccct cgtgacgttc ttcttcatcc tcctcctcat cttcattgct    420

gaggttgcaa tgctgtggtc gccttggtgt acaccacaat ggctgagcac ttcctgacgt    480

tgctggtaat gcctgccatc aanaaaagat tatgggttcc caggaanact tcactcaagt    540

gttggaacac caccatgaaa gggctcaagt gctgtggctt cnnccaacta tacggatttt    600

gaagantcac ctacttcaaa gaaaanagtg cctttccccc atttctgttg caattgacaa    660

acgtccccaa cacagccaat tgaaaacctg cacccaaccc aaanggtcc ccaaccanaa     720

attnaaggg                                                            729


<210> SEQ ID NO 14
<211> LENGTH: 816
<212> TYPE: DNA
<213> ORGANISM: Homo sapien
<220> FEATURE:
<221> NAME/KEY: misc_feature
<222> LOCATION: (1)...(816)
<223> OTHER INFORMATION: n = A,T,C or G

<400> SEQUENCE: 14

tgctcttcct caaagttgtt cttgttgcca taacaaccac cataggtaaa gcgggcgcag     60

tgttcgctga aggggttgta gtaccagcgc gggatgctct ccttgcagag tcctgtgtct    120

ggcaggtcca cgcagtgccc tttgtcactg gggaaatgga tgcgctggag ctcgtcaaag    180

ccactcgtgt atttttcaca ggcagcctcg tccgacgcgt cggggcagtt gggggtgtct    240

tcacactcca ggaaactgtc natgcagcag ccattgctgc agcggaactg ggtgggctga    300

cangtgccag agcacactgg atggcgcctt tccatgnnan gggccctgng ggaaagtccc    360

tganccccan anctgcctct caaangcccc accttgcaca ccccgacagg ctagaatgga    420

atcttcttcc cgaaaggtag ttnttcttgt tgcccaancc ancccentaa acaaactctt    480

gcanatctgc tccgnggggg tcntantacc ancgtgggaa aagaacccca ggcngcgaac    540

caancttgtt tggatncgaa gcnataatct nctnttctgc ttggtggaca gcaccantna    600

ctgtnnanct ttagnccntg gtcctcntgg gttgnncttg aacctaatcn ccnntcaact    660

gggacaaggt aantngccnt cctttnaatt cccnancntn ccccctggtt tggggttttn    720

cncnctccta ccccagaaan nccgtgttcc cccccaacta ggggccnaaa ccnnttnttc    780
```

-continued cacaaccctn ccccacccac gggttcngnt ggttng 816

<210> SEQ ID NO 15
<211> LENGTH: 783
<212> TYPE: DNA
<213> ORGANISM: Homo sapien
<220> FEATURE:
<221> NAME/KEY: misc_feature
<222> LOCATION: (1)...(783)
<223> OTHER INFORMATION: n = A,T,C or G

<400> SEQUENCE: 15
ccaaggcctg ggcaggcata nacttgaagg tacaacccca ggaacccctg gtgctgaagg 60
atgtggaaaa cacagattgg cgcctactgc ggggtgacac ggatgtcagg gtagagagga 120
aagacccaaa ccaggtggaa ctgtggggac tcaaggaang cacctacctg ttccagctga 180
cagtgactag ctcagaccac ccagaggaca cggccaacgt cacagtcact gtgctgtcca 240
ccaagcagac agaagactac tgcctcgcat ccaacaangt gggtcgctgc cggggctctt 300
tcccacgctg gtactatgac cccacggagc agatctgcaa gagtttcgtt tatggaggct 360
gcttgggcaa caagaacaac taccttcggg aagaagagtg cattctancc tgtcngggtg 420
tgcaaggtgg gcctttgana ngcanctctg ggctcangc gactttcccc cagggcccct 480
ccatggaaag gcgccatcca ntgttctctg gcacctgtca gcccacccag ttccgctgca 540
ncaatggctg ctgcatcnac antttcctng aattgtgaca acaccccca ntgcccccaa 600 ccctcccaac aaagcttccc tgttnaaaaa tacnccantt ggcttttnac aaacncccgg 660
cncctccntt ttccccnntn aacaaagggc nctngcnttt gaactgcccn aacccnggaa 720
tctnccnngg aaaaantncc ccccctggtt cctnnaancc cctccncnaa anctnccccc 780
ccc 783

<210> SEQ ID NO 16
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 16
gccccaattc cagctgccac accacccacg gtgactgcat tagttcggat gtcatacaaa 60
agctgattga agcaaccctc tactttttgg tcgtgagcct tttgcttggt gcaggtttca 120
ttggctgtgt tggtgacgtt gtcattgcaa cagaatgggg gaaaggcact gttctctttg 180
aagtagggtg agtcctcaaa atccgtatag ttggtgaagc cacagcactt gagccctttc 240
atggtggtgt tccacacttg agtgaagtct tcctgggaac cataatcttt cttgatggca 300
ggcactacca gcaacgtcag gaagtgctca gccattgtgg tgtacaccaa ggcgaccaca 360
gcagctgcaa cctcagcaat gaagatgagg aggaggatga agaagaacgt cncgagggca 420
cacttgctct ccgtcttagc accatagcag cccangaaac caagagcaaa gaccacaacg 480
ccngctgcga atgaaagaaa ntacccacgt tgacaaactg catggccact ggacgacagt 540
tggcccgaan atcttcagaa aagggatgcc ccatcgattg aacacccana tgcccactgc 600
cnacagggct gcnccncncn gaaagaatga gccattgaag aaggatcntc ntggtcttaa 660
tgaactgaaa ccntgcatgg tggcccctgt tcagggctct tggcagtgaa ttctganaaa 720

-continued

```
aaggaacngc ntnagccccc ccaaangana aaacaccccc gggtgttgcc ctgaattggc    780

ggccaaggan ccctgccccn g                                              801


<210> SEQ ID NO 17
<211> LENGTH: 740
<212> TYPE: DNA
<213> ORGANISM: Homo sapien
<220> FEATURE:
<221> NAME/KEY: misc_feature
<222> LOCATION: (1)...(740)
<223> OTHER INFORMATION: n = A,T,C or G

<400> SEQUENCE: 17

gtgagagcca ggcgtccctc tgcctgccca ctcagtggca acacccggga gctgttttgt     60

cctttgtgga gcctcagcag ttccctcttt cagaactcac tgccaagagc cctgaacagg    120

agccaccatg cagtgcttca gcttcattaa gaccatgatg atcctcttca atttgctcat    180

ctttctgtgt ggtgcagccc tgttggcagt gggcatctgg gtgtcaatcg atggggcatc    240

ctttctgaag atcttcgggc cactgtcgtc cagtgccatg cagtttgtca acgtgggcta    300

cttcctcatc gcagccggcg ttgtggtctt tgctcttggt ttcctgggct gctatggtgc    360

taagacggag agcaagtgtg ccctcgtgac gttcttcttc atcctcctcc tcatcttcat    420

tgctgaagtt gcagctgctg tggtcgcctt ggtgtacacc acaatggctg aaccattcct    480

gacgttgctg gtantgcctg ccatcaanaa agattatggg ttcccaggaa aaattcactc    540

aantntggaa caccnccatg aaaagggctc caatttctgn tggcttcccc aactataccg    600

gaattttgaa agantcnccc tacttccaaa aaaaaaanant tgcctttncc cccnttctgt    660

tgcaatgaaa acntcccaan acngccaatn aaaacctgcc cnnncaaaaa ggntcncaaa    720

caaaaaaant nnaagggttn                                                740


<210> SEQ ID NO 18
<211> LENGTH: 802
<212> TYPE: DNA
<213> ORGANISM: Homo sapien
<220> FEATURE:
<221> NAME/KEY: misc_feature
<222> LOCATION: (1)...(802)
<223> OTHER INFORMATION: n = A,T,C or G

<400> SEQUENCE: 18

ccgctggttg cgctggtcca gngnagccac gaagcacgtc agcatacaca gcctcaatca     60

caaggtcttc cagctgccgc acattacgca gggcaagagc ctccagcaac actgcatatg    120

ggatacactt tactttagca gccagggtga caactgagag gtgtcgaagc ttattcttct    180

gagcctctgt tagtggagga agattccggg cttcagctaa gtagtcagcg tatgtcccat    240

aagcaaacac tgtgagcagc cggaaggtag aggcaaagtc actctcagcc agctctctaa    300

cattgggcat gtccagcagt tctccaaaca cgtagacacc agnggcctcc agcacctgat    360

ggatgagtgt ggccagcgct gccccccttgg ccgacttggc taggagcaga aattgctcct    420

ggttctgccc tgtcaccttc acttccgcac tcatcactgc actgagtgtg ggggacttgg    480

gctcaggatg tccagagacg tggttccgcc ccctcnctta atgacaccgn ccanncaacc    540

gtcggctccc gccgantgng ttcgtcgtnc ctgggtcagg gtctgctggc cnctacttgc    600

aancttcgtc nggcccatgg aattcaccnc accggaactn gtangatcca ctnnttctat    660

aaccggncgc caccgcnnnt ggaactccac tcttnttncc tttacttgag ggttaaggtc    720

acccttnncg ttaccttggt ccaaaccntn ccntgtgtcg anatngtnaa tcnggnccna    780
```

tnccanccnc atangaagcc ng 802

<210> SEQ ID NO 19
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 19
cnaagcttcc aggtnacggg ccgcnaancc tgacccnagg tancanaang cagncngcgg 60
gagcccaccg tcacgnggng gngtctttat nggagggggc ggagccacat cnctggacnt 120
cntgacccca actccccncc ncncantgca gtgatgagtg cagaactgaa ggtnacgtgg 180
caggaaccaa gancaaannc tgctccnntc caagtcggcn nagggggcgg ggctggccac 240
gcncatccnt cnagtgctgn aaagccccnn cctgtctact tgtttggaga acngcnnnga 300
catgcccagn gttanataac nggcngagag tnantttgcc tctcccttcc ggctgcgcan 360
cgngtntgct tagnggacat aacctgacta cttaactgaa cccnngaatc tnccnccccct 420 ccactaagct cagaacaaaa aacttcgaca ccactcantt gtcacctgnc tgctcaagta 480
aagtgtaccc catncccaat gtntgctnga ngctctgncc tgcnttangt tcggtcctgg 540
gaagacctat caattnaagc tatgtttctg actgcctctt gctccctgna acaancnacc 600
cnncnntcca aggggggggnc ggcccccaat ccccccaacc ntnaattnan tttanccccn 660
cccccnggcc cggcctttta cnancntcnn nnacngggna aaaccnnngc tttncccaac 720
nnaatccncc t 731

<210> SEQ ID NO 20
<211> LENGTH: 754
<212> TYPE: DNA
<213> ORGANISM: Homo sapien
<220> FEATURE:
<221> NAME/KEY: misc_feature
<222> LOCATION: (1)...(754)
<223> OTHER INFORMATION: n = A,T,C or G

<400> SEQUENCE: 20
tttttttttt tttttttttt taaaaacccc ctccattnaa tgnaaacttc cgaaattgtc 60
caaccccctc ntccaaatnn ccntttccgg gngggggttc caaacccaan ttannttttgg 120 annttaaatt aaatnttnnt tggnggnnna anccnaatgt nangaaagtt naacccanta 180
tnancttnaa tncctggaaa ccngtngntt ccaaaaatnt ttaaccctta antccctccg 240
aaatngttna nggaaaaccc aanttctcnt aaggttgttt gaaggntnaa tnaaaanccc 300
nnccaattgt ttttngccac gcctgaatta attggnttcc gntgttttcc nttaaaanaa 360
ggnnancccc ggttantnaa tccccccnnc cccaattata ccgantttttt ttngaattgg 420 ganccccncgg gaattaacgg ggnnnntccc tnttgggggg cnggnncccc ccccntcggg 480
ggttngggnc aggncnnaat tgtttaaggg tccgaaaaat ccctccnaga aaaaaanctc 540
ccaggntgag nntngggttt ncccccccccc canggcccct ctcgnanagt tggggtttgg 600
ggggcctggg attttntttc ccctnttncc tccccccccc ccngggganag aggttngngt 660 tttgntcnnc ggccccnccn aagancttn ccganttnan ttaaatccnt gcctnggcga 720
agtccnttgn agggntaaan ggccccctnn cggg 754

-continued

<210> SEQ ID NO 21
<211> LENGTH: 755
<212> TYPE: DNA
<213> ORGANISM: Homo sapien
<220> FEATURE:
<221> NAME/KEY: misc_feature
<222> LOCATION: (1)...(755)
<223> OTHER INFORMATION: n = A,T,C or G

<400> SEQUENCE: 21
atcancccat gaccccnaac nngggaccnc tcanccggnc nnncnaccnc cggccnatca 60
nngtnagnnc actncnnttn natcacnccc cnccnactac gcccncnanc cnacgcncta 120
nncanatncc actganngcg cgangtngan ngagaaanct nataccanag ncaccanacn 180
ccagctgtcc nanaangcct nnnatacngg nnnatccaat ntgnancctc cnaagtattn 240
nncnncanat gattttcctn anccgattac ccntnccccc tancccctcc cccccaacna 300
cgaaggcnct ggnccnaagg nngcgncncc ccgctagntc cccnncaagt cncncnccta 360
aactcanccn nattacncgc ttcntgagta tcactccccg aatctcaccc tactcaactc 420
aaaaanatcn gatacaaaat aatncaagcc tgnttatnac actntgactg ggtctctatt 480
ttagnggtcc ntnaancntc ctaatacttc cagtctncct tcnccaattt ccnaanggct 540
ctttcngaca gcatnttttg gttcccnntt gggttcttan ngaattgccc ttcntngaac 600
gggctcntct tttccttcgg ttancctggn ttcnnccggc cagttattat ttcccntttt 660
aaattcntnc cntttanttt tggcnttcna aaccccccggc cttgaaaacg gccccctggt 720
aaaaggttgt tttganaaaa tttttgtttt gttcc 755

<210> SEQ ID NO 22
<211> LENGTH: 849
<212> TYPE: DNA
<213> ORGANISM: Homo sapien
<220> FEATURE:
<221> NAME/KEY: misc_feature
<222> LOCATION: (1)...(849)
<223> OTHER INFORMATION: n = A,T,C or G

<400> SEQUENCE: 22
tttttttttt tttttangtg tngtcgtgca ggtagaggct tactacaant gtgaanacgt 60
acgctnggan taangcgacc cganttctag ganncncccct aaaatcanac tgtgaagatn 120
atcctgnnna cggaanggtc accggnngat nntgctaggg tgnccnctcc cannncnttn 180
cataactcng nggccctgcc caccaccttc ggcggcccng ngnccgggcc cgggtcattn 240
gnnttaaccn cactnngcna ncggtttccn nccccnncng acccnggcga tccggggtnc 300
tctgtcttcc cctgnagncn anaaantggg ccncggnccc ctttacccct nnacaagcca 360
cngccntcta nccncngccc cccctccant nnggggggact gccnanngct ccgttnctng 420
nnaccccnnn gggtncctcg gttgtcgant cnaccgnang ccanggattc cnaaggaagg 480
tgcgttnttg gcccctaccc ttcgctncgg nncacccttc ccgacnanga nccgctcccg 540
cncnncgnng cctcncctcg caacacccgc nctcntcngt ncggnnnccc ccccacccgc 600
nccctcncnc ngncgnancn ctccnccncc gtctcannca ccacccccgcc ccgccaggcc 660 ntcanccacn ggnngacnng nagcncnntc gcnccgcgcn gcgncnccct cgccncngaa 720
ctncntcngg ccantnncgc tcaanccnna cnaaacgccg ctgcgcggcc cgnagcgncc 780
ncctccncga gtcctcccgn cttccnaccc angnnttccn cgaggacacn nnaccccgcc 840 nncangcgg 849

-continued

<210> SEQ ID NO 23
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 23
gcgcaaacta tacttcgctc gnactcgtgc gcctcgctnc tcttttcctc cgcaaccatg 60
tctgacnanc ccgattnggc ngatatcnan aagntcganc agtccaaact gantaacaca 120
cacacncnan aganaaatcc nctgccttcc anagtanacn attgaacnng agaaccangc 180
nggcgaatcg taatnaggcg tgcgccgcca atntgtcncc gtttattntn ccagcntcnc 240
ctnccnaccc tacntcttcn nagctgtcnn acccctngtn cgnacccccc naggtcggga 300
tcgggtttnn nntgaccgng cnncccctcc ccccntccat nacganccnc ccgcaccacc 360
nanngcncgc nccccgnnct cttcgccncc ctgtcctntn cccctgtngc ctggcncngn 420
accgcattga ccctcgccnn ctncnngaaa ncgnanacgt ccgggttgnn annancgctg 480
tgggnnngcg tctgcnccgc gttccttccn ncnncttcca ccatcttcnt tacngggtct 540
ccncgccntc tcnnncacnc cctgggacgc tntcctntgc ccccttnac tcccccccctt 600 cgncgtgncc cgnccccacc ntcatttnca nacgntcttc acaannncct ggntnnctcc 660
cnancngncn gtcanccnag ggaagggngg ggnnccnntg nttgacgttg nggngangtc 720
cgaanantcc tcnccntcan cnctacccct cgggcgnnct ctcngttncc aacttancaa 780
ntctcccccg ngngcncntc tcagcctcnc ccnccccnct ctctgcantg tnctctgctc 840
tnaccnntac gantnttcgn cnccctcttt cc 872

<210> SEQ ID NO 24
<211> LENGTH: 815
<212> TYPE: DNA
<213> ORGANISM: Homo sapien
<220> FEATURE:
<221> NAME/KEY: misc_feature
<222> LOCATION: (1)...(815)
<223> OTHER INFORMATION: n = A,T,C or G

<400> SEQUENCE: 24
gcatgcaagc ttgagtattc tatagngtca cctaaatanc ttggcntaat catggtcnta 60
nctgncttcc tgtgtcaaat gtatacnaan tanatatgaa tctnatntga caaganngta 120
tcntncatta gtaacaantg tnntgtccat cctgtcngan canattccca tnnattncgn 180
cgcattcncn gcncantatn taatngggaa ntcnnntnnn ncaccnncat ctatcntncc 240
gcnccctgac tggnagagat ggatnanttc tnntntgacc nacatgttca tcttggattn 300 aanancccccc cgcngnccac cggttngnng cnagccnntc ccaagacctc ctgtggaggt 360
aacctgcgtc aganncatca aacntgggaa acccgcnncc angtnnaagt ngnnncanan 420
gatcccgtcc aggnttnacc atcccttcnc agcgcccccct ttngtgcctt anagngnagc 480
gtgtccnanc cnctcaacat ganacgcgcc agnccanccg caattnggca caatgtcgnc 540
gaacccccta gggggantna tncaaanccc caggattgtc cncncangaa atcccncanc 600
cccnccctac ccnnctttgg gacngtgacc aantcccgga gtnccagtcc ggccngnctc 660
ccccaccggt nnccntgggg gggtgaanct cngnntcanc cngncgaggn ntcgnaagga 720

-continued

```
accggncctn ggncgaanng ancnntcnga agngccncnt cgtataaccc cccctcncca    780

nccnacngnt agntcccccc cngggtncgg aangg                               815
```

<210> SEQ ID NO 25
<211> LENGTH: 775
<212> TYPE: DNA
<213> ORGANISM: Homo sapien
<220> FEATURE:
<221> NAME/KEY: misc_feature
<222> LOCATION: (1)...(775)
<223> OTHER INFORMATION: n = A,T,C or G

<400> SEQUENCE: 25

```
ccgagatgtc tcgctccgtg gccttagctg tgctcgcgct actctctctt tctggcctgg     60

aggctatcca gcgtactcca aagattcagg tttactcacg tcatccagca gagaatggaa    120

agtcaaattt cctgaattgc tatgtgtctg ggtttcatcc atccgacatt gaanttgact    180

tactgaagaa tgganagaga attgaaaaag tggagcattc agacttgtct ttcagcaagg    240

actggtcttt ctatctcntg tactacactg aattcacccc cactgaaaaa gatgagtatg    300

cctgccgtgt gaaccatgtg actttgtcac agcccaagat agttaagtgg gatcgagaca    360

tgtaagcagn cnncatggaa gtttgaagat gccgcatttg gattggatga attccaaatt    420

ctgcttgctt gcnttttaat antgatatgc ntatacaccc taccctttat gnccccaaat    480

tgtaggggtt acatnantgt tcncntngga catgatcttc ctttataant ccnccnttcg    540

aattgcccgt cncccngttn ngaatgtttc cnnaaccacg gttggctccc ccaggtcncc    600

tcttacggaa gggcctgggc cnctttncaa ggttggggga accnaaaatt tcncttntgc    660

ccncccncca cnntcttgng nncncanttt ggaacccttc cnattcccct tggcctcnna    720

nccttnncta anaaaacttn aaancgtngc naaannttn acttcccccc ttacc          775
```

<210> SEQ ID NO 26
<211> LENGTH: 820
<212> TYPE: DNA
<213> ORGANISM: Homo sapien
<220> FEATURE:
<221> NAME/KEY: misc_feature
<222> LOCATION: (1)...(820)
<223> OTHER INFORMATION: n = A,T,C or G

<400> SEQUENCE: 26

```
anattantac agtgtaatct tttcccagag gtgtgtanag ggaacggggc ctagaggcat     60

cccanagata ncttatanca acagtgcttt gaccaagagc tgctgggcac atttcctgca    120

gaaaaggtgg cggtccccat cactcctcct ctcccatagc catcccagag gggtgagtag    180

ccatcangcc ttcggtggga gggagtcang gaaacaacan accacagagc anacagacca    240

ntgatgacca tgggcgggag cgagcctctt ccctgnaccg gggtggcana nganagccta    300

nctgaggggt cacactataa acgttaacga ccnagatnan cacctgcttc aagtgcaccc    360

ttcctacctg acnaccagng accnnnaact gcngcctggg gacagcnctg ggancagcta    420

acnnagcact cacctgcccc cccatggccg tncgcntccc tggtcctgnc aagggaagct    480

ccctgttgga attncgggga naccaaggga ncccccctcct ccanctgtga aggaaaaann    540

gatggaattt tnccccttccg gccnntcccc tcttccttta cacgcccccct nntactcntc    600

tccctctntt ntcctgncnc acttttnacc ccnnnatttc ccttnattga tcgganncctn    660

ganattccac tnncgcctnc cntcnatcng naanacnaaa nactntctna cccnggggat    720

gggnncctcg ntcatcctct ctttttcnct accnccnntt ctttgcctct ccttngatca    780
```

tccaaccntc gntggccntn ccccccccnnn tcctttnccc 820

<210> SEQ ID NO 27
<211> LENGTH: 818
<212> TYPE: DNA
<213> ORGANISM: Homo sapien
<220> FEATURE:
<221> NAME/KEY: misc_feature
<222> LOCATION: (1)...(818)
<223> OTHER INFORMATION: n = A,T,C or G

<400> SEQUENCE: 27
tctgggtgat ggcctcttcc tcctcaggga cctctgactg ctctgggcca aagaatctct 60
tgtttcttct ccgagcccca ggcagcggtg attcagccct gcccaacctg attctgatga 120
ctgcggatgc tgtgacggac ccaaggggca aatagggtcc cagggtccag ggaggggcgc 180
ctgctgagca cttccgcccc tcaccctgcc cagcccctgc catgagctct gggctgggtc 240
tccgcctcca gggttctgct cttccangca ngccancaag tggcgctggg ccacactggc 300
ttcttcctgc cccntccctg gctctgantc tctgtcttcc tgtcctgtgc angcnccttg 360
gatctcagtt tccctcnctc anngaactct gtttctgann tcttcantta actntgantt 420
tatnaccnan tggnctgtnc tgtcnnactt taatgggccn gaccggctaa tccctccctc 480
nctcccttcc anttcnnnna accngcttnc cntcntctcc ccntancccg ccngggaanc 540
ctcctttgcc ctnaccangg gccnnnaccg cccntnnctn gggggggcnng gtnnctncnc 600 ctgntnnccc cnctcncnnt tncctcgtcc cnncnncgcn nngcannttc ncngtcccnn 660
tnnctcttcn ngtntcgnaa ngntcncntn tnnnnngncn ngntnnntncn tccctctcnc 720 cnnntgnang tnnttnnnnc ncngnncccc nnnncnnnnn nggnnntnnn tctncncngc 780 cccnncccccc ngnattaagg cctccnntct ccggccnc 818

<210> SEQ ID NO 28
<211> LENGTH: 731
<212> TYPE: DNA
<213> ORGANISM: Homo sapien
<220> FEATURE:
<221> NAME/KEY: misc_feature
<222> LOCATION: (1)...(731)
<223> OTHER INFORMATION: n = A,T,C or G

<400> SEQUENCE: 28
aggaagggcg gagggatatt gtangggatt gagggatagg agnataangg gggaggtgtg 60
tcccaacatg anggtgnngt tctcttttga angagggttg ngtttttann ccnggtgggt 120
gattnaaccc cattgtatgg agnnaaaggn tttnagggat ttttcggctc ttatcagtat 180
ntanattcct gtnaatcgga aaatnatntt tcnncnggaa aatnttgctc ccatccgnaa 240
attnctcccg ggtagtgcat nttngggggn cngccangtt tcccaggctg ctanaatcgt 300
actaaagntt naagtgggan tncaaatgaa aacctnncac agagnatccn tacccgactg 360
tnnnttncct tcgccctntg actctgcnng agcccaatac ccnngngnat gtcncccngn 420
nnngcgncnc tgaaannnnc tcgnggctnn gancatcang gggtttcgca tcaaaagcnn 480
cgtttcncat naaggcactt tngcctcatc caaccnctng ccctcnncca tttngccgtc 540
nggttcncct acgctnnntng cncctnnntn ganattttnc ccgcctnggg naancctcct 600
gnaatgggta gggncttntc ttttnaccnn gnggtntact aatcnnctnc acgcntnctt 660
tctcnacccc cccccttttt caatcccanc ggcnaatggg gtctccccnn cganggggg 720

-continued

```
nnncccannc c                                                           731

<210> SEQ ID NO 29
<211> LENGTH: 822
<212> TYPE: DNA
<213> ORGANISM: Homo sapien
<220> FEATURE:
<221> NAME/KEY: misc_feature
<222> LOCATION: (1)...(822)
<223> OTHER INFORMATION: n = A,T,C or G

<400> SEQUENCE: 29

actagtccag tgtggtggaa ttccattgtg ttggggncnc ttctatgant antnttagat       60

cgctcanacc tcacancctc ccnacnangc ctataangaa nannaataga nctgtncnnt      120

atntntacnc tcatanncct cnnnacccac tccctcttaa cccntactgt gcctatngcn      180

tnnctantct ntgccgcctn cnanccaccn gtgggccnac cncnngnatt ctcnatctcc      240

tcnccatntn gcctananta ngtncatacc ctatacctac nccaatgcta nnnctaancn      300

tccatnantt annntaacta ccactgacnt ngactttcnc atnanctcct aatttgaatc      360

tactctgact cccacngcct annnattagc ancntccccc nacnatntct caaccaaatc      420

ntcaacaacc tatctanctg ttcnccaacc nttncctccg atccccnnac aacccccctc      480

ccaaataccc nccacctgac ncctaacccn caccatcccg gcaagccnan ggncatttan      540

ccactggaat cacnatngga naaaaaaaac ccnaactctc tancncnnat ctccctaana      600

aatnctcctn naatttactn ncantnccat caancccacn tgaaacnnaa cccctgtttt      660

tanatccctt ctttcgaaaa ccnaccettt annncccaac ctttngggcc cccccnctnc      720

ccnaatgaag gncncccaat cnangaaacg nccntgaaaa ancnaggcna anannntccg      780

canatcctat cccttanttn ggggnccctt ncccngggcc cc                         822

<210> SEQ ID NO 30
<211> LENGTH: 787
<212> TYPE: DNA
<213> ORGANISM: Homo sapien
<220> FEATURE:
<221> NAME/KEY: misc_feature
<222> LOCATION: (1)...(787)
<223> OTHER INFORMATION: n = A,T,C or G

<400> SEQUENCE: 30

cggccgcctg ctctggcaca tgcctcctga atggcatcaa aagtgatgga ctgcccattg       60

ctagagaaga ccttctctcc tactgtcatt atggagccct gcagactgag ggctcccctt      120

gtctgcagga tttgatgtct gaagtcgtgg agtgtggctt ggagctcctc atctacatna      180

gctggaagcc ctggagggcc tctctcgcca gcctccccct tctctccacg ctctccangg      240

acaccagggg ctccaggcag cccattattc ccagnangac atggtgtttc tccacgcgga      300

cccatggggc ctgnaaggcc agggtctcct ttgacaccat ctctcccgtc ctgcctggca      360

ggccgtggga tccactantt ctanaacggn cgccaccncg gtgggagctc cagcttttgt      420

tcccnttaat gaaggttaat tgcncgcttg gcgtaatcat nggtcanaac tntttcctgt      480

gtgaaattgt ttntcccctc ncnattccnc ncnacatacn aacccggaan cataaagtgt      540

taaagcctgg gggtngcctn nngaatnaac tnaactcaat taattgcgtt ggctcatggc      600

ccgctttccn ttcnggaaaa ctgtcntccc ctgcnttnnt gaatcggcca ccccccnggg      660

aaaagcggtt tgcnttttng ggggntcctt ccncttcccc cctcnctaan ccctncgcct      720

cggtcgttnc nggtngcggg gaangggnat nnnctcccnc naagggggng agnnngntat      780
```

ccccaaa 787

<210> SEQ ID NO 31
<211> LENGTH: 799
<212> TYPE: DNA
<213> ORGANISM: Homo sapien
<220> FEATURE:
<221> NAME/KEY: misc_feature
<222> LOCATION: (1)...(799)
<223> OTHER INFORMATION: n = A,T,C or G

<400> SEQUENCE: 31
tttttttttt tttttttggc gatgctactg tttaattgca ggaggtgggg gtgtgtgtac 60
catgtaccag ggctattaga agcaagaagg aaggagggag ggcagagcgc cctgctgagc 120
aacaaaggac tcctgcagcc ttctctgtct gtctcttggc gcaggcacat ggggaggcct 180
cccgcagggt gggggccacc agtccagggg tgggagcact acanggggtg ggagtgggtg 240
gtggctggtn cnaatggcct gncacanatc cctacgattc ttgacacctg gatttcacca 300
ggggaccttc tgttctccca nggnaacttc ntnnatctcn aaagaacaca actgtttctt 360
cngcanttct ggctgttcat ggaaagcaca ggtgtccnat ttnggctggg acttggtaca 420
tatggttccg gcccacctct cccntcnaan aagtaattca cccccccccn ccntctnttg 480
cctgggccct taantaccca caccggaact canttantta ttcatcttng gntgggcttg 540
ntnatcnccn cctgaangcg ccaagttgaa aggccacgcc gtncccnctc cccatagnan 600
nttttnncnt canctaatgc ccccccnggc aacnatccaa tcccccccn tgggggcccc 660 agcccanggc ccccgnctcg ggnnnccngn cncgnantcc ccaggntctc ccantcngnc 720
ccnnngcncc cccgcacgca gaacanaagg ntngagccnc cgcannnnnn nggtnncnac 780
ctcgcccccc ccnncgnng 799

<210> SEQ ID NO 32
<211> LENGTH: 789
<212> TYPE: DNA
<213> ORGANISM: Homo sapien
<220> FEATURE:
<221> NAME/KEY: misc_feature
<222> LOCATION: (1)...(789)
<223> OTHER INFORMATION: n = A,T,C or G

<400> SEQUENCE: 32
tttttttttt tttttttttt tttttttttt tttttttttt tttttttttt tttttttttt 60
ttttnccnag ggcaggttta ttgacaacct cncgggacac aancaggctg gggacaggac 120
ggcaacaggc tccggcggcg gcggcggcgg ccctacctgc ggtaccaaat ntgcagcctc 180
cgctcccgct tgatnttcct ctgcagctgc aggatgccnt aaaacagggc ctcggccntn 240
ggtgggcacc ctgggatttn aatttccacg ggcacaatgc ggtcgcancc cctcaccacc 300
nattaggaat agtggtntta cccnccnccg ttggcncact ccccntggaa accacttntc 360
gcggctccgg catctggtct taaaccttgc aaacnctggg gccctctttt tggttantnt 420
nccngccaca atcatnactc agactggcnc gggctggccc caaaaaancn ccccaaaacc 480
ggnccatgtc ttnncggggt tgctgcnatn tncatcacct cccgggcnca ncaggncaac 540
ccaaaagttc ttgnggcccn caaaaaanct ccgggggggnc ccagtttcaa caaagtcatc 600
ccccttggcc cccaaatcct cccccgntt nctgggtttg ggaacccacg cctctnnctt 660
tggnnggcaa gntggntccc ccttcgggcc cccggtgggc ccnnctctaa ngaaaacncc 720
ntcctnnnca ccatcccccc nngnnacgnc tancaangna tcccttttt tanaaacggg 780 cccccncg 789

<210> SEQ ID NO 33
<211> LENGTH: 793
<212> TYPE: DNA
<213> ORGANISM: Homo sapien
<220> FEATURE:
<221> NAME/KEY: misc_feature
<222> LOCATION: (1)...(793)
<223> OTHER INFORMATION: n = A,T,C or G

<400> SEQUENCE: 33
gacagaacat gttggatggt ggagcacctt tctatacgac ttacaggaca gcagatgggg 60
aattcatggc tgttggagca atanaacccc agttctacga gctgctgatc aaaggacttg 120
gactaaagtc tgatgaactt cccaatcaga tgagcatgga tgattggcca gaaatgaana 180
agaagtttgc agatgtattt gcaaagaaga cgaaggcaga gtggtgtcaa atctttgacg 240
gcacagatgc ctgtgtgact ccggttctga cttttgagga ggttgttcat catgatcaca 300
acaangaacg gggctcgttt atcaccantg aggagcagga cgtgagcccc cgccctgcac 360
ctctgctgtt aaacacccca gccatccctt ctttcaaaag ggatccacta cttctagagc 420
ggncgccacc gcggtggagc tccagctttt gttcccttta gtgagggtta attgcgcgct 480
tggcgtaatc atggtcatan ctgtttcctg tgtgaaattg ttatccgctc acaattccac 540
acaacatacg anccggaagc atnaaatttt aaagcctggn ggtngcctaa tgantgaact 600
nactcacatt aattggcttt gcgctcactg cccgctttcc agtccggaaa acctgtcctt 660
gccagctgcc nttaatgaat cnggccaccc cccggggaaa aggcngtttg cttnttgggg 720
cgcncttccc gctttctcgc ttcctgaant ccttcccccc ggtctttcgg cttgcggcna 780
acggtatcna cct 793

<210> SEQ ID NO 34
<211> LENGTH: 756
<212> TYPE: DNA
<213> ORGANISM: Homo sapien
<220> FEATURE:
<221> NAME/KEY: misc_feature
<222> LOCATION: (1)...(756)
<223> OTHER INFORMATION: n = A,T,C or G

<400> SEQUENCE: 34
gccgcgaccg gcatgtacga gcaactcaag ggcgagtgga accgtaaaag ccccaatctt 60
ancaagtgcg gggaanagct gggtcgactc aagctagttc ttctggagct caacttcttg 120
ccaaccacag ggaccaagct gaccaaacag cagctaattc tggcccgtga catactggag 180
atcggggccc aatggagcat cctacgcaan gacatcccct ccttcgagcg ctacatggcc 240
cagctcaaat gctactactt tgattacaan gagcagctcc ccgagtcagc ctatatgcac 300
cagctcttgg gcctcaacct cctcttcctg ctgtcccaga accgggtggc tgantnccac 360 acggganttgg ancggctgcc tgcccaanga catacanacc aatgtctaca tcnaccacca 420
gtgtcctgga gcaatactga tgganggcag ctaccncaaa gtnttcctgg ccnagggtaa 480 catccccccgc cgagagctac accttcttca ttgacatcct gctcgacact atcagggatg 540
aaaatcgcng ggttgctcca gaaaggctnc aanaanatcc ttttcnctga aggcccccgg 600
atncnctagt nctagaatcg gcccgccatc gcggtggganc ctccaacctt tcgttnccct 660
ttactgaggg ttnattgccg cccttggcgt tatcatggtc acnccngttn cctgtgttga 720

-continued aattnttaac cccccacaat tccacgccna cattng 756

<210> SEQ ID NO 35
<211> LENGTH: 834
<212> TYPE: DNA
<213> ORGANISM: Homo sapien
<220> FEATURE:
<221> NAME/KEY: misc_feature
<222> LOCATION: (1)...(834)
<223> OTHER INFORMATION: n = A,T,C or G

<400> SEQUENCE: 35
ggggatctct anatcnacct gnatgcatgg ttgtcggtgt ggtcgctgtc gatgaanatg 60
aacaggatct tgcccttgaa gctctcggct gctgtnttta agttgctcag tctgccgtca 120
tagtcagaca cnctcttggg caaaaaacan caggatntga gtcttgattt cacctccaat 180
aatcttcngg gctgtctgct cggtgaactc gatgacnang ggcagctggt tgtgtntgat 240
aaantccanc angttctcct tggtgacctc cccttcaaag ttgttccggc cttcatcaaa 300
cttctnnaan angannancc canctttgtc gagctggnat ttgganaaca cgtcactgtt 360
ggaaactgat cccaaatggt atgtcatcca tcgcctctgc tgcctgcaaa aaacttgctt 420
ggcncaaatc cgactccccn tccttgaaag aagccnatca cacccccctc cctggactcc 480
nncaangact ctnccgctnc cccntccnng cagggttggt ggcannccgg gcccntgcgc 540
ttcttcagcc agttcacnat nttcatcagc ccctctgcca gctgttntat tccttggggg 600
ggaanccgtc tctcccttcc tgaannaact ttgaccgtng gaatagccgc gcntcnccnt 660
acntnctggg ccgggttcaa antccctccn ttgncnntcn cctcgggcca ttctggattt 720
nccnaacttt ttccttcccc cnccccncgg ngtttggntt tttcatnggg ccccaactct 780
gctnttggcc antcccctgg gggcntntan cncccccctnt ggtcccntng ggcc 834

<210> SEQ ID NO 36
<211> LENGTH: 814
<212> TYPE: DNA
<213> ORGANISM: Homo sapien
<220> FEATURE:
<221> NAME/KEY: misc_feature
<222> LOCATION: (1)...(814)
<223> OTHER INFORMATION: n = A,T,C or G

<400> SEQUENCE: 36
cggncgcttt ccngccgcgc cccgtttcca tgacnaaggc tcccttcang ttaaatacnn 60
cctagnaaac attaatgggt tgctctacta atacatcata cnaaccagta agcctgccca 120
naacgccaac tcaggccatt cctaccaaag gaagaaaggc tggtctctcc accccctgta 180
ggaaaggcct gccttgtaag acaccacaat ncggctgaat ctnaagtctt gtgttttact 240
aatggaaaaa aaaaataaac aanaggtttt gttctcatgg ctgcccaccg cagcctggca 300
ctaaaacanc ccagcgctca cttctgcttg ganaaatatt ctttgctctt ttggacatca 360
ggcttgatgg tatcactgcc acntttccac ccagctgggc ncccttcccc catntttgtc 420
antganctgg aaggcctgaa ncttagtctc caaaagtctc ngcccacaag accggccacc 480
aggggangtc ntttncagtg gatctgccaa anantacccn tatcatcnnt gaataaaaag 540
gcccctgaac ganatgcttc cancancctt taagacccat aatcctngaa ccatggtgcc 600
cttccggtct gatccnaaag gaatgttcct gggtcccant ccctcctttg ttncttacgt 660
tgtnttggac ccntgctngn atnacccaan tganatcccc ngaagcaccc tnccccctggc 720

-continued

```
atttganttt cntaaattct ctgccctacn nctgaaagca cnattccctn ggcnccnaan    780

ggngaactca agaaggtctn ngaaaaacca cncn                                814


<210> SEQ ID NO 37
<211> LENGTH: 760
<212> TYPE: DNA
<213> ORGANISM: Homo sapien
<220> FEATURE:
<221> NAME/KEY: misc_feature
<222> LOCATION: (1)...(760)
<223> OTHER INFORMATION: n = A,T,C or G

<400> SEQUENCE: 37

gcatgctgct cttcctcaaa gttgttcttg ttgccataac aaccaccata ggtaaagcgg     60

gcgcagtgtt cgctgaaggg gttgtagtac cagcgcggga tgctctcctt gcagagtcct    120

gtgtctggca ggtccacgca atgccctttg tcactgggga aatggatgcg ctggagctcg    180

tcnaanccac tcgtgtattt ttcacangca gcctcctccg aagcntccgg gcagttgggg    240

gtgtcgtcac actccactaa actgtcgatn cancagccca ttgctgcagc ggaactgggt    300

gggctgacag gtgccagaac acactggatn ggcctttcca tggaagggcc tgggggaaat    360

cncctnancc caaactgcct ctcaaaggcc accttgcaca ccccgacagg ctagaaatgc    420

actcttcttc ccaaaggtag ttgttcttgt tgcccaagca ncctccanca aaccaaaanc    480

ttgcaaaatc tgctccgtgg gggtcatnnn taccanggtt ggggaaanaa acccggcngn    540

ganccncctt gtttgaatgc naaggnaata atcctcctgt cttgcttggg tggaanagca    600

caattgaact gttaacnttg ggccgngttc cnctngggtg gtctgaaact aatcaccgtc    660

actggaaaaa ggtangtgcc ttccttgaat tcccaaantt cccctngntt tgggtnnttt    720

ctcctctncc ctaaaaatcg tnttcccccc ccntanggcg                          760


<210> SEQ ID NO 38
<211> LENGTH: 724
<212> TYPE: DNA
<213> ORGANISM: Homo sapien
<220> FEATURE:
<221> NAME/KEY: misc_feature
<222> LOCATION: (1)...(724)
<223> OTHER INFORMATION: n = A,T,C or G

<400> SEQUENCE: 38

tttttttttt tttttttttt tttttttttt tttttaaaaa ccccctccat tgaatgaaaa     60

cttccnaaat tgtccaaccc cctcnnccaa atnnccattt ccgggggggg gttccaaacc    120

caaattaatt ttgganttta aattaaatnt tnattngggg aanaanccaa atgtnaagaa    180

aatttaaccc attatnaact taaatncctn gaaacccntg gnttccaaaa atttttaacc    240

cttaaatccc tccgaaattg ntaanggaaa accaaattcn cctaaggctn tttgaaggtt    300

ngatttaaac ccccttnant tnttttnacc cnngnctnaa ntatttngnt tccggtgttt    360

tcctnttaan cntnggtaac tcccgntaat gaannnccct aanccaatta aaccgaattt    420

tttttgaatt ggaaattccn ngggaattna ccggggtttt tcccntttgg gggccatncc    480

cccnctttcg gggtttgggn ntaggttgaa tttttnnang ncccaaaaaa ncccccaana    540

aaaaaactcc caagnnttaa ttngaatntc cccctcccca ggccttttgg gaaaggnggg    600

tttntggggg ccngggantt cnttccccc ttnccnccc ccccccnggt aaanggttat    660

ngnntttggt ttttgggccc cttnanggac cttccggatn gaaattaaat ccccgggncg    720

gccg                                                                 724
```

-continued

<210> SEQ ID NO 39
<211> LENGTH: 751
<212> TYPE: DNA
<213> ORGANISM: Homo sapien
<220> FEATURE:
<221> NAME/KEY: misc_feature
<222> LOCATION: (1)...(751)
<223> OTHER INFORMATION: n = A,T,C or G

<400> SEQUENCE: 39

```
ttttttttt tttttctttg ctcacattta atttttattt tgattttttt taatgctgca     60
caacacaata tttatttcat ttgtttcttt tatttcattt tatttgtttg ctgctgctgt    120
tttatttatt tttactgaaa gtgagaggga acttttgtgg ccttttttcc tttttctgta    180
ggccgcctta agctttctaa atttggaaca tctaagcaag ctgaanggaa aagggggttt    240
cgcaaaatca ctcgggggaa nggaaaggtt gctttgttaa tcatgcccta tggtgggtga    300
ttaactgctt gtacaattac ntttcacttt taattaattg tgctnaangc tttaattana    360
cttgggggtt ccctccccan accaaccccn ctgacaaaaa gtgccngccc tcaaatnatg    420
tcccggcnnt cnttgaaaca cacngcngaa ngttctcatt ntccccncnc caggtnaaaa    480
tgaagggtta ccatntttaa cnccacctcc acntggcnnn gcctgaatcc tcnaaaancn    540
ccctcaancn aattnctnng ccccggtcnc gcntnngtcc cncccgggct ccgggaantn    600
cacccccnga anncnntnnc naacnaaatt ccgaaaatat tcccnntcnc tcaattcccc    660
cnnagactnt cctcnncnan cncaattttc ttttnntcac gaacncgnnc cnnaaaatgn    720
nnnncncctc cnctngtccn naatcnccan c                                   751
```

<210> SEQ ID NO 40
<211> LENGTH: 753
<212> TYPE: DNA
<213> ORGANISM: Homo sapien
<220> FEATURE:
<221> NAME/KEY: misc_feature
<222> LOCATION: (1)...(753)
<223> OTHER INFORMATION: n = A,T,C or G

<400> SEQUENCE: 40

```
gtggtatttt ctgtaagatc aggtgttcct ccctcgtagg tttagaggaa acaccctcat     60
agatgaaaac ccccccgaga cagcagcact gcaactgcca agcagccggg gtaggagggg    120
cgccctatgc acagctgggc ccttgagaca gcagggcttc gatgtcaggc tcgatgtcaa    180
tggtctggaa gcggcggctg tacctgcgta ggggcacacc gtcagggccc accaggaact    240
tctcaaagtt ccaggcaacn tcgttgcgac acaccggaga ccaggtgatn agcttggggt    300
cggtcataan cgcggtggcg tcgtcgctgg gagctggcag ggcctcccgc aggaaggcna    360
ataaaaggtg cgcccccgca ccgttcanct cgcacttctc naanaccatg angttgggct    420
cnaacccacc accannccgg acttccttga nggaattccc aaatctcttc gntcttgggc    480
ttctnctgat gccctanctg gttgcccngn atgccaanca nccccaancc ccggggtcct    540
aaancacccn cctcctcntt tcatctgggt tnttntcccc ggaccntggt tcctctcaag    600
gganccccata tctcnaccan tactcaccnt nccccccccnt gnnacccanc cttctanngn    660
ttcccncccg ncctctggcc cntcaaanan gcttncacna cctgggtctg ccttcccccc    720
tnccctatct gnaccccncn tttgtctcan tnt                                 753
```

<210> SEQ ID NO 41

-continued

<211> LENGTH: 341
<212> TYPE: DNA
<213> ORGANISM: Homo sapien

<400> SEQUENCE: 41
actatatcca tcacaacaga catgcttcat cccatagact tcttgacata gcttcaaatg 60
agtgaaccca tccttgattt atatacatat atgttctcag tattttggga gcctttccac 120
ttctttaaac cttgttcatt atgaacactg aaaataggaa tttgtgaaga gttaaaaagt 180
tatagcttgt ttacgtagta agtttttgaa gtctacattc aatccagaca cttagttgag 240
tgttaaactg tgatttttaa aaaatatcat ttgagaatat tctttcagag gtattttcat 300
ttttactttt tgattaattg tgttttatat attagggtag t 341

<210> SEQ ID NO 42
<211> LENGTH: 101
<212> TYPE: DNA
<213> ORGANISM: Homo sapien

<400> SEQUENCE: 42
acttactgaa tttagttctg tgctcttcct tatttagtgt tgtatcataa atactttgat 60
gtttcaaaca ttctaaataa ataattttca gtggcttcat a 101

<210> SEQ ID NO 43
<211> LENGTH: 305
<212> TYPE: DNA
<213> ORGANISM: Homo sapien

<400> SEQUENCE: 43
acatctttgt tacagtctaa gatgtgttct taaatcacca ttccttcctg gtcctcaccc 60
tccagggtgg tctcacactg taattagagc tattgaggag tctttacagc aaattaagat 120
tcagatgcct tgctaagtct agagttctag agttatgttt cagaaagtct aagaaaccca 180
cctcttgaga ggtcagtaaa gaggacttaa tatttcatat ctacaaaatg accacaggat 240
tggatacaga acgagagtta tcctggataa ctcagagctg agtacctgcc cgggggccgc 300
tcgaa 305

<210> SEQ ID NO 44
<211> LENGTH: 852
<212> TYPE: DNA
<213> ORGANISM: Homo sapien
<220> FEATURE:
<221> NAME/KEY: misc_feature
<222> LOCATION: (1)...(852)
<223> OTHER INFORMATION: n = A,T,C or G

<400> SEQUENCE: 44
acataaatat cagagaaaag tagtctttga aatatttacg tccaggagtt ctttgtttct 60
gattatttgg tgtgtgtttt ggtttgtgtc caaagtattg gcagcttcag ttttcatttt 120
ctctccatcc tcgggcattc ttcccaaatt tatataccag tcttcgtcca tccacacgct 180
ccagaatttc tcttttgtag taatatctca tagctcggct gagcttttca taggtcatgc 240
tgctgttgtt cttcttttta ccccatagct gagccactgc ctctgatttc aagaacctga 300
agacgccctc agatcggtct tcccatttta ttaatcctgg gttcttgtct gggttcaaga 360
ggatgtcgcg gatgaattcc cataagtgag tccctctcgg gttgtgcttt ttggtgtggc 420
acttggcagg ggggtcttgc tcctttttca tatcaggtga ctctgcaaca ggaaggtgac 480
tggtggttgt catggagatc tgagcccggc agaaagtttt gctgtccaac aaatctactg 540

-continued

```
tgctaccata gttggtgtca tataaatagt tctngtcttt ccaggtgttc atgatggaag    600

gctcagtttg ttcagtcttg acaatgacat tgtgtgtgga ctggaacagg tcactactgc    660

actggccgtt ccacttcaga tgctgcaagt tgctgtagag gagntgcccc gccgtccctg    720

ccgcccgggt gaactcctgc aaactcatgc tgcaaaggtg ctcgccgttg atgtcgaact    780

cntggaaagg gatacaattg gcatccagct ggttggtgtc caggaggtga tggagccact    840

cccacacctg gt                                                         852
```

<210> SEQ ID NO 45
<211> LENGTH: 234
<212> TYPE: DNA
<213> ORGANISM: Homo sapien

<400> SEQUENCE: 45

```
acaacagacc cttgctcgct aacgacctca tgctcatcaa gttggacgaa tccgtgtccg     60

agtctgacac catccggagc atcagcattg cttcgcagtg ccctaccgcg gggaactctt    120

gcctcgtttc tggctggggt ctgctggcga acggcagaat gcctaccgtg ctgcagtgcg    180

tgaacgtgtc ggtggtgtct gaggaggtct gcagtaagct ctatgacccg ctgt          234
```

<210> SEQ ID NO 46
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 46

```
actttttatt taaatgttta taaggcagat ctatgagaat gatagaaaac atggtgtgta     60

atttgatagc aatattttgg agattacaga gttttagtaa ttaccaatta cacagttaaa    120

aagaagataa tatattccaa gcanatacaa aatatctaat gaaagatcaa ggcaggaaaa    180

tgantataac taattgacaa tggaaaatca attttaatgt gaattgcaca ttatccttta    240

aaagctttca aaanaaanaa ttattgcagt ctanttaatt caaacagtgt taaatggtat    300

caggataaan aactgaaggg canaaagaat taattttcac ttcatgtaac ncacccanat    360

ttacaatggc ttaaatgcan ggaaaaagca gtggaagtag ggaagtantc aaggtctttc    420

tggtctctaa tctgccttac tctttgggtg tggctttgat cctctggaga cagctgccag    480

ggctcctgtt atatccacaa tcccagcagc aagatgaagg gatgaaaaag gacacatgct    540

gccttccttt gaggagactt catctcactg gccaacactc agtcacatgt               590
```

<210> SEQ ID NO 47
<211> LENGTH: 774
<212> TYPE: DNA
<213> ORGANISM: Homo sapien
<220> FEATURE:
<221> NAME/KEY: misc_feature
<222> LOCATION: (1)...(774)
<223> OTHER INFORMATION: n = A,T,C or G

<400> SEQUENCE: 47

```
acaaggggc ataatgaagg agtggggana gattttaaag aaggaaaaaa aacgaggccc      60

tgaacagaat tttcctgnac aacggggctt caaaataatt ttcttgggga ggttcaagac    120

gcttcactgc ttgaaactta aatggatgtg ggacanaatt ttctgtaatg accctgaggg    180
```

-continued

```
cattacagac gggactctgg gaggaaggat aaacagaaag gggacaaagg ctaatcccaa    240

aacatcaaag aaaggaaggt ggcgtcatac ctcccagcct acacagttct ccagggctct    300

cctcatccct ggaggacgac agtggaggaa caactgacca tgtccccagg ctcctgtgtg    360

ctggctcctg gtcttcagcc cccagctctg gaagcccacc ctctgctgat cctgcgtggc    420

ccacactcct tgaacacaca tccccaggtt atattcctgg acatggctga acctcctatt    480

cctacttccg agatgccttg ctccctgcag cctgtcaaaa tcccactcac cctccaaacc    540

acggcatggg aagcctttct gacttgcctg attactccag catcttggaa caatccctga    600

ttccccactc cttagaggca agatagggtg gttaagagta gggctggacc acttggagcc    660

aggctgctgg cttcaaattn tggctcattt acgagctatg ggaccttggg caagtnatct    720

tcacttctat gggcntcatt ttgttctacc tgcaaaatgg gggataataa tagt          774
```

<210> SEQ ID NO 48
<211> LENGTH: 124
<212> TYPE: DNA
<213> ORGANISM: Homo sapien
<220> FEATURE:
<221> NAME/KEY: misc_feature
<222> LOCATION: (1)...(124)
<223> OTHER INFORMATION: n = A,T,C or G

<400> SEQUENCE: 48

```
canaaattga aattttataa aaaggcattt ttctcttata tccataaaat gatataattt     60

ttgcaantat anaaatgtgt cataaattat aatgttcctt aattacagct caacgcaact    120

tggt                                                                 124
```

<210> SEQ ID NO 49
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 49

```
gccgatgcta ctattttatt gcaggaggtg gggtgtttt tattattctc tcaacagctt     60

tgtggctaca ggtggtgtct gactgcatna aaaanttttt tacgggtgat tgcaaaaatt    120

ttagggcacc catatcccaa gcantgt                                        147
```

<210> SEQ ID NO 50
<211> LENGTH: 107
<212> TYPE: DNA
<213> ORGANISM: Homo sapien

<400> SEQUENCE: 50

```
acattaaatt aataaaagga ctgttggggt tctgctaaaa cacatggctt gatatattgc     60

atggtttgag gttaggagga gttaggcata tgttttggga gaggggt                  107
```

<210> SEQ ID NO 51
<211> LENGTH: 204
<212> TYPE: DNA
<213> ORGANISM: Homo sapien

<400> SEQUENCE: 51

```
gtcctaggaa gtctagggga cacacgactc tggggtcacg gggccgacac acttgcacgg     60

cgggaaggaa aggcagagaa gtgacaccgt caggggggaaa tgacagaaag gaaaatcaag    120
```

-continued

```
gccttgcaag gtcagaaagg ggactcaggg cttccaccac agccctgccc cacttggcca    180

cctccctttt gggaccagca atgt                                           204
```

<210> SEQ ID NO 52
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 52

```
acaaagataa catttatctt ataacaaaaa tttgatagtt ttaaaggtta gtattgtgta     60

gggtattttc caaaagacta aagagataac tcaggtaaaa agttagaaat gtataaaaca    120

ccatcagaca ggtttttaaa aacaacata ttacaaaatt agacaatcat ccttaaaaaa    180

aaaacttctt gtatcaattt cttttgttca aaatgactga cttaantatt tttaaatatt    240

tcanaaacac ttcctcaaaa attttcaana tggtagcttt canatgtncc ctcagtccca    300

atgttgctca gataaataaa tctcgtgaga acttaccacc caccacaagc tttctggggc    360

atgcaacagt gtcttttctt tncttttct tttttttttt ttacaggcac agaaactcat    420

caattttatt tggataacaa agggtctcca aattatattg aaaaataaat ccaagttaat    480

atcactcttg t                                                         491
```

<210> SEQ ID NO 53
<211> LENGTH: 484
<212> TYPE: DNA
<213> ORGANISM: Homo sapien
<220> FEATURE:
<221> NAME/KEY: misc_feature
<222> LOCATION: (1)...(484)
<223> OTHER INFORMATION: n = A,T,C or G

<400> SEQUENCE: 53

```
acataattta gcagggctaa ttaccataag atgctattta ttaanaggtn tatgatctga     60

gtattaacag ttgctgaagt ttggtatttt tatgcagcat tttctttttg ctttgataac    120

actacagaac ccttaaggac actgaaaatt agtaagtaaa gttcagaaac attagctgct    180

caatcaaatc tctacataac actatagtaa ttaaaacgtt aaaaaaaagt gttgaaatct    240

gcactagtat anaccgctcc tgtcaggata anactgcttt ggaacagaaa gggaaaaanc    300

agctttgant ttctttgtgc tgatangagg aaaggctgaa ttaccttgtt gcctctccct    360

aatgattggc aggtcnggta aatnccaaaa catattccaa ctcaacactt cttttccncg    420

tancttgant ctgtgtattc caggancagg cggatggaat gggccagccc ncggatgttc    480

cant                                                                 484
```

<210> SEQ ID NO 54
<211> LENGTH: 151
<212> TYPE: DNA
<213> ORGANISM: Homo sapien

<400> SEQUENCE: 54

```
actaaacctc gtgcttgtga actccataca gaaaacggtg ccatccctga acacggctgg     60

ccactgggta tactgctgac aaccgcaaca acaaaaacac aaatccttgg cactggctag    120

tctatgtcct ctcaagtgcc tttttgtttg t                                   151
```

-continued

<210> SEQ ID NO 55
<211> LENGTH: 91
<212> TYPE: DNA
<213> ORGANISM: Homo sapien

<400> SEQUENCE: 55
acctggcttg tctccgggtg gttcccggcg ccccccacgg tccccagaac ggacactttc 60
gccctccagt ggatactcga gccaaagtgg t 91

<210> SEQ ID NO 56
<211> LENGTH: 133
<212> TYPE: DNA
<213> ORGANISM: Homo sapien

<400> SEQUENCE: 56
ggcggatgtg cgttggttat atacaaatat gtcattttat gtaagggact tgagtatact 60
tggatttttg gtatctgtgg gttgggggga cggtccagga accaataccc catggatacc 120
aagggacaac tgt 133

<210> SEQ ID NO 57
<211> LENGTH: 147
<212> TYPE: DNA
<213> ORGANISM: Homo sapien
<220> FEATURE:
<221> NAME/KEY: misc_feature
<222> LOCATION: (1)...(147)
<223> OTHER INFORMATION: n = A,T,C or G

<400> SEQUENCE: 57
actctggaga acctgagccg ctgctccgcc tctgggatga ggtgatgcan gcngtggcgc 60
gactgggagc tgagcccttc cctttgcgcc tgcctcagag gattgttgcc gacntgcana 120
tctcantggg ctggatncat gcagggt 147

<210> SEQ ID NO 58
<211> LENGTH: 198
<212> TYPE: DNA
<213> ORGANISM: Homo sapien
<220> FEATURE:
<221> NAME/KEY: misc_feature
<222> LOCATION: (1)...(198)
<223> OTHER INFORMATION: n = A,T,C or G

<400> SEQUENCE: 58
acagggatat aggtttnaag ttattgtnat tgtaaaatac attgaatttt ctgtatactc 60
tgattacata catttatcct ttaaaaaaga tgtaaatctt aatttttatg ccatctatta 120
atttaccaat gagttacctt gtaaatgaga agtcatgata gcactgaatt ttaactagtt 180
ttgacttcta agtttggt 198

<210> SEQ ID NO 59
<211> LENGTH: 330
<212> TYPE: DNA
<213> ORGANISM: Homo sapien

<400> SEQUENCE: 59
acaacaaatg ggttgtgagg aagtcttatc agcaaaactg gtgatggcta ctgaaaagat 60
ccattgaaaa ttatcattaa tgattttaaa tgacaagtta tcaaaaactc actcaatttt 120
cacctgtgct agcttgctaa aatgggagtt aactctagag caaatatagt atcttctgaa 180
tacagtcaat aaatgacaaa gccagggcct acaggtggtt tccagacttt ccagacccag 240

-continued

```
cagaaggaat ctattttatc acatggatct ccgtctgtgc tcaaaatacc taatgatatt    300

tttcgtcttt attggacttc tttgaagagt                                     330


<210> SEQ ID NO 60
<211> LENGTH: 175
<212> TYPE: DNA
<213> ORGANISM: Homo sapien

<400> SEQUENCE: 60

accgtgggtg ccttctacat tcctgacggc tccttcacca acatctggtt ctacttcggc     60

gtcgtgggct ccttcctctt catcctcatc cagctggtgc tgctcatcga ctttgcgcac    120

tcctggaacc agcggtggct gggcaaggcc gaggagtgcg attcccgtgc ctggt         175


<210> SEQ ID NO 61
<211> LENGTH: 154
<212> TYPE: DNA
<213> ORGANISM: Homo sapien

<400> SEQUENCE: 61

accccacttt tcctcctgtg agcagtctgg acttctcact gctacatgat gagggtgagt     60

ggttgttgct cttcaacagt atcctcccct ttccggatct gctgagccgg acagcagtgc    120

tggactgcac agccccgggg ctccacattg ctgt                                154


<210> SEQ ID NO 62
<211> LENGTH: 30
<212> TYPE: DNA
<213> ORGANISM: Homo sapien

<400> SEQUENCE: 62

cgctcgagcc ctatagtgag tcgtattaga                                      30


<210> SEQ ID NO 63
<211> LENGTH: 89
<212> TYPE: DNA
<213> ORGANISM: Homo sapien

<400> SEQUENCE: 63

acaagtcatt tcagcaccct ttgctcttca aaactgacca tcttttatat ttaatgcttc     60

ctgtatgaat aaaaatggtt atgtcaagt                                       89


<210> SEQ ID NO 64
<211> LENGTH: 97
<212> TYPE: DNA
<213> ORGANISM: Homo sapien

<400> SEQUENCE: 64

accggagtaa ctgagtcggg acgctgaatc tgaatccacc aataaataaa ggttctgcag     60

aatcagtgca tccaggattg gtccttggat ctggggt                              97


<210> SEQ ID NO 65
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 65
```

-continued

```
acaacaanaa ntcccttctt taggccactg atggaaacct ggaaccccct tttgatggca     60

gcatggcgtc ctaggccttg acacagcggc tggggtttgg gctntcccaa accgcacacc    120

ccaaccctgg tctacccaca nttctggcta tgggctgtct ctgccactga acatcagggt    180

tcggtcataa natgaaatcc caanggggac agaggtcagt agaggaagct caatgagaaa    240

ggtgctgttt gctcagccag aaaacagctg cctggcattc gccgctgaac tatgaacccg    300

tgggggtgaa ctacccccan gaggaatcat gcctgggcga tgcaanggtg ccaacaggag    360

gggcgggagg agcatgt                                                   377
```

```
<210> SEQ ID NO 66
<211> LENGTH: 305
<212> TYPE: DNA
<213> ORGANISM: Homo sapien

<400> SEQUENCE: 66

acgcctttcc ctcagaattc agggaagaga ctgtcgcctg ccttcctccg ttgttgcgtg     60

agaacccgtg tgccccttcc caccatatcc accctcgctc catctttgaa ctcaaacacg    120

aggaactaac tgcaccctgg tcctctcccc agtccccagt tcaccctcca tccctcacct    180

tcctccactc taagggatat caacactgcc cagcacaggg gccctgaatt tatgtggttt    240

ttatatattt tttaataaga tgcactttat gtcatttttt aataaagtct gaagaattac    300

tgttt                                                                305
```

```
<210> SEQ ID NO 67
<211> LENGTH: 385
<212> TYPE: DNA
<213> ORGANISM: Homo sapien

<400> SEQUENCE: 67

actacacaca ctccacttgc ccttgtgaga cactttgtcc cagcacttta ggaatgctga     60

ggtcggacca gccacatctc atgtgcaaga ttgcccagca gacatcaggt ctgagagttc    120

ccctttttaaa aaaggggact tgcttaaaaa agaagtctag ccacgattgt gtagagcagc    180

tgtgctgtgc tggagattca cttttgagag agttctcctc tgagacctga tctttagagg    240

ctgggcagtc ttgcacatga gatggggctg gtctgatctc agcactcctt agtctgcttg    300

cctctcccag ggccccagcc tggccacacc tgcttacagg gcactctcag atgcccatac    360

catagtttct gtgctagtgg accgt                                          385
```

```
<210> SEQ ID NO 68
<211> LENGTH: 73
<212> TYPE: DNA
<213> ORGANISM: Homo sapien

<400> SEQUENCE: 68

acttaaccag atatattttt accccagatg gggatattct ttgtaaaaaa tgaaaataaa     60

gttttttttaa tgg                                                        73
```

```
<210> SEQ ID NO 69
<211> LENGTH: 536
<212> TYPE: DNA
<213> ORGANISM: Homo sapien
<220> FEATURE:
<221> NAME/KEY: misc_feature
<222> LOCATION: (1)...(536)
<223> OTHER INFORMATION: n = A,T,C or G

<400> SEQUENCE: 69
```

-continued

```
actagtccag tgtggtggaa ttccattgtg ttgggggctc tcaccctcct ctcctgcagc     60
tccagctttg tgctctgcct ctgaggagac catggcccag catctgagta ccctgctgct    120
cctgctggcc accctagctg tggccctggc ctggagcccc aaggaggagg ataggataat    180
cccgggtggc atctataacg cagacctcaa tgatgagtgg gtacagcgtg cccttcactt    240
cgccatcagc gagtataaca aggccaccaa agatgactac tacagacgtc cgctgcgggt    300
actaagagcc aggcaacaga ccgttggggg ggtgaattac ttcttcgacg tagaggtggg    360
ccgaaccata tgtaccaagt cccagcccaa cttggacacc tgtgccttcc atgaacagcc    420
agaactgcag aagaaacagt tgtgctcttt cgagatctac gaagttccct ggggagaaca    480
gaangtccct gggtgaaatc caggtgtcaa gaaatcctan ggatctgttg ccaggc        536
```

<210> SEQ ID NO 70
<211> LENGTH: 477
<212> TYPE: DNA
<213> ORGANISM: Homo sapien

<400> SEQUENCE: 70

```
atgaccccta acaggggccc tctcagccct cctaatgacc tccggcctag ccatgtgatt     60
tcacttccac tccataacgc tcctcatact aggcctacta accaacacac taaccatata    120
ccaatgatgg cgcgatgtaa cacgagaaag cacataccaa ggccaccaca caccacctgt    180
ccaaaaaggc cttcgatacg ggataatcct atttattacc tcagaagttt ttttcttcgc    240
agggattttt ctgagccttt taccactcca gcctagcccc taccccccaa ctaggagggc    300
actggccccc aacaggcatc accccgctaa atcccctaga agtcccactc ctaaacacat    360
ccgtattact cgcatcagga gtatcaatca cctgagctca ccatagtcta atagaaaaca    420
accgaaacca aattattcaa agcactgctt attacaattt tactgggtct ctattt        477
```

<210> SEQ ID NO 71
<211> LENGTH: 533
<212> TYPE: DNA
<213> ORGANISM: Homo sapien
<220> FEATURE:
<221> NAME/KEY: misc_feature
<222> LOCATION: (1)...(533)
<223> OTHER INFORMATION: n = A,T,C or G

<400> SEQUENCE: 71

```
agagctatag gtacagtgtg atctcagctt tgcaaacaca ttttctacat agatagtact     60
aggtattaat agatatgtaa agaaagaaat cacaccatta ataatggtaa gattggttta    120
tgtgatttta gtggtatttt tggcaccctt atatatgttt tccaaacttt cagcagtgat    180
attatttcca taacttaaaa agtgagtttg aaaaagaaaa tctccagcaa gcatctcatt    240
taaataaagg tttgtcatct ttaaaaatac agcaatatgt gactttttaa aaaagctgtc    300
aaataggtgt gaccctacta ataattatta gaaatacatt taaaaacatc gagtacctca    360
agtcagtttg ccttgaaaaa tatcaaatat aactcttaga gaaatgtaca taaaagaatg    420
cttcgtaatt ttggagtang aggttccctc ctcaattttg tatttttaaa aagtacatgg    480
taaaaaaaaa aattcacaac agtatataag gctgtaaaat gaagaattct gcc           533
```

<210> SEQ ID NO 72
<211> LENGTH: 511
<212> TYPE: DNA
<213> ORGANISM: Homo sapien
<220> FEATURE:

-continued

<221> NAME/KEY: misc_feature
<222> LOCATION: (1)...(511)
<223> OTHER INFORMATION: n = A,T,C or G

<400> SEQUENCE: 72
tattacggaa aaacacacca cataattcaa ctancaaaga anactgcttc agggcgtgta 60
aaatgaaagg cttccaggca gttatctgat taaagaacac taaaagaggg acaaggctaa 120
aagccgcagg atgtctacac tatancaggc gctatttggg ttggctggag gagctgtgga 180
aaacatggan agattggtgc tgganatcgc cgtggctatt cctcattgtt attacanagt 240
gaggttctct gtgtgcccac tggtttgaaa accgttctnc aataatgata gaatagtaca 300
cacatgagaa ctgaaatggc ccaaacccag aaagaaagcc caactagatc ctcagaanac 360
gcttctaggg acaataaccg atgaagaaaa gatggcctcc ttgtgccccc gtctgttatg 420
atttctctcc attgcagcna naaacccgtt cttctaagca aacncaggtg atgatggcna 480
aaatacaccc cctcttgaag naccnggagg a 511

<210> SEQ ID NO 73
<211> LENGTH: 499
<212> TYPE: DNA
<213> ORGANISM: Homo sapien
<220> FEATURE:
<221> NAME/KEY: misc_feature
<222> LOCATION: (1)...(499)
<223> OTHER INFORMATION: n = A,T,C or G

<400> SEQUENCE: 73
cagtgccagc actggtgcca gtaccagtac caataacagt gccagtgcca gtgccagcac 60
cagtggtggc ttcagtgctg gtgccagcct gaccgccact ctcacatttg ggctcttcgc 120
tggccttggt ggagctggtg ccagcaccag tggcagctct ggtgcctgtg gtttctccta 180
caagtgagat tttagatatt gttaatcctg ccagtctttc tcttcaagcc agggtgcatc 240
ctcagaaacc tactcaacac agcactctag gcagccacta tcaatcaatt gaagttgaca 300
ctctgcatta aatctatttg ccatttctga aaaaaaaaaa aaaaaaaggg cggccgctcg 360
antctagagg gcccgtttaa acccgctgat cagcctcgac tgtgccttct anttgccagc 420
catctgttgt ttgcccctcc cccgntgcct tccttgaccc tggaaagtgc cactcccact 480
gtcctttcct aantaaaat 499

<210> SEQ ID NO 74
<211> LENGTH: 537
<212> TYPE: DNA
<213> ORGANISM: Homo sapien
<220> FEATURE:
<221> NAME/KEY: misc_feature
<222> LOCATION: (1)...(537)
<223> OTHER INFORMATION: n = A,T,C or G

<400> SEQUENCE: 74
tttcatagga gaacacactg aggagatact tgaagaattt ggattcagcc gcgaagagat 60
ttatcagctt aactcagata aaatcattga aagtaataag gtaaaagcta gtctctaact 120
tccaggccca cggctcaagt gaatttgaat actgcattta cagtgtagag taacacataa 180
cattgtatgc atggaaacat ggaggaacag tattacagtg tcctaccact ctaatcaaga 240
aaagaattac agactctgat tctacagtga tgattgaatt ctaaaaatgg taatcattag 300
ggcttttgat ttataanact ttgggtactt atactaaatt atggtagtta tactgccttc 360
cagtttgctt gatatatttg ttgatattaa gattcttgac ttatattttg aatgggttct 420

-continued actgaaaaan gaatgatata ttcttgaaga catcgatata catttattta cactcttgat 480
tctacaatgt agaaaatgaa ggaaatgccc caaattgtat ggtgataaaa gtcccgt 537

<210> SEQ ID NO 75
<211> LENGTH: 467
<212> TYPE: DNA
<213> ORGANISM: Homo sapien
<220> FEATURE:
<221> NAME/KEY: misc_feature
<222> LOCATION: (1)...(467)
<223> OTHER INFORMATION: n = A,T,C or G

<400> SEQUENCE: 75
caaanacaat tgttcaaaag atgcaaatga tacactactg ctgcagctca caaacacctc 60
tgcatattac acgtacctcc tcctgctcct caagtagtgt ggtctatttt gccatcatca 120
cctgctgtct gcttagaaga acggctttct gctgcaangg agagaaatca taacagacgg 180
tggcacaagg aggccatctt ttcctcatcg gttattgtcc ctagaagcgt cttctgagga 240
tctagttggg ctttctttct gggtttgggc catttcantt ctcatgtgtg tactattcta 300
tcattattgt ataacggttt tcaaaccngt gggcacncag agaacctcac tctgtaataa 360
caatgaggaa tagccacggt gatctccagc accaaatctc tccatgttnt tccagagctc 420
ctccagccaa cccaaatagc cgctgctatn gtgtagaaca tccctgn 467

<210> SEQ ID NO 76
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 76
aagctgacag cattcgggcc gagatgtctc gctccgtggc cttagctgtg ctcgcgctac 60
tctctctttc tggcctggag gctatccagc gtactccaaa gattcaggtt tactcacgtc 120
atccagcaga gaatggaaag tcaaatttcc tgaattgcta tgtgtctggg tttcatccat 180
ccgacattga agttgactta ctgaagaatg gagagagaat tgaaaaagtg gagcattcag 240
acttgtcttt cagcaaggac tggtctttct atctcttgta ctacactgaa ttcaccccca 300
ctgaaaaaga tgagtatgcc tgccgtgtga accatgtgac tttgtcacag cccaagatng 360
ttnagtggga tcganacatg taagcagcan catgggaggt 400

<210> SEQ ID NO 77
<211> LENGTH: 248
<212> TYPE: DNA
<213> ORGANISM: Homo sapien

<400> SEQUENCE: 77
ctggagtgcc ttggtgtttc aagcccctgc aggaagcaga atgcaccttc tgaggcacct 60
ccagctgccc cggcgggga tgcgaggctc ggagcaccct tgcccggctg tgattgctgc 120
caggcactgt tcatctcagc ttttctgtcc ctttgctccc ggcaagcgct tctgctgaaa 180
gttcatatct ggagcctgat gtcttaacga ataaaggtcc catgctccac ccgaaaaaaa 240
aaaaaaaa 248

<210> SEQ ID NO 78

-continued

<211> LENGTH: 201
<212> TYPE: DNA
<213> ORGANISM: Homo sapien

<400> SEQUENCE: 78
actagtccag tgtggtggaa ttccattgtg ttgggcccaa cacaatggct acctttaaca 60
tcacccagac cccgccctgc ccgtgcccca cgctgctgct aacgacagta tgatgcttac 120
tctgctactc ggaaactatt tttatgtaat taatgtatgc tttcttgttt ataaatgcct 180
gatttaaaaa aaaaaaaaaa a 201

<210> SEQ ID NO 79
<211> LENGTH: 552
<212> TYPE: DNA
<213> ORGANISM: Homo sapien
<220> FEATURE:
<221> NAME/KEY: misc_feature
<222> LOCATION: (1)...(552)
<223> OTHER INFORMATION: n = A,T,C or G

<400> SEQUENCE: 79
tccttttgtt aggtttttga gacaacccta gacctaaact gtgtcacaga cttctgaatg 60
tttaggcagt gctagtaatt tcctcgtaat gattctgtta ttactttcct attctttatt 120
cctctttctt ctgaagatta atgaagttga aaattgaggt ggataaatac aaaaaggtag 180
tgtgatagta taagtatcta agtgcagatg aaagtgtgtt atatatatcc attcaaaatt 240
atgcaagtta gtaattactc agggttaact aaattacttt aatatgctgt tgaacctact 300
ctgttccttg gctagaaaaa attataaaca ggactttgtt agtttgggaa gccaaattga 360
taatattcta tgttctaaaa gttgggctat acataaanta tnaagaaata tggaatttta 420
ttcccaggaa tatggggttc atttatgaat antacccggg anagaagttt tgantnaaac 480
cngttttggt taatacgtta atatgtcctn aatnaacaag gcntgactta tttccaaaaa 540
aaaaaaaaaa aa 552

<210> SEQ ID NO 80
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 80
acagggattt gagatgctaa ggccccagag atcgtttgat ccaaccctct tattttcaga 60
ggggaaaatg gggcctagaa gttacagagc atctagctgg tgcgctggca cccctggcct 120
cacacagact cccgagtagc tgggactaca ggcacacagt cactgaagca ggccctgttt 180
gcaattcacg ttgccacctc caacttaaac attcttcata tgtgatgtcc ttagtcacta 240
aggttaaact ttcccaccca gaaaaggcaa cttagataaa atcttagagt actttcatac 300
tcttctaagt cctcttccag cctcactttg agtcctcctt gggggttgat aggaantntc 360
tcttggcttt ctcaataaaa tctctatcca tctcatgttt aatttggtac gcntaaaaat 420
gctgaaaaaa ttaaaatgtt ctggtttcnc tttaaaaaaa aaaaaaaaaa aaaaaa 476

<210> SEQ ID NO 81
<211> LENGTH: 232
<212> TYPE: DNA
<213> ORGANISM: Homo sapien -continued
<220> FEATURE:
<221> NAME/KEY: misc_feature
<222> LOCATION: (1)...(232)
<223> OTHER INFORMATION: n = A,T,C or G

<400> SEQUENCE: 81

```
tttttttttg tatgccntcn ctgtggngtt attgttgctg ccaccctgga ggagcccagt     60

ttcttctgta tctttctttt ctgggggatc ttcctggctc tgcccctcca ttcccagcct    120

ctcatcccca tcttgcactt ttgctagggt tggaggcgct ttcctggtag cccctcagag    180

actcagtcag cgggaataag tcctaggggt ggggggtgtg gcaagccggc ct            232
```

<210> SEQ ID NO 82
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 82

```
aggcgggagc agaagctaaa gccaaagccc aagaagagtg gcagtgccag cactggtgcc     60

agtaccagta ccaataacat gccagtgcca gtgccagcac cagtggtggc ttcagtgctg    120

gtgccagcct gaccgccact ctcacatttg ggctcttcgc tggccttggt ggagctggtg    180

ccagcaccag tggcagctct ggtgcctgtg gtttctccta caagtgagat tttagatatt    240

gttaatcctg ccagtctttc tcttcaagcc agggtgcatc ctcagaaacc tactcaacac    300

agcactctng gcagccacta tcaatcaatt gaagttgaca ctctgcatta aatctatttg    360

ccatttcaaa aaaaaaaaaa aaa                                            383
```

<210> SEQ ID NO 83
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 83

```
accgaattgg gaccgctggc ttataagcga tcatgtcctc cagtattacc tcaacgagca     60

gggagatcga gtctatacgc tgaagaaatt tgacccgatg ggacaacaga cctgctcagc    120

ccatcctgct cggttctccc cagatgacaa atactctcga caccgaatca ccatcaagaa    180

acgcttcaag gtgctcatga cccagcaacc gcgccctgtc ctctgagggt ccttaaactg    240

atgtcttttc tgccacctgt taccccctcgg agactccgta accaaactct tcggactgtg    300

agccctgatg cctttttgcc agccatactc tttggcntcc agtctctcgt ggcgattgat    360

tatgcttgtg tgaggcaatc atggtggcat cacccatnaa gggaacacat ttganttttt    420

tttcncatat tttaaattac naccagaata nttcagaata aatgaattga aaaactctta    480

aaaaaaaaaa aaaa                                                      494
```

<210> SEQ ID NO 84
<211> LENGTH: 380
<212> TYPE: DNA
<213> ORGANISM: Homo sapien
<220> FEATURE:
<221> NAME/KEY: misc_feature
<222> LOCATION: (1)...(380)

-continued

<223> OTHER INFORMATION: n = A,T,C or G

<400> SEQUENCE: 84
gctggtagcc tatggcgtgg ccacggangg gctcctgagg cacgggacag tgacttccca 60
agtatcctgc gccgcgtctt ctaccgtccc tacctgcaga tcttcgggca gattccccag 120
gaggacatgg acgtggccct catggagcac agcaactgct cgtcggagcc cggcttctgg 180
gcacaccctc ctggggccca ggcgggcacc tgcgtctccc agtatgccaa ctggctggtg 240
gtgctgctcc tcgtcatctt cctgctcgtg gccaacatcc tgctggtcac ttgctcattg 300
ccatgttcag ttacacattc ggcaaagtac agggcaacag cnatctctac tgggaaggcc 360
agcgttnccg cctcatccgg 380

<210> SEQ ID NO 85
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 85
gagttagctc ctccacaacc ttgatgaggt cgtctgcagt ggcctctcgc ttcataccgc 60
tnccatcgtc atactgtagg tttgccacca cctcctgcat cttggggcgg ctaatatcca 120
ggaaactctc aatcaagtca ccgtcnatna aacctgtggc tggttctgtc ttccgctcgg 180
tgtgaaagga tctccagaag gagtgctcga tcttccccac acttttgatg actttattga 240
gtcgattctg catgtccagc aggaggttgt accagctctc tgacagtgag gtcaccagcc 300
ctatcatgcc nttgaacgtg ccgaagaaca ccgagccttg tgtgggggt gnagtctcac 360 ccagattctg cattaccaga nagccgtggc aaaaganatt gacaactcgc ccaggnngaa 420
aaagaacacc tcctggaagt gctngccgct cctcgtccnt tggtggnngc gcntnccttt 480
t 481

<210> SEQ ID NO 86
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 86
aacatcttcc tgtataatgc tgtgtaatat cgatccgatn ttgtctgctg agaattcatt 60
acttggaaaa gcaacttnaa gcctggacac tggtattaaa attcacaata tgcaacactt 120
taaacagtgt gtcaatctgc tcccttactt tgtcatcacc agtctgggaa taagggtatg 180
ccctattcac acctgttaaa agggcgctaa gcatttttga ttcaacatct tttttttga 240 cacaagtccg aaaaaagcaa aagtaaacag ttnttaattt gttagccaat tcactttctt 300
catgggacag agccatttga tttaaaaagc aaattgcata atattgagct ttgggagctg 360
atatntgagc ggaagantag cctttctact tcaccagaca caactccttt catattggga 420
tgttnacnaa agttatgtct cttacagatg ggatgctttt gtggcaattc tg 472

<210> SEQ ID NO 87
<211> LENGTH: 413

-continued

<212> TYPE: DNA
<213> ORGANISM: Homo sapien
<220> FEATURE:
<221> NAME/KEY: misc_feature
<222> LOCATION: (1)...(413)
<223> OTHER INFORMATION: n = A,T,C or G

<400> SEQUENCE: 87
agaaaccagt atctctnaaa acaacctctc ataccttgtg gacctaattt tgtgtgcgtg 60
tgtgtgtgcg cgcatattat atagacaggc acatcttttt tacttttgta aaagcttatg 120
cctctttggt atctatatct gtgaaagttt taatgatctg ccataatgtc ttggggacct 180
ttgtcttctg tgtaaatggt actagagaaa acacctatnt tatgagtcaa tctagttngt 240
tttattcgac atgaaggaaa tttccagatn acaacactna caaactctcc cttgactagg 300
ggggacaaag aaaagcanaa ctgaacatna gaaacaattn cctggtgaga aattncataa 360
acagaaattg ggtngtatat tgaaananng catcattnaa acgttttttt ttt 413

<210> SEQ ID NO 88
<211> LENGTH: 448
<212> TYPE: DNA
<213> ORGANISM: Homo sapien
<220> FEATURE:
<221> NAME/KEY: misc_feature
<222> LOCATION: (1)...(448)
<223> OTHER INFORMATION: n = A,T,C or G

<400> SEQUENCE: 88
cgcagcgggt cctctctatc tagctccagc ctctcgcctg ccccactccc cgcgtcccgc 60
gtcctagccn accatggccg ggcccctgcg cgcccccgctg ctcctgctgg ccatcctggc 120
cgtggccctg gccgtgagcc ccgcggccgg ctccagtccc ggcaagccgc cgcgcctggt 180
gggaggccca tggaccccgc gtggaagaag aaggtgtgcg gcgtgcactg gactttgccg 240
tcggcnanta caacaaaccc gcaacnactt ttaccnagcn cgcgctgcag gttgtgccgc 300
cccaancaaa ttgttactng gggtaantaa ttcttggaag ttgaacctgg gccaaacnng 360
tttaccagaa ccnagccaat tngaacaatt ncccctccat aacagcccct tttaaaaagg 420
gaancantcc tgntcttttc caaatttt 448

<210> SEQ ID NO 89
<211> LENGTH: 463
<212> TYPE: DNA
<213> ORGANISM: Homo sapien
<220> FEATURE:
<221> NAME/KEY: misc_feature
<222> LOCATION: (1)...(463)
<223> OTHER INFORMATION: n = A,T,C or G

<400> SEQUENCE: 89
gaattttgtg cactggccac tgtgatggaa ccattgggcc aggatgcttt gagtttatca 60
gtagtgattc tgccaaagtt ggtgttgtaa catgagtatg taaaatgtca aaaaattagc 120
agaggtctag gtctgcatat cagcagacag tttgtccgtg tattttgtag ccttgaagtt 180
ctcagtgaca agttnnttct gatgcgaagt tctnattcca gtgttttagt cctttgcatc 240
tttnatgttn agacttgcct ctntnaaatt gcttttgtnt tctgcaggta ctatctgtgg 300
tttaacaaaa tagaannact tctctgcttn gaanatttga atatcttaca tctnaaaatn 360
aattctctcc ccatannaaa acccangccc ttggganaat ttgaaaaang gntccttcnn 420
aattcnnana anttcagntn tcatacaaca naacnggan c ccc 463

-continued

<210> SEQ ID NO 90
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 90
agggattgaa ggtctnttnt actgtcggac tgttcancca ccaactctac aagttgctgt 60
cttccactca ctgtctgtaa gcntnttaac ccagactgta tcttcataaa tagaacaaat 120
tcttcaccag tcacatcttc taggaccttt ttggattcag ttagtataag ctcttccact 180
tcctttgtta agacttcatc tggtaaagtc ttaagttttg tagaaaggaa tttaattgct 240
cgttctctaa caatgtcctc tccttgaagt atttggctga acaacccacc tnaagtccct 300
ttgtgcatcc attttaaata tacttaatag ggcattggtn cactaggtta aattctgcaa 360
gagtcatctg tctgcaaaag ttgcgttagt atatctgcca 400

<210> SEQ ID NO 91
<211> LENGTH: 480
<212> TYPE: DNA
<213> ORGANISM: Homo sapien
<220> FEATURE:
<221> NAME/KEY: misc_feature
<222> LOCATION: (1)...(480)
<223> OTHER INFORMATION: n = A,T,C or G

<400> SEQUENCE: 91
gagctcggat ccaataatct ttgtctgagg gcagcacaca tatncagtgc catggnaact 60
ggtctacccc acatgggagc agcatgccgt agntatataa ggtcattccc tgagtcagac 120
atgcctcttt gactaccgtg tgccagtgct ggtgattctc acacacctcc nnccgctctt 180
tgtggaaaaa ctggcacttg nctggaacta gcaagacatc acttacaaat tcacccacga 240
gacacttgaa aggtgtaaca aagcgactct tgcattgctt tttgtccctc cggcaccagt 300
tgtcaatact aacccgctgg tttgcctcca tcacatttgt gatctgtagc tctggataca 360
tctcctgaca gtactgaaga acttcttctt ttgtttcaaa agcaactctt ggtgcctgtt 420
ngatcaggtt cccatttccc agtccgaatg ttcacatggc atatnttact tcccacaaaa 480

<210> SEQ ID NO 92
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 92
atacagccca natcccacca cgaagatgcg cttgttgact gagaacctga tgcggtcact 60
ggtcccgctg tagccccagc gactctccac ctgctggaag cggttgatgc tgcactcctt 120
cccacgcagg cagcagcggg gccggtcaat gaactccact cgtggcttgg ggttgacggt 180
taantgcagg aagaggctga ccacctcgcg gtccaccagg atgcccgact gtgcgggacc 240
tgcagcgaaa ctcctcgatg gtcatgagcg ggaagcgaat gangcccagg gccttgccca 300
gaaccttccg cctgttctct ggcgtcacct gcagctgctg ccgctnacac tcggcctcgg 360
accagcggac aaacggcgtt gaacagccgc acctcacgga tgcccantgt gtcgcgctcc 420

-continued aggaacggcn ccagcgtgtc caggtcaatg tcggtgaanc ctccgcgggt aatggcg 477

<210> SEQ ID NO 93
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 93
gaacggctgg accttgcctc gcattgtgct gctggcagga ataccttggc aagcagctcc 60
agtccgagca gccccagacc gctgccgccc gaagctaagc ctgcctctgg ccttcccctc 120
cgcctcaatg cagaaccant agtgggagca ctgtgtttag agttaagagt gaacactgtn 180
tgattttact tgggaatttc ctctgttata tagcttttcc caatgctaat ttccaaacaa 240
caacaacaaa ataacatgtt tgcctgttna gttgtataaa agtangtgat tctgtatnta 300
aagaaaatat tactgttaca tatactgctt gcaanttctg tatttattgg tnctctggaa 360
ataaatatat tattaaa 377

<210> SEQ ID NO 94
<211> LENGTH: 495
<212> TYPE: DNA
<213> ORGANISM: Homo sapien
<220> FEATURE:
<221> NAME/KEY: misc_feature
<222> LOCATION: (1)...(495)
<223> OTHER INFORMATION: n = A,T,C or G

<400> SEQUENCE: 94
ccctttgagg ggttagggtc cagttcccag tggaagaaac aggccaggag aantgcgtgc 60
cgagctgang cagatttccc acagtgaccc cagagccctg ggctatagtc tctgacccct 120
ccaaggaaag accaccttct ggggacatgg gctggagggc aggacctaga ggcaccaagg 180
gaaggcccca ttccggggct gttccccgag gaggaaggga aggggctctg tgtgcccccc 240
acgaggaana ggccctgant cctgggatca nacacccctt cacgtgtatc cccacacaaa 300
tgcaagctca ccaaggtccc ctctcagtcc cttccctaca ccctgaacgg ncactggccc 360
acacccaccc agancancca cccgccatgg ggaatgtnct caaggaatcg cngggcaacg 420
tggactctng tcccnnaagg gggcagaatc tccaatagan gganngaacc cttgctnana 480
aaaaaaaana aaaaa 495

<210> SEQ ID NO 95
<211> LENGTH: 472
<212> TYPE: DNA
<213> ORGANISM: Homo sapien
<220> FEATURE:
<221> NAME/KEY: misc_feature
<222> LOCATION: (1)...(472)
<223> OTHER INFORMATION: n = A,T,C or G

<400> SEQUENCE: 95
ggttacttgg tttcattgcc accacttagt ggatgtcatt tagaaccatt ttgtctgctc 60
cctctggaag ccttgcgcag agcggacttt gtaattgttg gagaataact gctgaatttt 120
tagctgtttt gagttgattc gcaccactgc accacaactc aatatgaaaa ctatttnact 180
tatttattat cttgtgaaaa gtatacaatg aaaattttgt tcatactgta tttatcaagt 240

-continued

```
atgatgaaaa gcaatagata tatattcttt tattatgttn aattatgatt gccattatta    300

atcggcaaaa tgtggagtgt atgttctttt cacagtaata tatgcctttt gtaacttcac    360

ttggttattt tattgtaaat gaattacaaa attcttaatt taagaaaatg gtangttata    420

tttanttcan taatttcttt ccttgtttac gttaattttg aaaagaatgc at            472
```

<210> SEQ ID NO 96
<211> LENGTH: 476
<212> TYPE: DNA
<213> ORGANISM: Homo sapien
<220> FEATURE:
<221> NAME/KEY: misc_feature
<222> LOCATION: (1)...(476)
<223> OTHER INFORMATION: n = A,T,C or G

<400> SEQUENCE: 96

```
ctgaagcatt tcttcaaact tntctacttt tgtcattgat acctgtagta agttgacaat     60

gtggtgaaat ttcaaaatta tatgtaactt ctactagttt tactttctcc cccaagtctt    120

ttttaactca tgatttttac acacacaatc cagaacttat tatatagcct ctaagtcttt    180

attcttcaca gtagatgatg aaagagtcct ccagtgtctt gngcanaatg ttctagntat    240

agctggatac atacngtggg agttctataa actcatacct cagtgggact naaccaaaat    300

tgtgttagtc tcaattccta ccacactgag ggagcctccc aaatcactat attcttatct    360

gcaggtactc ctccagaaaa acngacaggg caggcttgca tgaaaaagtn acatctgcgt    420

tacaaagtct atcttcctca nangtctgtn aaggaacaat ttaatcttct agcttt        476
```

<210> SEQ ID NO 97
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 97

```
actctttcta atgctgatat gatcttgagt ataagaatgc atatgtcact agaatggata     60

aaataatgct gcaaacttaa tgttcttatg caaaatggaa cgctaatgaa acacagctta    120

caatcgcaaa tcaaaactca caagtgctca tctgttgtag atttagtgta ataagactta    180

gattgtgctc cttcggatat gattgtttct canatcttgg gcaatnttcc ttagtcaaat    240

caggctacta gaattctgtt attggatatn tgagagcatg aaatttttaa naatacactt    300

gtgattatna aattaatcac aaatttcact tatacctgct atcagcagct agaaaaacat    360

ntnnttttta natcaaagta ttttgtgttt ggaantgtnn aaatgaaatc tgaatgtggg    420

ttcnatctta ttttttcccn gacnactant tnctttttta gggnctattc tganccatc     479
```

<210> SEQ ID NO 98
<211> LENGTH: 461
<212> TYPE: DNA
<213> ORGANISM: Homo sapien

<400> SEQUENCE: 98

```
agtgacttgt cctccaacaa aaccccttga tcaagtttgt ggcactgaca atcagaccta     60

tgctagttcc tgtcatctat tcgctactaa atgcagactg gaggggacca aaaaggggca    120

tcaactccag ctggattatt ttggagcctg caaatctatt cctacttgta cggactttga    180

agtgattcag tttcctctac ggatgagaga ctggctcaag aatatcctca tgcagcttta    240
```

-continued

```
tgaagccact ctgaacacgc tggttatcta gatgagaaca gagaaataaa gtcagaaaat    300

ttacctggag aaaagaggct ttggctgggg accatcccat tgaaccttct cttaaggact    360

ttaagaaaaa ctaccacatg ttgtgtatcc tggtgccggc cgtttatgaa ctgaccaccc    420

tttggaataa tcttgacgct cctgaacttg ctcctctgcg a                        461
```

<210> SEQ ID NO 99
<211> LENGTH: 171
<212> TYPE: DNA
<213> ORGANISM: Homo sapien

<400> SEQUENCE: 99

```
gtggccgcgc gcaggtgttt cctcgtaccg cagggccccc tcccttcccc aggcgtccct     60

cggcgcctct gcgggcccga ggaggagcgg ctggcgggtg gggggagtgt gacccaccct    120

cggtgagaaa agccttctct agcgatctga gaggcgtgcc ttgggggtac c             171
```

<210> SEQ ID NO 100
<211> LENGTH: 269
<212> TYPE: DNA
<213> ORGANISM: Homo sapien

<400> SEQUENCE: 100

```
cggccgcaag tgcaactcca gctggggccg tgcggacgaa gattctgcca gcagttggtc     60

cgactgcgac gacggcggcg gcgacagtcg caggtgcagc gcgggcgcct ggggtcttgc    120

aaggctgagc tgacgccgca gaggtcgtgt cacgtcccac gaccttgacg ccgtcgggga    180

cagccggaac agagcccggt gaagcgggag gcctcgggga gcccctcggg aagggcggcc    240

cgagagatac gcaggtgcag gtggccgcc                                      269
```

<210> SEQ ID NO 101
<211> LENGTH: 405
<212> TYPE: DNA
<213> ORGANISM: Homo sapien

<400> SEQUENCE: 101

```
tttttttttt ttttggaatc tactgcgagc acagcaggtc agcaacaagt ttattttgca     60

gctagcaagg taacagggta gggcatggtt acatgttcag gtcaacttcc tttgtcgtgg    120

ttgattggtt tgtctttatg ggggcggggt ggggtagggg aaacgaagca aataacatgg    180

agtgggtgca ccctccctgt agaacctggt tacaaagctt ggggcagttc acctggtctg    240

tgaccgtcat tttcttgaca tcaatgttat tagaagtcag gatatctttt agagagtcca    300

ctgttctgga gggagattag ggtttcttgc caaatccaac aaaatccact gaaaaagttg    360

gatgatcagt acgaataccg aggcatattc tcatatcggt ggcca                    405
```

<210> SEQ ID NO 102
<211> LENGTH: 470
<212> TYPE: DNA
<213> ORGANISM: Homo sapien

<400> SEQUENCE: 102

```
tttttttttt tttttttttt tttttttttt tttttttttt tttttttttt tttttttttt     60

ggcacttaat ccatttttat ttcaaaatgt ctacaaattt aatcccatta tacggtattt    120

tcaaaatcta aattattcaa attagccaaa tccttaccaa ataataccca aaaatcaaaa    180

atatacttct ttcagcaaac ttgttacata aattaaaaaa atatatacgg ctggtgtttt    240
```

-continued caaagtacaa ttatcttaac actgcaaaca ttttaaggaa ctaaaataaa aaaaaacact 300
ccgcaaaggt taaagggaac aacaaattct tttacaacac cattataaaa atcatatctc 360
aaatcttagg ggaatatata cttcacacgg gatcttaact tttactcact ttgtttattt 420
ttttaaacca ttgtttgggc ccaacacaat ggaatccccc ctggactagt 470

<210> SEQ ID NO 103
<211> LENGTH: 581
<212> TYPE: DNA
<213> ORGANISM: Homo sapien

<400> SEQUENCE: 103
tttttttttt ttttttttga cccccctctt ataaaaaaca agttaccatt ttattttact 60
tacacatatt tattttataa ttggtattag atattcaaaa ggcagctttt aaaatcaaac 120
taaatggaaa ctgccttaga tacataattc ttaggaatta gcttaaaatc tgcctaaagt 180
gaaaatcttc tctagctctt ttgactgtaa atttttgact cttgtaaaac atccaaattc 240
atttttcttg tctttaaaat tatctaatct ttccattttt tccctattcc aagtcaattt 300
gcttctctag cctcatttcc tagctcttat ctactattag taagtggctt ttttcctaaa 360
agggaaaaca ggaagagaaa tggcacacaa aacaaacatt ttatattcat atttctacct 420
acgttaataa aatagcattt tgtgaagcca gctcaaaaga aggcttagat ccttttatgt 480
ccattttagt cactaaacga tatcaaagtg ccagaatgca aaaggtttgt gaacatttat 540
tcaaaagcta atataagata tttcacatac tcatctttct g 581

<210> SEQ ID NO 104
<211> LENGTH: 578
<212> TYPE: DNA
<213> ORGANISM: Homo sapien

<400> SEQUENCE: 104
tttttttttt tttttttttt tttttctctt cttttttttt gaaatgagga tcgagttttt 60
cactctctag atagggcatg aagaaaactc atctttccag ctttaaaata acaatcaaat 120
ctcttatgct atatcatatt ttaagttaaa ctaatgagtc actggcttat cttctcctga 180
aggaaatctg ttcattcttc tcattcatat agttatatca agtactacct tgcatattga 240
gaggtttttc ttctctattt acacatatat ttccatgtga atttgtatca aacctttatt 300
ttcatgcaaa ctagaaaata atgtttcttt tgcataagag aagagaacaa tatagcatta 360
caaaactgct caaattgttt gttaagttat ccattataat tagttggcag gagctaatac 420
aaatcacatt tacgacagca ataataaaac tgaagtacca gttaaatatc caaaataatt 480
aaaggaacat ttttagcctg ggtataatta gctaattcac tttacaagca tttattagaa 540
tgaattcaca tgttattatt cctagcccaa cacaatgg 578

<210> SEQ ID NO 105
<211> LENGTH: 538
<212> TYPE: DNA
<213> ORGANISM: Homo sapien

<400> SEQUENCE: 105
tttttttttt tttttcagta ataatcagaa caatatttat ttttatattt aaaattcata 60
gaaaagtgcc ttacatttaa taaaagtttg tttctcaaag tgatcagagg aattagatat 120
gtcttgaaca ccaatattaa tttgaggaaa atacaccaaa atacattaag taaattattt 180
aagatcatag agcttgtaag tgaaaagata aaatttgacc tcagaaactc tgagcattaa 240

-continued

```
aaatccacta ttagcaaata aattactatg gacttcttgc tttaattttg tgatgaatat    300

ggggtgtcac tggtaaacca acacattctg aaggatacat tacttagtga tagattctta    360

tgtactttgc taatacgtgg atatgagttg acaagtttct ctttcttcaa tcttttaagg    420

ggcgagaaat gaggaagaaa agaaaaggat tacgcatact gttctttcta tggaaggatt    480

agatatgttt cctttgccaa tattaaaaaa ataataatgt ttactactag tgaaaccc      538


<210> SEQ ID NO 106
<211> LENGTH: 473
<212> TYPE: DNA
<213> ORGANISM: Homo sapien

<400> SEQUENCE: 106

tttttttttt ttttttagtc aagtttctat ttttattata attaaagtct tggtcatttc     60

atttattagc tctgcaactt acatatttaa attaaagaaa cgttttagac aactgtacaa    120

tttataaatg taaggtgcca ttattgagta atatattcct ccaagagtgg atgtgtccct    180

tctcccacca actaatgaac agcaacatta gtttaatttt attagtagat atacactgct    240

gcaaacgcta attctcttct ccatccccat gtgatattgt gtatatgtgt gagttggtag    300

aatgcatcac aatctacaat caacagcaag atgaagctag gctgggcttt cggtgaaaat    360

agactgtgtc tgtctgaatc aaatgatctg acctatcctc ggtggcaaga actcttcgaa    420

ccgcttcctc aaaggcgctg ccacatttgt ggctctttgc acttgtttca aaa           473


<210> SEQ ID NO 107
<211> LENGTH: 1621
<212> TYPE: DNA
<213> ORGANISM: Homo sapien

<400> SEQUENCE: 107

cgccatggca ctgcagggca tctcggtcat ggagctgtcc ggcctggccc cgggcccgtt     60

ctgtgctatg gtcctggctg acttcggggc gcgtgtggta cgcgtggacc ggcccggctc    120

ccgctacgac gtgagccgct tgggccgggg caagcgctcg ctagtgctgg acctgaagca    180

gccgcgggga gccgccgtgc tgcggcgtct gtgcaagcgg tcggatgtgc tgctggagcc    240

cttccgccgc ggtgtcatgg agaaactcca gctgggccca gagattctgc agcgggaaaa    300

tccaaggctt atttatgcca ggctgagtgg atttggccag tcaggaagct tctgccggtt    360

agctggccac gatatcaact atttggcttt gtcaggtgtt ctctcaaaaa ttggcagaag    420

tggtgagaat ccgtatgccc cgctgaatct cctggctgac tttgctggtg gtggccttat    480

gtgtgcactg ggcattataa tggctctttt tgaccgcaca cgcactgaca agggtcaggt    540

cattgatgca aatatggtgg aaggaacagc atatttaagt tcttttctgt ggaaaactca    600

gaaatcgagt ctgtgggaag cacctcgagg acagaacatg ttggatggtg gagcaccttt    660

ctatacgact tacaggacag cagatgggga attcatggct gttggagcaa tagaacccca    720

gttctacgag ctgctgatca aaggacttgg actaaagtct gatgaacttc ccaatcagat    780

gagcatggat gattggccag aaatgaagaa gaagtttgca gatgtatttg caaagaagac    840

gaaggcagag tggtgtcaaa tctttgacgg cacagatgcc tgtgtgactc cggttctgac    900

ttttgaggag gttgttcatc atgatcacaa caaggaacgg ggctcgttta tcaccagtga    960

ggagcaggac gtgagccccc gccctgcacc tctgctgtta aacaccccag ccatcccttc   1020

tttcaaaagg gatcctttca taggagaaca cactgaggag atacttgaag aatttggatt   1080
```

-continued

```
cagccgcgaa gagatttatc agcttaactc agataaaatc attgaaagta ataaggtaaa   1140

agctagtctc taacttccag gcccacggct caagtgaatt tgaatactgc atttacagtg   1200

tagagtaaca cataacattg tatgcatgga aacatggagg aacagtatta cagtgtccta   1260

ccactctaat caagaaaaga attacagact ctgattctac agtgatgatt gaattctaaa   1320

aatggttatc attagggctt ttgatttata aaactttggg tacttatact aaattatggt   1380

agttattctg ccttccagtt tgcttgatat atttgttgat attaagattc ttgacttata   1440

ttttgaatgg gttctagtga aaaaggaatg atatattctt gaagacatcg atatacattt   1500

atttacactc ttgattctac aatgtagaaa atgaggaaat gccacaaatt gtatggtgat   1560

aaaagtcacg tgaaacaaaa aaaaaaaaaa aaaaaaaaaa aaaaaaaaaa aaaaaaaaaa   1620

a                                                                   1621


<210> SEQ ID NO 108
<211> LENGTH: 382
<212> TYPE: PRT
<213> ORGANISM: Homo sapien

<400> SEQUENCE: 108

Met Ala Leu Gln Gly Ile Ser Val Met Glu Leu Ser Gly Leu Ala Pro
 1               5                  10                  15

Gly Pro Phe Cys Ala Met Val Leu Ala Asp Phe Gly Ala Arg Val Val
            20                  25                  30

Arg Val Asp Arg Pro Gly Ser Arg Tyr Asp Val Ser Arg Leu Gly Arg
        35                  40                  45

Gly Lys Arg Ser Leu Val Leu Asp Leu Lys Gln Pro Arg Gly Ala Ala
    50                  55                  60

Val Leu Arg Arg Leu Cys Lys Arg Ser Asp Val Leu Leu Glu Pro Phe
65                  70                  75                  80

Arg Arg Gly Val Met Glu Lys Leu Gln Leu Gly Pro Glu Ile Leu Gln
                85                  90                  95

Arg Glu Asn Pro Arg Leu Ile Tyr Ala Arg Leu Ser Gly Phe Gly Gln
            100                 105                 110

Ser Gly Ser Phe Cys Arg Leu Ala Gly His Asp Ile Asn Tyr Leu Ala
        115                 120                 125

Leu Ser Gly Val Leu Ser Lys Ile Gly Arg Ser Gly Glu Asn Pro Tyr
    130                 135                 140

Ala Pro Leu Asn Leu Leu Ala Asp Phe Ala Gly Gly Gly Leu Met Cys
145                 150                 155                 160

Ala Leu Gly Ile Ile Met Ala Leu Phe Asp Arg Thr Arg Thr Asp Lys
                165                 170                 175

Gly Gln Val Ile Asp Ala Asn Met Val Glu Gly Thr Ala Tyr Leu Ser
            180                 185                 190

Ser Phe Leu Trp Lys Thr Gln Lys Ser Ser Leu Trp Glu Ala Pro Arg
        195                 200                 205

Gly Gln Asn Met Leu Asp Gly Gly Ala Pro Phe Tyr Thr Thr Tyr Arg
    210                 215                 220

Thr Ala Asp Gly Glu Phe Met Ala Val Gly Ala Ile Glu Pro Gln Phe
225                 230                 235                 240

Tyr Glu Leu Leu Ile Lys Gly Leu Gly Leu Lys Ser Asp Glu Leu Pro
                245                 250                 255

Asn Gln Met Ser Met Asp Asp Trp Pro Glu Met Lys Lys Lys Phe Ala
            260                 265                 270
```

-continued

```
Asp Val Phe Ala Lys Lys Thr Lys Ala Glu Trp Cys Gln Ile Phe Asp
        275                 280                 285

Gly Thr Asp Ala Cys Val Thr Pro Val Leu Thr Phe Glu Glu Val Val
    290                 295                 300

His His Asp His Asn Lys Glu Arg Gly Ser Phe Ile Thr Ser Glu Glu
305                 310                 315                 320

Gln Asp Val Ser Pro Arg Pro Ala Pro Leu Leu Leu Asn Thr Pro Ala
                325                 330                 335

Ile Pro Ser Phe Lys Arg Asp Pro Phe Ile Gly Glu His Thr Glu Glu
            340                 345                 350

Ile Leu Glu Glu Phe Gly Phe Ser Arg Glu Glu Ile Tyr Gln Leu Asn
        355                 360                 365

Ser Asp Lys Ile Ile Glu Ser Asn Lys Val Lys Ala Ser Leu
    370                 375                 380
```

<210> SEQ ID NO 109
<211> LENGTH: 1524
<212> TYPE: DNA
<213> ORGANISM: Homo sapien

<400> SEQUENCE: 109

```
ggcacgaggc tgcgccaggg cctgagcgga ggcgggggca gcctcgccag cgggggcccc     60

gggcctggcc atgcctcact gagccagcgc ctgcgcctct acctcgccga cagctggaac    120

cagtgcgacc tagtggctct cacctgcttc ctcctgggcg tgggctgccg gctgaccccg    180

ggtttgtacc acctgggccg cactgtcctc tgcatcgact tcatggtttt cacggtgcgg    240

ctgcttcaca tcttcacggt caacaaacag ctggggccca agatcgtcat cgtgagcaag    300

atgatgaagg acgtgttctt cttcctcttc ttcctcggcg tgtggctggt agcctatggc    360

gtggccacgg aggggctcct gaggccacgg gacagtgact tcccaagtat cctgcgccgc    420

gtcttctacc gtccctacct gcagatcttc gggcagattc cccaggagga catggacgtg    480

gccctcatgg agcacagcaa ctgctcgtcg gagcccggct tctgggcaca ccctcctggg    540

gcccaggcgg gcacctgcgt ctcccagtat gccaactggc tggtggtgct gctcctcgtc    600

atcttcctgc tcgtggccaa catcctgctg gtcaacttgc tcattgccat gttcagttac    660

acattcggca aagtacaggg caacagcgat ctctactgga aggcgcagcg ttaccgcctc    720

atccgggaat tccactctcg gcccgcgctg gccccgccct ttatcgtcat ctcccacttg    780

cgcctcctgc tcaggcaatt gtgcaggcga ccccggagcc cccagccgtc ctccccggcc    840

ctcgagcatt tccgggttta cctttctaag gaagccgagc ggaagctgct aacgtgggaa    900

tcggtgcata aggagaactt tctgctggca cgcgctaggg acaagcggga gagcgactcc    960

gagcgtctga agcgcacgtc ccagaaggtg gacttggcac tgaaacagct gggacacatc   1020

cgcgagtacg aacagcgcct gaaagtgctg gagcgggagg tccagcagtg tagccgcgtc   1080

ctggggtggg tggccgaggc cctgagccgc tctgccttgc tgccccccagg tgggccgcca   1140

ccccctgacc tgcctgggtc caaagactga gccctgctgg cggacttcaa ggagaagccc   1200

ccacagggga ttttgctcct agagtaaggc tcatctgggc ctcggccccc gcacctggtg   1260

gccttgtcct tgaggtgagc cccatgtcca tctgggccac tgtcaggacc acctttggga   1320

gtgtcatcct tacaaaccac agcatgcccg gctcctccca gaaccagtcc cagcctggga   1380

ggatcaaggc ctggatcccg ggccgttatc catctggagg ctgcagggtc cttggggtaa   1440

cagggaccac agacccctca ccactcacag attcctcaca ctggggaaat aaagccattt   1500
```

-continued

```
cagaggaaaa aaaaaaaaaa aaaa                                          1524

<210> SEQ ID NO 110
<211> LENGTH: 3410
<212> TYPE: DNA
<213> ORGANISM: Homo sapien

<400> SEQUENCE: 110

gggaaccagc ctgcacgcgc tggctccggg tgacagccgc gcgcctcggc caggatctga     60
gtgatgagac gtgtccccac tgaggtgccc cacagcagca ggtgttgagc atgggctgag    120
aagctggacc ggcaccaaag ggctggcaga aatgggcgcc tggctgattc ctaggcagtt    180
ggcggcagca aggaggagag gccgcagctt ctggagcaga gccgagacga agcagttctg    240
gagtgcctga acggcccccct gagccctacc cgcctggccc actatggtcc agaggctgtg    300
ggtgagccgc ctgctgcggc accggaaagc ccagctcttg ctggtcaacc tgctaacctt    360
tggcctggag gtgtgtttgg ccgcaggcat cacctatgtg ccgcctctgc tgctggaagt    420
gggggtagag gagaagttca tgaccatggt gctgggcatt ggtccagtgc tgggcctggt    480
ctgtgtcccg ctcctaggct cagccagtga ccactggcgt ggacgctatg gccgccgccg    540
gcccttcatc tgggcactgt ccttgggcat cctgctgagc ctctttctca tcccaagggc    600
cggctggcta gcagggctgc tgtgcccgga tcccaggccc ctggagctgg cactgctcat    660
cctgggcgtg gggctgctgg acttctgtgg ccaggtgtgc ttcactccac tggaggccct    720
gctctctgac ctcttccggg acccggacca ctgtcgccag gcctactctg tctatgcctt    780
catgatcagt cttgggggct gcctgggcta cctcctgcct gccattgact gggacaccag    840
tgccctggcc ccctacctgg gcacccagga ggagtgcctc tttggcctgc tcaccctcat    900
cttcctcacc tgcgtagcag ccacactgct ggtggctgag gaggcagcgc tgggccccac    960
cgagccagca gaagggctgt cggccccctc cttgtcgccc cactgctgtc catgccgggc   1020
ccgcttggct ttccggaacc tgggcgccct gcttccccgg ctgcaccagc tgtgctgccg   1080
catgccccgc accctgcgcc ggctcttcgt ggctgagctg tgcagctgga tggcactcat   1140
gaccttcacg ctgttttaca cggatttcgt gggcgagggg ctgtaccagg gcgtgcccag   1200
agctgagccg ggcaccgagg cccggagaca ctatgatgaa ggcgttcgga tgggcagcct   1260
ggggctgttc ctgcagtgcg ccatctccct ggtcttctct ctggtcatgg accggctggt   1320
gcagcgattc ggcactcgag cagtctattt ggccagtgtg gcagctttcc ctgtggctgc   1380
cggtgccaca tgcctgtccc acagtgtggc cgtggtgaca gcttcagccg ccctcaccgg   1440
gttcaccttc tcagccctgc agatcctgcc ctacacactg gcctccctct accaccggga   1500
gaagcaggtg ttcctgccca aataccgagg ggacactgga ggtgctagca gtgaggacag   1560
cctgatgacc agcttcctgc caggccctaa gcctggagct cccttcccta atggacacgt   1620
gggtgctgga ggcagtggcc tgctcccacc tccacccgcg ctctgcgggg cctctgcctg   1680
tgatgtctcc gtacgtgtgg tggtgggtga gcccaccgag gccagggtgg ttccgggccg   1740
gggcatctgc ctggacctcg ccatcctgga tagtgccttc ctgctgtccc aggtggcccc   1800
atccctgttt atgggctcca ttgtccagct cagccagtct gtcactgcct atatggtgtc   1860
tgccgcaggc ctgggtctgg tcgccattta ctttgctaca caggtagtat ttgacaagag   1920
cgacttggcc aaatactcag cgtagaaaac ttccagcaca ttggggtgga gggcctgcct   1980
cactgggtcc cagctccccg ctcctgttag ccccatgggg ctgccgggct ggccgccagt   2040
ttctgttgct gccaaagtaa tgtggctctc tgctgccacc ctgtgctgct gaggtgcgta   2100
```

gctgcacagc tgggggctgg ggcgtccctc tcctctctcc ccagtctcta gggctgcctg 2160
actggaggcc ttccaagggg gtttcagtct ggacttatac agggaggcca gaagggctcc 2220
atgcactgga atgcggggac tctgcaggtg gattacccag gctcagggtt aacagctagc 2280
ctcctagttg agacacacct agagaagggt ttttgggagc tgaataaact cagtcacctg 2340
gtttcccatc tctaagcccc ttaacctgca gcttcgttta atgtagctct tgcatgggag 2400
tttctaggat gaaacactcc tccatgggat ttgaacatat gacttatttg taggggaaga 2460
gtcctgaggg gcaacacaca agaaccaggt cccctcagcc cacagcactg tctttttgct 2520
gatccacccc cctcttacct tttatcagga tgtggcctgt tggtccttct gttgccatca 2580
cagagacaca ggcatttaaa tatttaactt atttatttaa caaagtagaa gggaatccat 2640
tgctagcttt tctgtgttgg tgtctaatat ttgggtaggg tgggggatcc ccaacaatca 2700
ggtcccctga gatagctggt cattgggctg atcattgcca gaatcttctt ctcctggggt 2760 ctggccccccc aaaatgccta acccaggacc ttggaaattc tactcatccc aaatgataat 2820
tccaaatgct gttacccaag gttagggtgt tgaaggaagg tagagggtgg ggcttcaggt 2880
ctcaacggct tccctaacca cccctcttct cttggcccag cctggttccc cccacttcca 2940
ctcccctcta ctctctctag gactgggctg atgaaggcac tgcccaaaat ttcccctacc 3000
cccaactttc ccctaccccc aactttcccc accagctcca caaccctgtt tggagctact 3060
gcaggaccag aagcacaaag tgcggtttcc caagcctttg tccatctcag cccccagagt 3120
atatctgtgc ttggggaatc tcacacagaa actcaggagc accccctgcc tgagctaagg 3180
gaggtcttat ctctcagggg gggtttaagt gccgtttgca ataatgtcgt cttatttatt 3240
tagcggggtg aatattttat actgtaagtg agcaatcaga gtataatgtt tatggtgaca 3300
aaattaaagg ctttcttata tgtttaaaaa aaaaaaaaaa aaaaaaaaaa aaaaaaaaaa 3360
aaaaaaaara aaaaaaaaaa aaaaaaaaaa aaaaaaataa aaaaaaaaaa 3410

<210> SEQ ID NO 111
<211> LENGTH: 1289
<212> TYPE: DNA
<213> ORGANISM: Homo sapien

<400> SEQUENCE: 111
agccaggcgt ccctctgcct gcccactcag tggcaacacc cgggagctgt tttgtccttt 60
gtggagcctc agcagttccc tctttcagaa ctcactgcca agagccctga acaggagcca 120
ccatgcagtg cttcagcttc attaagacca tgatgatcct cttcaatttg ctcatctttc 180
tgtgtggtgc agccctgttg gcagtgggca tctgggtgtc aatcgatggg gcatcctttc 240
tgaagatctt cgggccactg tcgtccagtg ccatgcagtt tgtcaacgtg ggctacttcc 300
tcatcgcagc cggcgttgtg gtctttgctc ttggtttcct gggctgctat ggtgctaaga 360
ctgagagcaa gtgtgccctc gtgacgttct tcttcatcct cctcctcatc ttcattgctg 420
aggttgcagc tgctgtggtc gccttggtgt acaccacaat ggctgagcac ttcctgacgt 480
tgctggtagt gcctgccatc aagaaagatt atggttccca ggaagacttc actcaagtgt 540
ggaacaccac catgaaaggg ctcaagtgct gtggcttcac caactatacg gattttgagg 600
actcacccta cttcaaagag aacagtgcct ttcccccatt ctgttgcaat gacaacgtca 660
ccaacacagc caatgaaacc tgcaccaagc aaaaggctca cgaccaaaaa gtagagggtt 720
gcttcaatca gcttttgtat gacatccgaa ctaatgcagt caccgtgggt ggtgtggcag 780

-continued

```
ctggaattgg gggcctcgag ctggctgcca tgattgtgtc catgtatctg tactgcaatc    840

tacaataagt ccacttctgc ctctgccact actgctgcca catgggaact gtgaagaggc    900

accctggcaa gcagcagtga ttgggggagg ggacaggatc taacaatgtc acttgggcca    960

gaatggacct gccctttctg ctccagactt ggggctagat agggaccact ccttttagcg   1020

atgcctgact ttccttccat tggtgggtgg atgggtgggg ggcattccag agcctctaag   1080

gtagccagtt ctgttgccca ttccccccagt ctattaaacc cttgatatgc cccctaggcc   1140

tagtggtgat cccagtgctc tactggggga tgagagaaag gcattttata gcctgggcat   1200

aagtgaaatc agcagagcct ctgggtggat gtgtagaagg cacttcaaaa tgcataaacc   1260

tgttacaatg ttaaaaaaaa aaaaaaaaa                                     1289
```

```
<210> SEQ ID NO 112
<211> LENGTH: 315
<212> TYPE: PRT
<213> ORGANISM: Homo sapien

<400> SEQUENCE: 112

Met Val Phe Thr Val Arg Leu Leu His Ile Phe Thr Val Asn Lys Gln
 1               5                  10                  15

Leu Gly Pro Lys Ile Val Ile Val Ser Lys Met Met Lys Asp Val Phe
            20                  25                  30

Phe Phe Leu Phe Phe Leu Gly Val Trp Leu Val Ala Tyr Gly Val Ala
        35                  40                  45

Thr Glu Gly Leu Leu Arg Pro Arg Asp Ser Asp Phe Pro Ser Ile Leu
    50                  55                  60

Arg Arg Val Phe Tyr Arg Pro Tyr Leu Gln Ile Phe Gly Gln Ile Pro
65                  70                  75                  80

Gln Glu Asp Met Asp Val Ala Leu Met Glu His Ser Asn Cys Ser Ser
                85                  90                  95

Glu Pro Gly Phe Trp Ala His Pro Pro Gly Ala Gln Ala Gly Thr Cys
            100                 105                 110

Val Ser Gln Tyr Ala Asn Trp Leu Val Val Leu Leu Leu Val Ile Phe
        115                 120                 125

Leu Leu Val Ala Asn Ile Leu Leu Val Asn Leu Leu Ile Ala Met Phe
    130                 135                 140

Ser Tyr Thr Phe Gly Lys Val Gln Gly Asn Ser Asp Leu Tyr Trp Lys
145                 150                 155                 160

Ala Gln Arg Tyr Arg Leu Ile Arg Glu Phe His Ser Arg Pro Ala Leu
                165                 170                 175

Ala Pro Pro Phe Ile Val Ile Ser His Leu Arg Leu Leu Leu Arg Gln
            180                 185                 190

Leu Cys Arg Arg Pro Arg Ser Pro Gln Pro Ser Ser Pro Ala Leu Glu
        195                 200                 205

His Phe Arg Val Tyr Leu Ser Lys Glu Ala Glu Arg Lys Leu Leu Thr
    210                 215                 220

Trp Glu Ser Val His Lys Glu Asn Phe Leu Leu Ala Arg Ala Arg Asp
225                 230                 235                 240

Lys Arg Glu Ser Asp Ser Glu Arg Leu Lys Arg Thr Ser Gln Lys Val
                245                 250                 255

Asp Leu Ala Leu Lys Gln Leu Gly His Ile Arg Glu Tyr Glu Gln Arg
            260                 265                 270

Leu Lys Val Leu Glu Arg Glu Val Gln Gln Cys Ser Arg Val Leu Gly
        275                 280                 285
```

-continued

```
Trp Val Ala Glu Ala Leu Ser Arg Ser Ala Leu Leu Pro Pro Gly Gly
    290                 295                 300

Pro Pro Pro Pro Asp Leu Pro Gly Ser Lys Asp
305                 310                 315


<210> SEQ ID NO 113
<211> LENGTH: 553
<212> TYPE: PRT
<213> ORGANISM: Homo sapien

<400> SEQUENCE: 113

Met Val Gln Arg Leu Trp Val Ser Arg Leu Leu Arg His Arg Lys Ala
 1               5                  10                  15

Gln Leu Leu Leu Val Asn Leu Leu Thr Phe Gly Leu Glu Val Cys Leu
            20                  25                  30

Ala Ala Gly Ile Thr Tyr Val Pro Pro Leu Leu Leu Glu Val Gly Val
        35                  40                  45

Glu Glu Lys Phe Met Thr Met Val Leu Gly Ile Gly Pro Val Leu Gly
    50                  55                  60

Leu Val Cys Val Pro Leu Leu Gly Ser Ala Ser Asp His Trp Arg Gly
65                  70                  75                  80

Arg Tyr Gly Arg Arg Arg Pro Phe Ile Trp Ala Leu Ser Leu Gly Ile
                85                  90                  95

Leu Leu Ser Leu Phe Leu Ile Pro Arg Ala Gly Trp Leu Ala Gly Leu
            100                 105                 110

Leu Cys Pro Asp Pro Arg Pro Leu Glu Leu Ala Leu Leu Ile Leu Gly
        115                 120                 125

Val Gly Leu Leu Asp Phe Cys Gly Gln Val Cys Phe Thr Pro Leu Glu
    130                 135                 140

Ala Leu Leu Ser Asp Leu Phe Arg Asp Pro Asp His Cys Arg Gln Ala
145                 150                 155                 160

Tyr Ser Val Tyr Ala Phe Met Ile Ser Leu Gly Gly Cys Leu Gly Tyr
                165                 170                 175

Leu Leu Pro Ala Ile Asp Trp Asp Thr Ser Ala Leu Ala Pro Tyr Leu
            180                 185                 190

Gly Thr Gln Glu Glu Cys Leu Phe Gly Leu Leu Thr Leu Ile Phe Leu
        195                 200                 205

Thr Cys Val Ala Ala Thr Leu Leu Val Ala Glu Glu Ala Ala Leu Gly
    210                 215                 220

Pro Thr Glu Pro Ala Glu Gly Leu Ser Ala Pro Ser Leu Ser Pro His
225                 230                 235                 240

Cys Cys Pro Cys Arg Ala Arg Leu Ala Phe Arg Asn Leu Gly Ala Leu
                245                 250                 255

Leu Pro Arg Leu His Gln Leu Cys Cys Arg Met Pro Arg Thr Leu Arg
            260                 265                 270

Arg Leu Phe Val Ala Glu Leu Cys Ser Trp Met Ala Leu Met Thr Phe
        275                 280                 285

Thr Leu Phe Tyr Thr Asp Phe Val Gly Glu Gly Leu Tyr Gln Gly Val
    290                 295                 300

Pro Arg Ala Glu Pro Gly Thr Glu Ala Arg Arg His Tyr Asp Glu Gly
305                 310                 315                 320

Val Arg Met Gly Ser Leu Gly Leu Phe Leu Gln Cys Ala Ile Ser Leu
                325                 330                 335

Val Phe Ser Leu Val Met Asp Arg Leu Val Gln Arg Phe Gly Thr Arg
```

-continued

```
        340                 345                 350

Ala Val Tyr Leu Ala Ser Val Ala Ala Phe Pro Val Ala Ala Gly Ala
            355                 360                 365

Thr Cys Leu Ser His Ser Val Ala Val Val Thr Ala Ser Ala Ala Leu
    370                 375                 380

Thr Gly Phe Thr Phe Ser Ala Leu Gln Ile Leu Pro Tyr Thr Leu Ala
385                 390                 395                 400

Ser Leu Tyr His Arg Glu Lys Gln Val Phe Leu Pro Lys Tyr Arg Gly
                405                 410                 415

Asp Thr Gly Gly Ala Ser Ser Glu Asp Ser Leu Met Thr Ser Phe Leu
            420                 425                 430

Pro Gly Pro Lys Pro Gly Ala Pro Phe Pro Asn Gly His Val Gly Ala
        435                 440                 445

Gly Gly Ser Gly Leu Leu Pro Pro Pro Pro Ala Leu Cys Gly Ala Ser
    450                 455                 460

Ala Cys Asp Val Ser Val Arg Val Val Val Gly Glu Pro Thr Glu Ala
465                 470                 475                 480

Arg Val Val Pro Gly Arg Gly Ile Cys Leu Asp Leu Ala Ile Leu Asp
                485                 490                 495

Ser Ala Phe Leu Leu Ser Gln Val Ala Pro Ser Leu Phe Met Gly Ser
            500                 505                 510

Ile Val Gln Leu Ser Gln Ser Val Thr Ala Tyr Met Val Ser Ala Ala
        515                 520                 525

Gly Leu Gly Leu Val Ala Ile Tyr Phe Ala Thr Gln Val Val Phe Asp
    530                 535                 540

Lys Ser Asp Leu Ala Lys Tyr Ser Ala
545                 550


<210> SEQ ID NO 114
<211> LENGTH: 241
<212> TYPE: PRT
<213> ORGANISM: Homo sapien

<400> SEQUENCE: 114

Met Gln Cys Phe Ser Phe Ile Lys Thr Met Met Ile Leu Phe Asn Leu
 1               5                  10                  15

Leu Ile Phe Leu Cys Gly Ala Ala Leu Leu Ala Val Gly Ile Trp Val
            20                  25                  30

Ser Ile Asp Gly Ala Ser Phe Leu Lys Ile Phe Gly Pro Leu Ser Ser
        35                  40                  45

Ser Ala Met Gln Phe Val Asn Val Gly Tyr Phe Leu Ile Ala Ala Gly
    50                  55                  60

Val Val Val Phe Ala Leu Gly Phe Leu Gly Cys Tyr Gly Ala Lys Thr
65                  70                  75                  80

Glu Ser Lys Cys Ala Leu Val Thr Phe Phe Phe Ile Leu Leu Leu Ile
                85                  90                  95

Phe Ile Ala Glu Val Ala Ala Ala Val Val Ala Leu Val Tyr Thr Thr
            100                 105                 110

Met Ala Glu His Phe Leu Thr Leu Leu Val Val Pro Ala Ile Lys Lys
        115                 120                 125

Asp Tyr Gly Ser Gln Glu Asp Phe Thr Gln Val Trp Asn Thr Thr Met
    130                 135                 140

Lys Gly Leu Lys Cys Cys Gly Phe Thr Asn Tyr Thr Asp Phe Glu Asp
145                 150                 155                 160
```

-continued

```
Ser Pro Tyr Phe Lys Glu Asn Ser Ala Phe Pro Pro Phe Cys Cys Asn
                165                 170                 175

Asp Asn Val Thr Asn Thr Ala Asn Glu Thr Cys Thr Lys Gln Lys Ala
            180                 185                 190

His Asp Gln Lys Val Glu Gly Cys Phe Asn Gln Leu Leu Tyr Asp Ile
        195                 200                 205

Arg Thr Asn Ala Val Thr Val Gly Gly Val Ala Ala Gly Ile Gly Gly
    210                 215                 220

Leu Glu Leu Ala Ala Met Ile Val Ser Met Tyr Leu Tyr Cys Asn Leu
225                 230                 235                 240

Gln
```

<210> SEQ ID NO 115
<211> LENGTH: 366
<212> TYPE: DNA
<213> ORGANISM: Homo sapien

<400> SEQUENCE: 115

```
gctctttctc tcccctcctc tgaatttaat tctttcaact tgcaatttgc aaggattaca     60

catttcactg tgatgtatat tgtgttgcaa aaaaaaaaaa gtgtctttgt ttaaaattac    120

ttggtttgtg aatccatctt gctttttccc cattggaact agtcattaac ccatctctga    180

actggtagaa aaacatctga agagctagtc tatcagcatc tgacaggtga attggatggt    240

tctcagaacc atttcaccca gacagcctgt ttctatcctg tttaataaat tagtttgggt    300

tctctacatg cataacaaac cctgctccaa tctgtcacat aaaagtctgt gacttgaagt    360

ttagtc                                                               366
```

<210> SEQ ID NO 116
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 116

```
acaaagatga accatttcct atattatagc aaaattaaaa tctacccgta ttctaatatt     60

gagaaatgag atnaaacaca atnttataaa gtctacttag agaagatcaa gtgacctcaa    120

agactttact attttcatat tttaagacac atgatttatc ctattttagt aacctggttc    180

atacgttaaa caaaggataa tgtgaacagc agagaggatt tgttggcaga aaatctatgt    240

tcaatctnga actatctana tcacagacat ttctattcct tt                       282
```

<210> SEQ ID NO 117
<211> LENGTH: 305
<212> TYPE: DNA
<213> ORGANISM: Homo sapien
<220> FEATURE:
<221> NAME/KEY: misc_feature
<222> LOCATION: (1)...(305)
<223> OTHER INFORMATION: n = A,T,C or G

<400> SEQUENCE: 117

```
acacatgtcg cttcactgcc ttcttagatg cttctggtca acatanagga acagggacca     60

tatttatcct ccctcctgaa acaattgcaa aataanacaa aatatatgaa acaattgcaa    120

aataaggcaa aatatatgaa acaacaggtc tcgagatatt ggaaatcagt caatgaagga    180
```

-continued

```
tactgatccc tgatcactgt cctaatgcag gatgtgggaa acagatgagg tcacctctgt    240

gactgcccca gcttactgcc tgtagagagt ttctangctg cagttcagac agggagaaat    300

tgggt                                                                305


<210> SEQ ID NO 118
<211> LENGTH: 71
<212> TYPE: DNA
<213> ORGANISM: Homo sapien
<220> FEATURE:
<221> NAME/KEY: misc_feature
<222> LOCATION: (1)...(71)
<223> OTHER INFORMATION: n = A,T,C or G

<400> SEQUENCE: 118

accaaggtgt ntgaatctct gacgtgggga tctctgattc ccgcacaatc tgagtggaaa     60

aantcctggg t                                                          71


<210> SEQ ID NO 119
<211> LENGTH: 212
<212> TYPE: DNA
<213> ORGANISM: Homo sapien
<220> FEATURE:
<221> NAME/KEY: misc_feature
<222> LOCATION: (1)...(212)
<223> OTHER INFORMATION: n = A,T,C or G

<400> SEQUENCE: 119

actccggttg gtgtcagcag cacgtggcat tgaacatngc aatgtggagc ccaaaccaca     60

gaaaatgggg tgaaattggc caactttcta tnaacttatg ttggcaantt tgccaccaac    120

agtaagctgg cccttctaat aaaagaaaat tgaaaggttt ctcactaanc ggaattaant    180

aatggantca aganactccc aggcctcagc gt                                  212


<210> SEQ ID NO 120
<211> LENGTH: 90
<212> TYPE: DNA
<213> ORGANISM: Homo sapien
<220> FEATURE:
<221> NAME/KEY: misc_feature
<222> LOCATION: (1)...(90)
<223> OTHER INFORMATION: n = A,T,C or G

<400> SEQUENCE: 120

actcgttgca natcaggggc cccccagagt caccgttgca ggagtccttc tggtcttgcc     60

ctccgccggc gcagaacatg ctggggtggt                                      90


<210> SEQ ID NO 121
<211> LENGTH: 218
<212> TYPE: DNA
<213> ORGANISM: Homo sapien
<220> FEATURE:
<221> NAME/KEY: misc_feature
<222> LOCATION: (1)...(218)
<223> OTHER INFORMATION: n = A,T,C or G

<400> SEQUENCE: 121

tgtancgtga anacgacaga nagggttgtc aaaaatggag aanccttgaa gtcattttga     60

gaataagatt tgctaaaaga tttggggcta aaacatggtt attgggagac atttctgaag    120

atatncangt aaattangga atgaattcat ggttcttttg ggaattcctt tacgatngcc    180

agcatanact tcatgtgggg atancagcta cccttgta                            218
```

-continued

<210> SEQ ID NO 122
<211> LENGTH: 171
<212> TYPE: DNA
<213> ORGANISM: Homo sapien

<400> SEQUENCE: 122
taggggtgta tgcaactgta aggacaaaaa ttgagactca actggcttaa ccaataaagg 60
catttgttag ctcatggaac aggaagtcgg atggtggggc atcttcagtg ctgcatgagt 120
caccaccccg gcggggtcat ctgtgccaca ggtccctgtt gacagtgcgg t 171

<210> SEQ ID NO 123
<211> LENGTH: 76
<212> TYPE: DNA
<213> ORGANISM: Homo sapien
<220> FEATURE:
<221> NAME/KEY: misc_feature
<222> LOCATION: (1)...(76)
<223> OTHER INFORMATION: n = A,T,C or G

<400> SEQUENCE: 123
tgtagcgtga agacnacaga atggtgtgtg ctgtgctatc caggaacaca tttattatca 60
ttatcaanta ttgtgt 76

<210> SEQ ID NO 124
<211> LENGTH: 131
<212> TYPE: DNA
<213> ORGANISM: Homo sapien

<400> SEQUENCE: 124
acctttcccc aaggccaatg tcctgtgtgc taactggccg gctgcaggac agctgcaatt 60
caatgtgctg ggtcatatgg aggggaggag actctaaaat agccaatttt attctcttgg 120
ttaagatttg t 131

<210> SEQ ID NO 125
<211> LENGTH: 432
<212> TYPE: DNA
<213> ORGANISM: Homo sapien

<400> SEQUENCE: 125
actttatcta ctggctatga aatagatggt ggaaaattgc gttaccaact ataccactgg 60
cttgaaaaag aggtgatagc tcttcagagg acttgtgact tttgctcaga tgctgaagaa 120
ctacagtctg catttggcag aaatgaagat gaatttggat taaatgagga tgctgaagat 180
ttgcctcacc aaacaaaagt gaaacaactg agagaaaatt ttcaggaaaa aagacagtgg 240
ctcttgaagt atcagtcact tttgagaatg tttcttagtt actgcatact tcatggatcc 300
catggtgggg gtcttgcatc tgtaagaatg gaattgattt tgcttttgca agaatctcag 360
caggaaacat cagaaccact attttctagc cctctgtcag agcaaacctc agtgcctctc 420
ctctttgctt gt 432

<210> SEQ ID NO 126
<211> LENGTH: 112
<212> TYPE: DNA
<213> ORGANISM: Homo sapien

<400> SEQUENCE: 126
acacaacttg aatagtaaaa tagaaactga gctgaaattt ctaattcact ttctaaccat 60
agtaagaatg atatttcccc ccagggatca ccaaatattt ataaaaattt gt 112

-continued

<210> SEQ ID NO 127
<211> LENGTH: 54
<212> TYPE: DNA
<213> ORGANISM: Homo sapien

<400> SEQUENCE: 127
accacgaaac cacaaacaag atggaagcat caatccactt gccaagcaca gcag 54

<210> SEQ ID NO 128
<211> LENGTH: 323
<212> TYPE: DNA
<213> ORGANISM: Homo sapien

<400> SEQUENCE: 128
acctcattag taattgtttt gttgtttcat ttttttctaa tgtctcccct ctaccagctc 60
acctgagata acagaatgaa aatggaagga cagccagatt tctcctttgc tctctgctca 120
ttctctctga agtctaggtt acccattttg gggacccatt ataggcaata aacacagttc 180
ccaaagcatt tggacagttt cttgttgtgt tttagaatgg ttttcctttt tcttagcctt 240
ttcctgcaaa aggctcactc agtcccttgc ttgctcagtg gactgggctc cccagggcct 300
aggctgcctt cttttccatg tcc 323

<210> SEQ ID NO 129
<211> LENGTH: 192
<212> TYPE: DNA
<213> ORGANISM: Homo sapien
<220> FEATURE:
<221> NAME/KEY: misc_feature
<222> LOCATION: (1)...(192)
<223> OTHER INFORMATION: n = A,T,C or G

<400> SEQUENCE: 129
acatacatgt gtgtatattt ttaaatatca cttttgtatc actctgactt tttagcatac 60
tgaaaacaca ctaacataat ttntgtgaac catgatcaga tacaacccaa atcattcatc 120
tagcacattc atctgtgata naaagatagg tgagtttcat ttccttcacg ttggccaatg 180
gataaacaaa gt 192

<210> SEQ ID NO 130
<211> LENGTH: 362
<212> TYPE: DNA
<213> ORGANISM: Homo sapien
<220> FEATURE:
<221> NAME/KEY: misc_feature
<222> LOCATION: (1)...(362)
<223> OTHER INFORMATION: n = A,T,C or G

<400> SEQUENCE: 130 cccttttta tggaatgagt agactgtatg tttgaanatt tanccacaac ctctttgaca 60
tataatgacg caacaaaaag gtgctgttta gtcctatggt tcagtttatg cccctgacaa 120
gtttccattg tgttttgccg atcttctggc taatcgtggt atcctccatg ttattagtaa 180
ttctgtattc cattttgtta acgcctggta gatgtaacct gctangaggc taactttata 240
cttatttaaa agctcttatt ttgtggtcat taaaatggca atttatgtgc agcactttat 300
tgcagcagga agcacgtgtg ggttggttgt aaagctcttt gctaatctta aaaagtaatg 360
gg 362

<210> SEQ ID NO 131
<211> LENGTH: 332

-continued

<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 131

```
cttttttgaaa gatcgtgtcc actcctgtgg acatcttgtt ttaatggagt ttcccatgca     60

gtangactgg tatggttgca gctgtccaga taaaaacatt tgaagagctc caaaatgaga    120

gttctcccag gttcgccctg ctgctccaag tctcagcagc agcctctttt aggaggcatc    180

ttctgaacta gattaaggca gcttgtaaat ctgatgtgat ttggtttatt atccaactaa    240

cttccatctg ttatcactgg agaaagccca gactccccan gacnggtacg gattgtgggc    300

atanaaggat tgggtgaagc tggcgttgtg gt                                  332
```

<210> SEQ ID NO 132
<211> LENGTH: 322
<212> TYPE: DNA
<213> ORGANISM: Homo sapien
<220> FEATURE:
<221> NAME/KEY: misc_feature
<222> LOCATION: (1)...(322)
<223> OTHER INFORMATION: n = A,T,C or G

<400> SEQUENCE: 132

```
acttttgcca ttttgtatat ataaacaatc ttgggacatt ctcctgaaaa ctaggtgtcc     60

agtggctaag agaactcgat ttcaagcaat tctgaaagga aaaccagcat gacacagaat    120

ctcaaattcc caaacagggg ctctgtggga aaaatgaggg aggacctttg tatctcgggt    180

tttagcaagt taaaatgaan atgacaggaa aggcttattt atcaacaaag agaagagttg    240

ggatgcttct aaaaaaaact ttggtagaga aaataggaat gctnaatcct agggaagcct    300

gtaacaatct acaattggtc ca                                             322
```

<210> SEQ ID NO 133
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 133

```
acaagccttc acaagtttaa ctaaattggg attaatcttt ctgtanttat ctgcataatt     60

cttgtttttc tttccatctg gctcctgggt tgacaatttg tggaaacaac tctattgcta    120

ctatttaaaa aaaatcacaa atctttccct ttaagctatg ttnaattcaa actattcctg    180

ctattcctgt tttgtcaaag aaattatatt tttcaaaata tgtntatttg tttgatgggt    240

cccacgaaac actaataaaa accacagaga ccagcctg                            278
```

<210> SEQ ID NO 134
<211> LENGTH: 121
<212> TYPE: DNA
<213> ORGANISM: Homo sapien
<220> FEATURE:
<221> NAME/KEY: misc_feature
<222> LOCATION: (1)...(121)
<223> OTHER INFORMATION: n = A,T,C or G

<400> SEQUENCE: 134

-continued

```
gtttanaaaa cttgtttagc tccatagagg aaagaatgtt aaactttgta ttttaaaaca     60

tgattctctg aggttaaact tggttttcaa atgttatttt tacttgtatt ttgcttttgg    120

t                                                                    121
```

<210> SEQ ID NO 135
<211> LENGTH: 350
<212> TYPE: DNA
<213> ORGANISM: Homo sapien
<220> FEATURE:
<221> NAME/KEY: misc_feature
<222> LOCATION: (1)...(350)
<223> OTHER INFORMATION: n = A,T,C or G

<400> SEQUENCE: 135

```
acttanaacc atgcctagca catcagaatc cctcaaagaa catcagtata atcctatacc     60

atancaagtg gtgactggtt aagcgtgcga caaaggtcag ctggcacatt acttgtgtgc    120

aaacttgata cttttgttct aagtaggaac tagtatacag tncctaggan tggtactcca    180

gggtgccccc caactcctgc agccgctcct ctgtgccagn ccctgnaagg aactttcgct    240

ccacctcaat caagccctgg gccatgctac ctgcaattgg ctgaacaaac gtttgctgag    300

ttcccaagga tgcaaagcct ggtgctcaac tcctggggcg tcaactcagt               350
```

<210> SEQ ID NO 136
<211> LENGTH: 399
<212> TYPE: DNA
<213> ORGANISM: Homo sapien
<220> FEATURE:
<221> NAME/KEY: misc_feature
<222> LOCATION: (1)...(399)
<223> OTHER INFORMATION: n = A,T,C or G

<400> SEQUENCE: 136

```
tgtaccgtga agacgacaga agttgcatgg cagggacagg gcagggccga ggccagggtt     60

gctgtgattg tatccgaata ntcctcgtga gaaaagataa tgagatgacg tgagcagcct    120

gcagacttgt gtctgccttc aanaagccag acaggaaggc cctgcctgcc ttggctctga    180

cctggcggcc agccagccag ccacaggtgg gcttcttcct tttgtggtga caacnccaag    240

aaaactgcag aggcccaggg tcaggtgtna gtgggtangt gaccataaaa caccaggtgc    300

tcccaggaac ccgggcaaag gccatcccca cctacagcca gcatgcccac tggcgtgatg    360

ggtgcagang gatgaagcag ccagntgttc tgctgtggt                           399
```

<210> SEQ ID NO 137
<211> LENGTH: 165
<212> TYPE: DNA
<213> ORGANISM: Homo sapien
<220> FEATURE:
<221> NAME/KEY: misc_feature
<222> LOCATION: (1)...(165)
<223> OTHER INFORMATION: n = A,T,C or G

<400> SEQUENCE: 137

```
actggtgtgg tnggggggtga tgctggtggt anaagttgan gtgacttcan gatggtgtgt    60

ggaggaagtg tgtgaacgta gggatgtaga ngttttggcc gtgctaaatg agcttcggga    120

ttggctggtc ccactggtgg tcactgtcat tggtggggtt cctgt                    165
```

<210> SEQ ID NO 138
<211> LENGTH: 338
<212> TYPE: DNA
<213> ORGANISM: Homo sapien
<220> FEATURE:
<221> NAME/KEY: misc_feature
<222> LOCATION: (1)...(338)
<223> OTHER INFORMATION: n = A,T,C or G

<400> SEQUENCE: 138

```
actcactgga atgccacatt cacaacagaa tcagaggtct gtgaaaacat taatggctcc     60

ttaacttctc cagtaagaat cagggacttg aaatggaaac gttaacagcc acatgcccaa    120

tgctgggcag tctcccatgc cttccacagt gaaagggctt gagaaaaatc acatccaatg    180

tcatgtgttt ccagccacac caaaaggtgc ttggggtgga gggctggggg catananggt    240

cangcctcag gaagcctcaa gttccattca gctttgccac tgtacattcc ccatntttaa    300

aaaaactgat gccttttttt tttttttttg taaaattc                            338
```

<210> SEQ ID NO 139
<211> LENGTH: 382
<212> TYPE: DNA
<213> ORGANISM: Homo sapien

<400> SEQUENCE: 139

```
gggaatcttg gtttttggca tctggtttgc ctatagccga ggccactttg acagaacaaa     60

gaaagggact tcgagtaaga aggtgattta cagccagcct agtgcccgaa gtgaaggaga    120

attcaaacag acctcgtcat tcctggtgtg agcctggtcg gctcaccgcc tatcatctgc    180

atttgcctta ctcaggtgct accggactct ggcccctgat gtctgtagtt tcacaggatg    240

ccttatttgt cttctacacc ccacagggcc ccctacttct tcggatgtgt ttttaataat    300

gtcagctatg tgccccatcc tccttcatgc cctccctccc tttcctacca ctgctgagtg    360

gcctggaact tgtttaaagt gt                                             382
```

<210> SEQ ID NO 140
<211> LENGTH: 200
<212> TYPE: DNA
<213> ORGANISM: Homo sapien
<220> FEATURE:
<221> NAME/KEY: misc_feature
<222> LOCATION: (1)...(200)
<223> OTHER INFORMATION: n = A,T,C or G

<400> SEQUENCE: 140

```
accaaanctt ctttctgttg tgttngattt tactataggg gtttngcttn ttctaaanat     60

acttttcatt taacancttt tgttaagtgt caggctgcac tttgctccat anaattattg    120

ttttcacatt tcaacttgta tgtgtttgtc tcttanagca ttggtgaaat cacatatttt    180

atattcagca taaaggagaa                                                200
```

<210> SEQ ID NO 141
<211> LENGTH: 335
<212> TYPE: DNA
<213> ORGANISM: Homo sapien
<220> FEATURE:
<221> NAME/KEY: misc_feature
<222> LOCATION: (1)...(335)
<223> OTHER INFORMATION: n = A,T,C or G

<400> SEQUENCE: 141

```
actttatttt caaaacactc atatgttgca aaaaacacat agaaaaataa agtttggtgg     60

gggtgctgac taaacttcaa gtcacagact tttatgtgac agattggagc agggtttgtt    120

atgcatgtag agaacccaaa ctaatttatt aaacaggata gaaacaggct gtctgggtga    180
```

-continued

```
aatggttctg agaaccatcc aattcacctg tcagatgctg atanactagc tcttcagatg    240

tttttctacc agttcagaga tnggttaatg actanttcca atggggaaaa agcaagatgg    300

attcacaaac caagtaattt taaacaaaga cactt                               335


<210> SEQ ID NO 142
<211> LENGTH: 459
<212> TYPE: DNA
<213> ORGANISM: Homo sapien
<220> FEATURE:
<221> NAME/KEY: misc_feature
<222> LOCATION: (1)...(459)
<223> OTHER INFORMATION: n = A,T,C or G

<400> SEQUENCE: 142

accaggttaa tattgccaca tatatccttt ccaattgcgg gctaaacaga cgtgtattta     60

gggttgttta aagacaaccc agcttaatat caagagaaat tgtgaccttt catggagtat    120

ctgatggaga aaacactgag ttttgacaaa tcttatttta ttcagatagc agtctgatca    180

cacatggtcc aacaacactc aaataataaa tcaaatatna tcagatgtta aagattggtc    240

ttcaaacatc atagccaatg atgccccgct tgcctataat ctctccgaca taaaaccaca    300

tcaacacctc agtggccacc aaaccattca gcacagcttc cttaactgtg agctgtttga    360

agctaccagt ctgagcacta ttgactatnt ttttcangct ctgaatagct ctagggatct    420

cagcangggt gggaggaacc agctcaacct tggcgtant                           459


<210> SEQ ID NO 143
<211> LENGTH: 140
<212> TYPE: DNA
<213> ORGANISM: Homo sapien

<400> SEQUENCE: 143

acatttcctt ccaccaagtc aggactcctg gcttctgtgg gagttcttat cacctgaggg     60

aaatccaaac agtctctcct agaaaggaat agtgtcacca accccaccca tctccctgag    120

accatccgac ttccctgtgt                                                140


<210> SEQ ID NO 144
<211> LENGTH: 164
<212> TYPE: DNA
<213> ORGANISM: Homo sapien
<220> FEATURE:
<221> NAME/KEY: misc_feature
<222> LOCATION: (1)...(164)
<223> OTHER INFORMATION: n = A,T,C or G

<400> SEQUENCE: 144

acttcagtaa caacatacaa taacaacatt aagtgtatat tgccatcttt gtcattttct     60

atctatacca ctctcccttc tgaaaacaan aatcactanc caatcactta tacaaatttg    120

aggcaattaa tccatatttg ttttcaataa ggaaaaaaag atgt                     164


<210> SEQ ID NO 145
<211> LENGTH: 303
<212> TYPE: DNA
<213> ORGANISM: Homo sapien
<220> FEATURE:
<221> NAME/KEY: misc_feature
<222> LOCATION: (1)...(303)
<223> OTHER INFORMATION: n = A,T,C or G

<400> SEQUENCE: 145

acgtagacca tccaactttg tatttgtaat ggcaaacatc cagnagcaat tcctaaacaa     60
```

-continued

```
actggagggt atttataccc aattatccca ttcattaaca tgccctcctc ctcaggctat    120

gcaggacagc tatcataagt cggcccaggc atccagatac taccatttgt ataaacttca    180

gtaggggagt ccatccaagt gacaggtcta atcaaaggag gaaatggaac ataagcccag    240

tagtaaaatn ttgcttagct gaaacagcca caaaagactt accgccgtgg tgattaccat    300

caa                                                                  303
```

<210> SEQ ID NO 146
<211> LENGTH: 327
<212> TYPE: DNA
<213> ORGANISM: Homo sapien
<220> FEATURE:
<221> NAME/KEY: misc_feature
<222> LOCATION: (1)...(327)
<223> OTHER INFORMATION: n = A,T,C or G

<400> SEQUENCE: 146

```
actgcagctc aattagaagt ggtctctgac tttcatcanc ttctccctgg gctccatgac     60

actggcctgg agtgactcat tgctctggtt ggttgagaga gctcctttgc caacaggcct    120

ccaagtcagg gctgggattt gtttcctttc cacattctag caacaatatg ctggccactt    180

cctgaacagg gagggtggga ggagccagca tggaacaagc tgccactttc taaagtagcc    240

agacttgccc ctgggcctgt cacacctact gatgaccttc tgtgcctgca ggatggaatg    300

taggggtgag ctgtgtgact ctatggt                                        327
```

<210> SEQ ID NO 147
<211> LENGTH: 173
<212> TYPE: DNA
<213> ORGANISM: Homo sapien
<220> FEATURE:
<221> NAME/KEY: misc_feature
<222> LOCATION: (1)...(173)
<223> OTHER INFORMATION: n = A,T,C or G

<400> SEQUENCE: 147

```
acattgtttt tttgagataa agcattgana gagctctcct taacgtgaca caatggaagg     60

actggaacac atacccacat ctttgttctg agggataatt ttctgataaa gtcttgctgt    120

atattcaagc acatatgtta tatattattc agttccatgt ttatagccta gtt           173
```

<210> SEQ ID NO 148
<211> LENGTH: 477
<212> TYPE: DNA
<213> ORGANISM: Homo sapien
<220> FEATURE:
<221> NAME/KEY: misc_feature
<222> LOCATION: (1)...(477)
<223> OTHER INFORMATION: n = A,T,C or G

<400> SEQUENCE: 148

```
acaaccactt tatctcatcg aatttttaac ccaaactcac tcactgtgcc tttctatcct     60

atgggatata ttatttgatg ctccatttca tcacacatat atgaataata cactcatact    120

gccctactac ctgctgcaat aatcacattc ccttcctgtc ctgaccctga agccattggg    180

gtggtcctag tggccatcag tccangcctg caccttgagc ccttgagctc cattgctcac    240

nccancccac ctcaccgacc ccatcctctt acacagctac ctccttgctc tctaacccca    300

tagattatnt ccaaattcag tcaattaagt tactattaac actctacccg acatgtccag    360

caccactggt aagccttctc cagccaacac acacacacac acacncacac acacacatat    420
```

```
ccaggcacag gctacctcat cttcacaatc acccctttaa ttaccatgct atggtgg        477

<210> SEQ ID NO 149
<211> LENGTH: 207
<212> TYPE: DNA
<213> ORGANISM: Homo sapien

<400> SEQUENCE: 149

acagttgtat tataatatca agaaataaac ttgcaatgag agcatttaag agggaagaac      60

taacgtattt tagagagcca aggaaggttt ctgtggggag tgggatgtaa ggtggggcct     120

gatgataaat aagagtcagc caggtaagtg ggtggtgtgg tatgggcaca gtgaagaaca    180

tttcaggcag agggaacagc agtgaaa                                         207

<210> SEQ ID NO 150
<211> LENGTH: 111
<212> TYPE: DNA
<213> ORGANISM: Homo sapien
<220> FEATURE:
<221> NAME/KEY: misc_feature
<222> LOCATION: (1)...(111)
<223> OTHER INFORMATION: n = A,T,C or G

<400> SEQUENCE: 150

accttgattt cattgctgct ctgatggaaa cccaactatc taatttagct aaaacatggg      60

cacttaaatg tggtcagtgt ttggacttgt taactantgg catctttggg t              111

<210> SEQ ID NO 151
<211> LENGTH: 196
<212> TYPE: DNA
<213> ORGANISM: Homo sapien

<400> SEQUENCE: 151

agcgcggcag gtcatattga acattccaga tacctatcat tactcgatgc tgttgataac      60

agcaagatgg ctttgaactc agggtcacca ccagctattg gaccttacta tgaaaaccat    120

ggataccaac cggaaaaccc ctatcccgca cagcccactg tggtccccac tgtctacgag    180

gtgcatccgg ctcagt                                                     196

<210> SEQ ID NO 152
<211> LENGTH: 132
<212> TYPE: DNA
<213> ORGANISM: Homo sapien

<400> SEQUENCE: 152

acagcacttt cacatgtaag aagggagaaa ttcctaaatg taggagaaag ataacagaac      60

cttccccttt tcatctagtg gtggaaacct gatgctttat gttgacagga atagaaccag    120

gagggagttt gt                                                         132

<210> SEQ ID NO 153
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 153

acaanaccca nganaggcca ctggccgtgg tgtcatggcc tccaaacatg aaagtgtcag      60

cttctgctct tatgtcctca tctgacaact ctttaccatt tttatcctcg ctcagcagga    120
```

-continued gcacatcaat aaagtccaaa gtcttggact tggccttggc ttggaggaag tcatcaacac 180
cctggctagt gagggtgcgg cgccgctcct ggatgacggc atctgtgaag tcgtgcacca 240
gtctgcaggc cctgtggaag cgccgtccac acggagtnag gaatt 285

<210> SEQ ID NO 154
<211> LENGTH: 333
<212> TYPE: DNA
<213> ORGANISM: Homo sapien

<400> SEQUENCE: 154
accacagtcc tgttgggcca gggcttcatg accctttctg tgaaaagcca tattatcacc 60
accccaaatt tttccttaaa tatctttaac tgaaggggtc agcctcttga ctgcaaagac 120
cctaagccgg ttacacagct aactcccact ggccctgatt tgtgaaattg ctgctgcctg 180
attggcacag gagtcgaagg tgttcagctc ccctcctccg tggaacgaga ctctgatttg 240
agtttcacaa attctcgggc cacctcgtca ttgctcctct gaaataaaat ccggagaatg 300
gtcaggcctg tctcatccat atggatcttc cgg 333

<210> SEQ ID NO 155
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 155
actggaaata ataaaaccca catcacagtg ttgtgtcaaa gatcatcagg gcatggatgg 60
gaaagtgctt tgggaactgt aaagtgccta acacatgatc gatgattttt gttataatat 120
ttgaatcacg gtgcatacaa actctcctgc ctgctcctcc tgggccccag ccccagcccc 180
atcacagctc actgctctgt tcatccaggc ccagcatgta gtggctgatt cttcttggct 240
gcttttagcc tccanaagtt tctctgaagc caaccaaacc tctangtgta aggcatgctg 300
gccctggt 308

<210> SEQ ID NO 156
<211> LENGTH: 295
<212> TYPE: DNA
<213> ORGANISM: Homo sapien

<400> SEQUENCE: 156
accttgctcg gtgcttggaa catattagga actcaaaata tgagatgata acagtgccta 60
ttattgatta ctgagagaac tgttagacat ttagttgaag attttctaca caggaactga 120
gaataggaga ttatgtttgg ccctcatatt ctctcctatc ctccttgcct cattctatgt 180
ctaatatatt ctcaatcaaa taaggttagc ataatcagga aatcgaccaa ataccaatat 240
aaaaccagat gtctatcctt aagattttca aatagaaaac aaattaacag actat 295

<210> SEQ ID NO 157
<211> LENGTH: 126
<212> TYPE: DNA
<213> ORGANISM: Homo sapien

<400> SEQUENCE: 157
acaagtttaa atagtgctgt cactgtgcat gtgctgaaat gtgaaatcca ccacatttct 60
gaagagcaaa acaaattctg tcatgtaatc tctatcttgg gtcgtgggta tatctgtccc 120
cttagt 126

<210> SEQ ID NO 158
<211> LENGTH: 442
<212> TYPE: DNA
<213> ORGANISM: Homo sapien
<220> FEATURE:
<221> NAME/KEY: misc_feature
<222> LOCATION: (1)...(442)
<223> OTHER INFORMATION: n = A,T,C or G

<400> SEQUENCE: 158
acccactggt cttggaaaca cccatcctta atacgatgat ttttctgtcg tgtgaaaatg 60
aanccagcag gctgccccta gtcagtcctt ccttccagag aaaaagagat ttgagaaagt 120
gcctgggtaa ttcaccatta atttcctccc ccaaactctc tgagtcttcc cttaatattt 180
ctggtggttc tgaccaaagc aggtcatggt ttgttgagca tttgggatcc cagtgaagta 240
natgtttgta gccttgcata cttagccctt cccacgcaca aacggagtgg cagagtggtg 300
ccaaccctgt tttcccagtc cacgtagaca gattcacagt gcggaattct ggaagctgga 360
nacagacggg ctctttgcag agccgggact ctgagangga catgagggcc tctgcctctg 420
tgttcattct ctgatgtcct gt 442

<210> SEQ ID NO 159
<211> LENGTH: 498
<212> TYPE: DNA
<213> ORGANISM: Homo sapien
<220> FEATURE:
<221> NAME/KEY: misc_feature
<222> LOCATION: (1)...(498)
<223> OTHER INFORMATION: n = A,T,C or G

<400> SEQUENCE: 159
acttccaggt aacgttgttg tttccgttga gcctgaactg atgggtgacg ttgtaggttc 60
tccaacaaga actgaggttg cagagcgggt agggaagagt gctgttccag ttgcacctgg 120
gctgctgtgg actgttgttg attcctcact acggcccaag gttgtggaac tggcanaaag 180
gtgtgttgtt gganttgagc tcgggcggct gtggtaggtt gtgggctctt caacaggggc 240
tgctgtggtg ccgggangtg aangtgttgt gtcacttgag cttggccagc tctggaaagt 300
antanattct tcctgaaggc cagcgcttgt ggagctggca ngggtcantg ttgtgtgtaa 360
cgaaccagtg ctgctgtggg tgggtgtana tcctccacaa agcctgaagt tatggtgtcn 420
tcaggtaana atgtggtttc agtgtccctg ggcngctgtg gaaggttgta nattgtcacc 480
aagggaataa gctgtggt 498

<210> SEQ ID NO 160
<211> LENGTH: 380
<212> TYPE: DNA
<213> ORGANISM: Homo sapien
<220> FEATURE:
<221> NAME/KEY: misc_feature
<222> LOCATION: (1)...(380)
<223> OTHER INFORMATION: n = A,T,C or G

<400> SEQUENCE: 160
acctgcatcc agcttccctg ccaaactcac aaggagacat caacctctag acagggaaac 60
agcttcagga tacttccagg agacagagcc accagcagca aaacaaatat tcccatgcct 120
ggagcatggc atagaggaag ctganaaatg tggggtctga ggaagccatt tgagtctggc 180

-continued

```
cactagacat ctcatcagcc acttgtgtga agagatgccc catgacccca gatgcctctc    240

ccacccttac ctccatctca cacacttgag ctttccactc tgtataattc taacatcctg    300

gagaaaaatg gcagtttgac cgaacctgtt cacaacggta gaggctgatt tctaacgaaa    360

cttgtagaat gaagcctgga                                                380
```

```
<210> SEQ ID NO 161
<211> LENGTH: 114
<212> TYPE: DNA
<213> ORGANISM: Homo sapien

<400> SEQUENCE: 161

actccacatc ccctctgagc aggcggttgt cgttcaaggt gtatttggcc ttgcctgtca     60

cactgtccac tggcccctta tccacttggt gcttaatccc tcgaaagagc atgt          114
```

```
<210> SEQ ID NO 162
<211> LENGTH: 177
<212> TYPE: DNA
<213> ORGANISM: Homo sapien

<400> SEQUENCE: 162

actttctgaa tcgaatcaaa tgatacttag tgtagtttta atatcctcat atatatcaaa     60

gttttactac tctgataatt ttgtaaacca ggtaaccaga acatccagtc atacagcttt    120

tggtgatata taacttggca ataacccagt ctggtgatac ataaaactac tcactgt      177
```

```
<210> SEQ ID NO 163
<211> LENGTH: 137
<212> TYPE: DNA
<213> ORGANISM: Homo sapien
<220> FEATURE:
<221> NAME/KEY: misc_feature
<222> LOCATION: (1)...(137)
<223> OTHER INFORMATION: n = A,T,C or G

<400> SEQUENCE: 163

catttataca gacaggcgtg aagacattca cgacaaaaac gcgaaattct atcccgtgac     60

canagaaggc agctacggct actcctacat cctggcgtgg gtggccttcg cctgcacctt    120

catcagcggc atgatgt                                                   137
```

```
<210> SEQ ID NO 164
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 164

cttatcacaa tgaatgttct cctgggcagc gttgtgatct ttgccacctt cgtgacttta     60

tgcaatgcat catgctattt catacctaat gagggagttc caggagattc aaccaggaaa    120

tgcatggatc tcaaaggaaa caaacaccca ataaactcgg agtggcagac tgacaactgt    180

gagacatgca cttgctacga aacagaaatt tcatgttgca cccttgtttc tacacctgtg    240

ggttatgaca aagacaactg ccaaagaatc ttcaagaagg aggactgcaa gtatatcgtg    300

gtggagaaga aggacccaaa aaagacctgt tctgtcagtg aatggataat ctaatgtgct    360

tctagtaggc acagggctcc caggccaggc ctcattctcc tctggcctct aatagtcaat    420
```

-continued

```
gattgtgtag ccatgcctat cagtaaaaag atntttgagc aaacacttt              469


<210> SEQ ID NO 165
<211> LENGTH: 195
<212> TYPE: DNA
<213> ORGANISM: Homo sapien
<220> FEATURE:
<221> NAME/KEY: misc_feature
<222> LOCATION: (1)...(195)
<223> OTHER INFORMATION: n = A,T,C or G

<400> SEQUENCE: 165

acagtttttt atanatatcg acattgccgg cacttgtgtt cagtttcata aagctggtgg     60

atccgctgtc atccactatt ccttggctag agtaaaaatt attcttatag cccatgtccc    120

tgcaggccgc ccgcccgtag ttctcgttcc agtcgtcttg gcacacaggg tgccaggact    180

tcctctgaga tgagt                                                     195


<210> SEQ ID NO 166
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 166

acatcttagt agtgtggcac atcagggggc catcagggtc acagtcactc atagcctcgc     60

cgaggtcgga gtccacacca ccggtgtagg tgtgctcaat cttgggcttg gcgcccacct    120

ttggagaagg gatatgctgc acacacatgt ccacaaagcc tgtgaactcg ccaaagaatt    180

tttgcagacc agcctgagca aggggcggat gttcagcttc agctcctcct tcgtcaggtg    240

gatgccaacc tcgtctangg tccgtgggaa gctggtgtcc acntcaccta caacctgggc    300

gangatctta taaagaggct ccnagataaa ctccacgaaa cttctctggg agctgctagt    360

nggggccttt ttggtgaact ttc                                            383


<210> SEQ ID NO 167
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 167

acagagccag accttggcca taaatgaanc agagattaag actaaacccc aagtcganat     60

tggagcagaa actggagcaa gaagtgggcc tggggctgaa gtagagacca aggccactgc    120

tatanccata cacagagcca actctcaggc caaggcnatg gttggggcag anccagagac    180

tcaatctgan tccaaagtgg tggctggaac actggtcatg acanaggcag tgactctgac    240

tgangtc                                                              247


<210> SEQ ID NO 168
<211> LENGTH: 273
<212> TYPE: DNA
<213> ORGANISM: Homo sapien
<220> FEATURE:
<221> NAME/KEY: misc_feature
<222> LOCATION: (1)...(273)
<223> OTHER INFORMATION: n = A,T,C or G
```

-continued

<400> SEQUENCE: 168

```
acttctaagt tttctagaag tggaaggatt gtantcatcc tgaaaatggg tttacttcaa      60
aatccctcan ccttgttctt cacnactgtc tatactgana gtgtcatgtt tccacaaagg     120
gctgacacct gagcctgnat tttcactcat ccctgagaag ccctttccag tagggtgggc     180
aattcccaac ttccttgcca caagcttccc aggctttctc ccctggaaaa ctccagcttg     240
agtcccagat acactcatgg gctgccctgg gca                                  273
```

<210> SEQ ID NO 169
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 169

```
acagccttgg cttccccaaa ctccacagtc tcagtgcaga aagatcatct tccagcagtc      60
agctcagacc agggtcaaag gatgtgacat caacagtttc tggtttcaga acaggttcta     120
ctactgtcaa atgacccccc atacttcctc aaaggctgtg gtaagttttg cacaggtgag     180
ggcagcagaa agggggtant tactgatgga caccatcttc tctgtatact ccacactgac     240
cttgccatgg gcaaaggccc ctaccacaaa aacaatagga tcactgctgg gcaccagctc     300
acgcacatca ctgacaaccg ggatggaaaa agaantgcca actttcatac atccaactgg     360
aaagtgatct gatactggat tcttaattac cttcaaaagc ttctgggggc catcagctgc     420
tcgaacactg a                                                          431
```

<210> SEQ ID NO 170
<211> LENGTH: 266
<212> TYPE: DNA
<213> ORGANISM: Homo sapien
<220> FEATURE:
<221> NAME/KEY: misc_feature
<222> LOCATION: (1)...(266)
<223> OTHER INFORMATION: n = A,T,C or G

<400> SEQUENCE: 170

```
acctgtgggc tgggctgtta tgcctgtgcc ggctgctgaa agggagttca gaggtggagc      60
tcaaggagct ctgcaggcat tttgccaanc ctctccanag canagggagc aacctacact     120
ccccgctaga aagacaccag attggagtcc tgggaggggg agttggggtg ggcatttgat     180
gtatacttgt cacctgaatg aangagccag agaggaanga gacgaanatg anattggcct     240
tcaaagctag ggtctggca ggtgga                                           266
```

<210> SEQ ID NO 171
<211> LENGTH: 1248
<212> TYPE: DNA
<213> ORGANISM: Homo sapien
<220> FEATURE:
<221> NAME/KEY: misc_feature
<222> LOCATION: (1)...(1248)
<223> OTHER INFORMATION: n = A,T,C or G

<400> SEQUENCE: 171

```
ggcagccaaa tcataaacgg cgaggactgc agcccgcact cgcagccctg gcaggcggca      60
ctggtcatgg aaaacgaatt gttctgctcg ggcgtcctgg tgcatccgca gtgggtgctg     120
```

-continued

```
tcagccgcac actgtttcca gaagtgagtg cagagctcct acaccatcgg gctgggcctg    180

cacagtcttg aggccgacca agagccaggg agccagatgg tggaggccag cctctccgta    240

cggcacccag agtacaacag acccttgctc gctaacgacc tcatgctcat caagttggac    300

gaatccgtgt ccgagtctga caccatccgg agcatcagca ttgcttcgca gtgccctacc    360

gcggggaact cttgcctcgt ttctggctgg ggtctgctgg cgaacggcag aatgcctacc    420

gtgctgcagt gcgtgaacgt gtcggtggtg tctgaggagg tctgcagtaa gctctatgac    480

ccgctgtacc accccagcat gttctgcgcc ggcggagggc aagaccagaa ggactcctgc    540

aacggtgact ctgggggggcc cctgatctgc aacgggtact tgcagggcct tgtgtctttc    600

ggaaaagccc cgtgtggcca agttggcgtg ccaggtgtct acaccaacct ctgcaaattc    660

actgagtgga tagagaaaac cgtccaggcc agttaactct ggggactggg aacccatgaa    720

attgaccccc aaatacatcc tgcggaagga attcaggaat atctgttccc agcccctcct    780

ccctcaggcc caggagtcca ggcccccagc ccctcctccc tcaaaccaag ggtacagatc    840

cccagcccct cctccctcag acccaggagt ccagaccccc cagcccctcc tccctcagac    900

ccaggagtcc agcccctcct ccctcagacc caggagtcca gaccccccag cccctcctcc    960

ctcagaccca ggggtccagg cccccaaccc ctcctccctc agactcagag gtccaagccc   1020

ccaacccntc attccccaga cccagaggtc caggtcccag cccctcntcc ctcagaccca   1080

gcggtccaat gccacctaga ctntccctgt acacagtgcc cccttgtggc acgttgaccc   1140

aaccttacca gttggttttt catttttngt ccctttcccc tagatccaga aataaagttt   1200

aagagaagng caaaaaaaaa aaaaaaaaaa aaaaaaaaaa aaaaaaaa                1248
```

<210> SEQ ID NO 172
<211> LENGTH: 159
<212> TYPE: PRT
<213> ORGANISM: Homo sapien
<220> FEATURE:
<221> NAME/KEY: VARIANT
<222> LOCATION: (1)...(159)
<223> OTHER INFORMATION: Xaa = Any Amino Acid

<400> SEQUENCE: 172

```
Met Val Glu Ala Ser Leu Ser Val Arg His Pro Glu Tyr Asn Arg Pro
 1               5                  10                  15

Leu Leu Ala Asn Asp Leu Met Leu Ile Lys Leu Asp Glu Ser Val Ser
            20                  25                  30

Glu Ser Asp Thr Ile Arg Ser Ile Ser Ile Ala Ser Gln Cys Pro Thr
        35                  40                  45

Ala Gly Asn Ser Cys Leu Val Ser Gly Trp Gly Leu Leu Ala Asn Gly
    50                  55                  60

Arg Met Pro Thr Val Leu Gln Cys Val Asn Val Ser Val Val Ser Glu
65                  70                  75                  80

Glu Val Cys Ser Lys Leu Tyr Asp Pro Leu Tyr His Pro Ser Met Phe
                85                  90                  95

Cys Ala Gly Gly Gly Gln Xaa Gln Xaa Asp Ser Cys Asn Gly Asp Ser
            100                 105                 110

Gly Gly Pro Leu Ile Cys Asn Gly Tyr Leu Gln Gly Leu Val Ser Phe
        115                 120                 125

Gly Lys Ala Pro Cys Gly Gln Val Gly Val Pro Gly Val Tyr Thr Asn
    130                 135                 140

Leu Cys Lys Phe Thr Glu Trp Ile Glu Lys Thr Val Gln Ala Ser
145                 150                 155
```

-continued

<210> SEQ ID NO 173
<211> LENGTH: 1265
<212> TYPE: DNA
<213> ORGANISM: Homo sapien
<220> FEATURE:
<221> NAME/KEY: misc_feature
<222> LOCATION: (1)...(1265)
<223> OTHER INFORMATION: n = A,T,C or G

<400> SEQUENCE: 173
ggcagcccgc actcgcagcc ctggcaggcg gcactggtca tggaaaacga attgttctgc 60
tcgggcgtcc tggtgcatcc gcagtgggtg ctgtcagccg cacactgttt ccagaactcc 120
tacaccatcg ggctgggcct gcacagtctt gaggccgacc aagagccagg gagccagatg 180
gtggaggcca gcctctccgt acggcaccca gagtacaaca gacccttgct cgctaacgac 240
ctcatgctca tcaagttgga cgaatccgtg tccgagtctg acaccatccg gagcatcagc 300
attgcttcgc agtgccctac cgcggggaac tcttgcctcg tttctggctg gggtctgctg 360
gcgaacggtg agctcacggg tgtgtgtctg ccctcttcaa ggaggtcctc tgcccagtcg 420
cgggggctga cccagagctc tgcgtcccag gcagaatgcc taccgtgctg cagtgcgtga 480
acgtgtcggt ggtgtctgag gaggtctgca gtaagctcta tgacccgctg taccacccca 540
gcatgttctg cgccggcgga gggcaagacc agaaggactc ctgcaacggt gactctgggg 600
ggcccctgat ctgcaacggg tacttgcagg gccttgtgtc tttcggaaaa gccccgtgtg 660
gccaagttgg cgtgccaggt gtctacacca acctctgcaa attcactgag tggatagaga 720
aaaccgtcca ggccagttaa ctctggggac tgggaaccca tgaaattgac cccccaaatac 780 atcctgcgga aggaattcag gaatatctgt tcccagcccc tcctccctca ggcccaggag 840
tccaggcccc cagcccctcc tccctcaaac caagggtaca gatccccagc ccctcctccc 900
tcagacccag gagtccagac cccccagccc ctcctccctc agacccagga gtccagcccc 960
tcctccntca gacccaggag tccagacccc ccagcccctc ctccctcaga cccaggggtt 1020
gaggccccca acccctcctc cttcagagtc agaggtccaa gcccccaacc cctcgttccc 1080
cagacccaga ggtnnaggtc ccagcccctc ttccntcaga cccagnggtc caatgccacc 1140
tagattttcc ctgnacacag tgccccccttg tggnangttg acccaacctt accagttggt 1200
ttttcatttt tngtcccttt cccctagatc cagaaataaa gtttaagaga ngngcaaaaa 1260
aaaaa 1265

<210> SEQ ID NO 174
<211> LENGTH: 1459
<212> TYPE: DNA
<213> ORGANISM: Homo sapien
<220> FEATURE:
<221> NAME/KEY: misc_feature
<222> LOCATION: (1)...(1459)
<223> OTHER INFORMATION: n = A,T,C or G

<400> SEQUENCE: 174
ggtcagccgc acactgtttc cagaagtgag tgcagagctc ctacaccatc gggctgggcc 60
tgcacagtct tgaggccgac caagagccag ggagccagat ggtggaggcc agcctctccg 120
tacggcaccc agagtacaac agacccttgc tcgctaacga cctcatgctc atcaagttgg 180
acgaatccgt gtccgagtct gacaccatcc ggagcatcag cattgcttcg cagtgcccta 240
ccgcggggaa ctcttgcctc gtttctggct ggggtctgct ggcgaacggt gagctcacgg 300

-continued

```
gtgtgtgtct gccctcttca aggaggtcct ctgcccagtc gcgggggctg acccagagct    360

ctgcgtccca ggcagaatgc ctaccgtgct gcagtgcgtg aacgtgtcgg tggtgtctga    420

ngaggtctgc antaagctct atgacccgct gtaccacccc ancatgttct gcgccggcgg    480

agggcaagac cagaaggact cctgcaacgt gagagagggg aaaggggagg gcaggcgact    540

cagggaaggg tggagaaggg ggagacagag acacacaggg ccgcatggcg agatgcagag    600

atggagagac acacagggag acagtgacaa ctagagagag aaactgagag aaacagagaa    660

ataaacacag gaataaagag aagcaaagga agagagaaac agaaacagac atggggaggc    720

agaaacacac acacatagaa atgcagttga ccttccaaca gcatggggcc tgagggcggt    780

gacctccacc caatagaaaa tcctcttata acttttgact ccccaaaaac ctgactagaa    840

atagcctact gttgacgggg agccttacca ataacataaa tagtcgattt atgcatacgt    900

tttatgcatt catgatatac ctttgttgga attttttgat atttctaagc tacacagttc    960

gtctgtgaat ttttttaaat tgttgcaact ctcctaaaat ttttctgatg tgtttattga   1020

aaaaatccaa gtataagtgg acttgtgcat tcaaaccagg gttgttcaag ggtcaactgt   1080

gtacccagag ggaaacagtg acacagattc atagaggtga aacacgaaga gaaacaggaa   1140

aaatcaagac tctacaaaga ggctgggcag ggtggctcat gcctgtaatc ccagcacttt   1200

gggaggcgag gcaggcagat cacttgaggt aaggagttca agaccagcct ggccaaaatg   1260

gtgaaatcct gtctgtacta aaaatacaaa agttagctgg atatggtggc aggcgcctgt   1320

aatcccagct acttgggagg ctgaggcagg agaattgctt gaatatggga ggcagaggtt   1380

gaagtgagtt gagatcacac cactatactc cagctggggc aacagagtaa gactctgtct   1440

caaaaaaaaa aaaaaaaaa                                                1459
```

<210> SEQ ID NO 175
<211> LENGTH: 1167
<212> TYPE: DNA
<213> ORGANISM: Homo sapien
<220> FEATURE:
<221> NAME/KEY: misc_feature
<222> LOCATION: (1)...(1167)
<223> OTHER INFORMATION: n = A,T,C or G

<400> SEQUENCE: 175

```
gcgcagccct ggcaggcggc actggtcatg gaaaacgaat tgttctgctc gggcgtcctg     60

gtgcatccgc agtgggtgct gtcagccgca cactgtttcc agaactccta caccatcggg    120

ctgggcctgc acagtcttga ggccgaccaa gagccaggga gccagatggt ggaggccagc    180

ctctccgtac ggcacccaga gtacaacaga ctcttgctcg ctaacgacct catgctcatc    240

aagttggacg aatccgtgtc cgagtctgac accatccgga gcatcagcat tgcttcgcag    300

tgccctaccg cggggaactc ttgcctcgtn tctggctggg gtctgctggc gaacggcaga    360

atgcctaccg tgctgcactg cgtgaacgtg tcggtggtgt ctgaggangt ctgcagtaag    420

ctctatgacc cgctgtacca ccccagcatg ttctgcgccg gcggagggca agaccagaag    480

gactcctgca acggtgactc tgggggggccc ctgatctgca acgggtactt gcagggcctt    540

gtgtctttcg gaaaagcccc gtgtggccaa cttggcgtgc caggtgtcta caccaacctc    600

tgcaaattca ctgagtggat agagaaaacc gtccagncca gttaactctg gggactggga    660

acccatgaaa ttgaccccca aatacatcct gcggaangaa ttcaggaata tctgttccca    720

gcccctcctc cctcaggccc aggagtccag gcccccagcc cctcctccct caaaccaagg    780

gtacagatcc ccagcccctc ctccctcaga cccaggagtc cagacccccc agcccctcnt    840
```

-continued

```
ccntcagacc caggagtcca gcccctcctc cntcagacgc aggagtccag accccccagc    900

ccntcntccg tcagacccag gggtgcaggc ccccaacccc tcntccntca gagtcagagg    960

tccaagcccc caacccctcg ttccccagac ccagaggtnc aggtcccagc ccctcctccc   1020

tcagacccag cggtccaatg ccacctagan tntccctgta cacagtgccc ccttgtggca   1080

ngttgaccca accttaccag ttggtttttc attttttgtc cctttcccct agatccagaa   1140

ataaagtnta agagaagcgc aaaaaaa                                       1167


<210> SEQ ID NO 176
<211> LENGTH: 205
<212> TYPE: PRT
<213> ORGANISM: Homo sapien
<220> FEATURE:
<221> NAME/KEY: VARIANT
<222> LOCATION: (1)...(205)
<223> OTHER INFORMATION: Xaa = Any Amino Acid

<400> SEQUENCE: 176

Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Leu Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Gly Arg Met
            100                 105                 110

Pro Thr Val Leu His Cys Val Asn Val Ser Val Val Ser Glu Xaa Val
        115                 120                 125

Cys Ser Lys Leu Tyr Asp Pro Leu Tyr His Pro Ser Met Phe Cys Ala
    130                 135                 140

Gly Gly Gly Gln Asp Gln Lys Asp Ser Cys Asn Gly Asp Ser Gly Gly
145                 150                 155                 160

Pro Leu Ile Cys Asn Gly Tyr Leu Gln Gly Leu Val Ser Phe Gly Lys
                165                 170                 175

Ala Pro Cys Gly Gln Leu Gly Val Pro Gly Val Tyr Thr Asn Leu Cys
            180                 185                 190

Lys Phe Thr Glu Trp Ile Glu Lys Thr Val Gln Xaa Ser
        195                 200                 205


<210> SEQ ID NO 177
<211> LENGTH: 1119
<212> TYPE: DNA
<213> ORGANISM: Homo sapien

<400> SEQUENCE: 177

gcgcactcgc agccctggca ggcggcactg gtcatggaaa acgaattgtt ctgctcgggc     60

gtcctggtgc atccgcagtg ggtgctgtca gccgcacact gtttccagaa ctcctacacc    120

atcgggctgg gcctgcacag tcttgaggcc gaccaagagc cagggagcca gatggtggag    180

gccagcctct ccgtacggca cccagagtac aacagaccct tgctcgctaa cgacctcatg    240
```

-continued

```
ctcatcaagt tggacgaatc cgtgtccgag tctgacacca tccggagcat cagcattgct    300
tcgcagtgcc ctaccgcggg gaactcttgc ctcgtttctg gctggggtct gctggcgaac    360
gatgctgtga ttgccatcca gtcccagact gtgggaggct gggagtgtga gaagctttcc    420
caaccctggc agggttgtac catttcggca acttccagtg caaggacgtc ctgctgcatc    480
ctcactgggt gctcactact gctcactgca tcacccggaa cactgtgatc aactagccag    540
caccatagtt ctccgaagtc agactatcat gattactgtg ttgactgtgc tgtctattgt    600
actaaccatg ccgatgttta ggtgaaatta gcgtcacttg gcctcaacca tcttggtatc    660
cagttatcct cactgaattg agatttcctg cttcagtgtc agccattccc acataatttc    720
tgacctacag aggtgaggga tcatatagct cttcaaggat gctggtactc ccctcacaaa    780
ttcatttctc ctgttgtagt gaaaggtgcg ccctctggag cctcccaggg tgggtgtgca    840
ggtcacaatg atgaatgtat gatcgtgttc ccattaccca aagcctttaa atccctcatg    900
ctcagtacac cagggcaggt ctagcatttc ttcatttagt gtatgctgtc cattcatgca    960
accacctcag gactcctgga ttctctgcct agttgagctc ctgcatgctg cctccttggg   1020
gaggtgaggg agagggccca tggttcaatg ggatctgtgc agttgtaaca cattaggtgc   1080
ttaataaaca gaagctgtga tgttaaaaaa aaaaaaaaa                          1119
```

<210> SEQ ID NO 178
<211> LENGTH: 164
<212> TYPE: PRT
<213> ORGANISM: Homo sapien
<220> FEATURE:
<221> NAME/KEY: VARIANT
<222> LOCATION: (1)...(164)
<223> OTHER INFORMATION: Xaa = Any Amino Acid

<400> SEQUENCE: 178

```
Met Glu Asn Glu Leu Phe Cys Ser Gly Val Leu Val His Pro Gln Trp
 1               5                  10                  15

Val Leu Ser Ala Ala His Cys Phe Gln Asn Ser Tyr Thr Ile Gly Leu
            20                  25                  30

Gly Leu His Ser Leu Glu Ala Asp Gln Glu Pro Gly Ser Gln Met Val
        35                  40                  45

Glu Ala Ser Leu Ser Val Arg His Pro Glu Tyr Asn Arg Pro Leu Leu
    50                  55                  60

Ala Asn Asp Leu Met Leu Ile Lys Leu Asp Glu Ser Val Ser Glu Ser
65                  70                  75                  80

Asp Thr Ile Arg Ser Ile Ser Ile Ala Ser Gln Cys Pro Thr Ala Gly
                85                  90                  95

Asn Ser Cys Leu Val Ser Gly Trp Gly Leu Leu Ala Asn Asp Ala Val
            100                 105                 110

Ile Ala Ile Gln Ser Xaa Thr Val Gly Gly Trp Glu Cys Glu Lys Leu
        115                 120                 125

Ser Gln Pro Trp Gln Gly Cys Thr Ile Ser Ala Thr Ser Ser Ala Arg
    130                 135                 140

Thr Ser Cys Cys Ile Leu Thr Gly Cys Ser Leu Leu Leu Thr Ala Ser
145                 150                 155                 160

Pro Gly Thr Leu
```

<210> SEQ ID NO 179
<211> LENGTH: 250
<212> TYPE: DNA

-continued

<213> ORGANISM: Homo sapien

<400> SEQUENCE: 179
ctggagtgcc ttggtgtttc aagcccctgc aggaagcaga atgcaccttc tgaggcacct 60
ccagctgccc ccggccgggg gatgcgaggc tcggagcacc cttgcccggc tgtgattgct 120
gccaggcact gttcatctca gcttttctgt ccctttgctc ccggcaagcg cttctgctga 180
aagttcatat ctggagcctg atgtcttaac gaataaaggt cccatgctcc acccgaaaaa 240
aaaaaaaaaa 250

<210> SEQ ID NO 180
<211> LENGTH: 202
<212> TYPE: DNA
<213> ORGANISM: Homo sapien

<400> SEQUENCE: 180
actagtccag tgtggtggaa ttccattgtg ttgggcccaa cacaatggct acctttaaca 60
tcacccagac cccgcccctg cccgtgcccc acgctgctgc taacgacagt atgatgctta 120
ctctgctact cggaaactat ttttatgtaa ttaatgtatg ctttcttgtt tataaatgcc 180
tgatttaaaa aaaaaaaaaa aa 202

<210> SEQ ID NO 181
<211> LENGTH: 558
<212> TYPE: DNA
<213> ORGANISM: Homo sapien
<220> FEATURE:
<221> NAME/KEY: misc_feature
<222> LOCATION: (1)...(558)
<223> OTHER INFORMATION: n = A,T,C or G

<400> SEQUENCE: 181
tccytttgkt naggtttkkg agacamccck agacctwaan ctgtgtcaca gacttcyngg 60
aatgtttagg cagtgctagt aatttcytcg taatgattct gttattactt tcctnattct 120
ttattcctct ttcttctgaa gattaatgaa gttgaaaatt gaggtggata aatacaaaaa 180
ggtagtgtga tagtataagt atctaagtgc agatgaaagt gtgttatata tatccattca 240
aaattatgca agttagtaat tactcagggt taactaaatt actttaatat gctgttgaac 300
ctactctgtt ccttggctag aaaaaattat aaacaggact ttgttagttt gggaagccaa 360
attgataata ttctatgttc taaaagttgg gctatacata aattattaag aaatatggaw 420
ttttattccc aggaatatgg kgttcatttt atgaatatta cscrggatag awgtwtgagt 480
aaaaycagtt ttggtwaata ygtwaatatg tcmtaaataa acaakgcttt gacttatttc 540
caaaaaaaaa aaaaaaa 558

<210> SEQ ID NO 182
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 182
acagggwttk grggatgcta agsccccrga rwtygtttga tccaaccctg gcttwttttc 60
agaggggaaa atggggccta gaagttacag mscatytagy tggtgcgmtg gcacccctgg 120
cstcacacag astcccgagt agctgggact acaggcacac agtcactgaa gcaggccctg 180

-continued

```
ttwgcaattc acgttgccac ctccaactta aacattcttc atatgtgatg tccttagtca    240

ctaaggttaa actttcccac ccagaaaagg caacttagat aaaatcttag agtactttca    300

tactmttcta agtcctcttc cagcctcact kkgagtcctm cytgggggtt gataggaant    360

ntctcttggc tttctcaata aartctctat ycatctcatg tttaatttgg tacgcatara    420

awtgstgara aaattaaaat gttctggtty mactttaaaa araaaaaaaa aaaaaaaaa     479
```

<210> SEQ ID NO 183
<211> LENGTH: 384
<212> TYPE: DNA
<213> ORGANISM: Homo sapien

<400> SEQUENCE: 183

```
aggcgggagc agaagctaaa gccaaagccc aagaagagtg gcagtgccag cactggtgcc     60

agtaccagta ccaataacag tgccagtgcc agtgccagca ccagtggtgg cttcagtgct    120

ggtgccagcc tgaccgccac tctcacattt gggctcttcg ctggccttgg tggagctggt    180

gccagcacca gtggcagctc tggtgcctgt ggtttctcct acaagtgaga ttttagatat    240

tgttaatcct gccagtcttt ctcttcaagc cagggtgcat cctcagaaac ctactcaaca    300

cagcactcta ggcagccact atcaatcaat tgaagttgac actctgcatt aratctattt    360

gccatttcaa aaaaaaaaaa aaaa                                            384
```

<210> SEQ ID NO 184
<211> LENGTH: 496
<212> TYPE: DNA
<213> ORGANISM: Homo sapien
<220> FEATURE:
<221> NAME/KEY: misc_feature
<222> LOCATION: (1)...(496)
<223> OTHER INFORMATION: n = A,T,C or G

<400> SEQUENCE: 184

```
accgaattgg gaccgctggc ttataagcga tcatgtyynt ccrgtatkac ctcaacgagc     60

agggagatcg agtctatacg ctgaagaaat ttgacccgat gggacaacag acctgctcag    120

cccatcctgc tcggttctcc ccagatgaca aatactctsg acaccgaatc accatcaaga    180

aacgcttcaa ggtgctcatg acccagcaac cgcgccctgt cctctgaggg tcccttaaac    240

tgatgtcttt tctgccacct gttacccctc ggagactccg taaccaaact cttcggactg    300

tgagccctga tgccttttttg ccagccatac tctttggcat ccagtctctc gtggcgattg    360

attatgcttg tgtgaggcaa tcatggtggc atcacccata aagggaacac atttgacttt    420

tttttctcat attttaaatt actacmagaw tattwmagaw waaatgawtt gaaaaactst    480

taaaaaaaaa aaaaaa                                                     496
```

<210> SEQ ID NO 185
<211> LENGTH: 384
<212> TYPE: DNA
<213> ORGANISM: Homo sapien

<400> SEQUENCE: 185

```
gctggtagcc tatggcgkgg cccacggagg ggctcctgag gccacggrac agtgacttcc     60

caagtatcyt gcgcsgcgtc ttctaccgtc cctacctgca gatcttcggg cagattcccc    120

aggaggacat ggacgtggcc ctcatggagc acagcaactg ytcgtcggag cccggcttct    180

gggcacaccc tcctggggcc caggcgggca cctgcgtctc ccagtatgcc aactggctgg    240
```

-continued

```
tggtgctgct cctcgtcatc ttcctgctcg tggccaacat cctgctggtc aacttgctca    300

ttgccatgtt cagttacaca ttcggcaaag tacagggcaa cagcgatctc tactgggaag    360

gcgcagcgtt accgcctcat ccgg                                           384


<210> SEQ ID NO 186
<211> LENGTH: 577
<212> TYPE: DNA
<213> ORGANISM: Homo sapien
<220> FEATURE:
<221> NAME/KEY: misc_feature
<222> LOCATION: (1)...(577)
<223> OTHER INFORMATION: n = A,T,C or G

<400> SEQUENCE: 186

gagttagctc ctccacaacc ttgatgaggt cgtctgcagt ggcctctcgc ttcataccgc     60

tnccatcgtc atactgtagg tttgccacca cytcctggca tcttggggcg gcntaatatt    120

ccaggaaact ctcaatcaag tcaccgtcga tgaaacctgt gggctggttc tgtcttccgc    180

tcggtgtgaa aggatctccc agaaggagtg ctcgatcttc cccacacttt tgatgacttt    240

attgagtcga ttctgcatgt ccagcaggag gttgtaccag ctctctgaca gtgaggtcac    300

cagccctatc atgccgttga mcgtgccgaa garcaccgag ccttgtgtgg gggkkgaagt    360

ctcacccaga ttctgcatta ccagagagcc gtggcaaaag acattgacaa actcgcccag    420

gtggaaaaag amcamctcct ggargtgctn gccgctcctc gtcmgttggt ggcagcgctw    480

tccttttgac acacaaacaa gttaaaggca ttttcagccc ccagaaantt gtcatcatcc    540

aagatntcgc acagcactna tccagttggg attaaat                             577


<210> SEQ ID NO 187
<211> LENGTH: 534
<212> TYPE: DNA
<213> ORGANISM: Homo sapien
<220> FEATURE:
<221> NAME/KEY: misc_feature
<222> LOCATION: (1)...(534)
<223> OTHER INFORMATION: n = A,T,C or G

<400> SEQUENCE: 187

aacatcttcc tgtataatgc tgtgtaatat cgatccgatn ttgtctgstg agaatycatw     60

actkggaaaa gmaacattaa agcctggaca ctggtattaa aattcacaat atgcaacact    120

ttaaacagtg tgtcaatctg ctcccyynac tttgtcatca ccagtctggg aakaagggta    180

tgccctattc acacctgtta aaagggcgct aagcattttt gattcaacat cttttttttt    240

gacacaagtc cgaaaaaagc aaaagtaaac agttatyaat ttgttagcca attcactttc    300

ttcatgggac agagccatyt gatttaaaaa gcaaattgca taatattgag cttygggagc    360

tgatatttga gcggaagagt agcctttcta cttcaccaga cacaactccc tttcatattg    420

ggatgttnac naaagtwatg tctctwacag atgggatgct tttgtggcaa ttctgttctg    480

aggatctccc agtttattta ccacttgcac aagaaggcgt tttcttcctc aggc          534


<210> SEQ ID NO 188
<211> LENGTH: 761
<212> TYPE: DNA
<213> ORGANISM: Homo sapien
<220> FEATURE:
<221> NAME/KEY: misc_feature
<222> LOCATION: (1)...(761)
<223> OTHER INFORMATION: n = A,T,C or G

<400> SEQUENCE: 188
```

-continued

```
agaaaccagt atctctnaaa acaacctctc ataccttgtg gacctaattt tgtgtgcgtg     60

tgtgtgtgcg cgcatattat atagacaggc acatcttttt tacttttgta aaagcttatg    120

cctctttggt atctatatct gtgaaagttt taatgatctg ccataatgtc ttggggacct    180

ttgtcttctg tgtaaatggt actagagaaa acacctatnt tatgagtcaa tctagttngt    240

tttattcgac atgaaggaaa tttccagatn acaacactna caaactctcc ctkgackarg    300

ggggacaaag aaaagcaaaa ctgamcataa raaacaatwa cctggtgaga arttgcataa    360

acagaaatwr ggtagtatat tgaarnacag catcattaaa rmgttwtktt wttctccctt    420

gcaaaaaaca tgtacngact tcccgttgag taatgccaag ttgttttttt tatnataaaa    480

cttgcccttc attacatgtt tnaaagtggt gtggtgggcc aaaatattga aatgatggaa    540

ctgactgata aagctgtaca aataagcagt gtgcctaaca agcaacacag taatgttgac    600

atgcttaatt cacaaatgct aatttcatta taaatgtttg ctaaaataca ctttgaacta    660

tttttctgtn ttcccagagc tgagatntta gattttatgt agtatnaagt gaaaaantac    720

gaaaataata acattgaaga aaaananaaa aaanaaaaaa a                        761
```

```
<210> SEQ ID NO 189
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 189

tttttttttt tttgccgatn ctactatttt attgcaggan gtgggggtgt atgcaccgca     60

caccggggct atnagaagca agaaggaagg agggagggca cagccccttg ctgagcaaca    120

aagccgcctg ctgccttctc tgtctgtctc ctggtgcagg cacatgggga gaccttcccc    180

aaggcagggg ccaccagtcc aggggtggga atacaggggg tgggangtgt gcataagaag    240

tgataggcac aggccacccg gtacagaccc ctcggctcct gacaggtnga tttcgaccag    300

gtcattgtgc cctgcccagg cacagcgtan atctggaaaa gacagaatgc tttccttttc    360

aaatttggct ngtcatngaa ngggcanttt tccaanttng gctnggtctt ggtacncttg    420

gttcggccca gctccncgtc caaaaantat tcacccnnct ccnaattgct tgcnggnccc    480

cc                                                                   482
```

```
<210> SEQ ID NO 190
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 190

tttttttttt ttttaaaaca gtttttcaca acaaaattta ttagaagaat agtggttttg     60

aaaactctcg catccagtga gaactaccat acaccacatt acagctngga atgtnctcca    120

aatgtctggt caaatgatac aatggaacca ttcaatctta cacatgcacg aaagaacaag    180

cgcttttgac atacaatgca caaaaaaaaa agggggggggg gaccacatgg attaaaattt    240

taagtactca tcacatacat taagacacag ttctagtcca gtcnaaaatc agaactgcnt    300
```

-continued

```
tgaaaaattt catgtatgca atccaaccaa agaacttnat tggtgatcat gantnctcta    360

ctacatcnac cttgatcatt gccaggaacn aaaagttnaa ancacncngt acaaaaanaa    420

tctgtaattn anttcaacct ccgtacngaa aaatnttnnt tatacactcc c             471


<210> SEQ ID NO 191
<211> LENGTH: 402
<212> TYPE: DNA
<213> ORGANISM: Homo sapien
<220> FEATURE:
<221> NAME/KEY: misc_feature
<222> LOCATION: (1)...(402)
<223> OTHER INFORMATION: n = A,T,C or G

<400> SEQUENCE: 191

gagggattga aggtctgttc tastgtcggm ctgttcagcc accaactcta acaagttgct     60

gtcttccact cactgtctgt aagcttttta acccagacwg tatcttcata aatagaacaa    120

attcttcacc agtcacatct tctaggacct ttttggattc agttagtata agctcttcca    180

cttcctttgt taagacttca tctggtaaag tcttaagttt tgtagaaagg aattyaattg    240

ctcgttctct aacaatgtcc tctccttgaa gtatttggct gaacaaccca cctaaagtcc    300

ctttgtgcat ccattttaaa tatacttaat agggcattgk tncactaggt taaattctgc    360

aagagtcatc tgtctgcaaa agttgcgtta gtatatctgc ca                       402


<210> SEQ ID NO 192
<211> LENGTH: 601
<212> TYPE: DNA
<213> ORGANISM: Homo sapien
<220> FEATURE:
<221> NAME/KEY: misc_feature
<222> LOCATION: (1)...(601)
<223> OTHER INFORMATION: n = A,T,C or G

<400> SEQUENCE: 192

gagctcggat ccaataatct ttgtctgagg gcagcacaca tatncagtgc catggnaact     60

ggtctacccc acatgggagc agcatgccgt agntatataa ggtcattccc tgagtcagac    120

atgcytyttt gaytaccgtg tgccaagtgc tggtgattct yaacacacyt ccatcccgyt    180

cttttgtgga aaaactggca cttktctgga actagcarga catcacttac aaattcaccc    240

acgagacact tgaaaggtgt aacaaagcga ytcttgcatt gctttttgtc cctccggcac    300

cagttgtcaa tactaacccg ctggtttgcc tccatcacat ttgtgatctg tagctctgga    360

tacatctcct gacagtactg aagaacttct tcttttgttt caaaagcarc tcttggtgcc    420

tgttggatca ggttcccatt tcccagtcyg aatgttcaca tggcatattt wacttcccac    480

aaaacattgc gatttgaggc tcagcaacag caaatcctgt tccggcattg gctgcaagag    540

cctcgatgta gccggccagc gccaaggcag gcgccgtgag ccccaccagc agcagaagca    600

g                                                                    601


<210> SEQ ID NO 193
<211> LENGTH: 608
<212> TYPE: DNA
<213> ORGANISM: Homo sapien
<220> FEATURE:
<221> NAME/KEY: misc_feature
<222> LOCATION: (1)...(608)
<223> OTHER INFORMATION: n = A,T,C or G

<400> SEQUENCE: 193

atacagccca natcccacca cgaagatgcg cttgttgact gagaacctga tgcggtcact     60
```

-continued

```
ggtcccgctg tagccccagc gactctccac ctgctggaag cggttgatgc tgcactcytt    120

cccaacgcag gcagmagcgg gsccggtcaa tgaactccay tcgtggcttg gggtkgacgg    180

tkaagtgcag gaagaggctg accacctcgc ggtccaccag gatgcccgac tgtgcgggac    240

ctgcagcgaa actcctcgat ggtcatgagc gggaagcgaa tgaggcccag ggccttgccc    300

agaaccttcc gcctgttctc tggcgtcacc tgcagctgct gccgctgaca ctcggcctcg    360

gaccagcgga caaacggcrt tgaacagccg cacctcacgg atgcccagtg tgtcgcgctc    420

caggammgsc accagcgtgt ccaggtcaat gtcggtgaag ccctccgcgg gtratggcgt    480

ctgcagtgtt tttgtcgatg ttctccaggc acaggctggc cagctgcggt tcatcgaaga    540

gtcgcgcctg cgtgagcagc atgaaggcgt tgtcggctcg cagttcttct tcaggaactc    600

cacgcaat                                                             608
```

<210> SEQ ID NO 194
<211> LENGTH: 392
<212> TYPE: DNA
<213> ORGANISM: Homo sapien
<220> FEATURE:
<221> NAME/KEY: misc_feature
<222> LOCATION: (1)...(392)
<223> OTHER INFORMATION: n = A,T,C or G

<400> SEQUENCE: 194

```
gaacggctgg accttgcctc gcattgtgct tgctggcagg gaataccttg gcaagcagyt     60

ccagtccgag cagccccaga ccgctgccgc ccgaagctaa gcctgcctct ggccttcccc    120

tccgcctcaa tgcagaacca gtagtgggag cactgtgttt agagttaaga gtgaacactg    180

tttgatttta cttgggaatt tcctctgtta tatagctttt cccaatgcta atttccaaac    240

aacaacaaca aaataacatg tttgcctgtt aagttgtata aaagtaggtg attctgtatt    300

taaagaaaat attactgtta catatactgc ttgcaatttc tgtatttatt gktnctstgg    360

aaataaatat agttattaaa ggttgtcant cc                                 392
```

<210> SEQ ID NO 195
<211> LENGTH: 502
<212> TYPE: DNA
<213> ORGANISM: Homo sapien
<220> FEATURE:
<221> NAME/KEY: misc_feature
<222> LOCATION: (1)...(502)
<223> OTHER INFORMATION: n = A,T,C or G

<400> SEQUENCE: 195

```
ccsttkgagg ggtkaggkyc cagttyccga gtggaagaaa caggccagga gaagtgcgtg     60

ccgagctgag gcagatgttc ccacagtgac ccccagagcc stgggstata gtytctgacc    120

cctcncaagg aaagaccacs ttctggggac atgggctgga gggcaggacc tagaggcacc    180

aagggaaggc cccattccgg ggstgttccc cgaggaggaa gggaagggc tctgtgtgcc     240

ccccasgagg aagaggccct gagtcctggg atcagacacc ccttcacgtg tatccccaca    300

caaatgcaag ctcaccaagg tcccctctca gtccccttcc stacaccctg amcggccact    360

gscscacacc cacccagagc acgccacccg ccatggggar tgtgctcaag gartcgcngg    420

gcarcgtgga catctngtcc cagaaggggg cagaatctcc aatagangga ctgarcmstt    480

gctnanaaaa aaaaanaaaa aa                                             502
```

<210> SEQ ID NO 196

-continued

<211> LENGTH: 665
<212> TYPE: DNA
<213> ORGANISM: Homo sapien
<220> FEATURE:
<221> NAME/KEY: misc_feature
<222> LOCATION: (1)...(665)
<223> OTHER INFORMATION: n = A,T,C or G

<400> SEQUENCE: 196
ggttacttgg tttcattgcc accacttagt ggatgtcatt tagaaccatt ttgtctgctc 60
cctctggaag ccttgcgcag agcggacttt gtaattgttg gagaataact gctgaatttt 120
wagctgtttk gagttgatts gcaccactgc acccacaact tcaatatgaa aacyawttga 180
actwatttat tatcttgtga aaagtataac aatgaaaatt ttgttcatac tgtattkatc 240
aagtatgatg aaaagcaawa gatatatatt cttttattat gttaaattat gattgccatt 300
attaatcggc aaaatgtgga gtgtatgttc ttttcacagt aatatatgcc ttttgtaact 360
tcacttggtt attttattgt aaatgartta caaaattctt aatttaagar aatggtatgt 420
watatttatt tcattaattt ctttcctkgt ttacgtwaat tttgaaaaga wtgcatgatt 480
tcttgacaga aatcgatctt gatgctgtgg aagtagtttg acccacatcc ctatgagttt 540
ttcttagaat gtataaaggt tgtagcccat cnaacttcaa agaaaaaaat gaccacatac 600
tttgcaatca ggctgaaatg tggcatgctn ttctaattcc aactttataa actagcaaan 660
aagtg 665

<210> SEQ ID NO 197
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 197
ttttnttttt ttttttttgc aggaaggatt ccatttattg tggatgcatt ttcacaatat 60
atgtttattg gagcgatcca ttatcagtga aaagtatcaa gtgtttataa natttttagg 120
aaggcagatt cacagaacat gctngtcngc ttgcagtttt acctcgtana gatnacagag 180
aattatagtc naaccagtaa acnaggaatt tacttttcaa aagattaaat ccaaactgaa 240
caaaattcta ccctgaaact tactccatcc aaatattgga ataanagtca gcagtgatac 300
attctcttct gaactttaga ttttctagaa aaatatgtaa tagtgatcag gaagagctct 360
tgttcaaaag tacaacnaag caatgttccc ttaccatagg ccttaattca aactttgatc 420
catttcactc ccatcacggg agtcaatgct acctgggaca cttgtatttt gttcatnctg 480
ancntggctt aa 492

<210> SEQ ID NO 198
<211> LENGTH: 478
<212> TYPE: DNA
<213> ORGANISM: Homo sapien
<220> FEATURE:
<221> NAME/KEY: misc_feature
<222> LOCATION: (1)...(478)
<223> OTHER INFORMATION: n = A,T,C or G

<400> SEQUENCE: 198
tttnttttgn atttcantct gtannaanta ttttcattat gtttattana aaaatatnaa 60
tgtntccacn acaaatcatn ttacntnagt aagaggccan ctacattgta caacatacac 120

-continued

```
tgagtatatt ttgaaaagga caagtttaaa gtanacncat attgccganc atancacatt    180

tatacatggc ttgattgata tttagcacag canaaactga gtgagttacc agaaanaaat    240

natatatgtc aatcngattt aagatacaaa acagatccta tggtacatan catcntgtag    300

gagttgtggc tttatgttta ctgaaagtca atgcagttcc tgtacaaaga gatggccgta    360

agcattctag tacctctact ccatggttaa gaatcgtaca cttatgttta catatgtnca    420

gggtaagaat tgtgttaagt naanttatgg agaggtccan gagaaaaatt tgatncaa      478
```

<210> SEQ ID NO 199
<211> LENGTH: 482
<212> TYPE: DNA
<213> ORGANISM: Homo sapien
<220> FEATURE:
<221> NAME/KEY: misc_feature
<222> LOCATION: (1)...(482)
<223> OTHER INFORMATION: n = A,T,C or G

<400> SEQUENCE: 199

```
agtgacttgt cctccaacaa aacccccttga tcaagtttgt ggcactgaca atcagaccta     60

tgctagttcc tgtcatctat tcgctactaa atgcagactg gaggggacca aaaaggggca    120

tcaactccag ctggattatt ttggagcctg caaatctatt cctacttgta cggactttga    180

agtgattcag tttcctctac ggatgagaga ctggctcaag aatatcctca tgcagcttta    240

tgaagccnac tctgaacacg ctggttatct nagatgagaa ncagagaaat aaagtcnaga    300

aaatttacct ggangaaaag aggctttngg ctggggacca tcccattgaa ccttctctta    360

anggacttta agaanaaact accacatgtn tgtngtatcc tggtgccngg ccgtttantg    420

aacntngacn ncacccttnt ggaatanant cttgacngcn tcctgaactt gctcctctgc    480

ga                                                                   482
```

<210> SEQ ID NO 200
<211> LENGTH: 270
<212> TYPE: DNA
<213> ORGANISM: Homo sapien
<220> FEATURE:
<221> NAME/KEY: misc_feature
<222> LOCATION: (1)...(270)
<223> OTHER INFORMATION: n = A,T,C or G

<400> SEQUENCE: 200

```
cggccgcaag tgcaactcca gctggggccg tgcggacgaa gattctgcca gcagttggtc     60

cgactgcgac gacggcggcg gcgacagtcg caggtgcagc gcgggcgcct ggggtcttgc    120

aaggctgagc tgacgccgca gaggtcgtgt cacgtcccac gaccttgacg ccgtcgggga    180

cagccggaac agagcccggt gaangcggga ggcctcgggg agcccctcgg gaagggcggc    240

ccgagagata cgcaggtgca ggtggccgcc                                     270
```

<210> SEQ ID NO 201
<211> LENGTH: 419
<212> TYPE: DNA
<213> ORGANISM: Homo sapien
<220> FEATURE:
<221> NAME/KEY: misc_feature
<222> LOCATION: (1)...(419)
<223> OTHER INFORMATION: n = A,T,C or G

<400> SEQUENCE: 201

```
tttttttttt ttttggaatc tactgcgagc acagcaggtc agcaacaagt ttattttgca     60
```

-continued

| | | |
|---|---|---|
| gctagcaagg taacagggta gggcatggtt acatgttcag gtcaacttcc tttgtcgtgg | 120 |
| ttgattggtt tgtctttatg ggggcggggt ggggtagggg aaancgaagc anaantaaca | 180 |
| tggagtgggt gcaccctccc tgtagaacct ggttacnaaa gcttgggggca gttcacctgg | 240 |
| tctgtgaccg tcattttctt gacatcaatg ttattagaag tcaggatatc ttttagagag | 300 |
| tccactgtnt ctggagggag attagggttt cttgccaana tccaancaaa atccacntga | 360 |
| aaaagttgga tgatncangt acngaatacc ganggcatan ttctcatant cggtggcca | 419 |

<210> SEQ ID NO 202
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 202

| | | |
|---|---|---|
| tttnttttt tttttttttt tttttttttt tttttttttt tttttttttt tttttttttt | 60 |
| tggcacttaa tccattttta tttcaaaatg tctacaaant ttnaatncnc cattatacng | 120 |
| gtnattttnc aaaatctaaa nnttattcaa atntnagcca aantccttac ncaaatnnaa | 180 |
| tacncncaaa aatcaaaaat atacntntct ttcagcaaac ttngttacat aaattaaaaa | 240 |
| aatatatacg gctggtgttt tcaaagtaca attatcttaa cactgcaaac atntttnnaa | 300 |
| ggaactaaaa taaaaaaaaa cactnccgca aaggttaaag ggaacaacaa attcntttta | 360 |
| caacancnnc nattataaaa atcatatctc aaatcttagg ggaatatata cttcacacng | 420 |
| ggatcttaac ttttactnca cttttgtttat ttttttanaa ccattgtntt gggcccaaca | 480 |
| caatggnaat nccnccncnc tggactagt | 509 |

<210> SEQ ID NO 203
<211> LENGTH: 583
<212> TYPE: DNA
<213> ORGANISM: Homo sapien
<220> FEATURE:
<221> NAME/KEY: misc_feature
<222> LOCATION: (1)...(583)
<223> OTHER INFORMATION: n = A,T,C or G

<400> SEQUENCE: 203

| | | |
|---|---|---|
| tttttttttt ttttttttga ccccccctctt ataaaaaaca agttaccatt ttattttact | 60 |
| tacacatatt tattttataa ttggtattag atattcaaaa ggcagctttt aaaatcaaac | 120 |
| taaatggaaa ctgccttaga tacataattc ttaggaatta gcttaaaatc tgcctaaagt | 180 |
| gaaaatcttc tctagctctt ttgactgtaa atttttgact cttgtaaaac atccaaattc | 240 |
| attttttcttg tctttaaaat tatctaatct ttccatttttt tccctattcc aagtcaattt | 300 |
| gcttctctag cctcatttcc tagctcttat ctactattag taagtggctt ttttcctaaa | 360 |
| agggaaaaca ggaagagana atggcacaca aaacaaacat tttatattca tatttctacc | 420 |
| tacgttaata aaatagcatt ttgtgaagcc agctcaaaag aaggcttaga tccttttatg | 480 |
| tccattttag tcactaaacg atatcnaaag tgccagaatg caaaaggttt gtgaacattt | 540 |
| attcaaaagc taatataaga tatttcacat actcatcttt ctg | 583 |

<210> SEQ ID NO 204
<211> LENGTH: 589
<212> TYPE: DNA
<213> ORGANISM: Homo sapien
<220> FEATURE:
<221> NAME/KEY: misc_feature
<222> LOCATION: (1)...(589)
<223> OTHER INFORMATION: n = A,T,C or G

<400> SEQUENCE: 204

```
tttttttttnt tttttttttt ttttttnctc ttcttttttt ttganaatga ggatcgagtt     60

tttcactctc tagatagggc atgaagaaaa ctcatctttc cagctttaaa ataacaatca    120

aatctcttat gctatatcat attttaagtt aaactaatga gtcactggct tatcttctcc    180

tgaaggaaat ctgttcattc ttctcattca tatagttata tcaagtacta ccttgcatat    240

tgagaggttt ttcttctcta tttacacata tatttccatg tgaatttgta tcaaaccttt    300

attttcatgc aaactagaaa ataatgtntt cttttgcata agagaagaga acaatatnag    360

cattacaaaa ctgctcaaat tgtttgttaa gnttatccat tataattagt tnggcaggag    420

ctaatacaaa tcacatttac ngacnagcaa taataaaact gaagtaccag ttaaatatcc    480

aaaataatta aaggaacatt tttagcctgg gtataattag ctaattcact ttacaagcat    540

ttattnagaa tgaattcaca tgttattatt ccntagccca acacaatgg              589
```

<210> SEQ ID NO 205
<211> LENGTH: 545
<212> TYPE: DNA
<213> ORGANISM: Homo sapien
<220> FEATURE:
<221> NAME/KEY: misc_feature
<222> LOCATION: (1)...(545)
<223> OTHER INFORMATION: n = A,T,C or G

<400> SEQUENCE: 205

```
tttttntttt ttttttcagt aataatcaga acaatattta tttttatatt taaaattcat     60

agaaaagtgc cttacattta ataaaagttt gtttctcaaa gtgatcagag gaattagata    120

tngtcttgaa caccaatatt aatttgagga aaatacacca aaatacatta agtaaattat    180

ttaagatcat agagcttgta agtgaaaaga taaaatttga cctcagaaac tctgagcatt    240

aaaaatccac tattagcaaa taaattacta tggacttctt gctttaattt tgtgatgaat    300

atggggtgtc actggtaaac caacacattc tgaaggatac attacttagt gatagattct    360

tatgtacttt gctanatnac gtggatatga gttgacaagt ttctctttct tcaatctttt    420

aaggggcnga ngaaatgagg aagaaaagaa aaggattacg catactgttc tttctatngg    480

aaggattaga tatgtttcct ttgccaatat taaaaaaata ataatgttta ctactagtga    540

aaccc                                                              545
```

<210> SEQ ID NO 206
<211> LENGTH: 487
<212> TYPE: DNA
<213> ORGANISM: Homo sapien
<220> FEATURE:
<221> NAME/KEY: misc_feature
<222> LOCATION: (1)...(487)
<223> OTHER INFORMATION: n = A,T,C or G

<400> SEQUENCE: 206

```
tttttttttt ttttttagtc aagtttctna tttttattat aattaaagtc ttggtcattt     60

catttattag ctctgcaact tacatattta aattaaagaa acgttnttag acaactgtna    120

caatttataa atgtaaggtg ccattattga gtanatatat tcctccaaga gtggatgtgt    180

cccttctccc accaactaat gaancagcaa cattagttta attttattag tagatnatac    240
```

-continued

```
actgctgcaa acgctaattc tcttctccat ccccatgtng atattgtgta tatgtgtgag    300

ttggtnagaa tgcatcanca atctnacaat caacagcaag atgaagctag gcntgggctt    360

tcggtgaaaa tagactgtgt ctgtctgaat caaatgatct gacctatcct cggtggcaag    420

aactcttcga accgcttcct caaaggcngc tgccacattt gtggcntctn ttgcacttgt    480

ttcaaaa                                                              487
```

<210> SEQ ID NO 207
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 207

```
tgaattggct aaaagactgc atttttanaa ctagcaactc ttatttcttt cctttaaaaa     60

tacatagcat taaatcccaa atcctattta aagacctgac agcttgagaa ggtcactact    120

gcatttatag gaccttctgg tggttctgct gttacntttg aantctgaca atccttgana    180

atctttgcat gcagaggagg taaaaggtat tggattttca cagaggaana acacagcgca    240

gaaatgaagg ggccaggctt actgagcttg tccactggag ggctcatggg tgggacatgg    300

aaaagaaggc agcctaggcc ctggggagcc ca                                  332
```

<210> SEQ ID NO 208
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 208

```
agggcgtggt gcggagggcg ttactgtttt gtctcagtaa caataaatac aaaaagactg     60

gttgtgttcc ggccccatcc aaccacgaag ttgatttctc ttgtgtgcag agtgactgat    120

tttaaaggac atggagcttg tcacaatgtc acaatgtcac agtgtgaagg gcacactcac    180

tcccgcgtga ttcacattta gcaaccaaca atagctcatg agtccatact tgtaaatact    240

tttggcagaa tacttnttga aacttgcaga tgataactaa gatccaagat atttcccaaa    300

gtaaatagaa gtgggtcata atattaatta cctgttcaca tcagcttcca tttacaagtc    360

atgagcccag acactgacat caaactaagc ccacttagac tcctcaccac cagtctgtcc    420

tgtcatcaga caggaggctg tcaccttgac caaattctca ccagtcaatc atctatccaa    480

aaaccattac ctgatccact tccggtaatg caccaccttg gtga                     524
```

<210> SEQ ID NO 209
<211> LENGTH: 159
<212> TYPE: DNA
<213> ORGANISM: Homo sapien

<400> SEQUENCE: 209

```
gggtgaggaa atccagagtt gccatggaga aaattccagt gtcagcattc ttgctccttg     60

tggccctctc ctacactctg gccagagata ccacagtcaa acctggagcc aaaaaggaca    120

caaaggactc tcgacccaaa ctgccccaga ccctctcca                           159
```

-continued

<210> SEQ ID NO 210
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 210
actccctggc agacaaaggc agaggagaga gctctgttag ttctgtgttg ttgaactgcc 60
actgaatttc tttccacttg gactattaca tgccanttga gggactaatg gaaaaacgta 120
tggggagatt ttanccaatt tangtntgta aatggggaga ctggggcagg cgggagagat 180
ttgcagggtg naaatgggan ggctggtttg ttanatgaac agggacatag gaggtaggca 240
ccaggatgct aaatca 256

<210> SEQ ID NO 211
<211> LENGTH: 264
<212> TYPE: DNA
<213> ORGANISM: Homo sapien
<220> FEATURE:
<221> NAME/KEY: misc_feature
<222> LOCATION: (1)...(264)
<223> OTHER INFORMATION: n = A,T,C or G

<400> SEQUENCE: 211
acattgtttt tttgagataa agcattgaga gagctctcct taacgtgaca caatggaagg 60
actggaacac atacccacat ctttgttctg agggataatt ttctgataaa gtcttgctgt 120
atattcaagc acatatgtta tatattattc agttccatgt ttatagccta gttaaggaga 180
ggggagatac attcngaaag aggactgaaa gaaatactca agtnggaaaa cagaaaaaga 240
aaaaaaggag caaatgagaa gcct 264

<210> SEQ ID NO 212
<211> LENGTH: 328
<212> TYPE: DNA
<213> ORGANISM: Homo sapien
<220> FEATURE:
<221> NAME/KEY: misc_feature
<222> LOCATION: (1)...(328)
<223> OTHER INFORMATION: n = A,T,C or G

<400> SEQUENCE: 212
acccaaaaat ccaatgctga atatttggct tcattattcc canattcttt gattgtcaaa 60
ggatttaatg ttgtctcagc ttgggcactt cagttaggac ctaaggatgc cagccggcag 120
gtttatatat gcagcaacaa tattcaagcg cgacaacagg ttattgaact tgcccgccag 180
ttnaatttca ttcccattga cttgggatcc ttatcatcag ccagagagat tgaaaattta 240
cccctacnac tctttactct ctgganaggg ccagtggtgg tagctataag cttggccaca 300
tttttttttc ctttattcct ttgtcaga 328

<210> SEQ ID NO 213
<211> LENGTH: 250
<212> TYPE: DNA
<213> ORGANISM: Homo sapien
<220> FEATURE:
<221> NAME/KEY: misc_feature
<222> LOCATION: (1)...(250)
<223> OTHER INFORMATION: n = A,T,C or G

<400> SEQUENCE: 213

-continued

```
acttatgagc agagcgacat atccnagtgt agactgaata aaactgaatt ctctccagtt     60

taaagcattg ctcactgaag ggatagaagt gactgccagg agggaaagta agccaaggct    120

cattatgcca aagganatat acatttcaat tctccaaact tcttcctcat tccaagagtt    180

ttcaatattt gcatgaacct gctgataanc catgttaana aacaaatatc tctctnacct    240

tctcatcggt                                                           250
```

```
<210> SEQ ID NO 214
<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 214

acccagaatc caatgctgaa tatttggctt cattattccc agattctttg attgtcaaag     60

gatttaatgt tgtctcagct tgggcacttc agttaggacc taaggatgcc agccggcagg    120

tttatatatg cagcaacaat attcaagcgc gacaacaggt tattgaactt gcccgccagt    180

tgaatttcat tcccattgac ttgggatcct tatcatcagc canagagatt gaaaatttac    240

ccctacgact ctttactctc tggagagggc cagtggtggt agctataagc ttggccacat    300

ttttttttcc tttattcctt tgtcagagat gcgattcatc catatgctan aaaccaacag    360

agtgactttt acaaaattcc tataganatt gtgaataaaa ccttacctat agttgccatt    420

actttgctct ccctaatata cctc                                           444
```

```
<210> SEQ ID NO 215
<211> LENGTH: 366
<212> TYPE: DNA
<213> ORGANISM: Homo sapien
<220> FEATURE:
<221> NAME/KEY: misc_feature
<222> LOCATION: (1)...(366)
<223> OTHER INFORMATION: n = A,T,C or G

<400> SEQUENCE: 215

acttatgagc agagcgacat atccaagtgt anactgaata aaactgaatt ctctccagtt     60

taaagcattg ctcactgaag ggatagaagt gactgccagg agggaaagta agccaaggct    120

cattatgcca aagganatat acatttcaat tctccaaact tcttcctcat tccaagagtt    180

ttcaatattt gcatgaacct gctgataagc catgttgaga aacaaatatc tctctgacct    240

tctcatcggt aagcagaggc tgtaggcaac atggaccata gcgaanaaaa aacttagtaa    300

tccaagctgt tttctacact gtaaccaggt ttccaaccaa ggtggaaatc tcctatactt    360

ggtgcc                                                               366
```

```
<210> SEQ ID NO 216
<211> LENGTH: 260
<212> TYPE: DNA
<213> ORGANISM: Homo sapien
<220> FEATURE:
<221> NAME/KEY: misc_feature
<222> LOCATION: (1)...(260)
<223> OTHER INFORMATION: n = A,T,C or G

<400> SEQUENCE: 216

ctgtataaac agaactccac tgcangaggg agggccgggc caggagaatc tccgcttgtc     60

caagacaggg gcctaaggag ggtctccaca ctgctnntaa gggctnttnc attttttttat    120
```

-continued

```
taataaaaag tnnaaaaggc ctcttctcaa cttttttccc ttnggctgga aaatttaaaa    180

atcaaaaatt tcctnaagtt ntcaagctat catatatact ntatcctgaa aaagcaacat    240

aattcttcct tccctccttt                                                260
```

<210> SEQ ID NO 217
<211> LENGTH: 262
<212> TYPE: DNA
<213> ORGANISM: Homo sapien
<220> FEATURE:
<221> NAME/KEY: misc_feature
<222> LOCATION: (1)...(262)
<223> OTHER INFORMATION: n = A,T,C or G

<400> SEQUENCE: 217

```
acctacgtgg gtaagtttan aaatgttata atttcaggaa naggaacgca tataattgta     60

tcttgcctat aattttctat tttaataagg aaatagcaaa ttggggtggg gggaatgtag    120

ggcattctac agtttgagca aaatgcaatt aaatgtggaa ggacagcact gaaaaatttt    180

atgaataatc tgtatgatta tatgtctcta gagtagattt ataattagcc acttacccta    240

atatccttca tgcttgtaaa gt                                             262
```

<210> SEQ ID NO 218
<211> LENGTH: 205
<212> TYPE: DNA
<213> ORGANISM: Homo sapien
<220> FEATURE:
<221> NAME/KEY: misc_feature
<222> LOCATION: (1)...(205)
<223> OTHER INFORMATION: n = A,T,C or G

<400> SEQUENCE: 218

```
accaaggtgg tgcattaccg gaantggatc aangacacca tcgtggccaa cccctgagca     60

cccctatcaa ctccctttg tagtaaactt ggaaccttgg aaatgaccag gccaagactc    120

aggcctcccc agttctactg acctttgtcc ttangtntna ngtccagggt tgctaggaaa    180

anaaatcagc agacacaggt gtaaa                                          205
```

<210> SEQ ID NO 219
<211> LENGTH: 114
<212> TYPE: DNA
<213> ORGANISM: Homo sapien

<400> SEQUENCE: 219

```
tactgttttg tctcagtaac aataaataca aaaagactgg ttgtgttccg gccccatcca     60

accacgaagt tgatttctct tgtgtgcaga gtgactgatt ttaaaggaca tgga          114
```

<210> SEQ ID NO 220
<211> LENGTH: 93
<212> TYPE: DNA
<213> ORGANISM: Homo sapien

<400> SEQUENCE: 220

```
actagccagc acaaaaggca gggtagcctg aattgctttc tgctctttac atttctttta     60

aaataagcat ttagtgctca gtccctactg agt                                  93
```

<210> SEQ ID NO 221
<211> LENGTH: 167
<212> TYPE: DNA
<213> ORGANISM: Homo sapien
<220> FEATURE:

<221> NAME/KEY: misc_feature
<222> LOCATION: (1)...(167)
<223> OTHER INFORMATION: n = A,T,C or G

<400> SEQUENCE: 221
actangtgca ggtgcgcaca aatatttgtc gatattccct tcatcttgga ttccatgagg 60
tcttttgccc agcctgtggc tctactgtag taagtttctg ctgatgagga gccagnatgc 120
cccccactac cttccctgac gctccccana aatcacccaa cctctgt 167

<210> SEQ ID NO 222
<211> LENGTH: 351
<212> TYPE: DNA
<213> ORGANISM: Homo sapien

<400> SEQUENCE: 222
agggcgtggt gcggagggcg gtactgacct cattagtagg aggatgcatt ctggcacccc 60
gttcttcacc tgtcccccaa tccttaaaag gccatactgc ataaagtcaa caacagataa 120
atgtttgctg aattaaagga tggatgaaaa aaattaataa tgaatttttg cataatccaa 180
ttttctcttt tatatttcta gaagaagttt ctttgagcct attagatccc gggaatcttt 240
taggtgagca tgattagaga gcttgtaggt tgcttttaca tatatctggc atatttgagt 300
ctcgtatcaa aacaatagat tggtaaaggt ggtattattg tattgataag t 351

<210> SEQ ID NO 223
<211> LENGTH: 383
<212> TYPE: DNA
<213> ORGANISM: Homo sapien
<220> FEATURE:
<221> NAME/KEY: misc_feature
<222> LOCATION: (1)...(383)
<223> OTHER INFORMATION: n = A,T,C or G

<400> SEQUENCE: 223
aaaacaaaca aacaaaaaaa acaattcttc attcagaaaa attatcttag ggactgatat 60
tggtaattat ggtcaattta atwrtrttkt ggggcatttc cttacattgt cttgacaaga 120
ttaaaatgtc tgtgccaaaa ttttgtattt tatttggaga cttcttatca aaagtaatgc 180
tgccaaagga agtctaagga attagtagtg ttcccmtcac ttgtttggag tgtgctattc 240
taaaagattt tgatttcctg gaatgacaat tatattttaa ctttggtggg ggaaanagtt 300
ataggaccac agtcttcact tctgatactt gtaaattaat cttttattgc acttgttttg 360
accattaagc tatatgttta aaa 383

<210> SEQ ID NO 224
<211> LENGTH: 320
<212> TYPE: DNA
<213> ORGANISM: Homo sapien

<400> SEQUENCE: 224
cccctgaagg cttcttgtta gaaaatagta cagttacaac caataggaac aacaaaaaga 60
aaaagtttgt gacattgtag tagggagtgt gtacccctta ctccccatca aaaaaaaaat 120
ggatacatgg ttaaaggata raagggcaat attttatcat atgttctaaa agagaaggaa 180
gagaaaatac tactttctcr aaatggaagc ccttaaaggt gctttgatac tgaaggacac 240
aaatgtggcc gtccatcctc ctttaragtt gcatgacttg gacacggtaa ctgttgcagt 300
tttaractcm gcattgtgac 320

-continued

<210> SEQ ID NO 225
<211> LENGTH: 1214
<212> TYPE: DNA
<213> ORGANISM: Homo sapien

<400> SEQUENCE: 225
gaggactgca gcccgcactc gcagccctgg caggcggcac tggtcatgga aaacgaattg 60
ttctgctcgg gcgtcctggt gcatccgcag tgggtgctgt cagccgcaca ctgtttccag 120
aactcctaca ccatcgggct gggcctgcac agtcttgagg ccgaccaaga gccagggagc 180
cagatggtgg aggccagcct ctccgtacgg cacccagagt acaacagacc cttgctcgct 240
aacgacctca tgctcatcaa gttggacgaa tccgtgtccg agtctgacac catccggagc 300
atcagcattg cttcgcagtg ccctaccgcg gggaactctt gcctcgtttc tggctggggt 360
ctgctggcga acggcagaat gcctaccgtg ctgcagtgcg tgaacgtgtc ggtggtgtct 420
gaggaggtct gcagtaagct ctatgacccg ctgtaccacc ccagcatgtt ctgcgccggc 480
ggagggcaag accagaagga ctcctgcaac ggtgactctg gggggcccct gatctgcaac 540
gggtacttgc agggccttgt gtctttcgga aaagccccgt gtggccaagt tggcgtgcca 600
ggtgtctaca ccaacctctg caaattcact gagtggatag agaaaaccgt ccaggccagt 660
taactctggg gactgggaac ccatgaaatt gacccccaaa tacatcctgc ggaaggaatt 720
caggaatatc tgttcccagc ccctcctccc tcaggcccag gagtccaggc ccccagcccc 780
tcctccctca aaccaagggt acagatcccc agcccctcct ccctcagacc caggagtcca 840 gacccccag cccctcctcc ctcagaccca ggagtccagc ccctcctccc tcagacccag 900
gagtccagac cccccagccc ctcctccctc agacccaggg gtccaggccc ccaacccctc 960
ctccctcaga ctcagaggtc caagccccca acccctcctt ccccagaccc agaggtccag 1020
gtcccagccc ctcctccctc agacccagcg gtccaatgcc acctagactc tccctgtaca 1080
cagtgccccc ttgtggcacg ttgacccaac cttaccagtt ggtttttcat tttttgtccc 1140
tttcccctag atccagaaat aaagtctaag agaagcgcaa aaaaaaaaaa aaaaaaaaaa 1200
aaaaaaaaaa aaaa 1214

<210> SEQ ID NO 226
<211> LENGTH: 119
<212> TYPE: DNA
<213> ORGANISM: Homo sapien

<400> SEQUENCE: 226
acccagtatg tgcagggaga cggaacccca tgtgacagcc cactccacca gggttcccaa 60
agaacctggc ccagtcataa tcattcatcc tgacagtggc aataatcacg ataaccagt 119

<210> SEQ ID NO 227
<211> LENGTH: 818
<212> TYPE: DNA
<213> ORGANISM: Homo sapien

<400> SEQUENCE: 227
acaattcata gggacgacca atgaggacag ggaatgaacc cggctctccc ccagccctga 60
tttttgctac atatggggtc ccttttcatt ctttgcaaaa acactgggtt ttctgagaac 120
acggacggtt cttagcacaa tttgtgaaat ctgtgtaraa ccgggctttg caggggagat 180
aattttcctc ctctggagga aaggtggtga ttgacaggca gggagacagt gacaaggcta 240
gagaaagcca cgctcggcct tctctgaacc aggatggaac ggcagacccc tgaaaacgaa 300

-continued

```
gcttgtcccc ttccaatcag ccacttctga gaacccccat ctaacttcct actggaaaag    360

agggcctcct caggagcagt ccaagagttt tcaaagataa cgtgacaact accatctaga    420

ggaaagggtg caccctcagc agagaagccg agagcttaac tctggtcgtt tccagagaca    480

acctgctggc tgtcttggga tgcgcccagc ctttgagagg ccactacccc atgaacttct    540

gccatccact ggacatgaag ctgaggacac tgggcttcaa cactgagttg tcatgagagg    600

gacaggctct gccctcaagc cggctgaggg cagcaaccac tctcctcccc tttctcacgc    660

aaagccattc ccacaaatcc agaccatacc atgaagcaac gagacccaaa cagtttggct    720

caagaggata tgaggactgt ctcagcctgg ctttgggctg acaccatgca cacacacaag    780

gtccacttct aggttttcag cctagatggg agtcgtgt                            818
```

<210> SEQ ID NO 228
<211> LENGTH: 744
<212> TYPE: DNA
<213> ORGANISM: Homo sapien

<400> SEQUENCE: 228

```
actggagaca ctgttgaact tgatcaagac ccagaccacc ccaggtctcc ttcgtgggat     60

gtcatgacgt ttgacatacc tttggaacga gcctcctcct tggaagatgg aagaccgtgt    120

tcgtggccga cctggcctct cctggcctgt ttcttaagat gcggagtcac atttcaatgg    180

taggaaaagt ggcttcgtaa aatagaagag cagtcactgt ggaactacca aatggcgaga    240

tgctcggtgc acattggggt gctttgggat aaaagattta tgagccaact attctctggc    300

accagattct aggccagttt gttccactga agcttttccc acagcagtcc acctctgcag    360

gctggcagct gaatggcttg ccggtggctc tgtggcaaga tcacactgag atcgatgggt    420

gagaaggcta ggatgcttgt ctagtgttct tagctgtcac gttggctcct tccaggttgg    480

ccagacggtg ttggccactc ccttctaaaa cacaggcgcc ctcctggtga cagtgacccg    540

ccgtggtatg ccttggccca ttccagcagt cccagttatg catttcaagt ttggggtttg    600

ttcttttcgt taatgttcct ctgtgttgtc agctgtcttc atttcctggg ctaagcagca    660

ttgggagatg tggaccagag atccactcct taagaaccag tggcgaaaga cactttcttt    720

cttcactctg aagtagctgg tggt                                           744
```

<210> SEQ ID NO 229
<211> LENGTH: 300
<212> TYPE: DNA
<213> ORGANISM: Homo sapien

<400> SEQUENCE: 229

```
cgagtctggg ttttgtctat aaagtttgat ccctcctttt ctcatccaaa tcatgtgaac     60

cattacacat cgaaataaaa gaaaggtggc agacttgccc aacgccaggc tgacatgtgc    120

tgcagggttg ttgtttttta attattattg ttagaaacgt cacccacagt ccctgttaat    180

ttgtatgtga cagccaactc tgagaaggtc ctatttttcc acctgcagag gatccagtct    240

cactaggctc ctccttgccc tcacactgga gtctccgcca gtgtgggtgc ccactgacat    300
```

<210> SEQ ID NO 230
<211> LENGTH: 301
<212> TYPE: DNA
<213> ORGANISM: Homo sapien

<400> SEQUENCE: 230

```
cagcagaaca aatacaaata tgaagagtgc aaagatctca taaaatctat gctgaggaat     60
```

-continued gagcgacagt tcaaggagga gaagcttgca gagcagctca agcaagctga ggagctcagg 120
caatataaag tcctggttca cactcaggaa cgagagctga cccagttaag ggagaagttg 180
cgggaaggga gagatgcctc cctctcattg aatgagcatc tccaggccct cctcactccg 240
gatgaaccgg acaagtccca ggggcaggac ctccaagaaa cagacctcgg ccgcgaccac 300
g 301

<210> SEQ ID NO 231
<211> LENGTH: 301
<212> TYPE: DNA
<213> ORGANISM: Homo sapien

<400> SEQUENCE: 231
gcaagcacgc tggcaaatct ctgtcaggtc agctccagag aagccattag tcattttagc 60
caggaactcc aagtccacat ccttggcaac tggggacttg cgcaggttag ccttgaggat 120
ggcaacacgg gacttctcat caggaagtgg gatgtagatg agctgatcaa gacggccagg 180
tctgaggatg gcaggatcaa tgatgtcagg ccggttggta ccgccaatga tgaacacatt 240
tttttttgtg gacatgccat ccatttctgt caggatctgg ttgatgactc ggtcagcagc 300
c 301

<210> SEQ ID NO 232
<211> LENGTH: 301
<212> TYPE: DNA
<213> ORGANISM: Homo sapien

<400> SEQUENCE: 232
agtaggtatt tcgtgagaag ttcaacacca aaactggaac atagttctcc ttcaagtgtt 60
ggcgacagcg gggcttcctg attctggaat ataactttgt gtaaattaac agccacctat 120
agaagagtcc atctgctgtg aaggagagac agagaactct gggttccgtc gtcctgtcca 180
cgtgctgtac caagtgctgg tgccagcctg ttacctgttc tcactgaaaa tctggctaat 240
gctcttgtgt atcacttctg attctgacaa tcaatcaatc aatggcctag agcactgact 300
g 301

<210> SEQ ID NO 233
<211> LENGTH: 301
<212> TYPE: DNA
<213> ORGANISM: Homo sapien

<400> SEQUENCE: 233
atgactgact tcccagtaag gctctctaag gggtaagtag gaggatccac aggatttgag 60
atgctaaggc cccagagatc gtttgatcca accctcttat tttcagaggg gaaaatgggg 120
cctagaagtt acagagcatc tagctggtgc gctggcaccc ctggcctcac acagactccc 180
gagtagctgg gactacaggc acacagtcac tgaagcaggc cctgttagca attctatgcg 240
tacaaattaa catgagatga gtagagactt tattgagaaa gcaagagaaa atcctatcaa 300
c 301

<210> SEQ ID NO 234
<211> LENGTH: 301
<212> TYPE: DNA
<213> ORGANISM: Homo sapien

<400> SEQUENCE: 234

-continued aggtcctaca catcgagact catccatgat tgatatgaat ttaaaaatta caagcaaaga 60
cattttattc atcatgatgc tttcttttgt ttcttctttt cgttttcttc tttttctttt 120
tcaatttcag caacatactt ctcaatttct tcaggattta aaatcttgag ggattgatct 180
cgcctcatga cagcaagttc aatgtttttg ccacctgact gaaccacttc caggagtgcc 240
ttgatcacca gcttaatggt cagatcatct gcttcaatgg cttcgtcagt atagttcttc 300
t 301

<210> SEQ ID NO 235
<211> LENGTH: 283
<212> TYPE: DNA
<213> ORGANISM: Homo sapien

<400> SEQUENCE: 235
tggggctgtg catcaggcgg gtttgagaaa tattcaattc tcagcagaag ccagaatttg 60
aattccctca tcttttaggg aatcatttac caggtttgga gaggattcag acagctcagg 120
tgctttcact aatgtctctg aacttctgtc cctctttgtt catggatagt ccaataaata 180
atgttatctt tgaactgatg ctcataggag agaatataag aactctgagt gatatcaaca 240
ttagggattc aaagaaatat tagatttaag ctcacactgg tca 283

<210> SEQ ID NO 236
<211> LENGTH: 301
<212> TYPE: DNA
<213> ORGANISM: Homo sapien

<400> SEQUENCE: 236
aggtcctcca ccaactgcct gaagcacggt taaaattggg aagaagtata gtgcagcata 60
aatactttta aatcgatcag atttccctaa cccacatgca atcttcttca ccagaagagg 120
tcggagcagc atcattaata ccaagcagaa tgcgtaatag ataaatacaa tggtatatag 180
tgggtagacg gcttcatgag tacagtgtac tgtggtatcg taatctggac ttgggttgta 240
aagcatcgtg taccagtcag aaagcatcaa tactcgacat gaacgaatat aaagaacacc 300
a 301

<210> SEQ ID NO 237
<211> LENGTH: 301
<212> TYPE: DNA
<213> ORGANISM: Homo sapien

<400> SEQUENCE: 237
cagtggtagt ggtggtggac gtggcgttgg tcgtggtgcc ttttttggtg cccgtcacaa 60
actcaatttt tgttcgctcc tttttggcct tttccaattt gtccatctca attttctggg 120
ccttggctaa tgcctcatag taggagtcct cagaccagcc atggggatca aacatatcct 180
ttgggtagtt ggtgccaagc tcgtcaatgg cacagaatgg atcagcttct cgtaaatcta 240
gggttccgaa attctttctt cctttggata atgtagttca tatccattcc ctcctttatc 300
t 301

<210> SEQ ID NO 238
<211> LENGTH: 301
<212> TYPE: DNA
<213> ORGANISM: Homo sapien

<400> SEQUENCE: 238
gggcaggttt tttttttttt ttttttgatg gtgcagaccc ttgctttatt tgtctgactt 60
gttcacagtt cagccccctg ctcagaaaac caacgggcca gctaaggaga ggaggaggca 120
ccttgagact tccggagtcg aggctctcca gggttcccca gcccatcaat cattttctgc 180
accccctgcc tgggaagcag ctccctgggg ggtgggaatg ggtgactaga agggatttca 240
gtgtgggacc cagggtctgt tcttcacagt aggaggtgga agggatgact aatttcttta 300
t 301

<210> SEQ ID NO 239
<211> LENGTH: 239
<212> TYPE: DNA
<213> ORGANISM: Homo sapien

<400> SEQUENCE: 239
ataagcagct agggaattct ttatttagta atgtcctaac ataaaagttc acataactgc 60
ttctgtcaaa ccatgatact gagctttgtg acaacccaga aataactaag agaaggcaaa 120
cataatacct tagagatcaa gaaacattta cacagttcaa ctgtttaaaa atagctcaac 180
attcagccag tgagtagagt gtgaatgcca gcatacacag tatacaggtc cttcaggga 239

<210> SEQ ID NO 240
<211> LENGTH: 300
<212> TYPE: DNA
<213> ORGANISM: Homo sapien

<400> SEQUENCE: 240
ggtcctaatg aagcagcagc ttccacattt taacgcaggt ttacggtgat actgtccttt 60
gggatctgcc ctccagtgga accttttaag gaagaagtgg gcccaagcta agttccacat 120
gctgggtgag ccagatgact tctgttccct ggtcactttc ttcaatgggg cgaatggggg 180
ctgccaggtt tttaaaatca tgcttcatct tgaagcacac ggtcacttca ccctcctcac 240
gctgtgggtg tactttgatg aaaataccca ctttgttggc ctttctgaag ctataatgtc 300

<210> SEQ ID NO 241
<211> LENGTH: 301
<212> TYPE: DNA
<213> ORGANISM: Homo sapien

<400> SEQUENCE: 241
gaggtctggt gctgaggtct ctgggctagg aagaggagtt ctgtggagct ggaagccaga 60
cctctttgga ggaaactcca gcagctatgt tggtgtctct gagggaatgc aacaaggctg 120
ctcctccatg tattggaaaa ctgcaaactg gactcaactg gaaggaagtg ctgctgccag 180
tgtgaagaac cagcctgagg tgacagaaac ggaagcaaac aggaacagcc agtcttttct 240
tcctcctcct gtcatacggt ctctctcaag catcctttgt tgtcaggggc ctaaaaggga 300
g 301

<210> SEQ ID NO 242
<211> LENGTH: 301
<212> TYPE: DNA
<213> ORGANISM: Homo sapien

<400> SEQUENCE: 242
ccgaggtcct gggatgcaac caatcactct gtttcacgtg acttttatca ccatacaatt 60
tgtggcattt cctcattttc tacattgtag aatcaagagt gtaaataaat gtatatcgat 120
gtcttcaaga atatatcatt cctttttcac tagaacccat tcaaaatata agtcaagaat 180

-continued cttaatatca acaaatatat caagcaaact ggaaggcaga ataactacca taatttagta 240
taagtaccca aagttttata aatcaaaagc cctaatgata accattttta gaattcaatc 300
a 301

<210> SEQ ID NO 243
<211> LENGTH: 301
<212> TYPE: DNA
<213> ORGANISM: Homo sapien

<400> SEQUENCE: 243
aggtaagtcc cagtttgaag ctcaaaagat ctggtatgag cataggctca tcgacgacat 60
ggtggcccaa gctatgaaat cagagggagg cttcatctgg gcctgtaaaa actatgatgg 120
tgacgtgcag tcggactctg tggcccaagg gtatggctct ctcggcatga tgaccagcgt 180
gctggtttgt ccagatggca agacagtaga agcagaggct gcccacggga ctgtaacccg 240
tcactaccgc atgttccaga aaggacagga gacgtccacc aatcccattg cttccatttt 300
t 301

<210> SEQ ID NO 244
<211> LENGTH: 300
<212> TYPE: DNA
<213> ORGANISM: Homo sapien

<400> SEQUENCE: 244
gctggtttgc aagaatgaaa tgaatgattc tacagctagg acttaacctt gaaatggaaa 60
gtcatgcaat cccatttgca ggatctgtct gtgcacatgc ctctgtagag agcagcattc 120
ccagggacct tggaaacagt tgacactgta aggtgcttgc tccccaagac acatcctaaa 180
aggtgttgta atggtgaaaa cgtcttcctt ctttattgcc ccttcttatt tatgtgaaca 240
actgtttgtc ttttgtgtat cttttttaaa ctgtaaagtt caattgtgaa aatgaatatc 300

<210> SEQ ID NO 245
<211> LENGTH: 301
<212> TYPE: DNA
<213> ORGANISM: Homo sapien

<400> SEQUENCE: 245
gtctgagtat ttaaaatgtt attgaaatta tccccaacca atgttagaaa agaaagaggt 60
tatatactta gataaaaaat gaggtgaatt actatccatt gaaatcatgc tcttagaatt 120
aaggccagga gatattgtca ttaatgtara cttcaggaca ctagagtata gcagccctat 180
gttttcaaag agcagagatg caattaaata ttgtttagca tcaaaaaggc cactcaatac 240
agctaataaa atgaaagacc taatttctaa agcaattctt tataatttac aaagttttaa 300
g 301

<210> SEQ ID NO 246
<211> LENGTH: 301
<212> TYPE: DNA
<213> ORGANISM: Homo sapien

<400> SEQUENCE: 246
ggtctgtcct acaatgcctg cttcttgaaa gaagtcggca ctttctagaa tagctaaata 60
acctgggctt attttaaaga actatttgta gctcagattg gttttcctat ggctaaaata 120
agtgcttctt gtgaaaatta aataaaacag ttaattcaaa gccttgatat atgttaccac 180
taacaatcat actaaatata ttttgaagta caaagtttga catgctctaa agtgacaacc 240

-continued caaatgtgtc ttacaaaaca cgttcctaac aaggtatgct ttacactacc aatgcagaaa 300
c 301

<210> SEQ ID NO 247
<211> LENGTH: 301
<212> TYPE: DNA
<213> ORGANISM: Homo sapien

<400> SEQUENCE: 247
aggtcctttg gcagggctca tggatcagag ctcaaactgg agggaaaggc atttcgggta 60
gcctaagagg gcgactggcg gcagcacaac caaggaaggc aaggttgttt cccccacgct 120
gtgtcctgtg ttcaggtgcg acacacaatc ctcatgggaa caggatcacc catgcgctgc 180
ccttgatgat caaggttggg gcttaagtgg attaagggag gcaagttctg ggttccttgc 240
cttttcaaac catgaagtca ggctctgtat ccctcctttt cctaactgat attctaacta 300
a 301

<210> SEQ ID NO 248
<211> LENGTH: 301
<212> TYPE: DNA
<213> ORGANISM: Homo sapien

<400> SEQUENCE: 248
aggtccttgg agatgccatt tcagccgaag gactcttctw ttcggaagta caccctcact 60
attaggaaga ttcttagggg taatttttct gaggaaggag aactagccaa cttaagaatt 120
acaggaagaa agtggtttgg aagacagcca aagaaataaa agcagattaa attgtatcag 180
gtacattcca gcctgttggc aactccataa aaacatttca gattttaatc ccgaatttag 240
ctaatgagac tggatttttg ttttttatgt tgtgtgtcgc agagctaaaa actcagttcc 300
c 301

<210> SEQ ID NO 249
<211> LENGTH: 301
<212> TYPE: DNA
<213> ORGANISM: Homo sapien

<400> SEQUENCE: 249
gtccagagga agcacctggt gctgaactag gcttgccctg ctgtgaactt gcacttggag 60
ccctgacgct gctgttctcc ccgaaaaacc cgaccgacct ccgcgatctc cgtcccgccc 120
ccagggagac acagcagtga ctcagagctg gtcgcacact gtgcctccct cctcaccgcc 180
catcgtaatg aattattttg aaaattaatt ccaccatcct ttcagattct ggatggaaag 240
actgaatctt tgactcagaa ttgtttgctg aaaagaatga tgtgactttc ttagtcattt 300
a 301

<210> SEQ ID NO 250
<211> LENGTH: 301
<212> TYPE: DNA
<213> ORGANISM: Homo sapien

<400> SEQUENCE: 250
ggtctgtgac aaggacttgc aggctgtggg aggcaagtga cccttaacac tacacttctc 60
cttatcttta ttggcttgat aaacataatt atttctaaca ctagcttatt tccagttgcc 120
cataagcaca tcagtacttt tctctggctg gaatagtaaa ctaaagtatg gtacatctac 180

-continued

```
ctaaaagact actatgtgga ataatacata ctaatgaagt attacatgat ttaaagacta    240

caataaaacc aaacatgctt ataacattaa gaaaaacaat aaagatacat gattgaaacc    300

a                                                                    301
```

<210> SEQ ID NO 251
<211> LENGTH: 301
<212> TYPE: DNA
<213> ORGANISM: Homo sapien

<400> SEQUENCE: 251

```
gccgaggtcc tacatttggc ccagtttccc cctgcatcct ctccagggcc cctgcctcat     60

agacaacctc atagagcata ggagaactgg ttgccctggg ggcaggggga ctgtctggat    120

ggcaggggtc ctcaaaaatg ccactgtcac tgccaggaaa tgcttctgag cagtacacct    180

cattgggatc aatgaaaagc ttcaagaaat cttcaggctc actctcttga aggcccggaa    240

cctctggagg ggggcagtgg aatcccagct ccaggacgga tcctgtcgaa aagatatcct    300

c                                                                    301
```

<210> SEQ ID NO 252
<211> LENGTH: 301
<212> TYPE: DNA
<213> ORGANISM: Homo sapien

<400> SEQUENCE: 252

```
gcaaccaatc actctgtttc acgtgacttt tatcaccata caatttgtgg catttcctca     60

ttttctacat tgtagaatca agagtgtaaa taaatgtata tcgatgtctt caagaatata    120

tcattccttt ttcactagga acccattcaa aatataagtc aagaatctta atatcaacaa    180

atatatcaag caaactggaa ggcagaataa ctaccataat ttagtataag tacccaaagt    240

tttataaatc aaaagcccta atgataacca tttttagaat tcaatcatca ctgtagaatc    300

a                                                                    301
```

<210> SEQ ID NO 253
<211> LENGTH: 301
<212> TYPE: DNA
<213> ORGANISM: Homo sapien

<400> SEQUENCE: 253

```
ttccctaaga agatgttatt ttgttgggtt ttgttccccc tccatctcga ttctcgtacc     60

caactaaaaa aaaaaaataa agaaaaaatg tgctgcgttc tgaaaaataa ctccttagct    120

tggtctgatt gttttcagac cttaaaatat aaacttgttt cacaagcttt aatccatgtg    180

gatttttttt cttagagaac cacaaaacat aaaaggagca agtcggactg aatacctgtt    240

tccatagtgc ccacagggta ttcctcacat tttctccata ggaaaatgct tttcccaag    300

g                                                                    301
```

<210> SEQ ID NO 254
<211> LENGTH: 301
<212> TYPE: DNA
<213> ORGANISM: Homo sapien

<400> SEQUENCE: 254

```
cgctgcgcct ttcccttggg ggaggggcaa ggccagaggg ggtccaagtg cagcacgagg     60

aacttgacca attcccttga agcgggtggg ttaaaccctg taaatgggaa caaaatcccc    120

ccaaatctct tcatcttacc ctggtggact cctgactgta gaatttttttg gttgaaacaa    180
```

-continued

```
gaaaaaaata aagctttgga cttttcaagg ttgcttaaca ggtactgaaa gactggcctc    240

acttaaactg agccaggaaa agctgcagat ttattaatgg gtgtgttagt gtgcagtgcc    300

t                                                                    301
```

<210> SEQ ID NO 255
<211> LENGTH: 302
<212> TYPE: DNA
<213> ORGANISM: Homo sapien

<400> SEQUENCE: 255

```
agcttttttt tttttttttt tttttttttt ttcattaaaa aatagtgctc tttattataa     60

attactgaaa tgtttctttt ctgaatataa atataaatat gtgcaaagtt tgacttggat    120

tgggattttg ttgagttctt caagcatctc ctaataccct caagggcctg agtagggggg    180

aggaaaaagg actggaggtg gaatctttat aaaaaacaag agtgattgag gcagattgta    240

aacattatta aaaaacaaga aacaaacaaa aaaatagaga aaaaaaccac cccaacacac    300

aa                                                                   302
```

<210> SEQ ID NO 256
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 256

```
gttccagaaa acattgaagg tggcttccca aagtctaact agggataccc cctctagcct     60

aggaccctcc tccccacacc tcaatccacc aaaccatcca taatgcaccc agataggccc    120

acccccaaaa gcctggacac cttgagcaca cagttatgac caggacagac tcatctctat    180

aggcaaatag ctgctggcaa actggcatta cctggtttgt ggggatgggg gggcaagtgt    240

gtggcctctc ggcctggtta gcaagaacat tcagggtagg cctaagttan tcgtgttagt    300

t                                                                    301
```

<210> SEQ ID NO 257
<211> LENGTH: 301
<212> TYPE: DNA
<213> ORGANISM: Homo sapien

<400> SEQUENCE: 257

```
gttgtggagg aactctggct tgctcattaa gtcctactga ttttcactat cccctgaatt     60

tccccactta tttttgtctt tcactatcgc aggccttaga agaggtctac ctgcctccag    120

tcttacctag tccagtctac cccctggagt tagaatggcc atcctgaagt gaaaagtaat    180

gtcacattac tcccttcagt gatttcttgt agaagtgcca atccctgaat gccaccaaga    240

tcttaatctt cacatcttta atcttatctc tttgactcct ctttacaccg gagaaggctc    300

c                                                                    301
```

<210> SEQ ID NO 258
<211> LENGTH: 301
<212> TYPE: DNA
<213> ORGANISM: Homo sapien
<220> FEATURE:
<221> NAME/KEY: misc_feature
<222> LOCATION: (1)...(301)

-continued

<223> OTHER INFORMATION: n = A,T,C or G

<400> SEQUENCE: 258
cagcagtagt agatgccgta tgccagcacg cccagcactc ccaggatcag caccagcacc 60
aggggcccag ccaccaggcg cagaagcaag ataaacagta ggctcaagac cagagccacc 120
cccagggcaa caagaatcca ataccaggac tgggcaaaat cttcaaagat cttaacactg 180
atgtctcggg cattgaggct gtcaataana cgctgatccc ctgctgtatg gtggtgtcat 240
tggtgatccc tgggagcgcc ggtggagtaa cgttggtcca tggaaagcag cgcccacaac 300
t 301

<210> SEQ ID NO 259
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 259
tcatatatgc aaacaaatgc agactangcc tcaggcagag actaaaggac atctcttggg 60
gtgtcctgaa gtgatttgga cccctgaggg cagacaccta agtaggaatc ccagtgggaa 120
gcaaagccat aaggaagccc aggattcctt gtgatcagga agtgggccag gaaggtctgt 180
tccagctcac atctcatctg catgcagcac ggaccggatg cgcccactgg gtcttggctt 240
ccctcccatc ttctcaagca gtgtccttgt tgagccattt gcatccttgg ctccaggtgg 300
c 301

<210> SEQ ID NO 260
<211> LENGTH: 301
<212> TYPE: DNA
<213> ORGANISM: Homo sapien

<400> SEQUENCE: 260 tttttttct ccctaaggaa aaagaaggaa caagtctcat aaaaccaaat aagcaatggt 60
aaggtgtctt aacttgaaaa agattaggag tcactggttt acaagttata attgaatgaa 120
agaactgtaa cagccacagt tggccatttc atgccaatgg cagcaaacaa caggattaac 180
tagggcaaaa taaataagtg tgtggaagcc ctgataagtg cttaataaac agactgattc 240
actgagacat cagtacctgc ccgggcggcc gctcgagccg aattctgcag atatccatca 300
c 301

<210> SEQ ID NO 261
<211> LENGTH: 301
<212> TYPE: DNA
<213> ORGANISM: Homo sapien

<400> SEQUENCE: 261
aaatattcga gcaaatcctg taactaatgt gtctccataa aaggctttga actcagtgaa 60
tctgcttcca tccacgattc tagcaatgac ctctcggaca tcaaagctcc tcttaaggtt 120
agcaccaact attccataca attcatcagc aggaaataaa ggctcttcag aaggttcaat 180
ggtgacatcc aatttcttct gataatttag attcctcaca accttcctag ttaagtgaag 240
ggcatgatga tcatccaaag cccagtggtc acttactcca gactttctgc aatgaagatc 300
a 301

<210> SEQ ID NO 262
<211> LENGTH: 301
<212> TYPE: DNA
<213> ORGANISM: Homo sapien

<400> SEQUENCE: 262
gaggagagcc tgttacagca tttgtaagca cagaatactc caggagtatt tgtaattgtc 60
tgtgagcttc ttgccgcaag tctctcagaa atttaaaaag atgcaaatcc ctgagtcacc 120
cctagacttc ctaaaccaga tcctctgggg ctggaacctg gcactctgca tttgtaatga 180
gggctttctg gtgcacacct aattttgtgc atctttgccc taaatcctgg attagtgccc 240
catcattacc cccacattat aatgggatag attcagagca gatactctcc agcaaagaat 300
c 301

<210> SEQ ID NO 263
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 263
tttagcttgt ggtaaatgac tcacaaaact gattttaaaa tcaagttaat gtgaattttg 60
aaaattacta cttaatccta attcacaata acaatggcat taaggtttga cttgagttgg 120
ttcttagtat tatttatggt aaataggctc ttaccacttg caaataactg gccacatcat 180
taatgactga cttcccagta aggctctcta aggggtaagt angaggatcc acaggatttg 240
agatgctaag gccccagaga tcgtttgatc caaccctctt attttcagag gggaaaatgg 300
g 301

<210> SEQ ID NO 264
<211> LENGTH: 301
<212> TYPE: DNA
<213> ORGANISM: Homo sapien

<400> SEQUENCE: 264
aaagacgtta aaccactcta ctaccacttg tggaactctc aaagggtaaa tgacaaascc 60
aatgaatgac tctaaaaaca atatttacat ttaatggttt gtagacaata aaaaaacaag 120
gtggatagat ctagaattgt aacattttaa gaaaaccata scatttgaca gatgagaaag 180
ctcaattata gatgcaaagt tataactaaa ctactatagt agtaaagaaa tacatttcac 240
acccttcata taaattcact atcttggctt gaggcactcc ataaaatgta tcacgtgcat 300
a 301

<210> SEQ ID NO 265
<211> LENGTH: 301
<212> TYPE: DNA
<213> ORGANISM: Homo sapien

<400> SEQUENCE: 265
tgcccaagtt atgtgtaagt gtatccgcac ccagaggtaa aactacactg tcatctttgt 60
cttcttgtga cgcagtattt cttctctggg gagaagccgg gaagtcttct cctggctcta 120
catattcttg gaagtctcta atcaactttt gttccatttg tttcatttct tcaggaggga 180

-continued

```
ttttcagttt gtcaacatgt tctctaacaa cacttgccca tttctgtaaa gaatccaaag    240

cagtccaagg ctttgacatg tcaacaacca gcataactag agtatccttc agagatacgg    300

c                                                                    301
```

<210> SEQ ID NO 266
<211> LENGTH: 301
<212> TYPE: DNA
<213> ORGANISM: Homo sapien

<400> SEQUENCE: 266

```
taccgtctgc ccttcctccc atccaggcca tctgcgaatc tacatgggtc ctcctattcg     60

acaccagatc actctttcct ctacccacag gcttgctatg agcaagagac acaacctcct    120

ctcttctgtg ttccagcttc ttttcctgtt cttcccaccc cttaagttct attcctgggg    180

atagagacac caatacccat aacctctctc ctaagcctcc ttataaccca gggtgcacag    240

cacagactcc tgacaactgg taaggccaat gaactgggag ctcacagctg gctgtgcctg    300

a                                                                    301
```

<210> SEQ ID NO 267
<211> LENGTH: 301
<212> TYPE: DNA
<213> ORGANISM: Homo sapien

<400> SEQUENCE: 267

```
aaagagcaca ggccagctca gcctgccctg gccatctaga ctcagcctgg ctccatgggg     60

gttctcagtg ctgagtccat ccaggaaaag ctcacctaga ccttctgagg ctgaatcttc    120

atcctcacag gcagcttctg agagcctgat attcctagcc ttgatggtct ggagtaaagc    180

ctcattctga ttcctctcct tcttttcttt caagttggct ttcctcacat ccctctgttc    240

aattcgcttc agcttgtctg ctttagccct catttccaga agcttcttct ctttggcatc    300

t                                                                    301
```

<210> SEQ ID NO 268
<211> LENGTH: 301
<212> TYPE: DNA
<213> ORGANISM: Homo sapien

<400> SEQUENCE: 268

```
aatgtctcac tcaactactt cccagcctac cgtggcctaa ttctgggagt tttcttctta     60

gatcttggga gagctggttc ttctaaggag aaggaggaag gacagatgta actttggatc    120

tcgaagagga agtctaatgg aagtaattag tcaacggtcc ttgtttagac tcttggaata    180

tgctgggtgg ctcagtgagc ccttttggag aaagcaagta ttattcttaa ggagtaacca    240

cttcccattg ttctactttc taccatcatc aattgtatat tatgtattct ttggagaact    300

a                                                                    301
```

<210> SEQ ID NO 269
<211> LENGTH: 301
<212> TYPE: DNA
<213> ORGANISM: Homo sapien

<400> SEQUENCE: 269

```
taacaatata cactagctat ctttttaact gtccatcatt agcaccaatg aagattcaat     60

aaaattacct ttattcacac atctcaaaac aattctgcaa attcttagtg aagtttaact    120

atagtcacag accttaaata ttcacattgt tttctatgtc tactgaaaat aagttcacta    180
```

-continued

```
cttttctgga tattctttac aaaatcttat taaaattcct ggtattatca cccccaatta    240

tacagtagca caaccacctt atgtagtttt tacatgatag ctctgtagaa gtttcacatc    300

t                                                                    301
```

```
<210> SEQ ID NO 270
<211> LENGTH: 301
<212> TYPE: DNA
<213> ORGANISM: Homo sapien

<400> SEQUENCE: 270

cattgaagag cttttgcgaa acatcagaac acaagtgctt ataaaattaa ttaagcctta     60

cacaagaata catattcctt ttatttctaa ggagttaaac atagatgtag ctgatgtgga    120

gagcttgctg gtgcagtgca tattggataa cactattcat ggccgaattg atcaagtcaa    180

ccaactcctt gaactggatc atcagaagaa gggtggtgca cgatatactg cactagataa    240

tggaccaacc aactaaattc tctcaccagg ctgtatcagt aaactggctt aacagaaaac    300

a                                                                    301
```

```
<210> SEQ ID NO 271
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 271

aaaaggttct cataagatta acaatttaaa taaatatttg atagaacatt ctttctcatt     60

tttatagctc atctttaggg ttgatattca gttcatgctt cccttgctgt tcttgatcca    120

gaattgcaat cacttcatca gcctgtattc gctccaattc tctataaagt gggtccaagg    180

tgaaccacag agccacagca cacctctttc ccttggtgac tgccttcacc ccatganggt    240

tctctcctcc agatganaac tgatcatgcg cccacatttt gggttttata gaagcagtca    300

c                                                                    301
```

```
<210> SEQ ID NO 272
<211> LENGTH: 301
<212> TYPE: DNA
<213> ORGANISM: Homo sapien

<400> SEQUENCE: 272

taaattgcta agccacagat aacaccaatc aaatggaaca aatcactgtc ttcaaatgtc     60

ttatcagaaa accaaatgag cctggaatct tcataatacc taaacatgcc gtatttagga    120

tccaataatt ccctcatgat gagcaagaaa aattctttgc gcacccctcc tgcatccaca    180

gcatcttctc caacaaatat aaccttgagt ggcttcttgt aatctatgtt ctttgttttc    240

ctaaggactt ccattgcatc tcctacaata ttttctctac gcaccactag aattaagcag    300

g                                                                    301
```

```
<210> SEQ ID NO 273
<211> LENGTH: 301
<212> TYPE: DNA
<213> ORGANISM: Homo sapien
<220> FEATURE:
<221> NAME/KEY: misc_feature
<222> LOCATION: (1)...(301)
```

-continued

<223> OTHER INFORMATION: n = A,T,C or G

<400> SEQUENCE: 273
acatgtgtgt atgtgtatct ttgggaaaan aanaagacat cttgtttayt attttttttgg 60 agagangctg ggacatggat aatcacwtaa tttgctayta tyactttaat ctgactygaa 120
gaaccgtcta aaaataaaat ttaccatgtc dtatattcct tatagtatgc ttatttcacc 180
ttytttctgt ccagagagag tatcagtgac ananatttma gggtgaamac atgmattggt 240
gggacttnty tttacngagm accctgcccg sgcgccctcg makcngantt ccgcsananc 300
t 301

<210> SEQ ID NO 274
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 274
cttatatact ctttctcaga ggcaaaagag gagatgggta atgtagacaa ttctttgagg 60
aacagtaaat gattattaga gagaangaat ggaccaagga gacagaaatt aacttgtaaa 120
tgattctctt tggaatctga atgagatcaa gaggccagct ttagcttgtg gaaaagtcca 180
tctaggtatg gttgcattct cgtcttcttt tctgcagtag ataatgaggt aaccgaaggc 240
aattgtgctt cttttgataa gaagctttct tggtcatatc aggaaattcc aganaaagtc 300
c 301

<210> SEQ ID NO 275
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 275
tcggtgtcag cagcacgtgg cattgaacat tgcaatgtgg agcccaaacc acagaaaatg 60
gggtgaaatt ggccaacttt ctattaactt atgttggcaa ttttgccacc aacagtaagc 120
tggcccttct aataaaagaa aattgaaagg tttctcacta aacggaatta agtagtggag 180
tcaagagact cccaggcctc agcgtacctg cccgggcggc cgctcgaagc cgaattctgc 240
agatatccat cacactggcg gncgctcgan catgcatcta gaaggnccaa ttcgccctat 300
a 301

<210> SEQ ID NO 276
<211> LENGTH: 301
<212> TYPE: DNA
<213> ORGANISM: Homo sapien

<400> SEQUENCE: 276
tgtacacata ctcaataaat aaatgactgc attgtggtat tattactata ctgattatat 60
ttatcatgtg acttctaatt agaaaatgta tccaaaagca aaacagcaga tatacaaaat 120
taaagagaca gaagatagac attaacagat aaggcaactt atacattgag aatccaaatc 180
caatacattt aaacatttgg gaaatgaggg ggacaaatgg aagccagatc aaatttgtgt 240

-continued

```
aaaactattc agtatgtttc ccttgcttca tgtctgagaa ggctctcctt caatggggat    300

g                                                                     301


<210> SEQ ID NO 277
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 277

tttgttgatg tcagtatttt attacttgcg ttatgagtgc tcacctggga aattctaaag     60

atacagagga cttggaggaa gcagagcaac tgaatttaat ttaaaagaag gaaaacattg    120

gaatcatggc actcctgata ctttcccaaa tcaacactct caatgcccca ccctcgtcct    180

caccatagtg gggagactaa agtggccacg gatttgcctt angtgtgcag tgcgttctga    240

gttcnctgtc gattacatct gaccagtctc ctttttccga agtccntccg ttcaatcttg    300

c                                                                     301


<210> SEQ ID NO 278
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 278

taccactaca ctccagcctg ggcaacagag caagacctgt ctcaaagcat aaaatggaat     60

aacatatcaa atgaaacagg gaaaatgaag ctgacaattt atggaagcca gggcttgtca    120

cagtctctac tgttattatg cattacctgg gaatttatat aagcccttaa taataatgcc    180

aatgaacatc tcatgtgtgc tcacaatgtt ctggcactat tataagtgct tcacaggttt    240

tatgtgttct tcgtaacttt atggantagg tactcggccg cgaacacgct aagccgaatt    300

c                                                                     301


<210> SEQ ID NO 279
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 279

aaagcaggaa tgacaaagct tgcttttctg gtatgttcta ggtgtattgt gacttttact     60

gttatattaa ttgccaatat aagtaaatat agattatata tgtatagtgt ttcacaaagc    120

ttagaccttt accttccagc caccccacag tgcttgatat ttcagagtca gtcattggtt    180

atacatgtgt agttccaaag cacataagct agaanaanaa atatttctag ggagcactac    240

catctgtttt cacatgaaat gccacacaca tagaactcca acatcaattt cattgcacag    300

a                                                                     301


<210> SEQ ID NO 280
```

<211> LENGTH: 301
<212> TYPE: DNA
<213> ORGANISM: Homo sapien

<400> SEQUENCE: 280
ggtactggag ttttcctccc ctgtgaaaac gtaactactg ttgggagtga attgaggatg 60
tagaaaggtg gtggaaccaa attgtggtca atggaaatag gagaatatgg ttctcactct 120
tgagaaaaaa acctaagatt agcccaggta gttgcctgta acttcagttt ttctgcctgg 180
gtttgatata gtttagggtt ggggttagat taagatctaa attacatcag gacaaagaga 240
cagactatta actccacagt taattaagga ggtatgttcc atgtttattt gttaaagcag 300
t 301

<210> SEQ ID NO 281
<211> LENGTH: 301
<212> TYPE: DNA
<213> ORGANISM: Homo sapien

<400> SEQUENCE: 281
aggtacaaga aggggaatgg gaaagagctg ctgctgtggc attgttcaac ttggatattc 60
gccgagcaat ccaaatcctg aatgaagggg catcttctga aaaaggagat ctgaatctca 120
atgtggtagc aatggcttta tcgggttata cggatgagaa gaactccctt tggagagaaa 180
tgtgtagcac actgcgatta cagctaaata acccgtattt gtgtgtcatg tttgcatttc 240
tgacaagtga aacaggatct tacgatggag ttttgtatga aaacaaagtt gcagtacctc 300
g 301

<210> SEQ ID NO 282
<211> LENGTH: 301
<212> TYPE: DNA
<213> ORGANISM: Homo sapien

<400> SEQUENCE: 282
caggtactac agaattaaaa tactgacaag caagtagttt cttggcgtgc acgaattgca 60
tccagaaccc aaaaattaag aaattcaaaa agacattttg tgggcacctg ctagcacaga 120
agcgcagaag caaagcccag gcagaaccat gctaacctta cagctcagcc tgcacagaag 180
cgcagaagca aagcccaggc agaaccatgc taaccttaca gctcagcctg cacagaagcg 240
cagaagcaaa gcccaggcag aacatgctaa ccttacagct cagcctgcac agaagcacag 300
a 301

<210> SEQ ID NO 283
<211> LENGTH: 301
<212> TYPE: DNA
<213> ORGANISM: Homo sapien

<400> SEQUENCE: 283
atctgtatac ggcagacaaa ctttatarag tgtagagagg tgagcgaaag gatgcaaaag 60
cactttgagg gctttataat aatatgctgc ttgaaaaaaa aaatgtgtag ttgatactca 120
gtgcatctcc agacatagta aggggttgct ctgaccaatc aggtgatcat tttttctatc 180
acttcccagg ttttatgcaa aaattttgtt aaattctata atggtgatat gcatctttta 240
ggaaacatat acatttttaa aaatctattt tatgtaagaa ctgacagacg aatttgcttt 300
g 301

-continued

<210> SEQ ID NO 284
<211> LENGTH: 301
<212> TYPE: DNA
<213> ORGANISM: Homo sapien

<400> SEQUENCE: 284
caggtacaaa acgctattaa gtggcttaga atttgaacat ttgtggtctt tatttacttt 60
gcttcgtgtg tgggcaaagc aacatcttcc ctaaatatat attaccaaga aaagcaagaa 120
gcagattagg tttttgacaa aacaaacagg ccaaaagggg gctgacctgg agcagagcat 180
ggtgagaggc aaggcatgag agggcaagtt tgttgtggac agatctgtgc ctactttatt 240
actggagtaa aagaaaacaa agttcattga tgtcgaagga tatatacagt gttagaaatt 300
a 301

<210> SEQ ID NO 285
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 285
acatcaccat gatcggatcc cccacccatt atacgttgta tgtttacata aatactcttc 60
aatgatcatt agtgttttaa aaaaaatact gaaaactcct tctgcatccc aatctctaac 120
caggaaagca aatgctattt acagacctgc aagccctccc tcaaacnaaa ctatttctgg 180
attaaatatg tctgacttct tttgaggtca cacgactagg caaatgctat ttacgatctg 240
caaaagctgt ttgaagagtc aaagccccca tgtgaacacg atttctggac cctgtaacag 300
t 301

<210> SEQ ID NO 286
<211> LENGTH: 301
<212> TYPE: DNA
<213> ORGANISM: Homo sapien

<400> SEQUENCE: 286
taccactgca ttccagcctg ggtgacagag tgagactccg tctccaaaaa aaactttgct 60
tgtatattat ttttgcctta cagtggatca ttctagtagg aaaggacagt aagatttttt 120
atcaaaatgt gtcatgccag taagagatgt tatattcttt tctcatttct tccccaccca 180
aaaataagct accatatagc ttataagtct caaatttttg ccttttacta aaatgtgatt 240
gtttctgttc attgtgtatg cttcatcacc tatattaggc aaattccatt ttttcccttg 300
t 301

<210> SEQ ID NO 287
<211> LENGTH: 301
<212> TYPE: DNA
<213> ORGANISM: Homo sapien

<400> SEQUENCE: 287
tacagatctg ggaactaaat attaaaaatg agtgtggctg gatatatgga gaatgttggg 60
cccagaagga acgtagagat cagatattac aacagctttg ttttgagggt tagaaatatg 120
aaatgatttg gttatgaacg cacagtttag gcagcagggc cagaatcctg accctctgcc 180
ccgtggttat ctcctcccca gcttggctgc ctcatgttat cacagtattc cattttgttt 240

-continued

```
gttgcatgtc ttgtgaagcc atcaagattt tctcgtctgt tttcctctca ttggtaatgc    300

t                                                                    301


<210> SEQ ID NO 288
<211> LENGTH: 301
<212> TYPE: DNA
<213> ORGANISM: Homo sapien

<400> SEQUENCE: 288

gtacacctaa ctgcaaggac agctgaggaa tgtaatgggc agccgctttt aaagaagtag     60

agtcaatagg aagacaaatt ccagttccag ctcagtctgg gtatctgcaa agctgcaaaa    120

gatctttaaa gacaatttca agagaatatt tccttaaagt tggcaatttg gagatcatac    180

aaaagcatct gcttttgtga tttaatttag ctcatctggc cactggaaga atccaaacag    240

tctgccttaa ttttggatga atgcatgatg gaaattcaat aatttagaaa gttaaaaaaa    300

a                                                                    301


<210> SEQ ID NO 289
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 289

ggtacactgt ttccatgtta tgtttctaca cattgctacc tcagtgctcc tggaaactta     60

gcttttgatg tctccaagta gtccaccttc atttaactct ttgaaactgt atcatctttg    120

ccaagtaaga gtggtggcct atttcagctg ctttgacaaa atgactggct cctgacttaa    180

cgttctataa atgaatgtgc tgaagcaaag tgcccatggt ggcggcgaan aagagaaaga    240

tgtgttttgt tttggactct ctgtggtccc ttccaatgct gtgggtttcc aaccagngga    300

a                                                                    301


<210> SEQ ID NO 290
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 290

acactgagct cttcttgata aatatacaga atgcttggca tatacaagat tctatactac     60

tgactgatct gttcatttct ctcacagctc ttacccccaa aagcttttcc accctaagtg    120

ttctgacctc cttttctaat cacagtaggg atagaggcag anccacctac aatgaacatg    180

gagttctatc aagaggcaga aacagcacag aatcccagtt ttaccattcg ctagcagtgc    240

tgccttgaac aaaaacattt ctccatgtct cattttcttc atgcctcaag taacagtgag    300

a                                                                    301


<210> SEQ ID NO 291
<211> LENGTH: 301
<212> TYPE: DNA
<213> ORGANISM: Homo sapien

<400> SEQUENCE: 291
```

-continued

```
caggtaccaa tttcttctat cctagaaaca tttcatttta tgttgttgaa acataacaac     60

tatatcagct agattttttt tctatgcttt acctgctatg gaaaatttga cacattctgc    120

tttactcttt tgtttatagg tgaatcacaa aatgtatttt tatgtattct gtagttcaat    180

agccatggct gtttacttca tttaatttat ttagcataaa gacattatga aaaggcctaa    240

acatgagctt cacttcccca ctaactaatt agcatctgtt atttcttaac cgtaatgcct    300

a                                                                    301
```

<210> SEQ ID NO 292
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 292

```
accttttagt agtaatgtct aataataaat aagaaatcaa ttttataagg tccatatagc     60

tgtattaaat aatttttaag tttaaaagat aaaataccat cattttaaat gttggtattc    120

aaaaccaaag natataaccg aaaggaaaaa cagatgagac ataaaatgat ttgcnagatg    180

ggaaatatag tasttyatga atgttnatta aattccagtt ataatagtgg ctacacactc    240

tcactacaca cacagacccc acagtcctat atgccacaaa cacatttcca taacttgaaa    300

a                                                                    301
```

<210> SEQ ID NO 293
<211> LENGTH: 301
<212> TYPE: DNA
<213> ORGANISM: Homo sapien

<400> SEQUENCE: 293

```
ggtaccaagt gctggtgcca gcctgttacc tgttctcact gaaaagtctg gctaatgctc     60

ttgtgtagtc acttctgatt ctgacaatca atcaatcaat ggcctagagc actgactgtt    120

aacacaaacg tcactagcaa agtagcaaca gctttaagtc taaatacaaa gctgttctgt    180

gtgagaattt tttaaaaggc tacttgtata ataacccttg tcatttttaa tgtacctcgg    240

ccgcgaccac gctaagccga attctgcaga tatccatcac actggcggcc gctcgagcat    300

g                                                                    301
```

<210> SEQ ID NO 294
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 294

```
tgacccataa caatatacac tagctatctt tttaactgtc catcattagc accaatgaag     60

attcaataaa attaccttta ttcacacatc tcaaaacaat tctgcaaatt cttagtgaag    120

tttaactata gtcacaganc ttaaatattc acattgtttt ctatgtctac tgaaaataag    180

ttcactactt ttctgggata ttctttacaa aatcttatta aaattcctgg tattatcacc    240

cccaattata cagtagcaca accaccttat gtagttttta catgatagct ctgtagaggt    300
```

-continued

```
t                                                                     301

<210> SEQ ID NO 295
<211> LENGTH: 305
<212> TYPE: DNA
<213> ORGANISM: Homo sapien

<400> SEQUENCE: 295

gtactctttc tctcccctcc tctgaattta attctttcaa cttgcaattt gcaaggatta      60

cacatttcac tgtgatgtat attgtgttgc aaaaaaaaaa gtgtctttgt ttaaaattac     120

ttggtttgtg aatccatctt gctttttccc cattggaact agtcattaac ccatctctga     180

actggtagaa aaacrtctga agagctagtc tatcagcatc tgacaggtga attggatggt     240

tctcagaacc atttcaccca gacagcctgt ttctatcctg tttaataaat tagtttgggt     300

tctct                                                                 305

<210> SEQ ID NO 296
<211> LENGTH: 301
<212> TYPE: DNA
<213> ORGANISM: Homo sapien

<400> SEQUENCE: 296

aggtactatg ggaagctgct aaaataatat ttgatagtaa aagtatgtaa tgtgctatct      60

cacctagtag taaactaaaa ataaactgaa actttatgga atctgaagtt attttccttg     120

attaaataga attaataaac caatatgagg aaacatgaaa ccatgcaatc tactatcaac     180

tttgaaaaag tgattgaacg aaccacttag ctttcagatg atgaacactg ataagtcatt     240

tgtcattact ataaatttta aaatctgtta ataagatggc ctatagggag gaaaaagggg     300

c                                                                     301

<210> SEQ ID NO 297
<211> LENGTH: 300
<212> TYPE: DNA
<213> ORGANISM: Homo sapien
<220> FEATURE:
<221> NAME/KEY: misc_feature
<222> LOCATION: (1)...(300)
<223> OTHER INFORMATION: n = A,T,C or G

<400> SEQUENCE: 297

actgagtttt aactggacgc caagcaggca aggctggaag gttttgctct ctttgtgcta      60

aaggttttga aaaccttgaa ggagaatcat tttgacaaga agtacttaag agtctagaga     120

acaaagangt gaaccagctg aaagctctcg ggggaanctt acatgtgttg ttaggcctgt     180

tccatcattg ggagtgcact ggccatccct caaaatttgt ctgggctggc ctgagtggtc     240

accgcacctc ggccgcgacc acgctaagcc gaattctgca gatatccatc acactggcgg     300

<210> SEQ ID NO 298
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 298

tatggggttt gtcacccaaa agctgatgct gagaaaggcc tccctggggc cccctcccgcg     60

ggcatctgag agacctggtg ttccagtgtt tctggaaatg ggtcccagtg ccgccggctg     120
```

tgaagctctc agatcaatca cgggaagggc ctggcggtgg tggccacctg gaaccaccct 180
gtcctgtctg tttacatttc actaycaggt tttctctggg cattacnatt tgttccccta 240
caacagtgac ctgtgcattc tgctgtggcc tgctgtgtct gcaggtggct ctcagcgagg 300
t 301

<210> SEQ ID NO 299
<211> LENGTH: 301
<212> TYPE: DNA
<213> ORGANISM: Homo sapien

<400> SEQUENCE: 299
gttttgagac ggagtttcac tcttgttgcc cagactggac tgcaatggca gggtctctgc 60
tcactgcacc ctctgcctcc caggttcgag caattctcct gcctcagcct cccaggtagc 120
tgggattgca ggctcacgcc accataccca gctaattttt ttgtattttt agtagagacg 180
gagtttcgcc atgttggcca gctggtctca aactcctgac ctcaagcgac ctgcctgcct 240
cggcctccca aagtgctgga attataggca tgagtcaaca cgcccagcct aaagatattt 300
t 301

<210> SEQ ID NO 300
<211> LENGTH: 301
<212> TYPE: DNA
<213> ORGANISM: Homo sapien

<400> SEQUENCE: 300
attcagtttt atttgctgcc ccagtatctg taaccaggag tgccacaaaa tcttgccaga 60
tatgtcccac acccactggg aaaggctccc acctggctac ttcctctatc agctgggtca 120
gctgcattcc acaaggttct cagcctaatg agtttcacta cctgccagtc tcaaaactta 180
gtaaagcaag accatgacat tccccccacgg aaatcagagt ttgccccacc gtcttgttac 240
tataaagcct gcctctaaca gtccttgctt cttcacacca atcccgagcg catcccccat 300
g 301

<210> SEQ ID NO 301
<211> LENGTH: 301
<212> TYPE: DNA
<213> ORGANISM: Homo sapien

<400> SEQUENCE: 301
ttaaattttt gagaggataa aaaggacaaa taatctagaa atgtgtcttc ttcagtctgc 60
agaggacccc aggtctccaa gcaaccacat ggtcaagggc atgaataatt aaaagttggt 120
gggaactcac aaagaccctc agagctgaga cacccacaac agtgggagct cacaaagacc 180
ctcagagctg agacacccac aacagtggga gctcacaaag accctcagag ctgagacacc 240
cacaacagca cctcgttcag ctgccacatg tgtgaataag gatgcaatgt ccagaagtgt 300
t 301

<210> SEQ ID NO 302
<211> LENGTH: 301
<212> TYPE: DNA
<213> ORGANISM: Homo sapien

<400> SEQUENCE: 302
aggtacacat ttagcttgtg gtaaatgact cacaaaactg attttaaaat caagttaatg 60

-continued

```
tgaattttga aaattactac ttaatcctaa ttcacaataa caatggcatt aaggtttgac    120

ttgagttggt tcttagtatt atttatggta aataggctct taccacttgc aaataactgg    180

ccacatcatt aatgactgac ttcccagtaa ggctctctaa ggggtaagta ggaggatcca    240

caggatttga gatgctaagg ccccagagat cgtttgatcc aaccctctta ttttcagagg    300

g                                                                    301
```

<210> SEQ ID NO 303
<211> LENGTH: 301
<212> TYPE: DNA
<213> ORGANISM: Homo sapien

<400> SEQUENCE: 303

```
aggtaccaac tgtggaaata ggtagaggat cattttttct ttccatatca actaagttgt     60

atattgtttt ttgacagttt aacacatctt cttctgtcag agattctttc acaatagcac    120

tggctaatgg aactaccgct tgcatgttaa aaatggtggt ttgtgaaatg atcataggcc    180

agtaacgggt atgtttttct aactgatctt ttgctcgttc caaagggacc tcaagacttc    240

catcgatttt atatctgggg tctagaaaag gagttaatct gttttccctc ataaattcac    300

c                                                                    301
```

<210> SEQ ID NO 304
<211> LENGTH: 301
<212> TYPE: DNA
<213> ORGANISM: Homo sapien

<400> SEQUENCE: 304

```
acatggatgt tattttgcag actgtcaacc tgaatttgta tttgcttgac attgcctaat     60

tattagtttc agtttcagct tacccacttt ttgtctgcaa catgcaraas agacagtgcc    120

ctttttagtg tatcatatca ggaatcatct cacattggtt tgtgccatta ctggtgcagt    180

gactttcagc cacttgggta aggtggagtt ggccatatgt ctccactgca aaattactga    240

ttttcctttt gtaattaata agtgtgtgtg tgaagattct ttgagatgag gtatatatct    300

c                                                                    301
```

<210> SEQ ID NO 305
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 305

```
gangtacagc gtggtcaagg taacaagaag aaaaaaatgt gagtggcatc ctgggatgag     60

cagggggaca gacctggaca gacacgttgt catttgctgc tgtgggtagg aaaatgggcg    120

taaaggagga gaaacagata caaaatctcc aactcagtat taaggtattc tcatgcctag    180

aatattggta gaaacaagaa tacattcata tggcaaataa ctaaccatgg tggaacaaaa    240

ttctgggatt taagttggat accaangaaa ttgtattaaa agagctgttc atggaataag    300

a                                                                    301
```

<210> SEQ ID NO 306
<211> LENGTH: 8
<212> TYPE: PRT
<213> ORGANISM: Homo sapien

-continued

<400> SEQUENCE: 306

Val Leu Gly Trp Val Ala Glu Leu
1 5

<210> SEQ ID NO 307
<211> LENGTH: 637
<212> TYPE: DNA
<213> ORGANISM: Homo sapien

<400> SEQUENCE: 307
acagggratg aagggaaagg gagaggatga ggaagccccc ctggggattt ggtttggtcc 60
ttgtgatcag gtggtctatg gggcttatcc ctacaaagaa gaatccagaa ataggggcac 120
attgaggaat gatacttgag cccaaagagc attcaatcat tgttttattt gccttmtttt 180
cacaccattg gtgagggagg gattaccacc ctggggttat gaagatggtt gaacacccca 240
cacatagcac cggagatatg agatcaacag tttcttagcc atagagattc acagcccaga 300
gcaggaggac gcttgcacac catgcaggat gacatggggg atgcgctcgg gattggtgtg 360
aagaagcaag gactgttaga ggcaggcttt atagtaacaa gacggtgggg caaactctga 420
tttccgtggg ggaatgtcat ggtcttgctt tactaagttt tgagactggc aggtagtgaa 480
actcattagg ctgagaacct tgtggaatgc acttgaccca sctgatagag gaagtagcca 540
ggtgggagcc tttcccagtg ggtgtgggac atatctggca agattttgtg gcactcctgg 600
ttacagatac tggggcagca aataaaactg aatcttg 637

<210> SEQ ID NO 308
<211> LENGTH: 647
<212> TYPE: DNA
<213> ORGANISM: Homo sapien
<220> FEATURE:
<221> NAME/KEY: misc_feature
<222> LOCATION: (1)...(647)
<223> OTHER INFORMATION: n = A,T,C or G

<400> SEQUENCE: 308
acgattttca ttatcatgta aatcgggtca ctcaaggggc caaccacagc tgggagccac 60
tgctcagggg aaggttcata tgggactttc tactgcccaa ggttctatac aggatataaa 120
ggngcctcac agtatagatc tggtagcaaa gaagaagaaa caaacactga tctctttctg 180
ccacccctct gacccttttgg aactcctctg accctttaga acaagcctac ctaatatctg 240
ctagagaaaa gaccaacaac ggcctcaaag gatctcttac catgaaggtc tcagctaatt 300
cttggctaag atgtgggttc cacattaggt tctgaatatg gggggaaggg tcaatttgct 360
cattttgtgt gtggataaag tcaggatgcc caggggccag agcaggggggc tgcttgcttt 420 gggaacaatg gctgagcata taaccatagg ttatggggaa caaaacaaca tcaaagtcac 480
tgtatcaatt gccatgaaga cttgagggac ctgaatctac cgattcatct taaggcagca 540
ggaccagttt gagtggcaac aatgcagcag cagaatcaat ggaaacaaca gaatgattgc 600
aatgtccttt tttttctcct gcttctgact tgataaaagg ggaccgt 647

<210> SEQ ID NO 309
<211> LENGTH: 460
<212> TYPE: DNA
<213> ORGANISM: Homo sapien

<400> SEQUENCE: 309
actttatagt ttaggctgga cattggaaaa aaaaaaaagc cagaacaaca tgtgatagat 60

-continued

```
aatatgattg gctgcacact tccagactga tgaatgatga acgtgatgga ctattgtatg    120
gagcacatct tcagcaagag ggggaaatac tcatcatttt tggccagcag ttgtttgatc    180
accaaacatc atgccagaat actcagcaaa ccttcttagc tcttgagaag tcaaagtccg    240
ggggaattta ttcctggcaa ttttaattgg actccttatg tgagagcagc ggctacccag    300
ctggggtggt ggagcgaacc cgtcactagt ggacatgcag tggcagagct cctggtaacc    360
acctagagga atacacaggc acatgtgtga tgccaagcgt gacacctgta gcactcaaat    420
ttgtcttgtt tttgtctttc ggtgtgtaag attcttaagt                          460
```

<210> SEQ ID NO 310
<211> LENGTH: 539
<212> TYPE: DNA
<213> ORGANISM: Homo sapien

<400> SEQUENCE: 310

```
acgggactta tcaaataaag ataggaaaag aagaaaactc aaatattata ggcagaaatg     60
ctaaaggttt taaaatatgt caggattgga agaaggcatg gataaagaac aaagttcagt    120
taggaaagag aaacacagaa ggaagagaca caataaaagt cattatgtat tctgtgagaa    180
gtcagacagt aagatttgtg ggaaatgggt tggtttgttg tatggtatgt attttagcaa    240
taatctttat ggcagagaaa gctaaaatcc tttagcttgc gtgaatgatc acttgctgaa    300
ttcctcaagg taggcatgat gaaggagggt ttagaggaga cacagacaca atgaactgac    360
ctagatagaa agccttagta tactcagcta ggaatagtga ttctgagggc acactgtgac    420
atgattatgt cattacatgt atggtagtga tggggatgat aggaaggaag aacttatggc    480
atattttcac ccccacaaaa gtcagttaaa tattgggaca ctaaccatcc aggtcaaga     539
```

<210> SEQ ID NO 311
<211> LENGTH: 526
<212> TYPE: DNA
<213> ORGANISM: Homo sapien
<220> FEATURE:
<221> NAME/KEY: misc_feature
<222> LOCATION: (1)...(526)
<223> OTHER INFORMATION: n = A,T,C or G

<400> SEQUENCE: 311

```
caaatttgag ccaatgacat agaattttac aaatcaagaa gcttattctg gggccatttc     60
ttttgacgtt ttctctaaac tactaaagag gcattaatga tccataaatt atattatcta    120
catttacagc atttaaaatg tgttcagcat gaaatattag ctacagggga agctaaataa    180
attaaacatg gaataaagat ttgtccttaa atataatcta caagaagact ttgatatttg    240
tttttcacaa gtgaagcatt cttataaagt gtcataacct ttttggggaa actatgggaa    300
aaaatgggga aactctgaag ggttttaagt atcttacctg aagctacaga ctccataacc    360
tctctttaca gggagctcct gcagccccta cagaaatgag tggctgagat tcttgattgc    420
acagcaagag cttctcatct aaaccctttc cctttttagt atctgtgtat caagtataaa    480
agttctataa actgtagtnt acttatttta atccccaaag cacagt                   526
```

<210> SEQ ID NO 312
<211> LENGTH: 500
<212> TYPE: DNA
<213> ORGANISM: Homo sapien
<220> FEATURE:
<221> NAME/KEY: misc_feature
<222> LOCATION: (1)...(500)

-continued

<223> OTHER INFORMATION: n = A,T,C or G

<400> SEQUENCE: 312
cctctctctc cccacccccct gactctagag aactgggttt tctcccagta ctccagcaat 60
tcatttctga aagcagttga gccactttat tccaaagtac actgcagatg ttcaaactct 120
ccatttctct ttcccttcca cctgccagtt ttgctgactc tcaacttgtc atgagtgtaa 180
gcattaagga cattatgctt cttcgattct gaagacaggc cctgctcatg gatgactctg 240
gcttcttagg aaaatatttt tcttccaaaa tcagtaggaa atctaaactt atcccctctt 300
tgcagatgtc tagcagcttc agacatttgg ttaagaaccc atgggaaaaa aaaaaatcct 360
tgctaatgtg gtttcctttg taaaccanga ttcttatttg nctggtatag aatatcagct 420
ctgaacgtgt ggtaaagatt tttgtgtttg aatataggag aaatcagttt gctgaaaagt 480
tagtcttaat tatctattgg 500

<210> SEQ ID NO 313
<211> LENGTH: 718
<212> TYPE: DNA
<213> ORGANISM: Homo sapien
<220> FEATURE:
<221> NAME/KEY: misc_feature
<222> LOCATION: (1)...(718)
<223> OTHER INFORMATION: n = A,T,C or G

<400> SEQUENCE: 313
ggagatttgt gtggtttgca gccgagggag accaggaaga tctgcatggt gggaaggacc 60
tgatgataca gaggtgagaa ataagaaagg ctgctgactt taccatctga ggccacacat 120
ctgctgaaat ggagataatt aacatcacta gaaacagcaa gatgacaata taatgtctaa 180
gtagtgacat gtttttgcac atttccagcc cttttaaata tccacacaca caggaagcac 240
aaaaggaagc acagagatcc ctgggagaaa tgcccggccg ccatcttggg tcatcgatga 300
gcctcgccct gtgcctgntc ccgcttgtga gggaaggaca ttagaaaatg aattgatgtg 360
ttccttaaag gatggcagga aaacagatcc tgttgtggat atttatttga acgggattac 420
agatttgaaa tgaagtcaca aagtgagcat taccaatgag aggaaaacag acgagaaaat 480
cttgatggtt cacaagacat gcaacaaaca aaatggaata ctgtgatgac acgagcagcc 540
aactggggag gagataccac ggggcagagg tcaggattct ggccctgctg cctaactgtg 600
cgttatacca atcatttcta tttctaccct caaacaagct gtngaatatc tgacttacgg 660
ttcttntggc ccacattttc atnatccacc ccntcntttt aannttantc caaantgt 718

<210> SEQ ID NO 314
<211> LENGTH: 358
<212> TYPE: DNA
<213> ORGANISM: Homo sapien

<400> SEQUENCE: 314
gtttatttac attacagaaa aaacatcaag acaatgtata ctatttcaaa tatatccata 60
cataatcaaa tatagctgta gtacatgttt tcattggtgt agattaccac aaatgcaagg 120
caacatgtgt agatctcttg tcttattctt ttgtctataa tactgtattg tgtagtccaa 180
gctctcggta gtccagccac tgtgaaacat gctcccttta gattaacctc gtggacgctc 240
ttgttgtatt gctgaactgt agtgccctgt attttgcttc tgtctgtgaa ttctgttgct 300
tctggggcat ttccttgtga tgcagaggac caccacacag atgacagcaa tctgaatt 358

-continued

<210> SEQ ID NO 315
<211> LENGTH: 341
<212> TYPE: DNA
<213> ORGANISM: Homo sapien

<400> SEQUENCE: 315
taccacctcc ccgctggcac tgatgagccg catcaccatg gtcaccagca ccatgaaggc 60
ataggtgatg atgaggacat ggaatgggcc cccaaggatg gtctgtccaa agaagcgagt 120
gacccccatt ctgaagatgt ctggaacctc taccagcagg atgatgatag ccccaatgac 180
agtcaccagc tccccgacca gccggatatc gtccttaggg gtcatgtagg cttcctgaag 240
tagcttctgc tgtaagaggg tgttgtcccg ggggctcgtg cggttattgg tcctgggctt 300
gagggggcgg tagatgcagc acatggtgaa gcagatgatg t 341

<210> SEQ ID NO 316
<211> LENGTH: 151
<212> TYPE: DNA
<213> ORGANISM: Homo sapien

<400> SEQUENCE: 316
agactgggca agactcttac gccccacact gcaatttggt cttgttgccg tatccattta 60
tgtgggcctt tctcgagttt ctgattataa acaccactgg agcgatgtgt tgactggact 120
cattcaggga gctctggttg caatattagt t 151

<210> SEQ ID NO 317
<211> LENGTH: 151
<212> TYPE: DNA
<213> ORGANISM: Homo sapien

<400> SEQUENCE: 317
agaactagtg gatcctaatg aaatacctga aacatatatt ggcatttatc aatggctcaa 60
atcttcattt atctctggcc ttaaccctgg ctcctgaggc tgcggccagc agatcccagg 120
ccagggctct gttcttgcca cacctgcttg a 151

<210> SEQ ID NO 318
<211> LENGTH: 151
<212> TYPE: DNA
<213> ORGANISM: Homo sapien

<400> SEQUENCE: 318
actggtggga ggcgctgttt agttggctgt tttcagaggg gtctttcgga gggacctcct 60
gctgcaggct ggagtgtctt tattcctggc gggagaccgc acattccact gctgaggctg 120
tgggggcggt ttatcaggca gtgataaaca t 151

<210> SEQ ID NO 319
<211> LENGTH: 151
<212> TYPE: DNA
<213> ORGANISM: Homo sapien

<400> SEQUENCE: 319
aactagtgga tccagagcta taggtacagt gtgatctcag ctttgcaaac acattttcta 60
catagatagt actaggtatt aatagatatg taaagaaaga aatcacacca ttaataatgg 120
taagattggg tttatgtgat tttagtgggt a 151

<210> SEQ ID NO 320
<211> LENGTH: 150
<212> TYPE: DNA

-continued

<213> ORGANISM: Homo sapien

<400> SEQUENCE: 320
aactagtgga tccactagtc cagtgtggtg gaattccatt gtgttggggt tctagatcgc 60
gagcggctgc cctttttttt tttttttttg ggggggaatt tttttttttt aatagttatt 120
gagtgttcta cagcttacag taaataccat 150

<210> SEQ ID NO 321
<211> LENGTH: 151
<212> TYPE: DNA
<213> ORGANISM: Homo sapien

<400> SEQUENCE: 321
agcaactttg tttttcatcc aggttatttt aggcttagga tttcctctca cactgcagtt 60
tagggtggca ttgtaaccag ctatggcata ggtgttaacc aaaggctgag taaacatggg 120
tgcctctgag aaatcaaagt cttcatacac t 151

<210> SEQ ID NO 322
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 322
atccagcatc ttctcctgtt tcttgccttc ctttttcttc ttcttasatt ctgcttgagg 60
tttgggcttg gtcagtttgc cacagggctt ggagatggtg acagtcttct ggcattcggc 120
attgtgcagg gctcgcttca nacttccagt t 151

<210> SEQ ID NO 323
<211> LENGTH: 151
<212> TYPE: DNA
<213> ORGANISM: Homo sapien
<220> FEATURE:
<221> NAME/KEY: misc_feature
<222> LOCATION: (1)...(151)
<223> OTHER INFORMATION: n = A,T,C or G

<400> SEQUENCE: 323
tgaggacttg tkttcttttt ctttattttt aatcctctta ckttgtaaat atattgccta 60
nagactcant tactacccag tttgtggttt twtgggagaa atgtaactgg acagttagct 120
gttcaatyaa aaagacactt ancccatgtg g 151

<210> SEQ ID NO 324
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 324
acctgtgtgg aatttcagct ttcctcatgc aaaaggattt tgtatccccg gcctacttga 60
agaagtggtc agctaaagga atccaggttg ttggttggac tgttaatacc tttgatgaaa 120
agagttacta cgaatcccat cttggttcca gctatatcac tgacagcatg gtagaagact 180
gcgaacctca cttctagact ttcacggtgg gacgaaacgg gttcagaaac tgccaggggc 240

-continued ctcatacagg gatatcaaaa taccctttgt gctacccagg ccctggggaa tcaggtgact 300
cacacaaatg caatagttgg tcactgcatt tttacctgaa ccaaagctaa acccggtgtt 360
gccaccatgc accatggcat gccagagttc aacactgttg ctcttgaaaa ttgggtctga 420
aaaaacgcac aagagcccct gccctgccct agctgangca c 461

<210> SEQ ID NO 325
<211> LENGTH: 400
<212> TYPE: DNA
<213> ORGANISM: Homo sapien

<400> SEQUENCE: 325
acactgtttc catgttatgt ttctacacat tgctacctca gtgctcctgg aaacttagct 60
tttgatgtct ccaagtagtc caccttcatt taactctttg aaactgtatc atctttgcca 120
agtaagagtg gtggcctatt tcagctgctt tgacaaaatg actggctcct gacttaacgt 180
tctataaatg aatgtgctga agcaaagtgc ccatggtggc ggcgaagaag agaaagatgt 240
gttttgtttt ggactctctg tggtcccttc caatgctgtg ggtttccaac caggggaagg 300 gtccctttttg cattgccaag tgccataacc atgagcacta cgctaccatg gttctgcctc 360
ctggccaagc aggctggttt gcaagaatga aatgaatgat 400

<210> SEQ ID NO 326
<211> LENGTH: 1215
<212> TYPE: DNA
<213> ORGANISM: Homo sapien

<400> SEQUENCE: 326
ggaggactgc agcccgcact cgcagccctg gcaggcggca ctggtcatgg aaaacgaatt 60
gttctgctcg ggcgtcctgg tgcatccgca gtgggtgctg tcagccgcac actgtttcca 120
gaactcctac accatcgggc tgggcctgca cagtcttgag gccgaccaag agccagggag 180
ccagatggtg gaggccagcc tctccgtacg gcacccagag tacaacagac ccttgctcgc 240
taacgacctc atgctcatca agttggacga atccgtgtcc gagtctgaca ccatccggag 300
catcagcatt gcttcgcagt gccctaccgc ggggaactct tgcctcgttt ctggctgggg 360
tctgctggcg aacggcagaa tgcctaccgt gctgcagtgc gtgaacgtgt cggtggtgtc 420
tgaggaggtc tgcagtaagc tctatgaccc gctgtaccac cccagcatgt tctgcgccgg 480
cggagggcaa gaccagaagg actcctgcaa cggtgactct gggggggccc tgatctgcaa 540
cgggtacttg cagggccttg tgtctttcgg aaaagccccg tgtggccaag ttggcgtgcc 600
aggtgtctac accaacctct gcaaattcac tgagtggata gagaaaaccg tccaggccag 660
ttaactctgg ggactgggaa cccatgaaat tgacccccaa atacatcctg cggaaggaat 720
tcaggaatat ctgttcccag cccctcctcc ctcaggccca ggagtccagg cccccagccc 780
ctcctccctc aaaccaaggg tacagatccc cagcccctcc tccctcagac ccaggagtcc 840 agaccccccca gcccctcctc cctcagaccc aggagtccag cccctcctcc ctcagaccca 900
ggagtccaga ccccccagcc cctcctccct cagacccagg ggtccaggcc cccaacccct 960
cctccctcag actcagaggt ccaagccccc aacccctcct tccccagacc cagaggtcca 1020
ggtcccagcc cctcctccct cagacccagc ggtccaatgc cacctagact ctccctgtac 1080
acagtgcccc cttgtggcac gttgacccaa ccttaccagt tggtttttca ttttttgtcc 1140
ctttccccta gatccagaaa taaagtctaa gagaagcgca aaaaaaaaaa aaaaaaaaaa 1200

-continued

```
aaaaaaaaaa aaaaa                                                        1215


<210> SEQ ID NO 327
<211> LENGTH: 220
<212> TYPE: PRT
<213> ORGANISM: Homo sapien

<400> SEQUENCE: 327

Glu Asp Cys Ser Pro His Ser Gln Pro Trp Gln Ala Ala Leu Val Met
 1               5                  10                  15

Glu Asn Glu Leu Phe Cys Ser Gly Val Leu Val His Pro Gln Trp Val
            20                  25                  30

Leu Ser Ala Ala His Cys Phe Gln Asn Ser Tyr Thr Ile Gly Leu Gly
        35                  40                  45

Leu His Ser Leu Glu Ala Asp Gln Glu Pro Gly Ser Gln Met Val Glu
    50                  55                  60

Ala Ser Leu Ser Val Arg His Pro Glu Tyr Asn Arg Pro Leu Leu Ala
65                  70                  75                  80

Asn Asp Leu Met Leu Ile Lys Leu Asp Glu Ser Val Ser Glu Ser Asp
                85                  90                  95

Thr Ile Arg Ser Ile Ser Ile Ala Ser Gln Cys Pro Thr Ala Gly Asn
            100                 105                 110

Ser Cys Leu Val Ser Gly Trp Gly Leu Leu Ala Asn Gly Arg Met Pro
        115                 120                 125

Thr Val Leu Gln Cys Val Asn Val Ser Val Val Ser Glu Glu Val Cys
    130                 135                 140

Ser Lys Leu Tyr Asp Pro Leu Tyr His Pro Ser Met Phe Cys Ala Gly
145                 150                 155                 160

Gly Gly Gln Asp Gln Lys Asp Ser Cys Asn Gly Asp Ser Gly Gly Pro
                165                 170                 175

Leu Ile Cys Asn Gly Tyr Leu Gln Gly Leu Val Ser Phe Gly Lys Ala
            180                 185                 190

Pro Cys Gly Gln Val Gly Val Pro Gly Val Tyr Thr Asn Leu Cys Lys
        195                 200                 205

Phe Thr Glu Trp Ile Glu Lys Thr Val Gln Ala Ser
    210                 215                 220


<210> SEQ ID NO 328
<211> LENGTH: 234
<212> TYPE: DNA
<213> ORGANISM: Homo sapien

<400> SEQUENCE: 328

cgctcgtctc tggtagctgc agccaaatca taaacggcga ggactgcagc ccgcactcgc      60

agccctggca ggcggcactg gtcatggaaa acgaattgtt ctgctcgggc gtcctggtgc     120

atccgcagtg ggtgctgtca gccacacact gtttccagaa ctcctacacc atcgggctgg     180

gcctgcacag tcttgaggcc gaccaagagc cagggagcca gatggtggag gcca           234


<210> SEQ ID NO 329
<211> LENGTH: 77
<212> TYPE: PRT
<213> ORGANISM: Homo sapien

<400> SEQUENCE: 329

Leu Val Ser Gly Ser Cys Ser Gln Ile Ile Asn Gly Glu Asp Cys Ser
 1               5                  10                  15
```

-continued

```
Pro His Ser Gln Pro Trp Gln Ala Ala Leu Val Met Glu Asn Glu Leu
            20                  25                  30

Phe Cys Ser Gly Val Leu Val His Pro Gln Trp Val Leu Ser Ala Thr
        35                  40                  45

His Cys Phe Gln Asn Ser Tyr Thr Ile Gly Leu Gly Leu His Ser Leu
    50                  55                  60

Glu Ala Asp Gln Glu Pro Gly Ser Gln Met Val Glu Ala
65                  70                  75


<210> SEQ ID NO 330
<211> LENGTH: 70
<212> TYPE: DNA
<213> ORGANISM: Homo sapien

<400> SEQUENCE: 330

cccaacacaa tggcccgatc ccatccctga ctccgccctc aggatcgctc gtctctggta      60

gctgcagcca                                                             70


<210> SEQ ID NO 331
<211> LENGTH: 22
<212> TYPE: PRT
<213> ORGANISM: Homo sapien

<400> SEQUENCE: 331

Gln His Asn Gly Pro Ile Pro Ser Leu Thr Pro Pro Ser Gly Ser Leu
 1               5                  10                  15

Val Ser Gly Ser Cys Ser
            20


<210> SEQ ID NO 332
<211> LENGTH: 2507
<212> TYPE: DNA
<213> ORGANISM: Homo sapien

<400> SEQUENCE: 332

tggtgccgct gcagccggca gagatggttg agctcatgtt cccgctgttg ctcctccttc      60

tgcccttcct tctgtatatg gctgcgcccc aaatcaggaa aatgctgtcc agtggggtgt     120

gtacatcaac tgttcagctt cctgggaaag tagttgtggt cacaggagct aatacaggta     180

tcgggaagga gacagccaaa gagctggctc agagaggagc tcgagtatat ttagcttgcc     240

gggatgtgga aaagggggaa ttggtggcca aagagatcca gaccacgaca gggaaccagc     300

aggtgttggt gcggaaactg gacctgtctg atactaagtc tattcgagct tttgctaagg     360

gcttcttagc tgaggaaaag cacctccacg ttttgatcaa caatgcagga gtgatgatgt     420

gtccgtactc gaagacagca gatggctttg agatgcacat aggagtcaac cacttgggtc     480

acttcctcct aacccatctg ctgctagaga aactaaagga atcagcccca tcaaggatag     540

taaatgtgtc ttccctcgca catcacctgg gaaggatcca cttccataac ctgcagggcg     600

agaaattcta caatgcaggc ctggcctact gtcacagcaa gctagccaac atcctcttca     660

cccaggaact ggcccggaga ctaaaaggct ctggcgttac gacgtattct gtacaccctg     720

gcacagtcca atctgaactg gttcggcact catctttcat gagatggatg tggtggcttt     780

tctccttttt catcaagact cctcagcagg gagcccagac cagcctgcac tgtgccttaa     840

cagaaggtct tgagattcta agtgggaatc atttcagtga ctgtcatgtg gcatgggtct     900

ctgcccaagc tcgtaatgag actatagcaa ggcggctgtg ggacgtcagt tgtgacctgc     960

tgggcctccc aatagactaa caggcagtgc cagttggacc caagagaaga ctgcagcaga    1020
```

-continued

```
ctacacagta cttcttgtca aaatgattct ccttcaaggt tttcaaaacc tttagcacaa   1080
agagagcaaa accttccagc cttgcctgct tggtgtccag ttaaaactca gtgtactgcc   1140
agattcgtct aaatgtctgt catgtccaga tttactttgc ttctgttact gccagagtta   1200
ctagagatat cataatagga taagaagacc ctcatatgac ctgcacagct cattttcctt   1260
ctgaaagaaa ctactaccta ggagaatcta agctatagca gggatgattt atgcaaattt   1320
gaactagctt ctttgttcac aattcagttc ctcccaacca accagtcttc acttcaagag   1380
ggccacactg caacctcagc ttaacatgaa taacaaagac tggctcagga gcagggcttg   1440
cccaggcatg gtggatcacc ggaggtcagt agttcaagac cagcctggcc aacatggtga   1500
aaccccacct ctactaaaaa ttgtgtatat ctttgtgtgt cttcctgttt atgtgtgcca   1560
agggagtatt ttcacaaagt tcaaaacagc cacaataatc agagatggag caaaccagtg   1620
ccatccagtc tttatgcaaa tgaaatgctg caaagggaag cagattctgt atatgttggt   1680
aactacccac caagagcaca tgggtagcag ggaagaagta aaaaaagaga aggagaatac   1740
tggaagataa tgcacaaaat gaagggacta gttaaggatt aactagccct ttaaggatta   1800
actagttaag gattaatagc aaaagayatt aaatatgcta acatagctat ggaggaattg   1860
agggcaagca cccaggactg atgaggtctt aacaaaaacc agtgtggcaa aaaaaaaaaa   1920
aaaaaaaaaa aaaaatccta aaaacaaaca aacaaaaaaa acaattcttc attcagaaaa   1980
attatcttag ggactgatat tggtaattat ggtcaattta ataatatttt ggggcatttc   2040
cttacattgt cttgacaaga ttaaaatgtc tgtgccaaaa ttttgtattt tatttggaga   2100
cttcttatca aaagtaatgc tgccaaagga agtctaagga attagtagtg ttcccatcac   2160
ttgtttggag tgtgctattc taaaagattt tgatttcctg gaatgacaat tatattttaa   2220
ctttggtggg ggaaagagtt ataggaccac agtcttcact tctgatactt gtaaattaat   2280
cttttattgc acttgttttg accattaagc tatatgttta gaaatggtca ttttacggaa   2340
aaattagaaa aattctgata atagtgcaga ataaatgaat taatgtttta cttaatttat   2400
attgaactgt caatgacaaa taaaaattct ttttgattat tttttgtttt catttaccag   2460
aataaaaacg taagaattaa aagtttgatt acaaaaaaaa aaaaaaa                 2507
```

<210> SEQ ID NO 333
<211> LENGTH: 3030
<212> TYPE: DNA
<213> ORGANISM: Homo sapien

<400> SEQUENCE: 333

```
gcaggcgact tgcgagctgg gagcgattta aaacgctttg gattcccccg gcctgggtgg     60
ggagagcgag ctgggtgccc cctagattcc ccgcccccgc acctcatgag ccgaccctcg    120
gctccatgga gcccggcaat tatgccacct tggatggagc caaggatatc gaaggcttgc    180
tgggagcggg aggggggcgg aatctggtcg cccactcccc tctgaccagc cacccagcgg    240
cgcctacgct gatgcctgct gtcaactatg ccccccttgga tctgccaggc tcggcggagc    300
cgccaaagca atgccaccca tgccctgggg tgccccaggg gacgtcccca gctcccgtgc    360
cttatggtta ctttggaggc gggtactact cctgccgagt gtcccggagc tcgctgaaac    420
cctgtgccca ggcagccacc ctggccgcgt accccgcgga gactcccacg gccggggaag    480
agtaccccag ycgccccact gagtttgcct tctatccggg atatccggga acctaccagc    540
ctatggccag ttacctggac gtgtctgtgg tgcagactct gggtgctcct ggagaaccgc    600
```

-continued

```
gacatgactc cctgttgcct gtggacagtt accagtcttg ggctctcgct ggtggctgga    660
acagccagat gtgttgccag ggagaacaga acccaccagg tccctttttgg aaggcagcat   720
ttgcagactc cagcgggcag caccctcctg acgcctgcgc ctttcgtcgc ggccgcaaga    780
aacgcattcc gtacagcaag gggcagttgc gggagctgga gcgggagtat gcggctaaca    840
agttcatcac caaggacaag aggcgcaaga tctcggcagc caccagcctc tcggagcgcc    900
agattaccat ctggtttcag aaccgccggg tcaaagagaa gaaggttctc gccaaggtga    960
agaacagcgc taccccttaa gagatctcct tgcctgggtg ggaggagcga aagtgggggt   1020
gtcctgggga gaccaggaac ctgccaagcc caggctgggg ccaaggactc tgctgagagg   1080
cccctagaga caacaccctt cccaggccac tggctgctgg actgttcctc aggagcggcc   1140
tgggtaccca gtatgtgcag ggagacggaa ccccatgtga cagcccactc caccagggtt   1200
cccaaagaac ctggcccagt cataatcatt catcctgaca gtggcaataa tcacgataac   1260
cagtactagc tgccatgatc gttagcctca tattttctat ctagagctct gtagagcact   1320
ttagaaaccg ctttcatgaa ttgagctaat tatgaataaa tttggaaggc gatccctttg   1380
cagggaagct ttctctcaga ccccccttcca ttacacctct caccctggta acagcaggaa   1440
gactgaggag aggggaacgg gcagattcgt tgtgtggctg tgatgtccgt ttagcatttt   1500
tctcagctga cagctgggta ggtggacaat tgtagaggct gtctcttcct ccctccttgt   1560
ccaccccata gggtgtaccc actggtcttg gaagcaccca tccttaatac gatgattttt   1620
ctgtcgtgtg aaaatgaagc cagcaggctg cccctagtca gtccttcctt ccagagaaaa   1680
agagatttga gaaagtgcct gggtaattca ccattaattt cctcccccaa actctctgag   1740
tcttccctta atatttctgg tggttctgac caaagcaggt catggtttgt tgagcatttg   1800
ggatcccagt gaagtagatg tttgtagcct tgcatactta gcccttccca ggcacaaacg   1860
gagtggcaga gtggtgccaa ccctgttttc ccagtccacg tagacagatt cacagtgcgg   1920
aattctggaa gctggagaca gacgggctct ttgcagagcc gggactctga gagggacatg   1980
agggcctctg cctctgtgtt cattctctga tgtcctgtac ctgggctcag tgcccggtgg   2040
gactcatctc ctggccgcgc agcaaagcca gcgggttcgt gctggtcctt cctgcacctt   2100
aggctggggg tggggggcct gccggcgcat tctccacgat tgagcgcaca ggcctgaagt   2160
ctggacaacc cgcagaaccg aagctccgag cagcgggtcg gtggcgagta gtggggtcgg   2220
tggcgagcag ttggtggtgg gccgcggccg ccactacctc gaggacattt ccctcccgga   2280
gccagctctc ctagaaaccc cgcggcggcc gccgcagcca agtgtttatg gcccgcggtc   2340
gggtgggatc ctagccctgt ctcctctcct gggaaggagt gagggtggga cgtgacttag   2400
acacctacaa atctatttac caaagaggag cccgggactg agggaaaagg ccaaagagtg   2460
tgagtgcatg cggactgggg gttcagggga agaggacgag gaggaggaag atgaggtcga   2520
tttcctgatt taaaaaatcg tccaagcccc gtggtccagc ttaaggtcct cggttacatg   2580
cgccgctcag agcaggtcac tttctgcctt ccacgtcctc cttcaaggaa gccccatgtg   2640
ggtagctttc aatatcgcag gttcttactc ctctgcctct ataagctcaa acccaccaac   2700
gatcgggcaa gtaaaccccc tccctcgccg acttcggaac tggcgagagt tcagcgcaga   2760
tgggcctgtg gggagggggc aagatagatg agggggagcg gcatggtgcg gggtgacccc   2820
ttggagagag gaaaaaggcc acaagagggg ctgccaccgc cactaacgga gatggccctg   2880
gtagagacct ttgggggtct ggaacctctg gactccccat gctctaactc ccacactctg   2940
ctatcagaaa cttaaacttg aggattttct ctgtttttca ctcgcaataa aytcagagca   3000
```

-continued aacaaaaaaa aaaaaaaaaa aaaactcgag 3030

<210> SEQ ID NO 334
<211> LENGTH: 2417
<212> TYPE: DNA
<213> ORGANISM: Homo sapien

<400> SEQUENCE: 334
ggcggccgct ctagagctag tgggatcccc cgggctgcac gaattcggca cgagtgagtt 60
ggagttttac ctgtattgtt ttaatttcaa caagcctgag gactagccac aaatgtaccc 120
agtttacaaa tgaggaaaca ggtgcaaaaa ggttgttacc tgtcaaaggt cgtatgtggc 180
agagccaaga tttgagccca gttatgtctg atgaacttag cctatgctct ttaaacttct 240
gaatgctgac cattgaggat atctaaactt agatcaattg cattttccct ccaagactat 300
ttacttatca atacaataat accaccttta ccaatctatt gttttgatac gagactcaaa 360
tatgccagat atatgtaaaa gcaacctaca agctctctaa tcatgctcac ctaaaagatt 420
cccgggatct aataggctca aagaaacttc ttctagaaat ataaaagaga aaattggatt 480
atgcaaaaat tcattattaa tttttttcat ccatccttta attcagcaaa catttatctg 540
ttgttgactt tatgcagtat ggccttttaa ggattggggg acaggtgaag aacggggtgc 600
cagaatgcat cctcctacta atgaggtcag tacacatttg cattttaaaa tgccctgtcc 660
agctgggcat ggtggatcat gcctgtaatc tcaacattgg aaggccaagg caggaggatt 720
gcttcagccc aggagttcaa gaccagcctg ggcaacatag aaagacccca tctctcaatc 780
aatcaatcaa tgccctgtct ttgaaaataa aactctttaa gaaaggttta atgggcaggg 840
tgtggtagct catgcctata atacagcact ttgggaggct gaggcaggag gatcacttta 900
gcccagaagt tcaagaccag cctgggcaac aagtgacacc tcatctcaat tttttaataa 960
aatgaataca tacataagga aagataaaaa gaaaagttta atgaaagaat acagtataaa 1020
acaaatctct tggacctaaa agtatttttg ttcaagccaa atattgtgaa tcacctctct 1080
gtgttgagga tacagaatat ctaagcccag gaaactgagc agaaagttca tgtactaact 1140
aatcaacccg aggcaaggca aaaatgagac taactaatca atccgaggca aggggcaaat 1200
tagacggaac ctgactctgg tctattaagc gacaactttc cctctgttgt atttttcttt 1260
tattcaatgt aaaaggataa aaactctcta aaactaaaaa caatgtttgt caggagttac 1320
aaaccatgac caactaatta tggggaatca taaaatatga ctgtatgaga tcttgatggt 1380
ttacaaagtg tacccactgt taatcacttt aaacattaat gaacttaaaa atgaatttac 1440
ggagattgga atgtttcttt cctgttgtat tagttggctc aggctgccat aacaaaatac 1500
cacagactgg gaggcttaag taacagaaat tcatttctca cagttctggg ggctggaagt 1560
ccacgatcaa ggtgcaggaa aggcaggctt cattctgagg cccctctctt ggctcacatg 1620
tggccaccct cccactgcgt gctcacatga cctctttgtg ctcctggaaa gagggtgtgg 1680
gggacagagg gaaagagaag gagagggaac tctctggtgt ctcgtctttc aaggacccta 1740
acctgggcca ctttggccca ggcactgtgg ggtggggggt tgtggctgct ctgctctgag 1800
tggccaagat aaagcaacag aaaaatgtcc aaagctgtgc agcaaagaca agccaccgaa 1860
cagggatctg ctcatcagtg tggggacctc caagtcggcc accctggagg caagccccca 1920
cagagcccat gcaaggtggc agcagcagaa gaagggaatt gtccctgtcc ttggcacatt 1980
cctcaccgac ctggtgatgc tggacactgc gatgaatggt aatgtggatg agaatatgat 2040

-continued ggactcccag aaaaggagac ccagctgctc aggtggctgc aaatcattac agccttcatc 2100
ctggggagga actgggggcc tggttctggg tcagagagca gcccagtgag ggtgagagct 2160
acagcctgtc ctgccagctg gatccccagt cccggtcaac cagtaatcaa ggctgagcag 2220
atcaggcttc ccggagctgg tcttgggaag ccagccctgg ggtgagttgg ctcctgctgt 2280
ggtactgaga caatattgtc ataaattcaa tgcgcccttg tatccctttt tctttttat 2340 ctgtctacat ctataatcac tatgcatact agtctttgtt agtgtttcta ttcmacttaa 2400
tagagatatg ttatact 2417

<210> SEQ ID NO 335
<211> LENGTH: 2984
<212> TYPE: DNA
<213> ORGANISM: Homo sapien

<400> SEQUENCE: 335
atccctcctt ccccactctc ctttccagaa ggcacttggg gtcttatctg ttggactctg 60
aaaacacttc aggcgccctt ccaaggcttc cccaaacccc taagcagccg cagaagcgct 120
cccgagctgc cttctcccac actcaggtga tcgagttgga gaggaagttc agccatcaga 180
agtacctgtc ggcccctgaa cgggcccacc tggccaagaa cctcaagctc acggagaccc 240
aagtgaagat atggttccag aacagacgct ataagactaa gcgaaagcag ctctcctcgg 300
agctgggaga cttggagaag cactcctctt tgccggccct gaaagaggag gccttctccc 360
gggcctccct ggtctccgtg tataacagct atccttacta cccatacctg tactgcgtgg 420
gcagctggag cccagctttt tggtaatgcc agctcaggtg acaaccatta tgatcaaaaa 480
ctgccttccc cagggtgtct ctatgaaaag cacaaggggc caaggtcagg gagcaagagg 540
tgtgcacacc aaagctattg gagatttgcg tggaaatctc asattcttca ctggtgagac 600
aatgaaacaa cagagacagt gaaagtttta atacctaagt cattccccca gtgcatactg 660
taggtcattt tttttgcttc tggctacctg tttgaagggg agagagggaa aatcaagtgg 720
tattttccag cactttgtat gattttggat gagctgtaca cccaaggatt ctgttctgca 780
actccatcct cctgtgtcac tgaatatcaa ctctgaaaga gcaaacctaa caggagaaag 840
gacaaccagg atgaggatgt caccaactga attaaactta agtccagaag cctcctgttg 900
gccttggaat atggccaagg ctctctctgt ccctgtaaaa gagaggggca aatagagagt 960
ctccaagaga acgccctcat gctcagcaca tatttgcatg ggagggggag atgggtggga 1020
ggagatgaaa atatcagctt ttcttattcc tttttattcc ttttaaaatg gtatgccaac 1080
ttaagtattt acagggtggc ccaaatagaa caagatgcac tcgctgtgat tttaagacaa 1140
gctgtataaa cagaactcca ctgcaagagg gggggccggg ccaggagaat ctccgcttgt 1200
ccaagacagg ggcctaagga gggtctccac actgctgcta ggggctgttg cattttttta 1260
ttagtagaaa gtggaaaggc ctcttctcaa cttttttccc ttgggctgga gaatttagaa 1320
tcagaagttt cctggagttt tcaggctatc atatatactg tatcctgaaa ggcaacataa 1380
ttcttccttc cctcctttta aaattttgtg ttccttttttg cagcaattac tcactaaagg 1440
gcttcatttt agtccagatt tttagtctgg ctgcacctaa cttatgcctc gcttatttag 1500
cccgagatct ggtctttttt tttttttttt tttttccgtc tccccaaagc tttatctgtc 1560
ttgacttttt aaaaaagttt gggggcagat tctgaattgg ctaaaagaca tgcattttta 1620
aaactagcaa ctcttatttc tttcctttaa aaatacatag cattaaatcc caaatcctat 1680
ttaaagacct gacagcttga gaaggtcact actgcattta taggaccttc tggtggttct 1740

-continued

```
gctgttacgt ttgaagtctg acaatccttg agaatctttg catgcagagg aggtaagagg   1800
tattggattt tcacagagga agaacacagc gcagaatgaa gggccaggct tactgagctg   1860
tccagtggag ggctcatggg tgggacatgg aaaagaaggc agcctaggcc ctggggagcc   1920
cagtccactg agcaagcaag ggactgagtg agccttttgc aggaaaaggc taagaaaaag   1980
gaaaaccatt ctaaaacaca acaagaaact gtccaaatgc tttgggaact gtgtttattg   2040
cctataatgg gtccccaaaa tgggtaacct agacttcaga gagaatgagc agagagcaaa   2100
ggagaaatct ggctgtcctt ccattttcat tctgttatct caggtgagct ggtagagggg   2160
agacattaga aaaaaatgaa acaacaaaac aattactaat gaggtacgct gaggcctggg   2220
agtctcttga ctccactact taattccgtt tagtgagaaa cctttcaatt ttcttttatt   2280
agaagggcca gcttactgtt ggtggcaaaa ttgccaacat aagttaatag aaagttggcc   2340
aatttcaccc cattttctgt ggtttgggct ccacattgca atgttcaatg ccacgtgctg   2400
ctgacaccga ccggagtact agccagcaca aaaggcaggg tagcctgaat tgctttctgc   2460
tctttacatt tcttttaaaa taagcattta gtgctcagtc cctactgagt actctttctc   2520
tcccctcctc tgaatttaat tctttcaact tgcaatttgc aaggattaca catttcactg   2580
tgatgtatat tgtgttgcaa aaaaaaaaaa aagtgtcttt gtttaaaatt acttggtttg   2640
tgaatccatc ttgctttttc cccattggaa ctagtcatta acccatctct gaactggtag   2700
aaaaacatct gaagagctag tctatcagca tctgacaggt gaattggatg gttctcagaa   2760
ccatttcacc cagacagcct gtttctatcc tgtttaataa attagtttgg gttctctaca   2820
tgcataacaa accctgctcc aatctgtcac ataaaagtct gtgacttgaa gtttagtcag   2880
cacccccacc aaactttatt tttctatgtg tttttgcaa catatgagtg ttttgaaaat    2940
aaagtaccca tgtctttatt agaaaaaaaa aaaaaaaaaa aaaa                    2984
```

```
<210> SEQ ID NO 336
<211> LENGTH: 147
<212> TYPE: PRT
<213> ORGANISM: Homo sapien

<400> SEQUENCE: 336

Pro Ser Phe Pro Thr Leu Leu Ser Arg Arg His Leu Gly Ser Tyr Leu
 1               5                  10                  15

Leu Asp Ser Glu Asn Thr Ser Gly Ala Leu Pro Arg Leu Pro Gln Thr
            20                  25                  30

Pro Lys Gln Pro Gln Lys Arg Ser Arg Ala Ala Phe Ser His Thr Gln
        35                  40                  45

Val Ile Glu Leu Glu Arg Lys Phe Ser His Gln Lys Tyr Leu Ser Ala
    50                  55                  60

Pro Glu Arg Ala His Leu Ala Lys Asn Leu Lys Leu Thr Glu Thr Gln
65                  70                  75                  80

Val Lys Ile Trp Phe Gln Asn Arg Arg Tyr Lys Thr Lys Arg Lys Gln
                85                  90                  95

Leu Ser Ser Glu Leu Gly Asp Leu Glu Lys His Ser Ser Leu Pro Ala
            100                 105                 110

Leu Lys Glu Glu Ala Phe Ser Arg Ala Ser Leu Val Ser Val Tyr Asn
        115                 120                 125

Ser Tyr Pro Tyr Tyr Pro Tyr Leu Tyr Cys Val Gly Ser Trp Ser Pro
    130                 135                 140

Ala Phe Trp
```

-continued

145

<210> SEQ ID NO 337
<211> LENGTH: 9
<212> TYPE: PRT
<213> ORGANISM: Homo sapien

<400> SEQUENCE: 337

Ala Leu Thr Gly Phe Thr Phe Ser Ala
1 5

<210> SEQ ID NO 338
<211> LENGTH: 9
<212> TYPE: PRT
<213> ORGANISM: Homo sapien

<400> SEQUENCE: 338

Leu Leu Ala Asn Asp Leu Met Leu Ile
1 5

<210> SEQ ID NO 339
<211> LENGTH: 318
<212> TYPE: PRT
<213> ORGANISM: Homo sapien

<400> SEQUENCE: 339

Met Val Glu Leu Met Phe Pro Leu Leu Leu Leu Leu Leu Pro Phe Leu
1 5 10 15

Leu Tyr Met Ala Ala Pro Gln Ile Arg Lys Met Leu Ser Ser Gly Val
20 25 30

Cys Thr Ser Thr Val Gln Leu Pro Gly Lys Val Val Val Val Thr Gly
35 40 45

Ala Asn Thr Gly Ile Gly Lys Glu Thr Ala Lys Glu Leu Ala Gln Arg
50 55 60

Gly Ala Arg Val Tyr Leu Ala Cys Arg Asp Val Glu Lys Gly Glu Leu
65 70 75 80

Val Ala Lys Glu Ile Gln Thr Thr Thr Gly Asn Gln Gln Val Leu Val
85 90 95

Arg Lys Leu Asp Leu Ser Asp Thr Lys Ser Ile Arg Ala Phe Ala Lys
100 105 110

Gly Phe Leu Ala Glu Glu Lys His Leu His Val Leu Ile Asn Asn Ala
115 120 125

Gly Val Met Met Cys Pro Tyr Ser Lys Thr Ala Asp Gly Phe Glu Met
130 135 140

His Ile Gly Val Asn His Leu Gly His Phe Leu Leu Thr His Leu Leu
145 150 155 160

Leu Glu Lys Leu Lys Glu Ser Ala Pro Ser Arg Ile Val Asn Val Ser
165 170 175

Ser Leu Ala His His Leu Gly Arg Ile His Phe His Asn Leu Gln Gly
180 185 190

Glu Lys Phe Tyr Asn Ala Gly Leu Ala Tyr Cys His Ser Lys Leu Ala
195 200 205

Asn Ile Leu Phe Thr Gln Glu Leu Ala Arg Arg Leu Lys Gly Ser Gly
210 215 220

Val Thr Thr Tyr Ser Val His Pro Gly Thr Val Gln Ser Glu Leu Val
225 230 235 240

Arg His Ser Ser Phe Met Arg Trp Met Trp Trp Leu Phe Ser Phe Phe
245 250 255

-continued

```
Ile Lys Thr Pro Gln Gln Gly Ala Gln Thr Ser Leu His Cys Ala Leu
            260                 265                 270

Thr Glu Gly Leu Glu Ile Leu Ser Gly Asn His Phe Ser Asp Cys His
        275                 280                 285

Val Ala Trp Val Ser Ala Gln Ala Arg Asn Glu Thr Ile Ala Arg Arg
    290                 295                 300

Leu Trp Asp Val Ser Cys Asp Leu Leu Gly Leu Pro Ile Asp
305                 310                 315


<210> SEQ ID NO 340
<211> LENGTH: 483
<212> TYPE: DNA
<213> ORGANISM: Homo sapien

<400> SEQUENCE: 340

gccgaggtct gccttcacac ggaggacacg agactgcttc ctcaagggct cctgcctgcc     60

tggacactgg tgggaggcgc tgtttagttg gctgttttca gaggggtctt tcggagggac    120

ctcctgctgc aggctggagt gtctttattc ctggcgggag accgcacatt ccactgctga    180

ggttgtgggg gcggtttatc aggcagtgat aaacataaga tgtcatttcc ttgactccgg    240

ccttcaattt tctctttggc tgacgacgga gtccgtggtg tcccgatgta actgacccct    300

gctccaaacg tgacatcact gatgctcttc tcgggggtgc tgatggcccg cttggtcacg    360

tgctcaatct cgccattcga ctcttgctcc aaactgtatg aagacacctg actgcacgtt    420

ttttctgggc ttccagaatt taaagtgaaa ggcagcactc ctaagctccg actccgatgc    480

ctg                                                                  483


<210> SEQ ID NO 341
<211> LENGTH: 344
<212> TYPE: DNA
<213> ORGANISM: Homo sapien

<400> SEQUENCE: 341

ctgctgctga gtcacagatt tcattataaa tagcctccct aaggaaaata cactgaatgc     60

tatttttact aaccattcta tttttataga aatagctgag agtttctaaa ccaactctct    120

gctgccttac aagtattaaa tattttactt ctttccataa agagtagctc aaaatatgca    180

attaatttaa taatttctga tgatggtttt atctgcagta atatgtatat catctattag    240

aatttactta atgaaaaact gaagagaaca aaatttgtaa ccactagcac ttaagtactc    300

ctgattctta acattgtctt taatgaccac aagacaacca acag                     344


<210> SEQ ID NO 342
<211> LENGTH: 592
<212> TYPE: DNA
<213> ORGANISM: Homo sapien

<400> SEQUENCE: 342

acagcaaaaa agaaactgag aagcccaaty tgctttcttg ttaacatcca cttatccaac     60

caatgtggaa acttcttata cttggttcca ttatgaagtt ggacaattgc tgctatcaca    120

cctggcaggt aaaccaatgc caagagagtg atggaaacca ttggcaagac tttgttgatg    180

accaggattg gaattttata aaaatattgt tgatgggaag ttgctaaagg gtgaattact    240

tccctcagaa gagtgtaaag aaaagtcaga gatgctataa tagcagctat tttaattggc    300

aagtgccact gtggaaagag ttcctgtgtg tgctgaagtt ctgaagggca gtcaaattca    360
```

-continued

```
tcagcatggg ctgtttggtg caaatgcaaa agcacaggtc tttttagcat gctggtctct    420

cccgtgtcct tatgcaaata atcgtcttct tctaaatttc tcctaggctt cattttccaa    480

agttcttctt ggtttgtgat gtctttttctg ctttccatta attctataaa atagtatggc    540

ttcagccacc cactcttcgc cttagcttga ccgtgagtct cggctgccgc tg            592
```

<210> SEQ ID NO 343
<211> LENGTH: 382
<212> TYPE: DNA
<213> ORGANISM: Homo sapien

<400> SEQUENCE: 343

```
ttcttgacct cctcctcctt caagctcaaa caccacctcc cttattcagg accggcactt     60

cttaatgttt gtggctttct ctccagcctc tcttaggagg ggtaatggtg gagttggcat    120

cttgtaactc tcctttctcc tttcttcccc tttctctgcc cgcctttccc atcctgctgt    180

agacttcttg attgtcagtc tgtgtcacat ccagtgattg ttttggtttc tgttcccttt    240

ctgactgccc aaggggctca gaaccccagc aatcccttcc tttcactacc ttcttttttg    300

ggggtagttg gaagggactg aaattgtggg gggaaggtag gaggcacatc aataaagagg    360

aaaccaccaa gctgaaaaaa aa                                             382
```

<210> SEQ ID NO 344
<211> LENGTH: 536
<212> TYPE: DNA
<213> ORGANISM: Homo sapien

<400> SEQUENCE: 344

```
ctgggcctga agctgtaggg taaatcagag gcaggcttct gagtgatgag agtcctgaga     60

caataggcca cataaacttg gctggatgga acctcacaat aaggtggtca cctcttgttt    120

gtttaggggg atgccaagga taaggccagc tcagttatat gaagagaagc agaacaaaca    180

agtctttcag agaaatggat gcaatcagag tgggatcccg gtcacatcaa ggtcacactc    240

caccttcatg tgcctgaatg gttgccaggt cagaaaaatc caccccttac gagtgcggct    300

tcgaccctat atcccccgcc cgcgtccctt tctccataaa attcttctta gtagctatta    360

ccttcttatt atttgatcta gaaattgccc tccttttacc cctaccatga gccctacaaa    420

caactaacct gccactaata gttatgtcat ccctcttatt aatcatcatc ctagccctaa    480

gtctggccta tgagtgacta caaaaaggat tagactgagc cgaataacaa aaaaaa        536
```

<210> SEQ ID NO 345
<211> LENGTH: 251
<212> TYPE: DNA
<213> ORGANISM: Homo sapien

<400> SEQUENCE: 345

```
acctttttgag gtctctctca ccacctccac agccaccgtc accgtgggat gtgctggatg     60

tgaatgaagc ccccatcttt gtgcctcctg aaaagagagt ggaagtgtcc gaggactttg    120

gcgtgggcca ggaaatcaca tcctacactg cccaggagcc agacacattt atggaacaga    180

aaataacata tcggatttgg agagacactg ccaactggct ggagattaat ccggacactg    240

gtgccatttc c                                                          251
```

<210> SEQ ID NO 346
<211> LENGTH: 282
<212> TYPE: DNA
<213> ORGANISM: Homo sapien -continued
<220> FEATURE:
<221> NAME/KEY: misc_feature
<222> LOCATION: (1)...(282)
<223> OTHER INFORMATION: n = A,T,C or G

<400> SEQUENCE: 346
cgcgtctctg acactgtgat catgacaggg gttcaaacag aaagtgcctg ggccctcctt 60
ctaagtcttg ttaccaaaaa aaggaaaaag aaaagatctt ctcagttaca aattctggga 120
agggagacta tacctggctc ttgccctaag tgagaggtct tccctcccgc accaaaaaat 180
agaaaggctt tctatttcac tggcccaggt agggggaagg agagtaactt tgagtctgtg 240
ggtctcattt cccaaggtgc cttcaatgct catnaaaacc aa 282

<210> SEQ ID NO 347
<211> LENGTH: 201
<212> TYPE: DNA
<213> ORGANISM: Homo sapien
<220> FEATURE:
<221> NAME/KEY: misc_feature
<222> LOCATION: (1)...(201)
<223> OTHER INFORMATION: n = A,T,C or G

<400> SEQUENCE: 347
acacacataa tattataaaa tgccatctaa ttggaaggag ctttctatca ttgcaagtca 60
taaatataac ttttaaaana ntactancag cttttaccta ngctcctaaa tgcttgtaaa 120
tctgagactg actggaccca cccagaccca gggcaaagat acatgttacc atatcatctt 180
tataaagaat ttttttttgt c 201

<210> SEQ ID NO 348
<211> LENGTH: 251
<212> TYPE: DNA
<213> ORGANISM: Homo sapien

<400> SEQUENCE: 348
ctgttaatca caacatttgt gcatcacttg tgccaagtga gaaaatgttc taaaatcaca 60
agagagaaca gtgccagaat gaaactgacc ctaagtccca ggtgcccctg ggcaggcaga 120
aggagacact cccagcatgg aggagggttt atcttttcat cctaggtcag gtctacaatg 180
ggggaaggtt ttattataga actcccaaca gcccacctca ctcctgccac ccacccgatg 240
gccctgcctc c 251

<210> SEQ ID NO 349
<211> LENGTH: 251
<212> TYPE: DNA
<213> ORGANISM: Homo sapien

<400> SEQUENCE: 349
taaaaatcaa gccatttaat tgtatctttg aaggtaaaca atatatggga gctggatcac 60
aacccctgag gatgccagag ctatgggtcc agaacatggt gtggtattat caacagagtt 120
cagaagggtc tgaactctac gtgttaccag agaacataat gcaattcatg cattccactt 180
agcaattttg taaaatacca gaaacagacc ccaagagtct ttcaagatga ggaaaattca 240
actcctggtt t 251

<210> SEQ ID NO 350
<211> LENGTH: 908
<212> TYPE: DNA
<213> ORGANISM: Homo sapien -continued

<400> SEQUENCE: 350
ctggacactt tgcgagggct tttgctggct gctgctgctg cccgtcatgc tactcatcgt 60
agcccgcccg gtgaagctcg ctgctttccc tacctcctta agtgactgcc aaacgcccac 120
cggctggaat tgctctggtt atgatgacag agaaaatgat ctcttcctct gtgacaccaa 180
cacctgtaaa tttgatgggg aatgtttaag aattggagac actgtgactt gcgtctgtca 240
gttcaagtgc aacaatgact atgtgcctgt gtgtggctcc aatggggaga gctaccagaa 300
tgagtgttac ctgcgacagg ctgcatgcaa acagcagagt gagatacttg tggtgtcaga 360
aggatcatgt gccacagtcc atgaaggctc tggagaaact agtcaaaagg agacatccac 420
ctgtgatatt tgccagtttg gtgcagaatg tgacgaagat gccgaggatg tctggtgtgt 480
gtgtaatatt gactgttctc aaaccaactt caatcccctc tgcgcttctg atgggaaatc 540
ttatgataat gcatgccaaa tcaaagaagc atcgtgtcag aaacaggaga aaattgaagt 600
catgtctttg ggtcgatgtc aagataacac aactacaact actaagtctg aagatgggca 660
ttatgcaaga acagattatg cagagaatgc taacaaatta gaagaaagtg ccagagaaca 720
ccacatacct tgtccggaac attacaatgg cttctgcatg catgggaagt gtgagcattc 780
tatcaatatg caggagccat cttgcaggtg tgatgctggt tatactggac aacactgtga 840
aaaaaaggac tacagtgttc tatacgttgt tcccggtcct gtacgatttc agtatgtctt 900
aatcgcag 908

<210> SEQ ID NO 351
<211> LENGTH: 472
<212> TYPE: DNA
<213> ORGANISM: Homo sapien

<400> SEQUENCE: 351
ccagttattt gcaagtggta agagcctatt taccataaat aatactaaga accaactcaa 60
gtcaaacctt aatgccattg ttattgtgaa ttaggattaa gtagtaattt tcaaaattca 120
cattaacttg attttaaaat cagwtttgyg agtcatttac cacaagctaa atgtgtacac 180
tatgataaaa acaaccattg tattcctgtt tttctaaaca gtcctaattt ctaacactgt 240
atatatcctt cgacatcaat gaactttgtt ttcttttact ccagtaataa agtaggcaca 300
gatctgtcca caacaaactt gccctctcat gccttgcctc tcaccatgct ctgctccagg 360 tcagcccccct tttggcctgt ttgttttgtc aaaaacctaa tctgcttctt gcttttcttg 420
gtaatatata tttagggaag atgttgcttt gcccacacac gaagcaaagt aa 472

<210> SEQ ID NO 352
<211> LENGTH: 251
<212> TYPE: DNA
<213> ORGANISM: Homo sapien

<400> SEQUENCE: 352
ctcaaagcta atctctcggg aatcaaacca gaaaagggca aggatcttag gcatggtgga 60
tgtggataag gccaggtcaa tggctgcaag catgcagaga aagaggtaca tcggagcgtg 120
caggctgcgt tccgtcctta cgatgaagac cacgatgcag tttccaaaca ttgccactac 180
atacatggaa aggaggggga agccaaccca gaaatgggct ttctctaatc ctgggatacc 240
aataagcaca a 251

<210> SEQ ID NO 353
<211> LENGTH: 436

-continued

<212> TYPE: DNA
<213> ORGANISM: Homo sapien

<400> SEQUENCE: 353
tttttttttt tttttttttt ttttttacaa caatgcagtc atttatttat tgagtatgtg 60
cacattatgg tattattact atactgatta tatttatcat gtgacttcta attaraaaat 120
gtatccaaaa gcaaaacagc agatatacaa aattaaagag acagaagata gacattaaca 180
gataaggcaa cttatacatt gacaatccaa atccaataca tttaaacatt tgggaaatga 240
gggggacaaa tggaagccar atcaaatttg tgtaaaacta ttcagtatgt ttcccttgct 300
tcatgtctga raaggctctc ccttcaatgg ggatgacaaa ctccaaatgc cacacaaatg 360
ttaacagaat actagattca cactggaacg ggggtaaaga agaaattatt ttctataaaa 420
gggctcctaa tgtagt 436

<210> SEQ ID NO 354
<211> LENGTH: 854
<212> TYPE: DNA
<213> ORGANISM: Homo sapien

<400> SEQUENCE: 354
ccttttctag ttcaccagtt ttctgcaagg atgctggtta gggagtgtct gcaggaggag 60
caagtctgaa accaaatcta ggaaacatag gaaacgagcc aggcacaggg ctggtgggcc 120
atcagggacc accctttggg ttgatatttt gcttaatctg catcttttga gtaagatcat 180
ctggcagtag aagctgttct ccaggtacat ttctctagct catgtacaaa aacatcctga 240
aggactttgt caggtgcctt gctaaaagcc agatgcgttc ggcacttcct tggtctgagg 300
ttaattgcac acctacaggc actgggctca tgctttcaag tattttgtcc tcactttagg 360
gtgagtgaaa gatccccatt ataggagcac ttgggagaga tcatataaaa gctgactctt 420
gagtacatgc agtaatgggg tagatgtgtg tggtgtgtct tcattcctgc aagggtgctt 480
gttagggagt gtttccagga ggaacaagtc tgaaaccaat catgaaataa atggtaggtg 540
tgaactggaa aactaattca aaagagagat cgtgatatca gtgtggttga tacaccttgg 600
caatatggaa ggctctaatt tgcccatatt tgaaataata attcagcttt ttgtaataca 660
aaataacaaa ggattgagaa tcatggtgtc taatgtataa aagacccagg aaacataaat 720
atatcaactg cataaatgta aaatgcatgt gacccaagaa ggccccaaag tggcagacaa 780
cattgtaccc attttccctt ccaaaatgtg agcggcgggc ctgctgcttt caaggctgtc 840
acacgggatg tcag 854

<210> SEQ ID NO 355
<211> LENGTH: 676
<212> TYPE: DNA
<213> ORGANISM: Homo sapien

<400> SEQUENCE: 355
gaaattaagt atgagctaaa ttccctgtta aaacctctag ggtgacagac tctcttcaac 60
caggtcaaag ctgatctttc tggaatgtca ccaaccaagg gcctatattt atcaaaagcc 120
atccacaagt catacctgga tgtcagcgaa gagggcacgg aggcagcagc agccactggg 180
gacagcatcg ctgtaaaaag cctaccaatg agagctcagt tcaaggcgaa ccaccccttc 240
ctgttcttta taaggcacac tcataccaac acgatcctat tctgtggcaa gcttgcctct 300
ccctaatcag atggggttga gtaaggctca gagttgcaga tgaggtgcag agacaatcct 360

-continued gtgactttcc cacggccaaa aagctgttca cacctcacgc acctctgtgc ctcagtttgc 420
tcatctgcaa aataggtcta ggatttcttc caaccatttc atgagttgtg aagctaaggc 480
tttgttaatc atggaaaaag gtagacttat gcagaaagcc tttctggctt tcttatctgt 540
ggtgtctcat ttgagtgctg tccagtgaca tgatcaagtc aatgagtaaa attttaaggg 600
attagatttt cttgacttgt atgtatctgt gagatcttga ataagtgacc tgacatctct 660
gcttaaagaa aaccag 676

<210> SEQ ID NO 356
<211> LENGTH: 574
<212> TYPE: DNA
<213> ORGANISM: Homo sapien

<400> SEQUENCE: 356
tttttttttt tttttcagga aaacattctc ttactttatt tgcatctcag caaaggttct 60
catgtggcac ctgactggca tcaaaccaaa gttcgtaggc caacaaagat gggccactca 120
caagcttccc atttgtagat ctcagtgcct atgagtatct gacacctgtt cctctcttca 180
gtctcttagg gaggcttaaa tctgtctcag gtgtgctaag agtgccagcc caaggkggtc 240
aaaagtccac aaaactgcag tctttgctgg gatagtaagc caagcagtgc ctggacagca 300
gagttctttt cttgggcaac agataaccag acaggactct aatcgtgctc ttattcaaca 360
ttcttctgtc tctgcctaga ctggaataaa aagccaatct ctctcgtggc acagggaagg 420
agatacaagc tcgtttacat gtgatagatc taacaaaggc atctaccgaa gtctggtctg 480
gatagacggc acagggagct cttaggtcag cgctgctggt tggaggacat tcctgagtcc 540
agctttgcag cctttgtgca acagtacttt ccca 574

<210> SEQ ID NO 357
<211> LENGTH: 393
<212> TYPE: DNA
<213> ORGANISM: Homo sapien

<400> SEQUENCE: 357
tttttttttt tttttttttt tttttttttt tacagaatat aratgcttta tcactgkact 60
taatatggkg kcttgttcac tatacttaaa aatgcaccac tcataaatat ttaattcagc 120
aagccacaac caaracttga ttttatcaac aaaaacccct aaatataaac ggsaaaaaag 180
atagatataa ttattccagt ttttttaaaa cttaaaarat attccattgc cgaattaara 240
araarataag tgttatatgg aaagaagggc attcaagcac actaaaraaa cctgaggkaa 300
gcataatctg tacaaaatta aactgtcctt tttggcattt taacaaattt gcaacgktct 360 ttttttctt tttctgtttt tttttttttt tac 393

<210> SEQ ID NO 358
<211> LENGTH: 630
<212> TYPE: DNA
<213> ORGANISM: Homo sapien

<400> SEQUENCE: 358
acagggtaaa caggaggatc cttgctctca cggagcttac attctagcag gaggacaata 60
ttaatgttta taggaaaatg atgagtttat gacaaaggaa gtagatagtg ttttacaaga 120
gcatagagta gggaagctaa tccagcacag ggaggtcaca gagacatccc taaggaagtg 180
gagtttaaac tgagagaagc aagtgcttaa actgaaggat gtgttgaaga agaagggaga 240
gtagaacaat ttgggcagag ggaaccttat agaccctaag gtgggaaggt tcaaagaact 300

-continued

```
gaaagagagc tagaacagct ggagccgttc tccggtgtaa agaggagtca aagagataag    360

attaaagatg tgaagattaa gatcttggtg gcattcaggg attggcactt ctacaagaaa    420

tcactgaagg gagtaatgtg acattacttt tcacttcagg atggccattc taactccagg    480

gggtagactg gactaggtaa gactggaggc aggtagacct cttctaaggc ctgcgatagt    540

gaaagacaaa aataagtggg gaaattcagg ggatagtgaa aatcagtagg acttaatgag    600

caagccagag gttcctccac aacaaccagt                                     630
```

<210> SEQ ID NO 359
<211> LENGTH: 620
<212> TYPE: DNA
<213> ORGANISM: Homo sapien

<400> SEQUENCE: 359

```
acagcattcc aaaatataca tctagagact aarrgtaaat gctctatagt gaagaagtaa     60

taattaaaaa atgctactaa tatagaaaat ttataatcag aaaaataaat attcagggag    120

ctcaccagaa gaataaagtg ctctgccagt tattaaagga ttactgctgg tgaattaaat    180

atggcattcc ccaagggaaa tagagagatt cttctggatt atgttcaata tttatttcac    240

aggattaact gttttaggaa cagatataaa gcttcgccac ggaagagatg gacaaagcac    300

aaagacaaca tgataccttta ggaagcaaca ctaccctttc aggcataaaa tttggagaaa    360

tgcaacatta tgcttcatga ataatatgta gaaagaaggt ctgatgaaaa tgacatcctt    420

aatgtaagat aactttataa gaattctggg tcaaataaaa ttctttgaag aaaacatcca    480

aatgtcattg acttatcaaa tactatcttg gcatataacc tatgaaggca aaactaaaca    540

aacaaaaagc tcacaccaaa caaaaccatc aacttatttt gtattctata acatacgaga    600

ctgtaaagat gtgacagtgt                                                620
```

<210> SEQ ID NO 360
<211> LENGTH: 431
<212> TYPE: DNA
<213> ORGANISM: Homo sapien

<400> SEQUENCE: 360

```
aaaaaaaaaa agccagaaca acatgtgata gataatatga ttggctgcac acttccagac     60

tgatgaatga tgaacgtgat ggactattgt atggagcaca tcttcagcaa gagggggaaa    120

tactcatcat ttttggccag cagttgtttg atcaccaaac atcatgccag aatactcagc    180

aaaccttctt agctcttgag aagtcaaagt ccgggggaat ttattcctgg caattttaat    240

tggactcctt atgtgagagc agcggctacc cagctggggt ggtggagcga acccgtcact    300

agtggacatg cagtggcaga gctcctggta accacctaga ggaatacaca ggcacatgtg    360

tgatgccaag cgtgacacct gtagcactca aatttgtctt gtttttgtct ttcggtgtgt    420

agattcttag t                                                         431
```

<210> SEQ ID NO 361
<211> LENGTH: 351
<212> TYPE: DNA
<213> ORGANISM: Homo sapien

<400> SEQUENCE: 361

```
acactgattt ccgatcaaaa gaatcatcat ctttaccttg acttttcagg gaattactga     60

actttcttct cagaagatag ggcacagcca ttgccttggc ctcacttgaa gggtctgcat    120
```

-continued

```
ttgggtcctc tggtctcttg ccaagtttcc cagccactcg agggagaaat atcgggaggt    180

ttgacttcct ccggggcttt cccgagggct tcaccgtgag ccctgcggcc ctcagggctg    240

caatcctgga ttcaatgtct gaaacctcgc tctctgcctg ctggacttct gaggccgtca    300

ctgccactct gtcctccagc tctgacagct cctcatctgt ggtcctgttg t             351
```

```
<210> SEQ ID NO 362
<211> LENGTH: 463
<212> TYPE: DNA
<213> ORGANISM: Homo sapien

<400> SEQUENCE: 362

acttcatcag gccataatgg gtgcctcccg tgagaatcca agcacctttg gactgcgcga     60

tgtagatgag ccggctgaag atcttgcgca tgcgcggctt cagggcgaag ttcttggcgc    120

ccccggtcac agaaatgacc aggttgggtg ttttcaggtg ccagtgctgg gtcagcagct    180

cgtaaaggat ttccgcgtcc gtgtcgcagg acagacgtat atacttccct ttcttcccca    240

gtgtctcaaa ctgaatatcc ccaaaggcgt cggtaggaaa ttccttggtg tgtttcttgt    300

agttccattt ctcactttgg ttgatctggg tgccttccat gtgctggctc tgggcatagc    360

cacacttgca cacattctcc ctgataagca cgatggtgtg gacaggaagg aaggatttca    420

ttgagcctgc ttatggaaac tggtattgtt agcttaaata gac                      463
```

```
<210> SEQ ID NO 363
<211> LENGTH: 653
<212> TYPE: DNA
<213> ORGANISM: Homo sapien
<220> FEATURE:
<221> NAME/KEY: misc_feature
<222> LOCATION: (1)...(653)
<223> OTHER INFORMATION: n = A,T,C or G

<400> SEQUENCE: 363

acccccgagt ncctgnctgg catactgnga acgaccaacg acacacccaa gctcggcctc     60

ctcttggnga ttctgggtga catcttcatg aatggcaacc gtgccagwga ggctgtcctc    120

tgggaggcac tacgcaagat gggactgcgt cctggggtga gacatcctct ccttggagat    180

ctaacgaaac ttctcaccta tgagttgtaa agcagaaata cctgnactac agacgagtgc    240

ccaacagcaa ccccccggaa gtatgagttc ctctrgggcc tccgttccta ccatgagasc    300

tagcaagatg naagtgttga gantcattgc agaggttcag aaaagagacc cntcgtgact    360

ggtctgcaca gttcatggag gctgcagatg aggccttgga tgctctggat gctgctgcag    420

ctgaggccga agcccgggct gaagcaagaa cccgcatggg aattggagat gaggctgtgt    480

ntgggccctg gagctgggat gacattgagt ttgagctgct gacctgggat gaggaaggag    540

attttggaga tccntggtcc agaattccat ttaccttctg ggccagatac caccagaatg    600

cccgctccag attccctcag acctttgccg gtcccattat tggtcstggt ggt           653
```

```
<210> SEQ ID NO 364
<211> LENGTH: 401
<212> TYPE: DNA
<213> ORGANISM: Homo sapien

<400> SEQUENCE: 364

actagaggaa agacgttaaa ccactctact accacttgtg gaactctcaa agggtaaatg     60

acaaagccaa tgaatgactc taaaaacaat atttacattt aatggtttgt agacaataaa    120

aaaacaaggt ggatagatct agaattgtaa cattttaaga aaaccatagc atttgacaga    180
```

-continued

```
tgagaaagct caattataga tgcaaagtta taactaaact actatagtag taaagaaata    240

catttcacac ccttcatata aattcactat cttggcttga ggcactccat aaaatgtatc    300

acgtgcatag taaatcttta tatttgctat ggcgttgcac tagaggactt ggactgcaac    360

aagtggatgc gcggaaaatg aaatcttctt caatagccca g                        401
```

<210> SEQ ID NO 365
<211> LENGTH: 356
<212> TYPE: DNA
<213> ORGANISM: Homo sapien

<400> SEQUENCE: 365

```
ccagtgtcat atttgggctt aaaatttcaa gaagggcact tcaaatggct ttgcatttgc     60

atgtttcagt gctagagcgt aggaatagac cctggcgtcc actgtgagat gttcttcagc    120

taccagagca tcaagtctct gcagcaggtc attcttgggt aaagaaatga cttccacaaa    180

ctctccatcc cctggctttg gcttcggcct tgcgttttcg gcatcatctc cgttaatggt    240

gactgtcacg atgtgtatag tacagtttga caagcctggg tccatacaga ccgctggaga    300

acattcggca atgtcccctt tgtagccagt ttcttcttcg agctcccgga gagcag        356
```

<210> SEQ ID NO 366
<211> LENGTH: 1851
<212> TYPE: DNA
<213> ORGANISM: Homo sapien

<400> SEQUENCE: 366

```
tcatcaccat tgccagcagc ggcaccgtta gtcaggtttt ctgggaatcc cacatgagta     60

cttccgtgtt cttcattctt cttcaatagc cataaatctt ctagctctgg ctggctgttt    120

tcacttcctt taagcctttg tgactcttcc tctgatgtca gctttaagtc ttgttctgga    180

ttgctgtttt cagaagagat ttttaacatc tgtttttctt tgtagtcaga aagtaactgg    240

caaattacat gatgatgact agaaacagca tactctctgg ccgtctttcc agatcttgag    300

aagatacatc aacattttgc tcaagtagag ggctgactat acttgctgat ccacaacata    360

cagcaagtat gagagcagtt cttccatatc tatccagcgc atttaaattc gctttttttct    420

tgattaaaaa tttcaccact tgctgttttt gctcatgtat accaagtagc agtggtgtga    480

ggccatgctt gttttttgat tcgatatcag caccgtataa gagcagtgct ttggccatta    540

atttatcttc attgtagaca gcatagtgta gagtggtatt tccatactca tctggaatat    600

ttggatcagt gccatgttcc agcaacatta acgcacattc atcttcctgg cattgtacgg    660

cctttgtcag agctgtcctc tttttgttgt caaggacatt aagttgacat cgtctgtcca    720

gcacgagttt tactacttct gaattcccat tggcagaggc cagatgtaga gcagtcctct    780

tttgcttgtc cctcttgttc acatccgtgt ccctgagcat gacgatgaga tcctttctgg    840

ggactttacc ccaccaggca gctctgtgga gcttgtccag atcttctcca tggacgtggt    900

acctgggatc catgaaggcg ctgtcatcgt agtctcccca agcgaccacg ttgctcttgc    960

cgctcccctg cagcagggga agcagtggca gcaccacttg cacctcttgc tcccaagcgt   1020

cttcacagag gagtcgttgt ggtctccaga agtgcccacg ttgctcttgc cgctccccct   1080

gtccatccag ggaggaagaa atgcaggaaa tgaaagatgc atgcacgatg gtatactcct   1140

cagccatcaa acttctggac agcaggtcac ttccagcaag gtggagaaag ctgtccaccc   1200

acagaggatg agatccagaa accacaatat ccattcacaa acaaacactt ttcagccaga   1260
```

-continued

```
cacaggtact gaaatcatgt catctgcggc aacatggtgg aacctaccca atcacacatc   1320

aagagatgaa gacactgcag tatatctgca caacgtaata ctcttcatcc ataacaaaat   1380

aatataattt tcctctggag ccatatggat gaactatgaa ggaagaactc cccgaagaag   1440

ccagtcgcag agaagccaca ctgaagctct gtcctcagcc atcagcgcca cggacaggar   1500

tgtgtttctt ccccagtgat gcagcctcaa gttatcccga agctgccgca gcacacggtg   1560

gctcctgaga aacaccccag ctcttccggt ctaacacagg caagtcaata aatgtgataa   1620

tcacataaac agaattaaaa gcaaagtcac ataagcatct caacagacac agaaaaggca   1680

tttgacaaaa tccagcatcc ttgtatttat tgttgcagtt ctcagaggaa atgcttctaa   1740

cttttcccca tttagtatta tgttggctgt gggcttgtca taggtggttt ttattacttt   1800

aaggtatgtc ccttctatgc ctgttttgct gagggtttta attctcgtgc c            1851
```

<210> SEQ ID NO 367
<211> LENGTH: 668
<212> TYPE: DNA
<213> ORGANISM: Homo sapien

<400> SEQUENCE: 367

```
cttgagcttc caaataygga agactggccc ttacacasgt caatgttaaa atgaatgcat     60

ttcagtattt tgaagataaa attrgtagat ctataccttg ttttttgatt cgatatcagc    120

accrtataag agcagtgctt tggccattaa tttatctttc attrtagaca gcrtagtgya    180

gagtggtatt tccatactca tctggaatat ttggatcagt gccatgttcc agcaacatta    240

acgcacattc atcttcctgg cattgtacgg cctgtcagta ttagacccaa aaacaaatta    300

catatcttag gaattcaaaa taacattcca cagctttcac caactagtta tatttaaagg    360

agaaaactca tttttatgcc atgtattgaa atcaaaccca cctcatgctg atatagttgg    420

ctactgcata cctttatcag agctgtcctc tttttgttgt caaggacatt aagttgacat    480

cgtctgtcca gcaggagttt tactacttct gaattcccat tggcagaggc cagatgtaga    540

gcagtcctat gagagtgaga agactttttta ggaaattgta gtgcactagc tacagccata    600

gcaatgattc atgtaactgc aaacactgaa tagcctgcta ttactctgcc ttcaaaaaaa    660

aaaaaaaa                                                             668
```

<210> SEQ ID NO 368
<211> LENGTH: 1512
<212> TYPE: DNA
<213> ORGANISM: Homo sapien

<400> SEQUENCE: 368

```
gggtcgccca gggggsgcgt gggctttcct cgggtgggtg tgggttttcc ctgggtgggg     60

tgggctgggc trgaatcccc tgctggggtt ggcaggtttt ggctgggatt gacttttytc    120

ttcaaacaga ttggaaaccc ggagttacct gctagttggt gaaactggtt ggtagacgcg    180

atctgttggc tactactggc ttctcctggc tgttaaaagc agatggtggt tgaggttgat    240

tccatgccgg ctgcttcttc tgtgaagaag ccatttggtc tcaggagcaa gatgggcaag    300

tggtgctgcc gttgcttccc ctgctgcagg gagagcggca agagcaacgt gggcacttct    360

ggagaccacg acgactctgc tatgaagaca ctcaggagca agatgggcaa gtggtgccgc    420

cactgcttcc cctgctgcag ggggagtggc aagagcaacg tgggcgcttc tggagaccac    480

gacgaytctg ctatgaagac actcaggaac aagatgggca agtggtgctg ccactgcttc    540

ccctgctgca gggggagcrg caagagcaag gtgggcgctt ggggagacta cgatgacagt    600
```

-continued gccttcatgg agcccaggta ccacgtccgt ggagaagatc tggacaagct ccacagagct 660
gcctggtggg gtaaagtccc cagaaaggat ctcatcgtca tgctcaggga cactgacgtg 720
aacaagaagg acaagcaaaa gaggactgct ctacatctgg cctctgccaa tgggaattca 780
gaagtagtaa aactcstgct ggacagacga tgtcaactta atgtccttga caacaaaaag 840
aggacagctc tgayaaaggc cgtacaatgc caggaagatg aatgtgcgtt aatgttgctg 900
gaacatggca ctgatccaaa tattccagat gagtatggaa ataccactct rcactaygct 960
rtctayaatg aagataaatt aatggccaaa gcactgctct tatayggtgc tgatatcgaa 1020
tcaaaaaaca aggtatagat ctactaattt tatcttcaaa atactgaaat gcattcattt 1080
taacattgac gtgtgtaagg gccagtcttc cgtatttgga agctcaagca taacttgaat 1140
gaaaatattt tgaaatgacc taattatctm agactttatt ttaaatattg ttattttcaa 1200
agaagcatta gagggtacag tttttttttt ttaaatgcac ttctggtaaa tacttttgtt 1260
gaaaacactg aatttgtaaa aggtaatact tactattttt caatttttcc ctcctaggat 1320 tttttttcccc taatgaatgt aagatggcaa aatttgccct gaaataggtt ttacatgaaa 1380
actccaagaa aagttaaaca tgtttcagtg aatagagatc ctgctccttt ggcaagttcc 1440
taaaaaacag taatagatac gaggtgatgc gcctgtcagt ggcaaggttt aagatatttc 1500
tgatctcgtg cc 1512

<210> SEQ ID NO 369
<211> LENGTH: 1853
<212> TYPE: DNA
<213> ORGANISM: Homo sapien

<400> SEQUENCE: 369
gggtcgccca gggggsgcgt gggctttcct cgggtgggtg tgggttttcc ctgggtgggg 60
tgggctgggc trgaatcccc tgctggggtt ggcaggtttt ggctgggatt gacttttytc 120
ttcaaacaga ttggaaaccc ggagttacct gctagttggt gaaactggtt ggtagacgcg 180
atctgttggc tactactggc ttctcctggc tgttaaaagc agatggtggt tgaggttgat 240
tccatgccgg ctgcttcttc tgtgaagaag ccatttggtc tcaggagcaa gatgggcaag 300
tggtgctgcc gttgcttccc ctgctgcagg gagagcggca agagcaacgt gggcacttct 360
ggagaccacg acgactctgc tatgaagaca ctcaggagca agatgggcaa gtggtgccgc 420
cactgcttcc cctgctgcag ggggagtggc aagagcaacg tgggcgcttc tggagaccac 480
gacgaytctg ctatgaagac actcaggaac aagatgggca agtggtgctg ccactgcttc 540
ccctgctgca gggggagcrg caagagcaag gtgggcgctt ggggagacta cgatgacagy 600
gccttcatgg akcccaggta ccacgtccrt ggagaagatc tggacaagct ccacagagct 660
gcctggtggg gtaaagtccc cagaaaggat ctcatcgtca tgctcaggga cackgaygtg 720
aacaagargg acaagcaaaa gaggactgct ctacatctgg cctctgccaa tgggaattca 780
gaagtagtaa aactcstgct ggacagacga tgtcaactta atgtccttga caacaaaaag 840
aggacagctc tgayaaaggc cgtacaatgc caggaagatg aatgtgcgtt aatgttgctg 900
gaacatggca ctgatccaaa tattccagat gagtatggaa ataccactct rcactaygct 960
rtctayaatg aagataaatt aatggccaaa gcactgctct tatayggtgc tgatatcgaa 1020
tcaaaaaaca agcatggcct cacaccactg ytacttggtr tacatgagca aaaacagcaa 1080
gtsgtgaaat ttttaatyaa gaaaaaagcg aatttaaaat gcrctggata gatatggaag 1140

-continued

```
ractgctctc atacttgctg tatgttgtgg atcagcaagt atagtcagcc ytctacttga   1200
gcaaaatrtt gatgtatctt ctcaagatct ggaaagacgg ccagagagta tgctgtttct   1260
agtcatcatc atgtaatttg ccagttactt tctgactaca aagaaaaaca gatgttaaaa   1320
atctcttctg aaaacagcaa tccagaacaa gacttaaagc tgacatcaga ggaagagtca   1380
caaaggctta aaggaagtga aaacagccag ccagaggcat ggaaactttt aaatttaaac   1440
ttttggttta atgttttttt tttttgcctt aataatatta gatagtccca aatgaaatwa   1500
cctatgagac taggctttga gaatcaatag attctttttt taagaatctt ttggctagga   1560
gcggtgtctc acgcctgtaa ttccagcacc ttgagaggct gaggtgggca gatcacgaga   1620
tcaggagatc gagaccatcc tggctaacac ggtgaaaccc catctctact aaaaatacaa   1680
aaacttagct gggtgtggtg gcgggtgcct gtagtcccag ctactcagga rgctgaggca   1740
ggagaatggc atgaacccgg gaggtggagg ttgcagtgag ccgagatccg ccactacact   1800
ccagcctggg tgacagagca agactctgtc tcaaaaaaaa aaaaaaaaaa aaa          1853
```

```
<210> SEQ ID NO 370
<211> LENGTH: 2184
<212> TYPE: DNA
<213> ORGANISM: Homo sapien

<400> SEQUENCE: 370
```

```
ggcacgagaa ttaaaaccct cagcaaaaca ggcatagaag ggacatacct taaagtaata     60
aaaaccacct atgacaagcc cacagccaac ataatactaa atggggaaaa gttagaagca    120
tttcctctga gaactgcaac aataaataca aggatgctgg attttgtcaa atgccttttc    180
tgtgtctgtt gagatgctta tgtgactttg cttttaattc tgtttatgtg attatcacat    240
ttattgactt gcctgtgtta gaccggaaga gctggggtgt ttctcaggag ccaccgtgtg    300
ctgcggcagc ttcgggataa cttgaggctg catcactggg gaagaaacac aytcctgtcc    360
gtggcgctga tggctgagga cagagcttca gtgtggcttc tctgcgactg gcttcttcgg    420
ggagttcttc cttcatagtt catccatatg gctccagagg aaaattatat tattttgtta    480
tggatgaaga gtattacgtt gtgcagatat actgcagtgt cttcatctct tgatgtgtga    540
ttgggtaggt tccaccatgt tgccgcagat gacatgattt cagtacctgt gtctggctga    600
aaagtgtttg tttgtgaatg gatattgtgg tttctggatc tcatcctctg tgggtggaca    660
gctttctcca ccttgctgga agtgacctgc tgtccagaag tttgatggct gaggagtata    720
ccatcgtgca tgcatctttc atttcctgca tttcttcctc cctggatgga caggggggagc   780
ggcaagagca acgtgggcac ttctggagac cacaacgact cctctgtgaa gacgcttggg    840
agcaagaggt gcaagtggtg ctgccactgc ttcccctgct gcaggggagc ggcaagagca    900
acgtggtcgc ttggggagac tacgatgaca gcgccttcat ggatcccagg taccacgtcc    960
atggagaaga tctggacaag ctccacagag ctgcctggtg gggtaaagtc cccagaaagg   1020
atctcatcgt catgctcagg gacacggatg tgaacaagag ggacaagcaa aagaggactg   1080
ctctacatct ggcctctgcc aatgggaatt cagaagtagt aaaactcgtg ctggacagac   1140
gatgtcaact taatgtcctt gacaacaaaa agaggacagc tctgacaaag gccgtacaat   1200
gccaggaaga tgaatgtgcg ttaatgttgc tggaacatgg cactgatcca aatattccag   1260
atgagtatgg aaataccact ctacactatg ctgtctacaa tgaagataaa ttaatggcca   1320
aagcactgct cttatacggt gctgatatcg aatcaaaaaa caagcatggc ctcacaccac   1380
tgctacttgg tatacatgag caaaaacagc aagtggtgaa atttttaatc aagaaaaaag   1440
```

-continued

```
cgaatttaaa tgcgctggat agatatggaa gaactgctct catacttgct gtatgttgtg   1500
gatcagcaag tatagtcagc cctctacttg agcaaaatgt tgatgtatct tctcaagatc   1560
tggaaagacg gccagagagt atgctgtttc tagtcatcat catgtaattt gccagttact   1620
ttctgactac aaagaaaaac agatgttaaa aatctcttct gaaaacagca atccagaaca   1680
agacttaaag ctgacatcag aggaagagtc acaaaggctt aaaggaagtg aaaacagcca   1740
gccagaggca tggaaacttt taaatttaaa cttttggttt aatgtttttt ttttttgcct   1800
taataatatt agatagtccc aaatgaaatw acctatgaga ctaggctttg agaatcaata   1860
gattcttttt ttaagaatct tttggctagg agcggtgtct cacgcctgta attccagcac   1920
cttgagaggc tgaggtgggc agatcacgag atcaggagat cgagaccatc ctggctaaca   1980
cggtgaaacc ccatctctac taaaaataca aaaacttagc tgggtgtggt ggcgggtgcc   2040
tgtagtccca gctactcagg argctgaggc aggagaatgg catgaacccg ggaggtggag   2100
gttgcagtga gccgagatcc gccactacac tccagcctgg gtgacagagc aagactctgt   2160
ctcaaaaaaa aaaaaaaaaa aaaa                                          2184
```

<210> SEQ ID NO 371
<211> LENGTH: 1855
<212> TYPE: DNA
<213> ORGANISM: Homo sapien
<220> FEATURE:
<221> NAME/KEY: misc_feature
<222> LOCATION: (1)...(1855)
<223> OTHER INFORMATION: n = A,T,C or G

<400> SEQUENCE: 371

```
tgcacgcatc ggccagtgtc tgtgccacgt acactgacgc cccctgagat gtgcacgccg     60
cacgcgcacg ttgcacgcgc ggcagcggct tggctggctt gtaacggctt gcacgcgcac    120
gccgcccccg cataaccgtc agactggcct gtaacggctt gcaggcgcac gccgcacgcg    180
cgtaacggct tggctgccct gtaacggctt gcacgtgcat gctgcacgcg cgttaacggc    240
ttggctggca tgtagccgct tggcttggct ttgcattytt tgctkggctk ggcgttgkty    300
tcttggattg acgcttcctc cttggatkga cgtttcctcc ttggatkgac gtttcytyty    360
tcgcgttcct ttgctggact tgacctttty tctgctgggt ttggcattcc tttggggtgg    420
gctgggtgtt ttctccgggg gggktkgccc ttcctggggt gggcgtgggk cgcccccagg    480
gggcgtgggc tttccccggg tgggtgtggg ttttcctggg gtggggtggg ctgtgctggg    540
atccccctgc tggggttggc agggattgac ttttttcttc aaacagattg gaaacccgga    600
gtaacntgct agttggtgaa actggttggt agacgcgatc tgctggtact actgtttctc    660
ctggctgtta aaagcagatg gtggctgagg ttgattcaat gccggctgct tcttctgtga    720
agaagccatt tggtctcagg agcaagatgg gcaagtggtg cgccactgct tcccctgctg    780
cagggggagc ggcaagagca acgtgggcac ttctggagac cacaacgact cctctgtgaa    840
gacgcttggg agcaagaggt gcaagtggtg ctgcccactg cttcccctgc tgcaggggag    900
cggcaagagc aacgtggkcg cttggggaga ctacgatgac agcgccttca tggakcccag    960
gtaccacgtc crtggagaag atctggacaa gctccacaga gctgcctggt ggggtaaagt   1020
ccccagaaag gatctcatcg tcatgctcag ggacactgay gtgaacaaga rggacaagca   1080
aaagaggact gctctacatc tggcctctgc caatgggaat tcagaagtag taaaactcgt   1140
gctggacaga cgatgtcaac ttaatgtcct tgacaacaaa aagaggacag ctctgacaaa   1200
```

-continued

```
ggccgtacaa tgccaggaag atgaatgtgc gttaatgttg ctggaacatg gcactgatcc   1260

aaatattcca gatgagtatg gaaataccac tctacactat gctgtctaca atgaagataa   1320

attaatggcc aaagcactgc tcttatacgg tgctgatatc gaatcaaaaa acaaggtata   1380

gatctactaa ttttatcttc aaaatactga aatgcattca ttttaacatt gacgtgtgta   1440

agggccagtc ttccgtattt ggaagctcaa gcataacttg aatgaaaata ttttgaaatg   1500

acctaattat ctaagacttt attttaaata ttgttatttt caaagaagca ttagagggta   1560

cagttttttt tttttaaatg cacttctggt aaatactttt gttgaaaaca ctgaatttgt   1620

aaaaggtaat acttactatt tttcaatttt tccctcctag gatttttttc ccctaatgaa   1680

tgtaagatgg caaaatttgc cctgaaatag gttttacatg aaaactccaa gaaaagttaa   1740

acatgtttca gtgaatagag atcctgctcc tttggcaagt tcctaaaaaa cagtaataga   1800

tacgaggtga tgcgcctgtc agtggcaagg tttaagatat ttctgatctc gtgcc        1855
```

<210> SEQ ID NO 372
<211> LENGTH: 1059
<212> TYPE: DNA
<213> ORGANISM: Homo sapien

<400> SEQUENCE: 372

```
gcaacgtggg cacttctgga gaccacaacg actcctctgt gaagacgctt gggagcaaga     60

ggtgcaagtg gtgctgccca ctgcttcccc tgctgcaggg gagcggcaag agcaacgtgg    120

gcgcttgrgg agactmcgat gacagygcct tcatggagcc caggtaccac gtccgtggag    180

aagatctgga caagctccac agagctgccc tggtggggta aagtccccag aaaggatctc    240

atcgtcatgc tcagggacac tgaygtgaac aagarggaca agcaaaagag gactgctcta    300

catctggcct ctgccaatgg gaattcagaa gtagtaaaac tcstgctgga cagacgatgt    360

caacttaatg tccttgacaa caaaaagagg acagctctga yaaaggccgt acaatgccag    420

gaagatgaat gtgcgttaat gttgctggaa catggcactg atccaaatat tccagatgag    480

tatggaaata ccactctrca ctaygctrtc tayaatgaag ataaattaat ggccaaagca    540

ctgctcttat ayggtgctga tatcgaatca aaaaacaagg tatagatcta ctaattttat    600

cttcaaaata ctgaaatgca ttcattttaa cattgacgtg tgtaagggcc agtcttccgt    660

atttggaagc tcaagcataa cttgaatgaa aatattttga aatgacctaa ttatctaaga    720

ctttatttta aatattgtta ttttcaaaga agcattagag ggtacagttt ttttttttta    780

aatgcacttc tggtaaatac ttttgttgaa aacactgaat ttgtaaaagg taatacttac    840

tatttttcaa tttttccctc ctaggatttt tttcccctaa tgaatgtaag atggcaaaat    900

ttgccctgaa ataggtttta catgaaaact ccaagaaaag ttaaacatgt ttcagtgaat    960

agagatcctg ctcctttggc aagttcctaa aaaacagtaa tagatacgag gtgatgcgcc   1020

tgtcagtggc aaggtttaag atatttctga tctcgtgcc                          1059
```

<210> SEQ ID NO 373
<211> LENGTH: 1155
<212> TYPE: DNA
<213> ORGANISM: Homo sapien

<400> SEQUENCE: 373

```
atggtggttg aggttgattc catgccggct gcctcttctg tgaagaagcc atttggtctc     60

aggagcaaga tgggcaagtg gtgctgccgt tgcttcccct gctgcaggga gagcggcaag    120

agcaacgtgg gcacttctgg agaccacgac gactctgcta tgaagacact caggagcaag    180
```

-continued

```
atgggcaagt ggtgccgcca ctgcttcccc tgctgcaggg ggagtggcaa gagcaacgtg    240

ggcgcttctg gagaccacga cgactctgct atgaagacac tcaggaacaa gatgggcaag    300

tggtgctgcc actgcttccc ctgctgcagg gggagcggca agagcaaggt gggcgcttgg    360

ggagactacg atgacagtgc cttcatggag cccaggtacc acgtccgtgg agaagatctg    420

gacaagctcc acagagctgc ctggtggggt aaagtcccca gaaaggatct catcgtcatg    480

ctcagggaca ctgacgtgaa caagaaggac aagcaaaaga ggactgctct acatctggcc    540

tctgccaatg ggaattcaga agtagtaaaa ctcctgctgg acagacgatg tcaacttaat    600

gtccttgaca acaaaaagag gacagctctg ataaaggccg tacaatgcca ggaagatgaa    660

tgtgcgttaa tgttgctgga acatggcact gatccaaata ttccagatga gtatggaaat    720

accactctgc actacgctat ctataatgaa gataaattaa tggccaaagc actgctctta    780

tatggtgctg atatcgaatc aaaaaacaag catggcctca caccactgtt acttggtgta    840

catgagcaaa aacagcaagt cgtgaaattt ttaatcaaga aaaaagcgaa tttaaatgca    900

ctggatagat atggaaggac tgctctcata cttgctgtat gttgtggatc agcaagtata    960

gtcagccttc tacttgagca aaatattgat gtatcttctc aagatctatc tggacagacg   1020

gccagagagt atgctgtttc tagtcatcat catgtaattt gccagttact ttctgactac   1080

aaagaaaaac agatgctaaa aatctcttct gaaaacagca atccagaaaa tgtctcaaga   1140

accagaaata aataa                                                    1155
```

```
<210> SEQ ID NO 374
<211> LENGTH: 2000
<212> TYPE: DNA
<213> ORGANISM: Homo sapien

<400> SEQUENCE: 374
```

```
atggtggttg aggttgattc catgccggct gcctcttctg tgaagaagcc atttggtctc     60

aggagcaaga tgggcaagtg gtgctgccgt tgcttcccct gctgcaggga gagcggcaag    120

agcaacgtgg gcacttctgg agaccacgac gactctgcta tgaagacact caggagcaag    180

atgggcaagt ggtgccgcca ctgcttcccc tgctgcaggg ggagtggcaa gagcaacgtg    240

ggcgcttctg gagaccacga cgactctgct atgaagacac tcaggaacaa gatgggcaag    300

tggtgctgcc actgcttccc ctgctgcagg gggagcggca agagcaaggt gggcgcttgg    360

ggagactacg atgacagtgc cttcatggag cccaggtacc acgtccgtgg agaagatctg    420

gacaagctcc acagagctgc ctggtggggt aaagtcccca gaaaggatct catcgtcatg    480

ctcagggaca ctgacgtgaa caagaaggac aagcaaaaga ggactgctct acatctggcc    540

tctgccaatg ggaattcaga agtagtaaaa ctcctgctgg acagacgatg tcaacttaat    600

gtccttgaca acaaaaagag gacagctctg ataaaggccg tacaatgcca ggaagatgaa    660

tgtgcgttaa tgttgctgga acatggcact gatccaaata ttccagatga gtatggaaat    720

accactctgc actacgctat ctataatgaa gataaattaa tggccaaagc actgctctta    780

tatggtgctg atatcgaatc aaaaaacaag catggcctca caccactgtt acttggtgta    840

catgagcaaa aacagcaagt cgtgaaattt ttaatcaaga aaaaagcgaa tttaaatgca    900

ctggatagat atggaaggac tgctctcata cttgctgtat gttgtggatc agcaagtata    960

gtcagccttc tacttgagca aaatattgat gtatcttctc aagatctatc tggacagacg   1020

gccagagagt atgctgtttc tagtcatcat catgtaattt gccagttact ttctgactac   1080
```

-continued

```
aaagaaaaac agatgctaaa aatctcttct gaaaacagca atccagaaca agacttaaag   1140
ctgacatcag aggaagagtc acaaaggttc aaaggcagtg aaaatagcca gccagagaaa   1200
atgtctcaag aaccagaaat aaataaggat ggtgatagag aggttgaaga agaaatgaag   1260
aagcatgaaa gtaataatgt gggattacta gaaaacctga ctaatggtgt cactgctggc   1320
aatggtgata atggattaat tcctcaaagg aagagcagaa cacctgaaaa tcagcaattt   1380
cctgacaacg aaagtgaaga gtatcacaga atttgcgaat tagtttctga ctacaaagaa   1440
aaacagatgc caaaatactc ttctgaaaac agcaacccag aacaagactt aaagctgaca   1500
tcagaggaag agtcacaaag gcttgagggc agtgaaaatg gccagccaga gctagaaaat   1560
tttatggcta tcgaagaaat gaagaagcac ggaagtactc atgtcggatt cccagaaaac   1620
ctgactaatg gtgccactgc tggcaatggt gatgatggat taattcctcc aaggaagagc   1680
agaacacctg aaagccagca atttcctgac actgagaatg aagagtatca cagtgacgaa   1740
caaaatgata ctcagaagca attttgtgaa gaacagaaca ctggaatatt acacgatgag   1800
attctgattc atgaagaaaa gcagatagaa gtggttgaaa aaatgaattc tgagctttct   1860
cttagttgta agaaagaaaa agacatcttg catgaaaata gtacgttgcg ggaagaaatt   1920
gccatgctaa gactggagct agacacaatg aaacatcaga gccagctaaa aaaaaaaaaa   1980
aaaaaaaaaa aaaaaaaaaa                                               2000
```

<210> SEQ ID NO 375
<211> LENGTH: 2040
<212> TYPE: DNA
<213> ORGANISM: Homo sapien

<400> SEQUENCE: 375

```
atggtggttg aggttgattc catgccggct gcctcttctg tgaagaagcc atttggtctc     60
aggagcaaga tgggcaagtg gtgctgccgt tgcttcccct gctgcaggga gagcggcaag    120
agcaacgtgg gcacttctgg agaccacgac gactctgcta tgaagacact caggagcaag    180
atgggcaagt ggtgccgcca ctgcttcccc tgctgcaggg ggagtggcaa gagcaacgtg    240
ggcgcttctg gagaccacga cgactctgct atgaagacac tcaggaacaa gatgggcaag    300
tggtgctgcc actgcttccc ctgctgcagg gggagcggca agagcaaggt gggcgcttgg    360
ggagactacg atgacagtgc cttcatggag cccaggtacc acgtccgtgg agaagatctg    420
gacaagctcc acagagctgc ctggtggggt aaagtcccca gaaaggatct catcgtcatg    480
ctcagggaca ctgacgtgaa caagaaggac aagcaaaaga ggactgctct acatctggcc    540
tctgccaatg ggaattcaga agtagtaaaa ctcctgctgg acagacgatg tcaacttaat    600
gtccttgaca acaaaaagag gacagctctg ataaaggccg tacaatgcca ggaagatgaa    660
tgtgcgttaa tgttgctgga acatggcact gatccaaata ttccagatga gtatggaaat    720
accactctgc actacgctat ctataatgaa gataaattaa tggccaaagc actgctctta    780
tatggtgctg atatcgaatc aaaaaacaag catggcctca caccactgtt acttggtgta    840
catgagcaaa aacagcaagt cgtgaaattt ttaatcaaga aaaaagcgaa tttaaatgca    900
ctggatagat atggaaggac tgctctcata cttgctgtat gttgtggatc agcaagtata    960
gtcagccttc tacttgagca aaatattgat gtatcttctc aagatctatc tggacagacg   1020
gccagagagt atgctgtttc tagtcatcat catgtaattt gccagttact ttctgactac   1080
aaagaaaaac agatgctaaa aatctcttct gaaaacagca atccagaaca agacttaaag   1140
ctgacatcag aggaagagtc acaaaggttc aaaggcagtg aaaatagcca gccagagaaa   1200
```

-continued

```
atgtctcaag aaccagaaat aaataaggat ggtgatagag aggttgaaga agaaatgaag   1260

aagcatgaaa gtaataatgt gggattacta gaaaacctga ctaatggtgt cactgctggc   1320

aatggtgata atggattaat tcctcaaagg aagagcagaa cacctgaaaa tcagcaattt   1380

cctgacaacg aaagtgaaga gtatcacaga atttgcgaat tagtttctga ctacaaagaa   1440

aaacagatgc caaaatactc ttctgaaaac agcaacccag aacaagactt aaagctgaca   1500

tcagaggaag agtcacaaag gcttgagggc agtgaaaatg gccagccaga gaaaagatct   1560

caagaaccag aaataaataa ggatggtgat agagagctag aaaattttat ggctatcgaa   1620

gaaatgaaga agcacggaag tactcatgtc ggattcccag aaaacctgac taatggtgcc   1680

actgctggca atggtgatga tggattaatt cctccaagga agagcagaac acctgaaagc   1740

cagcaatttc ctgacactga gaatgaagag tatcacagtg acgaacaaaa tgatactcag   1800

aagcaatttt gtgaagaaca gaacactgga atattacacg atgagattct gattcatgaa   1860

gaaaagcaga tagaagtggt tgaaaaaatg aattctgagc tttctcttag ttgtaagaaa   1920

gaaaaagaca tcttgcatga aaatagtacg ttgcgggaag aaattgccat gctaagactg   1980

gagctagaca caatgaaaca tcagagccag ctaaaaaaaa aaaaaaaaaa aaaaaaaaaa   2040
```

<210> SEQ ID NO 376
<211> LENGTH: 329
<212> TYPE: PRT
<213> ORGANISM: Homo sapien

<400> SEQUENCE: 376

```
Met Asp Ile Val Val Ser Gly Ser His Pro Leu Trp Val Asp Ser Phe
 1               5                  10                  15

Leu His Leu Ala Gly Ser Asp Leu Leu Ser Arg Ser Leu Met Ala Glu
            20                  25                  30

Glu Tyr Thr Ile Val His Ala Ser Phe Ile Ser Cys Ile Ser Ser Ser
        35                  40                  45

Leu Asp Gly Gln Gly Glu Arg Gln Glu Gln Arg Gly His Phe Trp Arg
    50                  55                  60

Pro Gln Arg Leu Leu Cys Glu Asp Ala Trp Glu Gln Glu Val Gln Val
65                  70                  75                  80

Val Leu Pro Leu Leu Pro Leu Leu Gln Gly Ser Gly Lys Ser Asn Val
                85                  90                  95

Val Ala Trp Gly Asp Tyr Asp Asp Ser Ala Phe Met Asp Pro Arg Tyr
            100                 105                 110

His Val His Gly Glu Asp Leu Asp Lys Leu His Arg Ala Ala Trp Trp
        115                 120                 125

Gly Lys Val Pro Arg Lys Asp Leu Ile Val Met Leu Arg Asp Thr Asp
    130                 135                 140

Val Asn Lys Arg Asp Lys Gln Lys Arg Thr Ala Leu His Leu Ala Ser
145                 150                 155                 160

Ala Asn Gly Asn Ser Glu Val Val Lys Leu Val Leu Asp Arg Arg Cys
                165                 170                 175

Gln Leu Asn Val Leu Asp Asn Lys Lys Arg Thr Ala Leu Thr Lys Ala
            180                 185                 190

Val Gln Cys Gln Glu Asp Glu Cys Ala Leu Met Leu Leu Glu His Gly
        195                 200                 205

Thr Asp Pro Asn Ile Pro Asp Glu Tyr Gly Asn Thr Thr Leu His Tyr
    210                 215                 220
```

-continued

```
Ala Val Tyr Asn Glu Asp Lys Leu Met Ala Lys Ala Leu Leu Leu Tyr
225                 230                 235                 240

Gly Ala Asp Ile Glu Ser Lys Asn Lys His Gly Leu Thr Pro Leu Leu
                245                 250                 255

Leu Gly Ile His Glu Gln Lys Gln Gln Val Val Lys Phe Leu Ile Lys
            260                 265                 270

Lys Lys Ala Asn Leu Asn Ala Leu Asp Arg Tyr Gly Arg Thr Ala Leu
        275                 280                 285

Ile Leu Ala Val Cys Cys Gly Ser Ala Ser Ile Val Ser Pro Leu Leu
    290                 295                 300

Glu Gln Asn Val Asp Val Ser Ser Gln Asp Leu Glu Arg Arg Pro Glu
305                 310                 315                 320

Ser Met Leu Phe Leu Val Ile Ile Met
                325
```

```
<210> SEQ ID NO 377
<211> LENGTH: 148
<212> TYPE: PRT
<213> ORGANISM: Homo sapien
<220> FEATURE:
<221> NAME/KEY: VARIANT
<222> LOCATION: (1)...(148)
<223> OTHER INFORMATION: Xaa = Any Amino Acid

<400> SEQUENCE: 377

Met Thr Xaa Pro Ser Trp Ser Pro Gly Thr Thr Ser Val Glu Lys Ile
 1               5                  10                  15

Trp Thr Ser Ser Thr Glu Leu Pro Trp Trp Gly Lys Val Pro Arg Lys
            20                  25                  30

Asp Leu Ile Val Met Leu Arg Asp Thr Asp Val Asn Lys Xaa Asp Lys
        35                  40                  45

Gln Lys Arg Thr Ala Leu His Leu Ala Ser Ala Asn Gly Asn Ser Glu
    50                  55                  60

Val Val Lys Leu Xaa Leu Asp Arg Arg Cys Gln Leu Asn Val Leu Asp
65                  70                  75                  80

Asn Lys Lys Arg Thr Ala Leu Xaa Lys Ala Val Gln Cys Gln Glu Asp
                85                  90                  95

Glu Cys Ala Leu Met Leu Leu Glu His Gly Thr Asp Pro Asn Ile Pro
            100                 105                 110

Asp Glu Tyr Gly Asn Thr Thr Leu His Tyr Ala Xaa Tyr Asn Glu Asp
        115                 120                 125

Lys Leu Met Ala Lys Ala Leu Leu Leu Tyr Gly Ala Asp Ile Glu Ser
    130                 135                 140

Lys Asn Lys Val
145
```

```
<210> SEQ ID NO 378
<211> LENGTH: 1719
<212> TYPE: PRT
<213> ORGANISM: Homo sapien

<400> SEQUENCE: 378

Met Val Val Glu Val Asp Ser Met Pro Ala Ala Ser Ser Val Lys Lys
 1               5                  10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45
```

-continued

```
His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
                85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Asp Ser Ala Phe
        115                 120                 125

Met Glu Pro Arg Tyr His Val Arg Gly Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
    210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Asn Val Ser Arg Thr Arg Asn Lys
    370                 375                 380

Pro Arg Thr His Met Val Val Glu Val Asp Ser Met Pro Ala Ala Ser
385                 390                 395                 400

Ser Val Lys Lys Pro Phe Gly Leu Arg Ser Lys Met Gly Lys Trp Cys
                405                 410                 415

Cys Arg Cys Phe Pro Cys Cys Arg Glu Ser Gly Lys Ser Asn Val Gly
            420                 425                 430

Thr Ser Gly Asp His Asp Asp Ser Ala Met Lys Thr Leu Arg Ser Lys
        435                 440                 445

Met Gly Lys Trp Cys Arg His Cys Phe Pro Cys Cys Arg Gly Ser Gly
    450                 455                 460
```

-continued

```
Lys Ser Asn Val Gly Ala Ser Gly Asp His Asp Asp Ser Ala Met Lys
465                 470                 475                 480

Thr Leu Arg Asn Lys Met Gly Lys Trp Cys Cys His Cys Phe Pro Cys
                485                 490                 495

Cys Arg Gly Ser Gly Lys Ser Lys Val Gly Ala Trp Gly Asp Tyr Asp
            500                 505                 510

Asp Ser Ala Phe Met Glu Pro Arg Tyr His Val Arg Gly Glu Asp Leu
        515                 520                 525

Asp Lys Leu His Arg Ala Ala Trp Trp Gly Lys Val Pro Arg Lys Asp
    530                 535                 540

Leu Ile Val Met Leu Arg Asp Thr Asp Val Asn Lys Lys Asp Lys Gln
545                 550                 555                 560

Lys Arg Thr Ala Leu His Leu Ala Ser Ala Asn Gly Asn Ser Glu Val
                565                 570                 575

Val Lys Leu Leu Leu Asp Arg Arg Cys Gln Leu Asn Val Leu Asp Asn
            580                 585                 590

Lys Lys Arg Thr Ala Leu Ile Lys Ala Val Gln Cys Gln Glu Asp Glu
        595                 600                 605

Cys Ala Leu Met Leu Leu Glu His Gly Thr Asp Pro Asn Ile Pro Asp
    610                 615                 620

Glu Tyr Gly Asn Thr Thr Leu His Tyr Ala Ile Tyr Asn Glu Asp Lys
625                 630                 635                 640

Leu Met Ala Lys Ala Leu Leu Leu Tyr Gly Ala Asp Ile Glu Ser Lys
                645                 650                 655

Asn Lys His Gly Leu Thr Pro Leu Leu Leu Gly Val His Glu Gln Lys
            660                 665                 670

Gln Gln Val Val Lys Phe Leu Ile Lys Lys Lys Ala Asn Leu Asn Ala
        675                 680                 685

Leu Asp Arg Tyr Gly Arg Thr Ala Leu Ile Leu Ala Val Cys Cys Gly
    690                 695                 700

Ser Ala Ser Ile Val Ser Leu Leu Leu Glu Gln Asn Ile Asp Val Ser
705                 710                 715                 720

Ser Gln Asp Leu Ser Gly Gln Thr Ala Arg Glu Tyr Ala Val Ser Ser
                725                 730                 735

His His His Val Ile Cys Gln Leu Leu Ser Asp Tyr Lys Glu Lys Gln
            740                 745                 750

Met Leu Lys Ile Ser Ser Glu Asn Ser Asn Pro Glu Gln Asp Leu Lys
        755                 760                 765

Leu Thr Ser Glu Glu Glu Ser Gln Arg Phe Lys Gly Ser Glu Asn Ser
    770                 775                 780

Gln Pro Glu Lys Met Ser Gln Glu Pro Glu Ile Asn Lys Asp Gly Asp
785                 790                 795                 800

Arg Glu Val Glu Glu Glu Met Lys Lys His Glu Ser Asn Asn Val Gly
                805                 810                 815

Leu Leu Glu Asn Leu Thr Asn Gly Val Thr Ala Gly Asn Gly Asp Asn
            820                 825                 830

Gly Leu Ile Pro Gln Arg Lys Ser Arg Thr Pro Glu Asn Gln Gln Phe
        835                 840                 845

Pro Asp Asn Glu Ser Glu Glu Tyr His Arg Ile Cys Glu Leu Val Ser
    850                 855                 860

Asp Tyr Lys Glu Lys Gln Met Pro Lys Tyr Ser Ser Glu Asn Ser Asn
865                 870                 875                 880

Pro Glu Gln Asp Leu Lys Leu Thr Ser Glu Glu Glu Ser Gln Arg Leu
```

-continued

```
                885                 890                 895

Glu Gly Ser Glu Asn Gly Gln Pro Glu Leu Glu Asn Phe Met Ala Ile
            900                 905                 910

Glu Glu Met Lys Lys His Gly Ser Thr His Val Gly Phe Pro Glu Asn
        915                 920                 925

Leu Thr Asn Gly Ala Thr Ala Gly Asn Gly Asp Asp Gly Leu Ile Pro
    930                 935                 940

Pro Arg Lys Ser Arg Thr Pro Glu Ser Gln Gln Phe Pro Asp Thr Glu
945                 950                 955                 960

Asn Glu Glu Tyr His Ser Asp Glu Gln Asn Asp Thr Gln Lys Gln Phe
                965                 970                 975

Cys Glu Glu Gln Asn Thr Gly Ile Leu His Asp Glu Ile Leu Ile His
            980                 985                 990

Glu Glu Lys Gln Ile Glu Val Val Glu Lys Met Asn Ser Glu Leu Ser
        995                 1000                1005

Leu Ser Cys Lys Lys Glu Lys Asp Ile Leu His Glu Asn Ser Thr Leu
    1010                1015                1020

Arg Glu Glu Ile Ala Met Leu Arg Leu Glu Leu Asp Thr Met Lys His
1025                1030                1035                1040

Gln Ser Gln Leu Pro Arg Thr His Met Val Val Glu Val Asp Ser Met
                1045                1050                1055

Pro Ala Ala Ser Ser Val Lys Lys Pro Phe Gly Leu Arg Ser Lys Met
            1060                1065                1070

Gly Lys Trp Cys Cys Arg Cys Phe Pro Cys Cys Arg Glu Ser Gly Lys
        1075                1080                1085

Ser Asn Val Gly Thr Ser Gly Asp His Asp Asp Ser Ala Met Lys Thr
    1090                1095                1100

Leu Arg Ser Lys Met Gly Lys Trp Cys Arg His Cys Phe Pro Cys Cys
1105                1110                1115                1120

Arg Gly Ser Gly Lys Ser Asn Val Gly Ala Ser Gly Asp His Asp Asp
                1125                1130                1135

Ser Ala Met Lys Thr Leu Arg Asn Lys Met Gly Lys Trp Cys Cys His
            1140                1145                1150

Cys Phe Pro Cys Cys Arg Gly Ser Gly Lys Ser Lys Val Gly Ala Trp
        1155                1160                1165

Gly Asp Tyr Asp Asp Ser Ala Phe Met Glu Pro Arg Tyr His Val Arg
    1170                1175                1180

Gly Glu Asp Leu Asp Lys Leu His Arg Ala Ala Trp Trp Gly Lys Val
1185                1190                1195                1200

Pro Arg Lys Asp Leu Ile Val Met Leu Arg Asp Thr Asp Val Asn Lys
                1205                1210                1215

Lys Asp Lys Gln Lys Arg Thr Ala Leu His Leu Ala Ser Ala Asn Gly
            1220                1225                1230

Asn Ser Glu Val Val Lys Leu Leu Leu Asp Arg Arg Cys Gln Leu Asn
        1235                1240                1245

Val Leu Asp Asn Lys Lys Arg Thr Ala Leu Ile Lys Ala Val Gln Cys
    1250                1255                1260

Gln Glu Asp Glu Cys Ala Leu Met Leu Leu Glu His Gly Thr Asp Pro
1265                1270                1275                1280

Asn Ile Pro Asp Glu Tyr Gly Asn Thr Thr Leu His Tyr Ala Ile Tyr
                1285                1290                1295

Asn Glu Asp Lys Leu Met Ala Lys Ala Leu Leu Leu Tyr Gly Ala Asp
            1300                1305                1310
```

-continued

```
Ile Glu Ser Lys Asn Lys His Gly Leu Thr Pro Leu Leu Leu Gly Val
        1315                1320                1325

His Glu Gln Lys Gln Gln Val Val Lys Phe Leu Ile Lys Lys Lys Ala
    1330                1335                1340

Asn Leu Asn Ala Leu Asp Arg Tyr Gly Arg Thr Ala Leu Ile Leu Ala
1345                1350                1355                1360

Val Cys Cys Gly Ser Ala Ser Ile Val Ser Leu Leu Leu Glu Gln Asn
                1365                1370                1375

Ile Asp Val Ser Ser Gln Asp Leu Ser Gly Gln Thr Ala Arg Glu Tyr
            1380                1385                1390

Ala Val Ser Ser His His His Val Ile Cys Gln Leu Leu Ser Asp Tyr
        1395                1400                1405

Lys Glu Lys Gln Met Leu Lys Ile Ser Ser Glu Asn Ser Asn Pro Glu
    1410                1415                1420

Gln Asp Leu Lys Leu Thr Ser Glu Glu Glu Ser Gln Arg Phe Lys Gly
1425                1430                1435                1440

Ser Glu Asn Ser Gln Pro Glu Lys Met Ser Gln Glu Pro Glu Ile Asn
                1445                1450                1455

Lys Asp Gly Asp Arg Glu Val Glu Glu Glu Met Lys Lys His Glu Ser
            1460                1465                1470

Asn Asn Val Gly Leu Leu Glu Asn Leu Thr Asn Gly Val Thr Ala Gly
        1475                1480                1485

Asn Gly Asp Asn Gly Leu Ile Pro Gln Arg Lys Ser Arg Thr Pro Glu
    1490                1495                1500

Asn Gln Gln Phe Pro Asp Asn Glu Ser Glu Glu Tyr His Arg Ile Cys
1505                1510                1515                1520

Glu Leu Val Ser Asp Tyr Lys Glu Lys Gln Met Pro Lys Tyr Ser Ser
                1525                1530                1535

Glu Asn Ser Asn Pro Glu Gln Asp Leu Lys Leu Thr Ser Glu Glu Glu
            1540                1545                1550

Ser Gln Arg Leu Glu Gly Ser Glu Asn Gly Gln Pro Glu Lys Arg Ser
        1555                1560                1565

Gln Glu Pro Glu Ile Asn Lys Asp Gly Asp Arg Glu Leu Glu Asn Phe
    1570                1575                1580

Met Ala Ile Glu Glu Met Lys Lys His Gly Ser Thr His Val Gly Phe
1585                1590                1595                1600

Pro Glu Asn Leu Thr Asn Gly Ala Thr Ala Gly Asn Gly Asp Asp Gly
                1605                1610                1615

Leu Ile Pro Pro Arg Lys Ser Arg Thr Pro Glu Ser Gln Gln Phe Pro
            1620                1625                1630

Asp Thr Glu Asn Glu Glu Tyr His Ser Asp Glu Gln Asn Asp Thr Gln
        1635                1640                1645

Lys Gln Phe Cys Glu Glu Gln Asn Thr Gly Ile Leu His Asp Glu Ile
    1650                1655                1660

Leu Ile His Glu Glu Lys Gln Ile Glu Val Val Glu Lys Met Asn Ser
1665                1670                1675                1680

Glu Leu Ser Leu Ser Cys Lys Lys Glu Lys Asp Ile Leu His Glu Asn
                1685                1690                1695

Ser Thr Leu Arg Glu Glu Ile Ala Met Leu Arg Leu Glu Leu Asp Thr
            1700                1705                1710

Met Lys His Gln Ser Gln Leu
        1715
```

<210> SEQ ID NO 379
<211> LENGTH: 656
<212> TYPE: PRT
<213> ORGANISM: Homo sapien

<400> SEQUENCE: 379

```
Met Val Val Glu Val Asp Ser Met Pro Ala Ala Ser Ser Val Lys Lys
 1               5                  10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
                85                  90                  95

Lys Met Gly Lys Trp Cys Cys His Cys Phe Pro Cys Cys Arg Gly Ser
            100                 105                 110

Gly Lys Ser Lys Val Gly Ala Trp Gly Asp Tyr Asp Asp Ser Ala Phe
        115                 120                 125

Met Glu Pro Arg Tyr His Val Arg Gly Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
    210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Gln Asp Leu Lys Leu Thr Ser Glu
    370                 375                 380
```

-continued

```
Glu Glu Ser Gln Arg Phe Lys Gly Ser Glu Asn Ser Gln Pro Glu Lys
385                 390                 395                 400

Met Ser Gln Glu Pro Glu Ile Asn Lys Asp Gly Asp Arg Glu Val Glu
                405                 410                 415

Glu Glu Met Lys Lys His Glu Ser Asn Asn Val Gly Leu Leu Glu Asn
            420                 425                 430

Leu Thr Asn Gly Val Thr Ala Gly Asn Gly Asp Asn Gly Leu Ile Pro
        435                 440                 445

Gln Arg Lys Ser Arg Thr Pro Glu Asn Gln Gln Phe Pro Asp Asn Glu
    450                 455                 460

Ser Glu Glu Tyr His Arg Ile Cys Glu Leu Val Ser Asp Tyr Lys Glu
465                 470                 475                 480

Lys Gln Met Pro Lys Tyr Ser Ser Glu Asn Ser Asn Pro Glu Gln Asp
                485                 490                 495

Leu Lys Leu Thr Ser Glu Glu Glu Ser Gln Arg Leu Glu Gly Ser Glu
            500                 505                 510

Asn Gly Gln Pro Glu Leu Glu Asn Phe Met Ala Ile Glu Glu Met Lys
        515                 520                 525

Lys His Gly Ser Thr His Val Gly Phe Pro Glu Asn Leu Thr Asn Gly
    530                 535                 540

Ala Thr Ala Gly Asn Gly Asp Asp Gly Leu Ile Pro Pro Arg Lys Ser
545                 550                 555                 560

Arg Thr Pro Glu Ser Gln Gln Phe Pro Asp Thr Glu Asn Glu Glu Tyr
                565                 570                 575

His Ser Asp Glu Gln Asn Asp Thr Gln Lys Gln Phe Cys Glu Glu Gln
            580                 585                 590

Asn Thr Gly Ile Leu His Asp Glu Ile Leu Ile His Glu Glu Lys Gln
        595                 600                 605

Ile Glu Val Val Glu Lys Met Asn Ser Glu Leu Ser Leu Ser Cys Lys
    610                 615                 620

Lys Glu Lys Asp Ile Leu His Glu Asn Ser Thr Leu Arg Glu Glu Ile
625                 630                 635                 640

Ala Met Leu Arg Leu Glu Leu Asp Thr Met Lys His Gln Ser Gln Leu
                645                 650                 655


<210> SEQ ID NO 380
<211> LENGTH: 671
<212> TYPE: PRT
<213> ORGANISM: Homo sapien

<400> SEQUENCE: 380

Met Val Val Glu Val Asp Ser Met Pro Ala Ala Ser Ser Val Lys Lys
 1               5                  10                  15

Pro Phe Gly Leu Arg Ser Lys Met Gly Lys Trp Cys Cys Arg Cys Phe
            20                  25                  30

Pro Cys Cys Arg Glu Ser Gly Lys Ser Asn Val Gly Thr Ser Gly Asp
        35                  40                  45

His Asp Asp Ser Ala Met Lys Thr Leu Arg Ser Lys Met Gly Lys Trp
    50                  55                  60

Cys Arg His Cys Phe Pro Cys Cys Arg Gly Ser Gly Lys Ser Asn Val
65                  70                  75                  80

Gly Ala Ser Gly Asp His Asp Asp Ser Ala Met Lys Thr Leu Arg Asn
                85                  90                  95

Lys Met Gly Lys Trp Cys Cys His Cys Phe Pro Cys Cys Arg Gly Ser
```

-continued

```
        100                 105                 110

Gly Lys Ser Lys Val Gly Ala Trp Gly Asp Tyr Asp Asp Ser Ala Phe
    115                 120                 125

Met Glu Pro Arg Tyr His Val Arg Gly Glu Asp Leu Asp Lys Leu His
    130                 135                 140

Arg Ala Ala Trp Trp Gly Lys Val Pro Arg Lys Asp Leu Ile Val Met
145                 150                 155                 160

Leu Arg Asp Thr Asp Val Asn Lys Lys Asp Lys Gln Lys Arg Thr Ala
                165                 170                 175

Leu His Leu Ala Ser Ala Asn Gly Asn Ser Glu Val Val Lys Leu Leu
            180                 185                 190

Leu Asp Arg Arg Cys Gln Leu Asn Val Leu Asp Asn Lys Lys Arg Thr
        195                 200                 205

Ala Leu Ile Lys Ala Val Gln Cys Gln Glu Asp Glu Cys Ala Leu Met
    210                 215                 220

Leu Leu Glu His Gly Thr Asp Pro Asn Ile Pro Asp Glu Tyr Gly Asn
225                 230                 235                 240

Thr Thr Leu His Tyr Ala Ile Tyr Asn Glu Asp Lys Leu Met Ala Lys
                245                 250                 255

Ala Leu Leu Leu Tyr Gly Ala Asp Ile Glu Ser Lys Asn Lys His Gly
            260                 265                 270

Leu Thr Pro Leu Leu Leu Gly Val His Glu Gln Lys Gln Gln Val Val
        275                 280                 285

Lys Phe Leu Ile Lys Lys Lys Ala Asn Leu Asn Ala Leu Asp Arg Tyr
    290                 295                 300

Gly Arg Thr Ala Leu Ile Leu Ala Val Cys Cys Gly Ser Ala Ser Ile
305                 310                 315                 320

Val Ser Leu Leu Leu Glu Gln Asn Ile Asp Val Ser Ser Gln Asp Leu
                325                 330                 335

Ser Gly Gln Thr Ala Arg Glu Tyr Ala Val Ser Ser His His His Val
            340                 345                 350

Ile Cys Gln Leu Leu Ser Asp Tyr Lys Glu Lys Gln Met Leu Lys Ile
        355                 360                 365

Ser Ser Glu Asn Ser Asn Pro Glu Gln Asp Leu Lys Leu Thr Ser Glu
    370                 375                 380

Glu Glu Ser Gln Arg Phe Lys Gly Ser Glu Asn Ser Gln Pro Glu Lys
385                 390                 395                 400

Met Ser Gln Glu Pro Glu Ile Asn Lys Asp Gly Asp Arg Glu Val Glu
                405                 410                 415

Glu Glu Met Lys Lys His Glu Ser Asn Asn Val Gly Leu Leu Glu Asn
            420                 425                 430

Leu Thr Asn Gly Val Thr Ala Gly Asn Gly Asp Asn Gly Leu Ile Pro
        435                 440                 445

Gln Arg Lys Ser Arg Thr Pro Glu Asn Gln Gln Phe Pro Asp Asn Glu
    450                 455                 460

Ser Glu Glu Tyr His Arg Ile Cys Glu Leu Val Ser Asp Tyr Lys Glu
465                 470                 475                 480

Lys Gln Met Pro Lys Tyr Ser Ser Glu Asn Ser Asn Pro Glu Gln Asp
                485                 490                 495

Leu Lys Leu Thr Ser Glu Glu Glu Ser Gln Arg Leu Glu Gly Ser Glu
            500                 505                 510

Asn Gly Gln Pro Glu Lys Arg Ser Gln Glu Pro Glu Ile Asn Lys Asp
        515                 520                 525
```

-continued

```
Gly Asp Arg Glu Leu Glu Asn Phe Met Ala Ile Glu Glu Met Lys Lys
    530                 535                 540

His Gly Ser Thr His Val Gly Phe Pro Glu Asn Leu Thr Asn Gly Ala
545                 550                 555                 560

Thr Ala Gly Asn Gly Asp Asp Gly Leu Ile Pro Pro Arg Lys Ser Arg
                565                 570                 575

Thr Pro Glu Ser Gln Gln Phe Pro Asp Thr Glu Asn Glu Glu Tyr His
            580                 585                 590

Ser Asp Glu Gln Asn Asp Thr Gln Lys Gln Phe Cys Glu Glu Gln Asn
        595                 600                 605

Thr Gly Ile Leu His Asp Glu Ile Leu Ile His Glu Glu Lys Gln Ile
    610                 615                 620

Glu Val Val Glu Lys Met Asn Ser Glu Leu Ser Leu Ser Cys Lys Lys
625                 630                 635                 640

Glu Lys Asp Ile Leu His Glu Asn Ser Thr Leu Arg Glu Glu Ile Ala
                645                 650                 655

Met Leu Arg Leu Glu Leu Asp Thr Met Lys His Gln Ser Gln Leu
            660                 665                 670
```

<210> SEQ ID NO 381
<211> LENGTH: 251
<212> TYPE: DNA
<213> ORGANISM: Homo sapien

<400> SEQUENCE: 381

```
ggagaagcgt ctgctggggc aggaaggggt ttccctgccc tctcacctgt ccctcaccaa      60

ggtaacatgc ttcccctaag ggtatcccaa cccaggggcc tcaccatgac ctctgagggg     120

ccaatatccc aggagaagca ttggggagtt gggggcaggt gaaggaccca ggactcacac     180

atcctgggcc tccaaggcag aggagagggt cctcaagaag gtcaggagga aaatccgtaa     240

caagcagtca g                                                          251
```

<210> SEQ ID NO 382
<211> LENGTH: 3279
<212> TYPE: DNA
<213> ORGANISM: Homo sapiens

<400> SEQUENCE: 382

```
cttcctgcag cccccatgct ggtgaggggc acgggcagga acagtggacc caacatggaa      60

atgctggagg gtgtcaggaa gtgatcgggc tctggggcag ggaggagggg tggggagtgt     120

cactgggagg ggacatcctg cagaaggtag gagtgagcaa acacccgctg caggggaggg     180

gagagccctg cggcacctgg gggagcagag ggagcagcac ctgcccaggc ctgggaggag     240

gggcctggag ggcgtgagga ggagcgaggg ggctgcatgg ctggagtgag ggatcagggg     300

cagggcgcga gatggcctca cacagggaag agagggcccc tcctgcaggg cctcacctgg     360

gccacaggag gacactgctt ttcctctgag gagtcaggag ctgtggatgg tgctggacag     420

aagaaggaca gggcctggct caggtgtcca gaggctgtcg ctggcttccc tttgggatca     480

gactgcaggg agggagggcg gcagggttgt ggggggagtg acgatgagga tgacctgggg     540

gtggctccag gccttgcccc tgcctgggcc ctcacccagc ctccctcaca gtctcctggc     600

cctcagtctc tcccctccac tccatcctcc atctggcctc agtgggtcat tctgatcact     660

gaactgacca tacccagccc tgcccacggc cctccatggc tccccaatgc cctggagagg     720

ggacatctag tcagagagta gtcctgaaga ggtggcctct gcgatgtgcc tgtgggggca     780
```

-continued

```
gcatcctgca gatggtcccg gccctcatcc tgctgacctg tctgcaggga ctgtcctcct    840
ggaccttgcc ccttgtgcag gagctggacc ctgaagtccc ctccccatag gccaagactg    900
gagccttgtt ccctctgttg gactccctgc ccatattctt gtgggagtgg gttctggaga    960
catttctgtc tgttcctgag agctgggaat tgctctcagt catctgcctg cgcggttctg   1020
agagatggag ttgcctaggc agttattggg gccaatcttt ctcactgtgt ctctcctcct   1080
ttacccttag ggtgattctg gggtccact tgtctgtaat ggtgtgcttc aaggtatcac    1140
atcatggggc cctgagccat gtgccctgcc tgaaaagcct gctgtgtaca ccaaggtggt   1200
gcattaccgg aagtggatca aggacaccat cgcagccaac ccctgagtgc ccctgtccca   1260
cccctacctc tagtaaattt aagtccacct cacgttctgg catcacttgg cctttctgga   1320
tgctggacac ctgaagcttg gaactcacct ggccgaagct cgagcctcct gagtcctact   1380
gacctgtgct ttctggtgtg gagtccaggg ctgctaggaa aaggaatggg cagacacagg   1440
tgtatgccaa tgtttctgaa atgggtataa tttcgtcctc tccttcggaa cactggctgt   1500
ctctgaagac ttctcgctca gtttcagtga ggacacacac aaagacgtgg gtgaccatgt   1560
tgtttgtggg gtgcagagat gggaggggtg gggcccaccc tggaagagtg gacagtgaca   1620
caaggtggac actctctaca gatcactgag gataagctgg agccacaatg catgaggcac   1680
acacacagca aggttgacgc tgtaaacata gcccacgctg tcctgggggc actgggaagc   1740
ctagataagg ccgtgagcag aaagaagggg aggatcctcc tatgttgttg aaggagggac   1800
tagggggaga aactgaaagc tgattaatta caggaggttt gttcaggtcc cccaaaccac   1860
cgtcagattt gatgatttcc tagcaggact tacagaaata aagagctatc atgctgtggt   1920
ttattatggt ttgttacatt gataggatac atactgaaat cagcaaacaa aacagatgta   1980
tagattagag tgtggagaaa acagaggaaa acttgcagtt acgaagactg gcaacttggc   2040
tttactaagt tttcagactg gcaggaagtc aaacctatta ggctgaggac cttgtggagt   2100
gtagctgatc cagctgatag aggaactagc caggtggggg cctttccctt tggatggggg   2160
gcatatccga cagttattct ctccaagtgg agacttacgg acagcatata attctccctg   2220
caaggatgta tgataatatg tacaaagtaa ttccaactga ggaagctcac ctgatcctta   2280
gtgtccaggg tttttactgg gggtctgtag gacgagtatg gagtacttga ataattgacc   2340
tgaagtcctc agacctgagg ttccctagag ttcaaacaga tacagcatgg tccagagtcc   2400
cagatgtaca aaaacaggga ttcatcacaa atcccatctt tagcatgaag ggtctggcat   2460
ggcccaaggc cccaagtata tcaaggcact tgggcagaac atgccaagga atcaaatgtc   2520
atctcccagg agttattcaa gggtgagccc tttacttggg atgtacaggc tttgagcagt   2580
gcagggctgc tgagtcaacc ttttattgta caggggatga gggaaaggga gaggatgagg   2640
aagcccccct ggggatttgg tttggtcttg tgatcaggtg gtctatgggg ctatccctac   2700
aaagaagaat ccagaaatag gggcacattg aggaatgata ctgagcccaa agagcattca   2760
atcattgttt tatttgcctt cttttcacac cattggtgag ggagggatta ccaccctggg   2820
gttatgaaga tggttgaaca ccccacacat agcaccggag atatgagatc aacagtttct   2880
tagccataga gattcacagc ccagagcagg aggacgctgc acaccatgca ggatgacatg   2940
ggggatgcgc tcgggattgg tgtgaagaag caaggactgt tagaggcagg ctttatagta   3000
acaagacggt ggggcaaact ctgatttccg tgggggaatg tcatggtctt gctttactaa   3060
gttttgagac tggcaggtag tgaaactcat taggctgaga accttgtgga atgcagctga   3120
```

-continued

```
cccagctgat agaggaagta gccaggtggg agcctttccc agtgggtgtg ggacatatct   3180

ggcaagattt tgtggcactc ctggttacag atactggggc agcaaataaa actgaatctt   3240

gttttcagac cttaaaaaaa aaaaaaaaaa aaaagtttt                          3279
```

<210> SEQ ID NO 383
<211> LENGTH: 154
<212> TYPE: PRT
<213> ORGANISM: Homo sapiens

<400> SEQUENCE: 383

```
Met Ala Gly Val Arg Asp Gln Gly Gln Gly Ala Arg Trp Pro His Thr
                 5                  10                  15

Gly Lys Arg Gly Pro Leu Leu Gln Gly Leu Thr Trp Ala Thr Gly Gly
            20                  25                  30

His Cys Phe Ser Ser Glu Glu Ser Gly Ala Val Asp Gly Ala Gly Gln
        35                  40                  45

Lys Lys Asp Arg Ala Trp Leu Arg Cys Pro Glu Ala Val Ala Gly Phe
    50                  55                  60

Pro Leu Gly Ser Asp Cys Arg Glu Gly Gly Arg Gln Gly Cys Gly Gly
 65                  70                  75                  80

Ser Asp Asp Glu Asp Asp Leu Gly Val Ala Pro Gly Leu Ala Pro Ala
                85                  90                  95

Trp Ala Leu Thr Gln Pro Pro Ser Gln Ser Pro Gly Pro Gln Ser Leu
            100                 105                 110

Pro Ser Thr Pro Ser Ser Ile Trp Pro Gln Trp Val Ile Leu Ile Thr
        115                 120                 125

Glu Leu Thr Ile Pro Ser Pro Ala His Gly Pro Pro Trp Leu Pro Asn
    130                 135                 140

Ala Leu Glu Arg Gly His Leu Val Arg Glu
145                 150
```

<210> SEQ ID NO 384
<211> LENGTH: 557
<212> TYPE: DNA
<213> ORGANISM: Homo sapiens

<400> SEQUENCE: 384

```
ggatcctcta gagcggccgc ctactactac taaattcgcg gccgcgtcga cgaagaagag     60

aaagatgtgt tttgttttgg actctctgtg gtcccttcca atgctgtggg tttccaacca    120

ggggaagggt cccttttgca ttgccaagtg ccataaccat gagcactact ctaccatggt    180

tctgcctcct ggccaagcag gctggtttgc aagaatgaaa tgaatgattc tacagctagg    240

acttaacctt gaaatggaaa gtcttgcaat cccatttgca ggatccgtct gtgcacatgc    300

ctctgtagag agcagcattc ccagggacct tggaaacagt tggcactgta aggtgcttgc    360

tccccaagac acatcctaaa aggtgttgta atggtgaaaa cgtcttcctt ctttattgcc    420

ccttcttatt tatgtgaaca actgtttgtc tttttttgta tctttttttaa actgtaaagt    480

tcaattgtga aaatgaatat catgcaaata aattatgcga tttttttttc aaagtaaaaa    540

aaaaaaaaaa aaaaaaa                                                   557
```

<210> SEQ ID NO 385
<211> LENGTH: 337
<212> TYPE: DNA
<213> ORGANISM: Homo sapiens

<400> SEQUENCE: 385

-continued

```
ttcccaggtg atgtgcgagg gaagacacat ttactatcct tgatggggct gattccttta      60

gtttctctag cagcagatgg gttaggagga agtgacccaa gtggttgact cctatgtgca     120

tctcaaagcc atctgctgtc ttcgagtacg gacacatcat cactcctgca ttgttgatca     180

aaacgtggag gtgcttttcc tcagctaaga agcccttagc aaaagctcga atagacttag     240

tatcagacag gtccagtttc cgcaccaaca cctgctggtt ccctgtcgtg gtctggatct     300

ctttggccac caattccccc ttttccacat cccggca                              337
```

<210> SEQ ID NO 386
<211> LENGTH: 300
<212> TYPE: DNA
<213> ORGANISM: Homo sapiens

<400> SEQUENCE: 386

```
gggcccgcta ccggcccagg ccccgcctcg cgagtcctcc tccccgggtg cctgcccgca      60

gcccgctcgg cccagagggt gggcgcgggg ctgcctctac cggctggcgg ctgtaactca     120

gcgaccttgg cccgaaggct ctagcaagga cccaccgacc ccagccgcgg cggcggcggc     180

gcggactttg cccggtgtgt ggggcggagc ggactgcgtg tccgcggacg ggcagcgaag     240

atgttagcct tcgctgccag gaccgtggac cgatcccagg gctgtggtgt aacctcagcc     300
```

<210> SEQ ID NO 387
<211> LENGTH: 537
<212> TYPE: DNA
<213> ORGANISM: Homo sapiens

<400> SEQUENCE: 387

```
gggccgagtc gggcaccaag ggactctttg caggcttcct tcctcggatc atcaaggctg      60

ccccctcctg tgccatcatg atcagcacct atgagttcgg caaaagcttc ttccagaggc     120

tgaaccagga ccggcttctg ggcggctgaa aggggcaagg aggcaaggac cccgtctctc     180

ccacggatgg ggagagggca ggaggagacc cagccaagtg ccttttcctc agcactgagg     240

gagggggctt gtttcccttc cctcccggcg acaagctcca gggcagggct gtccctctgg     300

gcggcccagc acttcctcag acacaacttc ttcctgctgc tccagtcgtg gggatcatca     360

cttacccacc ccccaagttc aagaccaaat cttccagctg ccccccttcgt gtttccctgt     420

gtttgctgta gctgggcatg tctccaggaa ccaagaagcc ctcagcctgg tgtagtctcc     480

ctgacccttg ttaattcctt aagtctaaag atgatgaact tcaaaaaaaa aaaaaaa        537
```

<210> SEQ ID NO 388
<211> LENGTH: 520
<212> TYPE: DNA
<213> ORGANISM: Homo sapiens

<400> SEQUENCE: 388

```
aggataattt ttaaaccaat caaatgaaaa aaacaaacaa acaaaaaagg aaatgtcatg      60

tgaggttaaa ccagtttgca ttcccctaat gtggaaaaag taagaggact actcagcact     120

gtttgaagat tgcctcttct acagcttctg agaattgtgt tatttcactt gccaagtgaa     180

ggaccccctc cccaacatgc cccagcccac ccctaagcat ggtcccttgt caccaggcaa     240

ccaggaaact gctacttgtg gacctcacca gagaccagga gggtttggtt agctcacagg     300

acttccccca ccccagaaga ttagcatccc atactagact catactcaac tcaactaggc     360

tcatactcaa ttgatggtta ttagacaatt ccatttcttt ctggttatta taaacagaaa     420
```

-continued

```
atctttcctc ttctcattac cagtaaaggc tcttggtatc tttctgttgg aatgatttct    480

atgaacttgt cttattttaa tggtgggttt tttttctggt                          520


<210> SEQ ID NO 389
<211> LENGTH: 365
<212> TYPE: DNA
<213> ORGANISM: Homo sapiens

<400> SEQUENCE: 389

cgttgcccca gtttgacaga aggaaaggcg gagcttattc aaagtctaga gggagtggag     60

gagttaaggc tggatttcag atctgcctgg ttccagccgc agtgtgccct ctgctccccc    120

aacgactttc caaataatct caccagcgcc ttccagctca ggcgtcctag aagcgtcttg    180

aagcctatgg ccagctgtct ttgtgttccc tctcacccgc ctgtcctcac agctgagact    240

cccaggaaac cttcagacta ccttcctctg ccttcagcaa ggggcgttgc ccacattctc    300

tgagggtcag tggaagaacc tagactccca ttgctagagg tagaaagggg aagggtgctg    360

gggag                                                                365


<210> SEQ ID NO 390
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 390

tgcctctcca tcctggcccc gacttctctg tcaggaaagt ggggatggac cccatctgca     60

tacacggntt ctcatgggtg tggaacatct ctgcttgcgg tttcaggaag gcctctggct    120

gctctangag tctgancnga ntcgttgccc cantntgaca naaggaaagg cggagcttat    180

tcaaagtcta gagggagtgg aggagttaag gctggatttc a                        221


<210> SEQ ID NO 391
<211> LENGTH: 325
<212> TYPE: DNA
<213> ORGANISM: Homo sapiens
<220> FEATURE:
<221> NAME/KEY: misc_feature
<222> LOCATION: (1)...(325)
<223> OTHER INFORMATION: n = A,T,C or G

<400> SEQUENCE: 391

tggagcaggt cccgaggcct ccctagagcc tggggccgac tctgtgncga tgcangcttt     60

ctctcgcgcc cagcctggag ctgctcctgg catctaccaa caatcagncg aggcgagcag    120

tagccagggc actgctgcca acagccagtc cnnataccat catgtnaccc ggtgngctct    180

naanttngat ntccanagcc ctacccatcn tagttctgct ctcccaccgg ntaccagccc    240

cactgcccag gaatcctaca gccagtaccc tgtcccgacg tctctaccta ccagtacgat    300

gagacctccg gctactacta tgacc                                          325


<210> SEQ ID NO 392
<211> LENGTH: 277
<212> TYPE: DNA
<213> ORGANISM: Homo sapiens
<220> FEATURE:
<221> NAME/KEY: misc_feature
<222> LOCATION: (1)...(277)
<223> OTHER INFORMATION: n = A,T,C or G
```

<400> SEQUENCE: 392
atattgttta actccttcct ttatatcttt taacattttc atggngaaag gttcacatct 60
agtctcactt nggcnagngn ctcctacttg agtctcttcc ccggcctgnn ccagtngnaa 120
antaccanga accgncatgn cttaanaacn ncctggtttn tgggttnntc aatgactgca 180
tgcagtgcac caccctgtcc actacgtgat gctgtaggat taaagtctca cagtgggcgg 240
ctgaggatac agcgccgcgt cctgtgttgc tggggaa 277

<210> SEQ ID NO 393
<211> LENGTH: 566
<212> TYPE: DNA
<213> ORGANISM: Homo sapiens

<400> SEQUENCE: 393
actagtccag tgtggtggaa ttcgcggccg cgtcgacgga caggtcagct gtctggctca 60
gtgatctaca ttctgaagtt gtctgaaaat gtcttcatga ttaaattcag cctaaacgtt 120
ttgccgggaa cactgcagag acaatgctgt gagtttccaa ccttagccca tctgcgggca 180
gagaaggtct agtttgtcca tcagcattat catgatatca ggactggtta cttggttaag 240
gaggggtcta ggagatctgt ccctttttaga gacaccttac ttataatgaa gtatttggga 300
gggtggtttt caaaagtaga aatgtcctgt attccgatga tcatcctgta aacattttat 360
catttattaa tcatccctgc ctgtgtctat tattatattc atatctctac gctggaaact 420
ttctgcctca atgtttactg tgcctttgtt tttgctagtt tgtgttgttg aaaaaaaaaa 480
cattctctgc ctgagtttta atttttgtcc aaagttattt taatctatac aattaaaagc 540
ttttgcctat caaaaaaaaa aaaaaa 566

<210> SEQ ID NO 394
<211> LENGTH: 384
<212> TYPE: DNA
<213> ORGANISM: Homo sapiens
<220> FEATURE:
<221> NAME/KEY: misc_feature
<222> LOCATION: (1)...(384)
<223> OTHER INFORMATION: n = A,T,C or G

<400> SEQUENCE: 394
gaacatacat gtcccggcac ctgagctgca gtctgacatc atcgccatca cgggcctcgc 60
tgcaaattng gaccgggcca aggctggact gctggagcgt gtgaaggagc tacaggccna 120
gcaggaggac cgggctttaa ggagttttaa gctgagtgtc actgtagacc ccaaatacca 180
tcccaagatt atcgggagaa agggggcagt aattacccaa atccggttgg agcatgacgt 240
gaacatccag tttcctgata aggacgatgg gaaccagccc caggaccaaa ttaccatcac 300
agggtacgaa aagaacacag aagctgccag ggatgctata ctgagaattg tgggtgaact 360
tgagcagatg gtttctgagg acgt 384

<210> SEQ ID NO 395
<211> LENGTH: 399
<212> TYPE: DNA
<213> ORGANISM: Homo sapiens

<400> SEQUENCE: 395
ggcaaaactg tgtgacctca ataagacctc gcagatccaa ggtcaagtat cagaagtgac 60
tctgaccttg gactccaaga cctacatcaa cagcctggct atattagatg atgagccagt 120

-continued

```
tatcagaggt ttcatcattg cggaaattgt ggagtctaag gaaatcatgg cctctgaagt    180

attcacgtct ttccagtacc ctgagttctc tatagagttg cctaacacag gcagaattgg    240

ccagctactt gtctgcaatt gtatcttcaa gaataccctg gccatccctt tgactgacgt    300

caagttctct ttggaaagcc tgggcatctc ctcactacag acctctgacc atgggacggt    360

gcagcctggt gagaccatcc aatcccaaat aaaatgcac                           399
```

```
<210> SEQ ID NO 396
<211> LENGTH: 403
<212> TYPE: DNA
<213> ORGANISM: Homo sapiens
<220> FEATURE:
<221> NAME/KEY: misc_feature
<222> LOCATION: (1)...(403)
<223> OTHER INFORMATION: n = A,T,C or G

<400> SEQUENCE: 396

tggagttntc agtgcaaaca agccataaag cttcagtagc aaattactgt ctcacagaaa     60

gacattttca acttctgctc cagctgctga taaaacaaat catgtgttta gcttgactcc    120

agacaaggac aacctgttcc ttcataactc tctagagaaa aaaaggagtt gttagtagat    180

actaaaaaaa gtggatgaat aatctggata tttttcctaa aaagattcct tgaaacacat    240

taggaaaatg gagggcctta tgatcagaat gctagaatta gtccattgtg ctgaagcagg    300

gtttagggga gggagtgagg gataaaagaa ggaaaaaaag aagagtgaga aaacctattt    360

atcaaagcag gtgctatcac tcaatgttag gccctgctct ttt                      403
```

```
<210> SEQ ID NO 397
<211> LENGTH: 100
<212> TYPE: DNA
<213> ORGANISM: Homo sapiens
<220> FEATURE:
<221> NAME/KEY: misc_feature
<222> LOCATION: (1)...(100)
<223> OTHER INFORMATION: n = A,T,C or G

<400> SEQUENCE: 397

actagtncag tgtggtggaa ttcgcggccg cgtcgaccta naanccatct ctatagcaaa     60

tccatccccg ctcctggttg gtnacagaat gactgacaaa                         100
```

```
<210> SEQ ID NO 398
<211> LENGTH: 278
<212> TYPE: DNA
<213> ORGANISM: Homo sapiens
<220> FEATURE:
<221> NAME/KEY: misc_feature
<222> LOCATION: (1)...(278)
<223> OTHER INFORMATION: n = A,T,C or G

<400> SEQUENCE: 398

gcggccgcgt cgacagcagt tccgccagcg ctcgcccctg ggtggggatg tgctgcacgc     60

ccacctggac atctggaagt cagcggcctg gatgaaagag cggacttcac ctggggcgat    120

tcactactgt gcctcgacca gtgaggagag ctggaccgac agcgaggtgg actcatcatg    180

ctccgggcag cccatccacc tgtggcagtt cctcaaggag ttgctactca agccccacag    240

ctatggccgc ttcattangt ggctcaacaa ggagaagg                            278
```

```
<210> SEQ ID NO 399
<211> LENGTH: 298
<212> TYPE: DNA
<213> ORGANISM: Homo sapiens
```

-continued

<220> FEATURE:
<221> NAME/KEY: misc_feature
<222> LOCATION: (1)...(298)
<223> OTHER INFORMATION: n = A,T,C or G

<400> SEQUENCE: 399
acggaggtgg aggaagcgnc cctgggatcg anaggatggg tcctgncatt gaccncctcn 60
ggggtgccng catggagcgc atgggcgcgg gcctgggcca cggcatggat cgcgtgggct 120
ccgagatcga gcgcatgggc ctggtcatgg accgcatggg ctccgtggag cgcatgggct 180
ccggcattga gcgcatgggc ccgctgggcc tcgaccacat ggcctccanc attgancgca 240
tgggccagac catggagcgc attggctctg gcgtggagcn catgggtgcc ggcatggg 298

<210> SEQ ID NO 400
<211> LENGTH: 548
<212> TYPE: DNA
<213> ORGANISM: Homo sapiens

<400> SEQUENCE: 400
acatcaacta cttcctcatt ttaaggtatg gcagttccct tcatcccctt ttcctgcctt 60
gtacatgtac atgtatgaaa tttccttctc ttaccgaact ctctccacac atcacaaggt 120
caaagaacca cacgcttaga agggtaagag ggcaccctat gaaatgaaat ggtgatttct 180
tgagtctctt ttttccacgt ttaaggggcc atggcaggac ttagagttgc gagttaagac 240
tgcagagggc tagagaatta tttcatacag gctttgaggc cacccatgtc acttatcccg 300
tataccctct caccatcccc ttgtctactc tgatgccccc aagatgcaac tgggcagcta 360
gttggcccca taattctggg cctttgttgt ttgttttaat tacttgggca tcccaggaag 420
ctttccagtg atctcctacc atgggccccc ctcctgggat caagcccctc ccaggccctg 480
tccccagccc ctcctgcccc agcccacccg cttgccttgg tgctcagccc tcccattggg 540
agcaggtt 548

<210> SEQ ID NO 401
<211> LENGTH: 355
<212> TYPE: DNA
<213> ORGANISM: Homo sapiens
<220> FEATURE:
<221> NAME/KEY: misc_feature
<222> LOCATION: (1)...(355)
<223> OTHER INFORMATION: n = A,T,C or G

<400> SEQUENCE: 401
actgtttcca tgttatgttt ctacacattg ctacctcagt gctcctggaa acttagcttt 60
tgatgtctcc aagtagtcca ccttcattta actctttgaa actgtatcat ctttgccaag 120
taagagtggt ggcctatttc agctgctttg acaaaatgac tggctcctga cttaacgttc 180
tataaatgaa tgtgctgaag caaagtgccc atggtggcgg cgaagaagan aaagatgtgt 240
tttgttttgg actctctgtg gtcccttcca atgctgnggg tttccaacca ggggaagggt 300 ccctttttgca ttgccaagtg ccataaccat gagcactact ctaccatggn tctgc 355

<210> SEQ ID NO 402
<211> LENGTH: 407
<212> TYPE: DNA
<213> ORGANISM: Homo sapiens
<220> FEATURE:
<221> NAME/KEY: misc_feature
<222> LOCATION: (1)...(407)
<223> OTHER INFORMATION: n = A,T,C or G

<400> SEQUENCE: 402

```
atggggcaag ctggataaag aaccaagacc cactggagta tgctgtcttc aagaaaccca     60
tctcacatgc ggtggcatac ataggctcaa aataaaggaa tggagaaaaa tatttcaagc    120
aaatggaaaa cagaaaaaag caggtgttgc actcctactt tctgacaaaa cagactatgc    180
gaataaagat aaaaaagaga aggacattac aaaggtggtc ctgacctttg ataaatctca    240
ttgcttgata ccaacctggg ctgttttaat tgcccaaacc aaaaggataa tttgctgagg    300
ttgtggagct tctcccctgc agagagtccc tgatctccca aaatttggtt gagatgtaag    360
gntgattttg ctgacaactc cttttctgaa gttttactca tttccaa                  407
```

<210> SEQ ID NO 403
<211> LENGTH: 303
<212> TYPE: DNA
<213> ORGANISM: Homo sapiens
<220> FEATURE:
<221> NAME/KEY: misc_feature
<222> LOCATION: (1)...(303)
<223> OTHER INFORMATION: n = A,T,C or G

<400> SEQUENCE: 403

```
cagtatttat agccnaactg aaaagctagt agcaggcaag tctcaaatcc aggcaccaaa     60
tcctaagcaa gagccatggc atggtgaaaa tgcaaaagga gagtctggcc aatctacaaa    120
tagagaacaa gacctactca gtcatgaaca aaaaggcaga caccaacatg gatctcatgg    180
gggattggat attgtaatta tagagcagga agatgacagt gatcgtcatt tggcacaaca    240
tcttaacaac gaccgaaacc cattatttac ataaacctcc attcggtaac catgttgaaa    300
gga                                                                 303
```

<210> SEQ ID NO 404
<211> LENGTH: 225
<212> TYPE: DNA
<213> ORGANISM: Homo sapiens

<400> SEQUENCE: 404

```
aagtgtaact tttaaaaatt tagtggattt tgaaaattct tagaggaaag taaaggaaaa     60
attgttaatg cactcattta cctttacatg gtgaaagttc tctcttgatc ctacaaacag    120
acattttcca ctcgtgtttc catagttgtt aagtgtatca gatgtgttgg gcatgtgaat    180
ctccaagtgc ctgtgtaata aataaagtat ctttatttca ttcat                    225
```

<210> SEQ ID NO 405
<211> LENGTH: 334
<212> TYPE: DNA
<213> ORGANISM: Homo sapiens
<220> FEATURE:
<221> NAME/KEY: misc_feature
<222> LOCATION: (1)...(334)
<223> OTHER INFORMATION: n = A,T,C or G

<400> SEQUENCE: 405

```
gagctgttat actgtgagtt ctactaggaa atcatcaaat ctgagggttg tctggaggac     60
ttcaatacac ctccccccat agtgaatcag cttccagggg gtccagtccc tctccttact    120
tcatccccat cccatgccaa aggaagaccc tccctccttg gctcacagcc ttctctaggc    180
ttcccagtgc ctccaggaca gagtgggtta tgttttcagc tccatccttg ctgtgagtgt    240
ctggtgcggt tgtgcctcca gcttctgctc agtgcttcat ggacagtgtc cagcccatgt    300
cactctccac tctctcanng tggatcccac ccct                                334
```

<210> SEQ ID NO 406
<211> LENGTH: 216
<212> TYPE: DNA
<213> ORGANISM: Homo sapiens
<220> FEATURE:
<221> NAME/KEY: misc_feature
<222> LOCATION: (1)...(216)
<223> OTHER INFORMATION: n = A,T,C or G

<400> SEQUENCE: 406
tttcatacct aatgagggag ttganatnac atnnaaccag gaaatgcatg gatctcaang 60
gaaacaaaca cccaataaac tcggagtggc agactgacaa ctgtgagaca tgcacttgct 120
acnaaacaca aatttnatgt tgcacccttg tttctacacc tgtgggttat gacaaagaca 180
actgccaaag aatnttcaag aaggaggact gccant 216

<210> SEQ ID NO 407
<211> LENGTH: 413
<212> TYPE: DNA
<213> ORGANISM: Homo sapiens

<400> SEQUENCE: 407
gctgacttgc tagtatcatc tgcattcatt gaagcacaag aacttcatgc cttgactcat 60
gtaaatgcaa taggattaaa aaataaattt gatatcacat ggaaacagac aaaaaatatt 120
gtacaacatt gcacccagtg tcagattcta cacctggcca ctcaggaagc aagagttaat 180
cccagaggtc tatgtcctaa tgtgttatgg caaatggatg tcatgcacgt accttcattt 240
ggaaaattgt catttgtcca tgtgacagtt gatacttatt cacatttcat atgggcaacc 300
tgccagacag gagaaagtct tcccatgtta aaagacattt attatcttgt tttcctgtca 360
tgggagttcc agaaaaagtt aaaacagaca atgggccagg ttctgtagta aag 413

<210> SEQ ID NO 408
<211> LENGTH: 183
<212> TYPE: DNA
<213> ORGANISM: Homo sapiens
<220> FEATURE:
<221> NAME/KEY: misc_feature
<222> LOCATION: (1)...(183)
<223> OTHER INFORMATION: n = A,T,C or G

<400> SEQUENCE: 408
ggagctngcc ctcaattcct ccatntctat gttancatat ttaatgtctt ttgnnattaa 60
tncttaacta gttaatcctt aaagggctan ntaatcctta actagtccct ccattgtgag 120
cattatcctt ccagtattcn ccttctnttt tatttactcc ttcctggcta cccatgtact 180 ntt 183

<210> SEQ ID NO 409
<211> LENGTH: 250
<212> TYPE: DNA
<213> ORGANISM: Homo sapiens
<220> FEATURE:
<221> NAME/KEY: misc_feature
<222> LOCATION: (1)...(250)
<223> OTHER INFORMATION: n = A,T,C or G

<400> SEQUENCE: 409
cccacgcatg ataagctctt tatttctgta agtcctgcta ggaaatcatc aaatctgacg 60
gtggtttggg ggacctgaac aaacctcctg taattaatca gctttcagtt tctcccccta 120
gtccctcctt caacaacata ggaggatcct ccccttcttt ctgctcacgg ccttatctag 180
gcttcccagt gcccccagga cagcgtgggc tatgtttaca gcgcntcctt gctggggggg 240 ggccntatgc 250

<210> SEQ ID NO 410
<211> LENGTH: 306
<212> TYPE: DNA
<213> ORGANISM: Homo sapiens
<220> FEATURE:
<221> NAME/KEY: misc_feature
<222> LOCATION: (1)...(306)
<223> OTHER INFORMATION: n = A,T,C or G

<400> SEQUENCE: 410
ggctggtttg caagaatgaa atgaatgatt ctacagctag gacttaacct tgaaatggaa 60
agtcttgcaa tcccatttgc aggatccgtc tgtgcacatg cctctgtaga gagcagcatt 120
cccagggacc ttggaaacag ttggcactgt aaggtgcttg ctccccaaga cacatcctaa 180
aaggtgttgt aatggtgaaa accgcttcct tctttattgc cccttcttat ttatgtgaac 240
nactggttgg cttttttgn atctttttta aactggaaag ttcaattgng aaaatgaata 300 tcntgc 306

<210> SEQ ID NO 411
<211> LENGTH: 261
<212> TYPE: DNA
<213> ORGANISM: Homo sapiens
<220> FEATURE:
<221> NAME/KEY: misc_feature
<222> LOCATION: (1)...(261)
<223> OTHER INFORMATION: n = A,T,C or G

<400> SEQUENCE: 411
agagatattn cttaggtnaa agttcataga gttcccatga actatatgac tggccacaca 60
ggatcttttg tatttaagga ttctgagatt ttgcttgagc aggattagat aaggctgttc 120
tttaaatgtc tgaaatggaa cagatttcaa aaaaaaaccc cacaatctag ggtgggaaca 180
aggaaggaaa gatgtgaata ggctgatggg caaaaaacca atttacccat cagttccagc 240
cttctctcaa ggngaggcaa a 261

<210> SEQ ID NO 412
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 412
gttcaatgtt acctgacatt tctacaacac cccactcacc gatgtattcg ttgcccagtg 60
ggaacatacc agcctgaatt tggaaaaaat aattgtgttt cttgcccagg aaatactacg 120
actgactttg atggctccac aaacataacc cagtgtaaaa acagaagatg tggaggggag 180
ctgggagatt tcactgggta cattgaattc ccaaactacc cangcaatta cccagccaac 240
a 241

<210> SEQ ID NO 413
<211> LENGTH: 231
<212> TYPE: DNA
<213> ORGANISM: Homo sapiens -continued
<220> FEATURE:
<221> NAME/KEY: misc_feature
<222> LOCATION: (1)...(231)
<223> OTHER INFORMATION: n = A,T,C or G

<400> SEQUENCE: 413
aactcttaca atccaagtga ctcatctgtg tgcttgaatc ctttccactg tctcatctcc 60
ctcatccaag tttctagtac cttctctttg ttgtgaagga taatcaaact gaacaacaaa 120
aagtttactc tcctcatttg gaacctaaaa actctcttct tcctgggtct gagggctcca 180
agaatccttg aatcanttct cagatcattg gggacaccan atcaggaacc t 231

<210> SEQ ID NO 414
<211> LENGTH: 234
<212> TYPE: DNA
<213> ORGANISM: Homo sapiens

<400> SEQUENCE: 414
actgtccatg aagcactgag cagaagctgg aggcacaacg caccagacac tcacagcaag 60
gatggagctg aaaacataac ccactctgtc ctggaggcac tgggaagcct agagaaggct 120
gtgagccaag gagggagggt cttcctttgg catgggatgg ggatgaagta aggagaggga 180
ctggaccccc tggaagctga ttcactatgg ggggaggtgt attgaagtcc tcca 234

<210> SEQ ID NO 415
<211> LENGTH: 217
<212> TYPE: DNA
<213> ORGANISM: Homo sapiens
<220> FEATURE:
<221> NAME/KEY: misc_feature
<222> LOCATION: (1)...(217)
<223> OTHER INFORMATION: n = A,T,C or G

<400> SEQUENCE: 415
gcataggatt aagactgagt atcttttcta cattctttta actttctaag gggcacttct 60
caaaacacag accaggtagc aaatctccac tgctctaagg ntctcaccac cactttctca 120
cacctagcaa tagtagaatt cagtcctact tctgaggcca gaagaatggt tcagaaaaat 180
antggattat aaaaaataac aattaagaaa aataatc 217

<210> SEQ ID NO 416
<211> LENGTH: 213
<212> TYPE: DNA
<213> ORGANISM: Homo sapiens
<220> FEATURE:
<221> NAME/KEY: misc_feature
<222> LOCATION: (1)...(213)
<223> OTHER INFORMATION: n = A,T,C or G

<400> SEQUENCE: 416
atgcatatnt aaagganact gcctcgcttt tagaagacat ctggnctgct ctctgcatga 60
ggcacagcag taaagctctt tgattcccag aatcaagaac tctccccttc agactattac 120
cgaatgcaag gtggttaatt gaaggccact aattgatgct caaatagaag gatattgact 180
atattggaac agatggagtc tctactacaa aag 213

<210> SEQ ID NO 417
<211> LENGTH: 303
<212> TYPE: DNA
<213> ORGANISM: Homo sapiens
<220> FEATURE:
<221> NAME/KEY: misc_feature
<222> LOCATION: (1)...(303)

-continued

<223> OTHER INFORMATION: n = A,T,C or G

<400> SEQUENCE: 417
nagtcttcag gcccatcagg gaagttcaca ctggagagaa gtcatacata tgtactgtat 60
gtgggaaagg ctttactctg agttcaaatc ttcaagccca tcagagagtc cacactggag 120
agaagccata caaatgcaat gagtgtggga agagcttcag gagggattcc cattatcaag 180
ttcatctagt ggtccacaca ggagagaaac cctataaatg tgagatatgt gggaagggct 240
tcantcaaag ttcgtatctt caaatccatc ngaaggncca cagtatanan aaacctttta 300
agt 303

<210> SEQ ID NO 418
<211> LENGTH: 328
<212> TYPE: DNA
<213> ORGANISM: Homo sapiens
<220> FEATURE:
<221> NAME/KEY: misc_feature
<222> LOCATION: (1)...(328)
<223> OTHER INFORMATION: n = A,T,C or G

<400> SEQUENCE: 418
tttttggcgg tggtggggca gggacgggac angagtctca ctctgttgcc caggctggag 60
tgcacaggca tgatctcggc tcactacaac ccctgcctcc catgtccaag cgattcttgt 120
gcctcagcct tccctgtagc tagaattaca ggcacatgcc accacaccca gctagttttt 180
gtatttttag tagagacagg gtttcaccat gttggccagg ctggtctcaa actcctnacc 240
tcagnggtca ggctggtctc aaactcctga cctcaagtga tctgcccacc tcagcctccc 300
aaagtgctan gattacaggc cgtgagcc 328

<210> SEQ ID NO 419
<211> LENGTH: 389
<212> TYPE: DNA
<213> ORGANISM: Homo sapiens
<220> FEATURE:
<221> NAME/KEY: misc_feature
<222> LOCATION: (1)...(389)
<223> OTHER INFORMATION: n = A,T,C or G

<400> SEQUENCE: 419
cctcctcaag acggcctgtg gtccgcctcc cggcaaccaa gaagcctgca gtgccatatg 60
acccctgagc catggactgg agcctgaaag gcagcgtaca ccctgctcct gatcttgctg 120
cttgtttcct ctctgtggct ccattcatag cacagttgtt gcactgaggc ttgtgcaggc 180
cgagcaaggc caagctggct caaagagcaa ccagtcaact ctgccacggt gtgccaggca 240
ccggttctcc agccaccaac ctcactcgct cccgcaaatg gcacatcagt tcttctaccc 300
taaaggtagg accaaagggc atctgctttt ctgaagtcct ctgctctatc agccatcacg 360
tggcagccac tcnggctgtg tcgacgcgg 389

<210> SEQ ID NO 420
<211> LENGTH: 408
<212> TYPE: DNA
<213> ORGANISM: Homo sapiens

<400> SEQUENCE: 420
gttcctccta actcctgcca gaaacagctc tcctcaacat gagagctgca cccctcctcc 60
tggccagggc agcaagcctt agccttggct tcttgtttct gcttttttc tggctagacc 120 gaagtgtact agccaaggag ttgaagtttg tgactttggt gtttcggcat ggagaccgaa 180

-continued

```
gtcccattga cacctttccc actgacccca taaaggaatc ctcatggcca caaggatttg    240

gccaactcac ccagctgggc atggagcagc attatgaact tggagagtat ataagaaaga    300

gatatagaaa attcttgaat gagtcctata aacatgaaca ggtttatatt cgaagcacag    360

acgttgaccg gactttgatg aagtgctatg acaaacctgg caagcccg                 408
```

```
<210> SEQ ID NO 421
<211> LENGTH: 352
<212> TYPE: DNA
<213> ORGANISM: Homo sapiens
<220> FEATURE:
<221> NAME/KEY: misc_feature
<222> LOCATION: (1)...(352)
<223> OTHER INFORMATION: n = A,T,C or G

<400> SEQUENCE: 421

gctcaaaaat ctttttactg atnggcatgg ctacacaatc attgactatt acggaggcca     60

gaggagaatg aggcctggcc tgggagccct gtgcctacta naagcacatt agattatcca    120

ttcactgaca gaacaggtct tttttgggtc cttcttctcc accacnatat acttgcagtc    180

ctccttcttg aagattcttt ggcagttgtc tttgtcataa cccacaggtg tagaaacaag    240

ggtgcaacat gaaatttctg tttcgtagca agtgcatgtc tcacaagttg gcangtctgc    300

cactccgagt ttattgggtg tttgtttcct ttgagatcca tgcatttcct gg            352
```

```
<210> SEQ ID NO 422
<211> LENGTH: 337
<212> TYPE: DNA
<213> ORGANISM: Homo sapiens

<400> SEQUENCE: 422

atgccaccat gctggcaatg cagcgggcgg tcgaaggcct gcatatccag cccaagctgg     60

cgatgatcga cggcaaccgt tgcccgaagt tgccgatgcc agccgaagcg gtggtcaagg    120

gcgatagcaa ggtgccggcg atcgcggcgg cgtcaatcct ggccaaggtc agccgtgatc    180

gtgaaatggc agctgtcgaa ttgatctacc cgggttatgg catcggcggg cataagggct    240

atccgacacc ggtgcacctg gaagccttgc agcggctggg gccgacgccg attcaccgac    300

gcttcttccg ccggtacggc tggcctatga aaattat                             337
```

```
<210> SEQ ID NO 423
<211> LENGTH: 310
<212> TYPE: DNA
<213> ORGANISM: Homo sapiens
<220> FEATURE:
<221> NAME/KEY: misc_feature
<222> LOCATION: (1)...(310)
<223> OTHER INFORMATION: n = A,T,C or G

<400> SEQUENCE: 423

gctcaaaaat ctttttactg atatggcatg gctacacaat cattgactat tagaggccag     60

aggagaatga ggcctggcct gggagccctg tgcctactan aagcncatta gattatccat    120

tcactgacag aacaggtctt ttttgggtcc ttcttctcca ccacgatata cttgcagtcc    180

tccttcttga agattctttg gcagttgtct ttgtcataac ccacaggtgt anaaacaagg    240

gtgcaacatg aaatttctgt ttcgtagcaa gtgcatgtct cacagttgtc aagtctgccc    300

tccgagttta                                                           310
```

```
<210> SEQ ID NO 424
```

-continued

<211> LENGTH: 370
<212> TYPE: DNA
<213> ORGANISM: Homo sapiens
<220> FEATURE:
<221> NAME/KEY: misc_feature
<222> LOCATION: (1)...(370)
<223> OTHER INFORMATION: n = A,T,C or G

<400> SEQUENCE: 424
gctcaaaaat ctttttactg ataggcatgg ctacacaatc attgactatt agaggccaga 60
ggagaatgag gcctggcctg ggagccctgt gcctactaga agcacattag attatccatt 120
cactgacaga acaggtcttt tttgggtcct tcttctccac cacgatatac ttgcagtcct 180
ccttcttgaa gattctttgg cagttgtctt tgtcataacc cacaggtgta gaaacatcct 240
ggttgaatct cctggaactc cctcattagg tatgaaatag catgatgcat tgcataaagt 300
cacgaaggtg gcaaagatca caacgctgcc cagganaaca ttcattgtga taagcaggac 360
tccgtcgacg 370

<210> SEQ ID NO 425
<211> LENGTH: 216
<212> TYPE: DNA
<213> ORGANISM: Homo sapiens
<220> FEATURE:
<221> NAME/KEY: misc_feature
<222> LOCATION: (1)...(216)
<223> OTHER INFORMATION: n = A,T,C or G

<400> SEQUENCE: 425
aattgctatn ntttattttg ccactcaaaa taattaccaa aaaaaaaaaa tnttaaatga 60
taacaacnca acatcaaggn aaananaaca ggaatggntg actntgcata aatnggccga 120
anattatcca ttatnttaag ggttgacttc aggntacagc acacagacaa acatgcccag 180
gaggntntca ggaccgctcg atgtnttntg aggagg 216

<210> SEQ ID NO 426
<211> LENGTH: 596
<212> TYPE: DNA
<213> ORGANISM: Homo sapiens

<400> SEQUENCE: 426
cttccagtga ggataaccct gttgccccgg gccgaggttc tccattaggc tctgattgat 60
tggcagtcag tgatggaagg gtgttctgat cattccgact gccccaaggg tcgctggcca 120
gctctctgtt ttgctgagtt ggcagtagga cctaatttgt taattaagag tagatggtga 180
gctgtccttg tattttgatt aacctaatgg ccttcccagc acgactcgga ttcagctgga 240
gacatcacgg caacttttaa tgaaatgatt tgaagggcca ttaagaggca cttcccgtta 300
ttaggcagtt catctgcact gataacttct tggcagctga gctggtcgga gctgtggccc 360
aaacgcacac ttggcttttg gttttgagat acaactctta atcttttagt catgcttgag 420
ggtggatggc cttttcagct ttaacccaat ttgcactgcc ttggaagtgt agccaggaga 480
atacactcat atactcgtgg gcttagaggc cacagcagat gtcattggtc tactgcctga 540
gtcccgctgg tcccatccca ggaccttcca tcggcgagta cctgggagcc cgtgct 596

<210> SEQ ID NO 427
<211> LENGTH: 107
<212> TYPE: DNA
<213> ORGANISM: Homo sapiens
<220> FEATURE:
<221> NAME/KEY: misc_feature -continued
<222> LOCATION: (1)...(107)
<223> OTHER INFORMATION: n = A,T,C or G

<400> SEQUENCE: 427
gaagaattca agttaggttt attcaaaggg cttacngaga atcctanacc caggncccag 60
cccgggagca gccttanaga gctcctgttt gactgcccgg ctcagng 107

<210> SEQ ID NO 428
<211> LENGTH: 38
<212> TYPE: DNA
<213> ORGANISM: Homo sapiens
<220> FEATURE:
<221> NAME/KEY: misc_feature
<222> LOCATION: (1)...(38)
<223> OTHER INFORMATION: n = A,T,C or G

<400> SEQUENCE: 428
gaacttccna anaangactt tattcactat tttacatt 38

<210> SEQ ID NO 429
<211> LENGTH: 544
<212> TYPE: DNA
<213> ORGANISM: Homo sapiens

<400> SEQUENCE: 429
ctttgctgga cggaataaaa gtggacgcaa gcatgacctc ctgatgaggg cgctgcattt 60
attgaagagc ggctgcagcc ctgcggttca gattaaaatc cgagaattgt atagacgccg 120
atatccacga actcttgaag gactttctga tttatccaca atcaaatcat cggttttcag 180
tttggatggt ggctcatcac ctgtagaacc tgacttggcc gtggctggaa tccactcgtt 240
gccttccact tcagttacac ctcactcacc atcctctcct gttggttctg tgctgcttca 300
agatactaag cccacatttg agatgcagca gccatctccc ccaattcctc ctgtccatcc 360
tgatgtgcag ttaaaaaatc tgccctttta tgatgtcctt gatgttctca tcaagcccac 420
gagtttagtt caaagcagta ttcagcgatt tcaagagaag ttttttattt ttgctttgac 480
acctcaacaa gttagagaga tatgcatatc cagggatttt ttgccaggtg gtaggagaga 540
ttat 544

<210> SEQ ID NO 430
<211> LENGTH: 507
<212> TYPE: DNA
<213> ORGANISM: Homo sapiens
<220> FEATURE:
<221> NAME/KEY: misc_feature
<222> LOCATION: (1)...(507)
<223> OTHER INFORMATION: n = A,T,C or G

<400> SEQUENCE: 430
cttatcncaa tggggctccc aaacttggct gtgcagtgga aactccgggg gaattttgaa 60
gaacactgac acccatcttc caccccgaca ctctgattta attgggctgc agtgagaaca 120
gagcatcaat ttaaaaagct gcccagaatg ttntcctggg cagcgttgtg atctttgccn 180
ccttcgtgac tttatgcaat gcatcatgct atttcatacc taatgaggga gttccaggag 240
attcaaccag gatgtttcta cncctgtggg ttatgacaaa gacaactgcc aaagaatntt 300
caagaaggag gactgcaagt atatcgtggt ggagaagaag gacccaaaaa agacctgttc 360
tgtcagtgaa tggataatct aatgtgcttc tagtaggcac agggctccca ggccaggcct 420
cattctcctc tggcctctaa tagtcaatga ttgtgtagcc atgcctatca gtaaaaagat 480

```
ttttgagcaa aaaaaaaaaa aaaaaaa                                          507


<210> SEQ ID NO 431
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 431

gaaaattcag aatggataaa aacaaatgaa gtacaaaata tttcagattt acatagcgat       60

aaacaagaaa gcacttatca ggaggactta caaatggaag tacactctan aaccatcatc      120

tatcatggct aaatgtgaga ttagcacagc tgtattattt gtacattgca aacacctaga      180

aagagatggg aaacaaaatc ccaggagttt tgtgtgtgga gtcctgggtt ttccaacaga      240

catcattcca gcattctgag attagggnga ttggggatca ttctggagtt ggaatgttca      300

acaaaagtga tgttgttagg taaaatgtac aacttctgga tctatgcaga cattgaaggt      360

gcaatgagtc tggcttttac tctgctgttt ct                                    392


<210> SEQ ID NO 432
<211> LENGTH: 387
<212> TYPE: DNA
<213> ORGANISM: Homo sapiens
<220> FEATURE:
<221> NAME/KEY: misc_feature
<222> LOCATION: (1)...(387)
<223> OTHER INFORMATION: n = A,T,C or G

<400> SEQUENCE: 432

ggtatccnta cataatcaaa tatagctgta gtacatgttt tcattggngt agattaccac       60

aaatgcaagg caacatgtgt agatctcttg tcttattctt ttgtctataa tactgtattg      120

ngtagtccaa gctctcggna gtccagccac tgngaaacat gctcccttta gattaacctc      180

gtggacnctn ttgttgnatt gtctgaactg tagngccctg tattttgctt ctgtctgnga      240

attctgttgc ttctggggca tttccttgng atgcagagga ccaccacaca gatgacagca      300

atctgaattg ntccaatcac agctgcgatt aagacatact gaaatcgtac aggaccggga      360

acaacgtata gaacactgga gtccttt                                          387


<210> SEQ ID NO 433
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n = A,T,C or G

<400> SEQUENCE: 433

ttcaactagc anagaanact gcttcagggn gtgtaaaatg aaaggcttcc acgcagttat       60

ctgattaaag aacactaaga gagggacaag gctagaagcc gcaggatgtc tacactatag      120

caggcnctat ttgggttggc tggaggagct gtggaaaaca tggagagatt ggcgctggag      180

atcgccgtgg ctattcctcn ttgntattac accagngagg ntctctgtnt gcccactggt      240

tnnaaaaccg ntatacaata atgatagaat aggacacaca t                          281


<210> SEQ ID NO 434
<211> LENGTH: 484
```

-continued

<212> TYPE: DNA
<213> ORGANISM: Homo sapiens

<400> SEQUENCE: 434
ttttaaaata agcatttagt gctcagtccc tactgagtac tctttctctc ccctcctctg 60
aatttaattc tttcaacttg caatttgcaa ggattacaca tttcactgtg atgtatattg 120
tgttgcaaaa aaaaaaaagt gtctttgttt aaaattactt ggtttgtgaa tccatcttgc 180
tttttcccca ttggaactag tcattaaccc atctctgaac tggtagaaaa acatctgaag 240
agctagtcta tcagcatctg acaggtgaat tggatggttc tcagaaccat ttcacccaga 300
cagcctgttt ctatcctgtt taataaatta gtttgggttc tctacatgca taacaaaccc 360
tgctccaatc tgtcacataa aagtctgtga cttgaagttt agtcagcacc cccaccaaac 420
tttatttttc tatgtgtttt ttgcaacata tgagtgtttt gaaaataaag tacccatgtc 480
ttta 484

<210> SEQ ID NO 435
<211> LENGTH: 424
<212> TYPE: DNA
<213> ORGANISM: Homo sapiens

<400> SEQUENCE: 435
gcgccgctca gagcaggtca ctttctgcct tccacgtcct ccttcaagga agccccatgt 60
gggtagcttt caatatcgca ggttcttact cctctgcctc tataagctca aacccaccaa 120
cgatcgggca agtaaacccc ctccctcgcc gacttcggaa ctggcgagag ttcagcgcag 180
atgggcctgt ggggaggggg caagatagat gagggggagc ggcatggtgc ggggtgaccc 240
cttggagaga ggaaaaaggc cacaagaggg gctgccaccg ccactaacgg agatggccct 300
ggtagagacc tttgggggtc tggaacctct ggactcccca tgctctaact cccacactct 360
gctatcagaa acttaaactt gaggattttc tctgtttttc actcgcaata aattcagagc 420
aaac 424

<210> SEQ ID NO 436
<211> LENGTH: 667
<212> TYPE: DNA
<213> ORGANISM: Homo sapiens
<220> FEATURE:
<221> NAME/KEY: misc_feature
<222> LOCATION: (1)...(667)
<223> OTHER INFORMATION: n = A,T,C or G

<400> SEQUENCE: 436
accttgggaa nactctcaca atataaaggg tcgtagactt tactccaaat tccaaaaagg 60
tcctggccat gtaatcctga aagttttccc aaggtagcta taaaatcctt ataagggtgc 120
agcctcttct ggaattcctc tgatttcaaa gtctcactct caagttcttg aaaacgaggg 180
cagttcctga aaggcaggta tagcaactga tcttcagaaa gaggaactgt gtgcaccggg 240
atgggctgcc agagtaggat aggattccag atgctgacac cttctggggg aaacagggct 300
gccaggtttg tcatagcact catcaaagtc cggtcaacgt ctgtgcttcg aatataaacc 360
tgttcatgtt tataggactc attcaagaat tttctatatc tctttcttat atactctcca 420
agttcataat gctgctccat gcccagctgg gtgagttggc caaatccttg tggccatgag 480
gattccttta tggggtcagt gggaaaggtg tcaatgggac ttcggtctcc atgccgaaac 540
accaaagtca caaacttcaa ctccttggct agtacacttc ggtctagcca gaaaaaaagc 600

-continued

```
agaaacaaga agccaaggct aaggcttgct gccctgccag gaggaggggt gcagctctca    660

tgttgag                                                              667
```

<210> SEQ ID NO 437
<211> LENGTH: 693
<212> TYPE: DNA
<213> ORGANISM: Homo sapiens

<400> SEQUENCE: 437

```
ctacgtctca accctcattt ttaggtaagg aatcttaagt ccaaagatat taagtgactc     60

acacagccag gtaaggaaag ctggattggc acactaggac tctaccatac cgggttttgt    120

taaagctcag gttaggaggc tgataagctt ggaaggaact tcagacagct ttttcagatc    180

ataaaagata attcttagcc catgttcttc tccagagcag acctgaaatg acagcacagc    240

aggtactcct ctattttcac ccctcttgct tctactctct ggcagtcaga cctgtgggag    300

gccatgggag aaagcagctc tctggatgtt tgtacagatc atggactatt ctctgtggac    360

catttctcca ggttacccta ggtgtcacta ttggggggac agccagcatc tttagctttc    420

atttgagttt ctgtctgtct tcagtagagg aaacttttgc tcttcacact tcacatctga    480

acacctaact gctgttgctc ctgaggtggt gaaagacaga tatagagctt acagtattta    540

tcctatttct aggcactgag ggctgtgggg taccttgtgg tgccaaaaca gatcctgttt    600

taaggacatg ttgcttcaga gatgtctgta actatctggg ggctctgttg gctctttacc    660

ctgcatcatg tgctctcttg gctgaaaatg acc                                 693
```

<210> SEQ ID NO 438
<211> LENGTH: 360
<212> TYPE: DNA
<213> ORGANISM: Homo sapiens

<400> SEQUENCE: 438

```
ctgcttatca caatgaatgt tctcctgggc agcgttgtga tctttgccac cttcgtgact     60

ttatgcaatg catcatgcta tttcatacct aatgagggag ttccaggaga ttcaaccagg    120

atgtttctac acctgtgggt tatgacaaag acaactgcca aagaatcttc aagaaggagg    180

actgcaagta tatctggtgg agaagaagga cccaaaaaag acctgttctg tcagtgaatg    240

gataatctaa tgtgcttcta gtaggcacag ggctcccagg ccaggcctca ttctcctctg    300

gcctctaata gtcaataatt gtgtagccat gcctatcagt aaaaagattt ttgagcaaac    360
```

<210> SEQ ID NO 439
<211> LENGTH: 431
<212> TYPE: DNA
<213> ORGANISM: Homo sapiens
<220> FEATURE:
<221> NAME/KEY: misc_feature
<222> LOCATION: (1)...(431)
<223> OTHER INFORMATION: n = A,T,C or G

<400> SEQUENCE: 439

```
gttcctnnta actcctgcca gaaacagctc tcctcaacat gagagctgca cccctcctcc     60

tggccagggc agcaagcctt agccttggct tcttgtttct gctttttttc tggctagacc    120

gaagtgtact agccaaggag ttgaagtttg tgactttggt gtttcggcat ggagaccgaa    180

gtcccattga cacctttccc actgacccca taaaggaatc ctcatggcca caaggatttg    240

gccaactcac ccagctgggc atggagcagc attatgaact tggagagtat ataagaaaga    300

gatatagaaa attcttgaat gagtcctata aacatgaaca ggtttatatt cgaagcacag    360
```

-continued acgttgaccg gactttgatg agtgctatga caaacctggc agcccgtcga cgcggccgcg 420
aatttagtag t 431

<210> SEQ ID NO 440
<211> LENGTH: 523
<212> TYPE: DNA
<213> ORGANISM: Homo sapiens

<400> SEQUENCE: 440
agagataaag cttaggtcaa agttcataga gttcccatga actatatgac tggccacaca 60
ggatcttttg tatttaagga ttctgagatt ttgcttgagc aggattagat aaggctgttc 120
tttaaatgtc tgaaatggaa cagatttcaa aaaaaaaccc cacaatctag ggtgggaaca 180
aggaaggaaa gatgtgaata ggctgatggg caaaaaacca atttacccat cagttccagc 240
cttctctcaa ggagaggcaa agaaaggaga tacagtggag acatctggaa agttttctcc 300
actggaaaac tgctactatc tgtttttata tttctgttaa aatatatgag gctacagaac 360
taaaaattaa aacctctttg tgtcccttgg tcctggaaca tttatgttcc ttttaaagaa 420
acaaaaatca aactttacag aaagatttga tgtatgtaat acatatagca gctcttgaag 480
tatatatatc atagcaaata agtcatctga tgagaacaag cta 523

<210> SEQ ID NO 441
<211> LENGTH: 430
<212> TYPE: DNA
<213> ORGANISM: Homo sapiens

<400> SEQUENCE: 441
gttcctccta actcctgcca gaaacagctc tcctcaacat gagagctgca cccctcctcc 60
tggccagggc agcaagcctt agccttggct tcttgtttct gctttttttc tggctagacc 120
gaagtgtact agccaaggag ttgaagtttg tgactttggt gtttcggcat ggagaccgaa 180
gtcccattga cacctttccc actgacccca taaaggaatc ctcatggcca caaggatttg 240
gccaactcac ccagctgggc atggagcagc attatgaact tggagagtat ataagaaaga 300
gatatagaaa attcttgaat gagtcctata aacatgaaca ggtttatatt cgaagcacag 360
acgttgaccg gactttgatg agtgctatga caaacctggc agcccgtcga cgcggccgcg 420
aatttagtag 430

<210> SEQ ID NO 442
<211> LENGTH: 362
<212> TYPE: DNA
<213> ORGANISM: Homo sapiens

<400> SEQUENCE: 442
ctaaggaatt agtagtgttc ccatcacttg tttggagtgt gctattctaa aagattttga 60
tttcctggaa tgacaattat attttaactt tggtggggga aagagttata ggaccacagt 120
cttcacttct gatacttgta aattaatctt ttattgcact tgttttgacc attaagctat 180
atgtttagaa atggtcattt tacggaaaaa ttagaaaaat tctgataata gtgcagaata 240
aatgaattaa tgttttactt aatttatatt gaactgtcaa tgacaaataa aaattctttt 300
tgattatttt ttgttttcat ttaccagaat aaaaactaag aattaaaagt ttgattacag 360
tc 362

<210> SEQ ID NO 443

-continued

<211> LENGTH: 624
<212> TYPE: DNA
<213> ORGANISM: Homo sapiens
<220> FEATURE:
<221> NAME/KEY: misc_feature
<222> LOCATION: (1)...(624)
<223> OTHER INFORMATION: n = A,T,C or G

<400> SEQUENCE: 443
tttttttttt gcaacacaat atacatcaca gtgaaatgtg taatccttgc aaattgcaag 60
ttgaaagaat taaattcaga ggaggggaga gaaagagtac tcagtaggga ctgagcacta 120
aatgcttatt ttaaaagaaa tgtaaagagc agaaagcaat tcaggctacc ctgccttttg 180
tgctggctag tactccggtc ggtgtcagca gcacgtggca ttgaacattg caatgtggag 240
cccaaaccac agaaaatggg gtgaaattgg ccaactttct attaacttgg cttcctgttt 300
tataaaatat tgtgaataat atcacctact tcaaagggca gttatgaggc ttaaatgaac 360
taacgcctac aaaacactta aacatagata acataggtgc aagtactatg tatctggtac 420
atggtaaaca tccttattat taaagtcaac gctaaaatga atgtgtgtgc atatgctaat 480
agtacagaga gagggcactt aaaccaacta agggcctgga gggaaggttt cctggaaaga 540
ngatgcttgt gctgggtcca aatcttggtc tactatgacc ttggccaaat tatttaaact 600
ttgtccctat ctgctaaaca gatc 624

<210> SEQ ID NO 444
<211> LENGTH: 425
<212> TYPE: DNA
<213> ORGANISM: Homo sapiens
<220> FEATURE:
<221> NAME/KEY: misc_feature
<222> LOCATION: (1)...(425)
<223> OTHER INFORMATION: n = A,T,C or G

<400> SEQUENCE: 444
gcacatcatt nntcttgcat tctttgagaa taagaagatc agtaaatagt tcagaagtgg 60
gaagctttgt ccaggcctgt gtgtgaaccc aatgttttgc ttagaaatag aacaagtaag 120
ttcattgcta tagcataaca caaaatttgc ataagtggtg gtcagcaaat ccttgaatgc 180
tgcttaatgt gagaggttgg taaaatcctt tgtgcaacac tctaactccc tgaatgtttt 240
gctgtgctgg gacctgtgca tgccagacaa ggccaagctg gctgaaagag caaccagcca 300
cctctgcaat ctgccacctc ctgctggcag gatttgtttt tgcatcctgt gaagagccaa 360
ggaggcacca gggcataagt gagtagactt atggtcgacg cggccgcgaa tttagtagta 420
gtaga 425

<210> SEQ ID NO 445
<211> LENGTH: 414
<212> TYPE: DNA
<213> ORGANISM: Homo sapiens
<220> FEATURE:
<221> NAME/KEY: misc_feature
<222> LOCATION: (1)...(414)
<223> OTHER INFORMATION: n = A,T,C or G

<400> SEQUENCE: 445
catgtttatg nttttggatt actttgggca cctagtgttt ctaaatcgtc tatcattctt 60
ttctgttttt caaaagcaga gatggccaga gtctcaacaa actgtatctt caagtctttg 120
tgaaattctt tgcatgtggc agattattgg atgtagtttc ctttaactag catataaatc 180
tggtgtgttt cagataaatg aacagcaaaa tgtggtggaa ttaccatttg gaacattgtg 240

-continued

```
aatgaaaaat tgtgtctcta gattatgtaa caaataacta tttcctaacc attgatcttt    300

ggatttttat aatcctactc acaaatgact aggcttctcc tcttgtattt tgaagcagtg    360

tgggtgctgg attgataaaa aaaaaaaaag tcgacgcggc cgcgaattta gtag          414
```

<210> SEQ ID NO 446
<211> LENGTH: 631
<212> TYPE: DNA
<213> ORGANISM: Homo sapiens
<220> FEATURE:
<221> NAME/KEY: misc_feature
<222> LOCATION: (1)...(631)
<223> OTHER INFORMATION: n = A,T,C or G

<400> SEQUENCE: 446

```
acaaattaga anaaagtgcc agagaacacc acataccttg tccggaacat tacaatggct     60

tctgcatgca tgggaagtgt gagcattcta tcaatatgca ggagccatct tgcaggtgtg    120

atgctggtta tactggacaa cactgtgaaa aaaaggacta cagtgttcta tacgttgttc    180

ccggtcctgt acgatttcag tatgtcttaa tcgcagctgt gattggaaca attcagattg    240

ctgtcatctg tgtggtggtc ctctgcatca caagggccaa actttaggta atagcattgg    300

actgagattt gtaaactttc caaccttcca ggaaatgccc cagaagcaac agaattcaca    360

gacagaagca aaatacaggg cactacagtt cagacaatac aacaagagcg tccacgaggt    420

taatctaaag ggagcatgtt tcacagtggc tggactaccg agagcttgga ctacacaata    480

cagtattata gacaaaagaa taagacaaga gatctacaca tgttgccttg catttgtggt    540

aatctacacc aatgaaaaca tgtactacag ctatatttga ttatgtatgg atatatttga    600

aatagtatac attgtcttga tgttttttct g                                   631
```

<210> SEQ ID NO 447
<211> LENGTH: 585
<212> TYPE: DNA
<213> ORGANISM: Homo sapiens
<220> FEATURE:
<221> NAME/KEY: misc_feature
<222> LOCATION: (1)...(585)
<223> OTHER INFORMATION: n = A,T,C or G

<400> SEQUENCE: 447

```
ccttgggaaa antntcacaa tataaagggt cgtagacttt actccaaatt ccaaaaaggt     60

cctggccatg taatcctgaa agttttccca aggtagctat aaaatcctta taagggtgca    120

gcctcttctg gaattcctct gatttcaaag tctcactctc aagttcttga aaacgagggc    180

agttcctgaa aggcaggtat agcaactgat cttcagaaag aggaactgtg tgcaccggga    240

tgggctgcca gagtaggata ggattccaga tgctgacacc ttctggggga aacagggctg    300

ccaggtttgt catagcactc atcaaagtcc ggtcaacgtc tgtgcttcga atataaacct    360

gttcatgttt ataggactca ttcaagaatt ttctatatct ctttcttata tactctccaa    420

gttcataatg ctgctccatg cccagctggg tgagttggcc aaatccttgt ggccatgagg    480

attcctttat ggggtcagtg ggaaaggtgt caatgggact tcggtctcca tgccgaaaca    540

ccaaagtcac aaacttcaac tccttggcta gtacacttcg gtcta                    585
```

<210> SEQ ID NO 448
<211> LENGTH: 93
<212> TYPE: DNA
<213> ORGANISM: Homo sapiens
<220> FEATURE:

-continued

<221> NAME/KEY: misc_feature
<222> LOCATION: (1)...(93)
<223> OTHER INFORMATION: n = A,T,C or G

<400> SEQUENCE: 448
tgctcgtggg tcattctgan nnccgaactg accntgccag ccctgccgan gggccnccat 60
ggctccctag tgccctggag aggangggc tag 93

<210> SEQ ID NO 449
<211> LENGTH: 706
<212> TYPE: DNA
<213> ORGANISM: Homo sapiens
<220> FEATURE:
<221> NAME/KEY: misc_feature
<222> LOCATION: (1)...(706)
<223> OTHER INFORMATION: n = A,T,C or G

<400> SEQUENCE: 449
ccaagttcat gctntgtgct ggacgctgga caggggggcaa aagcnnttgc tcgtgggtca 60
ttctgancac cgaactgacc atgccagccc tgccgatggt cctccatggc tccctagtgc 120
cctggagagg aggtgtctag tcagagagta gtcctggaag gtggcctctg ngaggagcca 180
cggggacagc atcctgcaga tggtcgggcg cgtcccattc gccattcagg ctgcgcaact 240
gttgggaagg gcgatcggtg cgggcctctt cgctattacg ccagctggcg aaagggggat 300
gtgctgcaag gcgattaagt tgggtaacgc cagggttttc ccagtcncga cgttgtaaaa 360
cgacggccag tgaattgaat ttaggtgacn ctatagaaga gctatgacgt cgcatgcacg 420
cgtacgtaag cttggatcct ctagagcggc cgcctactac tactaaattc gcggccgcgt 480
cgacgtggga tccncactga gagagtggag agtgacatgt gctggacnct gtccatgaag 540
cactgagcag aagctggagg cacaacgcnc cagacactca cagctactca ggaggctgag 600
aacaggttga acctgggagg tggaggttgc aatgagctga gatcaggccn ctgcncccca 660
gcatggatga cagagtgaaa ctccatctta aaaaaaaaaa aaaaaa 706

<210> SEQ ID NO 450
<211> LENGTH: 493
<212> TYPE: DNA
<213> ORGANISM: Homo sapiens

<400> SEQUENCE: 450
gagacggagt gtcactctgt tgcccaggct ggagtgcagc aagacactgt ctaagaaaaa 60
acagttttaa aaggtaaaac aacataaaaa gaaatatcct atagtggaaa taagagagtc 120
aaatgaggct gagaacttta caaagggatc ttacagacat gtcgccaata tcactgcatg 180
agcctaagta taagaacaac ctttggggag aaaccatcat ttgacagtga ggtacaattc 240
caagtcaggt agtgaaatgg gtggaattaa actcaaatta atcctgccag ctgaaacgca 300
agagacactg tcagagagtt aaaaagtgag ttctatccat gaggtgattc cacagtcttc 360
tcaagtcaac acatctgtga actcacagac caagttctta aaccactgtt caaactctgc 420
tacacatcag aatcacctgg agagctttac aaactcccat tgccgagggt cgacgcggcc 480
gcgaatttag tag 493

<210> SEQ ID NO 451
<211> LENGTH: 501
<212> TYPE: DNA
<213> ORGANISM: Homo sapiens
<220> FEATURE:
<221> NAME/KEY: misc_feature -continued
<222> LOCATION: (1)...(501)
<223> OTHER INFORMATION: n = A,T,C or G

<400> SEQUENCE: 451
gggcgcgtcc cattcgccat tcaggctgcg caactgttgg gaagggcgat cggtgcgggc 60
ctcttcgcta ttacgccagc tggcgaaagg gggatgtgct gcaaggcgat taagttgggt 120
aacgccaggg ttttcccagt cncgacgttg taaaacgacg gccagtgaat tgaatttagg 180
tgacnctata gaagagctat gacgtcgcat gcacgcgtac gtaagcttgg atcctctaga 240
gcggccgcct actactacta aattcgcggc cgcgtcgacg tgggatccnc actgagagag 300
tggagagtga catgtgctgg acnctgtcca tgaagcactg agcagaagct ggaggcacaa 360
cgcnccagac actcacagct actcaggagg ctgagaacag gttgaacctg ggaggtggag 420
gttgcaatga gctgagatca ggccnctgcn ccccagcatg gatgacagag tgaaactcca 480
tcttaaaaaa aaaaaaaaaa a 501

<210> SEQ ID NO 452
<211> LENGTH: 51
<212> TYPE: DNA
<213> ORGANISM: Homo sapiens
<220> FEATURE:
<221> NAME/KEY: misc_feature
<222> LOCATION: (1)...(51)
<223> OTHER INFORMATION: n = A,T,C or G

<400> SEQUENCE: 452
agacggtttc accnttacaa cnccttttag gatgggnntt ggggagcaag c 51

<210> SEQ ID NO 453
<211> LENGTH: 317
<212> TYPE: DNA
<213> ORGANISM: Homo sapiens
<220> FEATURE:
<221> NAME/KEY: misc_feature
<222> LOCATION: (1)...(317)
<223> OTHER INFORMATION: n = A,T,C or G

<400> SEQUENCE: 453
tacatcttgc tttttcccca ttggaactag tcattaaccc atctctgaac tggtagaaaa 60
acatctgaag agctagtcta tcagcatctg gcaagtgaat tggatggttc tcagaaccat 120
ttcacccana cagcctgttt ctatcctgtt taataaatta gtttgggttc tctacatgca 180
taacaaaccc tgctccaatc tgtcacataa aagtctgtga cttgaagttt antcagcacc 240
cccaccaaac tttatttttc tatgtgtttt ttgcaacata tgagtgtttt gaaaataagg 300
tacccatgtc tttatta 317

<210> SEQ ID NO 454
<211> LENGTH: 231
<212> TYPE: DNA
<213> ORGANISM: Homo sapiens

<400> SEQUENCE: 454
ttcgaggtac aatcaactct cagagtgtag tttccttcta tagatgagtc agcattaata 60
taagccacgc cacgctcttg aaggagtctt gaattctcct ctgctcactc agtagaacca 120
agaagaccaa attcttctgc atcccagctt gcaaacaaaa ttgttcttct aggtctccac 180
ccttcctttt tcagtgttcc aaagctcctc acaatttcat gaacaacagc t 231

<210> SEQ ID NO 455

-continued

```
<211> LENGTH: 231
<212> TYPE: DNA
<213> ORGANISM: Homo sapiens

<400> SEQUENCE: 455

taccaaagag ggcataataa tcagtctcac agtagggttc accatcctcc aagtgaaaaa     60

cattgttccg aatgggcttt ccacaggcta cacacacaaa acaggaaaca tgccaagttt    120

gtttcaacgc attgatgact tctccaagga tcttcctttg gcatcgacca cattcagggg    180

caaagaattt ctcatagcac agctcacaat acagggctcc tttctcctct a             231


<210> SEQ ID NO 456
<211> LENGTH: 231
<212> TYPE: DNA
<213> ORGANISM: Homo sapiens

<400> SEQUENCE: 456

ttggcaggta cccttacaaa gaagacacca taccttatgc gttattaggt ggaataatca     60

ttccattcag tattatcgtt attattcttg gagaaaccct gtctgtttac tgtaaccttt    120

tgcactcaaa ttcctttatc aggaataact acatagccac tatttacaaa gccattggaa    180

cctttttatt tggtgcagct gctagtcagt ccctgactga cattgccaag t             231


<210> SEQ ID NO 457
<211> LENGTH: 231
<212> TYPE: DNA
<213> ORGANISM: Homo sapiens
<220> FEATURE:
<221> NAME/KEY: misc_feature
<222> LOCATION: (1)...(231)
<223> OTHER INFORMATION: n = A,T,C or G

<400> SEQUENCE: 457

cgaggtaccc aggggtctga aaatctctnn tttantagtc gatagcaaaa ttgttcatca     60

gcattcctta atatgatctt gctataatta gatttttctc cattagagtt catacagttt    120

tatttgattt tattagcaat ctctttcaga agacccttga gatcattaag ctttgtatcc    180

agttgtctaa atcgatgcct catttcctct gaggtgtcgc tggcttttgt g             231


<210> SEQ ID NO 458
<211> LENGTH: 231
<212> TYPE: DNA
<213> ORGANISM: Homo sapiens

<400> SEQUENCE: 458

aggtctggtt ccccccactt ccactcccct ctactctctc taggactggg ctgggccaag     60

agaagagggg tggttaggga agccgttgag acctgaagcc ccaccctcta ccttccttca    120

acaccctaac cttgggtaac agcatttgga attatcattt gggatgagta gaatttccaa    180

ggtcctgggt taggcatttt ggggggccag accccaggag aagaagattc t             231


<210> SEQ ID NO 459
<211> LENGTH: 231
<212> TYPE: DNA
<213> ORGANISM: Homo sapiens

<400> SEQUENCE: 459

ggtaccgagg ctcgctgaca cagagaaacc ccaacgcgag gaaaggaatg gccagccaca     60

ccttcgcgaa acctgtggtg gcccaccagt cctaacggga caggacagag agacagagca    120

gccctgcact gttttccctc caccacagcc atcctgtccc tcattggctc tgtgctttcc    180
```

-continued actatacaca gtcaccgtcc caatgagaaa caagaaggag caccctccac a 231

<210> SEQ ID NO 460
<211> LENGTH: 231
<212> TYPE: DNA
<213> ORGANISM: Homo sapiens

<400> SEQUENCE: 460
gcaggtataa catgctgcaa caacagatgt gactaggaac ggccggtgac atggggaggg 60
cctatcaccc tattcttggg ggctgcttct tcacagtgat catgaagcct agcagcaaat 120
cccacctccc cacacgcaca cggccagcct ggagcccaca gaagggtcct cctgcagcca 180
gtggagcttg gtccagcctc cagtccaccc ctaccaggct taaggataga a 231

<210> SEQ ID NO 461
<211> LENGTH: 231
<212> TYPE: DNA
<213> ORGANISM: Homo sapiens

<400> SEQUENCE: 461
cgaggtttga gaagctctaa tgtgcagggg agccgagaag caggcggcct agggagggtc 60
gcgtgtgctc cagaagagtg tgtgcatgcc agaggggaaa caggcgcctg tgtgtcctgg 120
gtggggttca gtgaggagtg ggaaattggt tcagcagaac caagccgttg ggtgaataag 180
agggggattc catggcactg atagagccct atagtttcag agctgggaat t 231

<210> SEQ ID NO 462
<211> LENGTH: 231
<212> TYPE: DNA
<213> ORGANISM: Homo sapiens

<400> SEQUENCE: 462
aggtaccctc attgtagcca tgggaaaatt gatgttcagt ggggatcagt gaattaaatg 60
gggtcatgca agtataaaaa ttaaaaaaaa aagacttcat gcccaatctc atatgatgtg 120
gaagaactgt tagagagacc aacagggtag tgggttagag atttccagag tcttacattt 180
tctagaggag gtatttaatt tcttctcact catccagtgt tgtatttagg a 231

<210> SEQ ID NO 463
<211> LENGTH: 231
<212> TYPE: DNA
<213> ORGANISM: Homo sapiens

<400> SEQUENCE: 463
tactccagcc tggtgacaga gcgagaccct atcaccgccc cccaccccac caaaaaaaaa 60
actgagtaga caggtgtcct cttggcatgg taagtcttaa gtcccctccc agatctgtga 120
catttgacag gtgtcttttc ctctggacct cggtgtcccc atctgagtga gaaaaggcag 180
tggggaggtg gatcttccag tcgaagcggt atagaagccc gtgtgaaaag c 231

<210> SEQ ID NO 464
<211> LENGTH: 231
<212> TYPE: DNA
<213> ORGANISM: Homo sapiens

<400> SEQUENCE: 464
gtactctaag attttatcta agttgccttt tctgggtggg aaagtttaac cttagtgact 60
aaggacatca catatgaaga atgtttaagt tggaggtggc aacgtgaatt gcaaacaggg 120

-continued

```
cctgcttcag tgactgtgtg cctgtagtcc cagctactcg ggagtctgtg tgaggccagg    180

ggtgccagcg caccagctag atgctctgta acttctaggc cccattttcc c             231
```

<210> SEQ ID NO 465
<211> LENGTH: 231
<212> TYPE: DNA
<213> ORGANISM: Homo sapiens

<400> SEQUENCE: 465

```
catgttgttg tagctgtggt aatgctggct gcatctcaga cagggttaac ttcagctcct     60

gtggcaaatt agcaacaaat tctgacatca tatttatggt ttctgtatct ttgttgatga    120

aggatggcac aatttttgct tgtgttcata atatactcag attagttcag ctccatcaga    180

taaactggag acatgcagga cattagggta gtgttgtagc tctggtaatg a             231
```

<210> SEQ ID NO 466
<211> LENGTH: 231
<212> TYPE: DNA
<213> ORGANISM: Homo sapiens

<400> SEQUENCE: 466

```
caggtacctc tttccattgg atactgtgct agcaagcatg ctctccgggg tttttttaat     60

ggccttcgaa cagaacttgc cacataccca ggtataatag tttctaacat ttgcccagga    120

cctgtgcaat caaatattgt ggagaattcc ctagctggag aagtcacaaa gactataggc    180

aataatggag accagtccca caagatgaca accagtcgtt gtgtgcggct g             231
```

<210> SEQ ID NO 467
<211> LENGTH: 311
<212> TYPE: DNA
<213> ORGANISM: Homo sapiens

<400> SEQUENCE: 467

```
gtacaccctg gcacagtcca atctgaactg gttcggcact catctttcat gagatggatg     60

tggtggcttt tctccttttt catcaagact cctcagcagg gagcccagac cagcctgcac    120

tgtgccttaa cagaaggtct tgagattcta agtgggaatc atttcagtga ctgtcatgtg    180

gcatgggtct ctgcccaagc tcgtaatgag actatagcaa ggcggctgtg ggacgtcagt    240

tgtgacctgc tgggcctccc aatagactaa caggcagtgc cagttggacc caagagaaga    300

ctgcagcaga c                                                         311
```

<210> SEQ ID NO 468
<211> LENGTH: 3112
<212> TYPE: DNA
<213> ORGANISM: Homo sapiens

<400> SEQUENCE: 468

```
cattgtgttg ggagaaaaac agaggggaga tttgtgtggc tgcagccgag ggagaccagg     60

aagatctgca tggtgggaag gacctgatga tacagagttt gataggagac aattaaaggc    120

tggaaggcac tggatgcctg atgatgaagt ggactttcaa actggggcac tactgaaacg    180

atgggatggc cagagacaca ggagatgagt tggagcaagc tcaataacaa agtggttcaa    240

cgaggacttg gaattgcatg gagctggagc tgaagtttag cccaattgtt tactagttga    300

gtgaatgtgg atgattggat gatcatttct catctctgag cctcaggttc cccatccata    360

aaatgggata cacagtatga tctataaagt gggatatagt atgatctact tcactgggtt    420

atttgaagga tgaattgaga taatttattt caggtgccta gaacaatgcc cagattagta    480
```

-continued

```
catttggtgg aactgagaaa tggcataaca ccaaatttaa tatatgtcag atgttactat    540
gattatcatt caatctcata gttttgtcat ggcccaattt atcctcactt gtgcctcaac    600
aaattgaact gttaacaaag gaatctctgg tcctgggtaa tggctgagca ccactgagca    660
tttccattcc agttggcttc ttgggtttgc tagctgcatc actagtcatc ttaaataaat    720
gaagttttaa catttctcca gtgatttttt tatctcacct ttgaagatac tatgttatgt    780
gattaaataa agaacttgag aagaacaggt ttcattaaac ataaaatcaa tgtagacgca    840
aattttctgg atgggcaata cttatgttca caggaaatgc tttaaaatat gcagaagata    900
attaaatggc aatggacaaa gtgaaaaact tagacttttt tttttttttt ggaagtatct    960
ggatgttcct tagtcactta aaggagaact gaaaaatagc agtgagttcc acataatcca   1020
acctgtgaga ttaaggctct ttgtggggaa ggacaaagat ctgtaaattt acagtttcct   1080
tccaaagcca acgtcgaatt ttgaaacata tcaaagctct tcttcaagac aaataatcta   1140
tagtacatct ttcttatggg atgcacttat gaaaaatggt ggctgtcaac atctagtcac   1200
tttagctctc aaaatggttc attttaagag aaagttttag aatctcatat ttattcctgt   1260
ggaaggacag cattgtggct tggactttat aaggtcttta ttcaactaaa taggtgagaa   1320
ataagaaagg ctgctgactt taccatctga ggccacacat ctgctgaaat ggagataatt   1380
aacatcacta gaaacagcaa gatgacaata taatgtctaa gtagtgacat gtttttgcac   1440
atttccagcc cctttaaata tccacacaca caggaagcac aaaaggaagc acagagatcc   1500
ctgggagaaa tgcccggccg ccatcttggg tcatcgatga gcctcgccct gtgcctggtc   1560
ccgcttgtga gggaaggaca ttagaaaatg aattgatgtg ttccttaaag gatgggcagg   1620
aaaacagatc ctgttgtgga tatttatttg aacgggatta cagatttgaa atgaagtcac   1680
aaagtgagca ttaccaatga gaggaaaaca gacgagaaaa tcttgatggc ttcacaagac   1740
atgcaacaaa caaaatggaa tactgtgatg acatgaggca gccaagctgg ggaggagata   1800
accacggggc agagggtcag gattctggcc ctgctgccta aactgtgcgt tcataaccaa   1860
atcatttcat atttctaacc ctcaaaacaa agctgttgta atatctgatc tctacggttc   1920
cttctgggcc caacattctc catatatcca gccacactca tttttaatat ttagttccca   1980
gatctgtact gtgacctttc tacactgtag aataacatta ctcattttgt tcaaagaccc   2040
ttcgtgttgc tgcctaatat gtagctgact gtttttccta aggagtgttc tggcccaggg   2100
gatctgtgaa caggctggga agcatctcaa gatctttcca gggttatact tactagcaca   2160
cagcatgatc attacggagt gaattatcta atcaacatca tcctcagtgt ctttgcccat   2220
actgaaattc atttcccact tttgtgccca ttctcaagac ctcaaaatgt cattccatta   2280
atatcacagg attaactttt ttttttaacc tggaagaatt caatgttaca tgcagctatg   2340
ggaatttaat tacatatttt gttttccagt gcaaagatga ctaagtcctt tatccctccc   2400
ctttgtttga ttttttttcc agtataaagt taaaatgctt agccttgtac tgaggctgta   2460
tacagccaca gcctctcccc atccctccag ccttatctgt catcaccatc aacccctccc   2520
atgcacctaa acaaaatcta acttgtaatt ccttgaacat gtcaggcata cattattcct   2580
tctgcctgag aagctcttcc ttgtctctta aatctagaat gatgtaaagt tttgaataag   2640
ttgactatct tacttcatgc aaagaaggga cacatatgag attcatcatc acatgagaca   2700
gcaaatacta aaagtgtaat ttgattataa gagtttagat aaatatatga aatgcaagag   2760
ccacagaggg aatgtttatg gggcacgttt gtaagcctgg gatgtgaagc aaaggcaggg   2820
```

-continued

```
aacctcatag tatcttatat aatatacttc atttctctat ctctatcaca atatccaaca   2880

agcttttcac agaattcatg cagtgcaaat ccccaaaggt aacctttatc catttcatgg   2940

tgagtgcgct ttagaatttt ggcaaatcat actggtcact tatctcaact ttgagatgtg   3000

tttgtccttg tagttaattg aaagaaatag ggcactcttg tgagccactt tagggttcac   3060

tcctggcaat aaagaattta caaagagcaa aaaaaaaaaa aaaaaaaaaa aa           3112
```

<210> SEQ ID NO 469
<211> LENGTH: 2229
<212> TYPE: DNA
<213> ORGANISM: Homo sapiens

<400> SEQUENCE: 469

```
agctctttgt aaattcttta ttgccaggag tgaaccctaa agtggctcac aagagtgccc     60

tatttctttc aattaactac aaggacaaac acatctcaaa gttgagataa gtgaccagta    120

tgatttgcca aaattctaaa gcgcactcac catgaaatgg ataaaggtta cctttgggga    180

tttgcactgc atgaattctg tgaaaagctt gttggatatt gtgatagaga tagagaaatg    240

aagtatatta tataagatac tatgaggttc cctgcctttg cttcacatcc caggcttaca    300

aacgtgcccc ataaacattc cctctgtggc tcttgcattt catatattta tctaaactct    360

tataatcaaa tacactttta gtatttgctg tctcatgtga tgatgaatct catatgtgtc    420

ccttctttgc atgaagtaag atagtcaact tattcaaaac tttacatcat tctagattta    480

agagacaagg aagagcttct caggcagaag gaataatgta tgcctgacat gttcaaggaa    540

ttacaagtta gattttgttt aggtgcatgg gaggggttga tggtgatgac agataaggct    600

ggagggatgg ggagaggctg tggctgtata cagcctcagt acaaggctaa gcattttaac    660

tttatactgg aaaaaaaatc aaacaaaggg gagggataaa ggacttagtc atctttgcac    720

tggaaaacaa aatatgtaat taaattccca tagctgcatg taacattgaa ttcttccagg    780

ttaaaaaaaa agttaatcct gtgatattaa tggaatgaca ttttgaggtc ttgagaatgg    840

gcacaaaagt gggaaatgaa tttcagtatg ggcaaagaca ctgaggatga tgttgattag    900

ataattcact ccgtaatgat catgctgtgt gctagtaagt ataaccctgg aaagatcttg    960

agatgcttcc cagcctgttc acagatcccc tgggccagaa cactccttag gaaaaacagt   1020

cagctacata ttaggcagca acacgaaggg tctttgaaca aaatgagtaa tgttattcta   1080

cagtgtagaa aggtcacagt acagatctgg gaactaaata ttaaaaatga gtgtggctgg   1140

atatatggag aatgttgggc ccagaaggaa ccgtagagat cagatattac aacagctttg   1200

ttttgagggt tagaaatatg aaatgatttg gttatgaacg cacagtttag gcagcagggc   1260

cagaatcctg accctctgcc ccgtggttat ctcctcccca gcttggctgc ctcatgtcat   1320

cacagtattc cattttgttt gttgcatgtc ttgtgaagcc atcaagattt tctcgtctgt   1380

tttcctctca ttggtaatgc tcactttgtg acttcatttc aaatctgtaa tcccgttcaa   1440

ataaatatcc acaacaggat ctgttttcct gcccatcctt taaggaacac atcaattcat   1500

tttctaatgt ccttccctca caagcgggac caggcacagg gcgaggctca tcgatgaccc   1560

aagatggcgg ccgggcattt ctcccaggga tctctgtgct tccttttgtg cttcctgtgt   1620

gtgtggatat ttaaaggggc tggaaatgtg caaaaacatg tcactactta gacattatat   1680

tgtcatcttg ctgtttctag tgatgttaat tatctccatt tcagcagatg tgtggcctca   1740

gatggtaaag tcagcagcct ttcttatttc tcacctggaa atacatacga ccatttgagg   1800

agacaaatgg caaggtgtca gcataccctg aacttgagtt gagagctaca cacaatatta   1860
```

-continued ttggtttccg agcatcacaa acaccctctc tgtttcttca ctgggcacag aattttaata 1920
cttatttcag tgggctgttg gcaggaacaa atgaagcaat ctacataaag tcactagtgc 1980
agtgcctgac acacaccatt ctcttgaggt cccctctaga gatcccacag gtcatatgac 2040
ttcttgggga gcagtggctc acacctgtaa tcccagcact ttgggaggct gaggcaggtg 2100
ggtcacctga ggtcaggagt tcaagaccag cctggccaat atggtgaaac cccatctcta 2160
ctaaaaatac aaaaattagc tgggcgtgct ggtgcatgcc tgtaatccca gccccaacac 2220
aatggaatt 2229

<210> SEQ ID NO 470
<211> LENGTH: 2426
<212> TYPE: DNA
<213> ORGANISM: Homo sapiens

<400> SEQUENCE: 470
gtaaattctt tattgccagg agtgaaccct aaagtggctc acaagagtgc cctatttctt 60
tcaattaact acaaggacaa acacatctca aagttgagat aagtgaccag tatgatttgc 120
caaaattcta aagcgcactc accatgaaat ggataaaggt tacctttggg gatttgcact 180
gcatgaattc tgtgaaaagc ttgttggata ttgtgataga gatagagaaa tgaagtatat 240
tatataagat actatgaggt tccctgcctt tgcttcacat cccaggctta caaacgtgcc 300
ccataaacat tccctctgtg gctcttgcat ttcatatatt tatctaaact cttataatca 360
aattacactt ttagtatttg ctgtctcatg tgatgatgaa tctcatatgt gtcccttctt 420
tgcatgaagt aagatagtca acttattcaa aactttacat cattctagat ttaagagaca 480
aggaagagct tctcaggcag aaggaataat gtatgcctga catgttcaag gaattacaag 540
ttagattttg tttaggtgca tgggaggggt tgatggtgat gacagataag gctggaggga 600
tggggagagg ctgtggctgt atacagcctc agtacaaggc taagcatttt aactttatac 660
tggaaaaaaa atcaaacaaa ggggagggat aaaggactta gtcatctttg cactggaaaa 720
caaaatatgt aattaaattc ccatagctgc atgtaacatt gaattcttcc aggttaaaaa 780
aaaaagttaa tcctgtgata ttaatggaat gacattttga ggtcttgaga atgggcacaa 840
aagtgggaaa tgaatttcag tatgggcaaa gacactgagg atgatgttga ttagataatt 900
cactccgtaa tgatcatgct gtgtgctagt aagtataacc ctggaaagat cttgagatgc 960
ttcccagcct gttcacagat cccctgggcc agaacactcc ttaggaaaaa cagtcagcta 1020
catattaggc agcaacacga agggtctttg aacaaaatga gtaatgttat tctacagtgt 1080
agaaaggtca cagtacagat ctgggaacta aatattaaaa atgagtgtgg ctggatatat 1140
ggagaatgtt gggcccagaa ggaaccgtag agatcagata ttacaacagc tttgttttga 1200
gggttagaaa tatgaaatga tttggttatg aacgcacagt ttaggcagca gggccagaat 1260
cctgaccctc tgccccgtgg ttatctcctc cccagcttgg ctgcctcatg tcatcacagt 1320
attccatttt gtttgttgca tgtcttgtga agccatcaag attttctcgt ctgttttcct 1380
ctcattggta atgctcactt tgtgacttca tttcaaatct gtaatcccgt tcaaataaat 1440
atccacaaca ggatctgttt tcctgcccat cctttaagga acacatcaat tcattttcta 1500
atgtccttcc ctcacaagcg ggaccaggca cagggcgagg ctcatcgatg acccaagatg 1560
gcggccgggc atttctccca gggatctctg tgcttccttt tgtgcttcct gtgtgtgtgg 1620
atatttaaag gggctggaaa tgtgcaaaaa catgtcacta cttagacatt atattgtcat 1680

-continued

```
cttgctgttt ctagtgatgt taattatctc catttcagca gatgtgtggc ctcagatggt   1740

aaagtcagca gcctttctta tttctcacct ggaaatacat acgaccattt gaggagacaa   1800

atggcaaggt gtcagcatac cctgaacttg agttgagagc tacacacaat attattggtt   1860

tccgagcatc acaaacaccc tctctgtttc ttcactgggc acagaatttt aatacttatt   1920

tcagtgggct gttggcagga acaaatgaag caatctacat aaagtcacta gtgcagtgcc   1980

tgacacacac cattctcttg aggtcccctc tagagatccc acaggtcata tgacttcttg   2040

gggagcagtg gctcacacct gtaatcccag cactttggga ggctgaggca ggtgggtcac   2100

ctgaggtcag gagttcaaga ccagcctggc caatatggtg aaaccccatc tctactaaaa   2160

atacaaaaat tagctgggcg tgctggtgca tgcctgtaat cccagctact tgggaggctg   2220

aggcaggaga attgctggaa catgggaggc ggaggttgca gtgagctgta attgtgccat   2280

tgcactcgaa cctgggcgac agagtggaac tctgtttcca aaaaacaaac aaacaaaaaa   2340

ggcatagtca gatacaacgt gggtgggatg tgtaaataga agcaggatat aaagggcatg   2400

gggtgacggt tttgcccaac acaatg                                         2426
```

<210> SEQ ID NO 471
<211> LENGTH: 812
<212> TYPE: DNA
<213> ORGANISM: Homo sapiens

<400> SEQUENCE: 471

```
gaacaaaatg agtaatgtta ttctacagtg tagaaaggtc acagtacaga tctgggaact     60

aaatattaaa aatgagtgtg gctggatata tggagaatgt tgggcccaga aggaaccgta    120

gagatcagat attacaacag ctttgttttg agggttagaa atatgaaatg atttggttat    180

gaacgcacag tttaggcagc agggccagaa tcctgaccct ctgccccgtg gttatctcct    240

ccccagcttg gctgcctcat gtcatcacag tattccattt tgtttgttgc atgtcttgtg    300

aagccatcaa gattttctcg tctgttttcc tctcattggt aatgctcact ttgtgacttc    360

atttcaaatc tgtaatcccg ttcaaataaa tatccacaac aggatctgtt ttcctgccca    420

tcctttaagg aacacatcaa ttcattttct aatgtccttc cctcacaagc gggaccaggc    480

acagggcgag gctcatcgat gacccaagat ggcggccggg catttctccc agggatctct    540

gtgcttcctt ttgtgcttcc tgtgtgtgtg gatatttaaa ggggctggaa atgtgcaaaa    600

acatgtcact acttagacat tatattgtca tcttgctgtt tctagtgatg ttaattatct    660

ccatttcagc agatgtgtgg cctcagatgg taaagtcagc agcctttctt atttctcacc    720

tctgtatcat caggtccttc ccaccatgca gatcttcctg gtctccctcg gctgcagcca    780

cacaaatctc ccctctgttt ttctgatgcc ag                                  812
```

<210> SEQ ID NO 472
<211> LENGTH: 515
<212> TYPE: DNA
<213> ORGANISM: Homo sapiens
<220> FEATURE:
<221> NAME/KEY: misc_feature
<222> LOCATION: (1)...(515)
<223> OTHER INFORMATION: n = A,T,C or G

<400> SEQUENCE: 472

```
acggagactt attttctgat attgtctgca tatgtatgtt tttaagagtc tggaaatagt     60

cttatgactt tcctatcatg cttattaata aataatacag cccagagaag atgaaaatgg    120

gttccagaat tattggtcct tgcagcccgg tgaatctcag caagaggaac caccaactga    180
```

-continued

```
caatcaggat attgaacctg gacaagagag agaaggaaca cctccgatcg aagaacgtaa    240
agtagaaggt gattgccagg aaatggatct ggaaaagact cggagtgagc gtggagatgg    300
ctctgatgta aaagagaaga ctccacctaa tcctaagcat gctaagacta aagaagcagg    360
agatgggcag ccataagtta aaaagaagac aagctgaagc tacacacatg gctgatgtca    420
cattgaaaat gtgactgaaa atttgaaaat tctctcaata aagtttgagt tttctctgaa    480
gaaaaaaaaa naaaaaaaaa aaanaaaaan aaaaa                               515
```

<210> SEQ ID NO 473
<211> LENGTH: 5829
<212> TYPE: DNA
<213> ORGANISM: Homo sapiens

<400> SEQUENCE: 473

```
cgcatgccgg ggaagcccaa gctggctcga agagccacca gccacctgtg caagggtggg     60
cctggaccag ttggaccagc caccaagctc acctactcaa ggaagcaggg atggccaggt    120
tgcaacagcc tgagtggctg ccacctgata gctgatggag cagaggcctg aggaaaatca    180
gatggcacat ttagctcttt aatggatctt aagttaattt ttctataaag cacatggcac    240
cagtccatgc ctcagagctc gtatggcact gcggaccaca gcaggccgag ttcccaggat    300
tgccatccag gggggccttc tgtagccctg gccagacctt gcagaggtgg ctgggtgctc    360
tttgagcgag ctcggcctcc ctggcatgca caggccccag gtactgacac gctgctctga    420
gtgagcttgt cctgccttgg ctgccaccta actgctgatg gagcagcggc cttaggaaaa    480
gcaaatggcg ctgtagccca actttagggt agaagaagat gtaccatgtc cggccgctag    540
ttggtgactg gtgcacctgc tcctggcgta cccttgcaga ggtgggtggt tgctctttgg    600
ccagcttggc cttgcctggc atgcacaagc ctcagtgcaa caactgtcct acaaatggag    660
acacagagag gaaacaagca gcgggctcag gagcagggtg tgtgctgcct ttggggctcc    720
agtccatgcc tcgggtcgta tggtactgca ggcttcttgg ttgccaagag gcggaccaca    780
ggccttcttg aggaggactt tacgttcaag tgcagaaagc agccaaaatt accatccatg    840
agactaagcc ttctgtggcc ctggcgagac ttaaaatttg tgccaaggca ggacaagctc    900
actcggagca gcgtgtcagt agctggggcc tatgcatgcc gggcagggcc gggctggctg    960
aaggagcaac cagccacctc tgcaagggtg cgcctagtgc aggcggagca tccaccacct   1020
cacccgctcg aggaagtggg gatggccagg ttcccacagc ctgagtgtct gccaccttat   1080
tgctgatgga gcagaggcct taagaaaagc agatggcact gtggccctac ctttagggtg   1140
gaagaagtga tgtacatgtc cggacgctaa ttggtgactg gtacaccggc tcctgctaca   1200
cctttgcaga ggtggctggt tgctctttga gccagcttgt ccttgcccgg catgcacaag   1260
tttcagtgca acaactttgc cacaaatgga gccatataga ggaaacaaga agcaggttca   1320
ggagaagggt gtaccctgcc tttggggctc cagtccatgc ctcaggtgtc acatggcact   1380
gcgggcttct tggttgccag gaggcggacc acaggccatc ttggggagga ctttgtgttc   1440
aagtgcagaa agcagccagg attgccatcc agggggacct tctatagccc tggccaaacc   1500
ttgcaggggt gtctggttgc tctttgagcc ggcttggcct ccctggcatg cacgggcccc   1560
aggtgctggc acgctgctcc gagtgtgctt gtcctgcctt ggctgccacc tctgcggggg   1620
tgcgtctgga gggggtggac cggccaccaa ccttacccag tcaaggaagt ggatggccat   1680
gttcccacag cctgagtggc tgccacctga tggctgatgg agcaaaggcc ttaggaaaag   1740
```

-continued

```
cagatggccc ttggccctac ctttttgtta gaagaactga tgttccatgt cctgcagcga   1800
gtgaggttgg tggctgtgcc cccagctcct ggcgcgccct cgcagaggtg actggttgct   1860
ctttgggccc tcttggcctt gcccagcatg cacaagcctc agtgctacta ctgtgctaca   1920
aatggagcca tatagggggaa acgagcagcc atctcaggag caaggtgtat gctgcctttg   1980
ggggctccag tccttgcctc aagggtctta tgtcactgtg ggcttcttgg ttgtcaagag   2040
gcagaccata ggccgtcttg agagggactt tatgttcaag tgcagaaagc agccaggatt   2100
gccaccctcg ggactctgcc ttctgtggcc ctggccaaac ttagaatttg gccgtagaca   2160
ggacaggctc acttggagta gcgtgtccgt agctggggtc tgtgcatgcc gggcaaggcc   2220
gggctggctc ggggagcaac cagccacctc tgcgggggtg cgcctggagc aggtggagca   2280
gccaccagct cacccactcc aggaagccgg ggtagccagg ttcccaaggc ctgagtgggt   2340
gccacctaat ggctgaagaa acagaggcct tgggaaaacc agatggcact gtggccctac   2400
ctttatggta gaagagctga tttagcctga ctggcagcgt gtggggttgg tggctggtct   2460
gcctgctgct ggcgcatccg tgcaaggatg gctggttgcc ctttgagcca gcttgccctt   2520
gcccggcatg cgcaagcctc agtgcaacaa ctgtgctgca aatggggcca tatagaggaa   2580
aggagcagct ggctctggag catggtgtgc actccctttg ggccttcagt ccatgtctca   2640
tgggtcgtat gacactgcgg gcttgttggt tgccaagagg cagaccacag gtcatcttga   2700
ggaggacttt atgttccagt ccagaaagca gccagtggta ccacccaggg gacttgtgct   2760
tctgtgccca ggccagacgt agaatttgac aaagtcagga cggtctcagt cagagcggcg   2820
tgtcggtccc cggggcctgt gcatgccggg cagggccggg ctggcttggg gagcaagcag   2880
ccacctctgt taagggtgtg cctggagcag gtggagcagc caccaacctc acgcactgaa   2940
agaagcaggg atggccaggt tccaacatcc tgagtggctg ccacctgatg gctgatggag   3000
cagaggcctg aggaaaagca gatggcactg ctttgtagtg ctgttctttg tctctcttga   3060
tctttttcag ttaatgtctg ttttatcaga gactaggatt gcaaaccctg ctctttttttg   3120
ctttccattt gcttggtaaa tattcctcca tccctttatt ttaagcctat gtgtgtcttt   3180
gcacatgaga tgggtctcct gaatacagga caacaatggg tctttactct ttatccaact   3240
tgccagtctg tgtcttttaa ctggggcatt tagcccattt acatttaagt ttagtattgt   3300
tacatgtgaa atttatcctg tcatgatgtt gctagctttt tatttttccc attagtttgc   3360
agtttcttta tagtgtcaat ggtctttaca attcgatatg tttttgtagt ggctggtact   3420
ggtttttcct ttctacgttt agtgtctcct tcaggagctc ttgtaacaca agaatgtgga   3480
tttatttctt gtaaggtaaa tatgtggatt tatttcttgg gactgtattc tatggccttt   3540
accccaagaa tcattacttt ttaaaatgca attcaaatta gcataaaaca tttacagcct   3600
atggaaaggc ttgtggcatt agaatcctta tttataggat tattttgtgt ttttttgaga   3660
tatggtcttt gtcatcgagg cagaagtgcc gtggtttgat cataattcac cacagccctg   3720
aactcttgag tccaagccat ccttttgcct taatctccca accagttgga tctgcaggca   3780
taaggcatca tgcgtggcta attttttcac gttttttttt tttttttgtc gagattatgg   3840
tgtcactgtg ttgctctggc tgatctcaaa tgtttgacct caagggatct ttctgccacg   3900
gcctcctaaa gtgctaggat tatatgcatg atacaccatg cctattgtag agtattacat   3960
tattttcaaa gtcttattgt aagagccatt tattgccttt ggcctaaata actcaatata   4020
atatctctga aactttttttt tgacaaattt tggggcgtga tgatgagaga agggggtttg   4080
aaactttcta ataagagtta acttagagcc atttaagaaa ggaaaaaaca caaattatca   4140
```

-continued

```
gaaaaacaac agtaagatca agtgcaaaag ttctgtggca aagatgatga gagtaaagaa   4200
tatatgtttg tgactcatgg tggcttttac tttgttcttg aatttctgag tacgggttaa   4260
catttaaaga atctacatta tagataacat tttattgcaa gtaaatgtat ttcaaaattt   4320
gttattggtt ttgtatgaga ttattctcag cctacttcat tatcaagcta tattatttta   4380
ttaatgtagt tcgatgatct tacagcaaag ctgaaagctg tatcttcaaa atatgtctat   4440
ttgactaaaa agttattcaa caggagttat tatctataaa aaaaatacaa caggaatata   4500
aaaaacttga ggataaaaag atgttggaaa aagtaatatt aaatcttaaa aaacatatgg   4560
aaactacaca atggtgaaga cacattggtg aagtacaaaa atataaattg gatctagaag   4620
aaagggcaat gcaggcaata gaaaaattag tagaaatccc tttaaaggtt agtttgtaaa   4680
atcaggtaag tttatttata atttgctttc atttatttca ctgcaaatta tattttggat   4740
atgtatatat attgtgcttc ctctgcctgt cttacagcaa tttgccttgc agagttctag   4800
gaaaaaggtg gcatgtgttt ttactttcaa aatatttaaa tttccatcat tataacaaaa   4860
tcaatttttc agagtaatga ttctcactgt ggagtcattt gattattaag acccgttggc   4920
ataagattac atcctctgac tataaaaatc ctggaagaaa acctaggaaa tattcgtctg   4980
gacattgcac ttggcaatga atttatgggt aaccactgat ccacttccag tcactatcca   5040
tgagttttta tttccagata catgaaatca tatgagttga aactttcttt tgattgagca   5100
gtttggaaac cgtctttttg tagaatctgc aagtggatat ttggaaccct ttgaggccta   5160
tgctgaaaaa agaaatatct tcactacatg atgaccacca gcagcagctg ggaaaccag    5220
caccctgtgg aattccatac ggtgcataga atacatcctc ccttcagtcg gcttgggtca   5280
acttaggtca tgggccacct ggctgatagc agtttccaca gaaatgcttc aagatgaaag   5340
tggatgaccg ggccaccctc caccactgcc ctgtaagacc atgggacaca caggccacca   5400
gttcttttca tgtggtcatc ccctgttaga tgggagaaaa tacacctgcc tcatttttgt   5460
accttctgtg tgaacattcc acggcagact gtcgctaaat gtggatgaag aattgaatga   5520
atgaatgaat atgagagaaa atgaataaat ggttcagatc ctgggctgga aggctgtgta   5580
tgaggatggt gggtagagga gggtctgttt ttcttgcctt taagtcacta attgtcactt   5640
tggggcagga gcacaggctt tgaatgcaga ccgactggac tttaattctg gctttactag   5700
ttgtgattgt gtgaccttgt gaaagttact taaaccctct gtgcctgttt ctttatctgt   5760
aaaatggaga taataagatg tcaaaggact gtggtaagaa ttaaatgctt taaaaaaaaa   5820
aaaaaaaaa                                                           5829
```

<210> SEQ ID NO 474
<211> LENGTH: 1594
<212> TYPE: DNA
<213> ORGANISM: Homo sapiens

<400> SEQUENCE: 474

```
atttatggat cattaatgcc tctttagtag tttagagaaa acgtcaaaag aaatggcccc     60
agaataagct tcttgatttg taaaattcta tgtcattggc tcaaatttgt atagtatctc    120
aaaatataaa tatatagaca tctcagataa tatatttgaa atagcaaatt cctgttagaa    180
aataatagta cttaactaga tgagaataac aggtcgccat tatttgaatt gtctcctatt    240
cgtttttcat ttgttgtgtt actcatgttt tacttatgag ggatatatat aacttccact    300
gttttcagaa ttattgtatg cagtcagtat gagaatgcaa tttaagtttc cttgatgctt    360
```

-continued

```
tttcacactt ctattactag aaataagaat acagtaatat tggcaaagaa aattgaccag    420
ttcaataaaa ttttttagta aatctgattg aaaataaaca ttgcttatgg ctttcttaca    480
tcaatattgt tatgtcctag acaccttatc tgaaattacg gcttcaaaat tctaattatg    540
tgcaaatgtg taaaatatca atactttatg ttcaagctgg ggcctcttca ggcgtcctgg    600
gctgagagag aaagatgcta gctccgcaag ccggagaggg aacaccgcca cattgttaca    660
cggacacacc gccacgtgga cacatgacca gactcacatg tacagacaca cggagacatt    720
accacatgga gacaccgtca cacagtcaca cggacacact ggcatagtca catggacgga    780
cacacagaca tatggagaaa tcacatggac acaccaccac actatcacag ggacacagac    840
acacggagac atcaccacat ggacacactg tcacactacc acagggacac gagacatcac    900
actgtcacat ggacacacca tcacacacat gaacacaccg acacactgcc atatggacac    960
tggcacacac actgccacac tgtcacatgg acacacctcc acaccatcac accaccacac   1020
acactgcctg tggacacaag gacacacaga cactgtcaca cagatacaca aaacactgtc   1080
acacggagac atcaccatgc agatacacca ccactctggt gccgtctgaa ttaccctgct   1140
ggggggacag cagtggcata ctcatgccta agtgactggc tttcacccca gtagtgattg   1200
ccctccatca acactgccca ccccaggttg gggctacccc agcccatctt tacaaaacag   1260
ggcaaggtga actaatggag tgggtggagg agttggaaga aatcccagcg tcagtcaccg   1320
ggatagaatt cccaaggaac cctctttttg gaggatggtt tccatttctg gaggcgatct   1380
gccgacaggg tgaatgcctt cttgcttgtc ttctggggaa tcagagagag tccgttttgt   1440
ggtgggaaga gtgtggctgt gtactttgaa ctcctgtaaa ttctctgact catgtccaca   1500
aaaccaacag ttttgtgaat gtgtctggag gcaagggaag ggccactcag gatctatgtt   1560
gaagggaaga ggcctggggc tggagtattc gctt                               1594
```

<210> SEQ ID NO 475
<211> LENGTH: 2414
<212> TYPE: DNA
<213> ORGANISM: Homo sapiens
<220> FEATURE:
<221> NAME/KEY: unsure
<222> LOCATION: (33)
<223> OTHER INFORMATION: n=A,T,C or G

<400> SEQUENCE: 475

```
cccaacacaa tggctttata agaatgcttc acntgtgaaa aacaaatatc aaagtcttct     60
tgtagattat ttttaaggac aaatctttat tccatgttta atttatttag ctttccctgt    120
agctaatatt tcatgctgaa cacattttaa atgctgtaaa tgtagataat gtaatttatg    180
tatcattaat gcctctttag tagtttagag aaaacgtcaa aagaaatggc cccagaataa    240
gcttcttgat ttgtaaaatt ctatgtcatt ggctcaaatt tgtatagtat ctcaaaatat    300
aaatatatag acatctcaga taatatattt gaaatagcaa attcctgtta gaaaataata    360
gtacttaact agatgagaat aacaggtcgc cattatttga attgtctcct attcgttttt    420
catttgttgt gttactcatg ttttacttat gggggggatat atataacttc cgctgttttc    480
agaagtattg tatgcagtca gtatgagaat gcaatttaag tttccttgat gctttttcac    540
acttctatta ctagaaataa gaatacagta atattggcaa agaaaattga ccagttcaat    600
aaaatttttt agtaaatctg attgaaaata aacattgctt atggctttct tacatcaata    660
ttgttatgtc ctagacacct tatctgaaat tacggcttca aaattctaat tatgtgcaaa    720
tgtgtaaaat atcaatactt tatgttcaag ctggggcctc ttcaggcgtc ctgggctgag    780
```

-continued

```
agagaaagat gctagctccg caagccgggg agggaacacc gccacattgt tacatggaca    840
caccgccacg tggacacatg accagactca catgtacaga cacacggaga cattaccaca    900
tggagacacc gtcacacagt cacacgagca cactggcata gtcacatgga cggacacaca    960
gacatatgga gaaatcacac tgacacacca ccacactatc acagggacac agacacacgg   1020
agacatcacc acatggacac actgtcacac taccacaggg acacgagaca tcacactgtc   1080
acatggacac accatcacac acatgaacac accgacacac tgccatatgg acactgccac   1140
acacactgcc acactgtcac atggacacac ctccatacca tcacaccacc acacacactg   1200
ccatgtggac acaaggacac acagacactg tcacacagat acacaaaaca ctgtcacacg   1260
gagacatcac catgcagata caccaccaca tggacatagc accagacact ctgccacaca   1320
gatacaccac cacacagaaa tgcggacaca ctgccacaca gacaccacca catcgttgcc   1380
acactttcat gtgtcagctg gcggtgtggg ccccacgact ctgggctcta atcgagaaat   1440
tacttggaca tatagtgaag gcaaaatttt tttttatttt ctgggtaacc aagcgcgact   1500
ctgtctcaaa aaaagaaaaa aaaagcaata tactgtgtaa tcgttgacag cataattcac   1560
tattatgtag atcggagagc agaggattct gaatgcatga acatatcatt aacatttcaa   1620
tacattactc ataattactg atgaactaaa gagaaaccaa gaaattatgg tgatagttat   1680
attgacctgg agaaatgtag acacaaaaga accgtaagat gagaaatgtg ttaacacagt   1740
ctataagggc atgcaagaat aaaaataggg gagaaaacag gagagttttt caagagcttt   1800
ctggtcatgt aagtcaactt gtatcggtta atttttaaaa ggtttattta catgcaataa   1860
actgcacata cttcaattgt acattttggt aattcttggc atttgtagct ctataaaacc   1920
agcaacatat taaaatagca aacatatcca ttacctttac caccaaagtt ttcttgtgtt   1980
ttttctactc actttttcct gcctatcccc ccatctcttc cacaggtaac cactgatcca   2040
cttccagtca ctatccatga gtttttattt ccaaatacat gaaatcatat gaatttctgg   2100
tttttcctgt tggagcccaa ggagcaaggg cagaatgagg aacatgatgt ttcttwccga   2160
cagttactca tgacgtctcc atccaggact gagggggggca tccttctcca tctaggactg   2220
ggggcatcct tctccatcca gtattggggg tcatccttct ccatccagta ttgggggtca   2280
tcctcctcca tccaggacct gaggggtgtc cttttctgcg cttccttgga tggcagtctt   2340
tcccttcatg tttatagtra cttaccatta aatcactgtg ccgttttttc ctaaaataaa   2400
aaaaaaaaaa aaaa                                                     2414
```

<210> SEQ ID NO 476
<211> LENGTH: 3434
<212> TYPE: DNA
<213> ORGANISM: Homo sapiens

<400> SEQUENCE: 476

```
ctgtgctgca aatggggcca tatagaggaa aggagcagct ggctctggag catggtgtgc     60
actccctttg ggccttcagt ccatgtctca tgggtcgtat gacactgcgg gcttgttggt    120
tgccaagagg cagaccacag gtcatcttga ggaggacttt atgttccagt ccagaaagca    180
gccagtggta ccacccaggg gacttgtgct tctgtggccc aggccagacg tagaatttga    240
caaagtcagg acggtctcag tcagagcagc atgtcggtcc ccggggcctg tgcatgccgg    300
gcagggccag gctggcttaa ggagcaagca gccacctctg ttaggggtgt gcctggagca    360
ggtggagcag ccaccaacct cacgcactga aagaagcagg gatggccagg ttccaacatc    420
```

-continued

```
ctgagtggct gccacctgat ggctgatgga gcagaggcct gaggaaaagc agatggcact    480
gctttgtagt gctgttcttt gtctctcttg atctttttca gttaatgtct gttttatcag    540
agactaggat tgcaaaccct gctctttttt gctttccatt tgcttggtaa atattcctcc    600
atccctttat tttaagccta tgtgtgtctt tgcacatgag atgggtctcc tgaatacagg    660
acaacaatgg gtctttactc tttatccaac ttgccagtct gtgtctttta actggggcat    720
ttagcccatt tacatttaag tttagtattt gttacatgtg aaatttatcc tgtcatgatg    780
ttgctagctt tttatttttc ccattagttt gcagtttctt tatagtgtca atggtcttta    840
caattcgata tgtttttgta gtggctggta ctggtttttc ctttctacgt ttagtgtctc    900
cttcaggagc tcttgtaaca caagaatgtg gatttatttc ttgtaaggta aatatgtgga    960
tttattctgg gactgtattc tatggccttt accccaagaa tcattacttt ttaaaatgca   1020
attcaaatta gcataaaaca tttacagcct atggaaaggc ttgtggcatt agaatcctta   1080
tttataggat tattttgtgt tttttttgaga tatggtcttt gtcatcgagg cagaagtgcc  1140
gtggtttgat cataattcac cacagccctg aactcttgag tccaagccat ccttttgcct   1200
taatctccca accagttgga tctacaagca taaggcatca tgcgtggcta attttttcac   1260
gttttttttt tttttgtcga gattatggta tcactgtgtt gctctggctg atctcaaatg   1320
tttgacctca agggatcttt ctgccacagc ctcctaaagt gctaggatta tatgcatgat   1380
acaccatgcc tattgtagag tattacatta ttttcaaagt cttattgtaa gagccattta   1440
ttgcctttgg cctaaataac tcaatataat atctctgaaa cttttttttg acaaattttg   1500
gggcgtgatg atgagagaag ggggtttgaa actttctaat aagagttaac ttagagccat   1560
ttaagaaagg aaaaaacaca aattatcaga aaaacaacag taagatcaag tgcaaaagtt   1620
ctgtggcaaa gatgatgaga gtaaagaata tatgtttgtg actcatggtg gcttttactt   1680
tgttcttgaa tttctgagta cgggttaaca tttaaagaat ctacattata gataacattt   1740
tattgcaagt aaatgtattt caaaatttgt tattggtttt gtatgagatt attctcagcc   1800
tacttcatta tcaagctata ttattttatt aatgtagttc gatgatctta cagcaaagct   1860
gaaagctgta tcttcaaaat atgtctattt gactaaaaag ttattcaaca ggagttatta   1920
tctataaaaa aatacaacag gaatataaaa aacttgagga taaaaagatg ttggaaaaag   1980
taatattaaa tcttaaaaaa catatggaaa ctacacaatg gtgaagacac attggtgaag   2040
tacaaaaata taaattggat ctagaagaaa gggcaatgca ggcaatagaa aaattagtag   2100
aaatcccttt aaaggttagt ttgtaaaatc aggtaagttt atttataatt tgctttcatt   2160
tatttcactg caaattatat tttggatatg tatatatatt gtgcttcctc tgcctgtctt   2220
acagcaattt gccttgcaga gttctaggaa aaaggtggca tgtgtttttta ctttcaaaat  2280
atttaaattt ccatcattat aacaaaatca atttttcaga gtaatgattc tcactgtgga   2340
gtcatttgat tattaagacc cgttggcata agattacatc ctctgactat aaaaatcctg   2400
gaagaaaacc taggaaatat tcgtctggac attgcacttg gcaatgaatt tatgggcgct   2460
ttggaatcct gcagatataa taatgataat taaacaaaac actcagagaa actgccaacc   2520
ctaggatgaa gtatattgtt actgtgcttt gggattaaaa taagtaacta cagtttatag   2580
aacttttata ctgatacaca gacactaaaa agggaaaggg tttagatgag aagctctgct   2640
atgcaatcaa gaatctcagc cactcatttc tgtaggggct gcaggagctc cctgtaaaga   2700
gaggttatgg agtctgtagc ttcaggtaag atacttaaaa cccttcagag tttctccatt   2760
ttttcccata gtttccccaa aaaggttatg acactttata agaatgcttc acttgtgaaa   2820
```

-continued

```
aacaaatatc aaagtcttct tgtagattat ttttaaggac aaatctttat tccatgttta   2880

atttatttag ctttccctgt agctaatatt tcatgctgaa cacattttaa atgctgtaaa   2940

tgtagataat gtaatttatg tatcattaat gcctctttag tagtttagag aaaacgtcaa   3000

aagaaatggc cccagaataa gcttcttgat ttgtaaaatt ctatgtcatt ggctcaaatt   3060

tgtatagtat ctcaaaatat aaatatatag acatctcaga taatatattt gaaatagcaa   3120

attcctgtta gaaaataata gtacttaact agatgagaat aacaggtcgc cattatttga   3180

attgtctcct attcgttttt catttgttgt gttactcatg ttttacttat gggggggatat   3240

atataacttc cgctgttttc agaagtattg tatgcagtca gtatgagaat gcaatttaag   3300

tttccttgat gctttttcac acttctatta ctagaaataa gaatacagta atattggcaa   3360

agaaaattga ccagttcaat aaaatttttt agtaaatctg attgaaaata aaaaaaaaaa   3420

aaaaaaaaaa aaaa                                                     3434
```

<210> SEQ ID NO 477
<211> LENGTH: 140
<212> TYPE: PRT
<213> ORGANISM: Homo sapiens

<400> SEQUENCE: 477

```
Met Asp Gly His Thr Asp Ile Trp Arg Asn His Met Asp Thr Pro Pro
                5                   10                  15

His Tyr His Arg Asp Thr Asp Thr Arg Arg His His His Met Asp Thr
            20                  25                  30

Leu Ser His Tyr His Arg Asp Thr Arg His His Thr Val Thr Trp Thr
        35                  40                  45

His His His Thr His Glu His Thr Asp Thr Leu Pro Tyr Gly His Trp
    50                  55                  60

His Thr His Cys His Thr Val Thr Trp Thr His Leu His Thr Ile Thr
65                  70                  75                  80

Pro Pro His Thr Leu Pro Val Asp Thr Arg Thr His Arg His Cys His
                85                  90                  95

Thr Asp Thr Gln Asn Thr Val Thr Arg Arg His His His Ala Asp Thr
            100                 105                 110

Pro Pro Leu Trp Cys Arg Leu Asn Tyr Pro Ala Gly Gly Thr Ala Val
        115                 120                 125

Ala Tyr Ser Cys Leu Ser Asp Trp Leu Ser Pro Gln
    130                 135                 140
```

<210> SEQ ID NO 478
<211> LENGTH: 143
<212> TYPE: PRT
<213> ORGANISM: Homo sapiens

<400> SEQUENCE: 478

```
Met Tyr Arg His Thr Glu Thr Leu Pro His Gly Asp Thr Val Thr Gln
                5                   10                  15

Ser His Gly His Thr Gly Ile Val Thr Trp Thr Asp Thr Gln Thr Tyr
            20                  25                  30

Gly Glu Ile Thr Trp Thr His His His Thr Ile Thr Gly Thr Gln Thr
        35                  40                  45

His Gly Asp Ile Thr Thr Trp Thr His Cys His Thr Thr Thr Gly Thr
    50                  55                  60

Arg Asp Ile Thr Leu Ser His Gly His Thr Ile Thr His Met Asn Thr
```

-continued

```
 65                  70                  75                  80

Pro Thr His Cys His Met Asp Thr Gly Thr His Thr Ala Thr Leu Ser
                 85                  90                  95

His Gly His Thr Ser Thr Pro Ser His His His Thr His Cys Leu Trp
            100                 105                 110

Thr Gln Gly His Thr Asp Thr Val Thr Gln Ile His Lys Thr Leu Ser
        115                 120                 125

His Gly Asp Ile Thr Met Gln Ile His His His Ser Gly Ala Val
    130                 135                 140


<210> SEQ ID NO 479
<211> LENGTH: 222
<212> TYPE: PRT
<213> ORGANISM: Homo sapiens

<400> SEQUENCE: 479

Met Tyr Arg His Thr Glu Thr Leu Pro His Gly Asp Thr Val Thr Gln
                  5                  10                  15

Ser His Glu His Thr Gly Ile Val Thr Trp Thr Asp Thr Gln Thr Tyr
             20                  25                  30

Gly Glu Ile Thr Leu Thr His His His Thr Ile Thr Gly Thr Gln Thr
         35                  40                  45

His Gly Asp Ile Thr Thr Trp Thr His Cys His Thr Thr Thr Gly Thr
     50                  55                  60

Arg Asp Ile Thr Leu Ser His Gly His Thr Ile Thr His Met Asn Thr
 65                  70                  75                  80

Pro Thr His Cys His Met Asp Thr Ala Thr His Thr Ala Thr Leu Ser
                 85                  90                  95

His Gly His Thr Ser Ile Pro Ser His His His Thr His Cys His Val
            100                 105                 110

Asp Thr Arg Thr His Arg His Cys His Thr Asp Thr Gln Asn Thr Val
        115                 120                 125

Thr Arg Arg His His His Ala Asp Thr Pro Pro His Gly His Ser Thr
    130                 135                 140

Arg His Ser Ala Thr Gln Ile His His His Thr Glu Met Arg Thr His
145                 150                 155                 160

Cys His Thr Asp Thr Thr Thr Ser Leu Pro His Phe His Val Ser Ala
                165                 170                 175

Gly Gly Val Gly Pro Thr Thr Leu Gly Ser Asn Arg Glu Ile Thr Trp
            180                 185                 190

Thr Tyr Ser Glu Gly Lys Ile Phe Phe Tyr Phe Leu Gly Asn Gln Ala
        195                 200                 205

Arg Leu Cys Leu Lys Lys Arg Lys Lys Lys Gln Tyr Thr Val
    210                 215                 220


<210> SEQ ID NO 480
<211> LENGTH: 144
<212> TYPE: PRT
<213> ORGANISM: Homo sapiens

<400> SEQUENCE: 480

Met Glu Pro Tyr Arg Gly Asn Glu Gln Pro Ser Gln Glu Gln Gly Val
                  5                  10                  15

Cys Cys Leu Trp Gly Leu Gln Ser Leu Pro Gln Gly Ser Tyr Val Thr
             20                  25                  30

Val Gly Phe Leu Val Val Lys Arg Gln Thr Ile Gly Arg Leu Glu Arg
```

-continued

```
        35                  40                  45

Asp Phe Met Phe Lys Cys Arg Lys Gln Pro Gly Leu Pro Pro Ser Gly
     50                  55                  60

Leu Cys Leu Leu Trp Pro Trp Pro Asn Leu Glu Phe Gly Arg Arg Gln
 65                  70                  75                  80

Asp Arg Leu Thr Trp Ser Ser Val Ser Val Ala Gly Val Cys Ala Cys
                 85                  90                  95

Arg Ala Arg Pro Gly Trp Leu Gly Glu Gln Pro Ala Thr Ser Ala Gly
            100                 105                 110

Val Arg Leu Glu Gln Val Glu Gln Pro Pro Ala His Pro Leu Gln Glu
        115                 120                 125

Ala Gly Val Ala Arg Phe Pro Arg Pro Glu Trp Val Pro Pro Asn Gly
    130                 135                 140


<210> SEQ ID NO 481
<211> LENGTH: 167
<212> TYPE: PRT
<213> ORGANISM: Homo sapiens

<400> SEQUENCE: 481

Met His Gly Pro Gln Val Leu Ala Arg Cys Ser Glu Cys Ala Cys Pro
                  5                  10                  15

Ala Leu Ala Ala Thr Ser Ala Gly Val Arg Leu Glu Gly Val Asp Arg
             20                  25                  30

Pro Pro Thr Leu Pro Ser Gln Gly Ser Gly Trp Pro Cys Ser His Ser
        35                  40                  45

Leu Ser Gly Cys His Leu Met Ala Asp Gly Ala Lys Ala Leu Gly Lys
     50                  55                  60

Ala Asp Gly Pro Trp Pro Tyr Leu Phe Val Arg Arg Thr Asp Val Pro
 65                  70                  75                  80

Cys Pro Ala Ala Ser Glu Val Gly Gly Cys Ala Pro Ser Ser Trp Arg
                 85                  90                  95

Ala Leu Ala Glu Val Thr Gly Cys Ser Leu Gly Pro Leu Gly Leu Ala
            100                 105                 110

Gln His Ala Gln Ala Ser Val Leu Leu Leu Cys Tyr Lys Trp Ser His
        115                 120                 125

Ile Gly Glu Thr Ser Ser His Leu Arg Ser Lys Val Tyr Ala Ala Phe
    130                 135                 140

Gly Gly Ser Ser Pro Cys Leu Lys Gly Leu Met Ser Leu Trp Ala Ser
145                 150                 155                 160

Trp Leu Ser Arg Gly Arg Pro
                165


<210> SEQ ID NO 482
<211> LENGTH: 143
<212> TYPE: PRT
<213> ORGANISM: Homo sapiens

<400> SEQUENCE: 482

Met Glu Pro Tyr Arg Gly Asn Lys Lys Gln Val Gln Glu Lys Gly Val
                  5                  10                  15

Pro Cys Leu Trp Gly Ser Ser Pro Cys Leu Arg Cys His Met Ala Leu
             20                  25                  30

Arg Ala Ser Trp Leu Pro Gly Gly Gly Pro Gln Ala Ile Leu Gly Arg
        35                  40                  45

Thr Leu Cys Ser Ser Ala Glu Ser Ser Gln Asp Cys His Pro Gly Gly
```

-continued

```
     50                  55                  60

Pro Ser Ile Ala Leu Ala Lys Pro Cys Arg Gly Val Trp Leu Leu Phe
 65                  70                  75                  80

Glu Pro Ala Trp Pro Pro Trp His Ala Arg Ala Pro Gly Ala Gly Thr
                 85                  90                  95

Leu Leu Arg Val Cys Leu Ser Cys Leu Gly Cys His Leu Cys Gly Gly
            100                 105                 110

Ala Ser Gly Gly Gly Gly Pro Ala Thr Asn Leu Thr Gln Ser Arg Lys
        115                 120                 125

Trp Met Ala Met Phe Pro Gln Pro Glu Trp Leu Pro Pro Asp Gly
    130                 135                 140


<210> SEQ ID NO 483
<211> LENGTH: 143
<212> TYPE: PRT
<213> ORGANISM: Homo sapiens

<400> SEQUENCE: 483

Met Glu Thr Gln Arg Gly Asn Lys Gln Arg Ala Gln Glu Gln Gly Val
                  5                  10                  15

Cys Cys Leu Trp Gly Ser Ser Pro Cys Leu Gly Ser Tyr Gly Thr Ala
             20                  25                  30

Gly Phe Leu Val Ala Lys Arg Arg Thr Thr Gly Leu Leu Glu Glu Asp
         35                  40                  45

Phe Thr Phe Lys Cys Arg Lys Gln Pro Lys Leu Pro Ser Met Arg Leu
     50                  55                  60

Ser Leu Leu Trp Pro Trp Arg Asp Leu Lys Phe Val Pro Arg Gln Asp
 65                  70                  75                  80

Lys Leu Thr Arg Ser Ser Val Ser Val Ala Gly Ala Tyr Ala Cys Arg
                 85                  90                  95

Ala Gly Pro Gly Trp Leu Lys Glu Gln Pro Ala Thr Ser Ala Arg Val
            100                 105                 110

Arg Leu Val Gln Ala Glu His Pro Pro Pro His Pro Leu Glu Glu Val
        115                 120                 125

Gly Met Ala Arg Phe Pro Gln Pro Glu Cys Leu Pro Pro Tyr Cys
    130                 135                 140


<210> SEQ ID NO 484
<211> LENGTH: 30
<212> TYPE: PRT
<213> ORGANISM: Homo Sapien

<400> SEQUENCE: 484

Thr Ala Ala Ser Asp Asn Phe Gln Leu Ser Gln Gly Gly Gln Gly Phe
 1               5                  10                  15

Ala Ile Pro Ile Gly Gln Ala Met Ala Ile Ala Gly Gln Ile
            20                  25                  30


<210> SEQ ID NO 485
<211> LENGTH: 31
<212> TYPE: DNA
<213> ORGANISM: Artificial Sequence
<220> FEATURE:
<223> OTHER INFORMATION: Made in a lab

<400> SEQUENCE: 485

gggaagctta tcacctatgt gccgcctctg c                                 31
```

-continued

<210> SEQ ID NO 486
<211> LENGTH: 27
<212> TYPE: DNA
<213> ORGANISM: Artificial Sequence
<220> FEATURE:
<223> OTHER INFORMATION: Made in a lab

<400> SEQUENCE: 486
gcgaattctc acgctgagta tttggcc 27

<210> SEQ ID NO 487
<211> LENGTH: 36
<212> TYPE: DNA
<213> ORGANISM: Artificial Sequence
<220> FEATURE:
<223> OTHER INFORMATION: Made in a lab

<400> SEQUENCE: 487
cccgaattct tagctgccca tccgaacgcc ttcatc 36

<210> SEQ ID NO 488
<211> LENGTH: 33
<212> TYPE: DNA
<213> ORGANISM: Artificial Sequence
<220> FEATURE:
<223> OTHER INFORMATION: Made in a lab

<400> SEQUENCE: 488
gggaagcttc ttccccggct gcaccagctg tgc 33

<210> SEQ ID NO 489
<211> LENGTH: 19
<212> TYPE: PRT
<213> ORGANISM: Artificial Sequence
<220> FEATURE:
<223> OTHER INFORMATION: Made in a lab

<400> SEQUENCE: 489

Met Asp Arg Leu Val Gln Arg Phe Gly Thr Arg Ala Val Tyr Leu Ala
1 5 10 15

Ser Val Ala

<210> SEQ ID NO 490
<211> LENGTH: 20
<212> TYPE: PRT
<213> ORGANISM: Artificial Sequence
<220> FEATURE:
<223> OTHER INFORMATION: Made in a lab

<400> SEQUENCE: 490

Tyr Leu Ala Ser Val Ala Ala Phe Pro Val Ala Ala Gly Ala Thr Cys
1 5 10 15

Leu Ser His Ser
20

<210> SEQ ID NO 491
<211> LENGTH: 20
<212> TYPE: PRT
<213> ORGANISM: Artificial Sequence
<220> FEATURE:
<223> OTHER INFORMATION: Made in a lab

<400> SEQUENCE: 491

Thr Cys Leu Ser His Ser Val Ala Val Val Thr Ala Ser Ala Ala Leu
1 5 10 15

-continued

Thr Gly Phe Thr
20

<210> SEQ ID NO 492
<211> LENGTH: 20
<212> TYPE: PRT
<213> ORGANISM: Artificial Sequence
<220> FEATURE:
<223> OTHER INFORMATION: Made in a lab

<400> SEQUENCE: 492

Ala Leu Thr Gly Phe Thr Phe Ser Ala Leu Gln Ile Leu Pro Tyr Thr
1 5 10 15

Leu Ala Ser Leu
20

<210> SEQ ID NO 493
<211> LENGTH: 20
<212> TYPE: PRT
<213> ORGANISM: Artificial Sequence
<220> FEATURE:
<223> OTHER INFORMATION: Made in a lab

<400> SEQUENCE: 493

Tyr Thr Leu Ala Ser Leu Tyr His Arg Glu Lys Gln Val Phe Leu Pro
1 5 10 15

Lys Tyr Arg Gly
20

<210> SEQ ID NO 494
<211> LENGTH: 20
<212> TYPE: PRT
<213> ORGANISM: Artificial Sequence
<220> FEATURE:
<223> OTHER INFORMATION: Made in a lab

<400> SEQUENCE: 494

Leu Pro Lys Tyr Arg Gly Asp Thr Gly Gly Ala Ser Ser Glu Asp Ser
1 5 10 15

Leu Met Ile Ser
20

<210> SEQ ID NO 495
<211> LENGTH: 20
<212> TYPE: PRT
<213> ORGANISM: Artificial Sequence
<220> FEATURE:
<223> OTHER INFORMATION: Made in a lab

<400> SEQUENCE: 495

Asp Ser Leu Met Thr Ser Phe Leu Pro Gly Pro Lys Pro Gly Ala Pro
1 5 10 15

Phe Pro Asn Gly
20

<210> SEQ ID NO 496
<211> LENGTH: 21
<212> TYPE: PRT
<213> ORGANISM: Artificial Sequence
<220> FEATURE:
<223> OTHER INFORMATION: Made in a lab

<400> SEQUENCE: 496

Ala Pro Phe Pro Asn Gly His Val Gly Ala Gly Gly Ser Gly Leu Leu
1 5 10 15

-continued

Pro Pro Pro Pro Ala
20

<210> SEQ ID NO 497
<211> LENGTH: 20
<212> TYPE: PRT
<213> ORGANISM: Artificial Sequence
<220> FEATURE:
<223> OTHER INFORMATION: Made in a lab

<400> SEQUENCE: 497

Leu Leu Pro Pro Pro Pro Ala Leu Cys Gly Ala Ser Ala Cys Asp Val
1 5 10 15

Ser Val Arg Val
20

<210> SEQ ID NO 498
<211> LENGTH: 20
<212> TYPE: PRT
<213> ORGANISM: Artificial Sequence
<220> FEATURE:
<223> OTHER INFORMATION: Made in a lab

<400> SEQUENCE: 498

Asp Val Ser Val Arg Val Val Val Gly Glu Pro Thr Glu Ala Arg Val
1 5 10 15

Val Pro Gly Arg
20

<210> SEQ ID NO 499
<211> LENGTH: 20
<212> TYPE: PRT
<213> ORGANISM: Artificial Sequence
<220> FEATURE:
<223> OTHER INFORMATION: Made in a lab

<400> SEQUENCE: 499

Arg Val Val Pro Gly Arg Gly Ile Cys Leu Asp Leu Ala Ile Leu Asp
1 5 10 15

Ser Ala Phe Leu
20

<210> SEQ ID NO 500
<211> LENGTH: 20
<212> TYPE: PRT
<213> ORGANISM: Artificial Sequence
<220> FEATURE:
<223> OTHER INFORMATION: Made in a lab

<400> SEQUENCE: 500

Leu Asp Ser Ala Phe Leu Leu Ser Gln Val Ala Pro Ser Leu Phe Met
1 5 10 15

Gly Ser Ile Val
20

<210> SEQ ID NO 501
<211> LENGTH: 20
<212> TYPE: PRT
<213> ORGANISM: Artificial Sequence
<220> FEATURE:
<223> OTHER INFORMATION: Made in a lab

<400> SEQUENCE: 501

Phe Met Gly Ser Ile Val Gln Leu Ser Gln Ser Val Thr Ala Tyr Met

-continued

```
 1               5                  10                  15

Val Ser Ala Ala
            20


<210> SEQ ID NO 502
<211> LENGTH: 414
<212> TYPE: DNA
<213> ORGANISM: Homo Sapien
<220> FEATURE:
<221> NAME/KEY: misc_feature
<222> LOCATION: (1)...(414)
<223> OTHER INFORMATION: n = A,T,C or G

<400> SEQUENCE: 502

caccatggag acaggcctgc gctggctttt cctggtcgct gtgctcaaag gtgtccaatg      60

tcagtcggtg gaggagtccg gggtcgcct ggtcacgcct gggacacctt tgacantcac      120

ctgtagagtt tttggaatng acctcagtag caatgcaatg agctgggtcc gccaggctcc      180

agggaagggg ctggaatgga tcggagccat tgataattgt ccacantacg cgacctgggc      240

gaaaggccga ttnatnattt ccaaaacctn gaccacggtg gatttgaaaa tgaccagtcc      300

gacaaccgag gacacggcca cctatttttg tggcagaatg aatactggta atagtggttg      360

gaagaatatt tggggcccag gcaccctggt caccgtntcc tcagggcaac ctaa            414


<210> SEQ ID NO 503
<211> LENGTH: 379
<212> TYPE: DNA
<213> ORGANISM: Homo Sapiens
<220> FEATURE:
<221> NAME/KEY: misc_feature
<222> LOCATION: (1)...(379)
<223> OTHER INFORMATION: n = A,T,C or G

<400> SEQUENCE: 503

atncgatggt gcttggtcaa aggtgtccag tgtcagtcgg tggaggagtc cgggggtcgc      60

ctggtcacgc ctgggacacc cctgacactc acctgcaccg tntctggatt ngacatcagt     120

agctatggag tgagctgggt ccgccaggct ccagggaagg ggctggnata catcggatca     180

ttagtagtag tggtacattt tacgcgagct gggcgaaagg ccgattcacc atttccaaaa     240

cctngaccac ggtggatttg aaaatcacca gtttgacaac cgaggacacg gccacctatt     300

tntgtgccag agggggggttt aattataaag acatttgggg cccaggcacc ctggtcaccg     360

tntccttagg gcaacctaa                                                  379


<210> SEQ ID NO 504
<211> LENGTH: 19
<212> TYPE: PRT
<213> ORGANISM: Artificial Sequence
<220> FEATURE:
<223> OTHER INFORMATION: Made in a lab

<400> SEQUENCE: 504

Gly Phe Thr Asn Tyr Thr Asp Phe Glu Asp Ser Pro Tyr Phe Lys Glu
 1               5                  10                  15

Asn Ser Ala


<210> SEQ ID NO 505
<211> LENGTH: 20
<212> TYPE: PRT
<213> ORGANISM: Artificial Sequence
<220> FEATURE:
<223> OTHER INFORMATION: Made in a lab
```

-continued

<400> SEQUENCE: 505

Lys Glu Asn Ser Ala Phe Pro Pro Phe Cys Cys Asn Asp Asn Val Thr
1 5 10 15

Asn Thr Ala Asn
20

<210> SEQ ID NO 506
<211> LENGTH: 407
<212> TYPE: DNA
<213> ORGANISM: Homo Sapien

<400> SEQUENCE: 506
atggagacag gcctgcgctg gcttctcctg gtcgctgcgc tcaaaggtgt ccagtgtcag 60
tcgctggagg agtccggggg tcgcctggtc acgcctggga cacccctgac actcacctgc 120
accgtctctg gattctccct cagtagcaat gcaatgatct gggtccgcca ggctccaggg 180
aaggggctgg aatacatcgg atacattagt tatggtggta gcgcatacta cgcgagctgg 240
gtgaaaggcc gattcaccat ctccaaaacc tcgaccacgg tggatctgag aatgaccagt 300
ctgacaaccg aggacacggc cacctatttc tgtgccagaa atagtgattt tagtggtatg 360
ttgtggggcc caggcaccct ggtcaccgtc tcctcagggc aacctaa 407

<210> SEQ ID NO 507
<211> LENGTH: 422
<212> TYPE: DNA
<213> ORGANISM: Homo Sapien

<400> SEQUENCE: 507
atggagacag gcctgcgctg gcttctcctg gtcgctgtgc tcaaaggtgt ccagtgtcag 60
tcggtggagg agtccggggg tcgcctggtc acgcctggga cacccctgac actcacctgt 120
acagtctctg gattctccct cagcaactac gacctgaact gggtccgcca ggctccaggg 180
aaggggctgg aatggatcgg gatcattaat tatgttggta ggacggacta cgcgaactgg 240
gcaaaaggcc ggttcaccat ctccaaaacc tcgaccaccg tggatctcaa gatcgccagt 300
ccgacaaccg aggacacggc cacctatttc tgtgccagag ggtggaagtg cgatgagtct 360
ggtccgtgct tgcgcatctg ggcccaggc accctggtca ccgtctcctt agggcaacct 420
aa 422

<210> SEQ ID NO 508
<211> LENGTH: 411
<212> TYPE: DNA
<213> ORGANISM: Homo Sapiens
<220> FEATURE:
<221> NAME/KEY: misc_feature
<222> LOCATION: (1)...(411)
<223> OTHER INFORMATION: n = A,T,C or G

<400> SEQUENCE: 508
atggagacag gcctcgctgg cttctcctgg tcgctgtgct caaaggtgtc cagtgtcagt 60
cggtggagga gtccgggggt cgcctggtca cgcctgggac acccctgaca ctcacctgca 120
cagtctctgg aatcgacctc agtagctact gcatgagctg ggtccgccag gctccaggga 180
aggggctgga atggatcgga atcattggta ctcctggtga cacatactac gcgaggtggg 240
cgaaaggccg attcaccatc tccaaaacct cgaccacggt gcatntgaaa atcnccagtc 300
cgacaaccga ggacacggcc acctatttct gtgccagaga tcttcgggat ggtagtagta 360

-continued ctggttatta taaaatctgg ggcccaggca ccctggtcac cgtctccttg g 411

<210> SEQ ID NO 509
<211> LENGTH: 15
<212> TYPE: PRT
<213> ORGANISM: Artificial Sequence
<220> FEATURE:
<223> OTHER INFORMATION: Made in a lab

<400> SEQUENCE: 509

Leu Cys Lys Phe Thr Glu Trp Ile Glu Lys Thr Val Gln Ala Ser
1 5 10 15

<210> SEQ ID NO 510
<211> LENGTH: 15
<212> TYPE: PRT
<213> ORGANISM: Artificial Sequence
<220> FEATURE:
<223> OTHER INFORMATION: Made in a lab

<400> SEQUENCE: 510

Pro Glu Tyr Asn Arg Pro Leu Leu Ala Asn Asp Leu Met Leu Ile
1 5 10 15

<210> SEQ ID NO 511
<211> LENGTH: 15
<212> TYPE: PRT
<213> ORGANISM: Artificial Sequence
<220> FEATURE:
<223> OTHER INFORMATION: Made in a lab

<400> SEQUENCE: 511

Tyr His Pro Ser Met Phe Cys Ala Gly Gly Gly Gln Asp Gln Lys
1 5 10 15

<210> SEQ ID NO 512
<211> LENGTH: 15
<212> TYPE: PRT
<213> ORGANISM: Artificial Sequence
<220> FEATURE:
<223> OTHER INFORMATION: Made in a lab

<400> SEQUENCE: 512

Asp Ser Gly Gly Pro Leu Ile Cys Asn Gly Tyr Leu Gln Gly Leu
1 5 10 15

<210> SEQ ID NO 513
<211> LENGTH: 15
<212> TYPE: PRT
<213> ORGANISM: Artificial Sequence
<220> FEATURE:
<223> OTHER INFORMATION: Made in a lab

<400> SEQUENCE: 513

Ala Pro Cys Gly Gln Val Gly Val Pro Asx Val Tyr Thr Asn Leu
1 5 10 15

<210> SEQ ID NO 514
<211> LENGTH: 15
<212> TYPE: PRT
<213> ORGANISM: Artificial Sequence
<220> FEATURE:
<223> OTHER INFORMATION: Made in a lab

<400> SEQUENCE: 514

Leu Cys Lys Phe Thr Glu Trp Ile Glu Lys Thr Val Gln Ala Ser
1 5 10 15

<210> SEQ ID NO 515
<211> LENGTH: 15
<212> TYPE: PRT
<213> ORGANISM: Artificial Sequence
<220> FEATURE:
<223> OTHER INFORMATION: Made in a lab

<400> SEQUENCE: 515

Met Val Glu Ala Ser Leu Ser Val Arg His Pro Glu Tyr Asn Arg
1 5 10 15

<210> SEQ ID NO 516
<211> LENGTH: 15
<212> TYPE: PRT
<213> ORGANISM: Artificial Sequence
<220> FEATURE:
<223> OTHER INFORMATION: Made in a lab

<400> SEQUENCE: 516

Val Ser Glu Ser Asp Thr Ile Arg Ser Ile Ser Ile Ala Ser Gln
1 5 10 15

<210> SEQ ID NO 517
<211> LENGTH: 15
<212> TYPE: PRT
<213> ORGANISM: Artificial Sequence
<220> FEATURE:
<223> OTHER INFORMATION: Made in a lab

<400> SEQUENCE: 517

Glu Val Cys Ser Lys Leu Tyr Asp Pro Leu Tyr His Pro Ser Met
1 5 10 15

<210> SEQ ID NO 518
<211> LENGTH: 15
<212> TYPE: PRT
<213> ORGANISM: Artificial Sequence
<220> FEATURE:
<223> OTHER INFORMATION: Made in a lab

<400> SEQUENCE: 518

Arg Ala Glu Pro Gly Thr Glu Ala Arg Arg His Tyr Asp Glu Gly
1 5 10 15

<210> SEQ ID NO 519
<211> LENGTH: 17
<212> TYPE: PRT
<213> ORGANISM: Artificial Sequence
<220> FEATURE:
<223> OTHER INFORMATION: Made in a lab

<400> SEQUENCE: 519

Arg Ala Glu Pro Gly Thr Glu Ala Arg Arg Asn Tyr Asp Glu Gly Cys
1 5 10 15

Gly

<210> SEQ ID NO 520
<211> LENGTH: 25
<212> TYPE: PRT
<213> ORGANISM: Artificial Sequence
<220> FEATURE:
<223> OTHER INFORMATION: Made in a lab

<400> SEQUENCE: 520

Val Gly Glu Gly Leu Tyr Gln Gly Val Pro Arg Ala Glu Pro Gly Thr

-continued

```
 1               5                  10                  15

Glu Ala Arg Arg His Tyr Asp Glu Gly
            20                  25


<210> SEQ ID NO 521
<211> LENGTH: 21
<212> TYPE: PRT
<213> ORGANISM: Artificial Sequence
<220> FEATURE:
<223> OTHER INFORMATION: Made in a lab

<400> SEQUENCE: 521

Ala Pro Phe Pro Asn Gly His Val Gly Ala Gly Gly Ser Gly Leu Leu
 1               5                  10                  15

Pro Pro Pro Pro Ala
            20


<210> SEQ ID NO 522
<211> LENGTH: 20
<212> TYPE: PRT
<213> ORGANISM: Artificial Sequence
<220> FEATURE:
<223> OTHER INFORMATION: Made in a lab

<400> SEQUENCE: 522

Leu Leu Val Val Pro Ala Ile Lys Lys Asp Tyr Gly Ser Gln Glu Asp
 1               5                  10                  15

Phe Thr Gln Val
            20


<210> SEQ ID NO 523
<211> LENGTH: 254
<212> TYPE: PRT
<213> ORGANISM: Artificial Sequence
<220> FEATURE:
<223> OTHER INFORMATION: Made in a lab
<220> FEATURE:
<221> NAME/KEY: VARIANT
<222> LOCATION: (1)...(254)
<223> OTHER INFORMATION: Xaa = any amino acid

<400> SEQUENCE: 523

Met Ala Thr Ala Gly Asn Pro Trp Gly Trp Phe Leu Gly Tyr Leu Ile
 1               5                  10                  15

Leu Gly Val Ala Gly Ser Leu Val Ser Gly Ser Cys Ser Gln Ile Ile
            20                  25                  30

Asn Gly Glu Asp Cys Ser Pro His Ser Gln Pro Trp Gln Ala Ala Leu
        35                  40                  45

Val Met Glu Asn Glu Leu Phe Cys Ser Gly Val Leu Val His Pro Gln
    50                  55                  60

Trp Val Leu Ser Ala Thr His Cys Phe Gln Asn Ser Tyr Thr Ile Gly
65                  70                  75                  80

Leu Gly Leu His Ser Leu Glu Ala Asp Gln Glu Pro Gly Ser Gln Met
                85                  90                  95

Val Glu Ala Ser Leu Ser Val Arg His Pro Glu Tyr Asn Arg Pro Leu
            100                 105                 110

Leu Ala Asn Asp Leu Met Leu Ile Lys Leu Asp Glu Ser Val Ser Glu
        115                 120                 125

Ser Asp Thr Ile Arg Ser Ile Ser Ile Ala Ser Gln Cys Pro Thr Ala
    130                 135                 140

Gly Asn Ser Cys Leu Val Ser Gly Trp Gly Leu Leu Ala Asn Gly Arg
```

-continued

```
145                 150                 155                 160

Met Pro Thr Val Leu Gln Cys Val Asn Val Ser Val Val Ser Glu Glu
                165                 170                 175

Val Cys Ser Lys Leu Tyr Asp Pro Leu Tyr His Pro Ser Met Phe Cys
            180                 185                 190

Ala Gly Gly Gly Gln Xaa Gln Xaa Asp Ser Cys Asn Gly Asp Ser Gly
        195                 200                 205

Gly Pro Leu Ile Cys Asn Gly Tyr Leu Gln Gly Leu Val Ser Phe Gly
    210                 215                 220

Lys Ala Pro Cys Gly Gln Val Gly Val Pro Gly Val Tyr Thr Asn Leu
225                 230                 235                 240

Cys Lys Phe Thr Glu Trp Ile Glu Lys Thr Val Gln Ala Ser
                245                 250
```

<210> SEQ ID NO 524
<211> LENGTH: 765
<212> TYPE: DNA
<213> ORGANISM: Homo sapien

<400> SEQUENCE: 524

```
atggccacag caggaaatcc ctggggctgg ttcctggggt acctcatcct tggtgtcgca      60

ggatcgctcg tctctggtag ctgcagccaa atcataaacg gcgaggactg cagcccgcac     120

tcgcagccct ggcaggcggc actggtcatg gaaaacgaat tgttctgctc gggcgtcctg     180

gtgcatccgc agtgggtgct gtcagccgca cactgtttcc agaactccta caccatcggg     240

ctgggcctgc acagtcttga ggccgaccaa gagccaggga gccagatggt ggaggccagc     300

ctctccgtac ggcacccaga gtacaacaga cccttgctcg ctaacgacct catgctcatc     360

aagttggacg aatccgtgtc cgagtctgac accatccgga gcatcagcat tgcttcgcag     420

tgccctaccg cggggaactc ttgcctcgtt tctggctggg gtctgctggc gaacggcaga     480

atgcctaccg tgctgcagtg cgtgaacgtg tcggtggtgt ctgaggaggt ctgcagtaag     540

ctctatgacc cgctgtacca ccccagcatg ttctgcgccg gcggagggca agaccagaag     600

gactcctgca acggtgactc tggggggccc ctgatctgca acgggtactt gcagggcctt     660

gtgtctttcg gaaaagcccc gtgtggccaa gttggcgtgc caggtgtcta caccaacctc     720

tgcaaattca ctgagtggat agagaaaacc gtccaggcca gttaa                     765
```

<210> SEQ ID NO 525
<211> LENGTH: 254
<212> TYPE: PRT
<213> ORGANISM: Homo sapien

<400> SEQUENCE: 525

```
Met Ala Thr Ala Gly Asn Pro Trp Gly Trp Phe Leu Gly Tyr Leu Ile
 1               5                  10                  15

Leu Gly Val Ala Gly Ser Leu Val Ser Gly Ser Cys Ser Gln Ile Ile
            20                  25                  30

Asn Gly Glu Asp Cys Ser Pro His Ser Gln Pro Trp Gln Ala Ala Leu
        35                  40                  45

Val Met Glu Asn Glu Leu Phe Cys Ser Gly Val Leu Val His Pro Gln
    50                  55                  60

Trp Val Leu Ser Ala Ala His Cys Phe Gln Asn Ser Tyr Thr Ile Gly
65                  70                  75                  80

Leu Gly Leu His Ser Leu Glu Ala Asp Gln Glu Pro Gly Ser Gln Met
                85                  90                  95
```

-continued

```
Val Glu Ala Ser Leu Ser Val Arg His Pro Glu Tyr Asn Arg Pro Leu
            100                 105                 110

Leu Ala Asn Asp Leu Met Leu Ile Lys Leu Asp Glu Ser Val Ser Glu
        115                 120                 125

Ser Asp Thr Ile Arg Ser Ile Ser Ile Ala Ser Gln Cys Pro Thr Ala
    130                 135                 140

Gly Asn Ser Cys Leu Val Ser Gly Trp Gly Leu Leu Ala Asn Gly Arg
145                 150                 155                 160

Met Pro Thr Val Leu Gln Cys Val Asn Val Ser Val Val Ser Glu Glu
                165                 170                 175

Val Cys Ser Lys Leu Tyr Asp Pro Leu Tyr His Pro Ser Met Phe Cys
            180                 185                 190

Ala Gly Gly Gly Gln Asp Gln Lys Asp Ser Cys Asn Gly Asp Ser Gly
        195                 200                 205

Gly Pro Leu Ile Cys Asn Gly Tyr Leu Gln Gly Leu Val Ser Phe Gly
    210                 215                 220

Lys Ala Pro Cys Gly Gln Val Gly Val Pro Gly Val Tyr Thr Asn Leu
225                 230                 235                 240

Cys Lys Phe Thr Glu Trp Ile Glu Lys Thr Val Gln Ala Ser
                245                 250
```

<210> SEQ ID NO 526
<211> LENGTH: 963
<212> TYPE: DNA
<213> ORGANISM: Homo sapiens

<400> SEQUENCE: 526

```
atgagttcct gcaacttcac acatgccacc tttgtgctta ttggtatccc aggattagag      60

aaagcccatt tctgggttgg cttccccctc ctttccatgt atgtagtggc aatgtttgga     120

aactgcatcg tggtcttcat cgtaaggacg gaacgcagcc tgcacgctcc gatgtacctc     180

tttctctgca tgcttgcagc cattgacctg gccttatcca catccaccat gcctaagatc     240

cttgcccttt tctggtttga ttcccgagag attagctttg aggcctgtct tacccagatg     300

ttctttattc atgccctctc agccattgaa tccaccatcc tgctggccat ggcctttgac     360

cgttatgtgg ccatctgcca cccactgcgc catgctgcag tgctcaacaa tacagtaaca     420

gcccagattg gcatcgtggc tgtggtccgc ggatccctct ttttttcccc actgcctctg     480

ctgatcaagc ggctggcctt ctgccactcc aatgtcctct cgcactccta ttgtgtccac     540

caggatgtaa tgaagttggc ctatgcagac actttgccca atgtggtata tggtcttact     600

gccattctgc tggtcatggg cgtggacgta atgttcatct ccttgtccta ttttctgata     660

atacgaacgg ttctgcaact gccttccaag tcagagcggg ccaaggcctt tggaacctgt     720

gtgtcacaca ttggtgtggt actcgccttc tatgtgccac ttattggcct ctcagttgta     780

caccgctttg gaaacagcct tcatcccatt gtgcgtgttg tcatgggtga catctacctg     840

ctgctgcctc ctgtcatcaa tcccatcatc tatggtgcca aaaccaaaca gatcagaaca     900

cgggtgctgg ctatgttcaa gatcagctgt gacaaggact tgcaggctgt gggaggcaag     960

tga                                                                   963
```

<210> SEQ ID NO 527
<211> LENGTH: 320
<212> TYPE: PRT
<213> ORGANISM: Homo sapiens -continued

<400> SEQUENCE: 527

Met Ser Ser Cys Asn Phe Thr His Ala Thr Phe Val Leu Ile Gly Ile
5 10 15

Pro Gly Leu Glu Lys Ala His Phe Trp Val Gly Phe Pro Leu Leu Ser
20 25 30

Met Tyr Val Val Ala Met Phe Gly Asn Cys Ile Val Val Phe Ile Val
35 40 45

Arg Thr Glu Arg Ser Leu His Ala Pro Met Tyr Leu Phe Leu Cys Met
50 55 60

Leu Ala Ala Ile Asp Leu Ala Leu Ser Thr Ser Thr Met Pro Lys Ile
65 70 75 80

Leu Ala Leu Phe Trp Phe Asp Ser Arg Glu Ile Ser Phe Glu Ala Cys
85 90 95

Leu Thr Gln Met Phe Phe Ile His Ala Leu Ser Ala Ile Glu Ser Thr
100 105 110

Ile Leu Leu Ala Met Ala Phe Asp Arg Tyr Val Ala Ile Cys His Pro
115 120 125

Leu Arg His Ala Ala Val Leu Asn Asn Thr Val Thr Ala Gln Ile Gly
130 135 140

Ile Val Ala Val Val Arg Gly Ser Leu Phe Phe Phe Pro Leu Pro Leu
145 150 155 160

Leu Ile Lys Arg Leu Ala Phe Cys His Ser Asn Val Leu Ser His Ser
165 170 175

Tyr Cys Val His Gln Asp Val Met Lys Leu Ala Tyr Ala Asp Thr Leu
180 185 190

Pro Asn Val Val Tyr Gly Leu Thr Ala Ile Leu Leu Val Met Gly Val
195 200 205

Asp Val Met Phe Ile Ser Leu Ser Tyr Phe Leu Ile Ile Arg Thr Val
210 215 220

Leu Gln Leu Pro Ser Lys Ser Glu Arg Ala Lys Ala Phe Gly Thr Cys
225 230 235 240

Val Ser His Ile Gly Val Val Leu Ala Phe Tyr Val Pro Leu Ile Gly
245 250 255

Leu Ser Val Val His Arg Phe Gly Asn Ser Leu His Pro Ile Val Arg
260 265 270

Val Val Met Gly Asp Ile Tyr Leu Leu Leu Pro Pro Val Ile Asn Pro
275 280 285

Ile Ile Tyr Gly Ala Lys Thr Lys Gln Ile Arg Thr Arg Val Leu Ala
290 295 300

Met Phe Lys Ile Ser Cys Asp Lys Asp Leu Gln Ala Val Gly Gly Lys
305 310 315 320

<210> SEQ ID NO 528
<211> LENGTH: 20
<212> TYPE: DNA
<213> ORGANISM: Homo Sapien

<400> SEQUENCE: 528
actatggtcc agaggctgtg 20

<210> SEQ ID NO 529
<211> LENGTH: 20
<212> TYPE: DNA
<213> ORGANISM: Homo Sapien

<400> SEQUENCE: 529

-continued

```
atcacctatg tgccgcctct                                              20
```

<210> SEQ ID NO 530
<211> LENGTH: 1852
<212> TYPE: DNA
<213> ORGANISM: Homo sapiens

<400> SEQUENCE: 530

```
ggcacgagaa ttaaaaccct cagcaaaaca ggcatagaag ggacatacct taaagtaata     60
aaaaccacct atgacaagcc cacagccaac ataatactaa atggggaaaa gttagaagca    120
tttcctctga gaactgcaac aataaataca aggatgctgg attttgtcaa atgccttttc    180
tgtgtctgtt gagatgctta tgtgactttg cttttaattc tgtttatgtg attatcacat    240
ttattgactt gcctgtgtta gaccggaaga gctggggtgt ttctcaggag ccaccgtgtg    300
ctgcggcagc ttcgggataa cttgaggctg catcactggg gaagaaacac aytcctgtcc    360
gtggcgctga tggctgagga cagagcttca gtgtggcttc tctgcgactg gcttcttcgg    420
ggagttcttc cttcatagtt catccatatg gctccagagg aaaattatat tattttgtta    480
tggatgaaga gtattacgtt gtgcagatat actgcagtgt cttcatctct tgatgtgtga    540
ttgggtaggt tccaccatgt tgccgcagat gacatgattt cagtacctgt gtctggctga    600
aaagtgtttg tttgtgaatg gatattgtgg tttctggatc tcatcctctg tgggtggaca    660
gctttctcca ccttgctgga agtgacctgc tgtccagaag tttgatggct gaggagtata    720
ccatcgtgca tgcatctttc atttcctgca tttcttcctc cctggatgga caggggggagc    780
ggcaagagca acgtgggcac ttctggagac cacaacgact cctctgtgaa gacgcttggg    840
agcaagaggt gcaagtggtg ctgccactgc ttcccctgct gcagggggag cggcaagagc    900
aacgtggtcg cttggggaga ctacgatgac agcgccttca tggatcccag gtaccacgtc    960
catggagaag atctggacaa gctccacaga gctgcctggt ggggtaaagt ccccagaaag   1020
gatctcatcg tcatgctcag ggacacggat gtgaacaaga gggacaagca aaagaggact   1080
gctctacatc tggcctctgc caatgggaat tcagaagtag taaaactcgt gctggacaga   1140
cgatgtcaac ttaatgtcct tgacaacaaa aagaggacag ctctgacaaa ggccgtacaa   1200
tgccaggaag atgaatgtgc gttaatgttg ctggaacatg gcactgatcc aaatattcca   1260
gatgagtatg gaaataccac tctacactat gctgtctaca atgaagataa attaatggcc   1320
aaagcactgc tcttatacgg tgctgatatc gaatcaaaaa acaagcatgg cctcacacca   1380
ctgctacttg gtatacatga gcaaaaacag caagtggtga aatttttaat caagaaaaaa   1440
gcgaatttaa atgcgctgga tagatatgga agaactgctc tcatacttgc tgtatgttgt   1500
ggatcagcaa gtatagtcag ccctctactt gagcaaaatg ttgatgtatc ttctcaagat   1560
ctggaaagac ggccagagag tatgctgttt ctagtcatca tcatgtaatt tgccagttac   1620
tttctgacta caaagaaaaa cagatgttaa aaatctcttc tgaaaacagc aatccagaac   1680
aagacttaaa gctgacatca gaggaagagt cacaaaggct taaaggaagt gaaaacagcc   1740
agccagagct agaagattta tggctattga agaagaatga agaacacgga agtactcatg   1800
tgggattccc agaaaacctg actaacggtg ccgctgctgg caatggtgat ga           1852
```

<210> SEQ ID NO 531
<211> LENGTH: 879
<212> TYPE: DNA
<213> ORGANISM: Homo sapiens -continued

<400> SEQUENCE: 531

```
atgcatcttt catttcctgc atttcttcct ccctggatgg acagggggag cggcaagagc     60
aacgtgggca cttctggaga ccacaacgac tcctctgtga agacgcttgg gagcaagagg    120
tgcaagtggt gctgccactg cttcccctgc tgcaggggga gcggcaagag caacgtggtc    180
gcttggggag actacgatga cagcgccttc atggatccca ggtaccacgt ccatggagaa    240
gatctggaca agctccacag agctgcctgg tggggtaaag tccccagaaa ggatctcatc    300
gtcatgctca gggacacgga tgtgaacaag agggacaagc aaaagaggac tgctctacat    360
ctggcctctg ccaatgggaa ttcagaagta gtaaaactcg tgctggacag acgatgtcaa    420
cttaatgtcc ttgacaacaa aaagaggaca gctctgacaa aggccgtaca atgccaggaa    480
gatgaatgtg cgttaatgtt gctggaacat ggcactgatc caaatattcc agatgagtat    540
ggaaatacca ctctacacta tgctgtctac aatgaagata aattaatggc caaagcactg    600
ctcttatacg gtgctgatat cgaatcaaaa aacaagcatg gcctcacacc actgctactt    660
ggtatacatg agcaaaaaca gcaagtggtg aaatttttaa tcaagaaaaa agcgaattta    720
aatgcgctgg atagatatgg aagaactgct ctcatacttg ctgtatgttg tggatcagca    780
agtatagtca gccctctact tgagcaaaat gttgatgtat cttctcaaga tctggaaaga    840
cggccagaga gtatgctgtt tctagtcatc atcatgtaa                           879
```

<210> SEQ ID NO 532
<211> LENGTH: 292
<212> TYPE: PRT
<213> ORGANISM: Homo sapiens

<400> SEQUENCE: 532

```
Met His Leu Ser Phe Pro Ala Phe Leu Pro Pro Trp Met Asp Arg Gly
                5                   10                  15

Ser Gly Lys Ser Asn Val Gly Thr Ser Gly Asp His Asn Asp Ser Ser
            20                  25                  30

Val Lys Thr Leu Gly Ser Lys Arg Cys Lys Trp Cys Cys His Cys Phe
        35                  40                  45

Pro Cys Cys Arg Gly Ser Gly Lys Ser Asn Val Val Ala Trp Gly Asp
    50                  55                  60

Tyr Asp Asp Ser Ala Phe Met Asp Pro Arg Tyr His Val His Gly Glu
65                  70                  75                  80

Asp Leu Asp Lys Leu His Arg Ala Ala Trp Trp Gly Lys Val Pro Arg
                85                  90                  95

Lys Asp Leu Ile Val Met Leu Arg Asp Thr Asp Val Asn Lys Arg Asp
            100                 105                 110

Lys Gln Lys Arg Thr Ala Leu His Leu Ala Ser Ala Asn Gly Asn Ser
        115                 120                 125

Glu Val Val Lys Leu Val Leu Asp Arg Arg Cys Gln Leu Asn Val Leu
    130                 135                 140

Asp Asn Lys Lys Arg Thr Ala Leu Thr Lys Ala Val Gln Cys Gln Glu
145                 150                 155                 160

Asp Glu Cys Ala Leu Met Leu Leu Glu His Gly Thr Asp Pro Asn Ile
                165                 170                 175

Pro Asp Glu Tyr Gly Asn Thr Thr Leu His Tyr Ala Val Tyr Asn Glu
            180                 185                 190

Asp Lys Leu Met Ala Lys Ala Leu Leu Leu Tyr Gly Ala Asp Ile Glu
        195                 200                 205
```

-continued

```
Ser Lys Asn Lys His Gly Leu Thr Pro Leu Leu Leu Gly Ile His Glu
    210                 215                 220

Gln Lys Gln Gln Val Val Lys Phe Leu Ile Lys Lys Lys Ala Asn Leu
225                 230                 235                 240

Asn Ala Leu Asp Arg Tyr Gly Arg Thr Ala Leu Ile Leu Ala Val Cys
                245                 250                 255

Cys Gly Ser Ala Ser Ile Val Ser Pro Leu Leu Glu Gln Asn Val Asp
            260                 265                 270

Val Ser Ser Gln Asp Leu Glu Arg Arg Pro Glu Ser Met Leu Phe Leu
        275                 280                 285

Val Ile Ile Met
    290


<210> SEQ ID NO 533
<211> LENGTH: 801
<212> TYPE: DNA
<213> ORGANISM: Homo sapiens

<400> SEQUENCE: 533

atgtacaagc ttcagtgcaa caactgtgct acaaatggag ccacagagag gaaacaagca      60

gcaggctcag gagcagggta tgcgctgcct tcggctctcc aatccatgcc tcagggctcc     120

tatgccactg cacgattctt ggttgccaag aggccaacca caggccatct tgagaaggag     180

tttatgttcc actgcagaaa gcagccagga tcaccatcca ggggacttgg tcttctgtgg     240

ccctggccag acatagaatt tgtgccaagg caggacaagc tcactcagag cagcgtgtta     300

gtacctcaaa tctgtgcgtg ccagacaagg ccaaactggc tcaatgagca accagccacc     360

tctgcagggg tgcgtctgga ggaggtggac cagccaccaa ccttacccag tcaaggaagt     420

ggatggccat gttcccacag cctgagtggc tgccacctga tggctgatat agcaaaggcc     480

ttaggaaaag cagatggccc ttggccctac ctttttgtta gaagaactga tgttccatgt     540

cctgcagcga gtgaggttgg tggctgtgcc cccagctcct ggcacaccct cgcagaggtg     600

actggttgct ctttgagccc tcttagcctt gcccagcatg cacaagcctc agtgctacta     660

ctgtgctaca aatggagcca tataggggaa acgagcagcc atctcaggag caaggtgtat     720

gctgcctttg ggggctccag tccttgcctc aagggtctta tgtcactgtg ggcttcttgg     780

ttgccaagag gcagaccata g                                                801


<210> SEQ ID NO 534
<211> LENGTH: 266
<212> TYPE: PRT
<213> ORGANISM: Homo sapiens

<400> SEQUENCE: 534

Met Tyr Lys Leu Gln Cys Asn Asn Cys Ala Thr Asn Gly Ala Thr Glu
                  5                  10                  15

Arg Lys Gln Ala Ala Gly Ser Gly Ala Gly Tyr Ala Leu Pro Ser Ala
            20                  25                  30

Leu Gln Ser Met Pro Gln Gly Ser Tyr Ala Thr Ala Arg Phe Leu Val
        35                  40                  45

Ala Lys Arg Pro Thr Thr Gly His Leu Glu Lys Glu Phe Met Phe His
     50                  55                  60

Cys Arg Lys Gln Pro Gly Ser Pro Ser Arg Gly Leu Gly Leu Leu Trp
 65                  70                  75                  80

Pro Trp Pro Asp Ile Glu Phe Val Pro Arg Gln Asp Lys Leu Thr Gln
                 85                  90                  95
```

-continued

```
Ser Ser Val Leu Val Pro Gln Ile Cys Ala Cys Gln Thr Arg Pro Asn
            100                 105                 110

Trp Leu Asn Glu Gln Pro Ala Thr Ser Ala Gly Val Arg Leu Glu Glu
        115                 120                 125

Val Asp Gln Pro Pro Thr Leu Pro Ser Gln Gly Ser Gly Trp Pro Cys
    130                 135                 140

Ser His Ser Leu Ser Gly Cys His Leu Met Ala Asp Ile Ala Lys Ala
145                 150                 155                 160

Leu Gly Lys Ala Asp Gly Pro Trp Pro Tyr Leu Phe Val Arg Arg Thr
                165                 170                 175

Asp Val Pro Cys Pro Ala Ala Ser Glu Val Gly Gly Cys Ala Pro Ser
            180                 185                 190

Ser Trp His Thr Leu Ala Glu Val Thr Gly Cys Ser Leu Ser Pro Leu
        195                 200                 205

Ser Leu Ala Gln His Ala Gln Ala Ser Val Leu Leu Leu Cys Tyr Lys
    210                 215                 220

Trp Ser His Ile Gly Glu Thr Ser Ser His Leu Arg Ser Lys Val Tyr
225                 230                 235                 240

Ala Ala Phe Gly Gly Ser Ser Pro Cys Leu Lys Gly Leu Met Ser Leu
                245                 250                 255

Trp Ala Ser Trp Leu Pro Arg Gly Arg Pro
            260                 265
```

<210> SEQ ID NO 535
<211> LENGTH: 6082
<212> TYPE: DNA
<213> ORGANISM: Homo sapiens

<400> SEQUENCE: 535

```
cctccactat tacagcttat aggaaattac aatccacttt acaggcctca aaggttcatt     60

ctggccgagc ggacaggcgt ggcggccgga gccccagcat ccctgcttga ggtccaggag    120

cggagcccgc ggccactgcc gcctgatcag cgcgaccccg gcccgcgccc gccccgcccg    180

gcaagatgct gcccgtgtac caggaggtga agcccaaccc gctgcaggac gcgaacctct    240

gctcacgcgt gttcttctgg tggctcaatc ccttgtttaa aattggccat aaacggagat    300

tagaggaaga tgatatgtat tcagtgctgc cagaagaccg ctcacagcac cttggagagg    360

agttgcaagg gttctgggat aaagaagttt taagagctga gaatgacgca cagaagcctt    420

ctttaacaag agcaatcata aagtgttact ggaaatctta tttagttttg ggaattttta    480

cgttaattga ggaaagtgcc aaagtaatcc agcccatatt tttgggaaaa attattaatt    540

attttgaaaa ttatgatccc atggattctg tggctttgaa cacagcgtac gcctatgcca    600

cggtgctgac tttttgcacg ctcattttgg ctatactgca tcacttatat ttttatcacg    660

ttcagtgtgc tgggatgagg ttacgagtag ccatgtgcca tatgatttat cggaaggcac    720

ttcgtcttag taacatggcc atggggaaga caaccacagg ccagatagtc aatctgctgt    780

ccaatgatgt gaacaagttt gatcaggtga cagtgttctt acacttcctg tgggcaggac    840

cactgcaggc gatcgcagtg actgccctac tctggatgga gataggaata tcgtgccttg    900

ctgggatggc agttctaatc attctcctgc ccttgcaaag ctgttttggg aagttgttct    960

catcactgag gagtaaaact gcaactttca cggatgccag gatcaggacc atgaatgaag   1020

ttataactgg tataaggata ataaaaatgt acgcctggga aaagtcattt tcaaatctta   1080

ttaccaattt gagaaagaag gagatttcca agattctgag aagttcctgc ctcaggggga   1140
```

-continued

```
tgaatttggc ttcgtttttc agtgcaagca aaatcatcgt gtttgtgacc ttcaccacct   1200
acgtgctcct cggcagtgtg atcacagcca gccgcgtgtt cgtggcagtg acgctgtatg   1260
gggctgtgcg gctgacggtt accctcttct tcccctcagc cattgagagg gtgtcagagg   1320
caatcgtcag catccgaaga atccagacct tttgctact tgatgagata tcacagcgca    1380
accgtcagct gccgtcagat ggtaaaaaga tggtgcatgt gcaggatttt actgcttttt   1440
gggataaggc atcagagacc ccaactctac aaggcctttc ctttactgtc agacctggcg   1500
aattgttagc tgtggtcggc cccgtgggag cagggaagtc atcactgtta agtgccgtgc   1560
tcggggaatt ggccccaagt cacgggctgg tcagcgtgca tggaagaatt gcctatgtgt   1620
ctcagcagcc ctgggtgttc tcgggaactc tgaggagtaa tattttattt gggaagaaat   1680
acgaaaagga acgatatgaa aaagtcataa aggcttgtgc tctgaaaaag gatttacagc   1740
tgttggagga tggtgatctg actgtgatag gagatcgggg aaccacgctg agtggagggc   1800
agaaagcacg ggtaaacctt gcaagagcag tgtatcaaga tgctgacatc tatctcctgg   1860
acgatcctct cagtgcagta gatgcggaag ttagcagaca cttgttcgaa ctgtgtattt   1920
gtcaaatttt gcatgagaag atcacaattt tagtgactca tcagttgcag tacctcaaag   1980
ctgcaagtca gattctgata ttgaaagatg gtaaaatggt gcagaagggg acttacactg   2040
agttcctaaa atctggtata gattttggct cccttttaaa gaaggataat gaggaaagtg   2100
aacaacctcc agttccagga actcccacac taaggaatcg taccttctca gagtcttcgg   2160
tttggtctca acaatcttct agaccctcct tgaaagatgg tgctctggag agccaagata   2220
cagagaatgt cccagttaca ctatcagagg agaaccgttc tgaaggaaaa gttggttttc   2280
aggcctataa gaattacttc agagctggtg ctcactggat tgtcttcatt ttccttattc   2340
tcctaaacac tgcagctcag gttgcctatg tgcttcaaga ttggtggctt tcatactggg   2400
caaacaaaca aagtatgcta aatgtcactg taaatggagg aggaaatgta accgagaagc   2460
tagatcttaa ctggtactta ggaatttatt caggtttaac tgtagctacc gttctttttg   2520
gcatagcaag atctctattg gtattctacg tccttgttaa ctcttcacaa actttgcaca   2580
acaaaatgtt tgagtcaatt ctgaaagctc cggtattatt ctttgataga aatccaatag   2640
gaagaatttt aaatcgtttc tccaaagaca ttggacactt ggatgatttg ctgccgctga   2700
cgtttttaga tttcatccag acattgctac aagtggttgg tgtggtctct gtggctgtgg   2760
ccgtgattcc ttggatcgca atacccttgg ttccccttgg aatcattttc attttcttc    2820
ggcgatattt tttggaaacg tcaagagatg tgaagcgcct ggaatctaca actcggagtc   2880
cagtgttttc ccacttgtca tcttctctcc aggggctctg gaccatccgg gcatacaaag   2940
cagaagagag gtgtcaggaa ctgtttgatg cacaccagga tttacattca gaggcttggt   3000
tcttgttttt gacaacgtcc cgctggttcg ccgtccgtct ggatgccatc tgtgccatgt   3060
ttgtcatcat cgttgccttt gggtccctga ttctggcaaa aactctggat gccgggcagg   3120
ttggtttggc actgtcctat gccctcacgc tcatggggat gtttcagtgg tgtgttcgac   3180
aaagtgctga agttgagaat atgatgatct cagtagaaag ggtcattgaa tacacagacc   3240
ttgaaaaaga agcaccttgg gaatatcaga aacgcccacc accagcctgg ccccatgaag   3300
gagtgataat ctttgacaat gtgaacttca tgtacagtcc aggtgggcct ctggtactga   3360
agcatctgac agcactcatt aaatcacaag aaaaggttgg cattgtggga agaaccggag   3420
ctggaaaaag ttccctcatc tcagcccttt ttagattgtc agaacccgaa ggtaaaattt   3480
```

-continued ggattgataa gatcttgaca actgaaattg gacttcacga tttaaggaag aaaatgtcaa 3540
tcatacctca ggaacctgtt ttgttcactg gaacaatgag gaaaaacctg gatcccttta 3600
atgagcacac ggatgaggaa ctgtggaatg ccttacaaga ggtacaactt aaagaaacca 3660
ttgaagatct tcctggtaaa atggatactg aattagcaga atcaggatcc aattttagtg 3720
ttggacaaag acaactggtg tgccttgcca gggcaattct caggaaaaat cagatattga 3780
ttattgatga agcgacggca aatgtggatc caagaactga tgagttaata caaaaaaaat 3840
ccgggagaaa tttgcccact gcaccgtgct aaccattgca cacagattga acaccattat 3900
tgacagcgac aagataatgg ttttagattc aggaagactg aaagaatatg atgagccgta 3960
tgttttgctg caaaataaag agagcctatt ttacaagatg gtgcaacaac tgggcaaggc 4020
agaagccgct gccctcactg aaacagcaaa acaggtatac ttcaaaagaa attatccaca 4080
tattggtcac actgaccaca tggttacaaa cacttccaat ggacagccct cgaccttaac 4140
tattttcgag acagcactgt gaatccaacc aaaatgtcaa gtccgttccg aaggcatttg 4200
ccactagttt ttggactatg taaaccacat tgtacttttt tttactttgg caacaaatat 4260
ttatacatac aagatgctag ttcatttgaa tatttctccc aacttatcca aggatctcca 4320
gctctaacaa aatggtttat ttttatttaa atgtcaatag ttgtttttta aaatccaaat 4380
cagaggtgca ggccaccagt taaatgccgt ctatcaggtt ttgtgcctta agagactaca 4440
gagtcaaagc tcatttttaa aggagtagga cagagttgtc acaggttttt gttgttgttt 4500
ttattgcccc caaaattaca tgttaatttc catttatatc agggattcta tttacttgaa 4560
gactgtgaag ttgccatttt gtctcattgt tttctttgac ataactagga tccattattt 4620
cccctgaagg cttcttgtta gaaaatagta cagttacaac caataggaac aacaaaaaga 4680
aaaagtttgt gacattgtag tagggagtgt gtacccctta ctccccatca aaaaaaaaaa 4740
tggatacatg gttaaaggat agaagggcaa tattttatca tatgttctaa aagagaagga 4800
agagaaaata ctactttctc aaaatggaag cccttaaagg tgctttgata ctgaaggaca 4860
caaatgtgac cgtccatcct cctttagagt tgcatgactt ggacacggta actgttgcag 4920
ttttagactc agcattgtga cacttcccaa gaaggccaaa cctctaaccg acattcctga 4980
aatacgtggc attattcttt tttggatttc tcatttatgg aaggctaacc ctctgttgac 5040
tgtaagcctt ttggtttggg ctgtattgaa atcctttcta aattgcatga ataggctctg 5100
ctaacgtgat gagacaaact gaaaattatt gcaagcattg actataatta tgcagtacgt 5160
tctcaggatg catccagggg ttcattttca tgagcctgtc caggttagtt tactcctgac 5220
cactaatagc attgtcattt gggctttctg ttgaatgaat caacaaacca caatacttcc 5280
tgggaccttt tgtactttat ttgaactatg agtctttaat tttcctgat gatggtggct 5340
gtaatatgtt gagttcagtt tactaaaggt tttactatta tggtttgaag tggagtctca 5400
tgacctctca gaataaggtg tcacctccct gaaattgcat atatgtatat agacatgcac 5460
acgtgtgcat ttgtttgtat acatatattt gtccttcgta tagcaagttt tttgctcatc 5520
agcagagagc aacagatgtt ttattgagtg aagccttaaa aagcacacac cacacacagc 5580
taactgccaa aatacattga ccgtagtagc tgttcaactc ctagtactta gaaatacacg 5640
tatggttaat gttcagtcca acaaaccaca cacagtaaat gtttattaat agtcatggtt 5700
cgtattttag gtgactgaaa ttgcaacagt gatcataatg aggtttgtta aaatgatagc 5760
tatattcaaa atgtctatat gtttatttgg acttttgagg ttaaagacag tcatataaac 5820
gtcctgtttc tgttttaatg ttatcataga attttttaat gaaactaaat tcaattgaaa 5880
taaatgatag ttttcatctc caaaaaaaaa aaaaaaaagg gcggccgctc gagtctagag 5940
ggcccgttta aacccgctga tcagcctcga ctgtgccttc tagttgccag ccatctgttg 6000
tttgcccctc ccccgtgcct tccttgaccc tggaaggtgc cactcccact gtcctttcct 6060
aataaaatga ggaaattgca tc 6082

<210> SEQ ID NO 536
<211> LENGTH: 6140
<212> TYPE: DNA
<213> ORGANISM: Homo sapiens
<220> FEATURE:
<221> NAME/KEY: unsure
<222> LOCATION: (4535)
<223> OTHER INFORMATION: n=A,T,C or G

<400> SEQUENCE: 536
cagtggcgca gtctcagctc actgcagcct ccacctcctg tgttcaagca gtcctcctgc 60
ctcagccacc agactagcag gtctccccccg cctctttctt ggaaggacac ttgccattgg 120
atttaggacc cacttggata atccaggatg atgtcttcac tccaacatcc tcagtttaat 180
tccatgtgca aatacccttt tcccaaataa cattcaattc tttaccagga aaggtggctc 240
aatcccttgt ttaaaattgg ccataaacgg agattagagg aagatgatat gtattcagtg 300
ctgccagaag accgctcaca gcaccttgga gaggagttgc aagggttctg ggataaagaa 360
gttttaagag ctgagaatga cgcacagaag ccttctttaa caagagcaat cataaagtgt 420
tactggaaat cttatttagt tttgggaatt tttacgttaa ttgaggaaag tgccaaagta 480
atccagccca tatttttggg aaaaattatt aattattttg aaaattatga tcccatggat 540
tctgtggctt tgaacacagc gtacgcctat gccacggtgc tgactttttg cacgctcatt 600
ttggctatac tgcatcactt atattttat cacgttcagt gtgctgggat gaggttacga 660
gtagccatgt gccatatgat ttatcggaag gcacttcgtc ttagtaacat ggccatgggg 720
aagacaacca caggccagat agtcaatctg ctgtccaatg atgtgaacaa gtttgatcag 780
gtgacagtgt tcttacactt cctgtgggca ggaccactgc aggcgatcgc agtgactgcc 840
ctactctgga tggagatagg aatatcgtgc cttgctggga tggcagttct aatcattctc 900
ctgcccttgc aaagctgttt tgggaagttg ttctcatcac tgaggagtaa aactgcaact 960
ttcacggatg ccaggatcag gaccatgaat gaagttataa ctggtataag gataataaaa 1020
atgtacgcct gggaaaagtc attttcaaat cttattacca atttgagaaa gaaggagatt 1080
tccaagattc tgagaagttc ctgcctcagg gggatgaatt tggcttcgtt tttcagtgca 1140
agcaaaatca tcgtgtttgt gaccttcacc acctacgtgc tcctcggcag tgtgatcaca 1200
gccagccgcg tgttcgtggc agtgacgctg tatggggctg tgcggctgac ggttaccctc 1260
ttcttcccct cagccattga gagggtgtca gaggcaatcg tcagcatccg aagaatccag 1320
acctttttgc tacttgatga gatatcacag cgcaaccgtc agctgccgtc agatggtaaa 1380
aagatggtgc atgtgcagga ttttactgct tttgggata aggcatcaga gaccccaact 1440
ctacaaggcc tttcctttac tgtcagacct ggcgaattgt tagctgtggt cggccccgtg 1500
ggagcaggga agtcatcact gttaagtgcc gtgctcgggg aattggcccc aagtcacggg 1560
ctggtcagcg tgcatggaag aattgcctat gtgtctcagc agccctgggt gttctcggga 1620
actctgagga gtaatatttt atttgggaag aaatacgaaa aggaacgata tgaaaaagtc 1680
ataaaggctt gtgctctgaa aaaggattta cagctgttgg aggatggtga tctgactgtg 1740

-continued

```
ataggagatc ggggaaccac gctgagtgga gggcagaaag cacgggtaaa ccttgcaaga   1800
gcagtgtatc aagatgctga catctatctc ctggacgatc ctctcagtgc agtagatgcg   1860
gaagttagca gacacttgtt cgaactgtgt atttgtcaaa ttttgcatga gaagatcaca   1920
attttagtga ctcatcagtt gcagtacctc aaagctgcaa gtcagattct gatattgaaa   1980
gatggtaaaa tggtgcagaa ggggacttac actgagttcc taaaatctgg tatagatttt   2040
ggctcccttt taaagaagga taatgaggaa agtgaacaac ctccagttcc aggaactccc   2100
acactaagga atcgtacctt ctcagagtct tcggtttggt ctcaacaatc ttctagaccc   2160
tccttgaaag atggtgctct ggagagccaa gatacagaga atgtcccagt tacactatca   2220
gaggagaacc gttctgaagg aaaagttggt tttcaggcct ataagaatta cttcagagct   2280
ggtgctcact ggattgtctt cattttcctt attctcctaa acactgcagc tcaggttgcc   2340
tatgtgcttc aagattggtg gctttcatac tgggcaaaca aacaaagtat gctaaatgtc   2400
actgtaaatg gaggaggaaa tgtaaccgag aagctagatc ttaactggta cttaggaatt   2460
tattcaggtt taactgtagc taccgttctt tttggcatag caagatctct attggtattc   2520
tacgtccttg ttaactcttc acaaactttg cacaacaaaa tgtttgagtc aattctgaaa   2580
gctccggtat tattctttga tagaaatcca ataggaagaa ttttaaatcg tttctccaaa   2640
gacattggac acttggatga tttgctgccg ctgacgtttt tagatttcat ccagacattg   2700
ctacaagtgg ttggtgtggt ctctgtggct gtggccgtga ttccttggat cgcaataccc   2760
ttggttcccc ttggaatcat tttcattttt cttcggcgat attttttgga aacgtcaaga   2820
gatgtgaagc gcctggaatc tacaactcgg agtccagtgt tttcccactt gtcatcttct   2880
ctccaggggc tctggaccat ccgggcatac aaagcagaag agaggtgtca ggaactgttt   2940
gatgcacacc aggatttaca ttcagaggct tggttcttgt ttttgacaac gtcccgctgg   3000
ttcgccgtcc gtctggatgc catctgtgcc atgtttgtca tcatcgttgc ctttgggtcc   3060
ctgattctgg caaaaactct ggatgccggg caggttggtt tggcactgtc ctatgccctc   3120
acgctcatgg ggatgtttca gtggtgtgtt cgacaaagtg ctgaagttga gaatatgatg   3180
atctcagtag aaagggtcat tgaatacaca gaccttgaaa aagaagcacc ttgggaatat   3240
cagaaacgcc caccaccagc ctggccccat gaaggagtga taatctttga caatgtgaac   3300
ttcatgtaca gtccaggtgg gcctctggta ctgaagcatc tgacagcact cattaaatca   3360
caagaaaagg ttggcattgt gggaagaacc ggagctggaa aaagttccct catctcagcc   3420
ctttttagat tgtcagaacc cgaaggtaaa atttggattg ataagatctt gacaactgaa   3480
attggacttc acgatttaag gaagaaaatg tcaatcatac ctcaggaacc tgttttgttc   3540
actggaacaa tgaggaaaaa cctggatccc tttaatgagc acacggatga ggaactgtgg   3600
aatgccttac aagaggtaca acttaaagaa accattgaag atcttcctgg taaaatggat   3660
actgaattag cagaatcagg atccaatttt agtgttggac aaagacaact ggtgtgcctt   3720
gccagggcaa ttctcaggaa aaatcagata ttgattattg atgaagcgac ggcaaatgtg   3780
gatccaagaa ctgatgagtt aatacaaaaa aaaatccggg agaaatttgc ccactgcacc   3840
gtgctaacca ttgcacacag attgaacacc attattgaca gcgacaagat aatggtttta   3900
gattcaggaa gactgaaaga atatgatgag ccgtatgttt tgctgcaaaa taaagagagc   3960
ctattttaca agatggtgca acaactgggc aaggcagaag ccgctgccct cactgaaaca   4020
gcaaaacaga gatggggttt caccatgttg gccaggctgg tctcaaactc ctgacctcaa   4080
gtgatccacc tgccttggcc tcccaaactg ctgagattac aggtgtgagc caccacgccc   4140
```

-continued agcctgagta tacttcaaaa gaaattatcc acatattggt cacactgacc acatggttac 4200
aaacacttcc aatggacagc cctcgacctt aactattttc gagacagcac tgtgaatcca 4260
accaaaatgt caagtccgtt ccgaaggcat ttgccactag tttttggact atgtaaacca 4320
cattgtactt tttttactt tggcaacaaa tatttataca tacaagatgc tagttcattt 4380
gaatatttct cccaacttat ccaaggatct ccagctctaa caaaatggtt tatttttatt 4440
taaatgtcaa tagtkgkttt ttaaaatcca aatcagaggt gcaggccacc agttaaatgc 4500
cgtctatcag gttttgtgcc ttaagagact acagnagtca gaagctcatt tttaaaggag 4560
taggacagag ttgtcacagg tttttgttgg tgtttktatt gcccccaaaa ttacatgtta 4620
atttccattt atatcagggg attctattta cttgaagact gtgaagttgc cattttgtct 4680
cattgttttc tttgacatam ctaggatcca ttatttcccc tgaaggcttc ttgkagaaaa 4740
tagtacagtt acaaccaata ggaactamca aaaagaaaaa gtttgtgaca ttgtagtagg 4800
gagtgtgtac cccttactcc ccatcaaaaa aaaaaatgga tacatggtta aaggatagaa 4860
gggcaatatt ttatcatatg ttctaaaaga gaaggaagag aaaatactac tttctcaaaa 4920
tggaagccct taaaggtgct ttgatactga aggacacaaa tgtgaccgtc catcctcctt 4980
tagagttgca tgacttggac acggtaactg ttgcagtttt agactcagca ttgtgacact 5040
tcccaagaag gccaaacctc taaccgacat tcctgaaata cgtggcatta ttcttttttg 5100
gatttctcat ttaggaaggc taaccctctg ttgamtgtam kccttttggt ttgggctgta 5160
ttgaaatcct ttctaaattg catgaatagg ctctgctaac cgtgatgaga caaactgaaa 5220
attattgcaa gcattgacta taattatgca gtacgttctc aggatgcatc caggggttca 5280
ttttcatgag cctgtccagg ttagtttact cctgaccact aatagcattg tcatttgggc 5340
tttctgttga atgaatcaac aaaccacaat acttcctggg acctttgta ctttatttga 5400 actatgagtc tttaattttt cctgatgatg gtggctgtaa tatgttgagt tcagtttact 5460
aaaggtttta ctattatggt ttgaagggag tctcatgacc tctcagaaaa ggtgcacctc 5520
cctgaaattg catatatgta tatagacatg cacacgtgtg catttgtttg tatacatata 5580
tttgtccttc gtatagcaag ttttttgctc atcagcagag agcaacagat gttttattga 5640
gtgaagcctt aaaaagcaca caccacacac agctaactgc caaaatacat tgaccgtagt 5700
agctgttcaa ctcctagtac ttagaaatac acgtatggtt aatgttcagt ccaacaaacc 5760
acacacagta aatgtttatt aatagtcatg gttcgtattt taggtgactg aaattgcaac 5820
agtgatcata atgaggtttg ttaaaatgat agctatattc aaaatgtcta tatgtttatt 5880
tggacttttg aggttaaaga cagtcatata aacgtcctgt ttctgtttta atgttatcat 5940
agaatttttt aatgaaacta aattcaattg aaataaatga tagttttcat ctccaaaaaa 6000
aaaaaaaaag ggcggcccgc tcgagtctag agggcccggt ttaaacccgc tgatcagcct 6060
cgactgtgcc ttctagttgc cagccatctg ttgtttggcc ctcccccgtg ccttccttga 6120
ccctggaagg ggccactccc 6140

<210> SEQ ID NO 537
<211> LENGTH: 1228
<212> TYPE: PRT
<213> ORGANISM: Homo sapiens

<400> SEQUENCE: 537

Met Leu Pro Val Tyr Gln Glu Val Lys Pro Asn Pro Leu Gln Asp Ala
5 10 15

-continued

```
Asn Leu Cys Ser Arg Val Phe Phe Trp Trp Leu Asn Pro Leu Phe Lys
            20                  25                  30

Ile Gly His Lys Arg Arg Leu Glu Glu Asp Asp Met Tyr Ser Val Leu
        35                  40                  45

Pro Glu Asp Arg Ser Gln His Leu Gly Glu Glu Leu Gln Gly Phe Trp
    50                  55                  60

Asp Lys Glu Val Leu Arg Ala Glu Asn Asp Ala Gln Lys Pro Ser Leu
65                  70                  75                  80

Thr Arg Ala Ile Ile Lys Cys Tyr Trp Lys Ser Tyr Leu Val Leu Gly
                85                  90                  95

Ile Phe Thr Leu Ile Glu Glu Ser Ala Lys Val Ile Gln Pro Ile Phe
            100                 105                 110

Leu Gly Lys Ile Ile Asn Tyr Phe Glu Asn Tyr Asp Pro Met Asp Ser
        115                 120                 125

Val Ala Leu Asn Thr Ala Tyr Ala Tyr Ala Thr Val Leu Thr Phe Cys
    130                 135                 140

Thr Leu Ile Leu Ala Ile Leu His His Leu Tyr Phe Tyr His Val Gln
145                 150                 155                 160

Cys Ala Gly Met Arg Leu Arg Val Ala Met Cys His Met Ile Tyr Arg
                165                 170                 175

Lys Ala Leu Arg Leu Ser Asn Met Ala Met Gly Lys Thr Thr Thr Gly
            180                 185                 190

Gln Ile Val Asn Leu Leu Ser Asn Asp Val Asn Lys Phe Asp Gln Val
        195                 200                 205

Thr Val Phe Leu His Phe Leu Trp Ala Gly Pro Leu Gln Ala Ile Ala
    210                 215                 220

Val Thr Ala Leu Leu Trp Met Glu Ile Gly Ile Ser Cys Leu Ala Gly
225                 230                 235                 240

Met Ala Val Leu Ile Ile Leu Leu Pro Leu Gln Ser Cys Phe Gly Lys
                245                 250                 255

Leu Phe Ser Ser Leu Arg Ser Lys Thr Ala Thr Phe Thr Asp Ala Arg
            260                 265                 270

Ile Arg Thr Met Asn Glu Val Ile Thr Gly Ile Arg Ile Ile Lys Met
        275                 280                 285

Tyr Ala Trp Glu Lys Ser Phe Ser Asn Leu Ile Thr Asn Leu Arg Lys
    290                 295                 300

Lys Glu Ile Ser Lys Ile Leu Arg Ser Ser Cys Leu Arg Gly Met Asn
305                 310                 315                 320

Leu Ala Ser Phe Phe Ser Ala Ser Lys Ile Ile Val Phe Val Thr Phe
                325                 330                 335

Thr Thr Tyr Val Leu Leu Gly Ser Val Ile Thr Ala Ser Arg Val Phe
            340                 345                 350

Val Ala Val Thr Leu Tyr Gly Ala Val Arg Leu Thr Val Thr Leu Phe
        355                 360                 365

Phe Pro Ser Ala Ile Glu Arg Val Ser Glu Ala Ile Val Ser Ile Arg
    370                 375                 380

Arg Ile Gln Thr Phe Leu Leu Leu Asp Glu Ile Ser Gln Arg Asn Arg
385                 390                 395                 400

Gln Leu Pro Ser Asp Gly Lys Lys Met Val His Val Gln Asp Phe Thr
                405                 410                 415

Ala Phe Trp Asp Lys Ala Ser Glu Thr Pro Thr Leu Gln Gly Leu Ser
            420                 425                 430
```

-continued

```
Phe Thr Val Arg Pro Gly Glu Leu Leu Ala Val Val Gly Pro Val Gly
        435                 440                 445

Ala Gly Lys Ser Ser Leu Leu Ser Ala Val Leu Gly Glu Leu Ala Pro
    450                 455                 460

Ser His Gly Leu Val Ser Val His Gly Arg Ile Ala Tyr Val Ser Gln
465                 470                 475                 480

Gln Pro Trp Val Phe Ser Gly Thr Leu Arg Ser Asn Ile Leu Phe Gly
                485                 490                 495

Lys Lys Tyr Glu Lys Glu Arg Tyr Glu Lys Val Ile Lys Ala Cys Ala
            500                 505                 510

Leu Lys Lys Asp Leu Gln Leu Leu Glu Asp Gly Asp Leu Thr Val Ile
        515                 520                 525

Gly Asp Arg Gly Thr Thr Leu Ser Gly Gly Gln Lys Ala Arg Val Asn
    530                 535                 540

Leu Ala Arg Ala Val Tyr Gln Asp Ala Asp Ile Tyr Leu Leu Asp Asp
545                 550                 555                 560

Pro Leu Ser Ala Val Asp Ala Glu Val Ser Arg His Leu Phe Glu Leu
                565                 570                 575

Cys Ile Cys Gln Ile Leu His Glu Lys Ile Thr Ile Leu Val Thr His
            580                 585                 590

Gln Leu Gln Tyr Leu Lys Ala Ala Ser Gln Ile Leu Ile Leu Lys Asp
        595                 600                 605

Gly Lys Met Val Gln Lys Gly Thr Tyr Thr Glu Phe Leu Lys Ser Gly
    610                 615                 620

Ile Asp Phe Gly Ser Leu Leu Lys Lys Asp Asn Glu Glu Ser Glu Gln
625                 630                 635                 640

Pro Pro Val Pro Gly Thr Pro Thr Leu Arg Asn Arg Thr Phe Ser Glu
                645                 650                 655

Ser Ser Val Trp Ser Gln Gln Ser Ser Arg Pro Ser Leu Lys Asp Gly
            660                 665                 670

Ala Leu Glu Ser Gln Asp Thr Glu Asn Val Pro Val Thr Leu Ser Glu
        675                 680                 685

Glu Asn Arg Ser Glu Gly Lys Val Gly Phe Gln Ala Tyr Lys Asn Tyr
    690                 695                 700

Phe Arg Ala Gly Ala His Trp Ile Val Phe Ile Phe Leu Ile Leu Leu
705                 710                 715                 720

Asn Thr Ala Ala Gln Val Ala Tyr Val Leu Gln Asp Trp Trp Leu Ser
                725                 730                 735

Tyr Trp Ala Asn Lys Gln Ser Met Leu Asn Val Thr Val Asn Gly Gly
            740                 745                 750

Gly Asn Val Thr Glu Lys Leu Asp Leu Asn Trp Tyr Leu Gly Ile Tyr
        755                 760                 765

Ser Gly Leu Thr Val Ala Thr Val Leu Phe Gly Ile Ala Arg Ser Leu
    770                 775                 780

Leu Val Phe Tyr Val Leu Val Asn Ser Ser Gln Thr Leu His Asn Lys
785                 790                 795                 800

Met Phe Glu Ser Ile Leu Lys Ala Pro Val Leu Phe Phe Asp Arg Asn
                805                 810                 815

Pro Ile Gly Arg Ile Leu Asn Arg Phe Ser Lys Asp Ile Gly His Leu
            820                 825                 830

Asp Asp Leu Leu Pro Leu Thr Phe Leu Asp Phe Ile Gln Thr Leu Leu
        835                 840                 845

Gln Val Val Gly Val Val Ser Val Ala Val Ala Val Ile Pro Trp Ile
```

-continued

```
    850                 855                 860

Ala Ile Pro Leu Val Pro Leu Gly Ile Ile Phe Ile Phe Leu Arg Arg
865                 870                 875                 880

Tyr Phe Leu Glu Thr Ser Arg Asp Val Lys Arg Leu Glu Ser Thr Thr
                885                 890                 895

Arg Ser Pro Val Phe Ser His Leu Ser Ser Ser Leu Gln Gly Leu Trp
            900                 905                 910

Thr Ile Arg Ala Tyr Lys Ala Glu Glu Arg Cys Gln Glu Leu Phe Asp
        915                 920                 925

Ala His Gln Asp Leu His Ser Glu Ala Trp Phe Leu Phe Leu Thr Thr
    930                 935                 940

Ser Arg Trp Phe Ala Val Arg Leu Asp Ala Ile Cys Ala Met Phe Val
945                 950                 955                 960

Ile Ile Val Ala Phe Gly Ser Leu Ile Leu Ala Lys Thr Leu Asp Ala
                965                 970                 975

Gly Gln Val Gly Leu Ala Leu Ser Tyr Ala Leu Thr Leu Met Gly Met
            980                 985                 990

Phe Gln Trp Cys Val Arg Gln Ser Ala Glu Val Glu Asn Met Met Ile
        995                 1000                1005

Ser Val Glu Arg Val Ile Glu Tyr Thr Asp Leu Glu Lys Glu Ala Pro
    1010                1015                1020

Trp Glu Tyr Gln Lys Arg Pro Pro Pro Ala Trp Pro His Glu Gly Val
1025                1030                1035                1040

Ile Ile Phe Asp Asn Val Asn Phe Met Tyr Ser Pro Gly Gly Pro Leu
                1045                1050                1055

Val Leu Lys His Leu Thr Ala Leu Ile Lys Ser Gln Glu Lys Val Gly
            1060                1065                1070

Ile Val Gly Arg Thr Gly Ala Gly Lys Ser Ser Leu Ile Ser Ala Leu
        1075                1080                1085

Phe Arg Leu Ser Glu Pro Glu Gly Lys Ile Trp Ile Asp Lys Ile Leu
    1090                1095                1100

Thr Thr Glu Ile Gly Leu His Asp Leu Arg Lys Lys Met Ser Ile Ile
1105                1110                1115                1120

Pro Gln Glu Pro Val Leu Phe Thr Gly Thr Met Arg Lys Asn Leu Asp
                1125                1130                1135

Pro Phe Asn Glu His Thr Asp Glu Glu Leu Trp Asn Ala Leu Gln Glu
            1140                1145                1150

Val Gln Leu Lys Glu Thr Ile Glu Asp Leu Pro Gly Lys Met Asp Thr
        1155                1160                1165

Glu Leu Ala Glu Ser Gly Ser Asn Phe Ser Val Gly Gln Arg Gln Leu
    1170                1175                1180

Val Cys Leu Ala Arg Ala Ile Leu Arg Lys Asn Gln Ile Leu Ile Ile
1185                1190                1195                1200

Asp Glu Ala Thr Ala Asn Val Asp Pro Arg Thr Asp Glu Leu Ile Gln
                1205                1210                1215

Lys Lys Ser Gly Arg Asn Leu Pro Thr Ala Pro Cys
            1220                1225
```

<210> SEQ ID NO 538
<211> LENGTH: 1261
<212> TYPE: PRT
<213> ORGANISM: Homo sapiens

<400> SEQUENCE: 538

-continued

```
Met Tyr Ser Val Leu Pro Glu Asp Arg Ser Gln His Leu Gly Glu Glu
                5                   10                  15

Leu Gln Gly Phe Trp Asp Lys Glu Val Leu Arg Ala Glu Asn Asp Ala
            20                  25                  30

Gln Lys Pro Ser Leu Thr Arg Ala Ile Ile Lys Cys Tyr Trp Lys Ser
        35                  40                  45

Tyr Leu Val Leu Gly Ile Phe Thr Leu Ile Glu Glu Ser Ala Lys Val
    50                  55                  60

Ile Gln Pro Ile Phe Leu Gly Lys Ile Ile Asn Tyr Phe Glu Asn Tyr
65                  70                  75                  80

Asp Pro Met Asp Ser Val Ala Leu Asn Thr Ala Tyr Ala Tyr Ala Thr
                85                  90                  95

Val Leu Thr Phe Cys Thr Leu Ile Leu Ala Ile Leu His His Leu Tyr
            100                 105                 110

Phe Tyr His Val Gln Cys Ala Gly Met Arg Leu Arg Val Ala Met Cys
        115                 120                 125

His Met Ile Tyr Arg Lys Ala Leu Arg Leu Ser Asn Met Ala Met Gly
    130                 135                 140

Lys Thr Thr Thr Gly Gln Ile Val Asn Leu Leu Ser Asn Asp Val Asn
145                 150                 155                 160

Lys Phe Asp Gln Val Thr Val Phe Leu His Phe Leu Trp Ala Gly Pro
                165                 170                 175

Leu Gln Ala Ile Ala Val Thr Ala Leu Leu Trp Met Glu Ile Gly Ile
            180                 185                 190

Ser Cys Leu Ala Gly Met Ala Val Leu Ile Ile Leu Leu Pro Leu Gln
        195                 200                 205

Ser Cys Phe Gly Lys Leu Phe Ser Ser Leu Arg Ser Lys Thr Ala Thr
    210                 215                 220

Phe Thr Asp Ala Arg Ile Arg Thr Met Asn Glu Val Ile Thr Gly Ile
225                 230                 235                 240

Arg Ile Ile Lys Met Tyr Ala Trp Glu Lys Ser Phe Ser Asn Leu Ile
                245                 250                 255

Thr Asn Leu Arg Lys Lys Glu Ile Ser Lys Ile Leu Arg Ser Ser Cys
            260                 265                 270

Leu Arg Gly Met Asn Leu Ala Ser Phe Phe Ser Ala Ser Lys Ile Ile
        275                 280                 285

Val Phe Val Thr Phe Thr Thr Tyr Val Leu Leu Gly Ser Val Ile Thr
    290                 295                 300

Ala Ser Arg Val Phe Val Ala Val Thr Leu Tyr Gly Ala Val Arg Leu
305                 310                 315                 320

Thr Val Thr Leu Phe Phe Pro Ser Ala Ile Glu Arg Val Ser Glu Ala
                325                 330                 335

Ile Val Ser Ile Arg Arg Ile Gln Thr Phe Leu Leu Leu Asp Glu Ile
            340                 345                 350

Ser Gln Arg Asn Arg Gln Leu Pro Ser Asp Gly Lys Lys Met Val His
        355                 360                 365

Val Gln Asp Phe Thr Ala Phe Trp Asp Lys Ala Ser Glu Thr Pro Thr
    370                 375                 380

Leu Gln Gly Leu Ser Phe Thr Val Arg Pro Gly Glu Leu Leu Ala Val
385                 390                 395                 400

Val Gly Pro Val Gly Ala Gly Lys Ser Ser Leu Leu Ser Ala Val Leu
                405                 410                 415

Gly Glu Leu Ala Pro Ser His Gly Leu Val Ser Val His Gly Arg Ile
```

-continued

```
            420                 425                 430

Ala Tyr Val Ser Gln Gln Pro Trp Val Phe Ser Gly Thr Leu Arg Ser
        435                 440                 445

Asn Ile Leu Phe Gly Lys Lys Tyr Glu Lys Glu Arg Tyr Glu Lys Val
    450                 455                 460

Ile Lys Ala Cys Ala Leu Lys Lys Asp Leu Gln Leu Leu Glu Asp Gly
465                 470                 475                 480

Asp Leu Thr Val Ile Gly Asp Arg Gly Thr Thr Leu Ser Gly Gly Gln
                485                 490                 495

Lys Ala Arg Val Asn Leu Ala Arg Ala Val Tyr Gln Asp Ala Asp Ile
            500                 505                 510

Tyr Leu Leu Asp Asp Pro Leu Ser Ala Val Asp Ala Glu Val Ser Arg
        515                 520                 525

His Leu Phe Glu Leu Cys Ile Cys Gln Ile Leu His Glu Lys Ile Thr
    530                 535                 540

Ile Leu Val Thr His Gln Leu Gln Tyr Leu Lys Ala Ala Ser Gln Ile
545                 550                 555                 560

Leu Ile Leu Lys Asp Gly Lys Met Val Gln Lys Gly Thr Tyr Thr Glu
                565                 570                 575

Phe Leu Lys Ser Gly Ile Asp Phe Gly Ser Leu Leu Lys Lys Asp Asn
            580                 585                 590

Glu Glu Ser Glu Gln Pro Pro Val Pro Gly Thr Pro Thr Leu Arg Asn
        595                 600                 605

Arg Thr Phe Ser Glu Ser Ser Val Trp Ser Gln Gln Ser Ser Arg Pro
    610                 615                 620

Ser Leu Lys Asp Gly Ala Leu Glu Ser Gln Asp Thr Glu Asn Val Pro
625                 630                 635                 640

Val Thr Leu Ser Glu Glu Asn Arg Ser Glu Gly Lys Val Gly Phe Gln
                645                 650                 655

Ala Tyr Lys Asn Tyr Phe Arg Ala Gly Ala His Trp Ile Val Phe Ile
            660                 665                 670

Phe Leu Ile Leu Leu Asn Thr Ala Ala Gln Val Ala Tyr Val Leu Gln
        675                 680                 685

Asp Trp Trp Leu Ser Tyr Trp Ala Asn Lys Gln Ser Met Leu Asn Val
    690                 695                 700

Thr Val Asn Gly Gly Gly Asn Val Thr Glu Lys Leu Asp Leu Asn Trp
705                 710                 715                 720

Tyr Leu Gly Ile Tyr Ser Gly Leu Thr Val Ala Thr Val Leu Phe Gly
                725                 730                 735

Ile Ala Arg Ser Leu Leu Val Phe Tyr Val Leu Val Asn Ser Ser Gln
            740                 745                 750

Thr Leu His Asn Lys Met Phe Glu Ser Ile Leu Lys Ala Pro Val Leu
        755                 760                 765

Phe Phe Asp Arg Asn Pro Ile Gly Arg Ile Leu Asn Arg Phe Ser Lys
    770                 775                 780

Asp Ile Gly His Leu Asp Asp Leu Leu Pro Leu Thr Phe Leu Asp Phe
785                 790                 795                 800

Ile Gln Thr Leu Leu Gln Val Val Gly Val Val Ser Val Ala Val Ala
                805                 810                 815

Val Ile Pro Trp Ile Ala Ile Pro Leu Val Pro Leu Gly Ile Ile Phe
            820                 825                 830

Ile Phe Leu Arg Arg Tyr Phe Leu Glu Thr Ser Arg Asp Val Lys Arg
        835                 840                 845
```

-continued

```
Leu Glu Ser Thr Thr Arg Ser Pro Val Phe Ser His Leu Ser Ser Ser
    850                 855                 860

Leu Gln Gly Leu Trp Thr Ile Arg Ala Tyr Lys Ala Glu Glu Arg Cys
865                 870                 875                 880

Gln Glu Leu Phe Asp Ala His Gln Asp Leu His Ser Glu Ala Trp Phe
                885                 890                 895

Leu Phe Leu Thr Thr Ser Arg Trp Phe Ala Val Arg Leu Asp Ala Ile
            900                 905                 910

Cys Ala Met Phe Val Ile Ile Val Ala Phe Gly Ser Leu Ile Leu Ala
        915                 920                 925

Lys Thr Leu Asp Ala Gly Gln Val Gly Leu Ala Leu Ser Tyr Ala Leu
    930                 935                 940

Thr Leu Met Gly Met Phe Gln Trp Cys Val Arg Gln Ser Ala Glu Val
945                 950                 955                 960

Glu Asn Met Met Ile Ser Val Glu Arg Val Ile Glu Tyr Thr Asp Leu
                965                 970                 975

Glu Lys Glu Ala Pro Trp Glu Tyr Gln Lys Arg Pro Pro Pro Ala Trp
            980                 985                 990

Pro His Glu Gly Val Ile Ile Phe Asp Asn Val Asn Phe Met Tyr Ser
        995                 1000                1005

Pro Gly Gly Pro Leu Val Leu Lys His Leu Thr Ala Leu Ile Lys Ser
    1010                1015                1020

Gln Glu Lys Val Gly Ile Val Gly Arg Thr Gly Ala Gly Lys Ser Ser
1025                1030                1035                1040

Leu Ile Ser Ala Leu Phe Arg Leu Ser Glu Pro Glu Gly Lys Ile Trp
                1045                1050                1055

Ile Asp Lys Ile Leu Thr Thr Glu Ile Gly Leu His Asp Leu Arg Lys
            1060                1065                1070

Lys Met Ser Ile Ile Pro Gln Glu Pro Val Leu Phe Thr Gly Thr Met
        1075                1080                1085

Arg Lys Asn Leu Asp Pro Phe Asn Glu His Thr Asp Glu Glu Leu Trp
    1090                1095                1100

Asn Ala Leu Gln Glu Val Gln Leu Lys Glu Thr Ile Glu Asp Leu Pro
1105                1110                1115                1120

Gly Lys Met Asp Thr Glu Leu Ala Glu Ser Gly Ser Asn Phe Ser Val
                1125                1130                1135

Gly Gln Arg Gln Leu Val Cys Leu Ala Arg Ala Ile Leu Arg Lys Asn
            1140                1145                1150

Gln Ile Leu Ile Ile Asp Glu Ala Thr Ala Asn Val Asp Pro Arg Thr
        1155                1160                1165

Asp Glu Leu Ile Gln Lys Lys Ile Arg Glu Lys Phe Ala His Cys Thr
    1170                1175                1180

Val Leu Thr Ile Ala His Arg Leu Asn Thr Ile Ile Asp Ser Asp Lys
1185                1190                1195                1200

Ile Met Val Leu Asp Ser Gly Arg Leu Lys Glu Tyr Asp Glu Pro Tyr
                1205                1210                1215

Val Leu Leu Gln Asn Lys Glu Ser Leu Phe Tyr Lys Met Val Gln Gln
            1220                1225                1230

Leu Gly Lys Ala Glu Ala Ala Ala Leu Thr Glu Thr Ala Lys Gln Arg
        1235                1240                1245

Trp Gly Phe Thr Met Leu Ala Arg Leu Val Ser Asn Ser
    1250                1255                1260
```

-continued

<210> SEQ ID NO 539
<211> LENGTH: 10
<212> TYPE: PRT
<213> ORGANISM: Artificial Sequence
<220> FEATURE:
<223> OTHER INFORMATION: Made in a lab

<400> SEQUENCE: 539

Cys Leu Ser His Ser Val Ala Val Val Thr
1 5 10

<210> SEQ ID NO 540
<211> LENGTH: 9
<212> TYPE: PRT
<213> ORGANISM: Artificial Sequence
<220> FEATURE:
<223> OTHER INFORMATION: Made in a lab

<400> SEQUENCE: 540

Ala Val Val Thr Ala Ser Ala Ala Leu
1 5

<210> SEQ ID NO 541
<211> LENGTH: 14
<212> TYPE: PRT
<213> ORGANISM: Homo sapiens

<400> SEQUENCE: 541

Leu Ala Gly Leu Leu Cys Pro Asp Pro Arg Pro Leu Glu Leu
5 10

<210> SEQ ID NO 542
<211> LENGTH: 15
<212> TYPE: PRT
<213> ORGANISM: Homo sapiens

<400> SEQUENCE: 542

Thr Gln Val Val Phe Asp Lys Ser Asp Leu Ala Lys Tyr Ser Ala
5 10 15

<210> SEQ ID NO 543
<211> LENGTH: 12
<212> TYPE: PRT
<213> ORGANISM: Homo sapiens

<400> SEQUENCE: 543

Phe Met Gly Ser Ile Val Gln Leu Ser Gln Ser Val
5 10

<210> SEQ ID NO 544
<211> LENGTH: 18
<212> TYPE: PRT
<213> ORGANISM: Homo sapiens

<400> SEQUENCE: 544

Thr Tyr Val Pro Pro Leu Leu Leu Glu Val Gly Val Glu Glu Lys Phe
5 10 15

Met Thr

<210> SEQ ID NO 545
<211> LENGTH: 18
<212> TYPE: PRT
<213> ORGANISM: Homo sapiens

<400> SEQUENCE: 545

-continued

Met Asp Arg Leu Val Gln Arg Phe Gly Thr Arg Ala Val Tyr Leu Ala
5 10 15

Ser Val

<210> SEQ ID NO 546
<211> LENGTH: 29
<212> TYPE: PRT
<213> ORGANISM: Homo sapiens

<400> SEQUENCE: 546

Phe Val Gly Glu Gly Leu Tyr Gln Gly Val Pro Arg Ala Glu Pro Gly
5 10 15

Thr Glu Ala Arg Arg His Tyr Asp Glu Gly Val Arg Met
20 25

<210> SEQ ID NO 547
<211> LENGTH: 58
<212> TYPE: PRT
<213> ORGANISM: Homo sapiens

<400> SEQUENCE: 547

Val Ala Glu Glu Ala Ala Leu Gly Pro Thr Glu Pro Ala Glu Gly Leu
5 10 15

Ser Ala Pro Ser Leu Ser Pro His Cys Cys Pro Cys Arg Ala Arg Leu
20 25 30

Ala Phe Arg Asn Leu Gly Ala Leu Leu Pro Arg Leu His Gln Leu Cys
35 40 45

Cys Arg Met Pro Arg Thr Leu Arg Arg Leu
50 55

<210> SEQ ID NO 548
<211> LENGTH: 18
<212> TYPE: PRT
<213> ORGANISM: Homo sapiens

<400> SEQUENCE: 548

Ile Asp Trp Asp Thr Ser Ala Leu Ala Pro Tyr Leu Gly Thr Gln Glu
5 10 15

Glu Cys

<210> SEQ ID NO 549
<211> LENGTH: 18
<212> TYPE: PRT
<213> ORGANISM: Homo sapiens

<400> SEQUENCE: 549

Leu Glu Ala Leu Leu Ser Asp Leu Phe Arg Asp Pro Asp His Cys Arg
5 10 15

Gln Ala

<210> SEQ ID NO 550
<211> LENGTH: 14
<212> TYPE: PRT
<213> ORGANISM: Homo sapiens

<400> SEQUENCE: 550

Ser Asp His Trp Arg Gly Arg Tyr Gly Arg Arg Arg Pro Phe
5 10

<210> SEQ ID NO 551

-continued

```
<211> LENGTH: 11
<212> TYPE: PRT
<213> ORGANISM: Artificial Sequence
<220> FEATURE:
<223> OTHER INFORMATION: Made in a lab

<400> SEQUENCE: 551

Phe Asp Lys Ser Asp Leu Ala Lys Tyr Ser Ala
 1               5                  10
```

COMPOSITIONS AND METHODS FOR THE THERAPY AND DIAGNOSIS OF PROSTATE CANCER

TECHNICAL FIELD

The present invention relates generally to therapy and diagnosis of cancer, such as prostate cancer. The invention is more specifically related to polypeptides comprising at least a portion of a prostate-specific protein, and to polynucleotides encoding such polypeptides. Such polypeptides and polynucleotides may be used in vaccines and pharmaceutical compositions for prevention and treatment of prostate cancer, and for the diagnosis and monitoring of such cancers.

BACKGROUND OF THE INVENTION

Prostate cancer is the most common form of cancer among males, with an estimated incidence of 30% in men over the age of 50. Overwhelming clinical evidence shows that human prostate cancer has the propensity to metastasize to bone, and the disease appears to progress inevitably from androgen dependent to androgen refractory status, leading to increased patient mortality. This prevalent disease is currently the second leading cause of cancer death among men in the U.S.

In spite of considerable research into therapies for the disease, prostate cancer remains difficult to treat. Commonly, treatment is based on surgery and/or radiation therapy, but these methods are ineffective in a significant percentage of cases. Two previously identified prostate specific proteins—prostate specific antigen (PSA) and prostatic acid phosphatase (PAP)—have limited therapeutic and diagnostic potential. For example, PSA levels do not always correlate well with the presence of prostate cancer, being positive in a percentage of non-prostate cancer cases, including benign prostatic hyperplasia (BPH). Furthermore, PSA measurements correlate with prostate volume, and do not indicate the level of metastasis.

In spite of considerable research into therapies for these and other cancers, prostate cancer remains difficult to diagnose and treat effectively. Accordingly, there is a need in the art for improved methods for detecting and treating such cancers. The present invention fulfills these needs and further provides other related advantages.

SUMMARY OF THE INVENTION

Briefly stated, the present invention provides compositions and methods for the diagnosis and therapy of cancer, such as prostate cancer. In one aspect, the present invention provides polypeptides comprising at least a portion of a prostate-specific protein, or a variant thereof. Certain portions and other variants are immunogenic, such that the ability of the variant to react with antigen-specific antisera is not substantially diminished. Within certain embodiments, the polypeptide comprises at least an immunogenic portion of a prostate-specific protein, or a variant thereof, wherein the protein comprises an amino acid sequence that is encoded by a polynucleotide sequence selected from the group consisting of: (a) sequences recited in any one of SEQ ID NOs:1–111, 115–171, 173–175, 177, 179–305, 307–315, 326, 328, 330, 332–335, 340–375, 381, 382, 384–476, 524, 526, 530, 531, 533, 535 and 536; (b) sequences that hybridize to any of the foregoing sequences under moderately stringent conditions; and (c) complements of any of the sequence of (a) or (b). In certain specific embodiments, such a polypeptide comprises at least a portion, or variant thereof, of a protein that includes an amino acid sequence selected from the group consisting of sequences recited in any one of SEQ ID NO: 112–114, 172, 176, 178, 327, 329, 331, 336, 339, 376–380, 383, 477–483, 496, 504, 505, 519, 520, 522, 525, 527, 532, 534, 537–550.

The present invention further provides polynucleotides that encode a polypeptide as described above, or a portion thereof (such as a portion encoding at least 15 amino acid residues of a prostate-specific protein), expression vectors comprising such polynucleotides and host cells transformed or transfected with such expression vectors.

Within other aspects, the present invention provides pharmaceutical compositions comprising a polypeptide or polynucleotide as described above and a physiologically acceptable carrier.

Within a related aspect of the present invention, vaccines for prophylactic or therapeutic use are provided. Such vaccines comprise a polypeptide or polynucleotide as described above and an immunostimulant.

The present invention further provides pharmaceutical compositions that comprise: (a) an antibody or antigen-binding fragment thereof that specifically binds to a prostate-specific protein; and (b) a physiologically acceptable carrier. In certain embodiments, the present invention provides monoclonal antibodies that specifically bind to an amino acid sequence selected from the group consisting of SEQ ID NO: 496, 504, 505, 509–517, 522 and 541–550, together with monoclonal antibodies comprising a complementarity determining region selected from the group consisting of SEQ ID NO: 502, 503 and 506–508.

Within further aspects, the present invention provides pharmaceutical compositions comprising: (a) an antigen presenting cell that expresses a polypeptide as described above and (b) a pharmaceutically acceptable carrier or excipient. Antigen presenting cells include dendritic cells, macrophages, monocytes, fibroblasts and B cells.

Within related aspects, vaccines are provided that comprise: (a) an antigen presenting cell that expresses a polypeptide as described above and (b) an immunostimulant.

The present invention further provides, in other aspects, fusion proteins that comprise at least one polypeptide as described above, as well as polynucleotides encoding such fusion proteins.

Within related aspects, pharmaceutical compositions comprising a fusion protein, or a polynucleotide encoding a fusion protein, in combination with a physiologically acceptable carrier are provided.

Vaccines are further provided, within other aspects, that comprise a fusion protein, or a polynucleotide encoding a fusion protein, in combination with an immunostimulant.

Within further aspects, the present invention provides methods for inhibiting the development of a cancer in a patient, comprising administering to a patient a pharmaceutical composition or vaccine as recited above.

The present invention further provides, within other aspects, methods for removing tumor cells from a biological sample, comprising contacting a biological sample with T cells that specifically react with a prostate-specific protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a prostate-specific protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer in a patient, comprising administering to a patient an effective amount of a T cell population as described above.

The present invention further provides methods for inhibiting the development of a cancer in a patient, comprising the steps of: (a) incubating $CD4^+$ and/or $CD8^+$ T cells isolated from a patient with one or more of: (i) a polypeptide comprising at least an immunogenic portion of a prostate-specific protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

Within further aspects, the present invention provides methods for determining the presence or absence of a cancer in a patient, comprising: (a) contacting a biological sample obtained from a patient with a binding agent that binds to a polypeptide as recited above; (b) detecting in the sample an amount of polypeptide that binds to the binding agent; and (c) comparing the amount of polypeptide with a predetermined cut-off value, and therefrom determining the presence or absence of a cancer in the patient. Within preferred embodiments, the binding agent is an antibody, more preferably a monoclonal antibody. The cancer may be prostate cancer.

The present invention also provides, within other aspects, methods for monitoring the progression of a cancer in a patient. Such methods comprise the steps of: (a) contacting a biological sample obtained from a patient at a first point in time with a binding agent that binds to a polypeptide as recited above; (b) detecting in the sample an amount of polypeptide that binds to the binding agent; (c) repeating steps (a) and (b) using a biological sample obtained from the patient at a subsequent point in time; and (d) comparing the amount of polypeptide detected in step (c) with the amount detected in step (b) and therefrom monitoring the progression of the cancer in the patient.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a prostate-specific protein; (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, methods are provided for monitoring the progression of a cancer in a patient, comprising the steps of: (a) contacting a biological sample obtained from a patient with an oligonucleotide that hybridizes to a polynucleotide that encodes a prostate-specific protein; (b) detecting in the sample an amount of a polynucleotide that hybridizes to the oligonucleotide; (c) repeating steps (a) and (b) using a biological sample obtained from the patient at a subsequent point in time; and (d) comparing the amount of polynucleotide detected in step (c) with the amount detected in step (b) and therefrom monitoring the progression of the cancer in the patient.

Within further aspects, the present invention provides antibodies, such as monoclonal antibodies, that bind to a polypeptide as described above, as well as diagnostic kits comprising such antibodies. Diagnostic kits comprising one or more oligonucleotide probes or primers as described above are also provided.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS AND SEQUENCE IDENTIFIERS

FIG. 1 illustrates the ability of T cells to kill fibroblasts expressing the representative prostate-specific polypeptide P502S, as compared to control fibroblasts. The percentage lysis is shown as a series of effector:target ratios, as indicated.

FIGS. 2A and 2B illustrate the ability of T cells to recognize cells expressing the representative prostate-specific polypeptide P502S. In each case, the number of $\gamma$-interferon spots is shown for different numbers of responders. In FIG. 2A, data is presented for fibroblasts pulsed with the P2S-12 peptide, as compared to fibroblasts pulsed with a control E75 peptide. In FIG. 2B, data is presented for fibroblasts expressing P502S, as compared to fibroblasts expressing HER-2/neu.

FIG. 3 represents a peptide competition binding assay showing that the P1S#10 peptide, derived from P501S, binds HLA-A2. Peptide P1S#10 inhibits HLA-A2 restricted presentation of fluM58 peptide to CTL clone D150M58 in TNF release bioassay. D150M58 CTL is specific for the HLA-A2 binding influenza matrix peptide fluM58.

Figure 6A:
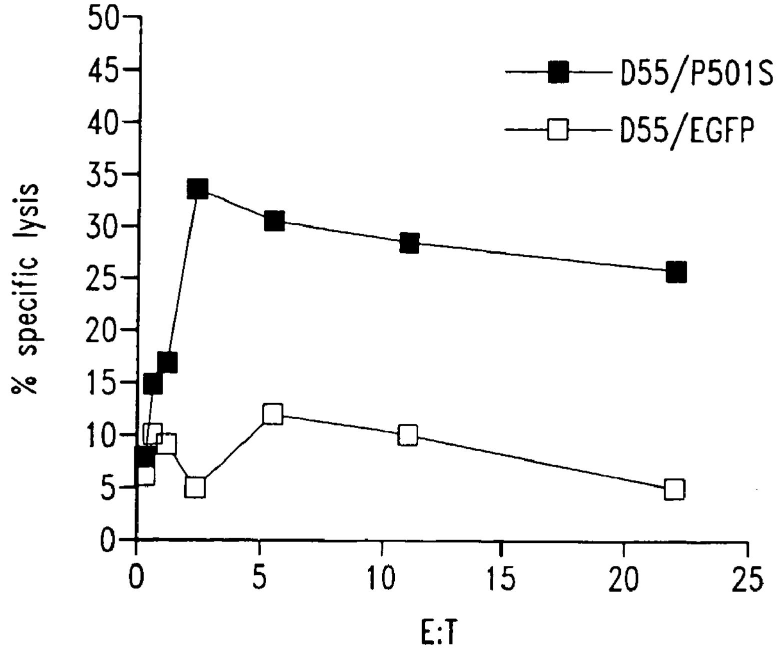
Figure 6B:
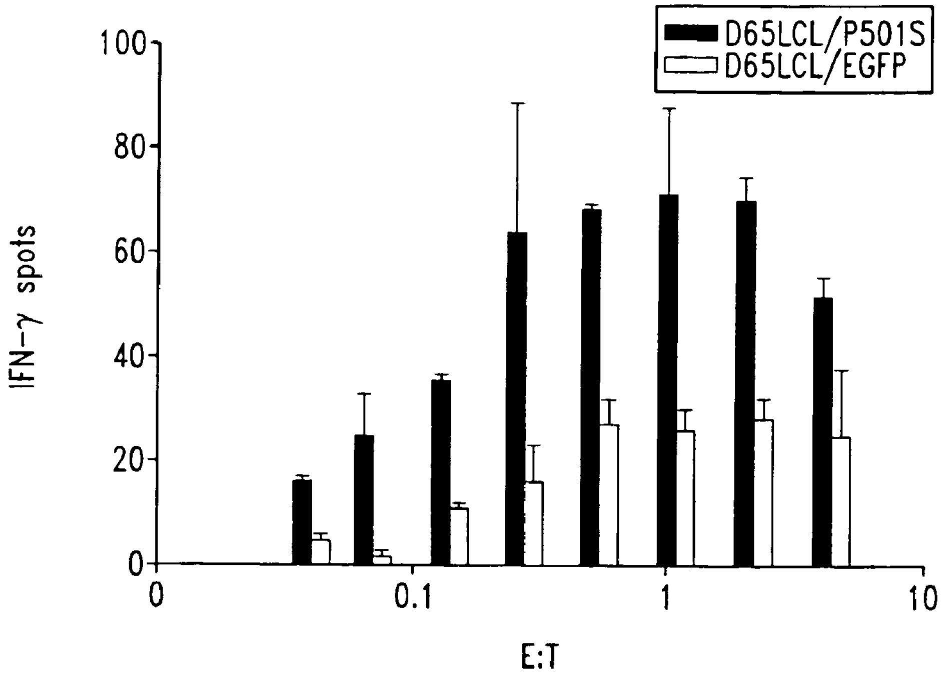

FIGS. 6A and 6B are graphs illustrating the specificity of a $CD8^+$ cell line (3A-1) for a representative prostate-specific antigen (P501S). FIG. 6A shows the results of a $^{51}$Cr release assay. The percent specific lysis is shown as a series of effector:target ratios, as indicated. FIG. 6B shows the production of interferon-gamma by 3A-1 cells stimulated with autologous B-LCL transduced with P501 S, at varying effector:target rations as indicated.

FIG. 7 is a Western blot showing the expression of P501 S in baculovirus.

Figure 8:
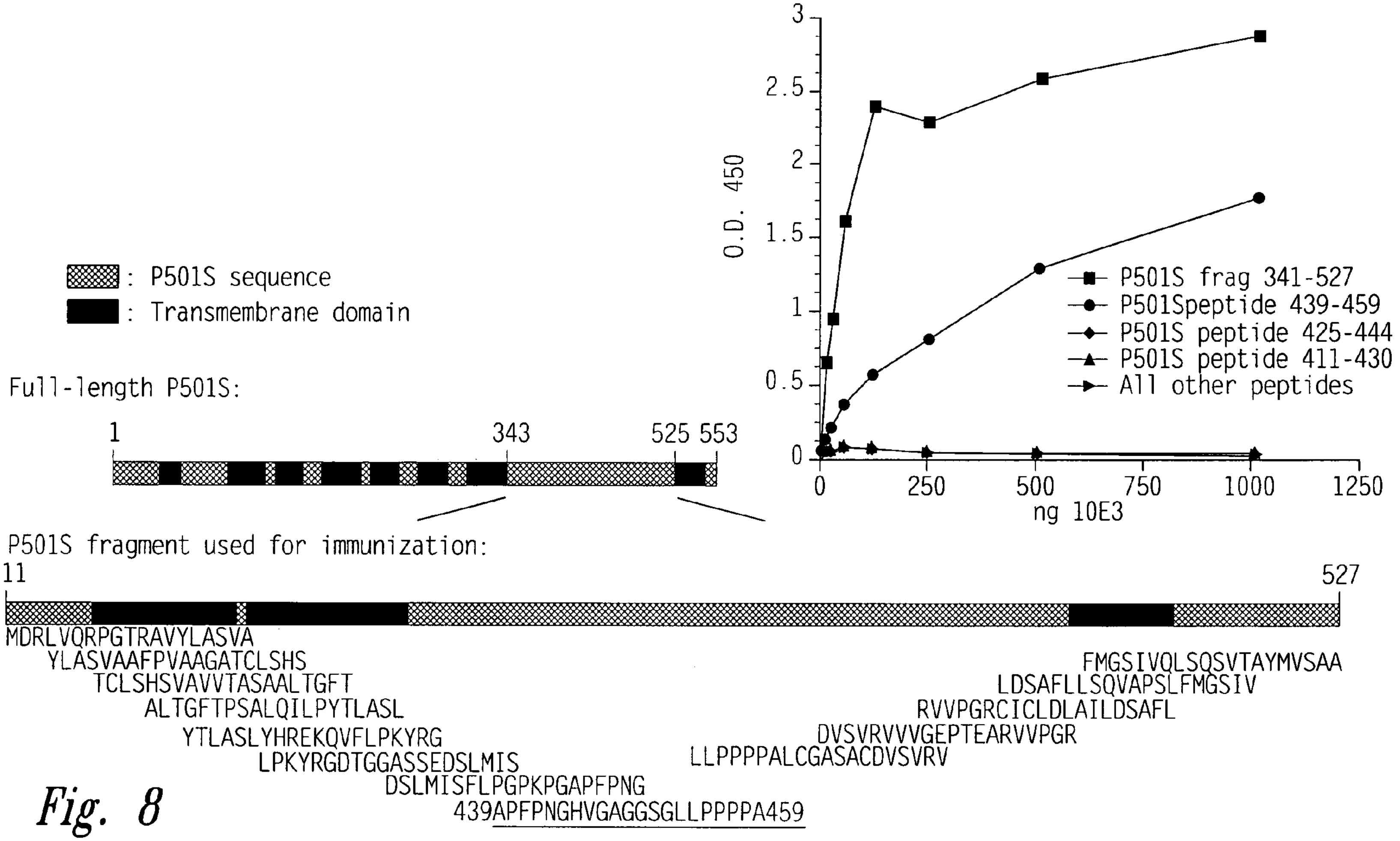

FIG. 8 illustrates the results of epitope mapping studies on P501 S. The peptides used in the study are shown from left to right at the bottom of the figure, as follows: MDRLVQRPGTRAVYLASVA (SEQ ID NO: 489), YLASVAAFPVAAGATCLSHS (SEQ ID NO: 490), TCLSHSVAVVTASAALTGFT (SEQ ID NO: 491), ALTGFTFSALQILPYTLASL (SEQ ID NO: 492), YTLASLYHREKQVFLPKYRG (SEQ ID NO: 493), LPKYRGDTGGASSEDSLMIS (SEQ ID NO: 494), DSLMTSFLPGPKPGAPFPNG (SEQ ID NO: 495), APFPNGHVGAGGSGLLPPPPA (SEQ ID NO: 496), LLPPPPALCGASACDVSVRV (SEQ ID NO: 497), DVSVRVVVGEPTEARVVPGR (SEQ ID NO: 498), RVVPGRGICLDLAILDSAFL (SEQ ID NO: 499), LDSAFLLSQVAPSLFMGSIV (SEQ ID NO: 500), FMGSIVQLSQSVTAYMVSAA (SEQ ID NO: 501).

FIG. 9 is a schematic representation of the P501S protein (SEQ ID NO: 113) showing the location of transmembrane domains and predicted intracellular and extracellular domains.

Figure 10:
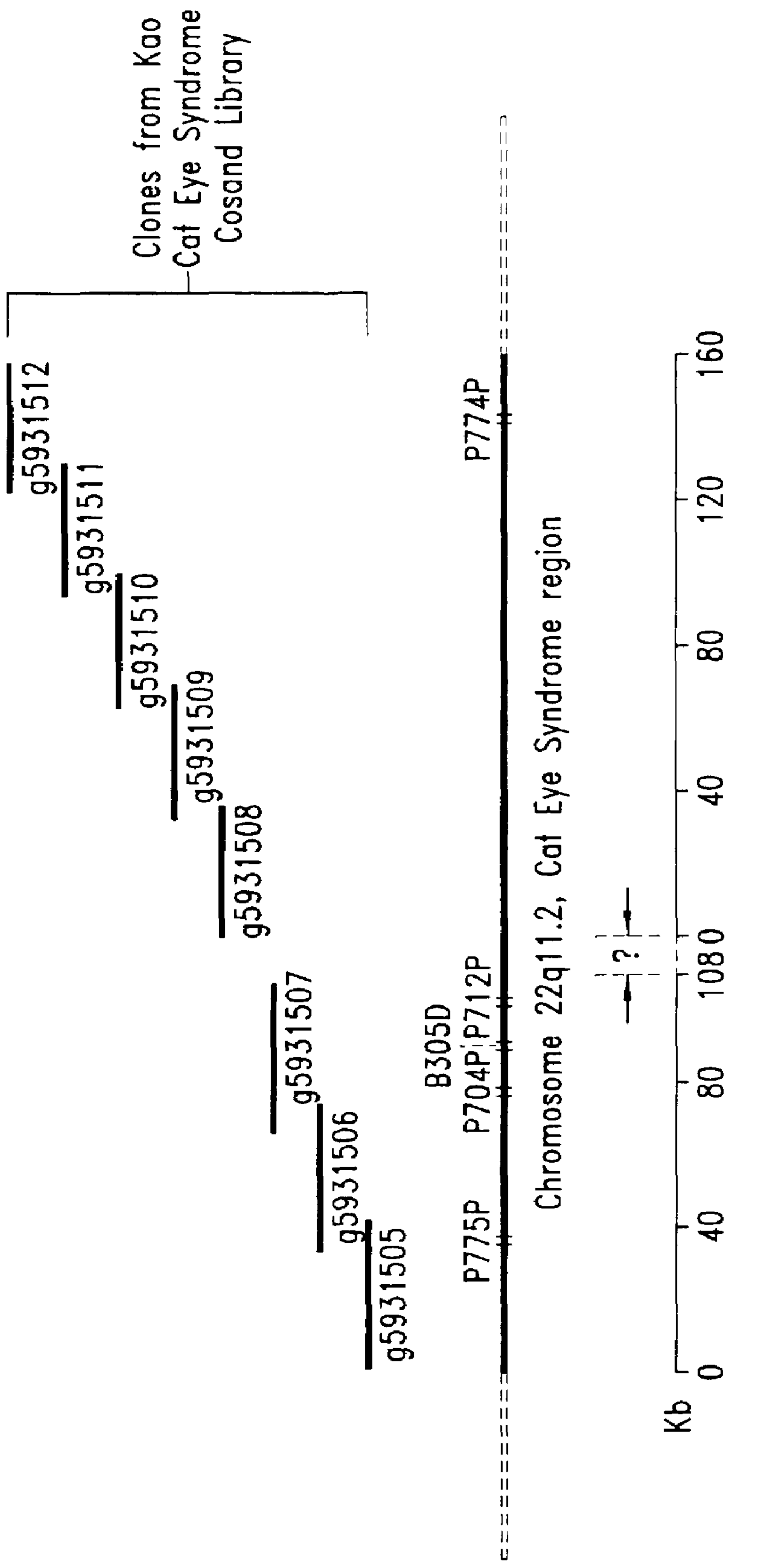

FIG. 10 is a genomic map showing the location of the prostate genes P775P, P704P, B305D, P712P and P774P within the Cat Eye Syndrome region of chromosome 22q11.2

Figure 11:
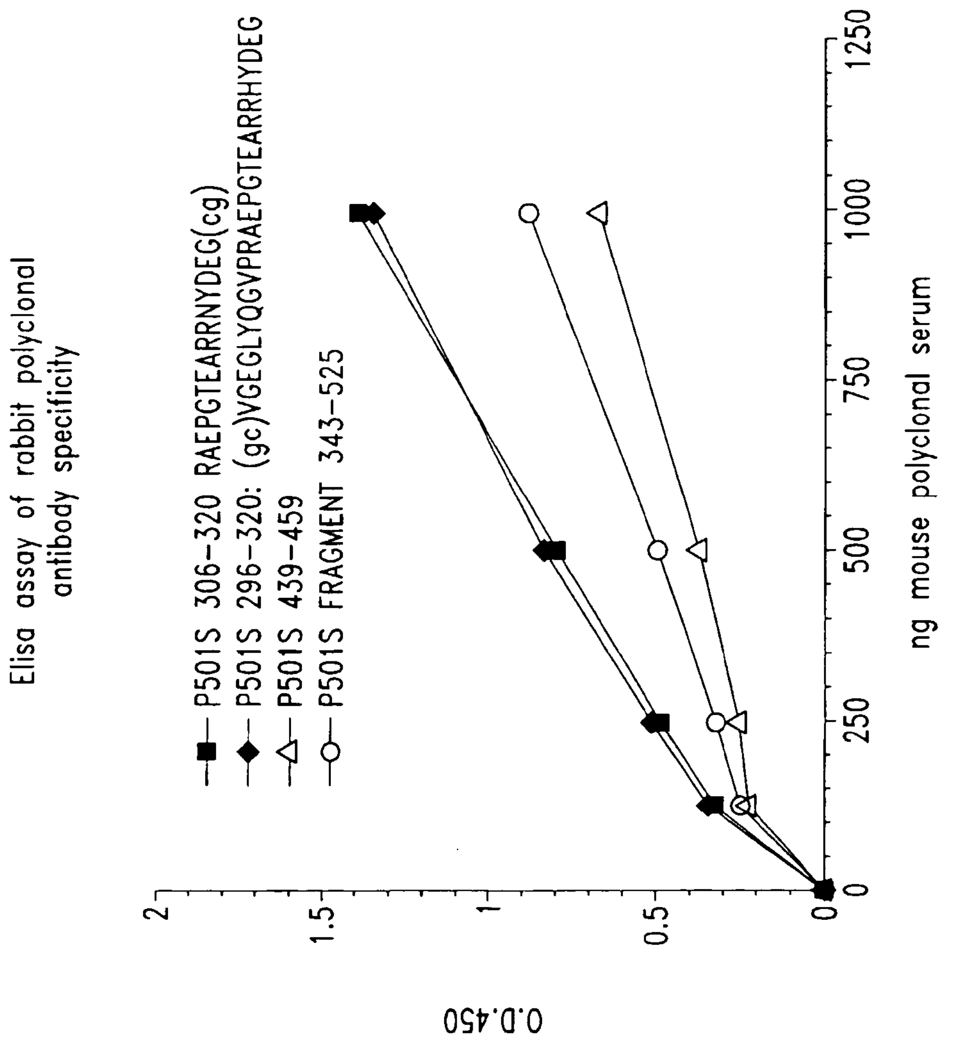

FIG. 11 shows the results of an ELISA assay to determine the specificity of rabbit polyclonal antisera raised against P501 S. The depicted sequence corresponding to peptide P501S 306–320 is set forth in SEQ ID NO: 519 and the sequence corresponding to P501S 296-320 is set forth in SEQ ID NO: 520.

SEQ ID NO: 1 is the determined cDNA sequence for F1-13

SEQ ID NO: 2 is the determined 3' cDNA sequence for F1-12

SEQ ID NO: 3 is the determined 5' cDNA sequence for F1-12

SEQ ID NO: 4 is the determined 3' cDNA sequence for F1-16

SEQ ID NO: 5 is the determined 3' cDNA sequence for H1-1

SEQ ID NO: 6 is the determined 3' cDNA sequence for H 1-9

SEQ ID NO: 7 is the determined 3' cDNA sequence for H1-4

SEQ ID NO: 8 is the determined 3' cDNA sequence for J1-17

SEQ ID NO: 9 is the determined 5' cDNA sequence for J1-17

SEQ ID NO: 10 is the determined 3' cDNA sequence for L1-12

SEQ ID NO: 11 is the determined 5' cDNA sequence for L1-12

SEQ ID NO: 12 is the determined 3' cDNA sequence for N1-1862

SEQ ID NO: 13 is the determined 5' cDNA sequence for N 1-1862

SEQ ID NO: 14 is the determined 3' cDNA sequence for J1-13

SEQ ID NO: 15 is the determined 5' cDNA sequence for J1-13

SEQ ID NO: 16 is the determined 3' cDNA sequence for J1-19

SEQ ID NO: 17 is the determined 5' cDNA sequence for J1-19

SEQ ID NO: 18 is the determined 3' cDNA sequence for J1-25

SEQ ID NO: 19 is the determined 5' cDNA sequence for J1-25

SEQ ID NO: 20 is the determined 5' cDNA sequence for J1-24

SEQ ID NO: 21 is the determined 3' cDNA sequence for J1-24

SEQ ID NO: 22 is the determined $^{51}$cDNA sequence for K1-58

SEQ ID NO: 23 is the determined 3' cDNA sequence for K1-58

SEQ ID NO: 24 is the determined 5' cDNA sequence for K1-63

SEQ ID NO: 25 is the determined 3' cDNA sequence for K1-63

SEQ ID NO: 26 is the determined 5' cDNA sequence for L1-4

SEQ ID NO: 27 is the determined 3' cDNA sequence for L1-4

SEQ ID NO: 28 is the determined 5' cDNA sequence for L1-14

SEQ ID NO: 29 is the determined 3' cDNA sequence for L1-14

SEQ ID NO: 30 is the determined 3' cDNA sequence for J1-12

SEQ ID NO: 31 is the determined 3' cDNA sequence for J1-16

SEQ ID NO: 32 is the determined 3' cDNA sequence for J1-21

SEQ ID NO: 33 is the determined 3' cDNA sequence for K1-48

SEQ ID NO: 34 is the determined 3' cDNA sequence for K1-55

SEQ ID NO: 35 is the determined 3' cDNA sequence for L1-2

SEQ ID NO: 36 is the determined 3' cDNA sequence for L1-6

SEQ ID NO: 37 is the determined 3' cDNA sequence for N1-1858

SEQ ID NO: 38 is the determined 3' cDNA sequence for N–1860

SEQ ID NO: 39 is the determined 3' cDNA sequence for N1-1861

SEQ ID NO: 40 is the determined 3' cDNA sequence for N1-1864

SEQ ID NO: 41 is the determined cDNA sequence for P5

SEQ ID NO: 42 is the determined cDNA sequence for P8

SEQ ID NO: 43 is the determined cDNA sequence for P9

SEQ ID NO: 44 is the determined cDNA sequence for P 18

SEQ ID NO: 45 is the determined cDNA sequence for P20

SEQ ID NO: 46 is the determined cDNA sequence for P29

SEQ ID NO: 47 is the determined cDNA sequence for P30

SEQ ID NO: 48 is the determined cDNA sequence for P34

SEQ ID NO: 49 is the determined cDNA sequence for P36

SEQ ID NO: 50 is the determined cDNA sequence for P38

SEQ ID NO: 51 is the determined cDNA sequence for P39

SEQ ID NO: 52 is the determined cDNA sequence for P42

SEQ ID NO: 53 is the determined cDNA sequence for P47

SEQ ID NO: 54 is the determined cDNA sequence for P49

SEQ ID NO: 55 is the determined cDNA sequence for P50

SEQ ID NO: 56 is the determined cDNA sequence for P53

SEQ ID NO: 57 is the determined cDNA sequence for P55

SEQ ID NO: 58 is the determined cDNA sequence for P60
SEQ ID NO: 59 is the determined cDNA sequence for P64
SEQ ID NO: 60 is the determined cDNA sequence for P65
SEQ ID NO: 61 is the determined cDNA sequence for P73
SEQ ID NO: 62 is the determined cDNA sequence for P75
SEQ ID NO: 63 is the determined cDNA sequence for P76
SEQ ID NO: 64 is the determined cDNA sequence for P79
SEQ ID NO: 65 is the determined cDNA sequence for P84
SEQ ID NO: 66 is the determined cDNA sequence for P68
SEQ ID NO: 67 is the determined cDNA sequence for P80
SEQ ID NO: 68 is the determined cDNA sequence for P82
SEQ ID NO: 69 is the determined cDNA sequence for U1-3064
SEQ ID NO: 70 is the determined cDNA sequence for U1-3065
SEQ ID NO: 71 is the determined cDNA sequence for V1-3692
SEQ ID NO: 72 is the determined cDNA sequence for 1A-3905
SEQ ID NO: 73 is the determined cDNA sequence for V1-3686
SEQ ID NO: 74 is the determined cDNA sequence for R1-2330
SEQ ID NO: 75 is the determined cDNA sequence for 1B-3976
SEQ ID NO: 76 is the determined cDNA sequence for V1-3679
SEQ ID NO: 77 is the determined cDNA sequence for 1G-4736
SEQ ID NO: 78 is the determined cDNA sequence for 1G-4738
SEQ ID NO: 79 is the determined cDNA sequence for 1G-4741
SEQ ID NO: 80 is the determined cDNA sequence for 1 G-4744
SEQ ID NO: 81 is the determined cDNA sequence for 1G-4734
SEQ ID NO: 82 is the determined cDNA sequence for 1H-4774
SEQ ID NO: 83 is the determined cDNA sequence for 1H-4781
SEQ ID NO: 84 is the determined cDNA sequence for 1H-4785
SEQ ID NO: 85 is the determined cDNA sequence for 1H-4787
SEQ ID NO: 86 is the determined cDNA sequence for 1H-4796
SEQ ID NO: 87 is the determined cDNA sequence for 1I-4807
SEQ ID NO: 88 is the determined cDNA sequence for 1H-4810
SEQ ID NO: 89 is the determined cDNA sequence for 1H-4811
SEQ ID NO: 90 is the determined cDNA sequence for 1J-4876
SEQ ID NO: 91 is the determined cDNA sequence for 1K-4884
SEQ ID NO: 92 is the determined cDNA sequence for 1K-4896
SEQ ID NO: 93 is the determined cDNA sequence for 1G-4761
SEQ ID NO: 94 is the determined cDNA sequence for 1 G-4762
SEQ ID NO: 95 is the determined cDNA sequence for 1H-4766
SEQ ID NO: 96 is the determined cDNA sequence for 1H-4770
SEQ ID NO: 97 is the determined cDNA sequence for 1H-4771
SEQ ID NO: 98 is the determined cDNA sequence for 1H-4772
SEQ ID NO: 99 is the determined cDNA sequence for 1 D-4297
SEQ ID NO: 100 is the determined cDNA sequence for 1D-4309
SEQ ID NO: 101 is the determined cDNA sequence for 1D.1-4278
SEQ ID NO: 102 is the determined cDNA sequence for 1D-4288
SEQ ID NO: 103 is the determined cDNA sequence for 1D-4283
SEQ ID NO: 104 is the determined cDNA sequence for 1D-4304
SEQ ID NO: 105 is the determined cDNA sequence for ID-4296
SEQ ID NO: 106 is the determined cDNA sequence for ID-4280
SEQ ID NO: 107 is the determined full length cDNA sequence for F1-12 (also referred to as P504S)
SEQ ID NO: 108 is the predicted amino acid sequence for F1-12
SEQ ID NO: 109 is the determined full length cDNA sequence for J 1-17
SEQ ID NO: 110 is the determined full length cDNA sequence for L1-12 (also referred to as P501 S)
SEQ ID NO: 111 is the determined full length cDNA sequence for N1-1862 (also referred to as P503S)
SEQ ID NO: 112 is the predicted amino acid sequence for J1-17
SEQ ID NO: 113 is the predicted amino acid sequence for L1-12 (also referred to as P501 S)
SEQ ID NO: 114 is the predicted amino acid sequence for N1-1862 (also referred to as P503S)
SEQ ID NO: 115 is the determined cDNA sequence for P89
SEQ ID NO: 116 is the determined cDNA sequence for P90
SEQ ID NO: 117 is the determined cDNA sequence for P92
SEQ ID NO: 118 is the determined cDNA sequence for P95
SEQ ID NO: 119 is the determined cDNA sequence for P98
SEQ ID NO: 120 is the determined cDNA sequence for P102
SEQ ID NO: 121 is the determined cDNA sequence for P110
SEQ ID NO: 122 is the determined cDNA sequence for P111
SEQ ID NO: 123 is the determined cDNA sequence for P114
SEQ ID NO: 124 is the determined cDNA sequence for P115
SEQ ID NO: 125 is the determined cDNA sequence for P116
SEQ ID NO: 126 is the determined cDNA sequence for P124
SEQ ID NO: 127 is the determined cDNA sequence for P126
SEQ ID NO: 128 is the determined cDNA sequence for P130
SEQ ID NO: 129 is the determined cDNA sequence for P133
SEQ ID NO: 130 is the determined cDNA sequence for P138
SEQ ID NO: 131 is the determined cDNA sequence for P143
SEQ ID NO: 132 is the determined cDNA sequence for P 151
SEQ ID NO: 133 is the determined cDNA sequence for P156
SEQ ID NO: 134 is the determined cDNA sequence for P157
SEQ ID NO: 135 is the determined cDNA sequence for P166
SEQ ID NO: 136 is the determined cDNA sequence for P176
SEQ ID NO: 137 is the determined cDNA sequence for P178
SEQ ID NO: 138 is the determined cDNA sequence for P179
SEQ ID NO: 139 is the determined cDNA sequence for P185
SEQ ID NO: 140 is the determined cDNA sequence for P192
SEQ ID NO: 141 is the determined cDNA sequence for P201
SEQ ID NO: 142 is the determined cDNA sequence for P204
SEQ ID NO: 143 is the determined cDNA sequence for P208
SEQ ID NO: 144 is the determined cDNA sequence for P211

SEQ ID NO: 145 is the determined cDNA sequence for P213
SEQ ID NO: 146 is the determined cDNA sequence for P219
SEQ ID NO: 147 is the determined cDNA sequence for P237
SEQ ID NO: 148 is the determined cDNA sequence for P239
SEQ ID NO: 149 is the determined cDNA sequence for P248
SEQ ID NO: 150 is the determined cDNA sequence for P251
SEQ ID NO: 151 is the determined cDNA sequence for P255
SEQ ID NO: 152 is the determined cDNA sequence for P256
SEQ ID NO: 153 is the determined cDNA sequence for P259
SEQ ID NO: 154 is the determined cDNA sequence for P260
SEQ ID NO: 155 is the determined cDNA sequence for P263
SEQ ID NO: 156 is the determined cDNA sequence for P264
SEQ ID NO: 157 is the determined cDNA sequence for P266
SEQ ID NO: 158 is the determined cDNA sequence for P270
SEQ ID NO: 159 is the determined cDNA sequence for P272
SEQ ID NO: 160 is the determined cDNA sequence for P278
SEQ ID NO: 161 is the determined cDNA sequence for P105
SEQ ID NO: 162 is the determined cDNA sequence for P107
SEQ ID NO: 163 is the determined cDNA sequence for P137
SEQ ID NO: 164 is the determined cDNA sequence for P194
SEQ ID NO: 165 is the determined cDNA sequence for P195
SEQ ID NO: 166 is the determined cDNA sequence for P196
SEQ ID NO: 167 is the determined cDNA sequence for P220
SEQ ID NO: 168 is the determined cDNA sequence for P234
SEQ ID NO: 169 is the determined cDNA sequence for P235
SEQ ID NO: 170 is the determined cDNA sequence for P243
SEQ ID NO: 171 is the determined cDNA sequence for P703P-DE 1
SEQ ID NO: 172 is the predicted amino acid sequence for P703P-DE1
SEQ ID NO: 173 is the determined cDNA sequence for P703P-DE2
SEQ ID NO: 174 is the determined cDNA sequence for P703P-DE6
SEQ ID NO: 175 is the determined cDNA sequence for P703P-DE13
SEQ ID NO: 176 is the predicted amino acid sequence for P703P-DE13
SEQ ID NO: 177 is the determined cDNA sequence for P703P-DE14
SEQ ID NO: 178 is the predicted amino acid sequence for P703P-DE14
SEQ ID NO: 179 is the determined extended cDNA sequence for 1G-4736
SEQ ID NO: 180 is the determined extended cDNA sequence for 1G-4738
SEQ ID NO: 181 is the determined extended cDNA sequence for 1G-4741
SEQ ID NO: 182 is the determined extended cDNA sequence for 1 G-4744
SEQ ID NO: 183 is the determined extended cDNA sequence for 1H-4774
SEQ ID NO: 184 is the determined extended cDNA sequence for 1H-4781
SEQ ID NO: 185 is the determined extended cDNA sequence for 1H-4785
SEQ ID NO: 186 is the determined extended cDNA sequence for 1H-4787
SEQ ID NO: 187 is the determined extended cDNA sequence for 1H-4796
SEQ ID NO: 188 is the determined extended cDNA sequence for 1H-4807
SEQ ID NO: 189 is the determined 3' cDNA sequence for 114810
SEQ ID NO: 190 is the determined 3' cDNA sequence for 1H-4811
SEQ ID NO: 191 is the determined extended cDNA sequence for 1I-4876
SEQ ID NO: 192 is the determined extended cDNA sequence for 1 K-4884
SEQ ID NO: 193 is the determined extended cDNA sequence for 1K-4896
SEQ ID NO: 194 is the determined extended cDNA sequence for 1 G-4761
SEQ ID NO: 195 is the determined extended cDNA sequence for 1 G-4762
SEQ ID NO: 196 is the determined extended cDNA sequence for 1H-4766
SEQ ID NO: 197 is the determined 3' cDNA sequence for 1H-4770
SEQ ID NO: 198 is the determined 3' cDNA sequence for 1H-4771
SEQ ID NO: 199 is the determined extended cDNA sequence for 1H-4772
SEQ ID NO: 200 is the determined extended cDNA sequence for ID-4309
SEQ ID NO: 201 is the determined extended cDNA sequence for 1 D.1-4278
SEQ ID NO: 202 is the determined extended cDNA sequence for 1 D-4288
SEQ ID NO: 203 is the determined extended cDNA sequence for 1D-4283
SEQ ID NO: 204 is the determined extended cDNA sequence for 1D-4304
SEQ ID NO: 205 is the determined extended cDNA sequence for 1 D-4296
SEQ ID NO: 206 is the determined extended cDNA sequence for 1D-4280
SEQ ID NO: 207 is the determined cDNA sequence for 10-d8fwd
SEQ ID NO: 208 is the determined cDNA sequence for 10-H10con
SEQ ID NO: 209 is the determined cDNA sequence for 11-C8rev
SEQ ID NO: 210 is the determined cDNA sequence for 7.g6fwd
SEQ ID NO: 211 is the determined cDNA sequence for 7.g6rev
SEQ ID NO: 212 is the determined cDNA sequence for 8-b5fwd
SEQ ID NO: 213 is the determined cDNA sequence for 8-b5rev
SEQ ID NO: 214 is the determined cDNA sequence for 8-b6fwd
SEQ ID NO: 215 is the determined cDNA sequence for 8-b6 rev
SEQ ID NO: 216 is the determined cDNA sequence for 8-d4fwd
SEQ ID NO: 217 is the determined cDNA sequence for 8-d9rev
SEQ ID NO: 218 is the determined cDNA sequence for 8-g3fwd
SEQ ID NO: 219 is the determined cDNA sequence for 8-g3rev
SEQ ID NO: 220 is the determined cDNA sequence for 8-h11rev
SEQ ID NO: 221 is the determined cDNA sequence for g-f12fwd
SEQ ID NO: 222 is the determined cDNA sequence for g-[3rev
SEQ ID NO: 223 is the determined cDNA sequence for P509S SEQ ID NO: 224 is the determined cDNA sequence for P5 1 0S SEQ ID NO: 225 is the determined cDNA sequence for P703DE5

SEQ ID NO: 226 is the determined cDNA sequence for 9-A11

SEQ ID NO: 227 is the determined cDNA sequence for 8-C6

SEQ ID NO: 228 is the determined cDNA sequence for 8-H7

SEQ ID NO: 229 is the determined cDNA sequence for JPTPN13

SEQ ID NO: 230 is the determined cDNA sequence for JPTPN14

SEQ ID NO: 231 is the determined cDNA sequence for JPTPN23

SEQ ID NO: 232 is the determined cDNA sequence for JPTPN24

SEQ ID NO: 233 is the determined cDNA sequence for JPTPN25

SEQ ID NO: 234 is the determined cDNA sequence for JPTPN30

SEQ ID NO: 235 is the determined cDNA sequence for JPTPN34

SEQ ID NO: 236 is the determined cDNA sequence for PTPN35

SEQ ID NO: 237 is the determined cDNA sequence for JPTPN36

SEQ ID NO: 238 is the determined cDNA sequence for JPTPN38

SEQ ID NO: 239 is the determined cDNA sequence for JPTPN39

SEQ ID NO: 240 is the determined cDNA sequence for JPTPN40

SEQ ID NO: 241 is the determined cDNA sequence for JPTPN41

SEQ ID NO: 242 is the determined cDNA sequence for JPTPN42

SEQ ID NO: 243 is the determined cDNA sequence for JPTPN45

SEQ ID NO: 244 is the determined cDNA sequence for JPTPN46

SEQ ID NO: 245 is the determined cDNA sequence for JPTPN51

SEQ ID NO: 246 is the determined cDNA sequence for JPTPN56

SEQ ID NO: 247 is the determined cDNA sequence for PTPN64

SEQ ID NO: 248 is the determined cDNA sequence for JPTPN65

SEQ ID NO: 249 is the determined cDNA sequence for JPTPN67

SEQ ID NO: 250 is the determined cDNA sequence for JPTPN76

SEQ ID NO: 251 is the determined cDNA sequence for JPTPN84

SEQ ID NO: 252 is the determined cDNA sequence for JPTPN85

SEQ ID NO: 253 is the determined cDNA sequence for JPTPN86

SEQ ID NO: 254 is the determined cDNA sequence for JPTPN87

SEQ ID NO: 255 is the determined cDNA sequence for JPTPN88

SEQ ID NO: 256 is the determined cDNA sequence for JP1F1

SEQ ID NO: 257 is the determined cDNA sequence for JP1 F2

SEQ ID NO: 258 is the determined cDNA sequence for JP1 C2

SEQ ID NO: 259 is the determined cDNA sequence for JP1B1

SEQ ID NO: 260 is the determined cDNA sequence for JP 1B2

SEQ ID NO: 261 is the determined cDNA sequence for JP1D3

SEQ ID NO: 262 is the determined cDNA sequence for JP1A4

SEQ ID NO: 263 is the determined cDNA sequence for JP1F5

SEQ ID NO: 264 is the determined cDNA sequence for JP 1 E6

SEQ ID NO: 265 is the determined cDNA sequence for JP1D6

SEQ ID NO: 266 is the determined cDNA sequence for JP1B5

SEQ ID NO: 267 is the determined cDNA sequence for JP I A6

SEQ ID NO: 268 is the determined cDNA sequence for JP I E8

SEQ ID NO: 269 is the determined cDNA sequence for JP1D7

SEQ ID NO: 270 is the determined cDNA sequence for JP I D9

SEQ ID NO: 271 is the determined cDNA sequence for JP1C10

SEQ ID NO: 272 is the determined cDNA sequence for JP1A9

SEQ ID NO: 273 is the determined cDNA sequence for JP1F12

SEQ ID NO: 274 is the determined cDNA sequence for JP1E12

SEQ ID NO: 275 is the determined cDNA sequence for JP1D11

SEQ ID NO: 276 is the determined cDNA sequence for JP1 C1

SEQ ID NO: 277 is the determined cDNA sequence for JP1 C12

SEQ ID NO: 278 is the determined cDNA sequence for JP1B12

SEQ ID NO: 279 is the determined cDNA sequence for JP1A12

SEQ ID NO: 280 is the determined cDNA sequence for JP8G2

SEQ ID NO: 281 is the determined cDNA sequence for JP8H1

SEQ ID NO: 282 is the determined cDNA sequence for JP8H2

SEQ ID NO: 283 is the determined cDNA sequence for JP8A3

SEQ ID NO: 284 is the determined cDNA sequence for JP8A4

SEQ ID NO: 285 is the determined cDNA sequence for JP8C3

SEQ ID NO: 286 is the determined cDNA sequence for JP8G4

SEQ ID NO: 287 is the determined cDNA sequence for JP8B6

SEQ ID NO: 288 is the determined cDNA sequence for JP8D6

SEQ ID NO: 289 is the determined cDNA sequence for JP8F5

SEQ ID NO: 290 is the determined cDNA sequence for JP8A8

SEQ ID NO: 291 is the determined cDNA sequence for JP8C7
SEQ ID NO: 292 is the determined cDNA sequence for JP8D7
SEQ ID NO: 293 is the determined cDNA sequence for P8D8
SEQ ID NO: 294 is the determined cDNA sequence for JP8E7
SEQ ID NO: 295 is the determined cDNA sequence for JP8F8
SEQ ID NO: 296 is the determined cDNA sequence for JP8G8
SEQ ID NO: 297 is the determined cDNA sequence for JP8B10
SEQ ID NO: 298 is the determined cDNA sequence for JP8C10
SEQ ID NO: 299 is the determined cDNA sequence for JP8E9
SEQ ID NO: 300 is the determined cDNA sequence for JP8E10
SEQ ID NO: 301 is the determined cDNA sequence for JP8F9
SEQ ID NO: 302 is the determined cDNA sequence for JP8H9
SEQ ID NO: 303 is the determined cDNA sequence for JP8C12
SEQ ID NO: 304 is the determined cDNA sequence for JP8E11
SEQ ID NO: 305 is the determined cDNA sequence for JP8E12
SEQ ID NO: 306 is the amino acid sequence for the peptide PS2#12
SEQ ID NO: 307 is the determined cDNA sequence for P711P
SEQ ID NO: 308 is the determined cDNA sequence for P712P
SEQ ID NO: 309 is the determined cDNA sequence for CLONE23
SEQ ID NO: 310 is the determined cDNA sequence for P774P
SEQ ID NO: 311 is the determined cDNA sequence for P775P
SEQ ID NO: 312 is the determined cDNA sequence for P715P
SEQ ID NO: 313 is the determined cDNA sequence for P710P
SEQ ID NO: 314 is the determined cDNA sequence for P767P
SEQ ID NO: 315 is the determined cDNA sequence for P768P
SEQ ID NO: 316–325 are the determined cDNA sequences of previously isolated genes
SEQ ID NO: 326 is the determined cDNA sequence for P703PDE5
SEQ ID NO: 327 is the predicted amino acid sequence for P703PDE5
SEQ ID NO: 328 is the determined cDNA sequence for P703P6.26
SEQ ID NO: 329 is the predicted amino acid sequence for P703P6.26
SEQ ID NO: 330 is the determined cDNA sequence for P703PX-23
SEQ ID NO: 331 is the predicted amino acid sequence for P703PX-23
SEQ ID NO: 332 is the determined full length cDNA sequence for P509S
SEQ ID NO: 333 is the determined extended cDNA sequence for P707P (also referred to as 11-C9)
SEQ ID NO: 334 is the determined cDNA sequence for P714P
SEQ ID NO: 335 is the determined cDNA sequence for P705P (also referred to as 9-F3)
SEQ ID NO: 336 is the predicted amino acid sequence for P705P
SEQ ID NO: 337 is the amino acid sequence of the peptide P1S#10
SEQ ID NO: 338 is the amino acid sequence of the peptide p5
SEQ ID NO: 339 is the predicted amino acid sequence of P509S
SEQ ID NO: 340 is the determined cDNA sequence for P778P
SEQ ID NO: 341 is the determined cDNA sequence for P786P
SEQ ID NO: 342 is the determined cDNA sequence for P789P
SEQ ID NO: 343 is the determined cDNA sequence for a clone showing homology to *Homo sapiens* MM46 mRNA
SEQ ID NO: 344 is the determined cDNA sequence for a clone showing homology to *Homo sapiens* TNF-alpha stimulated ABC protein (ABC50) mRNA
SEQ ID NO: 345 is the determined cDNA sequence for a clone showing homology to *Homo sapiens* mRNA for E-cadherin
SEQ ID NO: 346 is the determined cDNA sequence for a clone showing homology to Human nuclear-encoded mitochondrial serine hydroxymethyltransferase (SHMT)
SEQ ID NO: 347 is the determined cDNA sequence for a clone showing homology to *Homo sapiens* natural resistance-associated macrophage protein2 (NRAMP2)
SEQ ID NO: 348 is the determined cDNA sequence for a clone showing homology to *Homo sapiens* phosphoglucomutase-related protein (PGMRP)
SEQ ID NO: 349 is the determined cDNA sequence for a clone showing homology to Human mRNA for proteosome subunit p40
SEQ ID NO: 350 is the determined cDNA sequence for P777P
SEQ ID NO: 351 is the determined cDNA sequence for P779P
SEQ ID NO: 352 is the determined cDNA sequence for P790P
SEQ ID NO: 353 is the determined cDNA sequence for P784P
SEQ ID NO: 354 is the determined cDNA sequence for P776P
SEQ ID NO: 355 is the determined cDNA sequence for P780P
SEQ ID NO: 356 is the determined cDNA sequence for P544S
SEQ ID NO: 357 is the determined cDNA sequence for P745S
SEQ ID NO: 358 is the determined cDNA sequence for P782P
SEQ ID NO: 359 is the determined cDNA sequence for P783P
SEQ ID NO: 360 is the determined cDNA sequence for unknown 17984
SEQ ID NO: 361 is the determined cDNA sequence for P787P
SEQ ID NO: 362 is the determined cDNA sequence for P788P SEQ ID NO: 363 is the determined cDNA sequence for unknown 17994

SEQ ID NO: 364 is the determined cDNA sequence for P781P

SEQ ID NO: 365 is the determined cDNA sequence for P785P

SEQ ID NO: 366–375 are the determined cDNA sequences for splice variants of B305D.

SEQ ID NO: 376 is the predicted amino acid sequence encoded by the sequence of SEQ ID NO: 366.

SEQ ID NO: 377 is the predicted amino acid sequence encoded by the sequence of SEQ ID NO: 372.

SEQ ID NO: 378 is the predicted amino acid sequence encoded by the sequence of SEQ ID NO: 373.

SEQ ID NO: 379 is the predicted amino acid sequence encoded by the sequence of SEQ ID NO: 374.

SEQ ID NO: 380 is the predicted amino acid sequence encoded by the sequence of SEQ ID NO: 375.

SEQ ID NO: 381 is the determined cDNA sequence for B716P.

SEQ ID NO: 382 is the determined full-length cDNA sequence for P711P.

SEQ ID NO: 383 is the predicted amino acid sequence for P71 I P.

SEQ ID NO: 384 is the cDNA sequence for P1000C.

SEQ ID NO: 385 is the cDNA sequence for CGI-82.

SEQ ID NO:386 is the cDNA sequence for 23320.

SEQ ID NO:387 is the cDNA sequence for CGI-69.

SEQ ID NO:388 is the cDNA sequence for L-iditol-2-dehydrogenase.

SEQ ID NO:389 is the cDNA sequence for 23379.

SEQ ID NO:390 is the cDNA sequence for 23381.

SEQ ID NO:391 is the cDNA sequence for KIAA0122.

SEQ ID NO:392 is the cDNA sequence for 23399.

SEQ ID NO:393 is the cDNA sequence for a previously identified gene.

SEQ ID NO:394 is the cDNA sequence for HCLBP.

SEQ ID NO:395 is the cDNA sequence for transglutaminase.

SEQ ID NO:396 is the cDNA sequence for a previously identified gene.

SEQ ID NO:397 is the cDNA sequence for PAP.

SEQ ID NO:398 is the cDNA sequence for Ets transcription factor PDEF.

SEQ ID NO:399 is the cDNA sequence for hTGR.

SEQ ID NO:400 is the cDNA sequence for KIAA0295.

SEQ ID NO:401 is the cDNA sequence for 22545.

SEQ ID NO:402 is the cDNA sequence for 2’547.

SEQ ID NO:403 is the cDNA sequence for 22548.

SEQ ID NO:404 is the cDNA sequence for 22550.

SEQ ID NO:405 is the cDNA sequence for 22551.

SEQ ID NO:406 is the cDNA sequence for 22552.

SEQ ID NO:407 is the cDNA sequence for 22553.

SEQ ID NO:408 is the cDNA sequence for 22558.

SEQ ID NO:409 is the cDNA sequence for 22562.

SEQ ID NO:410 is the cDNA sequence for 22565.

SEQ ID NO:411 is the cDNA sequence for 22567.

SEQ ID NO:412 is the cDNA sequence for 22568.

SEQ ID NO:413 is the cDNA sequence for 22570.

SEQ ID NO:414 is the cDNA sequence for 22571.

SEQ ID NO:415 is the cDNA sequence for 22572.

SEQ ID NO:416 is the cDNA sequence for 22573.

SEQ ID NO:417 is the cDNA sequence for 22573.

SEQ ID NO:418 is the cDNA sequence for 22575.

SEQ ID NO:419 is the cDNA sequence for 22580.

SEQ ID NO:420 is the cDNA sequence for 22581.

SEQ ID NO:421 is the cDNA sequence for 22582.

SEQ ID NO:422 is the cDNA sequence for 22583.

SEQ ID NO:423 is the cDNA sequence for 22584.

SEQ ID NO:424 is the cDNA sequence for 22585.

SEQ ID NO:425 is the cDNA sequence for 22586.

SEQ ID NO:426 is the cDNA sequence for 22587.

SEQ ID NO:427 is the cDNA sequence for 22588.

SEQ ID NO:428 is the cDNA sequence for 22589.

SEQ ID NO:429 is the cDNA sequence for 22590.

SEQ ID NO:430 is the cDNA sequence for 22591.

SEQ ID NO:431 is the cDNA sequence for 22592.

SEQ ID NO:432 is the cDNA sequence for 22593.

SEQ ID NO:433 is the cDNA sequence for 22594.

SEQ ID NO:434 is the cDNA sequence for 22595.

SEQ ID NO:435 is the cDNA sequence for 22596.

SEQ ID NO:436 is the cDNA sequence for 22847.

SEQ ID NO:437 is the cDNA sequence for 22848.

SEQ ID NO:438 is the cDNA sequence for 22849.

SEQ ID NO:439 is the cDNA sequence for 22851.

SEQ ID NO:440 is the cDNA sequence for 22852.

SEQ ID NO:441 is the cDNA sequence for 22853.

SEQ ID NO:442 is the cDNA sequence for 22854.

SEQ ID NO:443 is the cDNA sequence for 22855.

SEQ ID NO:444 is the cDNA sequence for 22856.

SEQ ID NO:445 is the cDNA sequence for 22857.

SEQ ID NO:446 is the cDNA sequence for 23601.

SEQ ID NO:447 is the cDNA sequence for 23602.

SEQ ID NO:448 is the cDNA sequence for 23605.

SEQ ID NO:449 is the cDNA sequence for 23606.

SEQ ID NO:450 is the cDNA sequence for 23612.

SEQ ID NO:451 is the cDNA sequence for 23614.

SEQ ID NO:452 is the cDNA sequence for 23618.

SEQ ID NO:453 is the cDNA sequence for 23622.

SEQ ID NO:454 is the cDNA sequence for folate hydrolase.

SEQ ID NO:455 is the cDNA sequence for LIM protein.

SEQ ID NO:456 is the cDNA sequence for a known gene.

SEQ ID NO:457 is the cDNA sequence for a known gene.

SEQ ID NO:458 is the cDNA sequence for a previously identified gene.

SEQ ID NO:459 is the cDNA sequence for 23045.

SEQ ID NO:460 is the cDNA sequence for 23032.

SEQ ID NO:461 is the cDNA sequence for 23054.

SEQ ID NO:462–467 are cDNA sequences for known genes.

SEQ ID NO:468–471 are cDNA sequences for P710P.

SEQ ID NO:472 is a cDNA sequence for P1001° C.

SEQ ID NO: 473 is the determined cDNA sequence for a first splice variant of P775P (referred to as 27505).

SEQ ID NO: 474 is the determined cDNA sequence for a second splice variant of P775P (referred to as 19947).

SEQ ID NO: 475 is the determined cDNA sequence for a third splice variant of P775P (referred to as 19941).

SEQ ID NO: 476 is the determined cDNA sequence for a fourth splice variant of P775P (referred to as 19937).

SEQ ID NO: 477 is a first predicted amino acid sequence encoded by the sequence of SEQ ID NO: 474.

SEQ ID NO: 478 is a second predicted amino acid sequence encoded by the sequence of SEQ ID NO: 474.

SEQ ID NO: 479 is the predicted amino acid sequence encoded by the sequence of SEQ ID NO: 475.

SEQ ID NO: 480 is a first predicted amino acid sequence encoded by the sequence of SEQ ID NO: 473.

SEQ ID NO: 481 is a second predicted amino acid sequence encoded by the sequence of SEQ ID NO: 473.

SEQ ID NO: 482 is a third predicted amino acid sequence encoded by the sequence of SEQ ID NO: 473.

SEQ ID NO: 483 is a fourth predicted amino acid sequence encoded by the sequence of SEQ ID NO: 473.

SEQ ID NO: 484 is the first 30 amino acids of the *M tuberculosis* antigen Ra12.

SEQ ID NO: 485 is the PCR primer AW025.

SEQ ID NO: 486 is the PCR primer AW003.

SEQ ID NO: 487 is the PCR primer AW027.

SEQ ID NO: 488 is the PCR primer AW026.

SEQ ID NO: 489–501 are peptides employed in epitope mapping studies.

SEQ ID NO: 502 is the determined cDNA sequence of the complementarity determining region for the anti-P503S monoclonal antibody 20D4.

SEQ ID NO: 503 is the determined cDNA sequence of the complementarity determining region for the anti-P503S monoclonal antibody JA1.

SEQ ID NO: 504 & 505 are peptides employed in epitope mapping studies.

SEQ ID NO: 506 is the determined cDNA sequence of the complementarity determining region for the anti-P703P monoclonal antibody 8H2.

SEQ ID NO: 507 is the determined cDNA sequence of the complementarity determining region for the anti-P703P monoclonal antibody 7H8.

SEQ ID NO: 508 is the determined cDNA sequence of the complementarity determining region for the anti-P703P monoclonal antibody 2D4.

SEQ ID NO: 509–522 are peptides employed in epitope mapping studies.

SEQ ID NO: 523 is a mature form of P703P used to raise antibodies against P703P. SEQ ID NO: 524 is the putative full-length cDNA sequence of P703P.

SEQ ID NO: 525 is the predicted amino acid sequence encoded by SEQ ID NO: 524.

SEQ ID NO: 526 is the full-length cDNA sequence for P790P.

SEQ ID NO: 527 is the predicted amino acid sequence for P790P.

SEQ ID NO: 528 & 529 are PCR primers.

SEQ ID NO: 530 is the cDNA sequence of a splice variant of SEQ ID NO: 366.

SEQ ID NO: 531 is the cDNA sequence of the open reading frame of SEQ ID NO: 530.

SEQ ID NO: 532 is the predicted amino acid encoded by the sequence of SEQ ID NO: 531.

SEQ ID NO: 533 is the DNA sequence of a putative ORF of P775P.

SEQ ID NO: 534 is the predicted amino acid sequence encoded by SEQ ID NO: 533.

SEQ ID NO: 535 is a first full-length cDNA sequence for P510S.

SEQ ID NO: 536 is a second full-length cDNA sequence for P510S.

SEQ ID NO: 537 is the predicted amino acid sequence encoded by SEQ ID NO: 535.

SEQ ID NO: 538 is the predicted amino acid sequence encoded by SEQ ID NO: 536.

SEQ ID NO: 539 is the peptide P501S-370.

SEQ ID NO: 540 is the peptide P501 S-376.

SEQ ID NO: 541–550 are epitopes of P501 S.

SEQ ID NO: 551 corresponds to amino acids 543–553 of P501S.

DETAILED DESCRIPTION OF THE INVENTION

As noted above, the present invention is generally directed to compositions and methods for the therapy and diagnosis of cancer, such as prostate cancer. The compositions described herein may include prostate-specific polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a prostate-specific protein or a variant thereof. A "prostate-specific protein" is a protein that is expressed in normal prostate and/or prostate tumor cells at a level that is at least two fold, and preferably at least five fold, greater than the level of expression in a non-prostate normal tissue, as determined using a representative assay provided herein. Certain prostate-specific proteins are proteins that react detectably (within an immunoassay, such as an ELISA or Western blot) with antisera of a patient afflicted with prostate cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery of human prostate-specific proteins. Sequences of polynucleotides encoding certain prostate-specific proteins, or portions thereof, are provided in SEQ ID NOs:1–111, 115–171, 173–175, 177, 179–305, 307–315, 326, 328, 330, 332–335, 340–375, 381, 382, 384–476, 524, 526, 530, 531, 533, 535 and 536. Sequences of polypeptides comprising at least a portion of a prostate-specific protein are provided in SEQ ID NOs: 112–114, 172, 176, 178, 327, 329, 331, 336, 339, 376–380, 383, 477–483, 496, 504, 505, 519, 520, 522, 525, 527, 532, 534 and 537–550.

Prostate-Specific Protein Polynucleotides

Any polynucleotide that encodes a prostate-specific protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a prostate-specific protein. More preferably, a polynucleotide encodes an immunogenic portion of a prostate-specific protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a prostate-specific protein or a portion thereof) or may comprise a variant of such a sequence. Polynucleotide variants may contain one or more substitutions, additions, deletions and/or insertions such that the immunogenicity of the encoded polypeptide is not diminished, relative to a native protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native prostate-specific protein or a portion thereof. The term "variants" also encompasses homologous genes of xenogenic origin.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman, D. J. (1983) *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native prostate-specific protein (or a complementary sequence). Suitable moderately stringent conditions include prewashing in a solution of 5×SSC, 0.5% SDS, 1.0 mM EDTA (pH 8.0); hybridizing at 50° C.-65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least five fold greater in a prostate-specific than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as prostate-specific cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a prostate-specific cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as “rapid amplification of cDNA ends” or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, is it possible to obtain a full length cDNA sequence by analysis of sequences provided in an expressed sequence tag (EST) database, such as that available from GENBANK™.

Certain nucleic acid sequences of cDNA molecules encoding at least a portion of a prostate-specific protein are provided in SEQ ID NO: 1–111, 115–171, 173–175, 177, 179–305, 307–315, 326, 328, 330, 332–335, 340–375, 381, 382, 384–476, 524, 526, 530, 531, 533, 535 and 536. Isolation of these polynucleotides is described below. Each of these prostate-specific proteins was overexpressed in prostate tumor tissue.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., DNA 2:183, 1983). Alternatively, RNA molecules may be generated by in vitro or in vivo transcription of DNA sequences encoding a prostate-specific protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a prostate-specific polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). The polynucleotides may also be administered as naked plasmid vectors. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Prostate-Specific Polypeptides

Within the context of the present invention, polypeptides may comprise at least an immunogenic portion of a prostate-specific protein or a variant thereof, as described herein. As noted above, a "prostate-specific protein" is a protein that is expressed by normal prostate and/or prostate tumor cells. Proteins that are prostate-specific proteins also react detectably within an immunoassay (such as an ELISA) with antisera from a patient with prostate cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a prostate-specific protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native prostate-specific protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$]-labeled Protein A.

As noted above, a composition may comprise a variant of a native prostate-specific protein. A polypeptide "variant," as used herein, is a polypeptide that differs from a native prostate-specific protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein. Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutarnic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, higher eukaryotic and plant cells. Preferably, the host cells employed are *E. coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known prostate-specific protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

Within preferred embodiments, an immunological fusion partner is derived from protein D, a surface protein of the gram-negative bacterium *Haemophilus influenza* B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a prostate-specific protein. As used herein, an antibody, or antigen-binding fragment thereof, is said to "specifically bind" to a prostate-specific protein if it reacts at a detectable level (within, for example, an ELISA) with a prostate-specific protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as prostate cancer, using the representative assays provided herein. In other words, antibodies or other binding agents that bind to a prostate-specific protein will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Most preferably, antibodies employed in the inventive methods have the ability to induce lysis of tumor cells by activation of complement and mediation of antibody-dependent cellular cytotoxicity (ADCC). Antibodies of different classes and subclasses differ in these properties. For example, mouse antibodies of the IgG2a and IgG3 classes are capable of activating serum complement upon binding to target cells which express the antigen against which the antibodies were raised, and can mediate ADCC.

Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells.

A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

The preparation of mouse and rabbit monoclonal antibodies that specifically bind to polypeptides of the present invention is described in detail below. However, the antibodies of the present invention are not limited to those derived from mice. Human antibodies may also be employed in the inventive methods and may prove to be preferable. Such antibodies can be obtained using human hybridomas as described by Cote et al. (Monoclonal Antibodies and Cancer Therapy, Alan R. Lisa, p. 77, 1985). The present invention also encompasses antibodies made by recombinant means such as chimeric antibodies, wherein the variable region and constant region are derived from different species, and CDR-grafted antibodies, wherein the complementarity determining region is derived from a different species, as described in U.S. Pat. Nos. 4,816,567 and 5,225,539. Chimeric antibodies may be prepared by splicing genes for a mouse antibody molecule having a desired antigen specificity together with genes for a human antibody molecule having the desired biological activity, such as activation of human complement and mediation of ADCC (Morrison et al. *Proc. Natl. Acad. Sci. USA* 81:6851, 1984; Neuberger et al. *Nature* 312:604, 1984; Takeda et al. *Nature* 314:452, 1985).

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fe fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, *Pseudomonas* exotoxin, *Shigella* toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a prostate-specific protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ system, available from Nexell Therapeutics Inc., Irvine, Calif. (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a prostate-specific polypeptide, polynucleotide encoding a prostate-specific polypeptide and/or an antigen presenting cell (APC) that expresses such a polypeptide. Such stimulation is performed under conditions and for a time sufficient to permit the generation of T cells that are specific for the polypeptide. Preferably, a prostate-specific polypeptide or polynucleotide is present within a delivery vehicle, such as a microsphere, to facilitate the generation of specific T cells.

T cells are considered to be specific for a prostate-specific polypeptide if the T cells specifically proliferate, secrete cytokines or kill target cells coated with the polypeptide or expressing a gene encoding the polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a prostate-specific polypeptide (100 ng/ml —100 μg/ml, preferably 200 ng/ml–25 μg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a prostate-specific polypeptide, polynucleotide or polypeptide-expressing APC may be CD4+ and/or CD8+. Prostate-specific protein-specific T cells may be expanded using standard techniques. Within preferred embodiments, the T cells are derived from either a patient or a related, or unrelated, donor and are administered to the patient following stimulation and expansion.

For therapeutic purposes, CD4+ or CD8+ T cells that proliferate in response to a prostate-specific polypeptide, polynucleotide or APC can be expanded in number either in vitro or in vivo. Proliferation of such T cells in vitro may be accomplished in a variety of ways. For example, the T cells can be re-exposed to a prostate-specific polypeptide, or a short peptide corresponding to an immunogenic portion of such a polypeptide, with or without the addition of T cell growth factors, such as interleukin-2, and/or stimulator cells that synthesize a prostate-specific polypeptide. Alternatively, one or more T cells that proliferate in the presence of a prostate-specific protein can be expanded in number by cloning. Methods for cloning cells are well known in the art, and include limiting dilution.

Pharmaceutical Compositions and Vaccines

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and an immunostimulant. An immunostimulant may be any substance that enhances an immune response to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as *Bacillus*-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNFα, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule, sponge or gel (composed of polysaccharides for example) that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take-up, process and present antigens with high efficiency, and their ability to activate naïve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80, CD86 and 4-1BB).

APCs may generally be transfected with a polynucleotide encoding a prostate-specific protein (or portion or other variant thereof) such that the prostate-specific polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the prostate-specific polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as prostate cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such as polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperitoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 25 μg to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a prostate-specific protein generally correlate with an improved clinical outcome. Such immune responses may generally be evaluated using standard proliferation, cytotoxicity or cytokine assays, which may be performed using samples obtained from a patient before and after treatment.

Methods for Detecting Cancer

In general, a cancer may be detected in a patient based on the presence of one or more prostate-specific proteins and/or polynucleotides encoding such proteins in a biological sample (for example, blood, sera, urine and/or tumor biopsies) obtained from the patient. In other words, such proteins may be used as markers to indicate the presence or absence of a cancer such as prostate cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a prostate tumor sequence should be present at a level that is at least three fold higher in tumor tissue than in normal tissue.

There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length prostate-specific proteins and portions thereof to which the binding agent binds, as described above.

The solid support may be any material known to those of ordinary skill in the art to which the protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12-A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with prostate cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as prostate cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology. A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof. Preferably, the amount of antibody immobilized on the membrane ranges from about 25 ng to about 1 μg, and more preferably from about 50 ng to about 500 ng. Such tests can typically be performed with a very small amount of biological sample.

Of course, numerous other assay protocols exist that are suitable for use with the proteins or binding agents of the present invention. The above descriptions are intended to be exemplary only. For example, it will be apparent to those of ordinary skill in the art that the above protocols may be readily modified to use prostate-specific polypeptides to detect antibodies that bind to such polypeptides in a biological sample. The detection of such prostate-specific protein specific antibodies may correlate with the presence of a cancer.

A cancer may also, or alternatively, be detected based on the presence of T cells that specifically react with a prostate-specific protein in a biological sample. Within certain methods, a biological sample comprising $CD4^+$ and/or $CD8^+$ T cells isolated from a patient is incubated with a prostate-specific polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with prostate-specific polypeptide (e.g., 5–25 μg/ml). It may be desirable to incubate another aliquot of a T cell sample in the absence of prostate-specific polypeptide to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a prostate-specific protein in a biological sample. For example, at least two oligonucleotide primers may be employed in a polymerase chain reaction (PCR) based assay to amplify a portion of a prostate-specific cDNA derived from a biological sample, wherein at least one of the oligonucleotide primers is specific for (i.e., hybridizes to) a polynucleotide encoding the prostate-specific protein. The amplified cDNA is then separated and detected using techniques well known in the art, such as gel electrophoresis. Similarly, oligonucleotide probes that specifically hybridize to a polynucleotide encoding a prostate-specific protein may be used in a hybridization assay to detect the presence of polynucleotide encoding the protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a prostate-specific protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NO: 1–111, 115–171, 173–175, 177, 179–305, 307–315, 326, 328, 330, 332–335, 340–375, 381, 382, 384–476, 524, 526, 530, 531, 533, 535 and 536. Techniques for both PCR based assays and hybridization assays are well known in the art (see, for example, Mullis et al., *Cold Spring Harbor Symp. Quant. Biol.,* 51:263, 1987; Erlich ed., *PCR Technology, Stockton Press, NY,* 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple prostate-specific protein markers may be assayed within a given sample. It will be apparent that binding agents specific for different proteins provided herein may be combined within a single assay. Further, multiple primers or probes may be used concurrently. The selection of protein markers may be based on routine experiments to determine combinations that results in optimal sensitivity. In addition, or alternatively, assays for proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a prostate-specific protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a prostate-specific protein in a biological sample. Such kits generally comprise at least one oligonucleotide probe or primer, as described above, that hybridizes to a polynucleotide encoding a prostate-specific protein. Such an oligonucleotide may be used, for example, within a PCR or hybridization assay. Additional components that may be present within such kits include a second oligonucleotide and/or a diagnostic reagent or container to facilitate the detection of a polynucleotide encoding a prostate-specific protein.

The following Examples are offered by way of illustration and not by way of limitation.

EXAMPLES

Example 1

Isolation and Characterization of Prostate-Specific Polypeptides

This Example describes the isolation of certain prostate-specific polypeptides from a prostate tumor cDNA library.

A human prostate tumor cDNA expression library was constructed from prostate tumor poly A' RNA using a Superscript Plasmid System for cDNA Synthesis and Plasmid Cloning kit (BRL Life Technologies, Gaithersburg, Md. 20897) following the manufacturer's protocol. Specifically, prostate tumor tissues were homogenized with polytron (Kinematica, Switzerland) and total RNA was extracted using Trizol reagent (BRL Life Technologies) as directed by the manufacturer. The poly $A^+$ RNA was then purified using a Qiagen oligotex spin column mRNA purification kit (Qiagen, Santa Clarita, Calif. 91355) according to the manufacturer's protocol. First-strand cDNA was synthesized using the NotI/Oligo-dT18 primer. Double-stranded cDNA was synthesized, ligated with EcoRI/BAXI adaptors (Invitrogen, San Diego, Calif.) and digested with NotI. Following size fractionation with Chroma Spin-1000 columns (Clontech, Palo Alto, Calif.), the cDNA was ligated into the EcoRI/NotI site of pCDNA3.1 (Invitrogen) and transformed into ElectroMax *E. coli* DH10B cells (BRL Life Technologies) by electroporation.

Using the same procedure, a normal human pancreas cDNA expression library was prepared from a pool of six tissue specimens (Clontech). The cDNA libraries were characterized by determining the number of independent colonies, the percentage of clones that carried insert, the average insert size and by sequence analysis. The prostate tumor library contained $1.64\times10^7$ independent colonies, with 70% of clones having an insert and the average insert size being 1745 base pairs. The normal pancreas cDNA library contained $3.3\times10^6$ independent colonies, with 69% of clones having inserts and the average insert size being 1120 base pairs. For both libraries, sequence analysis showed that the majority of clones had a full length cDNA sequence and were synthesized from mRNA, with minimal rRNA and mitochondrial DNA contamination.

cDNA library subtraction was performed using the above prostate tumor and normal pancreas cDNA libraries, as described by Hara et al. (*Blood,* 84:189–199, 1994) with some modifications. Specifically, a prostate tumor-specific subtracted cDNA library was generated as follows. Normal pancreas cDNA library (70 μg) was digested with EcoRI, NotI, and SfuI, followed by a filling-in reaction with DNA polymerase Klenow fragment. After phenol-chloroform extraction and ethanol precipitation, the DNA was dissolved in 100 μl of $H_2O$, heat-denatured and mixed with 100 μl (100 μg) of Photoprobe biotin (Vector Laboratories, Burlingame, Calif.). As recommended by the manufacturer, the resulting mixture was irradiated with a 270 W sunlamp on ice for 20 minutes. Additional Photoprobe biotin (50 μl) was added and the biotinylation reaction was repeated. After extraction with butanol five times, the DNA was ethanol-precipitated and dissolved in 23 μl $H_2O$ to form the driver DNA.

To form the tracer DNA, 10 μg prostate tumor cDNA library was digested with BamHI and XhoI, phenol chloroform extracted and passed through Chroma spin-400 columns (Clontech). Following ethanol precipitation, the tracer DNA was dissolved in 5 PI $H_2O$. Tracer DNA was mixed with 15 μl driver DNA and 20 μl of 2× hybridization buffer (1.5 M NaCl/10 mM EDTA/50 mM HEPES pH 7.5/0.2% sodium dodecyl sulfate), overlaid with mineral oil, and heat-denatured completely. The sample was immediately transferred into a 68° C. water bath and incubated for 20 hours (long hybridization [LH]). The reaction mixture was then subjected to a streptavidin treatment followed by phenol/chloroform extraction. This process was repeated three more times. Subtracted DNA was precipitated, dissolved in 12 μl $H_2O$, mixed with 8 μl driver DNA and 20 μl of 2× hybridization buffer, and subjected to a hybridization at 68° C. for 2 hours (short hybridization [SH]). After removal of biotinylated double-stranded DNA, subtracted cDNA was ligated into BamHI/XhoI site of chloramphenicol resistant $pBCSK^+$ (Stratagene, La Jolla, Calif. 92037) and transformed into ElectroMax *E. Coli* DH10B cells by electroporation to generate a prostate tumor specific subtracted cDNA library (referred to as “prostate subtraction 1”).

To analyze the subtracted cDNA library, plasmid DNA was prepared from 100 independent clones, randomly picked from the subtracted prostate tumor specific library and grouped based on insert size. Representative cDNA clones were further characterized by DNA sequencing with a Perkin Elmer/Applied Biosystems Division Automated Sequencer Model 373A (Foster City, Calif.). Six cDNA clones, hereinafter referred to as F1-13, F1-12, F1-16, H1-1, H1-9 and H1-4, were shown to be abundant in the subtracted prostate-specific cDNA library. The determined 3' and 5' cDNA sequences for F1-12 are provided in SEQ ID NO: 2 and 3, respectively, with determined 3' cDNA sequences for F1-13, F1-16, H1-1, H1-9 and H1-4 being provided in SEQ ID NO: 1 and 4–7, respectively.

The cDNA sequences for the isolated clones were compared to known sequences in the gene bank using the EMBL and GENBANK™ databases (release 96). Four of the prostate tumor cDNA clones, F1-13, F1-16, H1-1, and H1-4, were determined to encode the following previously identified proteins: prostate specific antigen (PSA), human glandular kallikrein, human tumor expression enhanced gene, and mitochondria cytochrome C oxidase subunit II. H1-9 was found to be identical to a previously identified human autonomously replicating sequence. No significant homologies to the cDNA sequence for F1-12 were found.

Subsequent studies led to the isolation of a full-length cDNA sequence for F1-12. This sequence is provided in SEQ ID NO: 107, with the corresponding predicted amino acid sequence being provided in SEQ ID NO: 108.

To clone less abundant prostate tumor specific genes, cDNA library subtraction was performed by subtracting the prostate tumor cDNA library described above with the normal pancreas cDNA library and with the three most abundant genes in the previously subtracted prostate tumor specific cDNA library: human glandular kallikrein, prostate specific antigen (PSA), and mitochondria cytochrome C oxidase subunit II. Specifically, 1 μg each of human glandular kallikrein, PSA and mitochondria cytochrome C oxidase subunit II cDNAs in pCDNA3.1 were added to the driver DNA and subtraction was performed as described above to provide a second subtracted cDNA library hereinafter referred to as the “subtracted prostate tumor specific cDNA library with spike”.

Twenty-two cDNA clones were isolated from the subtracted prostate tumor specific cDNA library with spike. The determined 3' and 5' cDNA sequences for the clones referred to as J1-17, L1-12, N1-1862, J1-13, J1-19, J1-25, J1-24, K1-58, K1-63, L1-4 and L1-14 are provided in SEQ ID NOS: 8–9, 10–11, 12–13, 14–15, 16–17, 18–19, 20–21, 22–23, 24–25, 26–27 and 28–29, respectively. The determined 3' cDNA sequences for the clones referred to as J1-12, J1-16, J1-21, K148, K1-55, L1-2, L1-6, N1-1858, N1-1860, N1-1861, N1-1864 are provided in SEQ ID NOS: 3040, respectively. Comparison of these sequences with those in the gene bank as described above, revealed no significant homologies to three of the five most abundant DNA species, (J1-17, L1-12 and N1-1862; SEQ ID NOS: 8–9, 10–11 and 12–13, respectively). Of the remaining two most abundant species, one (J1-12; SEQ ID NO:30) was found to be identical to the previously identified human pulmonary surfactant-associated protein, and the other (K1-48; SEQ ID NO:33) was determined to have some homology to *R. norvegicus* mRNA for 2-arylpropionyl-CoA epimerase. Of the 17 less abundant cDNA clones isolated from the subtracted prostate tumor specific cDNA library with spike, four (J1-16, K1-55, L1-6 and N1-1864; SEQ ID NOS:31, 34, 36 and 40, respectively) were found to be identical to previously identified sequences, two (J1-21 and N1-1860; SEQ ID NOS: 32 and 38, respectively) were found to show some homology to non-human sequences, and two (L1-2 and N1-1861; SEQ ID NOS: 35 and 39, respectively) were found to show some homology to known human sequences. No significant homologies were found to the polypeptides J1-13, J1-19, J1-24, J1-25, K1-58, K1-63, L1-4, L1-14 (SEQ ID NOS: 14–15, 16–17, 20–21, 18–19, 22–23, 24–25, 26–27, 28–29, respectively).

Subsequent studies led to the isolation of full length cDNA sequences for J1-17, L1-12 and N1-1862 (SEQ ID NOS: 109–111, respectively). The corresponding predicted amino acid sequences are provided in SEQ ID NOS: 112–114. L1-12 is also referred to as P501 S.

In a further experiment, four additional clones were identified by subtracting a prostate tumor cDNA library with normal prostate cDNA prepared from a pool of three normal prostate poly A+ RNA (referred to as "prostate subtraction 2"). The determined cDNA sequences for these clones, hereinafter referred to as U1-3064, U1-3065, V1-3692 and 1A-3905, are provided in SEQ ID NO: 69–72, respectively. Comparison of the determined sequences with those in the gene bank revealed no significant homologies to U1-3065.

A second subtraction with spike (referred to as "prostate subtraction spike 2") was performed by subtracting a prostate tumor specific cDNA library with spike with normal pancreas cDNA library and further spiked with PSA, J I-17, pulmonary surfactant-associated protein, mitochondrial DNA, cytochrome c oxidase subunit II, N1-1862, autonomously replicating sequence, L1-12 and tumor expression enhanced gene. Four additional clones, hereinafter referred to as V1-3686, R1-2330, 1B-3976 and V1-3679, were isolated. The determined cDNA sequences for these clones are provided in SEQ ID NO:73–76, respectively. Comparison of these sequences with those in the gene bank revealed no significant homologies to V1-3686 and R1-2330.

Further analysis of the three prostate subtractions described above (prostate subtraction 2, subtracted prostate tumor specific cDNA library with spike, and prostate subtraction spike 2) resulted in the identification of sixteen additional clones, referred to as 1 G-4736, 1 G-4738, 1G-4741, 1G-4744, 1G4734, 1H-4774, 1H-4781, 1H-4785, 1H-4787, 1H-4796, 1I-4810, 1I-4811, 1J-4876, 1K-4884 and 1K4896. The determined cDNA sequences for these clones are provided in SEQ ID NOS: 77–92, respectively. Comparison of these sequences with those in the gene bank as described above, revealed no significant homologies to 1G-4741, 1G4734, 1I-4807, 1J-4876 and 1K4896 (SEQ ID NOS: 79, 81, 87, 90 and 92, respectively). Further analysis of the isolated clones led to the determination of extended cDNA sequences for 1G-4736, 1G-4738, 1G-4741, 1G-4744, 1H-4774, 1H-4781, 1H-4785, 1H-4787, 1H-4796, 1I-4807, 1I-4876, 1K-4884 and 1K-4896, provided in SEQ ID NOS: 179–188 and 191–193, respectively, and to the determination of additional partial cDNA sequences for 1I-4810 and I1-4811, provided in SEQ ID NOS: 189 and 190, respectively.

Additional studies with prostate subtraction spike 2 resulted in the isolation of three more clones. Their sequences were determined as described above and compared to the most recent GENBANK™. All three clones were found to have homology to known genes, which are Cysteine-rich protein, KIAA0242, and KIAA0280 (SEQ ID NO: 317, 319, and 320, respectively). Further analysis of these clones by Synteni microarray (Synteni, Palo Alto, Calif.) demonstrated that all three clones were over-expressed in most prostate tumors and prostate BPH, as well as in the majority of normal prostate tissues tested, but low expression in all other normal tissues.

An additional subtraction was performed by subtracting a normal prostate cDNA library with normal pancreas cDNA (referred to as "prostate subtraction 3"). This led to the identification of six additional clones referred to as 1G-4761, 1G-4762, 1H-4766, 1H-4770, 1H-4771 and 1H-4772 (SEQ ID NOS: 93–98). Comparison of these sequences with those in the gene bank revealed no significant homologies to 1G-4761 and 1H-4771 (SEQ ID NOS: 93 and 97, respectively). Further analysis of the isolated clones led to the determination of extended cDNA sequences for 1G-4761, 1G-4762, 1H-4766 and 1H-4772 provided in SEQ ID NOS: 194–196 and 199, respectively, and to the determination of additional partial cDNA sequences for 1H-4770 and 1H-4771, provided in SEQ ID NOS: 197 and 198, respectively.

Subtraction of a prostate tumor cDNA library, prepared from a pool of polyA+ RNA from three prostate cancer patients, with a normal pancreas cDNA library (prostate subtraction 4) led to the identification of eight clones, referred to as 1D-4297, 1D-4309, 1D.1-4278, 1D-4288, 1D-4283, 1D-4304, 1D-4296 and 1D-4280 (SEQ ID NOS: 99–107). These sequences were compared to those in the gene bank as described above. No significant homologies were found to 1D-4283 and 1D-4304 (SEQ ID NOS: 103 and 104, respectively). Further analysis of the isolated clones led to the determination of extended cDNA sequences for 1D-4309, 1D.1-4278, 1D-4288, 1D-4283, 1D-4304, 1D-4296 and 1D-4280, provided in SEQ ID NOS: 200–206, respectively.

cDNA clones isolated in prostate subtraction 1 and prostate subtraction 2, described above, were colony PCR amplified and their mRNA expression levels in prostate tumor, normal prostate and in various other normal tissues were determined using microarray technology (Synteni, Palo Alto, Calif.). Briefly, the PCR amplification products were dotted onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. This intensity correlates with the hybridization intensity. Two clones (referred to as P509S and P510S) were found to be over-expressed in prostate tumor and normal prostate and expressed at low levels in all other normal tissues tested (liver, pancreas, skin, bone marrow, brain, breast, adrenal gland, bladder, testes, salivary gland, large intestine, kidney, ovary, lung, spinal cord, skeletal muscle and colon). The determined cDNA sequences for P509S and P510S are provided in SEQ ID NO: 223 and 224, respectively. Comparison of these sequences with those in the gene bank as described above, revealed some homology to previously identified ESTs.

Additional, studies led to the isolation of the full-length cDNA sequence for P509S. This sequence is provided in SEQ ID NO: 332, with the corresponding predicted amino acid sequence being provided in SEQ ID NO: 339. Two variant full-length cDNA sequences for P510S are provided in SEQ ID NO: 535 and 536, with the corresponding predicted amino acid sequences being provided in SEQ ID NO: 537 and 538, respectively.

Example 2

Determination of Tissue Specificity of Prostate-Specific Polypeptides

Using gene specific primers, mRNA expression levels for the representative prostate-specific polypeptides F1-16, H1-1, J1-17 (also referred to as P502S), L1-12 (also referred to as P501 S), F1-12 (also referred to as P504S) and N1-1862 (also referred to as P503S) were examined in a variety of normal and tumor tissues using RT-PCR.

Briefly, total RNA was extracted from a variety of normal and tumor tissues using Trizol reagent as described above. First strand synthesis was carried out using 1–2 μg of total RNA with SuperScript II reverse transcriptase (BRL Life Technologies) at 42° C. for one hour. The cDNA was then amplified by PCR with gene-specific primers. To ensure the semi-quantitative nature of the RT-PCR, β-actin was used as an internal control for each of the tissues examined. First, serial dilutions of the first strand cDNAs were prepared and RT-PCR assays were performed using β-actin specific primers. A dilution was then chosen that enabled the linear range amplification of the β-actin template and which was sensitive enough to reflect the differences in the initial copy numbers. Using these conditions, the β-actin levels were determined for each reverse transcription reaction from each tissue. DNA contamination was minimized by DNase treatment and by assuring a negative PCR result when using first strand cDNA that was prepared without adding reverse transcriptase.

mRNA Expression levels were examined in four different types of tumor tissue (prostate tumor from 2 patients, breast tumor from 3 patients, colon tumor, lung tumor), and sixteen different normal tissues, including prostate, colon, kidney, liver, lung, ovary, pancreas, skeletal muscle, skin, stomach, testes, bone marrow and brain. F1-16 was found to be expressed at high levels in prostate tumor tissue, colon tumor and normal prostate, and at lower levels in normal liver, skin and testes, with expression being undetectable in the other tissues examined. H1-1 was found to be expressed at high levels in prostate tumor, lung tumor, breast tumor, normal prostate, normal colon and normal brain, at much lower levels in normal lung, pancreas, skeletal muscle, skin, small intestine, bone marrow, and was not detected in the other tissues tested. J1-17 (P502S) and L1-12 (P501S) appear to be specifically over-expressed in prostate, with both genes being expressed at high levels in prostate tumor and normal prostate but at low to undetectable levels in all the other tissues examined. N1-1862 (P503S) was found to be over-expressed in 60% of prostate tumors and detectable in normal colon and kidney. The RT-PCR results thus indicate that F1-16, H1-1, J1-17 (P502S), N1-1862 (P503S) and L1-12 (P501S) are either prostate specific or are expressed at significantly elevated levels in prostate.

Further RT-PCR studies showed that F1-12 (P504S) is over-expressed in 60% of prostate tumors, detectable in normal kidney but not detectable in all other tissues tested. Similarly, R1-2330 was shown to be over-expressed in 40% of prostate tumors, detectable in normal kidney and liver, but not detectable in all other tissues tested. U1-3064 was found to be over-expressed in 60% of prostate tumors, and also expressed in breast and colon tumors, but was not detectable in normal tissues.

RT-PCR characterization of R1-2330, U1-3064 and 1D-4279 showed that these three antigens are over-expressed in prostate and/or prostate tumors.

Northern analysis with four prostate tumors, two normal prostate samples, two BPH prostates, and normal colon, kidney, liver, lung, pancrease, skeletal muscle, brain, stomach, testes, small intestine and bone marrow, showed that L1-12 (P501 S) is over-expressed in prostate tumors and normal prostate, while being undetectable in other normal tissues tested. J1-17 (P502S) was detected in two prostate tumors and not in the other tissues tested. N1-1862 (P503 S) was found to be over-expressed in three prostate tumors and to be expressed in normal prostate, colon and kidney, but not in other tissues tested. F1-12 (P504S) was found to be highly expressed in two prostate tumors and to be undetectable in all other tissues tested.

The microarray technology described above was used to determine the expression levels of representative antigens described herein in prostate tumor, breast tumor and the following normal tissues: prostate, liver, pancreas, skin, bone marrow, brain, breast, adrenal gland, bladder, testes, salivary gland, large intestine, kidney, ovary, lung, spinal cord, skeletal muscle and colon. L1-12 (P501 S) was found to be over-expressed in normal prostate and prostate tumor, with some expression being detected in normal skeletal muscle. Both J1-12 and F1-12 (P504S) were found to be over-expressed in prostate tumor, with expression being lower or undetectable in all other tissues tested. N1-1862 (P503) was found to be expressed at high levels in prostate tumor and normal prostate, and at low levels in normal large intestine and normal colon, with expression being undetectable in all other tissues tested. R1-2330 was found to be over-expressed in prostate tumor and normal prostate, and to be expressed at lower levels in all other tissues tested. 1D-4279 was found to be over-expressed in prostate tumor and normal prostate, expressed at lower levels in normal spinal cord, and to be undetectable in all other tissues tested.

Further microarray analysis to specifically address the extent to which P501S (SEQ ID NO: 110) was expressed in breast tumor revealed moderate over-expression not only in breast tumor, but also in metastatic breast tumor (2/31), with negligible to low expression in normal tissues. This data suggests that P501 S may be over-expressed in various breast tumors as well as in prostate tumors.

The expression levels of 32 ESTs (expressed sequence tags) described by Vasmatzis et al. (*Proc. Natl. Acad. Sci. USA* 95:300–304, 1998) in a variety of tumor and normal tissues were examined by microarray technology as described above. Two of these clones (referred to as P1000C and P1001 C) were found to be over-expressed in prostate tumor and normal prostate, and expressed at low to undetectable levels in all other tissues tested (normal aorta, thymus, resting and activated PBMC, epithelial cells, spinal cord, adrenal gland, fetal tissues, skin, salivary gland, large intestine, bone marrow, liver, lung, dendritic cells, stomach, lymph nodes, brain, heart, small intestine, skeletal muscle, color, and kidney. The determined cDNA sequences for P1000C and P1001C are provided in SEQ ID NO: 384 and 472, respectively. The sequence of P1001C was found to show some homology to the previously isolated Human mRNA for JM27 protein. No significant homologies were found to the sequence of P1000C.

The expression of the polypeptide encoded by the full length cDNA sequence for F1-12 (also referred to as P504S; SEQ ID NO: 108) was investigated by immunohistochemical analysis. Rabbit-anti-P504S polyclonal antibodies were generated against the full length P504S protein by standard techniques. Subsequent isolation and characterization of the polyclonal antibodies were also performed by techniques well known in the art. Immunohistochemical analysis showed that the P504S polypeptide was expressed in 100% of prostate carcinoma samples tested (n=5).

The rabbit-anti-P504S polyclonal antibody did not appear to label benign prostate cells with the same cytoplasmic granular staining, but rather with light nuclear staining. Analysis of normal tissues revealed that the encoded polypeptide was found to be expressed in some, but not all normal human tissues. Positive cytoplasmic staining with rabbit-anti-P504S polyclonal antibody was found in normal human kidney, liver, brain, colon and lung-associated macrophages, whereas heart and bone marrow were negative.

This data indicates that the P504S polypeptide is present in prostate cancer tissues, and that there are qualitative and quantitative differences in the staining between benign prostatic hyperplasia tissues and prostate cancer tissues, suggesting that this polypeptide may be detected selectively in prostate tumors and therefore be useful in the diagnosis of prostate cancer.

Example 3

Isolation and Characterization of Prostate-Specific Polypeptides by PCR-Based Subtraction A cDNA subtraction library, containing cDNA from normal prostate subtracted with ten other normal tissue cDNAs (brain, heart, kidney, liver, lung, ovary, placenta, skeletal muscle, spleen and thymus) and then submitted to a first round of PCR amplification, was purchased from Clontech. This library was subjected to a second round of PCR amplification, following the manufacturer's protocol. The resulting cDNA fragments were subcloned into the vector pT7 Blue T-vector (Novagen, Madison, Wis.) and transformed into XL-1 Blue MRF' *E coli* (Stratagene). DNA was isolated from independent clones and sequenced using a Perkin Elmer/Applied Biosystems Division Automated Sequencer Model 373A.

Fifty-nine positive clones were sequenced. Comparison of the DNA sequences of these clones with those in the gene bank, as described above, revealed no significant homologies to 25 of these clones, hereinafter referred to as P5, P8, P9, P18, P20, P30, P34, P36, P38, P39, P42, P49, P50, P53, P55, P60, P64, P65, P73, P75, P76, P79 and P84. The determined cDNA sequences for these clones are provided in SEQ ID NO: 41–45, 47–52 and 54–65, respectively. P29, P47, P68, P80 and P82 (SEQ ID NO: 46, 53 and 66–68, respectively) were found to show some degree of homology to previously identified DNA sequences. To the best of the inventors' knowledge, none of these sequences have been previously shown to be present in prostate.

Further studies using the PCR-based methodology described above resulted in the isolation of more than 180 additional clones, of which 23 clones were found to show no significant homologies to known sequences. The determined cDNA sequences for these clones are provided in SEQ ID NO: 115–123, 127, 131, 137, 145, 147–151, 153, 156–158 and 160. Twenty-three clones (SEQ ID NO: 124–126, 128–130, 132–136, 138–144, 146, 152, 154, 155 and 159) were found to show some homology to previously identified ESTs. An additional ten clones (SEQ ID NO: 161–170) were found to have some degree of homology to known genes. Larger cDNA clones containing the P20 sequence represent splice variants of a gene referred to as P703P. The determined DNA sequence for the variants referred to as DE1, DE13 and DE14 are provided in SEQ ID NOS: 171, 175 and 177, respectively, with the corresponding predicted amino acid sequences being provided in SEQ ID NO: 172, 176 and 178, respectively. The determined cDNA sequence for an extended spliced form of P703 is provided in SEQ ID NO: 225. The DNA sequences for the splice variants referred to as DE2 and DE6 are provided in SEQ ID NOS: 173 and 174, respectively.

mRNA Expression levels for representative clones in tumor tissues (prostate (n=5), breast (n=2), colon and lung) normal tissues (prostate (n=5), colon, kidney, liver, lung (n=2), ovary (n=2), skeletal muscle, skin, stomach, small intestine and brain), and activated and non-activated PBMC was determined by RT-PCR as described above. Expression was examined in one sample of each tissue type unless otherwise indicated.

P9 was found to be highly expressed in normal prostate and prostate tumor compared to all normal tissues tested except for normal colon which showed comparable expression. P20, a portion of the P703P gene, was found to be highly expressed in normal prostate and prostate tumor, compared to all twelve normal tissues tested. A modest increase in expression of P20 in breast tumor (n=2), colon tumor and lung tumor was seen compared to all normal tissues except lung (1 of 2). Increased expression of P18 was found in normal prostate, prostate tumor and breast tumor compared to other normal tissues except lung and stomach. A modest increase in expression of P5 was observed in normal prostate compared to most other normal tissues. However, some elevated expression was seen in normal lung and PBMC. Elevated expression of P5 was also observed in prostate tumors (2 of 5), breast tumor and one lung tumor sample. For P30, similar expression levels were seen in normal prostate and prostate tumor, compared to six of twelve other normal tissues tested. Increased expression was seen in breast tumors, one lung tumor sample and one colon tumor sample, and also in normal PBMC. P29 was found to be over-expressed in prostate tumor (5 of 5) and normal prostate (5 of 5) compared to the majority of normal tissues. However, substantial expression of P29 was observed in normal colon and normal lung (2 of 2). P80 was found to be over-expressed in prostate tumor (5 of 5) and normal prostate (5 of 5) compared to all other normal tissues tested, with increased expression also being seen in colon tumor.

Further studies resulted in the isolation of twelve additional clones, hereinafter referred to as 10-d8,10-h10, 11-c8, 7-g6,8-b5,8-b6,8-d4,8-d9,8-g3,8-h11,9-f12 and 9-f3. The determined DNA sequences for 10-d8,10-h10, 11-c8, 8-d4, 8-d9,8-h11, 9-f12 and 9-f3 are provided in SEQ ID NO: 207, 208, 209, 216, 217, 220, 221 and 222, respectively. The determined forward and reverse DNA sequences for 7-g6, 8-b5,8-b6 and 8-g3 are provided in SEQ ID NO: 210 and 211; 212 and 213; 214 and 215; and 218 and 219, respectively. Comparison of these sequences with those in the gene bank revealed no significant homologies to the sequence of 9-f3. The clones 10-d8, 11-c8 and 8-h11 were found to show some homology to previously isolated ESTs, while 10-h10, 8-b5, 8-b6, 8-d4, 8-d9, 8-g3 and 9-F12 were found to show some homology to previously identified genes. Further characterization of 7-G6 and 8-G3 showed identity to the known genes PAP and PSA, respectively.

mRNA expression levels for these clones were determined using the micro-array technology described above. The clones 7-G6, 8-G3, 8-B5, 8-B6, 8-D4, 8-D9, 9-F3, 9-F12, 9-H3, 10-A2, 10-A4, 11-C9 and 11-F2 were found to be over-expressed in prostate tumor and normal prostate, with expression in other tissues tested being low or undetectable. Increased expression of 8-F 11 was seen in prostate tumor and normal prostate, bladder, skeletal muscle and colon. Increased expression of 10-H10 was seen in prostate tumor and normal prostate, bladder, lung, colon, brain and large intestine. Increased expression of 9-BI was seen in prostate tumor, breast tumor, and normal prostate, salivary gland, large intestine and skin, with increased expression of 11-C8 being seen in prostate tumor, and normal prostate and large intestine.

An additional cDNA fragment derived from the PCR-based normal prostate subtraction, described above, was found to be prostate specific by both micro-array technology and RT-PCR. The determined cDNA sequence of this clone (referred to as 9-A11) is provided in SEQ ID NO: 226. Comparison of this sequence with those in the public databases revealed 99% identity to the known gene HOXB13.

Further studies led to the isolation of the clones 8-C6 and 8-H7. The determined cDNA sequences for these clones are provided in SEQ ID NO: 227 and 228, respectively. These sequences were found to show some homology to previously isolated ESTs.

PCR and hybridization-based methodologies were employed to obtain longer cDNA sequences for clone P20 (also referred to as P703P), yielding three additional cDNA fragments that progressively extend the 5' end of the gene. These fragments, referred to as P703PDE5, P703P6.26, and P703PX-23 (SEQ ID NO: 326, 328 and 330, with the predicted corresponding amino acid sequences being provided in SEQ ID NO: 327, 329 and 331, respectively) contain additional 5' sequence. P703PDE5 was recovered by screening of a cDNA library (#141–26) with a portion of P703P as a probe. P703P6.26 was recovered from a mixture of three prostate tumor cDNAs and P703PX_23 was recovered from cDNA library (#438–48). Together, the additional sequences include all of the putative mature serine protease along with part of the putative signal sequence. The putative full-length cDNA sequence for P703P is provided in SEQ ID NO: 524, with the corresponding predicted amino acid sequence being provided in SEQ ID NO: 525.

Further studies using a PCR-based subtraction library of a prostate tumor pool subtracted against a pool of normal tissues (referred to as JP: PCR subtraction) resulted in the isolation of thirteen additional clones, seven of which did not share any significant homology to known GENBANK™ sequences. The determined cDNA sequences for these seven clones (P711P, P712P, novel 23, P774P, P775P, P710P and P768P) are provided in SEQ ID NO: 307–311, 313 and 315, respectively. The remaining six clones (SEQ ID NO: 316 and 321–325) were shown to share some homology to known genes. By microarray analysis, all thirteen clones showed three or more fold over-expression in prostate tissues, including prostate tumors, BPH and normal prostate as compared to normal non-prostate tissues. Clones P711P, P712P, novel 23 and P768P showed over-expression in most prostate tumors and BPH tissues tested (n=29), and in the majority of normal prostate tissues (n=4), but background to low expression levels in all normal tissues. Clones P774P, P775P and P710P showed comparatively lower expression and expression in fewer prostate tumors and BPH samples, with negative to low expression in normal prostate.

The full-length cDNA for P711P was obtained by employing the partial sequence of SEQ ID NO: 307 to screen a prostate cDNA library. Specifically, a directionally cloned prostate cDNA library was prepared using standard techniques. One million colonies of this library were plated onto LB/Amp plates. Nylon membrane filters were used to lift these colonies, and the cDNAs which were picked up by these filters were denatured and cross-linked to the filters by UV light. The P711P cDNA fragment of SEQ ID NO: 307 was radio-labeled and used to hybridize with these filters. Positive clones were selected, and cDNAs were prepared and sequenced using an automatic Perkin Elmer/Applied Biosystems sequencer. The determined full-length sequence of P711P is provided in SEQ ID NO: 382, with the corresponding predicted amino acid sequence being provided in SEQ ID NO: 383.

Using PCR and hybridization-based methodologies, additional cDNA sequence information was derived for two clones described above, 11-C9 and 9-F3, herein after referred to as P707P and P714P, respectively (SEQ ID NO: 333 and 334). After comparison with the most recent GENBANK™, P707P was found to be a splice variant of the known gene HoxB13. In contrast, no significant homologies to P714P were found.

Clones 8-B3, P89, P98, P130 and P201 (as disclosed in U.S. patent application Ser. No. 09/020,956, filed Feb. 9, 1998) were found to be contained within one contiguous sequence, referred to as P705P (SEQ ID NO: 335, with the predicted amino acid sequence provided in SEQ ID NO: 336), which was determined to be a splice variant of the known gene NKX 3.1.

Further studies on P775P resulted in the isolation of four additional sequences (SEQ ID NO: 473–476) which are all splice variants of the P775P gene. The sequence of SEQ ID NO: 474 was found to contain two open reading frames (ORFs). The predicted amino acid sequences encoded by these ORFs are provided in SEQ ID NO: 477 and 478. The cDNA sequence of SEQ ID NO: 475 was found to contain an ORF which encodes the amino acid sequence of SEQ ID NO: 479. The cDNA sequence of SEQ ID NO: 473 was found to contain four ORFs. The predicted amino acid sequences encoded by these ORFs are provided in SEQ ID NO: 480–483.

Subsequent studies led to the identification of a genomic region on chromosome 22q 11.2, known as the Cat Eye Syndrome region, that contains the five prostate genes P704P, P712P, P774P, P775P and B305D. The relative location of each of these five genes within the genomic region is shown in FIG. 10. This region may therefore be associated with malignant tumors, and other potential tumor genes may be contained within this region. These studies also led to the identification of a potential open reading frame (ORF) for P775P (provided in SEQ ID NO: 533), which encodes the amino acid sequence of SEQ ID NO: 534.

Example 4

Synthesis of Polypeptides

Polypeptides may be synthesized on a Perkin Elmer/Applied Biosystems 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid: ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

Example 5

Further Isolation and Characterization of Prostate-Specific Polypeptides by PCR-Based Subtraction A cDNA library generated from prostate primary tumor mRNA as described above was subtracted with cDNA from normal prostate. The subtraction was performed using a PCR-based protocol (Clontech), which was modified to generate larger fragments. Within this protocol, tester and driver double stranded cDNA were separately digested with five restriction enzymes that recognize six-nucleotide restriction sites (MluI, MscI, PvuII, SalI and StuI). This digestion resulted in an average cDNA size of 600 bp, rather than the average size of 300 bp that results from digestion with RsaI according to the Clontech protocol. This modification did not affect the subtraction efficiency. Two tester populations were then created with different adapters, and the driver library remained without adapters.

The tester and driver libraries were then hybridized using excess driver cDNA. In the first hybridization step, driver was separately hybridized with each of the two tester cDNA populations. This resulted in populations of (a) unhybridized tester cDNAs, (b) tester cDNAs hybridized to other tester cDNAs, (c) tester cDNAs hybridized to driver cDNAs and (d) unhybridized driver cDNAs. The two separate hybridization reactions were then combined, and rehybridized in the presence of additional denatured driver cDNA. Following this second hybridization, in addition to populations (a) through (d), a fifth population (e) was generated in which tester cDNA with one adapter hybridized to tester cDNA with the second adapter. Accordingly, the second hybridization step resulted in enrichment of differentially expressed sequences which could be used as templates for PCR amplification with adaptor-specific primers.

The ends were then filled in, and PCR amplification was performed using adaptor-specific primers. Only population (e), which contained tester cDNA that did not hybridize to driver cDNA, was amplified exponentially. A second PCR amplification step was then performed, to reduce background and further enrich differentially expressed sequences.

This PCR-based subtraction technique normalizes differentially expressed cDNAs so that rare transcripts that are overexpressed in prostate tumor tissue may be recoverable. Such transcripts would be difficult to recover by traditional subtraction methods.

In addition to genes known to be overexpressed in prostate tumor, seventy-seven further clones were identified. Sequences of these partial cDNAs are provided in SEQ ID NO: 29 to 305. Most of these clones had no significant homology to database sequences. Exceptions were JPTPN23 (SEQ ID NO: 231; similarity to pig valosin-containing protein), JPTPN30 (SEQ ID NO: 234; similarity to rat mRNA for proteasome subunit), JPTPN45 (SEQ ID NO: 243; similarity to rat norvegicus cytosolic NADP-dependent isocitrate dehydrogenase), JPTPN46 (SEQ ID NO: 244; similarity to human subclone H84 d4 DNA sequence), JP1D6 (SEQ ID NO: 265; similarity to *G. gallus* dynein light chain-A), JP8D6 (SEQ ID NO: 288; similarity to human BAC clone RG016J04), JP8F5 (SEQ ID NO: 289; similarity to human subclone H83 b5 DNA sequence), and JP8E9 (SEQ ID NO: 299; similarity to human Alu sequence).

Additional studies using the PCR-based subtraction library consisting of a prostate tumor pool subtracted against a normal prostate pool (referred to as PT-PN PCR subtraction) yielded three additional clones. Comparison of the cDNA sequences of these clones with the most recent release of GENBANK™ revealed no significant homologies to the two clones referred to as P715P and P767P (SEQ ID NO: 312 and 314). The remaining clone was found to show some homology to the known gene KIAA0056 (SEQ ID NO: 318). Using microarray analysis to measure mRNA expression levels in various tissues, all three clones were found to be over-expressed in prostate tumors and BPH tissues. Specifically, clone P715P was over-expressed in most prostate tumors and BPH tissues by a factor of three or greater, with elevated expression seen in the majority of normal prostate samples and in fetal tissue, but negative to low expression in all other normal tissues. Clone P767P was over-expressed in several prostate tumors and BPH tissues, with moderate expression levels in half of the normal prostate samples, and background to low expression in all other normal tissues tested.

Further analysis, by microarray as described above, of the PT-PN PCR subtraction library and of a DNA subtraction library containing cDNA from prostate tumor subtracted with a pool of normal tissue cDNAs, led to the isolation of 27 additional clones (SEQ ID NO: 340–365 and 381) which were determined to be over-expressed in prostate tumor. The clones of SEQ ID NO: 341, 342, 345, 347, 348, 349, 351, 355–359, 361, 362 and 364 were also found to be expressed in normal prostate. Expression of all 26 clones in a variety of normal tissues was found to be low or undetectable, with the exception of P544S (SEQ ID NO: 356) which was found to be expressed in small intestine. Of the 26 clones, 10 (SEQ ID NO: 340–349) were found to show some homology to previously identified sequences. No significant homologies were found to the clones of SEQ ID NO: 350, 351 and 353–365.

Further studies on the clone of SEQ ID NO: 352 (referred to as P790P) led to the isolation of the full-length cDNA sequence of SEQ ID NO: 526. The corresponding predicted amino acid is provided in SEQ ID NO: 527. Data from two quantitative PCR experiments indicated that P790P is over-expressed in 11/15 tested prostate tumor samples and is expressed at low levels in spinal cord, with no expression being seen in all other normal samples tested. Data from further PCR experiments and microarray experiments showed over-expression in normal prostate and prostate tumor with little or no expression in other tissues tested. P790P was subsequently found to show significant homology to a previously identified G-protein coupled prostate tissue receptor.

Example 6

Peptide Priming of Mice and Propagation of CTL Lines 6.1. This Example illustrates the preparation of a CTL cell line specific for cells expressing the P502S gene.

Mice expressing the transgene for human HLA A2 Kb (provided by Dr L. Sherman, The Scripps Research Institute, La Jolla, Calif.) were immunized with P2S# 12 peptide (VLGWVAEL; SEQ ID NO: 306), which is derived from the P502S gene (also referred to herein as J1-17, SEQ ID NO: 8), as described by Theobald et al., *Proc. Natl. Acad. Sci. USA* 92:11993–11997, 1995 with the following modifications. Mice were immunized with 100 μg of P2S#12 and 120 μg of an I-$A^b$ binding peptide derived from hepatitis B Virus protein emulsified in incomplete Freund's adjuvant. Three weeks later these mice were sacrificed and using a nylon mesh single cell suspensions prepared. Cells were then resuspended at $6\times10^6$ cells/ml in complete media (RPMI-1640; Gibco BRL, Gaithersburg, Md.) containing 10% FCS, 2 mM Glutamine (Gibco BRL), sodium pyruvate (Gibco BRL), non-essential amino acids (Gibco BRL), $2\times10^{-5}$ M 2-mercaptoethanol, 50 U/ml penicillin and streptomycin, and cultured in the presence of irradiated (3000 rads) P2S#12-pulsed (5 mg/ml P2S#12 and 10 mg/ml β2-microglobulin) LPS blasts (A2 transgenic spleens cells cultured in the presence of 7 μg/ml dextran sulfate and 25 μg/ml LPS for 3 days). Six days later, cells ($5\times10^5$/ml) were restimulated with $2.5\times10^6$/ml peptide pulsed irradiated (20,000 rads) EL4A2 Kb cells (Sherman et al, *Science* 258:815–818, 1992) and $3\times10^6$/ml A2 transgenic spleen feeder cells. Cells were cultured in the presence of 20 U/ml IL-2. Cells continued to be restimulated on a weekly basis as described, in preparation for cloning the line.

Figure 1:
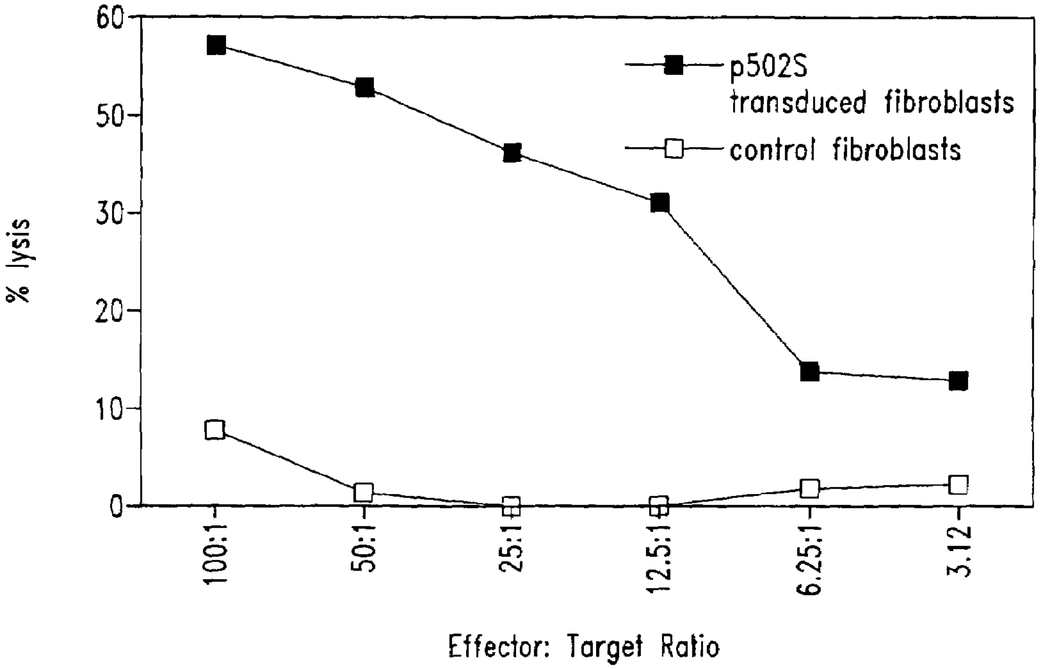

P2S#12 line was cloned by limiting dilution analysis with peptide pulsed EL4 A2 Kb tumor cells ($1\times10^4$ cells/well) as stimulators and A2 transgenic spleen cells as feeders ($5\times10^5$ cells/well) grown in the presence of 30 U/ml IL-2. On day 14, cells were restimulated as before. On day 21, clones that were growing were isolated and maintained in culture. Several of these clones demonstrated significantly higher reactivity (lysis) against human fibroblasts (HLA A2 Kb expressing) transduced with P502S than against control fibroblasts. An example is presented in FIG. 1.

This data indicates that P2S #12 represents a naturally processed epitope of the P502S protein that is expressed in the context of the human HLA A2 Kb molecule.

6.2. This Example illustrates the preparation of murine CTL lines and CTL clones specific for cells expressing the P501S gene.

Figure 3:
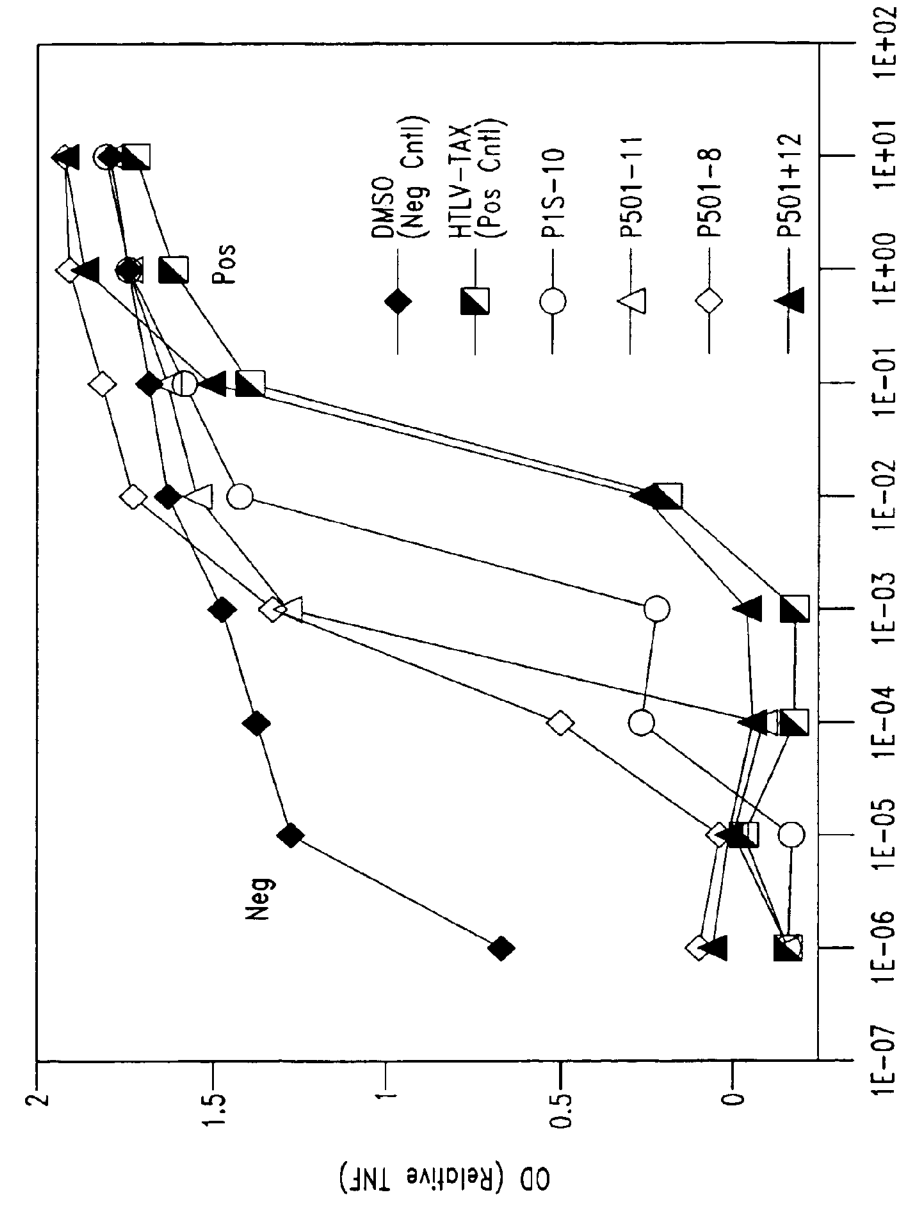

This series of experiments were performed similarly to that described above. Mice were immunized with the P1S#10 peptide (SEQ ID NO: 337), which is derived from the P501S gene (also referred to herein as L1-12, SEQ ID NO: 110). The P1S#10 peptide was derived by analysis of the predicted polypeptide sequence for P501S for potential HLA-A2 binding sequences as defined by published HLA-A2 binding motifs (Parker, K C, et al, *J. Immunol.,* 152:163, 1994). P1S#10 peptide was synthesized as described in Example 4, and empirically tested for HLA-A2 binding using a T cell based competition assay. Predicted A2 binding peptides were tested for their ability to compete HLA-A2 specific peptide presentation to an HLA-A2 restricted CTL clone (D150M58), which is specific for the HLA-A2 binding influenza matrix peptide fluM58. D150M58 CTL secretes TNF in response to self-presentation of peptide fluM58. In the competition assay, test peptides at 100–200 μg/ml were added to cultures of Dl 50M58 CTL in order to bind HLA-A2 on the CTL. After thirty minutes, CTL cultured with test peptides, or control peptides, were tested for their antigen dose response to the fluM58 peptide in a standard TNF bioassay. As shown in FIG. 3, peptide P1 S#10 competes HLA-A2 restricted presentation of fluM58, demonstrating that peptide P1S#10 binds HLA-A2.

Figure 4:
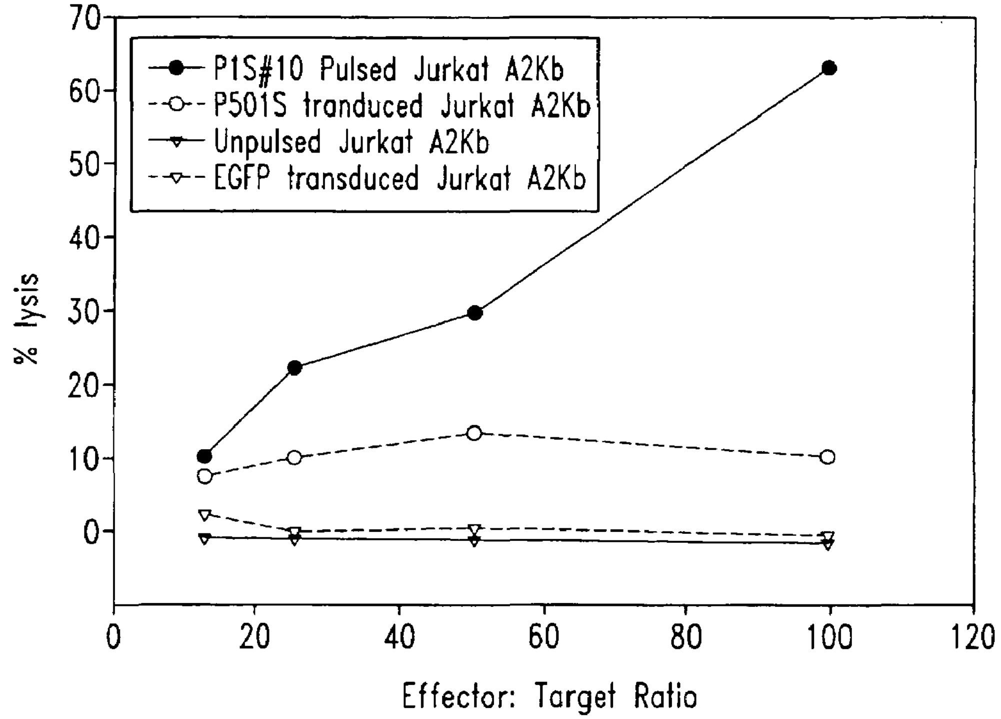
FIG. 4 illustrates the ability of T cell lines generated from P1 S#10 immunized mice to specifically lyse P1 S#10-pulsed Jurkat A2 Kb targets and P501 S-transduced Jurkat A2 Kb targets, as compared to EGFP-transduced Jurkat A2 Kb. The percent lysis is shown as a series of effector to target ratios, as indicated.

Mice expressing the transgene for human HLA A2 Kb were immunized as described by Theobald et al. (*Proc. Natl. Acad. Sci. USA* 92:11993–11997, 1995) with the following modifications. Mice were immunized with 62.5 μg of PIS #10 and 120 μg of an I-Ab binding peptide derived from Hepatitis B Virus protein emulsified in incomplete Freund's adjuvant. Three weeks later these mice were sacrificed and single cell suspensions prepared using a nylon mesh. Cells were then resuspended at $6\times10^6$ cells/ml in complete media (as described above) and cultured in the presence of irradiated (3000 rads) P1S#10-pulsed (2 μg/ml P1S#10 and 10 mg/ml β2-microglobulin) LPS blasts (A2 transgenic spleens cells cultured in the presence of 7 μg/ml dextran sulfate and 25 μg/ml LPS for 3 days). Six days later cells ($5\times10^5$/ml) were restimulated with $2.5\times10^6$/ml peptide-pulsed irradiated (20,000 rads) EL4A2 Kb cells, as described above, and $3\times10^6$/ml A2 transgenic spleen feeder cells. Cells were cultured in the presence of 20 U/ml IL-2. Cells were restimulated on a weekly basis in preparation for cloning. After three rounds of in vitro stimulations, one line was generated that recognized P1S#10-pulsed Jurkat A2 Kb targets and P501 S-transduced Jurkat targets as shown in FIG. 4.

Figure 5:
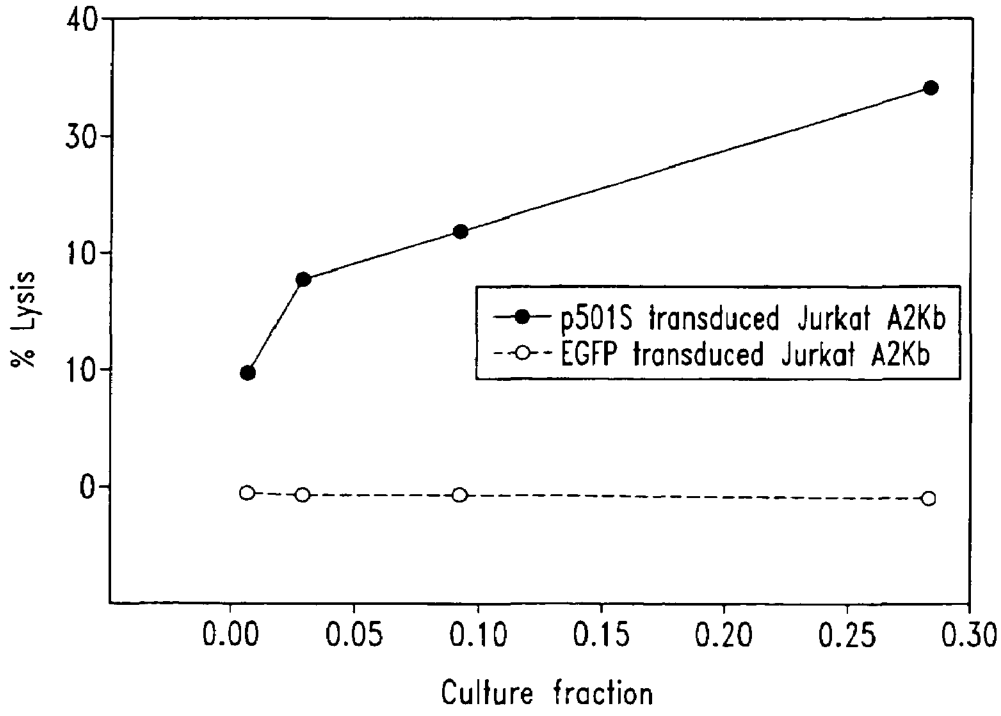
FIG. 5 illustrates the ability of a T cell clone to recognize and specifically lyse Jurkat A2 Kb cells expressing the representative prostate-specific polypeptide P501 S, thereby demonstrating that the P1S#10 peptide may be a naturally processed epitope of the P501S polypeptide.

A P1S#10-specific CTL line was cloned by limiting dilution analysis with peptide pulsed EL4 A2 Kb tumor cells ($1\times10^4$ cells/well) as stimulators and A2 transgenic spleen cells as feeders ($5\times10^5$ cells/well) grown in the presence of 30 U/ml IL-2. On day 14, cells were restimulated as before. On day 21, viable clones were isolated and maintained in culture. As shown in FIG. 5, five of these clones demonstrated specific cytolytic reactivity against P501 S-transduced Jurkat A2 Kb targets. This data indicates that PI S#10 represents a naturally processed epitope of the P501 S protein that is expressed in the context of the human HLA-A2.1 molecule.

Example 7

Priming of CTL In Vivo Using Naked DNA Immunization with a Prostate Antigen

The prostate-specific antigen L1-12, as described above, is also referred to as P501 S. HLA A2 Kb μg mice (provided by Dr L. Sherman, The Scripps Research Institute, La Jolla, Calif.) were immunized with 100 μg P501S in the vector VR1012 either intramuscularly or intradermally. The mice were immunized three times, with a two week interval between immunizations. Two weeks after the last immunization, immune spleen cells were cultured with Jurkat A2 Kb-P501S transduced stimulator cells. CTL lines were stimulated weekly. After two weeks of in vitro stimulation, CTL activity was assessed against P501S transduced targets. Two out of 8 mice developed strong anti-P501S CTL responses. These results demonstrate that P501S contains at least one naturally processed HLA-A2-restricted CTL epitope.

Example 8

Ability of Human T Cells to Recognize Prostate-Specific Polypeptides

This Example illustrates the ability of T cells specific for a prostate tumor polypeptide to recognize human tumor.

Figure 2A:
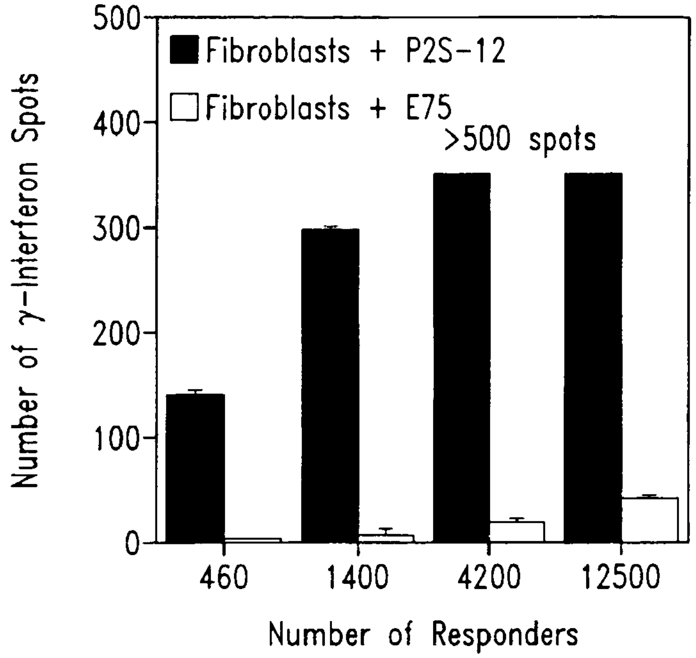
Figure 2B:
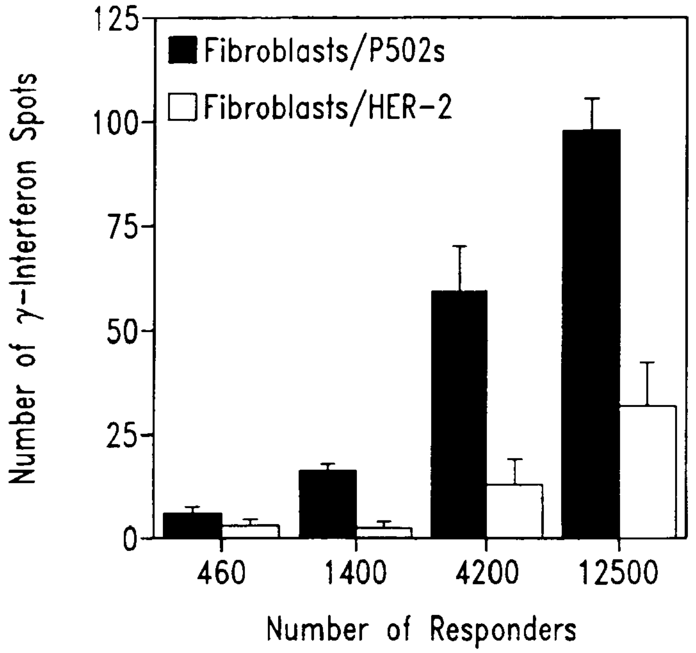

Human CD8' T cells were primed in vitro to the P2s-12 peptide (SEQ ID NO: 306) derived from P502S (also referred to as J1-17) using dendritic cells according to the protocol of Van Tsai et al. (*Critical Reviews in Immunology* 18:65–75, 1998). The resulting CD8+ T cell microcultures were tested for their ability to recognize the P2S-12 peptide presented by autologous fibroblasts or fibroblasts which were transduced to express the P502S gene in a γ-interferon ELISPOT assay (see Lalvani et al., *J. Exp. Med.* 186: 859–865, 1997). Briefly, titrating numbers of T cells were assayed in duplicate on $10^4$ fibroblasts in the presence of 3 μg/ml human 2-microglobulin and 1 μg/ml $P2S^{12}$ peptide or control E75 peptide. In addition, T cells were simultaneously assayed on autologous fibroblasts transduced with the P502S gene or as a control, fibroblasts transduced with HER-2/neu. Prior to the assay, the fibroblasts were treated with 10 ng/ml γ-interferon for 48 hours to upregulate class I MHC expression. One of the microcultures (#5) demonstrated strong recognition of both peptide pulsed fibroblasts as well as transduced fibroblasts in a γ-interferon ELISPOT assay. FIG. 2A demonstrates that there was a strong increase in the number of γ-interferon spots with increasing numbers of T cells on fibroblasts pulsed with the P2S-12 peptide (solid bars) but not with the control E75 peptide (open bars). This shows the ability of these T cells to specifically recognize the P2S-12 peptide. As shown in FIG. 2B, this microculture also demonstrated an increase in the number of γ-interferon spots with increasing numbers of T cells on fibroblasts transduced to express the P502S gene but not the HER-2/neu gene. These results provide additional confirmatory evidence that the P2S-12 peptide is a naturally processed epitope of the P502S protein. Furthermore, this also demonstrates that there exists in the human T cell repertoire, high affinity T cells which are capable of recognizing this epitope. These T cells should also be capable of recognizing human tumors which express the P502S gene.

Example 9

Elicitation of Prostate Antigen-Specific CTL Responses in Human Blood

This Example illustrates the ability of a prostate-specific antigen to elicit a CTL response in blood of normal humans.

Autologous dendritic cells (DC) were differentiated from monocyte cultures derived from PBMC of normal donors by growth for five days in RPMI medium containing 10% human serum, 50 ng/ml GMCSF and 30 ng/ml IL-4. Following culture, DC were infected overnight with recombinant P501S-expressing vaccinia virus at an M.O.I. of 5 and matured for 8 hours by the addition of 2 micrograms/ml $CD^{+8}$ ligand. Virus was inactivated by UV irradiation, $CD^{8+}$ cells were isolated by positive selection using magnetic beads, and priming cultures were initiated in 24-well plates. Following five stimulation cycles using autologous fibroblasts retrovirally transduced to express P501S and CD80, CD8+ lines were identified that specifically produced interferon-gamma when stimulated with autologous P501S-transduced fibroblasts. The P501 S-specific activity of cell line 3A-1 could be maintained following additional stimulation cycles on autologous B-LCL transduced with P501 S. Line 3A-1 was shown to specifically recognize autologous B-LCL transduced to express P501 S, but not EGFP-transduced autologous B-LCL, as measured by cytotoxicity assays ($^{51}Cr$ release) and-interferon-gamma production (Interferon-gamma Elispot; see above and Lalvani et al., *J. Exp. Med* 186:859–865, 1997). The results of these assays are presented in FIGS. 6A and 6B.

Example 10

Identification of a Naturally Processed CTL Epitope Contained within a Prostate-Specific Antigen The 9-mer peptide p5 (SEQ ID NO: 338) was derived from the P703P antigen (also referred to as P20). The p5 peptide is immunogenic in human HLA-A2 donors and is a naturally processed epitope. Antigen specific human CD8+ T cells can be primed following repeated in vitro stimulations with monocytes pulsed with p5 peptide. These CTL specifically recognize p5-pulsed and P703P-transduced target cells in both ELISPOT (as described above) and chromium release assays. Additionally, immunization of HLA-A2 Kb transgenic mice with p5 leads to the generation of CTL lines which recognize a variety of HLA-A2 Kb or HLA-A2 transduced target cells expressing P703P.

Initial studies demonstrating that p5 is a naturally processed epitope were done using HLA-A2 Kb transgenic mice. HLA-A2 Kb transgenic mice were immunized subcutaneously in the footpad with 100 μg of p5 peptide together with 140 μg of hepatitis B virus core peptide (a Th peptide) in Freund's incomplete adjuvant. Three weeks post immunization, spleen cells from immunized mice were stimulated in vitro with peptide-pulsed LPS blasts. CTL activity was assessed by chromium release assay five days after primary in vitro stimulation. Retrovirally transduced cells expressing the control antigen P703P and HLA-A2 Kb were used as targets. CTL lines that specifically recognized both p5-pulsed targets as well as P703P-expressing targets were identified.

Human in vitro priming experiments demonstrated that the p5 peptide is immunogenic in humans. Dendritic cells (DC) were differentiated from monocyte cultures derived from PBMC of normal human donors by culturing for five days in RPMI medium containing 10% human serum, 50 ng/ml human GM-CSF and 30 ng/ml human IL-4. Following culture, the DC were pulsed with 1 μg/ml p5 peptide and cultured with CD8+ T cell enriched PBMC. CTL lines were restimulated on a weekly basis with p5-pulsed monocytes. Five to six weeks after initiation of the CTL cultures, CTL recognition of p5-pulsed target cells was demonstrated. CTL were additionally shown to recognize human cells transduced to express P703P, demonstrating that p5 is a naturally processed epitope.

Example 11

Expression of a Breast Tumor-Derived Antigen in Prostate

Isolation of the antigen B305D from breast tumor by differential display is described in U.S. patent application Ser. No. 08/700,014, filed Aug. 20, 1996. Several different splice forms of this antigen were isolated. The determined cDNA sequences for these splice forms are provided in SEQ ID NO: 366–375, with the predicted amino acid sequences corresponding to the sequences of SEQ ID NO: 292, 298 and 301–303 being provided in SEQ ID NO: 299–306, respectively. In further studies, a splice variant of the cDNA sequence of SEQ ID NO: 366 was isolated which was found to contain an additional guanine residue at position 884 (SEQ ID NO: 530), leading to a frameshift in the open reading frame. The determined DNA sequence of this ORF is provided in SEQ ID NO: 531. This frameshift generates a protein sequence (provided in SEQ ID NO: 532) of 293 amino acids that contains the C-terminal domain common to the other isoforms of B305D but that differs in the N-terminal region.

The expression levels of B305D in a variety of tumor and normal tissues were examined by real time PCR and by Northern analysis. The results indicated that B305D is highly expressed in breast tumor, prostate tumor, normal prostate and normal testes, with expression being low or undetectable in all other tissues examined (colon tumor, lung tumor, ovary tumor, and normal bone marrow, colon, kidney, liver, lung, ovary, skin, small intestine, stomach).

Example 12

Generation of Human CTL In Vitro Using Whole Gene Priming and Stimulation Techniques with Prostate-Specific Antigen Using in vitro whole-gene priming with P501 S-vaccinia infected DC (see, for example, Yee et al, *The Journal of Immunology,* 157(9):4079–86, 1996), human CTL lines were derived that specifically recognize autologous fibroblasts transduced with P501S (also known as L1-12), as determined by interferon-γ ELISPOT analysis as described above. Using a panel of HLA-mismatched B-LCL lines transduced with P501S, these CTL lines were shown to be likely restricted to HLAB class I allele. Specifically, dendritic cells (DC) were differentiated from monocyte cultures derived from PBMC of normal human donors by growing for five days in RPMI medium containing 10% human serum, 50 ng/ml human GM-CSF and 30 ng/ml human IL-4. Following culture, DC were infected overnight with recombinant P501S vaccinia virus at a multiplicity of infection (M.O.I) of five, and matured overnight by the addition of 3 μg/ml CD40 ligand. Virus was inactivated by UV irradiation. CD8+ T cells were isolated using a magnetic bead system, and priming cultures were initiated using standard culture techniques. Cultures were restimulated every 7–10 days using autologous primary fibroblasts retrovirally transduced with P501S and CD80. Following four stimulation cycles, CD8+ T cell lines were identified that specifically produced interferon-γ when stimulated with P501S and CD80-transduced autologous fibroblasts. A panel of HLA-mismatched B-LCL lines transduced with P501S were generated to define the restriction allele of the response. By measuring interferon-γ in an ELISPOT assay, the P501S specific response was shown to be likely restricted by HLA B alleles. These results demonstrate that a CD8+ CTL response to P501S can be elicited.

To identify the epitope(s) recognized, cDNA encoding P501S was fragmented by various restriction digests, and sub-cloned into the retroviral expression vector pBIB-KS. Retroviral supernatants were generated by transfection of the helper packaging line Phoenix-Ampho. Supernatants were then used to transduce Jurkat/A2 Kb cells for CTL screening. CTL were screened in IFN-gamma ELISPOT assays against these A2 Kb targets transduced with the "library" of P501S fragments. Initial positive fragments P501S/H3 and P501S/F2 were sequenced and found to encode amino acids 106–553 and amino acids 136–547, respectively, of SEQ ID NO: 113. A truncation of H3 was made to encode amino acid residues 106–351 of SEQ ID NO: 113, which was unable to stimulate the CTL, thus localizing the epitope to amino acid residues 351–547. Additional fragments encoding amino acids 1–472 (Fragment A) and amino acids 1–351 (Fragment B) were also constructed. Fragment A but not Fragment B stimulated the CTL thus localizing the epitope to amino acid residues 351–472. Overlapping 20-mer and 18-mer peptides representing this region were tested by pulsing Jurkat/A2 Kb cells versus CTL in an IFN-gamma assay. Only peptides P501S-369(20) and P501S-369(18) stimulated the CTL. Nine-mer and 10-mer peptides representing this region were synthesized and similarly tested. Peptide P501 S-370 (SEQ ID NO: 539) was the minimal 9-mer giving a strong response. Peptide P501 S-376 (SEQ ID NO: 540) also gave a weak response, suggesting that it might represent a cross-reactive epitope.

In subsequent studies, the ability of primary human B cells transduced with P501S to prime MHC class I-restricted, P501S-specific, autologous CD8 T cells was examined. Primary B cells were derived from PBMC of a homozygous HLA-A2 donor by culture in CD40 ligand and IL-4, transduced at high frequency with recombinant P501S in the vector pBIB, and selected with blastocidin-S. For in vitro priming, purified CD8+ T cells were cultured with autologous CD40 ligand+IL-4 derived, P501S-transduced B cells in a 96-well microculture format. These CTL microcultures were re-stimulated with P501S-transduced B cells and then assayed for specificity. Following this initial screen, microcultures with significant signal above background were cloned on autologous EBV-transformed B cells (BLCL), also transduced with P501 S. Using IFN-gamma ELISPOT for detection, several of these CD8 T cell clones were found to be specific for P501 S, as demonstrated by reactivity to BLCL/P501S but not BLCL transduced with control antigen. It was further demonstrated that the anti-PSO1S CD8 T cell specificity is HLA-A2-restricted. First, antibody blocking experiments with anti-HLA-A,B,C monoclonal antibody (W6.32), anti-HLA-A,B,C monoclonal antibody (B1.23.2) and a control monoclonal antibody showed that only the anti-HLA-A,B,C antibody blocked recognition of P501S-expressing autologous BLCL. Secondly, the anti-P501S CTL also recognized an HLA-A2 matched, heterologous BLCL transduced with P501S, but not the corresponding EGFP transduced control BLCL.

Example 13

Identification of Prostate-Specific Antigens by Microarray Analysis

This Example describes the isolation of certain prostate-specific polypeptides from a prostate tumor cDNA library.

A human prostate tumor cDNA expression library as described above was screened using microarray analysis to identify clones that display at least a three fold over-expression in prostate tumor and/or normal prostate tissue, as compared to non-prostate normal tissues (not including testis). 372 clones were identified, and 319 were successfully sequenced. Table I presents a summary of these clones, which are shown in SEQ ID NOs:385–400. Of these sequences SEQ ID NOs:386, 389, 390 and 392 correspond to novel genes, and SEQ ID NOs: 393 and 396 correspond to previously identified sequences. The others (SEQ ID NOs:385, 387, 388, 391, 394, 395 and 397–400) correspond to known sequences, as shown in Table 1.

TABLE I

Summary of Prostate Tumor Antigens

| Known Genes | Previously Identified Genes | Novel Genes |
|---|---|---|
| T-cell gamma chain | P504S | 23379 (SEQ ID NO:389) |
| Kallikrein | P1000C | 23399 (SEQ ID NO:392) |
| Vector | P501S | 23320 (SEQ ID NO:386) |
| CGI-82 protein mRNA (23319; SEQ ID NO:385) | P503S | 23381 (SEQ ID NO:390) |
| PSA | P510S | |
| Ald. 6 Dehyd. | P784P | |
| L-iditol-2 dehydrogenase (23376; SEQ ID NO:388) | P502S | |
| Ets transcription factor PDEF (22672; SEQ ID NO:398) | P706P | |
| hTGR (22678; SEQ ID NO:399) | 19142.2, bangur.seq (22621; SEQ ID NO:396) | |
| KIAA0295(22685; SEQ ID NO:400) | 5566.1 Wang (23404; SEQ ID NO:393) | |
| Prostatic Acid Phosphatase (22655; SEQ ID NO:397) | P712P | |
| transglutaminase (22611; SEQ ID NO:395) | P778P | |
| HDLBP (23508; SEQ ID NO:394) | | |
| CGI-69 Protein(23367; SEQ ID NO:387) | | |
| KIAA0122(23383; SEQ ID NO:391) | | |
| TEEG | | |

CGI-82 showed 4.06 fold over-expression in prostate tissues as compared to other normal tissues tested. It was over-expressed in 43% of prostate tumors, 25% normal prostate, not detected in other normal tissues tested. L-iditol-2 dehydrogenase showed 4.94 fold over-expression in prostate tissues as compared to other normal tissues tested. It was over-expressed in 90% of prostate tumors, 100% of normal prostate, and not detected in other normal tissues tested. Ets transcription factor PDEF showed 5.55 fold over-expression in prostate tissues as compared to other normal tissues tested. It was over-expressed in 47% prostate tumors, 25% normal prostate and not detected in other normal tissues tested. hTGR1 showed 9.11 fold over-expression in prostate tissues as compared to other normal tissues tested. It was over-expressed in 63% of prostate tumors and is not detected in normal tissues tested including normal prostate. KIAA0295 showed 5.59 fold over-expression in prostate tissues as compared to other normal tissues tested. It was over-expressed in 47% of prostate tumors, low to undetectable in normal tissues tested including normal prostate tissues. Prostatic acid phosphatase showed 9.14 fold over-expression in prostate tissues as compared to other normal tissues tested. It was over-expressed in 67% of prostate tumors, 50% of normal prostate, and not detected in other normal tissues tested. Transglutaminase showed 14.84 fold over-expression in prostate tissues as compared to other normal tissues tested It was over-expressed in 30% of prostate tumors, 50% of normal prostate, and is not detected in other normal tissues tested. High density lipoprotein binding protein (HDLBP) showed 28.06 fold over-expression in prostate tissues as compared to other normal tissues tested. It was over-expressed in 97% of prostate tumors, 75% of normal prostate, and is undetectable in all other normal tissues tested. CGI-69 showed 3.56 fold over-expression in prostate tissues as compared to other normal tissues tested. It is a low abundant gene, detected in more than 90% of prostate tumors, and in 75% normal prostate tissues. The expression of this gene in normal tissues was very low. KIAA0122 showed 4.24 fold over-expression in prostate tissues as compared to other normal tissues tested. It was over-expressed in 57% of prostate tumors, it was undetectable in all normal tissues tested including normal prostate tissues. 19142.2 bangur showed 23.25 fold over-expression in prostate tissues as compared to other normal tissues tested. It was over-expressed in 97% of prostate tumors and 100% of normal prostate. It was undetectable in other normal tissues tested. 5566.1 Wang showed 3.31 fold over-expression in prostate tissues as compared to other normal tissues tested. It was over-expressed in 97% of prostate tumors, 75% normal prostate and was also over-expressed in normal bone marrow, pancreas, and activated PBMC. Novel clone 23379 showed 4.86 fold over-expression in prostate tissues as compared to other normal tissues tested. It was detectable in 97% of prostate tumors and 75% normal prostate and is undetectable in all other normal tissues tested. Novel clone 23399 showed 4.09 fold over-expression in prostate tissues as compared to other normal tissues tested. It was over-expressed in 27% of prostate tumors and was undetectable in all normal tissues tested including normal prostate tissues. Novel clone 23320 showed 3.15 fold over-expression in prostate tissues as compared to other normal tissues tested. It was detectable in all prostate tumors and 50% of normal prostate tissues. It was also expressed in normal colon and trachea. Other normal tissues do not express this gene at high level.

Example 14

Identification of Prostate-Specific Antigens by Electronic Subtraction

This Example describes the use of an electronic subtraction technique to identify prostate-specific antigens.

Potential prostate-specific genes present in the GENBANK™ human EST database were identified by electronic subtraction (similar to that described by Vasmatizis et al., *Proc. Natl. Acad. Sci. USA* 95:300–304, 1998). The sequences of EST clones (43,482) derived from various prostate libraries were obtained from the GENBANK™ public human EST database. Each prostate EST sequence was used as a query sequence in a BLASTN (National Center for Biotechnology Information) search against the human EST database. All matches considered identical (length of matching sequence>100 base pairs, density of identical matches over this region>70%) were grouped (aligned) together in a cluster. Clusters containing more than 200 ESTs were discarded since they probably represented repetitive elements or highly expressed genes such as those for ribosomal proteins. If two or more clusters shared common ESTs, those clusters were grouped together into a "supercluster," resulting in 4,345 prostate superclusters.

Records for the 479 human cDNA libraries represented in the GENBANK™ release were downloaded to create a database of these cDNA library records. These 479 cDNA libraries were grouped into three groups: Plus (normal prostate and prostate tumor libraries, and breast cell line libraries, in which expression was desired), Minus (libraries from other normal adult tissues, in which expression was not desirable), and Other (libraries from fetal tissue, infant tissue, tissues found only in women, non-prostate tumors and cell lines other than prostate cell lines, in which expression was considered to be irrelevant). A summary of these library groups is presented in Table II.

TABLE II

Prostate cDNA Libraries and ESTs

| Library | # of Libraries | # of ESTs |
|---|---|---|
| Plus | 25 | 43,482 |
| Normal | 11 | 18,875 |
| Tumor | 11 | 21,769 |
| Cell lines | 3 | 2,838 |
| Minus | 166 | |
| Other | 287 | |

Each supercluster was analyzed in terms of the ESTs within the supercluster. The tissue source of each EST clone was noted and used to classify the superclusters into four groups: Type 1-EST clones found in the Plus group libraries only; no expression detected in Minus or Other group libraries; Type 2-EST clones derived from the Plus and Other group libraries only; no expression detected in the Minus group; Type 3-EST clones derived from the Plus, Minus and Other group libraries, but the number of ESTs derived from the Plus group is higher than in either the Minus or Other groups; and Type 4-EST clones derived from Plus, Minus and Other group libraries, but the number derived from the Plus group is higher than the number derived from the Minus group. This analysis identified 4,345 breast clusters (see Table III). From these clusters, 3,172 EST clones were ordered from Research Genetics, Inc., and were received as frozen glycerol stocks in 96-well plates.

TABLE III

| Prostate Cluster Summary | | |
|---|---|---|
| Type | # of Superclusters | # of ESTs Ordered |
| 1 | 688 | 677 |
| 2 | 2899 | 2484 |
| 3 | 85 | 11 |
| 4 | 673 | 0 |
| Total | 4345 | 3172 |

The EST clone inserts were PCR-amplified using amino-linked PCR primers for Synteni microarray analysis. When more than one PCR product was obtained for a particular clone, that PCR product was not used for expression analysis. In total, 2,528 clones from the electronic subtraction method were analyzed by microarray analysis to identify electronic subtraction breast clones that had high levels of tumor vs. normal tissue mRNA. Such screens were performed using a Synteni (Palo Alto, Calif.) microarray, according to the manufacturer's instructions (and essentially as 10 described by Schena et al., *Proc. Natl. Acad. Sci. USA* 93:10614–10619, 1996 and Heller et al., *Proc. Natl. Acad. Sci. USA* 94:2150–2155, 1997). Within these analyses, the clones were arrayed on the chip, which was then probed with fluorescent probes generated from normal and tumor prostate cDNA, as well as various other normal tissues. The slides were scanned and the fluorescence intensity was measured.

Clones with an expression ratio greater than 3 (i.e., the level in prostate tumor and normal prostate mRNA was at least three times the level in other normal tissue mRNA) were identified as prostate tumor-specific sequences (Table IV). The sequences of these clones are provided in SEQ ID NO: 401–453, with certain novel sequences shown in SEQ ID NO: 407, 413, 416–419, 422, 426, 427 and 450.

TABLE IV

| Prostate-tumor Specific Clones | | |
|---|---|---|
| SEQ ID NO. | Sequence Designation | Comments |
| 401 | 22545 | previously identified P1000C |
| 402 | 22547 | previously identified P704P |
| 403 | 22548 | known |
| 404 | 22550 | known |
| 405 | 22551 | PSA |
| 406 | 22552 | prostate secretory protein 94 |
| 407 | 22553 | novel |
| 408 | 22558 | previously identified P509S |
| 409 | 22562 | glandular kallikrein |
| 410 | 22565 | previously identified P1000C |
| 411 | 22567 | PAP |
| 412 | 22568 | B1006C (breast tumor antigen) |
| 413 | 22570 | novel |
| 414 | 22571 | PSA |
| 415 | 22572 | previously identified P706P |
| 416 | 22573 | novel |
| 417 | 22574 | novel |
| 418 | 22575 | novel |
| 419 | 22580 | novel |
| 420 | 22581 | PAP |
| 421 | 22582 | prostatic secretory protein 94 |
| 422 | 22583 | novel |
| 423 | 22584 | prostatic secretory protein 94 |
| 424 | 22585 | prostatic secretory protein 94 |
| 425 | 22586 | known |
| 426 | 22587 | novel |

TABLE IV-continued

| Prostate-tumor Specific Clones | | |
|---|---|---|
| SEQ ID NO. | Sequence Designation | Comments |
| 427 | 22588 | novel |
| 428 | 22589 | PAP |
| 429 | 22590 | known |
| 430 | 22591 | PSA |
| 431 | 22592 | known |
| 432 | 22593 | Previously identified P777P |
| 433 | 22594 | T cell receptor gamma chain |
| 434 | 22595 | Previously identified P705P |
| 435 | 22596 | Previously identified P707P |
| 436 | 22847 | PAP |
| 437 | 22848 | known |
| 438 | 22849 | prostatic secretory protein 57 |
| 439 | 22851 | PAP |
| 440 | 22852 | PAP |
| 441 | 22853 | PAP |
| 442 | 22854 | previously identified P509S |
| 443 | 22855 | previously identified P705P |
| 444 | 22856 | previously identified P774P |
| 445 | 22857 | PSA |
| 446 | 23601 | previously identified P777P |
| 447 | 23602 | PSA |
| 448 | 23605 | PSA |
| 449 | 23606 | PSA |
| 450 | 23612 | novel |
| 451 | 23614 | PSA |
| 452 | 23618 | previously identified P1000C |
| 453 | 23622 | previously identified P705P |

Example 15

Further Identification of Prostate-Specific Antigens by Microarray Analysis

This Example describes the isolation of additional prostate-specific polypeptides from a prostate tumor cDNA library.

A human prostate tumor cDNA expression library as described above was screened using microarray analysis to identify clones that display at least a three fold over-expression in prostate tumor and/or normal prostate tissue, as compared to non-prostate normal tissues (not including testis). 142 clones were identified and sequenced. Certain of these clones are shown in SEQ ID NO: 454–467. Of these sequences, SEQ ID NO: 459461 represent novel genes. The others (SEQ ID NO: 454–458 and 461–467) correspond to known sequences.

Example 16

Further Characterization of Prostate-Specific Antigen P710P

This Example describes the full length cloning of P710P.

The prostate cDNA library described above was screened with the P710P fragment described above. One million colonies were plated on LB/Ampicillin plates. Nylon membrane filters were used to lift these colonies, and the cDNAs picked up by these filters were then denatured and cross-linked to the filters by UV light. The P710P fragment was radiolabeled and used to hybridize with the filters. Positive cDNA clones were selected and their cDNAs recovered and sequenced by an automatic Perkin Elmer/Applied Biosystems Division Sequencer. Four sequences were obtained, and are presented in SEQ ID NO: 468–471 These sequences appear to represent different splice variants of the P710P gene.

Example 17

Protein Expression of the Prostate-Specific Antigen P501 S

This example describes the expression and purification of the prostate-specific antigen P501S in *E. coli*, baculovirus and mammalian cells.

a) Expression in *E. coli*

Expression of the full-length form of P501S was attempted by first cloning P501S without the leader sequence (amino acids 36–553 of SEQ ID NO: 113) down-stream of the first 30 amino acids of the *M tuberculosis* antigen Ra12 (SEQ ID NO: 484) in pET17b. Specifically, P501S DNA was used to perform PCR using the primers AW025 (SEQ ID NO: 485) and AW003 (SEQ ID NO: 486). AW025 is a sense cloning primer that contains a HindIII site. AW003 is an antisense cloning primer that contains an EcoRI site. DNA amplification was performed using 5 μl 10×Pfu buffer, 1 μl 20 mM dNTPs, 1 μl each of the PCR primers at 10 μM concentration, 4011 water, 1 μl Pfu DNA polymerase (Stratagene, La Jolla, Calif.) and 1 μl DNA at 100 ng/μl. Denaturation at 95° C. was performed for 30 sec, followed by 10 cycles of 95° C. for 30 sec, 60° C. for 1 min and by 72° C. for 3 min. 20 cycles of 95° C. for 30 sec, 65° C. for 1 min and by 72° C. for 3 min, and lastly by I cycle of 72° C. for 10 min. The PCR product was cloned to Ra12 m/pET17b using HindIII and EcoRI. The sequence of the resulting fusion construct (referred to as Ra12-P501S—F) was confirmed by DNA sequencing.

The fusion construct was transformed into BL21(DE3) pLysE, pLysS and CodonPlus *E. coli* (Stratagene) and grown overnight in LB broth with kanamycin. The resulting culture was induced with IPTG. Protein was transferred to PVDF membrane and blocked with 5% non-fat milk (in PBS-Tween buffer), washed three times and incubated with mouse anti-His tag antibody (Clontech) for 1 hour. The membrane was washed 3 times and probed with HRP-Protein A (Zymed) for 30 min. Finally, the membrane was washed 3 times and developed with ECL (Amersham). No expression was detected by Western blot. Similarly, no expression was detected by Western blot when the Ral2-PSO1S-F fusion was used for expression in BL21CodonPlus by CE6 phage (Invitrogen).

An N-terminal fragment of P501S (amino acids 36–325 of SEQ ID NO: 113) was cloned down-stream of the first 30 amino acids of the *M tuberculosis* antigen Ral2 in pET17b as follows. P501S DNA was used to perform PCR using the primers AW025 (SEQ ID NO: 485) and AW027 (SEQ ID NO: 487). AW027 is an antisense cloning primer that contains an EcoRI site and a stop codon. DNA amplification was performed essentially as described above. The resulting PCR product was cloned to Ral2 in pET17b at the HindIII and EcoRI sites. The fusion construct (referred to as Ral2-P501 S—N) was confirmed by DNA sequencing.

The Ra12-P501S—N fusion construct was used for expression in BL21(DE3)pLysE, pLysS and CodonPlus, essentially as described above. Using Western blot analysis, protein bands were observed at the expected molecular weight of 36 kDa. Some high molecular weight bands were also observed, probably due to aggregation of the recombinant protein. No expression was detected by Western blot when the Ral2-P501S—F fusion was used for expression in BL21CodonPlus by CE6 phage.

A fusion construct comprising a C-terminal portion of P501S (amino acids 257–553 of SEQ ID NO: 113) located down-stream of the first 30 amino acids of the *M tuberculosis* antigen Ral2 (SEQ ID NO: 484) was prepared as follows. P501S DNA was used to perform PCR using the primers AW026 (SEQ ID NO: 488) and AW003 (SEQ ID NO: 486). AW026 is a sense cloning primer that contains a HindIII site. DNA amplification was performed essentially as described above. The resulting PCR product was cloned to Ral2 in pET17b at the HindIII and EcoRI sites. The sequence for the fusion construct (referred to as Ral2-P501 S—C) was confirmed.

The Ral2-P501S—C fusion construct was used for expression in BL21(DE3)pLysE, pLysS and CodonPlus, as described above. A small amount of protein was detected by Western blot, with some molecular weight aggregates also being observed. Expression was also detected by Western blot when the Ral2-P501S—C fusion was used for expression in BL21CodonPlus induced by CE6 phage.

b) Expression of P501 S in Baculovirus

The Bac-to-Bac baculovirus expression system (BRL Life Technologies, Inc.) was used to express P501S protein in insect cells. Full-length P501S (SEQ ID NO: 113) was amplified by PCR and cloned into the XbaI site of the donor plasmid pFastBacI. The recombinant bacmid and baculovirus were prepared according to the manufacturer's isntructions. The recombinant baculovirus was amplified in Sf9 cells and the high titer viral stocks were utilized to infect High Five cells (Invitrogen) to make the recombinant protein. The identity of the full-length protein was confirmed by N-terminal sequencing of the recombinant protein and by Western blot analysis (FIG. 7). Specifically, 0.6 million High Five cells in 6-well plates were infected with either the unrelated control virus BV/ECD_PD (lane 2), with recombinant baculovirus for P501 S at different amounts or MOIs (lanes 4–8), or were uninfected (lane 3). Cell lysates were run on SDS-PAGE under reducing conditions and analyzed by Western blot with the anti-P501S monoclonal antibody P501S-10E3-G4D3 (prepared as described below). Lane 1 is the biotinylated protein molecular weight marker (BioLabs).

The localization of recombinant P501S in the insect cells was investigated as follows. The insect cells overexpressing P501S were fractionated into fractions of nucleus, mitochondria, membrane and cytosol. Equal amounts of protein from each fraction were analyzed by Western blot with a monoclonal antibody against P501S. Due to the scheme of fractionation, both nucleus and mitochondria fractions contain some plasma membrane components. However, the membrane fraction is basically free from mitochondria and nucleus. P501S was found to be present in all fractions that contain the membrane component, suggesting that P501S may be associated with plasma membrane of the insect cells expressing the recombinant protein.

c) Expression of P501 S in mammalian cells

Full-length P501S (553AA) was cloned into various mammalian expression vectors, including pCEP4 (Invitrogen), pVR1012 (Vical, San Diego, Calif.) and a modified form of the retroviral vector pBMN, referred to as pBIB. Transfection of P50 μl/pCEP4 and P501S/pVR1012 into HEK293 fibroblasts was carried out using the Fugene transfection reagent (Boehringer Mannheim). Briefly, 2 μl of Fugene reagent was diluted into 100 μl of serum-free media and incubated at room temperature for 5–10 min. This mixture was added to 1 μg of P501S plasmid DNA, mixed briefly and incubated for 30 minutes at room temperature. The Fugene/DNA mixture was added to cells and incubated for 24–48 hours. Expression of recombinant P501 S in transfected HEK293 fibroblasts was detected by means of Western blot employing a monoclonal antibody to P501 S.

Transfection of p501 S/pCEP4 into CHO-K cells (American Type Culture Collection, Rockville, Md.) was carried out using GenePorter transfection reagent (Gene Therapy Systems, San Diego, Calif.). Briefly, 15 μl of -GenePorter was diluted in 500 μl of serum-free media and incubated at room temperature for 10 min. The GenePorter/media mixture was added to 2 μg of plasmid DNA that was diluted in 500 μl of serum-free media, mixed briefly and incubated for 30 min at room temperature. CHO-K cells were rinsed in PBS to remove serum proteins, and the GenePorter/DNA mix was added and incubated for 5 hours. The transfected cells were then fed an equal volume of 2× media and incubated for 24–48 hours.

FACS analysis of P501S transiently infected CHO-K cells, demonstrated surface expression of P501S. Expression was detected using rabbit polyclonal antisera raised against a P501S peptide, as described below. Flow cytometric analysis was performed using a FaCScan (Becton Dickinson), and the data were analyzed using the Cell Quest program.

Example 18

Preparation and Characterization of Antibodies Against Prostate-Specific Polypeptides a) Preparation and Characterization of Antibodies against P501S A murine monoclonal antibody directed against the carboxy-terminus of the prostate-specific antigen P501S was prepared as follows.

A truncated fragment of P501S (amino acids 355–526 of SEQ ID NO: 113) was generated and cloned into the pET28b vector (Novagen) and expressed in *E. coli* as a thioredoxin fusion protein with a histidine tag. The trx-P501S fusion protein was purified by nickel chromatography, digested with thrombin to remove the trx fragment and further purified by an acid precipitation procedure followed by reverse phase HPLC.

Mice were immunizied with truncated P501S protein. Serum bleeds from mice that potentially contained anti-P501S polyclonal sera were tested for P501S-specific reactivity using ELISA assays with purified P501S and trx-P501S proteins. Serum bleeds that appeared to react specifically with P501S were then screened for P501S reactivity by Western analysis. Mice that contained a P501S-specific antibody component were sacrificed and spleen cells were used to generate anti-P501S antibody producing hybridomas using standard techniques. Hybridoma supernatants were tested for P501S-specific reactivity initially by ELISA, and subsequently by FACS analysis of reactivity with P501S transduced cells. Based on these results, a monoclonal hybridoma referred to as 10E3 was chosen for further subcloning. A number of subclones were generated, tested for specific reactivity to P501S using ELISA and typed for IgG isotype. The results of this analysis are shown below in Table V. Of the 16 subclones tested, the monoclonal antibody 10E3-G4-D3 was selected for further study.

TABLE V

Isotype analysis of murine anti-P501S monoclonal antibodies

| Hybridoma clone | Isotype | Estimated [Ig] in supernatant (μg/ml) |
|---|---|---|
| 4D11 | IgG1 | 14.6 |
| 1G1 | IgG1 | 0.6 |
| 4F6 | IgG1 | 72 |
| 4H5 | IgG1 | 13.8 |
| 4H5-E12 | IgG1 | 10.7 |
| 4H5-EH2 | IgG1 | 9.2 |
| 4H5-H2-A10 | IgG1 | 10 |
| 4H5-H2-A3 | IgG1 | 12.8 |
| 4H5-H2-A10-G6 | IgG1 | 13.6 |
| 4H5-H2-B11 | IgG1 | 12.3 |
| 10E3 | IgG2a | 3.4 |
| 10E3-D4 | IgG2a | 3.8 |
| 10E3-D4-G3 | IgG2a | 9.5 |
| 10E3-D4-G6 | IgG2a | 10.4 |
| 10E3-E7 | IgG2a | 6.5 |
| 8H12 | IgG2a | 0.6 |

The specificity of 10E3-G4-D3 for P501S was examined by FACS analysis. Specifically, cells were fixed (2% formaldehyde, 10 minutes), permeabilized (0.1% saponin, 10 minutes) and stained with 10E3-G4-D3 at 0.5–1 μg/ml, followed by incubation with a secondary, FITC-conjugated goat anti-mouse Ig antibody (Pharmingen, San Diego, Calif.). Cells were then analyzed for FITC fluorescence using an Excalibur fluorescence activated cell sorter. For FACS analysis of transduced cells, B-LCL were retrovirally transduced with P501S. For analysis of infected cells, B-LCL were infected with a vaccinia vector that expresses P501 S. To demonstrate specificity in these assays, B-LCL transduced with a different antigen (P703P) and uninfected B-LCL vectors were utilized. 10E3-G4-D3 was shown to bind with P501 S-transduced B-LCL and also with P501 S-infected B-LCL, but not with either uninfected cells or P703P-transduced cells.

To determine whether the epitope recognized by 10E3-G4-D3 was found on the surface or in an intracellular compartment of cells, B-LCL were transduced with P501S or HLA-B8 as a control antigen and either fixed and permeabilized as described above or directly stained with 10E3-G4-D3 and analyzed as above. Specific recognition of P501S by 10E3-G4-D3 was found to require permeabilization, suggesting that the epitope recognized by this antibody is intracellular.

The reactivity of 10E3-G4-D3 with the three prostate tumor cell lines Lncap, PC-3 and DU-145, which are known to express high, medium and very low levels of P501 S, respectively, was examined by permeabilizing the cells and treating them as described above. Higher reactivity of 10E3-G4-D3 was seen with Lncap than with PC-3, which in turn showed higher reactivity that DU-145. These results are in agreement with the real time PCR and demonstrate that the antibody specifically recognizes P501S in these tumor cell lines and that the epitope recognized in prostate tumor cell lines is also intracellular.

Specificity of 10E3-G4-D3 for P501S was also demonstrated by Western blot analysis. Lysates from the prostate tumor cell lines Lncap, DU-145 and PC-3, from P501S-transiently transfected HEK293 cells, and from non-transfected HEK293 cells were generated. Western blot analysis of these lysates with 10E3-G4-D3 revealed a 46 kDa immunoreactive band in Lncap, PC-3 and P501S-transfected HEK cells, but not in DU-145 cells or non-transfected HEK293 cells. P501S mRNA expression is consistent with these results since semi-quantitative PCR analysis revealed that P501S mRNA is expressed in Lncap, to a lesser but detectable level in PC-3 and not at all in DU-145 cells. Bacterially expressed and purified recombinant P501S (referred to as P501SStr2) was recognized by 10E3-G4-D3 (24 kDa), as was full-length P501S that was transiently expressed in HEK293 cells using either the expression vector VR1012 or pCEP4. Although the predicted molecular weight of P501S is 60.5 kDa, both transfected and "native" P501S run at a slightly lower mobility due to its hydrophobic nature.

Immunohistochemical analysis was performed on prostate tumor and a panel of normal tissue sections (prostate, adrenal, breast, cervix, colon, duodenum, gall bladder, ileum, kidney, ovary, pancreas, parotid gland, skeletal muscle, spleen and testis). Tissue samples were fixed in formalin solution for 24 hours and embedded in paraffin before being sliced into 10 micron sections. Tissue sections were permeabilized and incubated with 10E3-G4-D3 antibody for 1 hr. HRP-labeled anti-mouse followed by incubation with DAB chromogen was used to visualize P501 S immunoreactivity. P501S was found to be highly expressed in both normal prostate and prostate tumor tissue but was not detected in any of the other tissues tested.

To identify the epitope recognized by 10E3-G4-D3, an epitope mapping approach was pursued. A series of 13 overlapping 20–21 mers (5 amino acid overlap; SEQ ID NO: 489–501) was synthesized that spanned the fragment of P501 S used to generate 10E3-G4-D3. Flat bottom 96 well microtiter plates were coated with either the peptides or the P501 S fragment used to immunize mice, at I microgram/ml for 2 hours at 37° C. Wells were then aspirated and blocked with phosphate buffered saline containing 1% (w/v) BSA for 2 hours at room temperature, and subsequently washed in PBS containing 0.1% Tween 20 (PBST). Purified antibody 10E3-G4-D3 was added at 2 fold dilutions (1000 ng–16 ng) in PBST and incubated for 30 minutes at room temperature. This was followed by washing 6 times with PBST and subsequently incubating with HRP-conjugated donkey anti-mouse IgG (H+L)Affinipure F(ab') fragment (Jackson Immunoresearch, West Grove, Pa.) at 1:20000 for 30 minutes. Plates were then washed and is incubated for 15 minutes in tetramethyl benzidine. Reactions were stopped by the addition of IN sulfuric acid and plates were read at 450 nm using an ELISA plate reader. As shown in FIG. 8, reactivity was seen with the peptide of SEQ ID NO: 496 (corresponding to amino acids 439–459 of P501S) and with the PSOIS fragment but not with the remaining peptides, demonstrating that the epitope recognized by 10E3-G4-D3 is localized to amino acids 439–459 of SEQ ID NO: 113.

In order to further evaluate the tissue specificity of P501 S, multi-array immunohistochemical analysis was performed on approximately 4700 different human tissues encompassing all the major normal organs as well as neoplasias derived from these tissues. Sixty-five of these human tissue samples were of prostate origin. Tissue sections 0.6 mm in diameter were formalin-fixed and paraffin embedded. Samples were pretreated with HIER using 10 mM citrate buffer pH 6.0 and boiling for 10 min. Sections were stained with 10E3-G4-D3 and P501S immunoreactivity was visualized with HRP. All the 65 prostate tissues samples (5 normal, 55 untreated prostate tumors, 5 hormone refractory prostate tumors) were positive, showing distinct perinuclear staining. All other tissues examined were negative for P501 S expression.

b) Preparation and Characterization of Antibodies against P503S

A fragment of P503S (amino acids 113–241 of SEQ ID NO: 114) was expressed and purified from bacteria essentially as described above for P501S and used to immunize both rabbits and mice. Mouse monoclonal antibodies were isolated using standard hybridoma technology as described above. Rabbit monoclonal antibodies were isolated using Selected Lymphocyte Antibody Method (SLAM) technology at Immgenics Pharmaceuticals (Vancouver, BC, Canada). Table V1, below, lists the monoclonal antibodies that were developed against P503S.

TABLE VI

| Antibody | Species |
|---|---|
| 20D4 | Rabbit |
| JA1 | Rabbit |
| 1A4 | Mouse |
| 1C3 | Mouse |
| 1C9 | Mouse |
| 1D12 | Mouse |
| 2A11 | Mouse |
| 2H9 | Mouse |
| 4H7 | Mouse |
| 8A8 | Mouse |
| 8D10 | Mouse |
| 9C12 | Mouse |
| 6D12 | Mouse |

The DNA sequences encoding the complementarity determining regions (CDRs) for the rabbit monoclonal antibodies 20D4 and JA1 were determined and are provided in SEQ ID NO: 502 and 503, respectively.

In order to better define the epitope binding region of each of the antibodies, a series of overlapping peptides were generated that span amino acids 109–213 of SEQ ID NO: 114. These peptides were used to epitope map the anti-P503S monoclonal antibodies by ELISA as follows. The recombinant fragment of P503S that was employed as the immunogen was used as a positive control. Ninety-six well microtiter plates were coated with either peptide or recombinant antigen at 20 ng/well overnight at 4° C. Plates were aspirated and blocked with phosphate buffered saline containing 1% (w/v) BSA for 2 hours at room temperature then washed in PBS containing 0.1% Tween 20 (PBST). Purified rabbit monoclonal antibodies diluted in PBST were added to the wells and incubated for 30 min at room temperature. This was followed by washing 6 times with PBST and incubation with Protein-A HRP conjugate at a 1:2000 dilution for a further 30 min. Plates were washed six times in PBST and incubated with tetramethylbenzidine (TMB) substrate for a further 15 min. The reaction was stopped by the addition of IN sulfuric acid and plates were read at 450 nm using at ELISA plate reader. ELISA with the mouse monoclonal antibodies was performed with supernatants from tissue culture run neat in the assay.

All of the antibodies bound to the recombinant P503S fragment, with the exception of the negative control SP2 supernatant. 20D4, JAI and 1D12 bound strictly to peptide #2101 (SEQ ID NO: 504), which corresponds to amino acids 151–169 of SEQ ID NO: 114. 1C3 bound to peptide #2102 (SEQ ID NO: 505), which corresponds to amino acids 165–184 of SEQ ID NO: 114. 9C12 bound to peptide #2099 (SEQ ID NO: 522), which corresponds to amino acids 120–139 of SEQ ID NO: 114. The other antibodies bind to regions that were not examined in these studies.

Subsequent to epitope mapping, the antibodies were tested by FACS analysis on a cell line that stably expressed P503S to confirm that the antibodies bind to cell surface epitopes. Cells stably transfected with a control plasmid were employed as a negative control. Cells were stained live with no fixative. 0.5 μg of anti-P503S monoclonal antibody was added and cells were incubated on ice for 30 min before being washed twice and incubated with a FITC-labelled goat anti-rabbit or mouse secondary antibody for 20 min. After being washed twice, cells were analyzed with an Excalibur fluorescent activated cell sorter. The monoclonal antibodies 1C3, 1D12, 9C12, 20D4 and JA1, but not 8D3, were found to bind to a cell surface epitope of P503S.

In order to determine which tissues express P503S, immunohistochemical analysis was performed, essentially as described above, on a panel of normal tissues (prostate, adrenal, breast, cervix, colon, duodenum, gall bladder, ileum, kidney, ovary, pancreas, parotid gland, skeletal muscle, spleen and testis). HRP-labeled anti-mouse or anti-rabbit antibody followed by incubation with TMB was used to visualize P503S immunoreactivity. P503S was found to be highly expressed in prostate tissue, with lower levels of expression being observed in cervix, colon, ileum and kidney, and no expression being observed in adrenal, breast, duodenum, gall bladder, ovary, pancreas, parotid gland, skeletal muscle, spleen and testis.

Western blot analysis was used to characterize anti-P503S monoclonal antibody specificity. SDS-PAGE was performed on recombinant (rec) P503S expressed in and purified from bacteria and on lysates from HEKC293 cells transfected with full length P503S. Protein was transferred to nitrocellulose and then Western blotted with each of the anti-P503S monoclonal antibodies (20D4, JA1, 1D12, 6D12 and 9C12) at an antibody concentration of 1 μg/ml. Protein was detected using horse radish peroxidase (HRP) conjugated to either a goat anti-mouse monoclonal antibody or to protein A-sepharose. The monoclonal antibody 20D4 detected the appropriate molecular weight 14 kDa recombinant P503S (amino acids 113–241) and the 23.5 kDa species in the HEK293 cell lysates transfected with full length P503S. Other anti-P503S monoclonal antibodies displayed similar specificity by Western blot.

c) Preparation and Characterization of Antibodies against P703P

Rabbits were immunized with either a truncated (P703Ptr1; SEQ ID NO: 172) or full-length mature form (P703Pf1; SEQ ID NO: 523) of recombinant P703P protein was expressed in and purified from bacteria as described above. Affinity purified polyclonal antibody was generated using immunogen P703Pfl or P703Ptrl attached to a solid support. Rabbit monoclonal antibodies were isolated using SLAM technology at Immgenics Pharmaceuticals. Table VII below lists both the polyclonal and monoclonal antibodies that were generated against P703P.

TABLE VII

| Antibody | Immunogen | Species/type |
|---|---|---|
| Aff. Purif. P703P (truncated); #2594 | P703Ptrl | Rabbit polyclonal |
| Aff. Purif. P703P (full length); #9245 | P703Pfl | Rabbit polyclonal |
| 2D4 | P703Ptrl | Rabbit monoclonal |
| 8H2 | P703Ptrl | Rabbit monoclonal |
| 7H8 | P703Ptrl | Rabbit monoclonal |

The DNA sequences encoding the complementarity determining regions (CDRs) for the rabbit monoclonal antibodies 8H2, 7H8 and 2D4 were determined and are provided in SEQ ID NO: 506–508, respectively.

Epitope mapping studies were performed as described above. Monoclonal antibodies 2D4 and 7H8 were found to specifically bind to the peptides of SEQ ID NO: 509 (corresponding to amino acids 145–159 of SEQ ID NO: 172) and SEQ ID NO: 510 (corresponding to amino acids 11–25 of SEQ ID NO: 172), respectively. The polyclonal antibody 2594 was found to bind to the peptides of SEQ ID NO: 511–514, with the polyclonal antibody 9427 binding to the peptides of SEQ ID NO: 515–517. The specificity of the anti-P703P antibodies was determined by Western blot analysis as follows. SDS-PAGE was performed on (1) bacterially expressed recombinant antigen; (2) lysates of HEK293 cells and Ltk−/− cells either untransfected or transfected with a plasmid expressing full length P703P; and (3) supernatant isolated from these cell cultures. Protein was transferred to nitrocellulose and then Western blotted using the anti-P703P polyclonal antibody #2594 at an antibody concentration of 1 μg/ml. Protein was detected using horse radish peroxidase (HRP) conjugated to an anti-rabbit antibody. A 35 kDa immunoreactive band could be observed with recombinant P703P. Recombinant P703P runs at a slightly higher molecular weight since it is epitope tagged. In lysates and supernatants from cells transfected with full length P703P, a 30 kDa band corresponding to P703P was observed. To assure specificity, lysates from HEK293 cells stably transfected with a control plasmid were also tested and were negative for P703P expression. Other anti-P703P antibodies showed similar results.

Immunohistochemical studies were performed as described above, using anti-P703P monoclonal antibody. P703P was found to be expressed at high levels in normal prostate and prostate tumor tissue but was not detectable in all other tissues tested (breast tumor, lung tumor and normal kidney).

Example 19

Characterization of Cell Surface Expression and Chromosome Localization of the Prostate-Specific Antigen P501 S This example describes studies demonstrating that the prostate-specific antigen P501S is expressed on the surface of cells, together with studies to determine the probable chromosomal location of P501 S.

The protein P501S (SEQ ID NO: 113) is predicted to have 11 transmembrane domains. Based on the discovery that the epitope recognized by the anti-P501S monoclonal antibody 10E3-G4-D3 (described above in Example 17) is intracellular, it was predicted that following transmembrane determinants would allow the prediction of extracellular domains of P501 S. FIG. 9 is a schematic representation of the P501S protein showing the predicted location of the transmembrane domains and the intracellular epitope described in Example 17. Underlined sequence represents the predicted transmembrane domains, bold sequence represents the predicted extracellular domains, and italized sequence represents the predicted intracellular domains. Sequence that is both bold and underlined represents sequence employed to generate polyclonal rabbit serum. The location of the transmembrane domains was predicted using HHMTOP as described by Tusnady and Simon (Principles Governing Amino Acid Composition of Integral Membrane Proteins: Applications to Topology Prediction, *J. Mol. Biol.* 283:489–506, 1998).

Based on FIG. 9, the P501 S domain flanked by the transmembrane domains corresponding to amino acids 274–295 and 323–342 is predicted to be extracellular. The peptide of SEQ ID NO: 518 corresponds to amino acids 306–320 of P501S and lies in the predicted extracellular domain. The peptide of SEQ ID NO: 519, which is identical to the peptide of SEQ ID NO: 518 with the exception of the substitution of the histidine with an asparginine, was synthesized as described above. A Cys-Gly was added to the C-terminus of the peptide to facilitate conjugation to the carrier protein. Cleavage of the peptide from the solid support was carried out using the following cleavage mixture: trifluoroacetic acid:ethanediol:thioanisol:water:phenol (40:1:2:2:3). After cleaving for two hours, the peptide was precipitated in cold ether. The peptide pellet was then dissolved in 10% v/v acetic acid and lyophilized prior to purification by C 18 reverse phase hplc. A gradient of 5–60% acetonitrile (containing 0.05% TFA) in water (containing 0.05% TFA) was used to elute the peptide. The purity of the peptide was verified by hplc and mass spectrometry, and was determined to be >95%. The purified peptide was used to generate rabbit polyclonal antisera as described above.

Surface expression of P501S was examined by FACS analysis. Cells were stained with the polyclonal anti-P501S peptide serum at 10 μg/ml, washed, incubated with a secondary FITC-conjugated goat anti-rabbit Ig antibody (ICN), washed and analyzed for FITC fluorescence using an Excalibur fluorescence activated cell sorter. For FACS analysis of transduced cells, B-LCL were retrovirally transduced with P501 S. To demonstrate specificity in these assays, B-LCL transduced with an irrelevant antigen (P703P) or nontransduced were stained in parallel. For FACS analysis of prostate tumor cell lines, Lncap, PC-3 and DU-145 were utilized. Prostate tumor cell lines were dissociated from tissue culture plates using cell dissociation medium and stained as above. All samples were treated with propidium iodide (PI) prior to FACS analysis, and data was obtained from PI-excluding (i.e. intact and non-permeabilized) cells. The rabbit polyclonal serum generated against the peptide of SEQ ID NO: 519 was shown to specifically recognize the surface of cells transduced to express P501S, demonstrating that the epitope recognized by the polyclonal serum is extracellular.

To determine biochemically if P501S is expressed on the cell surface, peripheral membranes from Lncap cells were isolated and subjected to Western blot analysis. Specifically, Lncap cells were lysed using a dounce homogenizer in 5 ml of homogenization buffer (250 mM sucrose, 10 mM HEPES, 1 mM EDTA, pH 8.0, 1 complete protease inhibitor tablet (Boehringer Mannheim)). Lysate samples were spun at 1000 g for 5 min at 4° C. The supernatant was then spun at 8000 g for 10 min at 4° C. Supernatant from the 8000 g spin was recovered and subjected to a 100,000 g spin for 30 min at 4° C. to recover peripheral membrane. Samples were then separated by SDS-PAGE and Western blotted with the mouse monoclonal antibody 10E3-G4-D3 (described above in Example 17) using conditions described above. Recombinant purified P501S, as well as HEK293 cells transfected with and over-expressing P501S were included as positive controls for P501S detection. LCL cell lysate was included as a negative control. P501S could be detected in Lncap total cell lysate, the 8000 g (internal membrane) fraction and also in the 00,000 g (plasma membrane) fraction. These results indicate that P501S is expressed at, and localizes to, the peripheral membrane.

To demonstrate that the rabbit polyclonal antiserum generated to the peptide of SEQ ID NO: 519 specifically recognizes this peptide as well as the corresponding native peptide of SEQ ID NO: 518, ELISA analyses were performed. For these analyses, flat-bottomed 96 well microtiter plates were coated with either the peptide of SEQ ID NO: 519, the longer peptide of SEQ ID NO: 520 that spans the entire predicted extracellular domain, the peptide of SEQ ID NO: 521 which represents the epitope recognized by the P501S-specific antibody 10E3-G4-D3, or a P501S fragment (corresponding to amino acids 355–526 of SEQ ID NO: 113) that does not include the immunizing peptide sequence, at 1 μg/ml for 2 hours at 37° C. Wells were aspirated, blocked with phosphate buffered saline containing 1% (w/v) BSA for 2 hours at room temperature and subsequently washed in PBS containing 0.1% Tween 20 (PBST). Purified anti-P501S polyclonal rabbit serum was added at 2 fold dilutions (1000 ng–125 ng) in PBST and incubated for 30 min at room temperature. This was followed by washing 6 times with PBST and incubating with HRP-conjugated goat anti-rabbit IgG (H+ L) Affinipure F(ab') fragment at 1:20000 for 30 min. Plates were then washed and incubated for 15 min in tetramethyl benzidine. Reactions were stopped by the addition of IN sulfuric acid and plates were read at 450 nm using an ELISA plate reader. As shown in FIG. 11, the anti-P501 S polyclonal rabbit serum specifically recognized the peptide of SEQ ID NO: 519 used in the immunization as well as the longer peptide of SEQ ID NO: 520, but did not recognize the irrelevant P501 S-derived peptides and fragments.

In further studies, rabbits were immunized with peptides derived from the P501S sequence and predicted to be either extracellular or intracellular, as shown in FIG. 9. Polyclonal rabbit sera were isolated and polyclonal antibodies in the serum were purified, as described above. To determine specific reactivity with P501S, FACS analysis was employed, utilizing either B-LCL transduced with P501S or the irrelevant antigen P703P, of B-LCL infected with vaccinia virus-expressing P501S. For surface expression, dead and non-intact cells were excluded from the analysis as described above. For intracellular staining, cells were fixed and permeabilized as described above. Rabbit polyclonal serum generated against the peptide of SEQ ID NO: 548, which corresponds to amino acids 181–198 of P501S, was found to recognize a surface epitope of P501S. Rabbit polyclonal serum generated against the peptide SEQ ID NO: 551, which corresponds to amino acids 543–553 of P501S, was found to recognize an epitope that was either potentially extracellular or intracellular since in different experiments intact or permeabilized cells were recognized by the polyclonal sera. Based on similar deductive reasoning, the sequences of SEQ ID NO: 541–547, 549 and 550, which correspond to amino acids 109–122, 539–553, 509–520, 37–54, 342–359, 295–323, 217–274, 143–160 and 75–88, respectively, of P501S, can be considered to be potential surface epitopes of P501S recognized by antibodies.

The chromosomal location of P501S was determined using the GeneBridge 4 Radiation Hybrid panel (Research Genetics). The PCR primers of SEQ ID NO: 528 and 529 were employed in PCR and DNA pools from the hybrid panel according to the manufacturer's directions. After 38 cycles of amplification, the reaction products were separated on a 1.2% agarose gel, and the results were analyzed through the Whitehead Institute/MIT Center for Genome Research web, server to determine the probable chromosomal location.

From the foregoing, it will be appreciated that, although specific embodiments of the invention have been described herein for the purposes of illustration, various modifications may be made without deviating from the spirit and scope of the invention. Accordingly, the present invention is not limited except as by the appended claims.

The invention claimed is:

1. An isolated polypeptide consisting of a portion of SEQ ID NO: 113 wherein the portion consists of at least amino acid residues 106–553 of SEQ ID NO: 113, amino acid residues 136–547 of SEQ ID NO: 113, amino acid residues 351–547 of SEQ ID NO: 113 or amino acid residues 351–472 of SEQ ID NO: 113.

2. An isolated polypeptide consisting of amino acid residues 106–553 of SEQ ID NO: 113, amino acid residues 136–547 of SEQ ID NO: 113, amino acid residues 351–547 of SEQ ID NO: 113 or amino acid residues 351–472 of SEQ ID NO: 113.

3. A fusion protein comprising at least one polypeptide according to claim 1.

4. A fusion protein according to claim 3, wherein the fusion protein comprises an expression enhancer that increases expression of the fusion protein in a host cell transfected with a polynucleotide encoding the fusion protein.

5. A fusion protein according to claim 3, wherein the fusion protein comprises a T helper epitope that is not present within the polypeptide of claim 1.

6. A fusion protein according to claim 3, wherein the fusion protein comprises an affinity tag.

* * * * *